United States Patent [19]
Boriack-Sjodin et al.

[11] Patent Number: 6,117,663
[45] Date of Patent: Sep. 12, 2000

[54] CRYSTAL OF A RAS-SOS COMPLEX

[75] Inventors: Ann Boriack-Sjodin, Waltham, Mass.; S. Mariana Margarit, Setauket; Dafna Bar-Sagi, Stony Brook, both of N.Y.; Philip Cole, Baltimore, Md.; John Kuriyan, Riverdale, N.Y.

[73] Assignees: The Rockefeller University, New York; The Research Foundation of State University of New York, Albany, both of N.Y.

[21] Appl. No.: 09/356,952

[22] Filed: Jul. 19, 1999

Related U.S. Application Data

[60] Provisional application No. 60/093,631, Jul. 21, 1998.

[51] Int. Cl.⁷ .................................................. C12N 9/14
[52] U.S. Cl. ............................. 435/195; 530/350; 435/18
[58] Field of Search ....................... 435/195, 18; 530/350

[56] References Cited

PUBLICATIONS

Boriack–Sjordin et al. "The structure basis of the activation of Ras by Sos" Nature, 394, 337–343, Jul. 1998.
Zheng et al. "The solution structure of the pleckstrin homology domain of human SOS1" J. Biol. Chem. 272, 30340–30344, Nov. 1997.
Tong et al. "Crystal structure at 2.2 A resolution of the catalytic domains of normal ras protein and oncogenic mutant complex with GDP" J. Mol. Biol. 217, 503–516, 1991.
Kraulis et al. "Solution structure and dynamics of Ras p21.GDP determined by heternuclear . . . " Biochemistry 33, 3515–3531, 1994.
Soisson et al. "Crystal structure of the Dbl and Pleckstrin homology domains from the human son of sevenless protein" Cell 95, 259–268, Oct. 1998.
de Vos et al. "Three–dimentional structure of oncogenic protein : Catalytic . . . " Science 239, 888–893, Feb. 1988.
Pai et al. "Structure of the guanine–nucleotide–binding domain of the Ha–ras . . . " Nature 341, 209–214, Sep. 1989.
Bar–Sugi, *Trends Endocrin. Metab.*, 5:165–169 (1994).
Bernstein et al., *Archives of Biochemistry & Biophysics*, 185:584–591 (1978).
Bourne et al., *Nature* , 349:1''17–127 (1991).
Boguski and McCormick, *Nature*, 366:643–654 (1993).
Brandmeier et al. *Helv. Chim. Acta.* 77: 70 (1994).
Brager et al., *Structure*, 5:325–336 (1997).
Buday and Downward, *Cell*, 73:611–620 (1993.
Bugg et al., *Scientific American*, Dec.:92–98 (1993).
Carson, *J. Appl. Cryst.*, 24:958–961 (1991).
Chardin et al., *Science*, 260:1338–1343 (1993).
Chen et al., *Oncogene* 9:2691–2698 (1994).
Cherfils et al., *Nature*, 392:101–105 (1998).
Collaborative Computing Project, N. The CCP4 Suite: Programs for protein cyrstallography. *Acta Cryst.*, D50:760–763 (1994).

Cowtan, Joint CCP4 and ESF–EACBM Newsletter on Protein Crystallography, 31:34–38 (1994).
Crochet et al., *J. Biol. Chem.*, 271:17234–17240 (1996).
Dunbrack et al., *Folding & Design*, 2:27–42 (1997).;
Feigel, *J. Am. Chem. Soc.* 108:181 (1986).
Gale et al., *Nature*, 363:88–92 (1993).
Gante, *Angew. Chem. Int. Ed. Engl.* 33:1699–1720 (1994).
Genin, and Johnston, *J. Am. Chem. Soc.* 114:8778 (1992).
Haney and Broach, *J. Biol. Chem.*, 269:16541–16548 (1994).
Harrison et al., *Science*, 276:431–435 (1997).
Holm and Sander, *J. Mol. Biol.*, 233:123–138 (1993).
Jones et al., *Acta Crystallogr.*, A47:110–119 (1991).
Jurnak, *Science*, 230:32–36 (1985).
Kawashima et al., *Nature*, 379:511–518 (1996).
Kemp, and Stiles, *Tetrahedron Lett.* 29:5057 (1988).
Lai et al., *Mol. Cell. Biol.*, 13:1345–1352 (1993).
Lenzen et al., *Biochemistry* 37:7420–7430 (1998).
Medema et al., *Molec. Cell. Biol.*, 13:155–162 (1993).
Milburn et al., *Science*, 247:939–945 (1990).
Mitsou et al., *EMBO J.*, 11:2391–2397 (1992).
Mosteller et al., *Molec. Cell. Biol.*, 14:1104–1112 (1994).
Mossessova et al., *Cell.* 92:415–423 (1998).
Nagai et al., *Tetrahedron* 49:3577 (1993).
Nicholls et al., *Proteins: Struct. Funct. and Genetics*, 11:281–296 (1991).
Nicholson et al. *Nature* 376:37 (1995).
Otwinowski and Minor, *Meth. Enzymol.*, 276:307–326 (1997).
Pai et al., *EMBO J.*, 9:2351–2359 (1990).
Poullet et al., *Eur. J. Biochem.*, 227:537–544 (1995).
Powers et al., *Molec. and Cell. Biol.*, 9:390–395 (1989.
Renault et al., *Nature*, 392:97–101 (1998).
Ripka et al., *Tetrahedron* 49:3593 (1993).
Rotunda et al. *Nature Structural Biology* 3:619–625 (1996).
Sato,and Nagai *J. Chem. Soc. Perkin Trans.* 1:1231 (1986).
Scheffzek et al., *Nature*, 384:591–596 (1996).
Schlessinger, *Trends Biochem. Sci.*, 18:273–275 (1994).
Segal et al., *Proc. Natl. Acad. Sci.*, 90:5564–5568 (1993).
Yu and Schreiber, *Nature*, 376:788–791 (1995).
Wagner, and Feigel, *Tetrahedron* 49:10831 (1993).
Wang et al., *Nat. Struct. Biol.*, 4:650–656 (1997.
Westbrook and Naday, *Meth. Enzymol.*, 276:244–268 (1997).

*Primary Examiner*—Ponnathapu Achutamurthy
*Assistant Examiner*—Nashaat T. Nashed
*Attorney, Agent, or Firm*—Klauber & Jackson

[57] ABSTRACT

A detailed three-dimensional structure for the complex formed between Ras and the Son of sevenless (Sos) protein is provided. Crystals of this complex are also included in the invention. The present invention further provides procedures for identifying agents that can inhibit tumor proliferation through the use of rational drug design predicated on the crystals and crystallographic data disclosed.

10 Claims, 16 Drawing Sheets

(7 of 16 Drawing Sheet(s) Filed in Color)

Ras-Sos  Ras-GTP

Schematic of GTP in Sos-Ras complex

R=analogs of the ribose triphosphate moiety

Further Analogs and Proposed Mechanisms of inhibition

8 → 9

10 → 11

12 → 13

14 → 15

16 → 17

Modifications of ribose-phosphate moiety    X= guanine or derivatives discussed above

18

19

20

21

Y=hydrogen bonding group such as $CO_2^-$, OH

22

23

Y=hydrogen bonding group such as $CO_2^-$, OH

Z=hydrophobic group such as alkyl or aryl

24  Ras β-turn

25

26

27

28

29

Z=alkyl or aryl group

CRYSTAL OF A RAS-SOS COMPLEX

CROSS-REFERENCE TO RELATED APPLICATIONS

The present application is a non-provisional application claiming the priority of copending provisional U.S. Ser. No. 60/093,631 filed Jul. 21, 1998, the disclosure of which is hereby incorporated by reference in its entirety. Applicants claim the benefits of this application under 35 U.S.C. §119(e).

GOVERNMENTAL SUPPORT

The research leading to the present invention was supported, at least in part, by a grant from National Institutes of Health, Grant No. F32 DK09664-1. Accordingly, the Government may have certain rights in the invention.

FIELD OF THE INVENTION

The present invention provides a crystal of a complex of Ras with the Son of sevenless (Sos) protein. The three-dimensional structural information is included in the invention. The interaction between these two proteins plays a key role in the regulation of cell proliferation. Therefore, the present invention provides procedures for identifying agents that can inhibit tumor proliferation through the use of rational drug design predicated on the crystallographic data.

BACKGROUND OF THE INVENTION

Ras proteins are highly conserved guanine nucleotide binding enzymes that couple cell surface receptors to intracellular signaling pathways controlling cell proliferation and differentiation [Bourne et al., *Nature*, 349:117–127 (1991); Boguski and McCormick, *Nature*, 366:643–654 (1993)]. Ras proteins act as molecular switches by cycling between an active GTP-bound state and an inactive GDP-bound state. The nucleotide bound state of Ras is not determined by intrinsic equilibrium with cytoplasmic pools of guanine nucleotides but by the relative activities of two classes of regulatory proteins: GTPase activating proteins (GAPs) and guanine nucleotide exchange factors (GEFs). Exchange factors promote the activation of Ras by catalyzing exchange of GDP for GTP, whereas activating proteins control the conversion of Ras to the inactive state by stimulating the hydrolysis of GTP to GDP [Boguski and McCormick, *Nature*, 366:643–654 (1993)].

Cell surface receptors that signal via tyrosine kinases activate Ras by stimulating the guanine nucleotide exchange reaction [Medema et al., *Molec. Cell. Biol.*, 13:155–162 (1993); Buday and Downward, *Cell*, 73:611–620 (1993); Gale et al., *Nature*, 363:88–92 (1993)]. Genetic and biochemical studies have indicated that this reaction is controlled by the Ras guanine nucleotide exchange factor Son of sevenless (Sos) [Bar-Sagi, *Trends Endocrin. Metab.*, 5:165–169 (1994)]. Following ligand binding, Sos is recruited from the cytoplasm to the activated receptor in a phosphotyrosine-dependent manner through adapter proteins such as Grb2. Grb2 contains SH3 domains that are bound constitutively to a C-terminal proline-rich region of Sos, and the Grb2-Sos complex is recruited to activated receptors by interactions between the SH2 domain of Grb2 and phosphotyrosine residues on the receptor [Schlessinger, *Trends Biochem. Sci.*, 18:273–275 (1994)]. Since Ras is localized to the membrane, receptor activation results in an increase in the effective concentration of Sos in the vicinity of Ras, thereby facilitating the exchange of bound guanine nucleotide for free cellular guanine nuzleotides. The cellular concentrations of GTP are ~10 fold higher than that of GDP, and Sos-mediated guanine nucleotide exchange on Ras thus leads to transient accumulation of active GTP-bound Ras molecules.

Sos proteins are large (Mr~150 kD) and contain several functional domains [Chardin et al., *Science*, 260:1338–1343 (1993)]. They are expressed in a wide range of tissues, consistent with their role as activators of the ubiquitously expressed Ras genes. The region of Sos that is functional for nucleotide exchange on Ras spans about 500 residues, and contains blocks of sequence that are conserved in other Ras-specific nucleotide exchange factors such as Cdc25, Sdc25 and Ras guanine nucleotide release factor (GRF) [Boguski and McCormick, *Nature*, 366:643–654 (1993); Poullet et al., *Eur. J. Biochem.*, 227:537–544 (1995)] (FIG. 1). Biochemical studies on these proteins have shown that the Ras-exchange factor complex is stable in the absence of nucleotides, and that the complex is dissociated by the re-binding of either GDP or GTP [Powers et al., *Molec. and Cell. Biol.*, 9:390–395 (1989); Mistou et al., *EMBO J.*, 11:2391–2397 (1992); Lai et al., *Mol. Cell. Biol.*, 13:1345–1352 (1993); Haney and Broach, *J. Biol. Chem.*, 269:16541–16548 (1994)]. The principal role for the exchange factor is to facilitate nucleotide release, and it does not appear to control the preferential rebinding of GTP over GDP to a significant extent [Haney and Broach, *J. Biol. Chem.*, 269:16541–16548 (1994); Klebe et al., *Biochemistry*, 34:12543–12552 (1995)].

The utilization of nucleotide exchange to control the timing of critical molecular events is a mechanism that is common to many different cellular regulators. In addition to small guanine nucleotide binding proteins (G-proteins) homologous to Ras, such as the Arf, Rab, Rho, Rac and Ran, nucleotide exchange is also crucial to the timing cycles of the heterotrimeric G-proteins and ribosomal elongation factor Tu, which have catalytic cores that are structurally and functionally similar to Ras [Bourne et al., *Nature*, 349:117–127 (1991)]. Nucleotide exchange is also critical to the cycles of the protein chaperones of the DnaK/Hsp70 family, which utilize ATP to bind and release peptides and are unrelated in sequence or structure to the GTPases [Harrison et al., *Science*, 276:431435 (1997)].

In contrast to the high degree of structural conservation seen in the GTPases, there are distinct families of nucleotide exchange factors that are unrelated to each other. The structures of several small G-protein exchange factors have been determined in isolation, revealing a variety of protein architectures (Mss4 [Yu and Schreiber, *Nature*, 376:788–791 (1995)], ARNO/Sec7 [Mossessova et al., *Cell*, 92:415423 (1998); Cherfils et al., *Nature*, 392:101–105 (1998)] and RCC1 [Renault et al., *Nature*, 392:97–101 (1998)]). At the present time the structure of only one nucleotide exchange factor bound to its cognate guanine nucleotide binding proteins has been determined, that of EF-Tu bound to its exchange factor EF-Ts [Wang et al., *Nat. Struct. Biol.*, 4:650–656 (1997); Kawashima et al., *Nature*, 379:511–518 (1996)]. In addition, the structure of the ATPase domain of DnaK bound to its exchange factor GrpE has also been determined [Harrison et al., *Science*, 276:431–435 (1997)]. No structural information is available on Ras-type small G-proteins complexed with their nucleotide exchange factors.

One means of modulating cellular proliferation and/or differentiation is to either inhibit or facilitate the Ras-Sos interaction. Therefore, there is a need to identify agonists or antagonists to the Ras-Sos complex. Unfortunately, such identification has heretofore relied on serendipity and/or systematic screening of large numbers of natural and synthetic compounds. A far superior method of drug-screening relies on structure based drug design. In this case, the three dimensional structure of Ras-Sos complex is determined and potential agonists and/or potential antagonists are designed with the aid of computer modeling [Bugg et al., *Scientific American*, Dec.:92–98 (1993); West et al., *TIPS*, 16:67–74 (1995); Dunbrack et al., *Folding & Design*, 2:27–42 (1997)]. However, heretofore the three-dimensional structure of the Ras-Sos complex has remained unknown. Therefore, there is a need for obtaining a crystal of a Ras-Sos complex with sufficient quality to allow high quality crystallographic data to be obtained. Furthermore there is a need for the determination of the three-dimensional structure of such crystals. Finally, there is a need for procedures for related structural based drug design predicated on such crystallographic data.

The citation of any reference herein should not be construed as an admission that such reference is available as "Prior Art" to the instant application.

SUMMARY OF THE INVENTION

The present invention provides crystals of the Ras-Son of sevenless protein-protein binding complex (Ras-Sos complex). In addition, the present invention also provides detailed three-dimensional structural data for tie Ras-Sos complex. Since the interaction between Ras and Sos plays a key role in the regulation of cell propagation and differentiation, the structural data obtained for the Ras-Sos complex can be used for the rational design of drugs that modulate cell proliferation. Therefore, the present invention further provides methods of identifying agonists or antagonists of the Ras-Sos complex which can be used in the regulation of cellular proliferation and/or differentiation. In a particular embodiment, such methodology can be used in the identification of drugs that inhibit tumor proliferation.

One aspect of the present invention provides crystals of the Ras-Sos complex that can effectively diffract X-rays for the determination of the atomic coordinates of the complex to a resolution of better than 5.0 Angstroms. In a preferred embodiment the crystal effectively diffracts X-rays for the determination of the atomic coordinates of the protein-ligand complex to a resolution of better than 3.0 Angstroms. In a particular embodiment the crystal effectively diffracts X-rays for the determination of the atomic coordinates of the protein-ligand complex to a resolution of 2.8 Angstroms.

In one embodiment, the crystal of the Ras-Sos complex comprises a full length Ras and a full length Sos. In a preferred embodiment of this type the full length Ras has the amino acid sequence of SEQ ID No:1 or the amino acid sequence of SEQ ID No:1 having one or more conservative amino acid substitutions and the fall length Sos has the amino acid sequence of SEQ ID NO:2 or the amino acid sequence of SEQ ID NO:2 having one or more conservative amino acid substitutions. In another embodiment, the Ras-Sos complex comprises a full length Ras and a fragment of the Sos which minimally contains a Sos catalytic domain. In yet another embodiment, the Ras-Sos complex comprises a full length Sos and a fragment of the Ras which minimally contains the Sos contacting region.

In a related feature of the invention the crystal of the Ras-Sos complex comprises a Ras fragment, and a Sos fragment. In one such embodiment the Ras fragment comprises a Sos contacting region and the Sos fragment comprises a Sos catalytic domain. In a particular embodiment of this type the Sos catalytic domain comprises the amino acid sequence of amino acids 781 to 1017 of SEQ ID NO:2. In another embodiment the Sos catalytic domain comprises amino acid sequence of amino acid 781 to 1017 of SEQ ID NO:2 having one or more conservative amino acid substitutions. In a preferred embodiment of this type the Sos fragment contains amino acids 752 to 1044 of the amino acid sequence of SEQ ID NO:2. In a related embodiment the Sos fragment contains amino acids 752 to 1044 of SEQ ID NO:2 having one or more conservative amino acid substitutions. In a particular embodiment the Sos fragment comprises the Sos catalytic domain and an N-Domain. In a preferred embodiment of this type the Sos fragment comprises the amino acid sequence of amino acids 564 to 1049 of SEQ ID NO:2. In yet another embodiment the Sos fragment comprises the amino acid sequence of amino acid 564 to 1049 of SEQ ID NO:2 having one or more conservative amino acid substitutions.

In another particular embodiment the crystal of the Ras-Sos complex comprises a Ras fragment containing the Sos contacting region halving the amino acid sequence of amino acids 5 to 105 of SEQ ID NO:1. In another embodiment, the crystal comprises a Ras fragment that further comprises the amino acid sequence of amino acids 1 to 4 and 106 to 166 of SEQ ID NO:1 (i.e., the Ras fragment comprises amino acids 1 to 166 of SEQ ID NO:1). In another embodiment, the Ras fragment contains a Sos contacting region having the amino acid sequence of amino acid 5 to 105 of SEQ ID NO:1 having one or more conservative amino acid substitutions. In a related embodiment, the Ras fragment further comprises amino acids 1 to 4 and 106 to 166 of SEQ ID NO:1 having one or more conservative amino acid substitutions (i.e., the Ras fragment comprises amino acids 1 to 166 of SEQ ID NO:1 having one or more conservative amino acid substitutions). In still another embodiment of this type the crystal comprises a Ras fragment that contains amino acids 5 to 160 of the amino acid sequence of SEQ ID NO:1. In a related embodiment the crystal comprises a Ras fragment that contains amino acids 5 to 160 of SEQ ID NO:1 having one or more conservative amino acid substitutions.

In a preferred embodiment the crystal comprises a Ras fragment comprising amino acids 1 to 166 of SEQ ID NO:1 or a Ras fragment comprising amino acids 1 to 166 of SEQ ID NO:1 having one or more conservative amino acid substitutions and a Sos fragment comprising the amino acid sequence of amino acids 564 to 1049 of SEQ ID NO:2, or the amino acid sequence of amino acid 564 to 1049 of SEQ ID NO:2 having one or more conservative amino acid substitutions.

A crystal of the present invention may take a variety of forms all of which are included in the present invention. In one embodiment the crystal has a space group of I4 or I422 and a unit cell of dimensions of a=124.6 Å, b=124.6 Å and c=314.9 Å. In a preferred embodiment the crystal has a space group of I422 and a unit cell of dimensions of a=142.7 Å, b=142.7 Å and c=207.9 Å.

The present invention further provides portions of Ras and Sos that not only bind to form a Ras-Sos complex, but in addition, form complexes that are amenable to crystallization. Preferably, these portions (e.g., Ras and/or Sos fragments) are soluble in aqueous solutions. Therefore this aspect of the present invention provides a Ras fragment that comprises the Sos contacting region. In a particular embodiment of this type, the Ras fragment contains amino acids 5 to 105 of the amino acid sequence of SEQ ID NO:1. In a related embodiment the Ras fragment contains amino acids 5 to 105 of SEQ ID NO:1 having one or more conservative amino acid substitutions. In a preferred embodiment of this type the Ras fragment contains amino acids 5 to 160 of the amino acid sequence of SEQ ID NO:1. In a related embodiment the Ras fragment contains amino acids 5 to 160 of SEQ ID NO:1 having one or more conservative amino acid substitutions. In a more preferred embodiment of this type the Ras fragment contains amino acids 1 to 166 of the amino acid sequence of SEQ ID NO:1. In a related embodiment the Ras fragment contains amino acids 1 to 166 of SEQ ID NO:1 having one or more conservative amino acid substitutions.

In another embodiment a Sos fragment of the present invention comprises the Sos catalytic domain. In a particular embodiment of this type, the Sos fragment contains amino acids 781 to 1017 of the amino acid sequence of SEQ ID NO:2. In a related embodiment the Sos fragment contains amino acids 781 to 1017 of SEQ ID NO:2 having one or more conservative amino acid substitutions. In a preferred embodiment of this type the Sos fragment contains amino acids 752 to 1044 of the amino acid sequence of SEQ ID NO:2. In a related embodiment the Sos fragment contains amino acids 752 to 1044 of SEQ ID NO:2 having one or more conservative amino acid substitutions. In a more preferred embodiment of this type the Sos fragment contains amino acids 564 to 1049 of the amino acid sequence of SEQ ID NO:2. In a related embodiment the Sos fragment contains amino acids 564 to 1049 of SEQ ID NO:2 having one or more conservative amino acid substitutions.

The present invention also includes nucleic acids encoding the Ras fragments and Sos fragments of the present invention. In a particular embodiment of this type, the nucleic acid encodes a Ras fragment that contains amino acids 5 to 105 of the amino acid sequence of SEQ ID NO:1. In a related embodiment the nucleic acid encodes a Ras fragment that contains amino acids 5 to 105 of SEQ ID NO:1 having one or more conservative amino acid substitutions. In a preferred embodiment of this type the nucleic acid encodes a Ras fragment that contains amino acids 5 to 160 of the amino acid sequence of SEQ ID NO:1. In a related embodiment the nucleic acid encodes a Ras fragment that contains amino acids 5 to 160 of SEQ ID NO:1 having one or more conservative amino acid substitutions. In a more preferred embodiment of this type the nucleic acid encodes a Ras fragment that contains amino acids 1 to 166 of the amino acid sequence of SEQ ID NO:1. In a related embodiment the nucleic acid encodes a Ras fragment that contains amino acids 1 to 166 of SEQ ID NO:1 having one or more conservative amino acid substitutions.

In another embodiment the nucleic acid encodes a Sos fragment of the present invention that comprises the Sos catalytic domain. In a particular embodiment of this type, the nucleic acid encodes a Sos fragment that contains amino acids 781 to 1017 of the amino acid sequence of SEQ ID NO:2. In a related embodiment the nucleic acid encodes a Sos fragment that contains amino acids 781 to 1017 of SEQ ID NO:2 having one or more conservative amino acid substitutions. In a preferred embodiment of this type the nucleic acid encodes a Sos fragment that contains amino acids 752 to 1044 of the amino acid sequence of SEQ ID NO:2. In a related embodiment the nucleic acid encodes a Sos fragment that contains amino acids 752 to 1044 of SEQ ID NO:2 having one or more conservative amino acid substitutions. In a more preferred embodiment of this type the nucleic acid encodes a Sos fragment that contains amino acids 564 to 1049 of the amino acid sequence of SEQ ID NO:2. In a related embodiment the nucleic acid encodes a Sos fragment that contains amino acids 564 to 1049 of SEQ ID NO:2 having one or more conservative amino acid substitutions.

The present invention also provides expression vectors which comprise a nucleic acid of the present invention (as exemplified above) operatively associated with an expression control sequence. The present invention further includes a cell transfected or transformed with an expression vector of the present invention. In one such embodiment the cell is a prokaryotic cell. In a preferred embodiment of this type the prokaryotic cell is an *E. coli* cell. In another embodiment the cell is a eukaryotic cell. In one such embodiment of this type the eukaryotic cell is an insect cell. In another such embodiment the eukaryotic cell is a vertebrate cell. In a preferred embodiment the vertebrate cell is a mammalian cell.

The present invention also includes methods of expressing the nucleic acids of the present invention comprising culturing a cell that expresses the Ras fragment or Sos fragment of the present invention, for example, in an appropriate cell culture medium under conditions that provide for expression of the protein by the cell. Any of the cells mentioned above may be employed in this method. In a particular embodiment the cell is an *E.coli* cell which has been manipulated to express a Ras fragment or Sos fragment of the present invention. In a preferred embodiment, the method further includes the step of purifying the Ras fragment or Sos fragment.

The present invention further includes methods of using the Ras fragments and Sos fragments of the present invention to grow a crystal of the Ras-Sos complex. One such method comprises contacting the Ras fragment and Sos fragment under conditions in which a Ras-Sos complex is formed and growing the crystal of the Ras-Sos complex. Preferably the crystal effectively diffracts X-rays for the determination of the atomic coordinates of the protein-ligand complex to a resolution of better than 5.0 Angstroms. In one such embodiment the Ras fragment is between about 100 to 170 amino acids and contains amino acids 5 to 105 of SEQ ID NO:1, or amino acids 5 to 105 of SEQ ID NO:1 having one or more conservative amino acid substitutions. In another embodiment the Sos fragment is between about 230 to 500 amino acids and contains amino acids 781 to 1017 of SEQ ID NO:2, or the amino acids 781 to 1017 of SEQ ID NO:2 having one or more conservative amino acid substitutions.

In a particular embodiment the crystal is grown by vapor diffusion. In one such embodiment the crystal is grown by hanging-drop vapor diffusion. In another embodiment the crystal is grown by sitting-drop vapor diffusion. Standard micro and/or macro seeding may be used to obtain a crystal of X-ray quality, i.e. a crystal that will diffract to allow resolution better than 5.0 Angstoms. Although the full length Ras protein and any number of Ras fragment, containing the Sos contacting region may be used, preferably the Ras fragment comprises amino acids 5 to 160 of SEQ ID NO:1. Similarly in a preferred embodiment a Sos fragment is used comprising amino acids 752 to 1044 of the amino acid sequence of SEQ ID NO:2.

Still another aspect of the present invention comprises a method of using a crystal of the present invention and/or a dataset comprising the three-dimensional coordinates obtained from the crystal in a drug screening assay. Example 2 below, exemplifies the use of such information to rationally design potentially important compounds that in turn can minimally be used as starting points in the drug screens.

In addition, the present invention provides three-dimensional coordinates for the Ras-Sos complex. In a particular embodiment the coordinates are for the human Ras-Sos complex as disclosed in Table 3. Thus the data set of Table 3, below, is part of the present invention. Furthermore, the data set of Table 3, below, in a computer readable form is also part of the present invention. In addition, methods of using such coordinates (including in computer readable form) in the drug assays and drug screens as exemplified herein, are also part of the present invention. In a particular embodiment of this type, the coordinates contained in the data set of Table 3, below, can be used to identify potential modulators of the Ras-Sos interaction. In one such embodiment the potential modulator is an inhibitor of the Sos nucleotide exchange reaction with Ras.

Accordingly, the present invention provides methods of identifying an agent or drug that stabilizes the Ras-Sos complex, or alternatively inhibit the formation of the Ras-Sos complex (see Example 2, below). The identification of such drugs can aid in the treatment of cancer, since activated Ras is involved in the proliferation of tumor cells, and the association and subsequent dissociation of Sos from Ras is a required step for the activation of Ras.

One such embodiment comprises selecting a potential agent that can stabilize the Ras-Sos complex by performing rational drug design with the three-dimensional coordinates determined for the crystal. Preferably the selection is performed in conjunction with computer modeling. The potential agent is then contacted with the Ras-Sos complex and the stability of the Ras-Sos complex is determined. A potential agent (or drug) is selected as an agent (or drug) that can stabilize the Ras-Sos complex when there is an increase in the stability of the Ras-Sos complex.

In a particular embodiment of this type, the method further comprises growing a supplemental crystal containing a Ras-Sos complex formed in the presence of the potential agent. Preferably the resulting crystal effectively diffracts X-rays for the determination of the atomic coordinates of the protein-ligand complex to a resolution of better than 5.0 Angstroms (more preferably better than 3.0 Angstroms). The three-dimensional coordinates of the supplemental crystal is determined with molecular replacement analysis and a second generation agent (or drug) is selected by performing rational drug design with the three-dimensional coordinates determined for the supplemental crystal. Preferably, the selection is performed in conjunction with computer modeling.

As should be readily apparent the three-dimensional structure of a supplemental crystal can be determined by molecular replacement analysis or multiwavelength anomalous dispersion or multiple isomorphous replacement. A candidate drug is then selected by performing rational drug design with the three-dimensional structure determined for the supplemental crystal, preferably in conjunction with computer modeling. The candidate drug can then be tested in a large number of drug screening assays using standard biochemical methodology exemplified herein.

The present invention further provides methods of selecting an agent that inhibits the binding of GTP to the Ras protein contained in a Ras-Sos complex using a crystal of the present invention or a dataset comprising the three-dimensional coordinates obtained from the crystal. One such embodiment comprises selecting a potential agent by performing rational drug design with the three-dimensional coordinates determined for the crystal. Preferably the selection is performed in conjunction with computer modeling. The potential agent is then contacted with (i) a Ras-Sos complex, and (ii) GTP or a GTP analog, under conditions in which the Ras-Sos complex can bind GTP and/or the GTP analog in the absence of the agent. The binding affinity of the Ras-Sos complex with GTP and/or the GTP analog is determined. A potential agent is selected as an agent that inhibits the binding of GTP to a Ras contained in a Ras-Sos complex when there is a decrease in the binding affinity of GTP or the GTP analog with the Ras in the presence of the agent. In a particular embodiment of this type, labeled GTP or a labeled GTP analog is used, and the binding affinity of GTP and/or the GTP analog for Ras is determined through the detection of the label.

In a particular embodiment of this type, the method further comprises growing a supplemental crystal containing a Ras-Sos complex formed in the presence of the potential agent. The crystal grown effectively diffracts X-rays for the determination of the atomic coordinates of the protein-ligand complex to a resolution of better than 5.0 Angstroms (preferably better than 3.0 Angstroms). The three-dimensional coordinates of the supplemental crystal is determined with molecular replacement analysis and a second generation agent (or drug) is selected by performing rational drug design with the three-dimensional coordinates determined for the supplemental crystal. Preferably, the selection is performed in conjunction with computer modeling. As discussed above, the three-dimensional structure of a supplemental crystal can be determined by molecular replacement analysis or multiwavelength anomalous dispersion or multiple isomorphous replacement and the candidate drug can then be selected by performing rational drug design with the three-dimensional structure determined for the supplemental crystal, preferably in conjunction with computer modeling. The candidate drug can then be tested in a large number of drug screening assays using standard biochemical methodology exemplified herein.

The present invention further provides methods of identifying agents (or drugs) that inhibit the formation of the Ras-Sos complex using a crystal of the present invention, and/or a dataset comprising the three-dimensional coordinates obtained from the crystal. One such embodiment comprises the selection of a potential agent that mimics a structural feature of Ras formed when Ras is bound to Sos. The selection is performed using rational drug design with the three-dimensional coordinates determined for the crystal. Preferably the selection is performed in conjunction with computer modeling. The potential agent is then contacted with either Sos alone or Sos in the presence of Ras under conditions in which the Ras-Sos complex can form in the absence of the potential agent. In the former case, after the contacting of the Sos with the agent, the Sos and potential agent are then contacted with Ras under conditions in which the Ras-Sos complex can form in the absence of the potential agent. The binding affinity of Ras for Sos is then determined (e.g., measured) and a potential agent is identified as an agent that inhibits the formation of the Ras-Sos complex when there is an decrease in the binding affinity of Ras for Sos.

In a particular embodiment of this type, the structural feature of Ras formed when Ras is bound to Sos is the β-turn of amino acids 64 to 67 of SEQ ID NO:1 as described in Example 2, below.

Computer analysis may be performed with one or more of the computer programs including: QUANTA, CHARMM, INSIGHT, SYBYL, MACROMODEL and ICM [Dunbrack et al., *Folding & Design*, 2:27–42 (1997)]. In a further embodiment of this aspect of the invention, an initial drug screening assay is performed using the three-dimensional structure so obtained, preferably along with a docking computer program. Such computer modeling can be performed with one or more Docking programs such as DOC, GRAM and AUTO DOCK [Dunbrack et al., *Folding & Design*, 2:2742 (1997)].

It should be understood that in all of the drug screening assays provided herein, a number of iterative cycles of any or all of the steps may be performed to optimize the selection. For example, assays and drug screens that monitor the nucleotide exchange rate of Ras catalyzed by Sos in the presence and/or absence of a potential modulator (or potential drug) are also included in the present invention and can be employed as the sole assay or drug screen, or more preferably as a single step in a multi-step protocol for identifying modulators of Ras-dependent cellular proliferation and the like.

The present invention further provides the novel agents (modulators or drugs) that are identified by a method of the present invention, along with the method of using agents (modulators or drugs) identified by a method of the present invention, for inhibiting Ras-dependent cellular proliferation.

Accordingly, it is a principal object of the present invention to provide a crystal containing the Ras-Sos complex.

It is a further object of the present invention to provide the three-dimensional coordinates of the Ras-Sos complex.

It is a further object of the present invention to provide soluble fragments of Sos that bind Ras.

It is a further object of the present invention to provide soluble fragments of Ras that bind Sos.

It is a further object of the present invention to provide methods of identifying drugs that can modulate cellular proliferation.

It is a further object of the present invention to provide methods for the rational design of drugs that stabilize the Ras-Sos complex It is a further object of the present invention to provide methods for the rational design of drugs that bind to Sos and prevent it from interacting with Ras.

These and other aspects of the present invention will be better appreciated by reference to the following drawings and Detailed Description.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIG. 2A shows a ribbon diagram of the Ras-Sos complex. The N-Domain of Sos (residues 568 to 741) is blue; the catalytic domain (residues 752 to 1044) is green; Ras is shaded gray. Conserved regions among Ras family exchange factors are indicated and shaded red (SCR I, SCR2, and SCR3 [Boguski and McCormick, *Nature*, 366:643–654 (1993)]) and cyan (SCR0 [Lai et al., *Mol. Cell. Biol.*, 13:1345–1352 (1993)]). Disordered residues of Sos (591–596, 654–675, 742–751) are shown as dotted lines. All ribbon diagrams were generated using RIBBONS [Carson, *J. Appl. Cryst.*, 24:958–961 (1991)]. FIG. 2B shows the Ras-Sos complex with the catalytic domain of Sos depicted as a molecular surface. The N-Domain is shown as a ribbon with the same color scheme as FIG. 2A,); disordered residues connecting the N-Domain and the catalytic domain are not represented. Conserved residues Ile 956 and Phe 958 in the catalytic domain that form a hydrophobic interface with the N-Domain are labeled. The polypeptide backbone is shown in white, except the P-loop and surrounding residues (1–25) which are red and the Switch 1 (residues 25–40) and Switch 2 (residues 57–75) segments which are orange. This and all figures with molecular surfaces were generated using GRASP [Nicholls et al., *Proteins: Struct. Funct. and Genetics*, 11:281–296 (1991)].

FIG. 4A shows the structure of Ras in the Ras-Sos complex. Residues that form direct interactions with Sos are shown as red spheres; additional residues at the interface are shown as orange spheres. The primary sequence of Ras is shown above with the Switch 1 and Switch 2 regions indicated. GTP and magnesium ion are shown for reference purposes only. FIG. 4B shows the interface surface of Ras; the orientation of Ras is the same as FIG. 4A. The surface is colored using a gradient: bright orange indicates atoms <4 Å from Sos, white indicates atoms >7 Å from Sos, lighter shades of orange indicate intermediate distances. Sos (N-Domain deleted) is shown as a green ribbon.

FIG. 5A depicts selected interactions between Ras and GTP (521P [the code for the coordinates for the 1.35 Å structure of Ras (1–166) bound to a GTP analogue in the Protein Data Bank, Pai et al., *EMBO J.*, 9:2351–2359 (1990)]). Backbone atoms of Ras residues 10–15 (P-loop), 28–35 (Switch 1), and 57–62 (Switch 2) and selected side chains are shown and labeled; water molecules are depicted as red spheres. Selected interactions are shown as dotted lines. GTP is shaded pink and magnesium ion is shown as a magenta sphere. FIG. 5B depicts selected interactions between Ras and Sos in the same orientation as in FIG. 5A. Backbone atoms of Ras residues 10–15, 28–35 and 57–62 and selected side chains are shown and labeled; only helix αH of Sos and selected side chains are shown. GTP and magnesium ion are shown for reference purposes only. FIG. 5C depicts the GTP binding site on the surface of Ras in Ras-GTP (521P [Pai et al., *EMBO J.*, 9:2351–2359 (1990)]). GTP is shaded pink and the magnesium ion is a magenta sphere. The side chain of Tyrosine32 was deleted from the surface calculations in the interests of clarity. FIG. 5D depicts the surface of Ras in the Ras-Sos complex with the backbone of Sos as a green ribbon. Ras is in a slightly different orientation than Ras-GTP in FIG. 5C). The GTP and magnesium ion are shown for reference purposes only.

FIG. 6A is a schematic of the Switch 2 region in Ras-GTP. FIG. 6B is a schematic of the Switch 2 region in Ras-Sos. The loop containing residues 57–67 of Ras is rearranged to form a new series of β-turns and new inter- and intramolecular interactions. Hydrogen bonds are shown as dashed lines, hydrophobic interactions re shown as solid arcs. Magnesium is shown for reference purposes only. FIGS. 6C–6D show that the Switch 2 region of Ras in the Ras-Sos complex is superimposed on the surface of Sos. Selected residues of Sos that make important interactions with Ras are indicated with black labels; residues of Ras are indicated with orange labels. Magnesium and nucleotide are shown for reference purposes only.

DETAILED DESCRIPTION OF THE INVENTION

The present invention provides crystals of a complex (if human H-Ras with the Ras guanine nucleotide exchange factor region of the Son of sevenless protein, Sos. Moreover, the present invention provides the structural determination of such crystals by X-ray crystallography. In one such embodiment, the structure of the crystal has been determined at a resolution of 2.8 Å.

The impetus for the present invention was partially based on the fact that the proliferation of cells is critically dependent on the activation state of Ras, and that the nucleotide exchange factor region of Sos is required for the activation of Ras. The present invention therefore employs the three-dimensional structural determination of the Ras-Sos complex disclosed herein, for identifying drugs that can modulate the proliferation of cells. In a particular embodiment, the three-dimensional structural information is used in the design of an inhibitor of cell proliferation for the treatment of cancer.

As a nucleotide exchange factor, Sos functions under two apparently conflicting imperatives. On the one hand, the interaction between Sos and Ras must be sufficiently strong so as to dislodge the tightly bound nucleotide. However, too tight an interaction between Ras and Sos would lead to dead-end complexes, and so the Ras-Sos complex needs to be poised for subsequent displacement by incoming nucleotides. The structure of the Ras-Sos complex disclosed herein demonstrates that Ras and Sos meet these demands by forming a tight complex that is anchored at one end of the nucleotide binding site, where phosphate and magnesium are normally bound. The interface between Sos and Ras is mainly hydrophilic, suggesting a ready unzippering via water mediated displacements of the coordinating sidechains. The main interacting elements of Sos avoid direct occlusion of the nucleotide binding site, excepting the region where the terminal phosphate groups and the magnesium ion are bound. This architectural feature of the complex provides opportunities for incoming nucleotides to reverse the process by competing for the groups that ligate the phosphate and metal ion.

The structural determinations of the present invention show that nucleotide release is facilitated by a large Sos-mediated displacement of the Switch 1 region of Ras, which is responsible for stabilizing the nucleotide in Ras. The conformation of Ras in the complex is inconsistent with nucleotide binding being due to changes in the Switch 1 and Switch 2 regions. The Switch 2 segment is completely buried in the Ras-Sos interface, and changes in its structure result in the disruption of the binding sites for the phosphate groups of the nucleotide and the associated magnesium ion. Sos does not impede the binding sites for the base and the ribose of GTP or GDP, and thus the Ras-Sos complex maintains a structure that permits nucleotide release and rebinding.

Figure 8A:
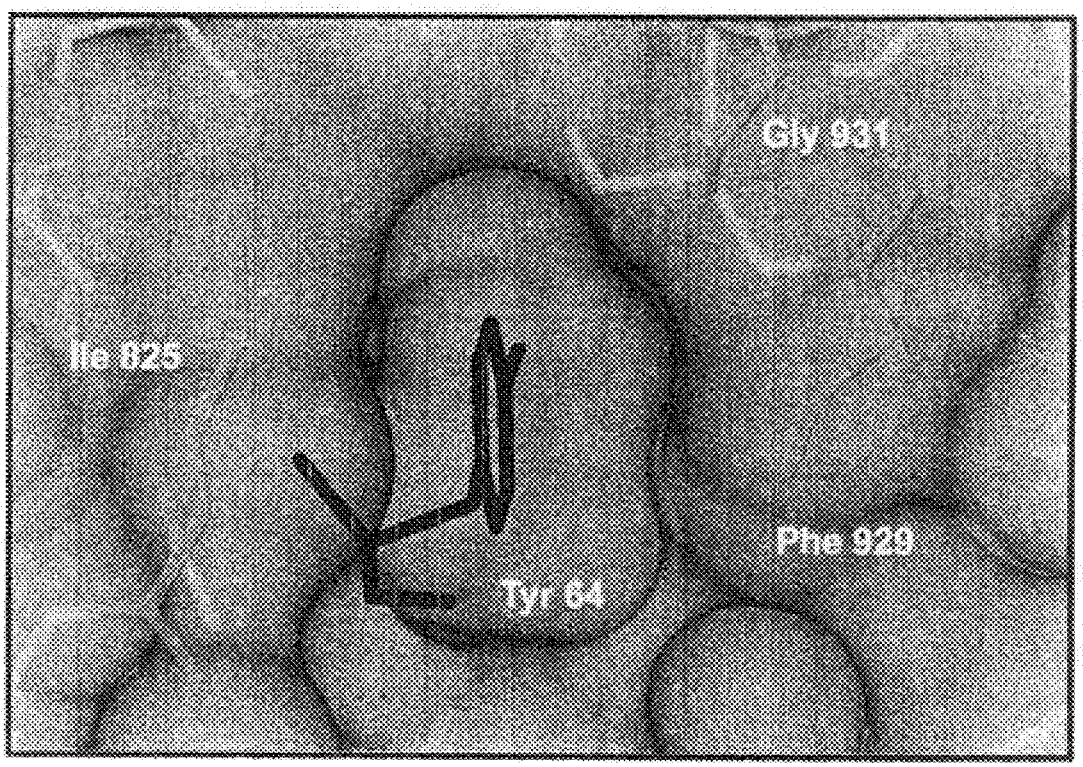
FIG. 8A is the surface presentation of the hydrophobic pocket of the Sos catalytic domain (Sos-CD). Sos residues are indicated in blue and Ras residues are in purple.
Figure 8B:
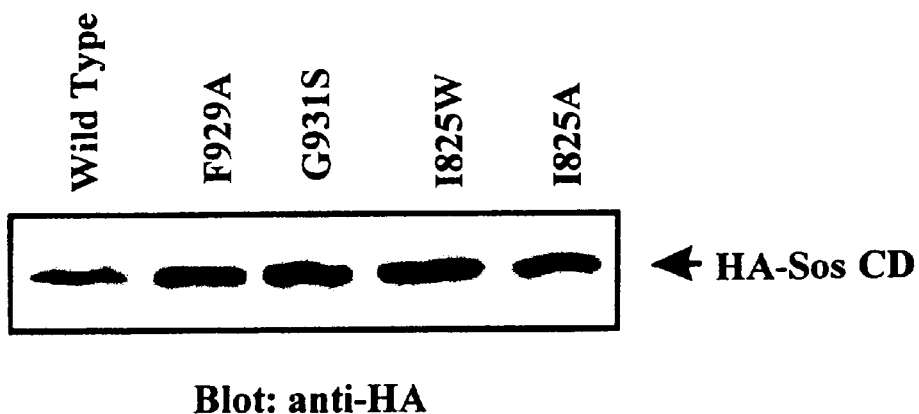
FIG. 8B depicts the expression of Sos-CD mutants. COS1 cells were transfected with cDNAs encoding HA-tagged Sos-CD containing the indicated point mutations. The cells were lysed and protein expression was detected by immunoblotting using anti-HA antibodies.
Figure 8C:
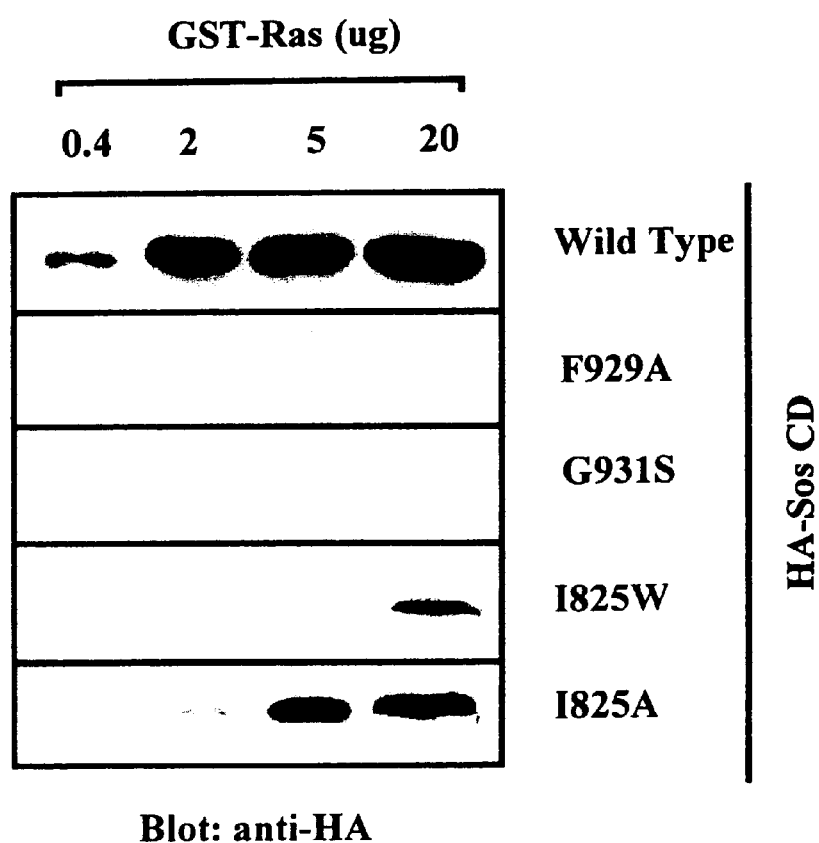
FIG. 8C shows that the interactions at the hydrophobic pocket are critical for Ras-Sos binding. Cell lysates containing the indicated HA-Sos-CD mutants were incubated with increasing concentrations of GST-Ras protein immobilized on glutathione beads. The beads were washed to remove unbound material and bound proteins were eluted by incubation with SDS sample buffer. The samples were analyzed by immunoblotting with anti-HA antibodies.

Through site-directed mutagenesis specific substitutions of SOS residues which comprise the hydrophobic pocket of SOS (FIG. 8A) have been shown to abolish or reduce binding to Ras (see FIG. 8C). These findings indicate that the interaction between Ras and Sos is critically dependent on hydrophobic contacts occurring within a small and well-defined region. Therefore, inhibitors that target this region are likely to be effective inhibitors of Ras-Sos interactions. Such inhibitors can be identified through the methods disclosed herein.

Thus, the structural information provided by the present invention facilitates the design of inhibitors that can block the activation of Ras by Sos. For example, hydrophobic compounds that bind to the core hydrophobic region at the heart of the binding site for Ras on Sos may be effective inhibitors of Sos action e.g., a drug that acts as the mimetic of the region of Ras that binds to the hydrophobic pocket of Sos. Alternatively, nucleotide analogs that are designed to recognize the altered nucleotide binding site in the Ras-Sos complex may help to stabilize the Ras-Sos complex, mimicking the action of dominant negative alleles of Ras.

Therefore, the present invention provides methods of identifying agents or drugs that can be used to control the proliferative status of cells, and in particular the proliferation of tumor cells. For example, small-molecule inhibitors of the nucleotide exchange region of Sos can be designed for use as drugs in the treatment of cancer. Similarly, nucleotide analogs can be designed that stabilize the Ras-Sos complex.

Therefore, if appearing herein, the following terms shall have the definitions set out below:

As used herein the term "Ras-Sos complex" denotes the tight protein-protein complex formed between Ras and Sos in the absence of nucleotides. Although the Ras-Sos complex is naturally formed by the full length Ras and Sos proteins, as used herein, the Ras-Sos complex also includes complexes that minimally contain a Sos catalytic domain and the Sos contacting domain of Ras. The three-dimensional structure of the human Ras-Sos complex is disclosed in Example 1, below.

As used herein a "Sos contacting region" of Ras is the region of the Ras protein that is directly involved in binding the nucleotide exchange factor region of Sos In the human Ras, this region comprises amino acid residues 5–105 of SEQ ID NO:1.

As used herein a "Ras fragment" of the invention that contains a "Sos contacting region" is a fragment of the Ras protein that comprises the portion of the protein that is directly involved in binding the nucleotide exchange domain of Sos.

As used herein, the terms "catalytic domain" of Sos or the "nucleotide exchange factor region" of Sos or the "nucleotide exchange domain" of Sos are terms that are used interchangeably and denote the portion of Sos that binds to Ras and is directly involved in the nucleotide exchange of Ras, (i.e., the release of GDP from Ras). The catalytic domain of Sos can span about 500 amino acid residues, and is exemplified by amino acid residues 781–1017 of SEQ ID NO:2 of human Sos.

As used herein an "active fragment of a Sos" is used interchangeably with the phrase "Sos active fragment" and is a fragment of Sos that minimally contains the catalytic domain of a Sos.

As used herein the "N-Domain" of a Sos is a region of the Sos protein that plays a key role in the stabilization of the Sos catalytic domain. The Sos N-Domain comprises amino acid residues 568–741 of SEQ ID NO:2 of human Sos.

As used herein a "GTP analog" is a small organic molecule (less than 3 Kd) that contains several structural features of guanosine 5'triphosphate but differs from GTP by one or more functional substitutions. Similarly, a "GDP analog" is a small organic molecule (less than 3 Kd) that contains several structural features of guanosine 5'diphosphate but differs from GDP by one or more functional substitutions. Examples of such analogs include those described in Example 2, below.

As used herein a "soluble" Sos fragment or Ras fragment is a fragment of Ras or Sos that is soluble in a buffered aqueous solution at a concentration of about 0.5 mg/ml.

As used herein a "small molecule β-turn mimic" of Ras is used interchangeably with a "β-turn small molecule mimic" of Ras and is a small molecule (less than 3 Kd) that mimics the conformational change in Ras that takes place upon Ras binding of Sos including those described herein. Such small molecule β-turn mimics are exemplified in Example 2, below.

As used herein a "β-turn of amino acids" is a unit of protein secondary structure that is maintained by a hydrogen bond between a backbone carbonyl oxygen from a given amino acid residue at position X in the amino acid sequence and a backbone NH from a residue at the position of X+4 in the amino acid sequence. A β-turn of amino amino acids is exemplified in FIG. 7E.

As used herein the term "about" means within 10 to 15%, preferably within 5 to 10%. For example an amino acid sequence that contains about 60 amino acid residues can contain between 51 to 69 amino acid residues to, more preferably 57 to 63 amino acid residues.

Genes Encoding Ras or Sos Proteins

The present invention contemplates isolation of a gene encoding either a Ras or a Sos of the invention, including a full length, i.e., naturally occurring form of the Ras or Sos from any eukaryote. The present invention further provides for subsequent modification of that coding region of the gene to generate a fragment of the Ras or Sos that will form a Ras-Sos complex. As used herein, the term "gene" refers to an assembly of nucleotides that encode a polypeptide, and includes cDNA and genomic DNA nucleic acids.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

A "vector" is a replicon, such as plasmid, phage or cosmid, to which another DNA segment may be attached so as to bring about the replication of the attached segment.

A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only tie sequence in the 5' to 3'direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6× SCC High stringency hybridization conditions correspond to the highest $T_m$, e.g., 50% formamide, 5× or 6× SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 12 nucleotides; preferably at least about 18 nucleotides: and more preferably the length is at least about 27 nucleotides; and most preferably 36 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic MRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) [Reeck et al., Cell, 50:667 (1987)].

Accordingly, the term "sequence similarity" in all its grammatical forms refers to the degree of identity or correspondence between nucleic acid or amino acid sequences of proteins that do not share a common evolutionary origin [see Reeck et al., 1987, supra]. However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than 30% of the amino acids are identical, or greater than about 60% are similar (functionally identical). Preferably, the similar or homologous sequences are identified by alignment using, for example, the GCG (Genetics Computer Group, Program Manual for the GCG Package, *Version* 7, Madison, Wis.) pileup program.

The term "corresponding to" is used herein to refer similar or homologous sequences, whether the exact position is identical or different from the molecule to which the similarity or homology is measured. Thus, the term "corresponding to" refers to the sequence similarity, and not the numbering of the amino acid residues or nucleotide bases.

A gene encoding a Ras or Sos, whether genomic DNA or cDNA, can be isolated from any source, particularly from a human cDNA or genomic library. In view and in conjunction with the present teachings, methods Well known in the art, as described above can be used for obtaining Ras or Sos genes from any source [see, e.g., Sambrook et al., 1989, supra].

Accordingly, any eucaryotic cell potentially can serve as the nucleic acid source for the molecular cloning of an Ras or Sos gene. The DNA may be obtained by standard procedures known in the art from cloned DNA (e.g., a DNA "library"), and preferably is obtained from a cDNA library prepared from tissues with high level expression of the protein by chemical synthesis, by cDNA cloning, or by the cloning of genomic DNA, or fragments thereof, purified from the desired cell [See, for example, Sambrook et al., 1989, supra; Glover, D. M. (ed.), 1985, DNA Cloning: A Practical Approach, MRL Press, Ltd., Oxford, U.K. Vol. I, II]. Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

The present invention also relates to cloning vectors containing genes encoding analogs and derivatives of Ras or Sos including and more preferably the Sos and Ras fragments of the present invention, that can form Ras-Sos complexes. Included are homologs of Ras and Sos and fragments thereof, from other species. Therefore the production and use of derivatives and analogs related to Ras and Sos are within the scope of the present invention.

Ras and Sos derivatives can be made by altering encoding nucleic acid sequences by substitutions, additions or deletions that provide for functionally equivalent molecules. Preferably, derivatives are made that are capable of forming crystals of the Ras-Sos complex that effectively diffract X-rays for the determination of the atomic coordinates of the protein-ligand complex to a resolution of better than 5.0 Angstroms, preferably to a resolution of better than 3 Angstroms.

Due to the degeneracy of nucleotide coding sequences, other DNA sequences which encode substantially the same amino acid sequence as a Ras or Sos gene may be used in the practice of the present invention. These include but are not limited to allelic genes, homologous genes from other species, and nucleotide sequences comprising all or portions of Ras and/or Sos genes which are altered by the substitution of different codons that encode the same amino acid residue within the sequence, thus producing a silent change. Likewise, the Ras or Sos derivatives of the invention include, but are not limited to, those containing, as a primary amino acid sequence, all or part of the amino acid sequence of a Ras or a Sos protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced at a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

The genes encoding Ras or Sos derivatives and analogs of the invention can be produced by various methods known in the art. The manipulations which result in their production can occur at the gene or protein level. For example, the cloned Ras or Sos gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of Ras or Sos, care should be taken to ensure that the modified gene remains within the same translational reading frame as the Ras or Sos gene, uninterrupted by translational stop signals, in the gene region where the desired activity is encoded.

Additionally, the Ras or Sos-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated Ras or Sos gene product. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis [see Higuchi, 1989, "Using PCR to Engineer DNA", in *PCR Technology: Principles and Applications for DNA Amplification*, H. Erlich, ed., Stockton Press, Chapter 6, pp. 61–70].

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E.* coli, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. Coli* and *Saccharomyces cerevisiae* by linking sequences from an *E. coli* plasmid with sequences from the yeast 2μ plasmid.

In an alternative method, the desired gene may be identified and isolated after insertion into a suitable cloning vector in a "shot gun" approach. Enrichment for the desired gene, for example, by size fractionation, can be done before insertion into the cloning vector.

Expression of Ras and Sos

The nucleotide sequence coding for Ras or Sos, a fragment of Ras or Sos or a derivative or analog thereof, including a functionally active derivative, such as a chimeric protein, thereof, can be inserted into an appropriate expression vector, i.e., a vector which contains the necessary elements for the transcription and translation of the inserted protein-coding sequence. Such elements are termed herein a "promoter." Thus, the nucleic acid encoding a Ras or Sos of the invention or a fragment thereof is operationally associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding Ras or Sos and/or its flanking regions.

Potential host-vector systems include but are not limited to mammalian cell systems infected with virus (e.g., vaccinia virus, adenovirus, etc.); insect cell systems infected with virus (e.g., baculovirus); microorganismns such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant Ras or Sos protein of the invention, or Ras or Sos fragment, derivative, chimeric construct, or analog thereof, may be expressed chromosomally, after integration of the coding sequence by recombination. In this regard, any of a number of amplification systems may be used to achieve high levels of stable gene expression [See Sambrook et al., 1989, supra].

The cell containing the recombinant vector comprising the nucleic acid encoding Ras or Sos is cultured in an appropriate cell culture medium under conditions that provide for expression of Ras or Sos by the cell.

Any of the methods previously described for the insertion of DNA fragments into a cloning vector may be used to construct expression vectors containing a gene consisting of appropriate transcriptional/translational control signals and the protein coding sequences. These methods may include in vitro) recombinant DNA and synthetic techniques and in vivo recombination (genetic recombination).

Expression of Ras or Sos protein may be controlled by any promoter/enhancer element known in the art, but these regulatory elements must be functional in the host selected for expression. Promoters which may be used to control Ras or Sos gene expression include, but are not limited to, the ST40 early promoter region [Benoist and Chambon, *Nature*, 290:304–310 (1981)]. the promoter contained in the 3' long terminal repeat of Rous sarcoma virus [Yamamoto et al., *Cell,* 22:787–797 (1980)], the herpes thymidine kinase promoter Wagner et al., *Proc. Natl. Acad. Sci. U.S.A.,* 78:1441–1445 (1981)], the regulatory sequences of the metallothionein gene [Brinster et al., *Nature* 296:39–42 (1982)]; prokaryotic expression vectors such as the β-lactamase promoter [Villa-Kamaroff, et al., *Proc. Natl. Acad. Sci. U.S.A.,* 75:3727–3731 (1978)], or the tac promoter [DeBoer, et al., *Proc. Natl. Acad. Sci. U.S.A.,* 80:21–25 (1983)]; see also "Useful proteins from recombinant bacteria" in Scientific American, 242:74–94 (1980); promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue Specificity and have been utilized in transgenic animals: elastase I gene control region which is active in pancreatic acinar cells [Swift et al., *Cell,* 38:639–646 (1984); Ornitz et al., *Cold Spring Harbor Symp. Quant. Biol.,* 50:399–409 (1986); MacDonald, *Hepatology,* 7:425–515 (1987)]; insulin gene control region which is active in pancreatic beta cells [Hanahan, *Nature,* 315:115–122 (1985)], imminoglobulin gene control region which is active in lymphoid cells [Grosschedl et al.. *Cell,* 38:647–658 (1984); Adames et al., *Nature,* 318:533–538 (1985); Alexander et al., *Mol. Cell. Biol.,* 7:1436–1444 (1987)], mouse mammary tumor virus control region which is active in testicular, breast, lymphoid and mast cells [Leder et al., *Cell,* 45:485495 (1986)], albumin gene control region which is active in liver [Pirikert et al., *Genes and Devel.,* 1:268–276 (1987)], alpha-fetoprotein gene control region which is active in liver [Krumlauf et al., *Mol. Cell. Biol.,* 5:1639–1648 (1985); Hammer et al., *Science,* 235:53–58 (1987)], alpha 1-antitrypsin gene control region which is active in the liver [Kelsey et al., *Genes and Devel.,* 1:161–171 (1987)], beta-globin gene control region which is active in myeloid cells [Mogram et al., *Nature,* 315:338–340 (1985); Kollias et al., *Cell,* 46:89–94 (1986)], myelin basic protein gene control region which is active in oligodendrocyte cells in the brain [Readhead et al., *Cell,* 48:703–712 (1987)], myosin light chain-2 gene control region which is active in skeletal muscle [Sani, *Nature,* 314:283–286 (1985)], and gonadotropic releasing hormone gene control region which is active in the hypothalamus [Mason et al., *Science,* 234:1372–1378 (1986)].

Expression vectors containing a nucleic acid encoding an Ras or Sos of the invention can be identified by four general approaches: (a) PCR amplification of the desired plasmid DNA or specific mRNA, (b) nucleic acid hybridization, (c)

presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosilase activity, thymidine kinase activity, resistance to antibiotics, transformation phenotype, occlusion body formation in baculovirus, etc.) caused by the insertion of foreign genes in the vector. In another example, if the nucleic acid encoding Ras or Sos is inserted within the "selection marker" gene sequence of the vector, recombinants containing the Ras or Sos insert can be identified by the absence of the selection marker gene function. In the fourth approach, recombinant expression vectors can be identified by assaying for the activity, biochemical, or immunological characteristics of the gene product expressed by the recombinant, provided that the expressed protein assumes a functionally active conformation.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col El, pCR1, pBR322, pMal-C2, pET, pGEX [Smith et al., *Gene*, 67:31–40 (1988)], pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2µ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamH1 cloning site; Summers), pVL1393 (BamH1, SmaI, XbaI, EcoR1, NotI, XmaIII, BglII, and PstI cloning site; Invitrogen, pVL1392 (BglII, PstI, NotI, XmaIII, EcoRI, XbaI, SmaI, and BamH1 cloning site; Summers and Invitrogen), and pBlueBacIII (BamnH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen(195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, *Current Protocols in Molecular Biology*, 16.12 (1991). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamHI cloning site, inducible methallothionein IIa gene promoter, hygromycin selectable marker: Invitrogen), pREP8 (BamH1, XhoI, NotI, HinIII, NheI, and KpnI cloning site, RSV-LTR promoter, histidinol selectable marker; Invitrogen), pREP9 (KpnI, MeI, HindIII, NotI, XhoI, SfiI, and BamHI cloning site, RSV-LTR promoter, G418 selectable marker; Invitrogen), and pEB-VHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufinar, 1991, supra) for use according to the invention include but are not limited to pSC11 (SmaI cloning site, TK- and β-gal selection), pMJ601 (SalI, SmaI, AfiI, NarI, BspMII, BamH1, ApaI, NheI, SacII, KpnI, and HindIII cloning site; TK- and β-gal selection), and pTKgptFIS (EcoRI, PstI, SalI, AccI, HindII, SbaI, BamHI, and Hpa cloning site, TK or XPRT selection).

Yeast expression systems can also be used according to the invention to express the Ras or Sos protein. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with Pro-Bond resin and cleaved with enterokinase; Invitrogen), to mention just two, can be employed according to the invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter [see, e.g., Wu et al., *J. Biol. Chem.*, 267:963–967 (1992); Wu and Wu, *J. Biol. Chem.*, 263:14621–14624 (1988); Hartmut et al., Canadian Patent Application No. 2,012,311, filed Mar. 15, 1990).

Peptide Synthesis

Synthetic polypeptides, prepared using the well known techniques of solid phase, liquid phase, or peptide condensation techniques, or any combination thereof, can include natural and unnatural amino acids. Amino acids used for peptide synthesis may be standard Boc ($N^\alpha$-amino protected $N^\alpha$-t-butyloxycarbonyl) amino acid resin with the standard deprotecting, neutralization, coupling and wash protocols of the original solid phase procedure of Merrifield [*J. Am. Chem. Soc.*, 85:2149–2154 (1963)], or the base-labile $N^\alpha$-amino protected 9-fluorenylmethoxycarbonyl (Fmoc) amino acids first described by Carpino and Han [*J. Org. Chem.*, 37:3403–3409 (1972)]. Both Fmoc and Boc $N^\alpha$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other $N^\alpha$-protecting groups that are familiar to those skilled in this art. Solid phase peptide synthesis may be accomplished by techniques familiar to those in the art and provided, for example, in Stewart and Young, 1984, Solid Phase Synthesis, Second Edition, Pierce Chemical Co., Rockford, Ill.; Fields and Noble, 1990, Int. J. Pept. Protein Res. 35:161–214, or using automated synthesizers, such as sold by ABS. Thus, polypeptides of the invention may comprise D-amino acids, a combination of D- and L-amino acids, and various "designer" amino acids (e.g., β-methyl amino acids, Cα-methyl amino acids, and Na-methyl amino acids, etc.) to convey special properties. Synthetic amino acids include ornithine for lysine, fluorophenylalanine for phenylalanine, and norleucine for leucine or isoleucine. Additionally, by assigning specific amino acids at specific coupling steps, α-helices, β turns, β sheets, γ-turns, and cyclic peptides can be generated.

Isolation and Crystallization of the Ras-Sos complex

The present invention provides Ras fragments and Sos fragments that retain their ability to form a protein-protein complex (a Ras-Sos complex) and in addition can be crystallized into a crystal that effectively diffracts X-rays for the determination of the atomic coordinates of the Ras-Sos complex to a resolution of better than 5.0 Angstroms. The Ras and Sos fragments (plus an initiator methionine when appropriate) can be expressed either as described below in Example 1, or as described above. The Ras fragments of the present invention are constructed to contain the Sos contacting region whereas the Sos fragments are constructed to retain all of the Sos catalytic domain. Generally additional portions of the two proteins are also retained. Thus, in Example 1 below, the Ras fragment contains the N-terminal 166 amino acids of SEQ ID NO:1, whereas the Sos contacting region of human Ras is contained by amino acids 5 to 105 of SEQ ID NO:1. Similarly, whereas the Sos catalytic domain of human Sos comprises amino acids 781–1017 of SEQ ID NO:2, the Sos fragment used in Example 1 below, contains amino acids 564–1049 of SEQ ID NO:2. Of course, the specific Ras and Sos fragments provided herein serve only as examples, since the crystallization process can tolerate a broad range of fragment lengths. Therefore, any person with skill in the art of protein crystallization having the present teachings and without undue experimentation could crystallize a large number of alternative forms of the Ras-Sos complex from a variety of different Ras and Sos fragments, or alternatively using either or both the full length Ras and Sos. As mentioned above, Ras and Sos, and Ras and Sos fragments having conservative substitutions in their amino acid sequence are also included in the invention, including a selenomethionine substituted form.

In addition, crystals can be prepared using modified fragments of Ras and Sos and are fully contemplated by the present invention. For example, a number of mutations in Ras have highlighted the importance of the Switch 1 and Switch 2 regions in the interaction with nucleotide exchange factors [Mistou et al., *EMBO J.*, 11:2391–2397 (1992); Verrotti et al., *EMBO J.*, 11:2855–2862 (1992); Segal et al., *Proc. Natl. Acad. Sci.*, 90:5564–5568 (1993); Mosteller et al., *Molec. Cell. Biol.*, 14:1104–1112 (1994); Segal etal., *Eur. J. Biochem.*, 228:96–101 (1995); Leonardsen et al., *Oncogene*, 13:2177–2187 (1996); Crechet et al., *J. Biol. Chem.*, 271:17234–17240 (1996); Quilliam et al., *J. Biol. Chem.*, 271:11076–11082 (1996)]. The importance of helix a3 (residues 102–105) has also been noted [Segal et al., *Proc. Natl. Acad. Sci.*, 90:5564–5568 (1993); Segal et al., *Eur. J. Biochem.*, 228:96–101 (1995); Leonardsen et al., *Oncogene*, 13:2177–2187 (1996)]. Similarly, in the structure of the Ras-Sos complex disclosed in Example 1 below, Glu 62 and 63 of SEQ ID NO:1 appear to be crucial to the interact ion with Sos and are therefore candidates for modification for generating crystals the Ras-Sos complex having a substantially different structural configuration. Similarly, dominant negative mutants of Ras have been identified that appear to act by binding to and sequestering nucleotide exchange factors [Feig and Cooper, *Molec. Cell. Biol.*, 8:3235–3243 (1988); Chen et al., *Oncogene*, 9:2691–2698 (1994)]. The most straightforward explanation of the action of these mutations is that they destabilize nucleotide binding [Haney and Broach, *J. Biol. Chem.*, 269:16541–16548 (1994); Chen et al., *Oncogene*, 9:2691–2698 (1994); Powers et al., *Cell*, 65:1225–1231 (1991)], thereby increasing the apparent affinity of Ras for Sos or other exchange factors. Some of the dominant negative mutations may, in addition, result in stronger interactions between Ras and the exchange factor. For example, Ser 17 in SEQ ID NO:1 forms a hydrogen bond with Glu 942 in SEQ ID NO:2, in FIG. 5B, below. In addition the mutation of Ser 17 of SEQ ID NO:1 to Asn 17 results in a dominant negative Ras, and Asn at this position in Ras may be positioned so as to interact more strongly with Glu 942 of SEQ ID NO:2.

In addition, substitution of Arg 80, Asn 81 of *S. cerevisiae* Ras2p (Arg 73, Thr 74 in SEQ ID NO:1) with Asp-Asp in the mutant (Ser 17→Asn) results in a loss of sensitivity to the corresponding *S. cerevisiae* nucleotide exchange protein Sdc25 and reversion of the dominant negative phenotype [Creclet et al., *J. Biol. Chem.*, 271:17234–17240 (1996)]. In the Ras-Sos complex, Arg 73 of SEQ ID NO:1 (Arg 80 in Ras2p) is involved in interactions with two residues of Sos (SEQ ID NO:2) (FIG. 6A), and a mutation to Asp would clearly be disruptive.

Crystals of the Ras-Sos complex can be grown by a number of techniques including batch crystallization, vapor diffusion (either by sitting drop or hanging drop) and by microdialysis. Seeding of the crystals in some instances is required to obtain X-ray quality crystals. Standard micro and/or macro seeding of crystals may therefore be used. Exemplified below is the hanging-drop vapor diffusion procedure. Hanging drops of Ras-Sos complex (2.5 μl, 10 mg/ml) in 20 mM Tris, pH=8.0, 100 mM NaCl were mixed with an equal amount of reservoir buffer containing 2.7–3.2M sodium formate and 100 mM Tris buffer, pH=8.0, and kept at 4° C. Crystal showers appeared after 1–2 days with large single crystals growing to full size (0.3×0.3×0.15 mm$^3$) within 2–3 weeks. Crystals were harvested in 3.5M sodium formate and 100 mM Tris buffer, pH=8.0 and cryoprotected in 3.5M sodium formate, 100 mM Tris buffer, pH=8.0, 10% (w/v) sucrose, and 10% (v/v) ethylene glycol before flash freezing in liquid propane.

Once a crystal of the present invention is grown, X-ray diffraction data can be collected. In Example 1 below, this analysis were measured at Brookhaven National Laboratories on beamline X25 using the Brandies 2×2 (four module) CCD-based detector [Westbrook and Naday, *Meth. Enzymol.,* 276:244–268 (1997)]. A mercury derivative data set (PCMB) was measured at Cornell High Energy Synchrotron Source on beamline F2 using the Q1 CCD-based detector (ADSC). Data processing was performed using Denzo and data reduction was performed using Scalepack [Otwinowski and Minor, *Meth. Enzymol.,* 276:307–326 (1997)]. MIR phases were calculated using MLPHARE as implemented in the CCP4 suite of programs [Collaborative Computing Project, N. The CCP4 Suite: Programs for protein cyrstallography. *Acta Cryst.,* D50:760–763 (1994)]. Solvent flattening was performed using DM [Cowtan, *Joint CCP4 and ESF-EACBM Newsletter on Protein Crystallography,* 31:34–38 (1994)].

Alternative methods may also be used. For example, crystals can be characterized by using X-rays produced in a conventional source (such as a sealed tube or a rotating anode) or using a synchrotron source. Methods of characterization include, but are not limited to, precision photography, oscillation photography and diffractometer data collection. Selenium-Methionine may be used in place of PCMB derivitization as described in Example 1, and multiwavelength anomalous dispersion data [Hendrickson, *Science,* 254:51–58 (1991)] can be collected on CHESS F2, using reverse-beam geometry to record Friedel pairs at four X-ray wavelengths, corresponding to two remote points above and below the Se absorption edge ($\lambda_1$ and $\lambda_4$) and the absorption edge inflection point ($\lambda_2$ and peak ($\lambda_3$). Data can be processed using DENZO and SCALEPACK (Z. Otwinowski and W. Minor). Selenium sites can be located using SHELXS-90 in Patterson search mode (G. M. Sheldrick). Experimental phases ($\alpha_{MAD}$) can be estimated via a multiple isomorphous replacement/anomalous scattering strategy using MLPHARE (Z. Otwinowski, Southwestern University of Texas, Dallas) with three of the wavelengths treated as derivatives and one ($\lambda_2$) treated as the parent for example. Alternatively, X-PLOR [Brüger, X-PLOR v. 3.1 Manual, New Haven: Yale University, (1993B)] or Heavy [T. Terwilliger, Los Alamos National Laboratory] may be used.

After density modification and non-crystallographic averaging, the protein can be built into a electron density map using the program O [Jones et al., *Acta Cryst.,* A47:110–119 (1991)]. Coordinates for the GTP bound form of Ras (521P) [Pai et al., *EMBO J.,* 9:2351–2359 (1990)] can be obtained from the Protein Data Bank [Bernstein et al., *Archives of Biochemistry & Biophysics,* 185:584591 (1978)]. The molecule, with Switch 1 and Switch 2 regions deleted, was fit into density in Example 1. After an initial round of model building and positional refinement using CNS with bulk solvent corrections and anisotropic B-factor scaling protocols utilized, phase combination methods using Sigma [Read, *Acta Cryst.,* A42:140–149 (1986)] can result in a much improved map. In Example 1, below the Switch 2 region of Ras, the catalytic domain of Sos, and the N-terminal helices of Sos were built by this methodology. Electron density maps based on multiple simulated annealing models [Brünger et al., *Structure,* 5:325–336 (1997)] allowed the remaining regions of Ras and Sos to be placed into density, Example 1, below. Residues 564–567 (N-terminal), 591–597, 654–675, 742–751, and 1045–1049 (C-terminal) are disordered and not modeled in Sos; no residues of Ras are disordered. For the crystal structure of Example 1, the Ramachandran plot showed 89% of all residues are in the most favored regions and no residues are in disallowed regions.

Protein-Structure Based Design of Modulators of Cellular Proliferation

Once the three-dimensional structure of a crystal comprising a Ras-Sos complex is determined, (e.g., see the coordinates in Table 3 below) a potential modulator of Ras activity, can be examined through the use of computer modeling using a docking program such as GRAM, DOCK, or AUTODOCK [Dunbrack et al., 1997, supra], to identify potential modulators of the Ras-Sos nucleotide exchange interaction. This procedure can include computer fitting of potential modulators to the Ras-Sos complex to ascertain how well the shape and the chemical structure of the potential modulator will bind to either the nucleolide exchange region of Sos or to the Ras-Sos complex, e.g., to act as a stabilizer. [Bugg et al., *Scientfic American,* Dec.:92–98 (1993); West et al., *TIPS,* 16:67–74 (1995)]. Computer programs can also be employed to estimate the attraction, repulsion, and steric hindrance of the two binding partners (e.g., the Ras-Sos complex and a potential stabilizer). Generally the tighter the fit, the lower the steric hindrances, and the greater the attractive forces, the more potent the potential modulator since these properties are consistent with a tighter binding constant. Furthermore, the more specificity in the design of a potential drug the more likely that the drug will not interact as well with other proteins. This will mininize potential side-effects due to unwanted interactions with other proteins.

Initially GTP analogs, for example, can be systematically modified by computer modeling programs until one or more promising potential analogs are identified. Examples of GTP analogs that have been designed in view of the structural information provided by the present invention are included in Example 2, below. In addition systematic modification of selected analogs can then be systematically modified by computer modeling programs until one or more potential analogs are identified. Such analysis has been shown to be effective in the development of HIV protease inhibitors [Lam et al., *Science* 263:380–384 (1994); Wlodawer et al., *Ann. Rev. Biochem.* 62:543–585 (1993); Appelt, *Perspectives in Drug Discovery and Design* 1:23–48 (1993); Erickson, *Perspectives in Drug Discovery and Design* 1:109–128 (1993)]. Alternatively a potential modulator could be obtained by initially screening a random peptide library produced by recombinant bacteriophage for example, [Scott and Smith, *Science,* 249:386–390 (1990); Cwirla et al., *Proc. Natl. Acad. Sci.,* 87:6378–6382 (1990); Devlin et al., *Science,* 249:404–406 (1990)]. A peptide selected in this manner would then be systematically modified by computer modeling programs as described above, and then treated analogously to a structural analog as described below.

Figure 7A:
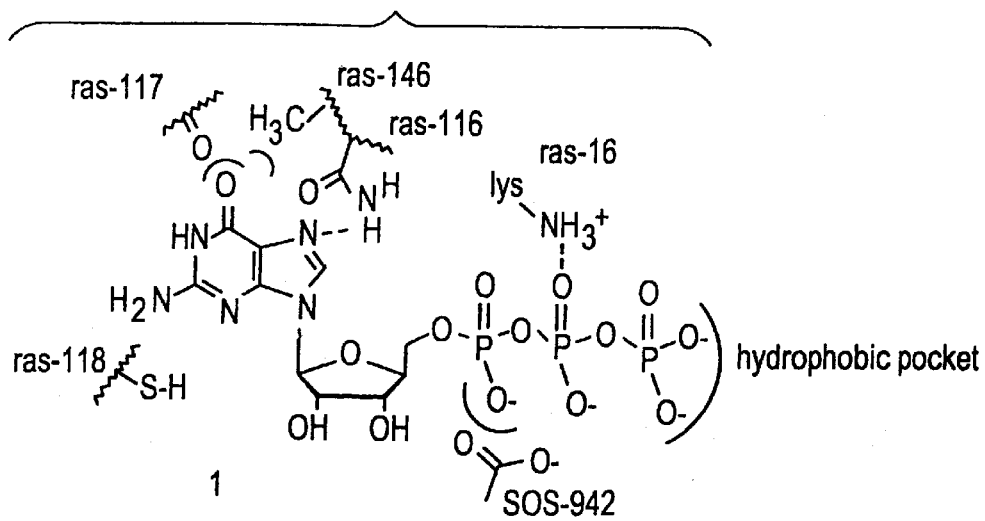
FIG. 7A shows a schematic of GTP bound in the Ras-Sos complex.
Figure 7B:
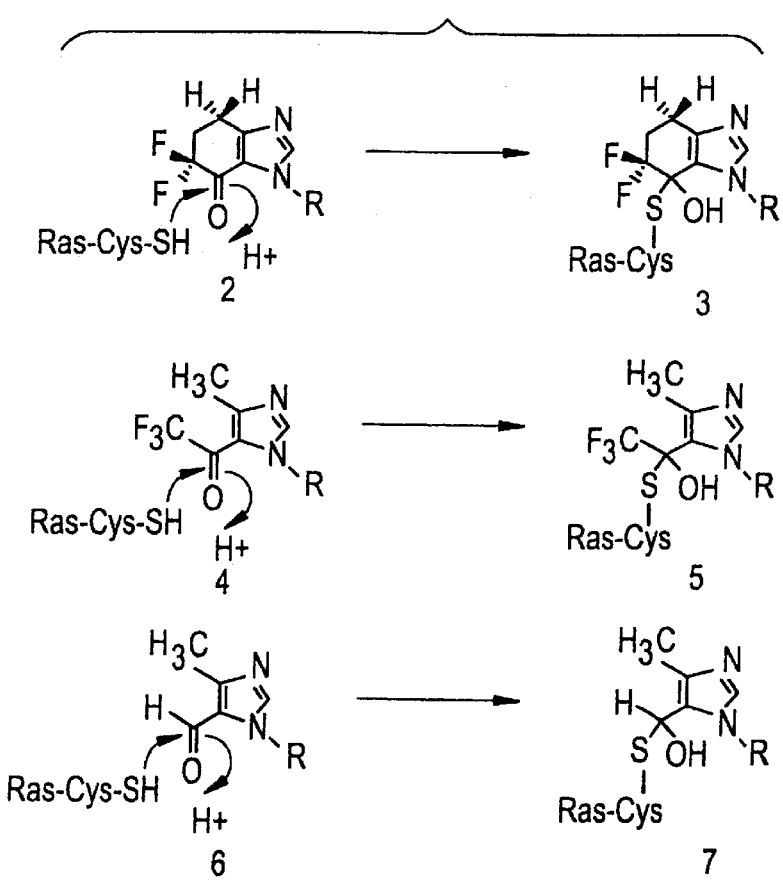
FIGS. 7B–7C shows putative inhibitors and modes of inhibition of the Ras-Sos interaction.
Figure 7C:
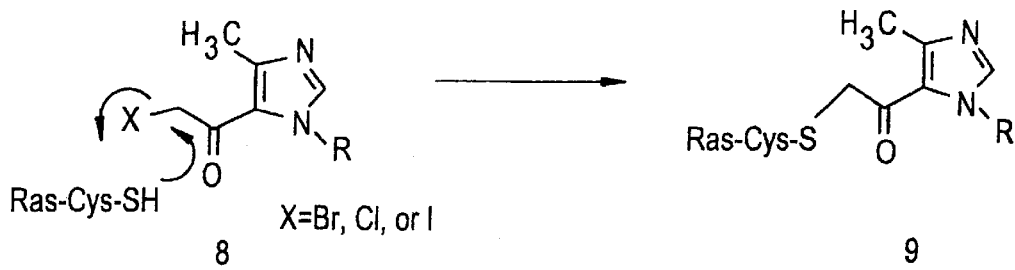
Figure 7C:
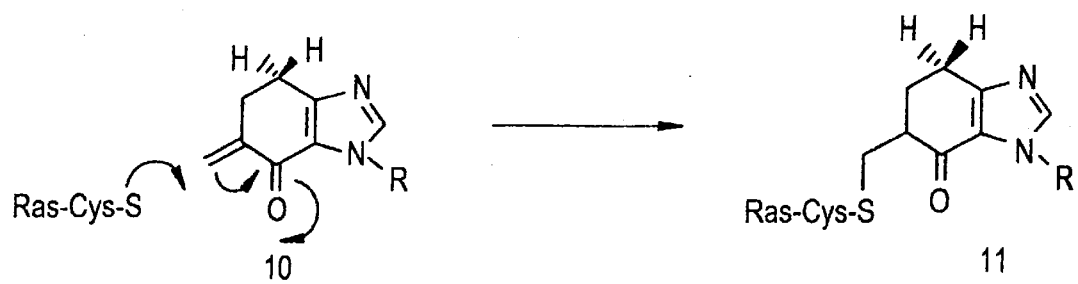
Figure 7C:
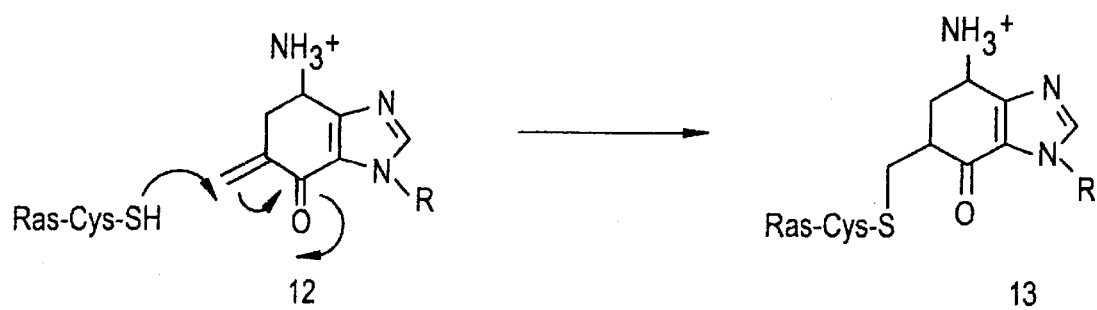
Figure 7C:
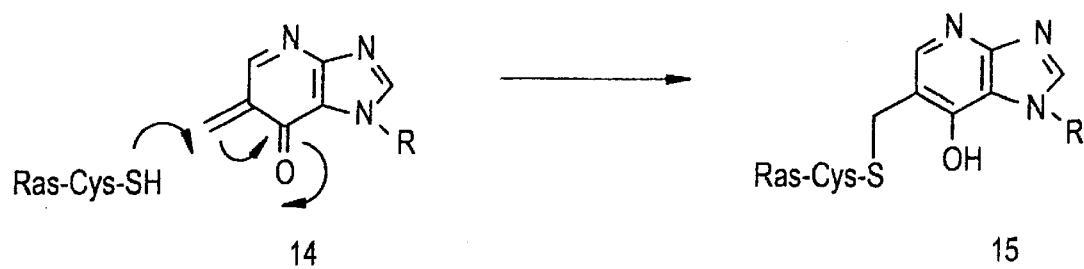
Figure 7C:
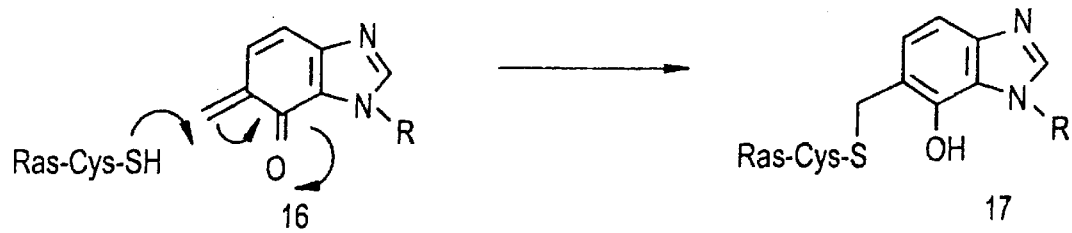
Figure 7D:
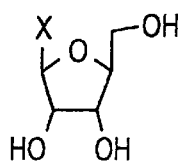
FIG. 7D shows potential inhibitors that assume that guanine binding would induce the Sos-free conformation of Ras, i.e., modifying the guanosine analogs at sites other than on the purine.
Figure 7D:
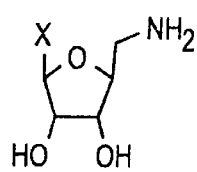
Figure 7D:
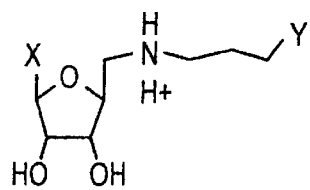
Figure 7D:
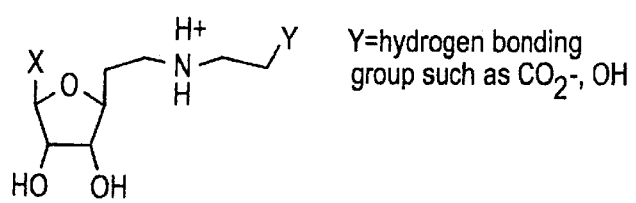
Figure 7D:
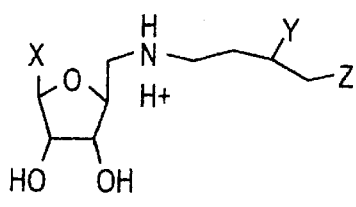
Figure 7D:
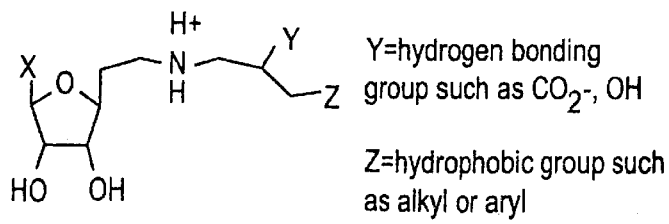
Figure 7E:
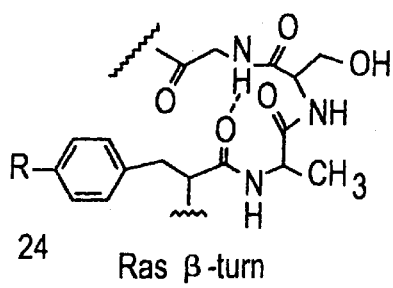
FIG. 7E depicts putative inhibitors of Sos that mimick the β-turn of Ras.
Figure 7E:
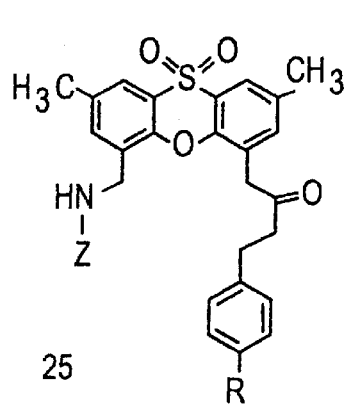
Figure 7E:
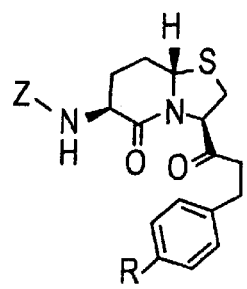
Figure 7E:
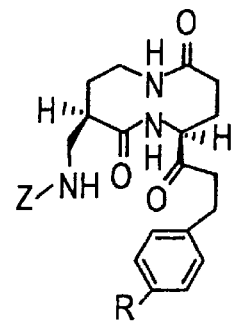
Figure 7E:
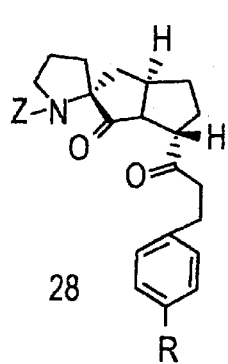
Figure 7E:
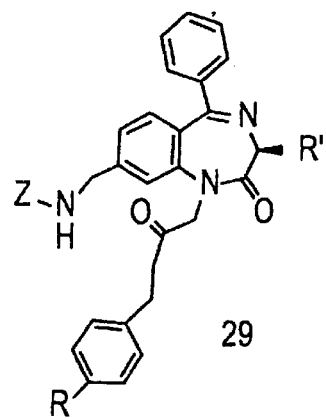

Another example of a potential modulator is compound that is a β-turn small molecule mimic, as exemplified in FIG. 7E. The β-turn small molecule mimic is designed to simulate the conformational change in Ras which appears to take place when Ras binds to Sos, as disclosed herein. Countless modifications of such a β-turn small molecule mimic can be made, any one of which could lead to a useful drug. Each modification requires additional chemical steps, which while being reasonable for the synthesis of a few of these compounds, quickly becomes overwhelming if all of these compounds need to be synthesized. However, through the use of the three-dimensional structure disclosed herein and computer modeling, a large number of these compounds can be rapidly screened on the computer monitor screen, and a few likely candidates can be determined without the laborious synthesis of untold numbers of compounds.

Once a potential modulator is identified it can be either selected from a library of chemicals as are commercially available from most large chemical companies including Merck, GlaxoWelcome, Bristol Meyers Squib, Monsanto/Searle, Eli Lilly, Novartis and Pharmacia UpJohn, or alternatively the potential modulator may be synthesized de novo. As mentioned above, the de novo synthesis of one or even a relatively small group of specific compounds is reasonable in the art of drug design. The potential modulator can be placed into a standard binding assay with Sos and/or Ras, or fragments of Sos and Ras which contain the portions of these proteins involved in their protein-protein interaction. The Ras fragments and Sos fragments can be synthesized by either standard peptide synthesis described above, or generated through recombinant DNA technology or classical proteolysis. Alternatively the corresponding full-length proteins may be used in these assays.

For example, the Sos catalytic domain can be attached to a solid support. Methods for placing the Sos catalytic domain on the solid support are well known in the art and include such things as linking biotin to the Sos catalytic domain and linidng avidin to the solid support. The solid support can be washed to remove unreacted species. A solution of a labeled potential modulator can be contacted with the solid support. The solid support is washed again to remove the potential modulator not bound to the support. The amount of labeled potential modulator remaining with the solid support and thereby bound to the Sos catalytic domain can be determined. Alternatively, or in addition, the dissociation constant between the labeled potential modulator and the Sos catalytic domain can be determined. Suitable labels are exemplified below.

In another aspect of the present invention a potential modulator is assayed for its ability to stabilize the Ras-Sos complex. A modulator that stabilizes the Ras-Sos complex is selected as an inhibitor of Ras activation (i.e., an inhibitor of cellular proliferation).

In a particular embodiment, the effect of a potential modulator on the catalytic activity of Sos is determined. In one such embodiment, Ras or a fragment thereof (e.g., a fragment of the Ras which contains the Sos contacting region and the nucleotide binding domain) is contacted with Sos (or a fragment thereof containing the catalytic domain) in the presence of a labeled nucleotide.

In a particular embodiment, isothermal calorimetry can be used to determine the stability of the Ras-Sos complex in the absence and presence of the potential modulator.

In another embodiment, a Biacore machine can be used to determine the binding constant of the Ras-Sos complex in the presence and absence of the potential modulator. In a particular embodiment of this type, Ras or a fragment thereof (e.g., a fragment of the Ras which minimally contains the Sos contacting region) can be immobilized on a sensor chip. Sos or a fragment thereof (e.g., a fragment which contains the Sos catalytic domain) can then be contacted with (e.g., flowed over) the sensor chip to form a Ras-Sos complex.

For example, Ras can be immobilized on a sensor chip and Sos can then be flowed over the sensor chip to form the Ras-Sos complex. The dissociation constant for the Ras-Sos complex can be determined by monitoring changes in the refractive index with respect to time as buffer is passed over the chip. [O'Shannessy et al. Anal. Biochem. 212:457–468 (1993); Schuster et al., Nature 365:343–347 (1993)]. Scatchard Plots, for example, can be used in the analysis of the response functions using different concentrations of Sos. Flowing a potential modulator at various concentrations over the Ras-Sos complex and monitoring the response function (e.g., the change in the refractive index with respect to time) allows the Ras-Sos complex dissociation constant to be determined in the presence of the potential modulator and thereby indicates whether the potential modulator is either an inhibitor, or an agonist of the Ras-Sos complex. Alternatively, the potential modulator can be flowed over the immobilized Ras with the Sos in order to determine if it effects the Ras-Sos binding.

In a particular embodiment Ras can be used which is free of nucleotides. In a related embodiment, nucleotide-free Ras can be prepared after the Ras is immobilized on the sensor chip. In one such embodiment a solution of approximately 40 mM EDTA is passed over the immobilized Ras to remove the ions (e.g., $Mg^{+2}$) involved in nucleotide binding. Alternatively, the analogous procedure can be performed using the an immobilized Sos (or fragment thereof) on the sensor chip and contacting Ras (or fragment thereof) with the sensor chip to form a Ras-Sos complex.

In still another embodiment, the binding affinity can be determined for an immobilized Ras, or Ras fragment that contains the Sos contacting region of Ras and a labeled, free Sos (or Sos fragment that minimally contains the Sos catalytic domain) in the absence and presence of the potential modulator. In a related embodiment, the binding affinity can be determined for an immobilized Sos, or Sos fragment (that minimally contains the Sos catalytic domain) and a labeled, free Ras (or Ras fragment that contains the Sos contacting region of Ras) in the absence and presence of the potential modulator. In yet another embodiment, the binding affinity of a potential modulator (preferably labeled) for the Sos catalytic domain can be determined using an immobilized Sos, or Sos fragment (that minimally contains the Sos catalytic domain) in the absence and presence of the potential modulator.

In a particular embodiment, GTP binding to Ras can be determined using labeled GTP or an appropriate labeled GTP analog in the absence and presence of the potential modulator.

In a preferred embodiment, the effect of the potential modulator on the catalytic activity of Sos is determined (either independently, or subsequent to a binding assay as exemplified above). In one such embodiment, the rate of the Sos-mediated guanine nucleotide exchange of Ras is determined. For example, a recombinant Ras protein can be incubated with Sos in the presence of labeled nucleotide. The amount of nucleotide bound to Ras is then determined. This assay can be performed using a real-time assay e.g., with a fluorescent analog of GDP or GTP and e.g., relying on the difference in quenching of the fluorescence when the nucleotide is bound to Ras and when it is free in solution. Alternatively, the determination can include the withdrawal of aliquots from the incubation mixture at defined intervals and subsequent placing of the aliquots on nitrocellulose paper in a nitrocellulose filter binding assay [Chardin et al., *Science* 260:1338–1343 (1993)]. In a particular embodiment the potential modulator is selected when it is an inhibitor of the Sos exchange reaction, i.e., the rate of nucleotide release by Ras is decreased.

When suitable potential modulators are identified, a supplemental crystal can be grown which comprises the Ras-Sos complex and the potential modulator.

Preferably the crystal effectively diffracts X-rays for the determination of the atomic coordinates of the protein-ligand complex to a resolution of better than 5.0 Angstroms, more preferably better than 3.0 Angstroms. The three-dimensional structure of the supplemental crystal is determined by Molecular Replacement Analysis. Molecular replacement involves using a known three-dimensional structure as a search model to determine the structure of a closely related molecule or protein-ligand complex in a new crystal form. The measured X-ray diffraction properties of the new crystal are compared with the search model structure to compute the position and orientation of the protein in the new crystal. Computer programs that can be used include: X-PLOR (see above), CNS, (Crystallography and NMR System, a next level of XPLOR), and AMORE [J. Navaza, *Acta Crystallographics ASO,* 157–163 (1994)]. Once the position and orientation are known an electron density map can be calculated using the search model to provide X-ray phases. Thereafter, the electron density is inspected for structural differences and the search model is modified to conform to the new structure. Using this approach, it will be possible to use the claimed crystal of the Ras-Sos complexes to solve the three-dimensional structures of any Ras-Sos complex having a pre-ascertained amino acid sequence. Other computer programs that can be used to solve the structures of the Ras-Sos complexes from other organisms include: QUANTA, CHARMM; INSIGHT; SYBYL; MACROMODE; and ICM.

A candidate drug can be selected by performing rational drug design with the three-dimensional structure determined for the supplemental crystal, preferably in conjunction with computer modeling discussed above. The candidate drug (e.g., a potential modulator of Ras activation) can then be assayed as exemplified above, or in situ. A candidate drug can be identified as a drug, for example, if it inhibits cellular proliferation in a cell. The cell can be either isolated from an animal, including a transformed cultured cell; or alternatively, in a living animal. Preferably the cell is an isolated cell such as a HeLa cell or a NIH/3T3 cell.

A potential modulator (e.g., a candidate drug) would be expected to interfere with a growth factor-induced effect that is dependent on Ras. Therefore, an assay that can measure a Ras-dependent effect may be used to identify a candidate drug. Examples of assays involving growth factor-induced effects that are dependent on Ras include but are not limited to cell growth assays, and assays that involve transcriptional activation of a specific promoter. In the latter case, the activation of the promoter can be monitored through the use of a reporter gene that encodes a marker protein, e.g., luciferase, green fluorescent protein, β-Gal, CAT etc. Suitable cells for performing such assays include mouse or rat fibroblasts (NIH3T3, REF-52, Rat-1); cell lines that over-express a receptor tyrosine kinase (e.g., an A431 human epidermoid carcinoma cell which overexpresses the EGF receptor); and cell lines that are derived from tumors arising in transgenic mice (e.g., MG 1361 is a breast carcinoma cell line obtained from the MMTV-neu transgenic mouse [Sacco et al., *Breast Cancer Res. Treat.,* 47:171–180 (1998)]). In one such embodiment the potential modulator (e.g., the candidate drug) is contacted with the cell and the rate of cell proliferation is determined (e.g., measuring doubling time). An inhibitor of the Sos nucleotide exchange reaction is identified if the rate of cellular proliferation is decreased.

In an alternative embodiment, the transcriptional activation of a reporter gene can be determined in the absence and presence of the potential modulator. The transcription of the reporter gene can be detected by either the enzymatic activity of the translated protein (e.g., luciferase) or the a detectable property of the translated protein (e.g., the fluorescence of green fluorescence protein). An inhibitor of the Sos nucleotide exchange reaction would cause a decrease of the activation of the promoter and therefore a decrease in the enzymatic activity or protein fluorescence respectively.

The present invention further provides methods of testing a potential modulator (e.g., the candidate drug) in mouse-tumor models of cancer. One such embodiment involves a nude-mouse xenograft assay. One such nude-mouse xenograft assay model monitors tumor formation following subcantaneous implantation of transformed cells [Blair et al., *Science* 218: 1122–1125 (1982)]. Cells that can be used for this assay include those that are transformed by the overexpression of Ras or a growth factor receptor. The ability of the potential modulator to inhibit tumor formation or growth is then ascertained. In one embodiment the size of the tumor is monitored by determining the tumor size and/or weight. The potential modulators can be administered by a variety of ways including orally, subcutaneously, or intraperitoneally. Generally, at least two groups of animals are used in the assay, with at least one group being a control group which is administered the administration vehicle without the potential modulator.

The present invention also provides methods of testing a potential modulator (e.g., the candidate drug) in a transgenic mouse assay. Transgenic mice are produced that express a transforming agent (e.g., a growth factor receptor) under the control of a tissue specific promoter. Such mice develop carcinomas that have genetic and pathological features that closely resemble human cancers. For example, in a MMTV-neu transgenic mouse lineage, 100% of the female mice develop mammary adenocarcinomas [Sacco et al., *Gene Therapy* 2:493497 (1995); Sacco et al., *Gene Therapy* 5:383–393 (1998)]. The ability of the potential modulator to inhibit tumor formation or growth is then ascertained. In one embodiment the size of the tumor is monitored by determining the tumor size and/or weight. The potential modulators can be administered by a variety of ways including orally, subcutaneously, or intraperitoneally. Generally, at least two groups of animals are used in the assay, with at least one group being a control group which is administered the administration vehicle without the potential modulator.

For all of the drug screening assays described herein further refinements to the structure of the drug will generally be necessary and can be made by the successive iterations of any and/or all of the steps provided by the particular drug screening assay.

Labels

Suitable labels include enzymes, fluorophores (e.g., fluorescence isothiocyanate (FITC), phycoerythrin (PE), Texas red (TR), rhodamine, free or chelated lanthanide series salts, especially $Eu^{3+}$, to name a few fluorophoies and including fluorescent GTP and GDP analogs such as mantGTP and mantGDP, chromophores, radioisotopes, chelating agents, dyes, colloidal gold, latex particles, ligands (e.g., biotin), and chemiluminescent agents. When a control marker is employed, the same or different labels may be used for the receptor and control marker.

In the instance where a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, 125I, $^{131}I$, and $^{186}Re$ are used, known currently available counting procedures may be utilized. In the instance where the label is an enzyme, detection may be accomplished by any of the presently utilized calorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932 and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present inveniton. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70:419439 (1980) and in U.S. Pat. No. 4,857,453.

Suitable enzymes include, but are not limited to, alkaline phosphatase and horseradish peroxidase. Other labels for use in the invention include magnetic beads or magnetic resonance imaging labels.

In another embodiment, a phosphorylation site can be created on an antibody of the invention for labeling with $^{32}P$, e.g., as described in European Patent No. 0372707 (application No. 89311108.8) by Sidney Pestka, or U.S. Pat. No. 5,459,240, issued Oct. 17, 1995 to Foxwell et al.

As exemplified herein, proteins, including antibodies, can be labeled by metabolic labeling. Metabolic labeling occurs during in vitro incubation of the cells that express the protein in the presence of culture medium supplemented with a metabolic label, such as $[^{35}S]$-methionine or $[^{32}P]$-orthophosphate. In addition to metabolic (or biosynthetic) labeling with $[^{35}S]$-methionine, the invention further contemplates labeling with $[^{14}C]$-amino acids and $[^{3}H]$-amino acids (with the tritium substituted at non-labile positions).

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE 1

STRUCTURAL BASIS FOR THE ACTIVATION OF RAS BY SOS

Summary

In order to clarify the molecular mechanism of the activation of Ras by Sos the crystal structure of the complex of a C-terminally truncated form of human H-Ras (residues 1–166, hereafter referred to as Ras), with the guanine nucleotide-exchange factor region of human Sos1 (residues 564–1049, hereafter referred to as Sos) was determined. The structure reveals that Sos interacts extensively with Ras and stabilizes it in a nucleotide-free state by displacing the residues that coordinate the magnesium ion and the phosphate groups of the nucleotide and by partially occluding the magnesium binding site. The structure also suggests a pathway for the rebinding of nucleotides to Ras, with consequent release of Sos, a process that is crucial for the functioning of Sos as a nucleotide exchanger rather than a binding inhibitor.

Methods

Expression and Purification: *E. coli* cells (BL21-DE3) A ere transformed with a pProEX HTb vector (Life Technologies) containing Ras (residues 1–166) linked to an N-terminal polyhistidine tag using the BamH I and Xho I restriction sites. Protein production was induced with 250 mM IPTG at a cell density of $O.D._{600}=0.5$. Protein was expressed at 30° C. for 6 hours. Cells were harvested by centrifugation, resuspended in 20 mM Tris, pH=8.0, 300 mM NaCl at 4° C., flash frozen and stored at −80° C. until needed. Once thawed, cells were lysed using a french press (EmulsiFlex-C5, Avestin, Inc), cell debris was removed by centrifugation, and resulting cell lysate loaded onto a charged nickel binding( column (HisBind; Novagen) pre-equilibrated with 20 mM Tris, pH=8.0, 500 mM NaCl, and 20 mM imidazole. Protein was eluted using an imidazole gradient. Fractions containing Ras were pooled, dialyzed into Buffer A (20 mM Tris, pH=8.0, 100 mM NaCl), and concentrated. The polyhistidine tag was cleaved by tobacco etch virus (TEV) in Buffer A at 4° C. for 48 hours. After cleavage, protein was passed over a charged nickel binding column preequilibrated with Buffer A to remove uncleaved protein. Fractions containing pure Ras were pooled and concentrated. Expression and purification of Sos (residues 564–1049) was performed as above, with an additional purification step utilizing a HiQ (Biorad) column preequilibrated with Buffer A. Fractions containing Sos were concentrated in Buffer A.

The Ras-Sos complex was formed by incubating concentrated Sos with 3–5 fold excess Ras in Buffer A for 1 hour at 4° C. Protein was loaded onto a Sephadex 75 gel filtration column (Pharmacia Biotech) preequilibrated with Buffer A. Fractions containing complex were pooled and concentrated to 10 mg/ml. Approximately 30 mgs of purified complex could be obtained from 16 liters of *E. coli* cell culture grown in LB expressing Sos, the limiting reagent.

Crystallization, data collection, and data processing: Hanging drops of Ras-Sos complex (2.5 µL, 10 mg/ml) in Buffer A were mixed with an equal amount of reservoir buffer containing 2.7–3.2M sodium formate and 100 mM Tris buffer, pH=8.0, and kept at 4° C. Crystal showers appeared after 1–2 days with large single crystals growing to full size (0.3×0.3×0.15 mm³) within 2–3 weeks. The crystals contain 1 heterodimeric complex per asymmetric unit an([ belong to space group I422 (a=b=142.7 Å, c=207.9 Å). Crystals were harvested in 3.5M sodium formate and 100 mM Tris buffer, pH=8.0 and cryoprotected in 3.5M sodium formate, 100 mM Tris buffer, pH=8.0, 10% (w/v) sucrose, and 10% (v/v) ethylene glycol before flash freezing in liquid propane. Heavy atom derivatives were prepared by soaking crystals in harvesting buffer containing heavy atom solutions. Crystals were also obtained from sodium/potassium phosphate (space group I422, a=b=142 Å, c=315 Å). However, due to the limited diffraction from these crystals (3.8 Å resolution), structure determination was not pursued.

All but one of the data sets used in this analysis were measured at Brookhaven National Laboratories on beamline X25 using the Brandies 2×2 (four module) CCD-based detector Westbrook and Naday, *Meth. Enzymol.*, 276:244–268 (1997)]. A mercury derivative data set (PCMB) was measured at Cornell High Energy Synchrotron Source on beamline F2 using the Q1 CCD-based detector (ADSC). Data processing was performed using Denzo and data reduction was performed using Scalepack [Otwinowski and Minor, *Meth. Enzymol.*, 276:307–326 (1997)]. MIR phases were calculated using MLPHARE as implemented in the CCP4 suite of programs [Collaborative Computing Project, N. The CCP4 Suite: Programs for protein cyrstallography. *Acta Cryst.*, D50:760–763 (1994)]. Solvent flattening was performed using DM [Cowtan, *Joint CCP4 and ESF-EACBM Newsletter on Protein Crystallography*, 31:34–38 (1994)].

Model Building and Refinement: Model building was performed using O [Jones et al, *Acta Crystallogr.*, A47:110–119 (1991)]. Coordinates for the GTP bound form of Ras (521P) [Pai et al., *EMBO J.*, 9:2351–2359 (1990)] were obtained from the Protein Data Bank [Bernstein et al., *Archives of Biochemistry & Biophysics*, 185:584–591 (1978)] and the molecule, with Switch 1 and Switch 2 regions deleted, was fit into density. After an initial round of model building and positional refinement using CNS with bulk solvent corrections and anisotropic B-factor scaling protocols utilized, phase combination methods using Sigmaa [Read, *Acta Cryst.*, A42:140–149 (1986)] resulted in a much improved map into which the Switch 2 region of Ras, the catalytic domain of Sos, and the N-terminal helices of Sos were built. Electron density maps based on multiple simulated annealing models [Brünger et al., *Structure*, 5:325–336 (1997)] allowed the remaining regions of Ras and Sos to be placed into density. Residues 564–567 (N-terminal), 591–597, 654–675, 742–751, and 1045–1049 (C-terminal) are disordered and not modeled in Sos; no residues of Ras are disordered. The Ramachandran plot shows 89% of all residues are in the most favored regions and no residues are in disallowed regions.

Results

Structure Determination: Ras and Sos form a tight complex in the absence of nucleotides. Crystals of this complex were obtained (I-centered tetragonal, a=b=142.7 Å, c=207.9 Å) with one Ras-Sos complex ($M_r$=75 kD) in the asymmetric unit. The structure was determined by multiple isomorphous replacement using 9 heavy atom derivatives (Tables 1 and 2). The molecular model was refined against data to 2.8 Å, resulting in a crystallographic R-value of 22.2% (free R-value of 28.1%). The final model includes 439 residues of Sos, 166 residues of Ras, and 26 water molecules. There is no nucleotide or magnesium present in the crystals. The coordinates for the human Ras-Sos complex are compiled in the data set in Table 3.

TABLE 1

Data collection, structure determination and refinement statistics

| Data set | Resolution (Å) | Observations Total/Unique | $R_{sym}$* (%) | Completeness (%) | $R_{iso}$† (%) | Sites (No.) | Phasing Power‡ |
|---|---|---|---|---|---|---|---|
| Native | 2.8 | 283114/26562 | 5.3 (28.7) | 99.3 (99.9) | | | |
| PCMB⁺ | 3.1 | 616299/19766 | 7.7 (28.9) | 93.4 (87.9) | 22.8 | 5 | 1.68 |
| Baker's Dimercurial⁺ | 3.25 | 640979/16988 | 7.6 (19.3) | 96.9 (98.6) | 21.5 | 6 | 0.80 |
| EMTS⁺ | 3.25 | 634455/17174 | 7.3 (35.1) | 95.4 (97.2) | 20.0 | 4 | 1.94 |
| Trimethyl Lead Acetate⁺ | 2.9 | 523356/23842 | 5.9 (27.0) | 98.2 (9.93) | 22.5 | 6 | 0.77 |
| Selenomethionine | 3.0 | 543633/21735 | 6.5 (29.7) | 96.1 (93.2) | 15.4 | 10 | 1.44 |
| Gold Cyanide⁺ | 3.05 | 368880/20927 | 5.4 (28.6) | 98.3 (96.5) | 33.5 | 3 | 1.46 |
| Platinum Terpyridine | 3.25 | 240941/16915 | 10.6 (36.7) | 98.9 (99.3) | 18.5 | 6 | 1.35 |
| Osmium Chloride | 3.1 | 202555/20025 | 6.8 (29.4) | 99.6 (99.9) | 23.5 | 4 | 1.55 |
| PCMB/Trimethyl Lead Acetate⁺ | 3.3 | 571428/16485 | 7.8 (30.0) | 99.8 (99.5) | 26.6 | 9 | 1.91 |

Overall Figure of Merit# = 0.70

TABLE 2

Refinement Statistics

| | Resolution | | | | | rmsd from ideal values | |
|---|---|---|---|---|---|---|---|
| Data Set | (Å) | Reflections | Total atoms | R-factor¶/$R_{free}$ | | bonds (Å) | angles (°) |
| Native | 30–2.8 | 26502 | 5010 | 0.222/0.281 | | 0.007 | 1.26 |

*$R_{sym}$ = 100 × Σ|I − <I>|/ΣI, where I is the integrated intensity of a given reflection. For $R_{sym}$ and completeness, numbers in parentheses refer to data in the highest resolution shell.
†$R_{iso}$ = 100 × Σ|$F_{PH}$ − $F_P$|/Σ$F_P$, where $F_{PH}$ and $F_P$ are the derivative and native structure factor amplitudes, respectively.
‡Phasing power = Σ|$F_{PH(calc)}$|²/Σ{|$F_{PH(obs)}$ − $F_{P(calc)}$|²}^½.
⁺Anomolous data was used in the phasing of these derivatives.
Figure of Merit = <|ΣP(α)$e^{iα}$/ΣP(α)|>, where α is the phase and P(α) is the phase probability distribution.
¶R-factor = Σ|$F_P$ − $F_{P(calc)}$|/Σ$F_P$; $R_{free}$ was calculated with 5% of the data.

Structure of Sos: The structure of the Ras exchange factor region of Sos (residues 568 to 1044) consists of two distinct α-helical structural domains (FIG. 2). The amino-terminal domain (N-Domain, residues 568 to 741) does not interact with Ras, and appears to play a purely structural role. The carboxy- terminal domain (residues 752 to 1044) contains within it all the residues that interact with Ras, and this region will be referred to as the catalytic domain. Analyses of the exchange factor activity of Cdc25, Sdc25 and Sos have shown that the relatively well conserved C-terminal catalytic domain suffices for catalytic activity [Chardin et al., *Science*, 260:1338–1343 (1993)]. However, recombinant fragments of Sos that span the catalytic domain, but which lack some or all of the N-Domain, are expressed poorly and have low solubility, whereas the fragment used for the structure determination includes both domains and results in relatively high yields of soluble protein. The formation of a Ras-Sos complex results in the protection from proteolysis of both the N- and catalytic domains, suggesting that they stabilize each other during complex formation.

Figure 2A:
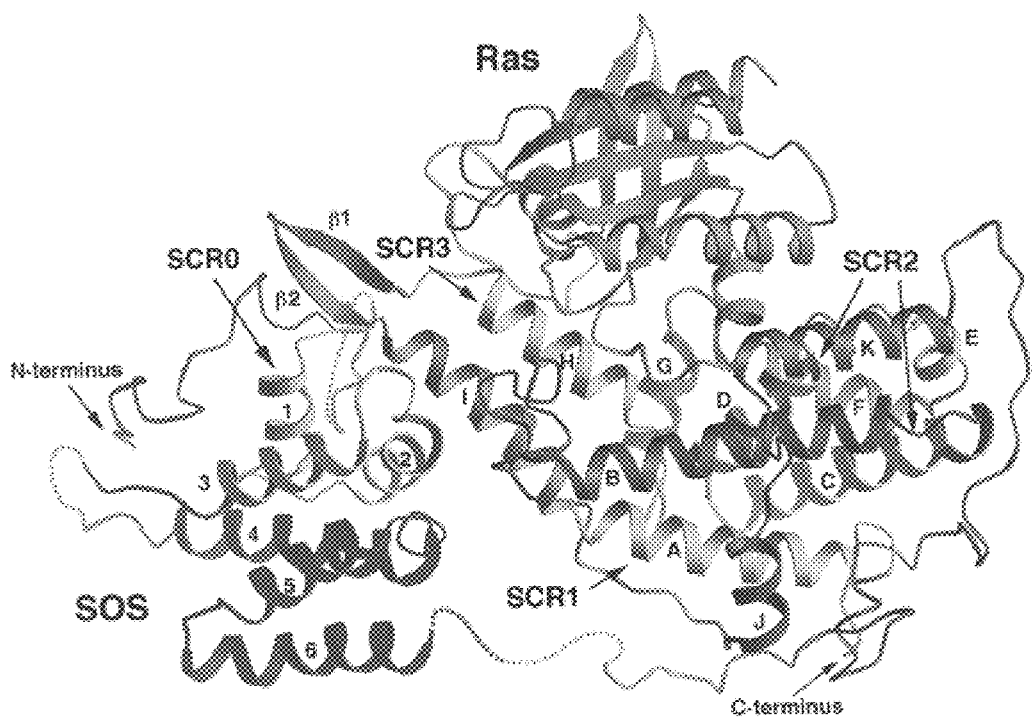
FIGS. 2A–2B show the complex of H-Ras with the exchange factor region of human Sos1.
Figure 2B:
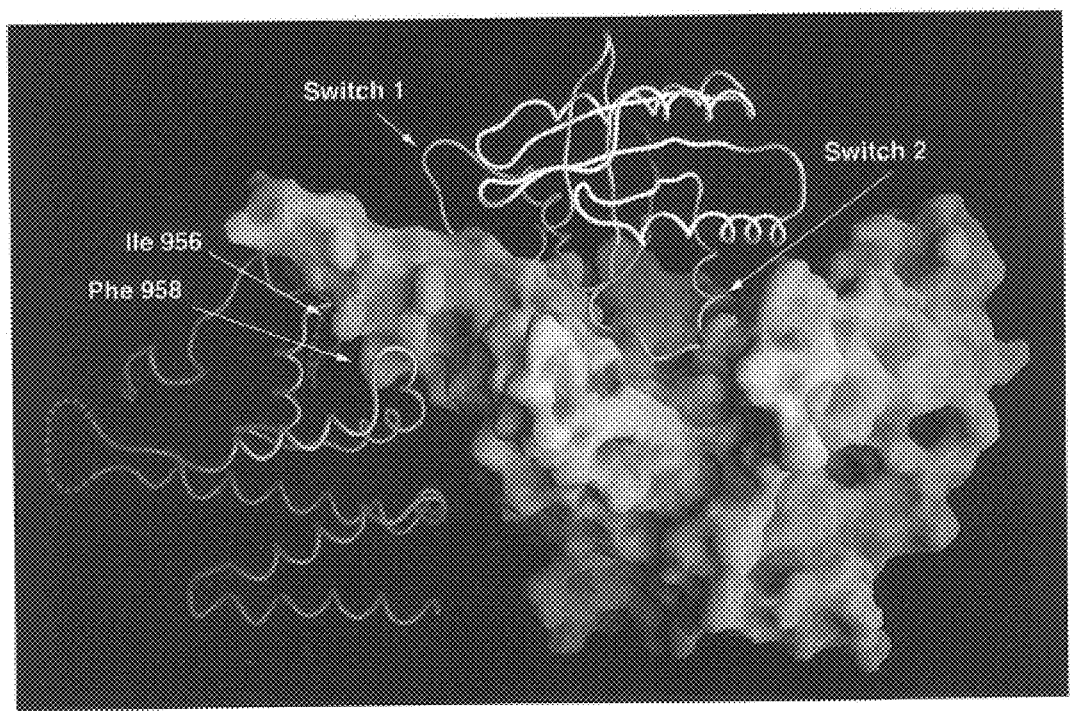

The interaction between the two domains of Sos is localized to one end of the catalytic domain. The N-Domain contains six helices ((α1 to α6). Helices α3 to α6 form a 4-helix bundle that supports helices α1 and α2. α1 and α2 together form a small hydrophobic groove into which are inserted two conserved hydrophobic sidechains from the catalytic domain (Ile 956 and Phe 9158; FIG. 2B). The packing of these sidechains into the α1–α2 groove, along with several adjacent inter-domain interactions, is likely to be important for the stability and correct placement of a hairpin structure formed by helices αH and αI in the catalytic domain (FIG. 2). This hairpin protrudes from the core of the catalytic domain, and helix αH plays a key role in the nucleotide exchange mechanism.

The structure of the catalytic domain consists of a series of helical hairpins that pack against each other, with no significant similarity to proteins in the databank (based on a DALI search [Holm and Sander, *J. Mol. Biol.*, 233:123–138 (1993)]). In particular, there is no structural similarity between this domain and the catalytic domain of Ras guanine activating protein [Scheffzek et al., *Nature*, 384:591–596 (1996)] which is also α-helical. Helices αA to αG, along with αJ and αK, form a compact core region, out of which is extruded the hairpin formed by helices αH and αI. It is this projection out of the core that appears to require interaction with the N-Domain for stabilization.

Figure 1A:
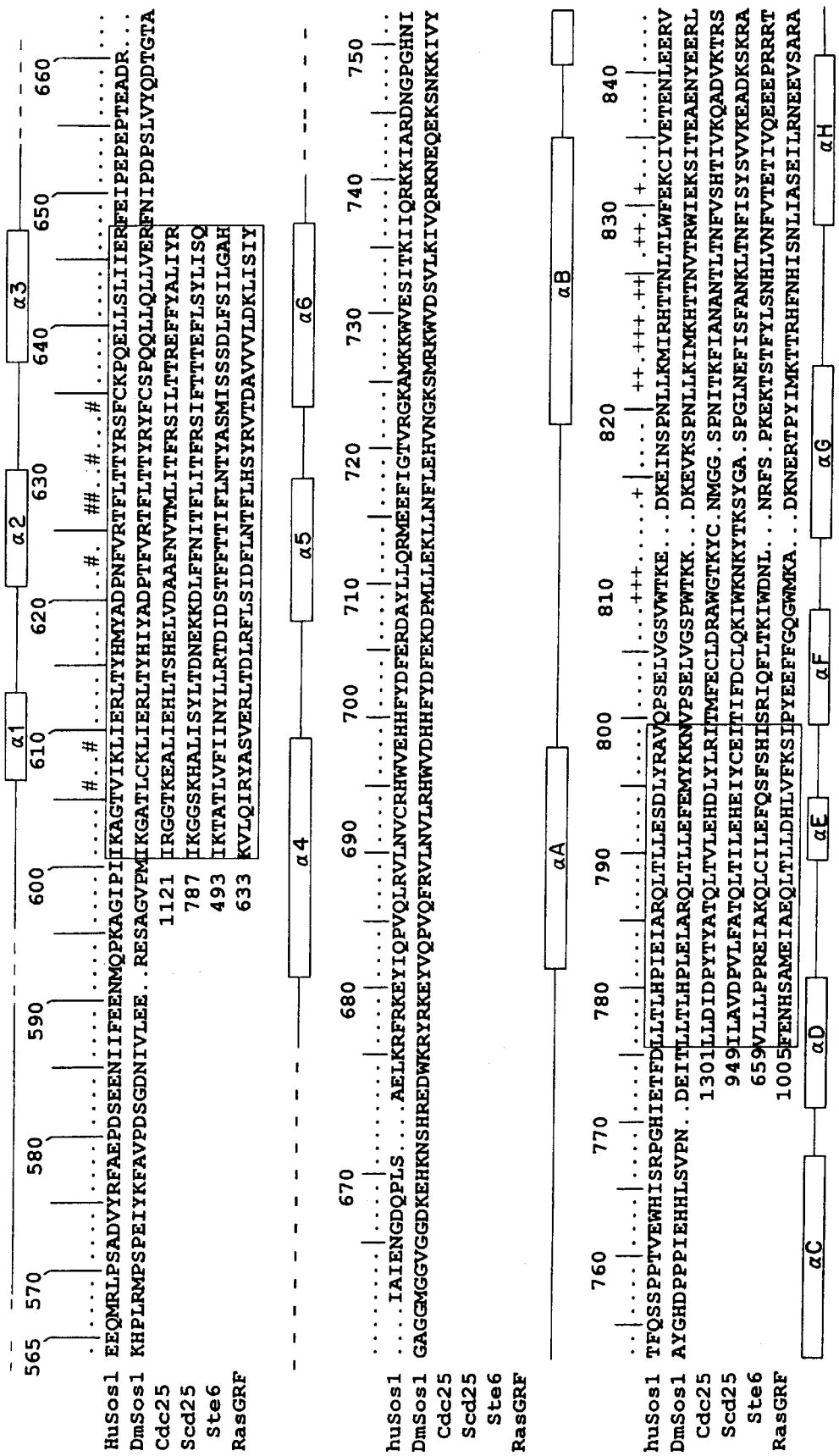
FIG. 1 shows the sequence alignment of Ras-binding exchange factors shown with the secondary structure and residue numbers of Sos indicated. The secondary structure elements (α-helices are shown as rectangles, β-sheets are shown as arrows, coil regions are shown as a solid line, disordered residues are shown as dashed lines) of the N-Domain are blue and of the catalytic domain are green. Conserved regions SCR 1–3 are shaded with red, SCR0 is shaded with blue. Residues of Sos at the Ras interface are indicated with +; residues in the N-Domain that form the hydrophobic core with the catalytic domain are indicated with #. Sequences have been omitted where the sequence similarity between exchange factors is low; residue numbers are indicated at the beginning of alignments.
Figure 1B:
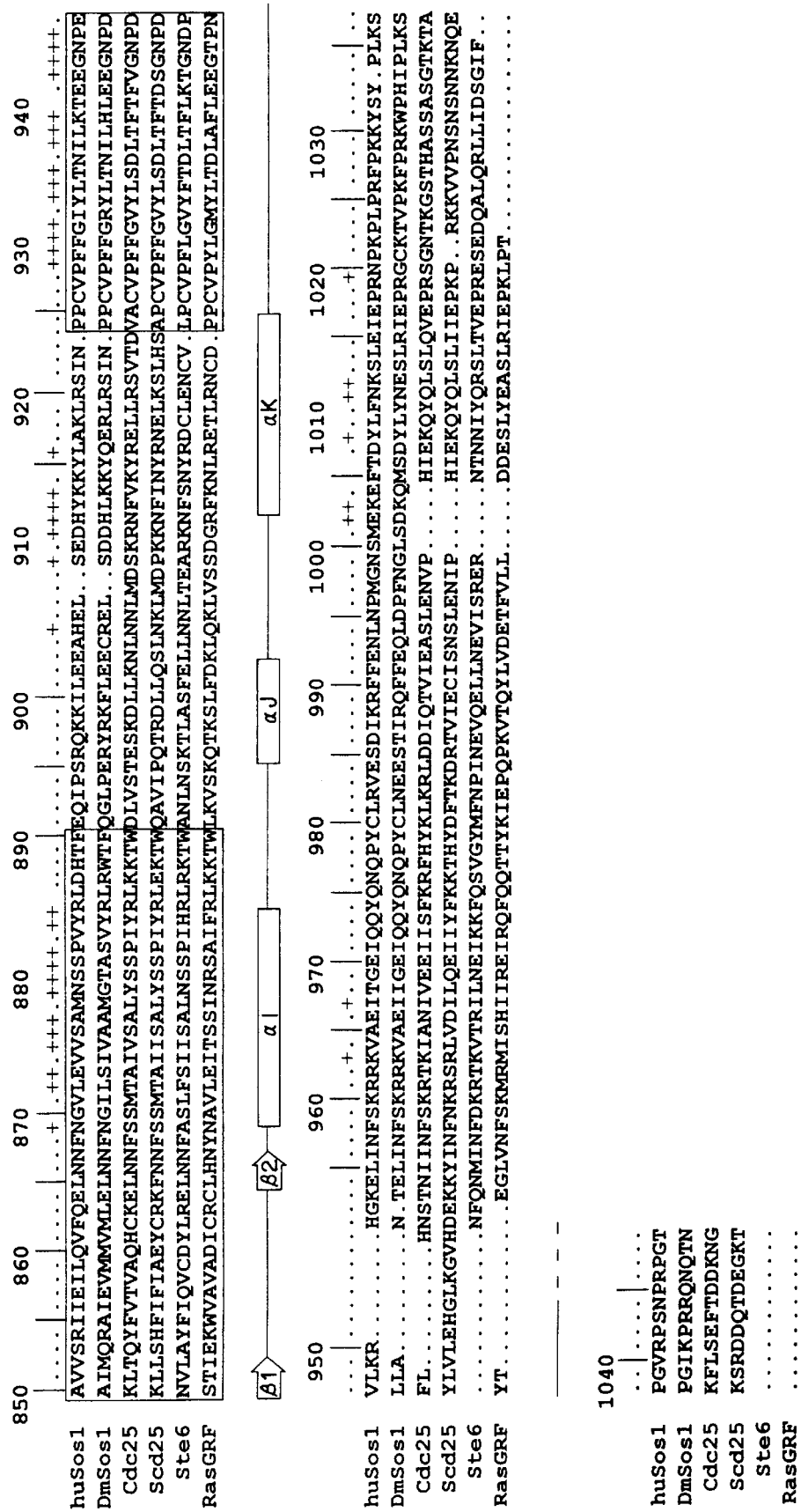

Structural Relationship between Sos and other nucleotide exchange factors for Ras: Sos is related in sequence to the yeast proteins Cdc25, Sdc25, and the mammalian exchange factor (FIG. 1). The structure of the Ras nucleotide exchange factor region of Sos described here is likely to be a good model for the general architecture of these guanine nucleotide exchange factors. Three regions of sequence conservation within the catalytic domain had been identified previously, and are named structurally conserved regions (SCR) 1–3 [Boguski and McCormick, *Nature*, 366:643–654 (1993)]. These regions are either important for the structural integrity of the domain (SCR1, helix αA and SCR2, helix αC) or for the interaction with Ras (SCR2 helix αD and SCR3; FIG. 2A). The region of the N-Domain spanning helices α1, α2 and α3 is highly conserved among Ras-specific nucleotide exchange factors (SCR0 in FIG. 2A) [Lai et al., *Mol. Cell. Biol.*, 13:1345–1352 (1993)]. This sequence conservation argues for a conservation between Sos, Cdc25, Sdc25, and RasGRF for the particular relative arrangement of the N-Domain and the catalytic domain that is seen in Sos. The hydrophobic nature of the groove between helices α1 and α2 is conserved, as are the residues on the catalytic domain that interact with the groove and the adjoining surface of the N-Domain.

Figure 3A:
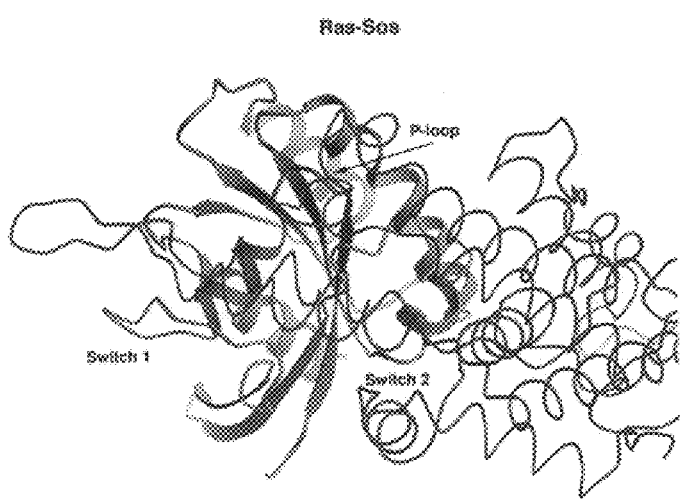
FIGS. 3A–3B show the comparison of Ras complexed with Sos (FIG. 3A) and b) GTP (FIG. 3B) [Pai et al., *EMBO J.*, 9:2351–2359 (1991))]. The coloring scheme for Ras is the same as FIG. 2B.; GTP is pink and the magnesium ion is shown as a magenta sphere. Sos is shown as a green ribbon; the PDB code for GTP-Ras used for these figures is also indicated. Secondary structure elements of Ras that are important in nucleotide binding and Sos binding are labeled.
Figure 3B:
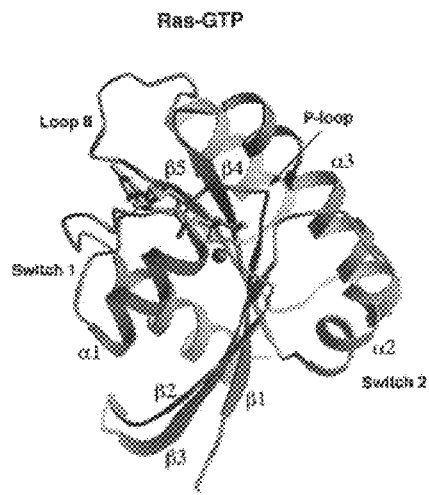

Structure of the Ras-SOS interface: The structure of Ras in the nucleotide bound form consists of a six-stranded β sheet, flanked by 5 α-helices (FIG. 3). Two segments of Ras, Switch 1 (residues 25–40) and Switch 2 (residues 57–75), adopt distinct conformations in the GDP and GTP bound states [Melburn et al., *Science*, 247:939–945 (1990)]. In the nucleotide bound forms, Switch 1 interacts with the base, the ribose group, the phosphates, and the magnesium ion. The Switch 2 region includes the loop following β3 and helix α2 and interacts with the magnesium ion and the phosphate of GTP.

Figure 4A:
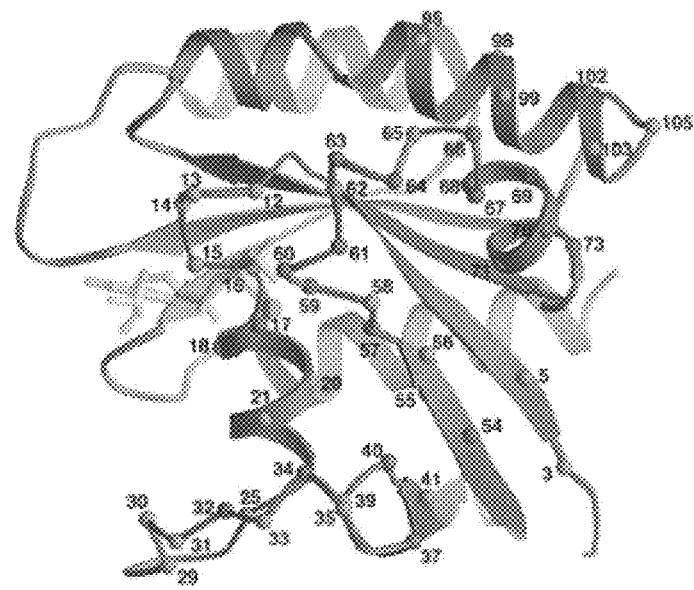
FIGS. 4A–4C show the interface surfaces of the Ras-Sos complex.
Figure 4B:
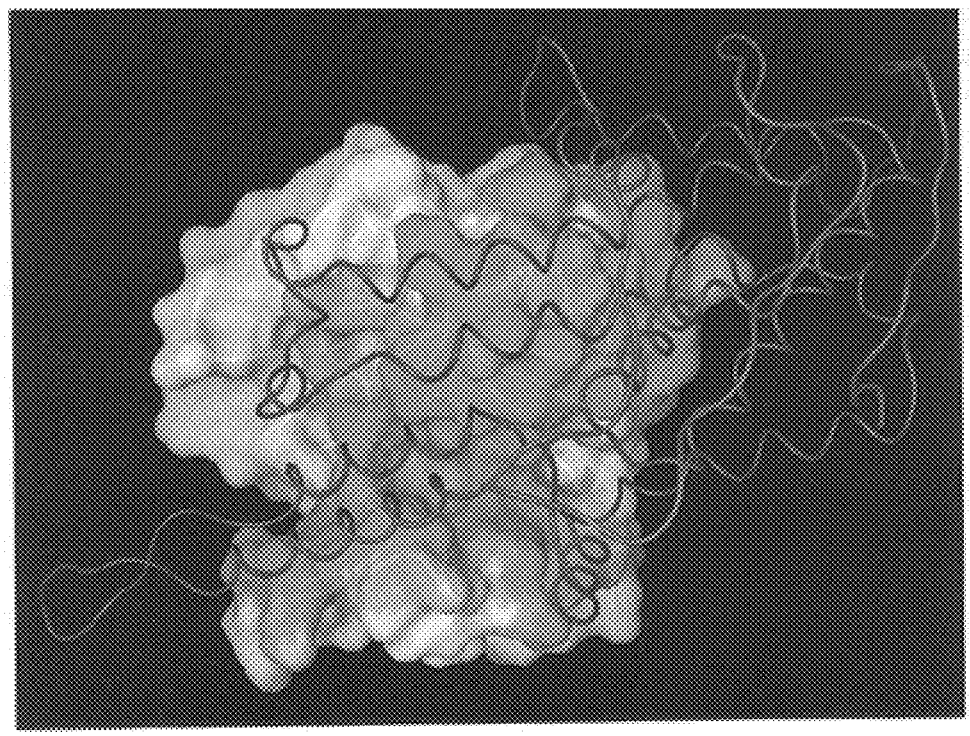
Figure 4C:
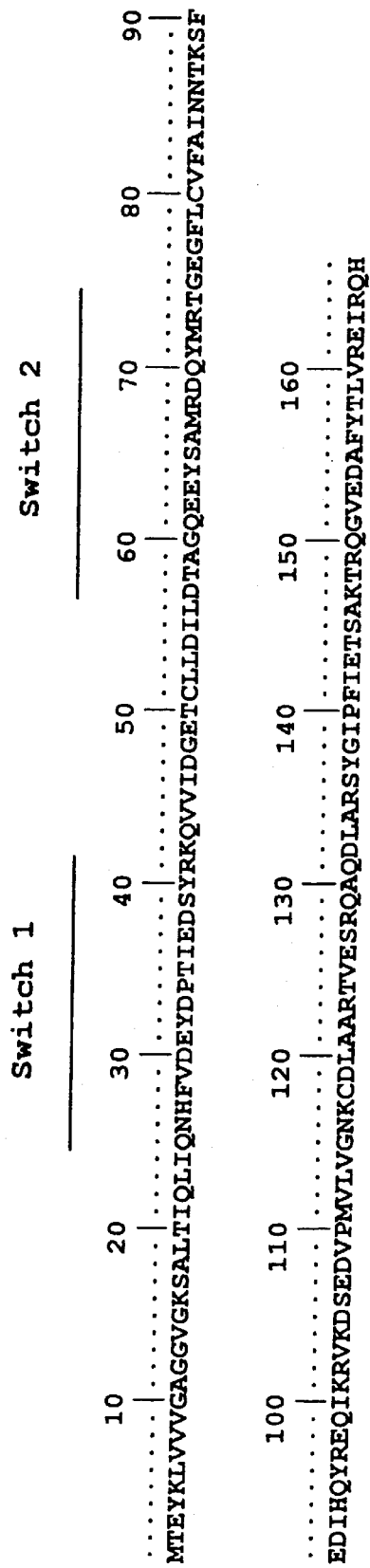

The overall shape of the catalytic domain of Sos is that of an oblong bowl (FIG. 2). The conserved regions SCR 1–3 are in the center of the bowl, which forms the binding site for Ras (FIG. 2B). The regions of Ras that interact most closely with Sos include the P-loop region (strand β1, the P-loop and helix α1), the Switch 1 region and the Switch 2 region. Additional interactions are seen with helix α3 (residues 95–105; FIGS. 4A and 4B). The interface between Ras and Sos is very extensive, with 3,600 $Å^2$ of surface area buried in the complex. At the heart of the interface between Switch 2 and Sos is a cluster of three hydrophobic sidechains from Ras (Tyr 64, Met 67 and Tyr 71) that are buried into the hydrophobic core of Sos at the base of the binding site. Surrounding this hydrophobic anchor is an array of polar and charged interactions between Sos and Ras that results in almost (every external sidechain of Switch 2 being coordinated by Sos. The interaction surf ace is primarily hydrophilic, with less than 25% of the buried surface area corresponding to hydrophobic and aromatic residues.

The most obvious effect of Sos binding to Ras is the opening of the nucleotide binding site due to the displacement of Switch 1 by the insertion of the helical hairpin formed by αH and αI (FIG. 5). Although the changes in the Switch 1 segment are large, there are few specific interactions between Ras and Sos in this region. Only three residues of Sos (Lys 913, Asn 936 and Asn 944) are involved in direct hydrogen bonds and only two residues (His 911 and Lys 939) are involved in hydrophobic van der Waals contacts or stacking interactions with Switch 1 residues. Of these five residues, four (His 911, Lys 913, Asn 936 and Lys 939) are not conserved among Ras exchange factors, suggestive that the helical hairpin plays a steric rather than a sequence specific role in keeping the Switch 1 region distant from the nucleotide binding site. Consistent with this idea, the temperature factors in the Switch 1 region are relatively high (average backbone B-value of 81 $Å^2$ for Switch 1, compared to 46 $Å^2$ for the entire Ras backbone).

Figure 6A:
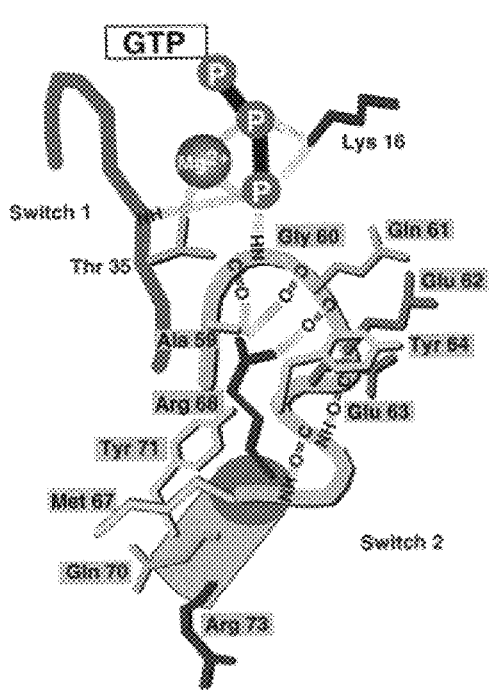
FIGS. 6A–6D show the differences in the Switch 2 regions of Ras-GTP (521P [Pai et al., *EMBO J.*, 9:2351–2359 (1990)]) and Ras-Sos.
Figure 6B:
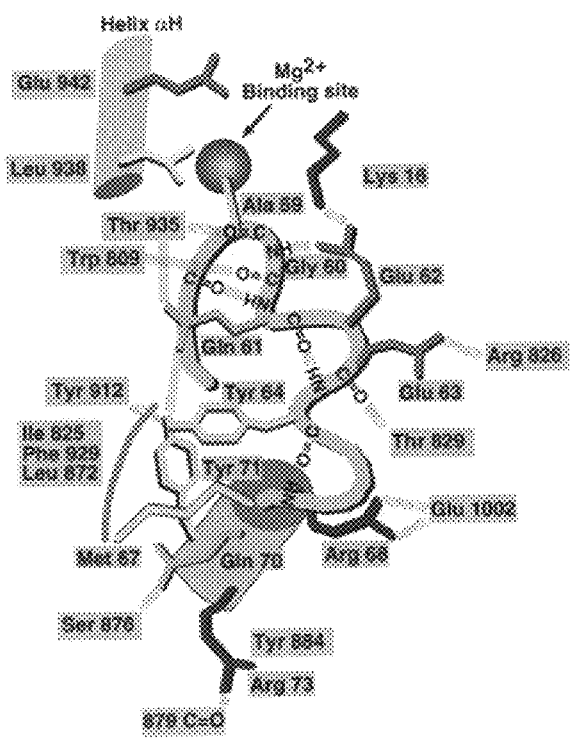
Figures 6C, 6D:
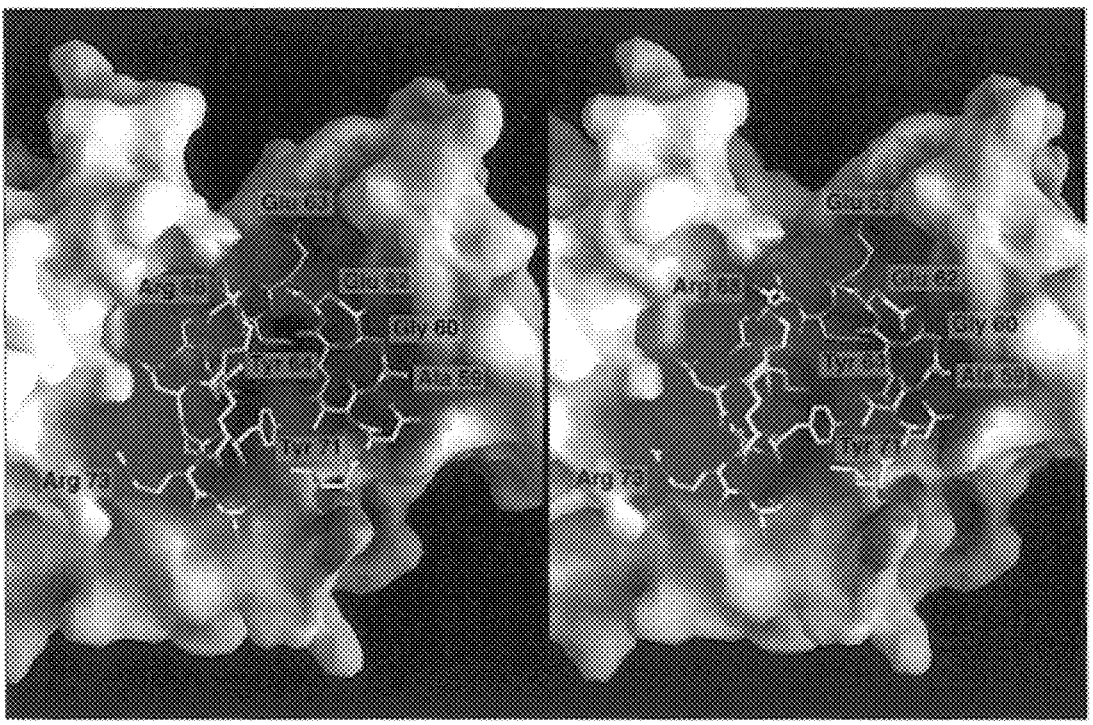

In contrast to the loose interaction between Sos and the Switch 1 region, the Switch 2 region is held in a very tight embrace by Sos. The temperature factors for all atoms of Switch 2 are low (34 $Å^2$, compared with the average value of 49 $Å^2$ for all of Ras). The C-terminal end of Switch 2 is farthest from the nucleotide binding site, and sidechains in this region interact with Sos but do not change their position significantly. However, closer to the nucleotide binding site the interactions between Sos and the sidechains of Switch 2 results in a restructuring of the polypeptide backbone connecting β3 and α2 (FIGS. 6A and 6B). The restructuring of the backbone is a crucial determinant of nucleotide exclusion.

Switch 1 and Switch 2 are the only regions of Ras in which structural changes are directly induced by Sos. Comparison of the structure of Ras in the Ras-Sos complex with that of the nucleotide bound forms shows that there are also structural changes in the loops that bind the nucleotide base (Loop 8, between β5 and α5, residues 118–123) and the phosphate (the P-loop, residues 10 to 15). The changes in these loops appear to be a simple consequence of the absence of nucleotide.

Structural Changes at the Nucleotide Binding Site: The modes of binding of GTP and GDP to Ras are very similar [Milburn et al., *Science*, 247: 939–945 (1990)]. β-strand 1 leads into the phosphate binding loop (P-loop), which contains a sequence motif ($GX_4GKT$) that is seen in many nucleotide binding proteins. The structural element encompassing β1, the P-loop and α1 is common to many nucleotide binding proteins, and is colored red in FIGS. 2B and 3. The phosphate groups of the nucleotide are cradled between the P-loop and helix a1 such that the helix dipole of α1 interacts favorably with the negatively charged phosphates. An important component of the phosphate binding site is a magnesium ion, which coordinates the β phosphate (and the γ phosphate in GTP). In the GTP complex, octahedral coordination of the $Me^{2+}$ ion is completed by the sidechains of Ser 17 and Thr 35 of Ras and two water molecules [Pai et al., *EMBO J.*, 9:2351–2359 (1990)]. The guanine base is recognized by sidechains presented by the two loops immediately following strands β4 and β6. The ribose ring interacts mainly with the Switch 1 region.

Figure 5A:
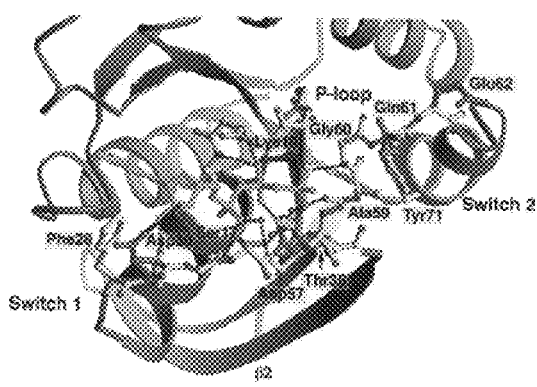
FIGS. 5A–5D shows the interactions at the nucleotide binding site.

The conformation of helix a2 in the Switch 2 region differs greatly in the GDP- and GTP-bound forms of Ras. The sensitivity of Switch 2 to the presence of GTP versus GDP is a consequence of the coordination of the terminal phosphate of GTP by the backbone amide nitrogen of Gly 60 (FIGS. 5A and 6A). In the Ras-GDP complex, the backbone is not engaged in such interactions, presumably allowing α2 to rotate away. The conformation of the Switch 2 region in the Ras-Sos complex can be compared to that seen in the GTP-bound form of Ras, since the Switch 2 region is less well ordered in the GDP bound form [Milburn et al., *Science*, 247:939–945 (1990)]. The GTP-bound form is also a natural structure for comparison to the nucleotide-free structure of Ras in the Sos complex, since it represents the structure of Ras when the binding site is fully ligated.

The changes in the structure of Switch 1 and Switch 2 that are induced by Sos result in the exclusion of nucleotide by disruption of the magnesium and phosphate binding sites, and removal of the interactions between Switch 1 and the nucleotide (FIG. 5). Three specific features of the Switch 2 conformation are correlated with disruption of nucleotide binding. The backbone conformation in the central region of Switch 2 is compressed in the Ras-Sos complex due to the formation of three consecutive β turns (between residues 58 to 61, 61 to 64 and 64 to 67; an S-shaped curve with β turns between residues 62 and 65 and also 64 and 67 is present in the GTP bound form of Ras, FIGS. 6A and 6B). As a consequence of the first β turn, the methyl sidechain of Ala 59 is turned in towards the phosphate binding site and occludes the position that would be occupied by the $Mg^{2+}$ ion in nucleotide complexes. In the GTP-bound form, the amide nitrogen of Gly 60 coordinates an oxygen atom of the terminal phosphate in the GTP complex. Due to the formation of the second β turn, the sidechain of Glu 62 moves from a position distant from the phosphate binding site to one where it now coordinates both the amide nitrogen of Gly 60 and the sidechain of Lys 16 (part of the conserved Walker motif, Lys 16 normally coordinates the oxygen atoms of the phosphates, FIGS. 5A and 6A).

In the GTP bound form the polypeptide backbone of the β3-α2 loop adopts a conformation wherein three carbonyl groups (that of 59, 60, 61) are pointed inwards. The resultant anion hole coordinates the sidechain of Arg 68, and positions the methyl group of Ala 59 away from the magnesium binding site. In the Sos complex, Arg 68 is removed from this internal location by interactions with Glu 1002 of Sos, and the anion hole is disrupted by the formation of the first two β turns in the structure (FIGS. 6A and 6B).

Figure 5B:
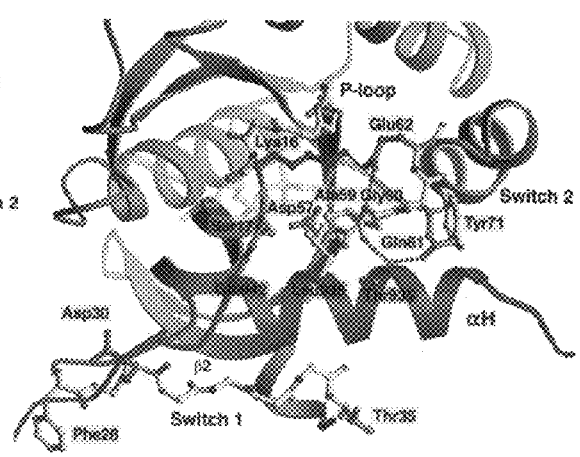
Figure 5C:
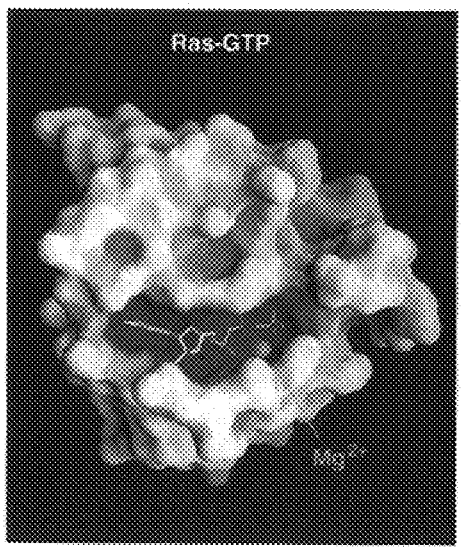

The change in the Switch 1 region of Ras when bound to Sos is drastic. The C-terminal region of helix α1 is shortened by about 1 helical turn. Switch 1 normally rises up from the end of α1 towards the P-loop region, so as to sandwich the nucleotide between it and the rest of Ras (FIGS. 5A and 5C). In the nucleotide complexes, Switch 1 approaches the Switch 2 region closely and strand β2 in Switch 1 forms an antiparallel interaction with strand β3, which leads into Switch 2. In the Sos complex, this anti-parallel β-sheet interaction is completely disrupted and strand β2 is melted, and Switch 1 is completely removed from the nucleotide binding site (FIGS. 5B and 5D).

Figure 5D:
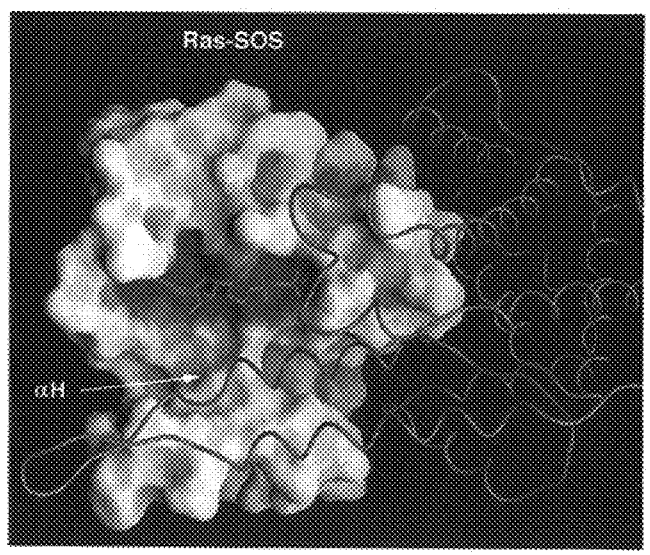

One important aspect of the insertion of the hairpin into the Switch 1 region is that it does not result in a significant occlusion of the nucleotide binding site (FIG. 5D). Rather, the main effect of this structural distortion is to break the network of direct and water-mediated hydrogen bonds that form between Switch 1 and the nucleotide, which is an effective method for destabilizing the nucleotide. In the GDP and GTP complexes, Phe 28 of Ras interacts with the guanine base through a perpendicular aromatic-aromatic interaction (FIG. 5A). Mutations at this position (Phe 28→Leu) result in a 18-fold increase in the intrinsic rate of dissociation of nucleotide from Ras [Mistou et al., *EMBO J.*, 11:2391–2397 (1992)]. In the Sos complex, the Ca atom of Phe 28 moves 9.6 Å and the sidechain no longer interacts with the nucleotide binding site (FIG. 5B). Moreover, two sidechains presented by helix αH of Sos, Leu 938 and Glu 942, directly impede the binding of magnesium and phosphate, respectively. The carboxylate group of Glu 942 is positioned near the location of the a phosphate of GTP or GDP in the nucleotide bound forms of Ras, and in the SOS complex Glu 942 forms a hydrogen bond with Ser 17 of Ras, a ligand of the magnesium ion in the nucleotide complexes of Ras. Leu 938 further increases the hydrophobicity of the magnesium binding site in the Sos complex, which is also occupied by Ala 59 from Switch 2.

Implications for the Reaction Mechanism: The mechanism of nucleotide release by the catalytic domain of murine Cdc25 has been investigated recently using fluorescently labeled nucleotides [Lenzen et al., *Biochemistry* 37:7420–7430 (1998)]. The affinity of Cdc25 for nucleotide-free Ras ($K_d$=4.6 nM) is found to be several orders of magnitude higher than that for nucleotide bound Ras, and the maximal acceleration by Cdc25 of the rate of dissociation of nucleotide is greater than 10,000-fold. Cdc25 acts primarily by facilitating the dissociation of nucleotide, with no preference for GTP or GDP.

Kinetic analysis of the association of nucleotides shows that the reaction proceeds via the formation ternary complex of a loosely bound nucleotide and Ras-Cdc25 followed by a conversion to a form in which the nucleotide is tightly bound to Ras [Lenzen et al., *Biochemistry* 37:7420–7430 (1998)]. In light of the structure of the Ras-Sos complex, the first step can be interpreted as the interaction of the base and the ribose of the nucleotide with the part of the Ras binding site that is not occluded by Sos. The second step would involve a conformational change in the Switch 2 segment and release of Switch 1, resulting in the restructuring of a competent binding site for phosphate and magnesium. It is expected that Sos would dissociate from Ras in parallel or after the second step. These studies also show that the mechanism by which Cdc25 displaces the nucleotide does not depend solely on expulsion of the magnesium [Lenzen et al., *Biochemistry* 37:7420–743( (1998)]. This is consistent with the Ras-Sos structure, since the mechanism involves both the removal of the Switch 1-nucleotide interactions as well as interference with the phosphate groups.

Analysis of Ras Mutations: The interaction of Ras with Cdc25 and Sdc25 has been studied extensively by mutagenesis and biochemical methods. However, no studies detailing the thermodynamics and kinetics of Sos and Ras and effects of Sos mutations have been reported as yet. Although SOS, Cde25 and Sdc25 are likely to share the same general features of the mechanism of nucleotide release, the relatively low sequence identity between them (FIG. 1) means that comparisons must be made cautiously.

The structure of the Ras-Sos complex is consistent with a number of mutations in Ras that have highlighted the importance of the Switch 1 and Switch 2 regions in the interaction with nucleotide exchange factors [Mistou et al., EMBO J., 11:2391–2397 (1992); Verrotti et al., EMBO J., 11:2855–2862 (1992); Segal et al., Proc. Natl. Acad. Sci., 90:5564–5568 (1993); Mosteller et al., Molec. Cell. Biol., 14:1104–1112 (1994); Segal et al., Eur. J. Biochem., 228:96–101 (1995); Leonardsen et al., Oncogene, 13:2177–2187 (1996); Crechet et al., J. Biol. Chem., 271:17234–17240 (1996); Quilliam et al., J. Biol. Chem., 271:11076–11082 (1996)]. The importance of helix α3 (residues 102–105) has also been noted [Segal et al., Proc. Natl. Acad Sci., 90:5564–5568 (1993); Segal et al., Eur. J. Biochem., 228:96–101 (1995); Leonardsen et al., Oncogene, 13:2177–2187 (1996)]. The importance of Switch 2 for the recognition of the exchange factor is demonstrated by the analysis of mutations in residues that are not directly involved in nucleotide binding, but which are affected in GDP-GTP exchange. Mutation of Glu 62 and Glu 63 to histidine had no significant effect on the stability of the Ras-GDP complex [Mitsou et al., EMBO J., 11:2391–2397 (1992)]. However, both Ras mutants were severely compromised in their ability to be activated by Sdc25 [Mitsou et al., EMBO J., 11:2391–2397 (1992)]. In the structure of the Ras-Sos complex, Glu 62 and 63 of Ras are both seen to be crucial to the interaction with Sos (FIGS. 5B and 6B).

Of particular interest are dominant negative mutants of Ras that appear to act by binding to and sequestering nucleotide exchange factors [Feig and Cooper, Molec. Cell. Biol., 8:3235–3243 (1988); Chen et al., Oncogene, 9:2691–2698 (1994)]. The most straightforward explanation of the action of these mutations is that they destabilize nucleotide binding [Haney and Broach, J. Biol. Chem., 269:16541–16548 (1994); Chen et al., Oncogene, 9:2691–2698 (1994); Powers et al., Cell, 65:1225–1231 (1991)], thereby increasing the apparent affinity of Ras for Sos or other exchange factors. Some of the dominant negative mutations may, in addition, result in stronger interactions between Ras and the exchange factor. For example, Ser 17 in Ras forms a hydrogen bond with Glu 942 in Sos (FIG. 5B). Mutation of Ser 17 to Asn 17 results in a dominant negative Ras, and Asn at this position in Ras may be positioned so as to interact more strongly with Glu 942 of Sos.

That the dominant negative mutant Ras proteins act by binding to the exchange factor is also suggested by the fact that mutations at residues that are important for the formation of the Ras-Sos interface result in a reversion of the dominant negative behavior [Mosteller et al., Molec. Cell. Biol., 14:1104–1112 (1994); Crechet et al., J. Biol. Chem., 271:17234–17240 (1996)]. For example, in S. cerevisiae Ras2p, Ser 24→Asn (corresponding to Ser 17→Asn in H-Ras) is a dominant negative mutation [Chen et al., Oncogene 9:2691–2698 (1994)]. Substitution of Arg 80, Asn 81 (Arg 73, Thr 74 in H-Ras) with Asp-Asp in the mutant (Ser 24→Asn) Ras2p results in a loss of sensitivity to Sdc25 and reversion of the dominant negative phenotype [Crechet et al., J. Biol. Chem., 271:17234–17240 (1996)]. In the Ras-Sos complex, Arg 73 (Arg 80 in Ras2p) is involved in interactions with two residues of Sos (FIG. 6A), and mutation to Asp would clearly be disruptive.

Comparison with EF-Tu/EF-Ts and GrpE/DnaK: At present, only two other structures of nucleotide binding proteins complexed to their exchange factors are known: EF-Tu-EF-Ts and GrpE-DnaK. EF-Tu is a GTPase that contains a nucleotide binding domain that is topologically similar to Ras as well as two additional domains [Jurnak, Science, 230:32–36 (1985)]. The EF-Tu-EF-Ts complex, like the Ras-Sos complex, stimulates nucleotide release by disrupting the interactions of the phosphate groups of the nucleotide, leaving the binding site for the base and ribose unimpeded [Wang et al., Nat. Struct. Biol., 4:650–656 (1997); Kawashima et al., Nature, 379:511–518 (1996)]. Reorientation of a peptide bond in the phosphate binding P-loop, induced by EF-Ts binding, results in the placement of a carbonyl oxygen in a position where it would collide with the β phosphate of the nucleotide. In addition, conformational changes in the Switch 2 region remove sidechains that interact with the magnesium ion via water molecules.

Strikingly, E. coli EF-Ts introduces a C-terminal α-helix into the region of the nucleotide binding site near the Switch 1 region [Kawashima et al., Nature, 379:511–518 (1996)]. However, this helix is further removed from the nucleotide binding site than helix αI in Sos, and no corresponding helix is seen in EF-Ts from Thermus thermophilus [Wang et al., Nat. Struct. Biol., 4:650–656 (1997)]. In contrast to Ras, the Switch 1 region of nucleotide-bound EF-Tu does not interact extensively with the nucleotide binding site. Consequently, disruption of the Switch 1 structure does not appear to be a major component of the mechanism of EF-Ts action.

The mechanism of nucleotide release from DnaK by GrpE is fundamentally different from that seen in Ras and EF-Tu. The ATPase domain of DnaK is much larger than Ras (166 residues for Ras compared to 383 residues for DnaK) and contains two subdomains that form a deep cleft in which nucleotide binds. GrpE acts by binding to the mouth of the cleft and wedging apart the two sides of the binding site [Harrison et al., Science, 276:431–435 (1997)].

EXAMPLE 2

IDENTIFYING MEDICINAL CHEMICALS FOR RATIONAL DRUG DESIGN USING THE THREE-DIMENSIONAL STRUCTURE OF THE RAS-SOS COMPLEX

Introduction

Through the use of the threedimensional structure of the Ras-Sos complex, described in Example 1, potential drugs can be rationally designed to inhibit the conversion of the inactive form of Ras (Ras-GDP) to the active form (Ras-GTP). This aspect of the present invention takes advantage of the requisite role of the nucleotide exchange factor of Sos to catalyze this conversion. Since the active form of Ras is required for cellular proliferation, such drugs can be used to inhibit the proliferation of cancer cells, for example. Therefore compounds that e.g., (i) stabilize the Ras-Sos complex, and thereby prevent GTP from binding Ras, or (ii) inhibit the nucleotide exchange factor of Sos, can used in the development of drugs that inhibit the activation of Ras. Once such compounds are synthesized, they can be experimentally tested and then further refined by the methodology exemplified above.

Analogs of the Nucleoside Component of GTP as stabilizers of Ras-Sos: From Example 1, above, it is known that the purine binding loop of Ras undergoes a major conformational change upon binding to Sos. In so doing, electronic repulsion of the guanine carbonyl (0–6) by a Ras-backbone carbonyl (lys-117) and potentially a Ras-side-chain alanine methyl (ala-146) could take place [1, FIG. 7A.] At the same time, the 7-N of the guanine appears to be able to make a hydrogen bond with a Ras-side-chain amide (asn-116). Importantly, a cysteine (cys-118) swings out in this new structure which is positioned not far from the 3-N of guanine. While the cysteine thiol may have the opportunity to form an H-bond with the 3-N, it affords other more interesting opportunities as described below.

Compound 2 [FIG. 7B] incorporates a guanine analog which has three important differences in the 6-membered ring. (i) the 3-N is replaced with a carbonyl; (ii) the 0–6 is replaced by an sp3 center with 2 hydrogen atoms; and (iii) the 1 and 2 positions of the ring now are replaced by an all carbon ring and include a difluoro substitution at the 2-position. These changes should allow better accommodation of the Ras protein vis-à-vis the 6-position because of the lack of steric or electronic repulsion. The incorporation of the α-difluoroketone functionality seems poised to undergo nucleophilic attack by the Ras-cysteine thiol to afford the ketalic structure in 3 [FIG. 7B]. Such structures are stable because of the well-known tendency of fluoroketones to exist as hydrated structures. This would be a covalent but somewhat reversible interaction.

Compound 4 [FIG. 7B] is a close relative of Compound 3. It lacks the guanine N-1 atom and may be considered a flexible guanosine analog. Since the absolute requirements are not known, this increase in flexibility nay allow a tighter fit into Ras. In addition, the additional fluorine in the trifluoroketone functionality should drive the equilibrium between ketone (4) and thioketal (5) [FIG. 7B] more toward the thioketal (5) as compared to the case with Compound 2.

Compound 6 [FIG. 7B] is a further modification of Compound 4. In 6, the trifluoromethyl-group is replaced by a hydrogen. This aldehyde 6 should still be able to undergo thio-ketal formation giving 7 [FIG. 7] because of the known reactivity of such functional groups. However, the lack of a trifluoromethyl group may also be beneficial in the case of unforeseen steric or electronic repulsion of this grouping.

Compound 8 [FIG. 7C] is related to Compounds 4 and 6. Replacement of the hydrogen atom (or trifluoromethyl) with a mono-haloniethyl may afford the possibility of irreversible alkylation of the Ras cysteine thiol to produce Compound 9 [FIG. 7C]. Unlike thioketal formation, $S_N2$ displacement of the halide (chloride, bromide, iodide; fluoride is a relatively poor leaving group for such reactions) should be kinetically as well as thermodynamically stable. Such irreversible inactivation of Ras may be desirable because new protein would have to be synthesized to recover biological function.

Compound 10 [FIG. 7C] has similarities to Compound 2 but by incorporation of the exomethylene instead of the difluoro-substitution, reactivity would be expected to be quite different. It is reasonable to predict that Compound 10 could be a potent Michael acceptor which would result in the formation of 11 [FIG. 7C]. Again, 11 would be expected to be very stable like 9 and would thus lead to permanent Ras inactivation.

In place of hydrogen atoms at the 6-position of Compounds 2 and 10, Compound 12 [FIG. 7C] contains an amino group. Such an amine may be able to form a stabilizing hydrogen bond with the Ras backbone carbonyl and therefore result in greater binding energy. Although 12 is shown with the exomethylene function as 10 and could potentially form 13 [FIG. 7C], there is no reason that the amino group could not be used along with the other congeners described above.

Likewise, Compounds 14 and 16 [FIG. 7C] place different steric requirements at the guanine 6-position that might serendipitously be well-tolerated. Perhaps more importantly, they would be expected to be even more chemically reactive as Michael acceptors than 10 and 12 because of the formation of an aromatic ring in the reaction as exemplified by the production of 15 and 17 [FIG. 7C]. Such aromatization might help accelerate the reactions of 14 and 16 leading to Ras-inactivation.

Instead of the assumption that the binding pocket of Ras would be altered when a purine were to bind, it is conceivable that the guanine binding would induce the Sos-free conformation of Ras. Thus, guanine may end up being the preferred substructure for nucleoside inhibitor design.

Modifications of the Ribose Triphosphate Structure: The structure of 1 [FIG. 7A] illustrates that the triphosphate of GTP might be very poorly accommodated in a Ras-Sos complex. Thus, the focus of attention could be on replacements of this portion of the molecule. Note that all of the purine derivatives described above could be interfaced with the ribose triphosphate substitutions described below.

To start with, just the standard ribose ring could be employed. The deletion of the triphosphate completely resulting in 18 [FIG. 7D] could allow favorable binding. Moreover, the amine function in 19 [FIG. 7D] could potentially allow a hydrogen bond with the Ras-carboxylate near the α-phosphate position. Repositioning of the amino-function, extension of the tether and the placement of suitable hydrogen bond acceptors (Y) in Compounds 20–23 [FIG. 7D] are logical derivatives to target. The use of hydrophobic substitutions in the terminus of the molecules (Z of 22 and 23) may be important to interact with the hydrophobic side chains that are found in Ras in the Ras-Sos complex. It should also be mentioned that for inhibitor design purposes the ribose ring could be truncated since there are no obvious contacts with this group.

β-Turn Mimics that Bind to Sos: With the aid of the three-dimensional structure of the Ras-Sos complex, Example 1, above, binding partners for Sos which will inhibit the binding of Sos and Ras can be rationally designed. For example, upon binding to Sos, a conformational change in Ras appears to take place which results in the formation of a β-turn from amino acids 64 to 67 (24) [FIG. 7E]. Amino acid 64 contains a tyrosine which appears to make a key hydrophobic interaction with Sos. Also of potential importance is a hydrophobic methionine which emerges from the C-terminal side of the β-turn. There are a large number of β-turn small molecule mimics which have been designed and synthesized and shown to be effective. These compounds hold the amine and carboxy-terminus in relatively fixed positions that mimic those of the real turn. At this time, it is not possible to predict with confidence whether the one or more of Compounds 25–29 [FIG. 7E] would complement the Sos binding surface so all types would need to be screened. The key additions to these known compounds would be to place an aromatic at the N-terminal side of the turn and probably a hydrophobic substituent (aryl or alyl) at the C-terminal side.

It is important to emphasize that the compounds presented throughout the present Disclosure, are simply used to illustrate potential starting points for identifying drugs that can be used for treating diseases involving Ras. Any person having skill in the art of medicinal chemistry would readily realize that although the compounds exemplified above, are an excellent starting point for the drug screens, it is highly unlikely that any of the listed compounds will themselves be successful drug candidates.

Relevant References Include:

Silverman, R. B. The Organic Chemistry of Drug Design and Drug Action. *Academic Press,* New York, 1992.

Nicholson et al. *Nature* 376:37 (1995).

Rotunda et al. *Nature Structural Biology* 3:619–625 (1996).

Gante, *Angew. Chem. Int. Ed. Engl.* 33:1699–1720 (1994).

Feigel, *J. Am. Chem. Soc.* 108:181 (1986).

Wagner, and Feigel, *Tetrahedron* 49:10831 (1993).

Brandmeier et al. *Helv. Chim. Acta.* 77: 70 (1994).

Sato, and Nagai *J. Chem. Soc. Perkin Trans.* 1:1231 (19)86).

Nagai et al., *Tetrahedron* 49:3577 (1993).

Kemp, and Stites, *Tetrahedron Lett.* 29:5057 (1988).

Genin, and Johnson, *J. Am. Chem. Soc.* 114:8778 (1992).

Ripka et al., *Tetrahedron* 49:3593 (1993).

The present invention is not to be limited in scope by tie specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

TABLE 3

PDB Coordinates for the Ras-Sos Structure:
DATA SET FOR REFINED COORDINATES

REMARK coordinates from minimization refinement
REMARK refinement resolution: 30.0–2.8 A
REMARK starting     r = 0.2223 free_r = 0.2807
REMARK final        r = 0.2220 free_r = 0.2811
REMARK rmsd bonds = 0.006712     rmsd angles = 1.25899
REMARK wa = 2.83987
REMARK target = mlf cycles = 1 steps = 300
REMARK sg = I422 a = 142.73 b = 142.73 c = 207.89 alpha = 90 beta = 90 gamma = 90
REMARK parameter file 1 : CNS_TOPPAR:protein.param
REMARK parameter file 2 : CNS_TOPPAR:water.param
REMARK molecular structure file: rsa4_gen.psf
REMARK input coordinates: rsa4_gen.pdb
REMARK reflection file = nat3_Rfree.hkl_xplor
REMARK ncs = none
REMARK B-correction resolution: 6.0–2.8
REMARK initial B-factor correction applied to fobs:
REMARK    B11 =    −6.191   B22 =   −6.191   B33 =   12.382
REMARK    B12 =     0.000   B13 =    0.000   B23 =    0.000
REMARK B-factor correction applied to coordinate array B: 1.267
                                    REMARK bulk solvent: density level=0.272909 e/A^3,
                                    B-factor= 10.7814 A^2
REMARK reflections with |Fobs|/sigma_F < 0.0 rejected
REMARK reflections with |Fobs| > 10000 * rms(Fobs) rejected
REMARK theoretical total number of refl. in resol. range:       26748     (100.0%)
REMARK number of unobserved reflections (no entry or |F| = 0):    246       (0.9%)
REMARK number of reflections rejected:                              0       (0.0%)
REMARK total number of reflections used:                        26502      (99.1%)
REMARK number of reflections in working set:                    25175      (94.1%)
REMARK number of reflections in test set:                        1327       (5.0%)
REMARK FILENAME="rsa4_min.pdb"
REMARK DATE: 03-Apr-98     15:43:51     created by user: boriacp

| ATOM | 1  | CB  | ARG | 568 | 65.030 | 36.388 | 12.267 | 1.00 | 86.85  | sos |
|------|----|-----|-----|-----|--------|--------|--------|------|--------|-----|
| ATOM | 2  | CG  | ARG | 568 | 64.365 | 35.070 | 12.634 | 1.00 | 85.46  | sos |
| ATOM | 3  | CD  | ARG | 568 | 63.268 | 35.255 | 13.671 | 1.00 | 81.64  | sos |
| ATOM | 4  | NE  | ARG | 568 | 62.720 | 33.976 | 14.118 | 0.00 | 83.05  | sos |
| ATOM | 5  | CZ  | ARG | 568 | 63.295 | 33.188 | 15.022 | 0.00 | 82.83  | sos |
| ATOM | 6  | NH1 | ARG | 568 | 64.442 | 33.540 | 15.587 | 0.00 | 83.01  | sos |
| ATOM | 7  | NH2 | ARG | 568 | 62.724 | 32.039 | 15.359 | 0.00 | 83.01  | sos |
| ATOM | 8  | C   | ARG | 568 | 66.656 | 37.661 | 10.841 | 1.00 | 92.14  | sos |
| ATOM | 9  | O   | ARG | 568 | 67.860 | 37.822 | 10.643 | 1.00 | 91.54  | sos |
| ATOM | 10 | N   | ARG | 568 | 67.174 | 35.327 | 11.569 | 1.00 | 88.89  | sos |
| ATOM | 11 | CA  | ARG | 568 | 66.093 | 36.276 | 11.164 | 1.00 | 90.80  | sos |
| ATOM | 12 | N   | LEU | 569 | 65.773 | 38.655 | 10.781 | 1.00 | 94.54  | sos |
| ATOM | 13 | CA  | LEU | 569 | 66.162 | 40.032 | 10.484 | 1.00 | 96.99  | sos |
| ATOM | 14 | CB  | LEU | 569 | 66.058 | 40.306 | 8.973  | 1.00 | 96.57  | sos |
| ATOM | 15 | CG  | LEU | 569 | 65.071 | 39.506 | 8.106  | 0.00 | 96.72  | sos |
| ATOM | 16 | CD1 | LEU | 569 | 63.639 | 39.621 | 8.612  | 0.00 | 96.66  | sos |
| ATOM | 17 | CD2 | LEU | 569 | 65.162 | 39.988 | 6.668  | 0.00 | 96.66  | sos |
| ATOM | 18 | C   | LEU | 569 | 65.318 | 41.034 | 11.278 | 1.00 | 98.72  | sos |
| ATOM | 19 | O   | LEU | 569 | 64.288 | 41.509 | 10.798 | 1.00 | 99.61  | sos |
| ATOM | 20 | N   | PRO | 570 | 65.742 | 41.360 | 12.517 | 1.00 | 100.00 | sos |
| ATOM | 21 | CD  | PRO | 570 | 66.924 | 40.814 | 13.210 | 1.00 | 101.82 | sos |
| ATOM | 22 | CA  | PRO | 570 | 65.026 | 42.306 | 13.383 | 1.00 | 98.66  | sos |
| ATOM | 23 | CB  | PRO | 570 | 65.670 | 42.066 | 14.747 | 1.00 | 99.43  | sos |
| ATOM | 24 | CG  | PRO | 570 | 67.082 | 41.759 | 14.387 | 1.00 | 101.26 | sos |

TABLE 3-continued

PDB Coordinates for the Ras-Sos Structure:
DATA SET FOR REFINED COORDINATES

| ATOM | 25 | C | PRO | 570 | 65.172 | 43.756 | 12.932 | 1.00 | 96.84 | sos |
|---|---|---|---|---|---|---|---|---|---|---|
| ATOM | 26 | O | PRO | 570 | 65.841 | 44.041 | 11.939 | 1.00 | 94.96 | sos |
| ATOM | 27 | N | SER | 571 | 64.556 | 44.667 | 13.677 | 1.00 | 96.14 | sos |
| ATOM | 28 | CA | SER | 571 | 64.596 | 46.087 | 13.349 | 1.00 | 96.60 | sos |
| ATOM | 29 | CB | SER | 571 | 63.583 | 46.853 | 14.195 | 1.00 | 98.88 | sos |
| ATOM | 30 | CG | SER | 571 | 62.264 | 46.422 | 13.900 | 1.00 | 101.55 | sos |
| ATOM | 31 | C | SER | 571 | 65.975 | 46.748 | 13.414 | 1.00 | 96.15 | sos |
| ATOM | 32 | O | SER | 571 | 66.964 | 46.121 | 13.804 | 1.00 | 94.52 | sos |
| ATOM | 33 | N | ALA | 572 | 66.011 | 48.031 | 13.053 | 1.00 | 96.56 | sos |
| ATOM | 34 | CA | ALA | 572 | 67.241 | 48.825 | 12.992 | 1.00 | 97.38 | sos |
| ATOM | 35 | CB | ALA | 572 | 66.997 | 50.088 | 12.162 | 1.00 | 95.98 | sos |
| ATOM | 36 | C | ALA | 572 | 67.978 | 49.193 | 14.286 | 1.00 | 97.38 | sos |
| ATOM | 37 | O | ALA | 572 | 68.924 | 49.987 | 14.232 | 1.00 | 98.97 | sos |
| ATOM | 38 | N | ASP | 573 | 67.577 | 48.630 | 15.428 | 1.00 | 94.68 | sos |
| ATOM | 39 | CA | ASP | 573 | 68.233 | 48.927 | 16.708 | 1.00 | 92.01 | sos |
| ATOM | 40 | CB | ASP | 573 | 69.754 | 48.656 | 16.596 | 1.00 | 91.55 | sos |
| ATOM | 41 | CG | ASP | 573 | 70.607 | 49.655 | 17.361 | 0.00 | 91.98 | sos |
| ATOM | 42 | OD1 | ASP | 573 | 71.130 | 50.591 | 16.727 | 0.00 | 92.02 | sos |
| ATOM | 43 | OD2 | ASP | 573 | 70.776 | 49.498 | 18.586 | 0.00 | 92.02 | sos |
| ATOM | 44 | C | ASP | 573 | 67.907 | 50.334 | 17.231 | 1.00 | 91.71 | sos |
| ATOM | 45 | O | ASP | 573 | 67.975 | 50.584 | 18.431 | 1.00 | 90.14 | sos |
| ATOM | 46 | N | VAL | 574 | 67.570 | 51.241 | 16.314 | 1.00 | 93.56 | sos |
| ATOM | 47 | CA | VAL | 574 | 67.189 | 52.618 | 16.638 | 1.00 | 93.77 | sos |
| ATOM | 48 | CB | VAL | 574 | 67.535 | 53.589 | 15.470 | 1.00 | 96.52 | sos |
| ATOM | 49 | CG1 | VAL | 574 | 67.317 | 55.045 | 15.889 | 1.00 | 97.68 | sos |
| ATOM | 50 | CG2 | VAL | 574 | 68.980 | 53.370 | 15.013 | 1.00 | 96.04 | sos |
| ATOM | 51 | C | VAL | 574 | 65.671 | 52.628 | 16.899 | 1.00 | 92.97 | sos |
| ATOM | 52 | O | VAL | 574 | 65.047 | 53.687 | 16.978 | 1.00 | 94.05 | sos |
| ATOM | 53 | N | TYR | 575 | 65.095 | 51.429 | 17.026 | 1.00 | 91.05 | sos |
| ATOM | 54 | CA | TYR | 575 | 63.668 | 51.233 | 17.297 | 1.00 | 86.99 | sos |
| ATOM | 55 | CB | TYR | 575 | 62.864 | 51.093 | 15.989 | 1.00 | 88.09 | sos |
| ATOM | 56 | CG | TYR | 575 | 62.862 | 52.290 | 15.063 | 0.00 | 88.43 | sos |
| ATOM | 57 | CD1 | TYR | 575 | 63.770 | 52.375 | 14.008 | 0.00 | 88.72 | sos |
| ATOM | 58 | CE1 | TYR | 575 | 63.755 | 53.453 | 13.127 | 0.00 | 88.91 | sos |
| ATOM | 59 | CD2 | TYR | 575 | 61.933 | 53.319 | 15.217 | 0.00 | 88.72 | sos |
| ATOM | 60 | CE2 | TYR | 575 | 61.908 | 54.404 | 14.340 | 0.00 | 88.91 | sos |
| ATOM | 61 | CZ | TYR | 575 | 62.823 | 54.463 | 13.298 | 0.00 | 88.97 | sos |
| ATOM | 62 | OH | TYR | 575 | 62.812 | 55.528 | 12.428 | 0.00 | 89.07 | sos |
| ATOM | 63 | C | TYR | 575 | 63.486 | 49.929 | 18.088 | 1.00 | 84.03 | sos |
| ATOM | 64 | O | TYR | 575 | 62.369 | 49.406 | 18.159 | 1.00 | 83.83 | sos |
| ATOM | 65 | N | ARG | 576 | 64.548 | 49.432 | 18.729 | 1.00 | 79.53 | sos |
| ATOM | 66 | CA | ARG | 576 | 64.444 | 48.154 | 19.432 | 1.00 | 76.12 | sos |
| ATOM | 67 | CB | ARG | 576 | 64.435 | 47.058 | 18.366 | 1.00 | 71.29 | sos |
| ATOM | 68 | CG | ARG | 576 | 63.082 | 46.552 | 17.964 | 1.00 | 62.74 | sos |
| ATOM | 69 | CD | ARG | 576 | 62.651 | 45.477 | 18.898 | 1.00 | 57.01 | sos |
| ATOM | 70 | NE | ARG | 576 | 61.576 | 45.928 | 19.762 | 1.00 | 54.20 | sos |
| ATOM | 71 | CZ | ARG | 576 | 60.933 | 45.135 | 20.611 | 1.00 | 57.03 | sos |
| ATOM | 72 | NH1 | ARG | 576 | 61.263 | 43.851 | 20.724 | 1.00 | 52.90 | sos |
| ATOM | 73 | NH2 | ARG | 576 | 59.911 | 45.613 | 21.302 | 1.00 | 59.79 | sos |
| ATOM | 74 | C | ARG | 576 | 65.458 | 47.731 | 20.517 | 1.00 | 77.98 | sos |
| ATOM | 75 | O | ARG | 576 | 66.225 | 48.530 | 21.063 | 1.00 | 75.52 | sos |
| ATOM | 76 | N | PHE | 577 | 65.342 | 46.443 | 20.860 | 1.00 | 79.44 | sos |
| ATOM | 77 | CA | PHE | 577 | 66.186 | 45.702 | 21.804 | 1.00 | 76.34 | sos |
| ATOM | 78 | CB | PHE | 577 | 65.344 | 44.685 | 22.600 | 1.00 | 74.10 | sos |
| ATOM | 79 | CG | PHE | 577 | 64.490 | 45.287 | 23.683 | 1.00 | 70.97 | sos |
| ATOM | 80 | CD1 | PHE | 577 | 63.486 | 46.199 | 23.382 | 1.00 | 68.95 | sos |
| ATOM | 81 | CD2 | PHE | 577 | 64.690 | 44.929 | 25.013 | 1.00 | 67.32 | sos |
| ATOM | 82 | CE1 | PHE | 577 | 62.696 | 46.747 | 24.390 | 1.00 | 67.33 | sos |
| ATOM | 83 | CE2 | PHE | 577 | 63.906 | 45.471 | 26.021 | 1.00 | 65.54 | sos |
| ATOM | 84 | CZ | PHE | 577 | 62.908 | 46.381 | 25.710 | 1.00 | 65.61 | sos |
| ATOM | 85 | C | PHE | 577 | 67.085 | 44.886 | 20.868 | 1.00 | 77.81 | sos |
| ATOM | 86 | O | PHE | 577 | 67.724 | 43.911 | 21.277 | 1.00 | 79.06 | sos |
| ATOM | 87 | N | ALA | 57B | 67.057 | 45.265 | 19.592 | 1.00 | 77.34 | sos |
| ATOM | 88 | CA | ALA | 578 | 67.801 | 44.615 | 18.525 | 1.00 | 76.91 | sos |
| ATOM | 89 | CB | ALA | 578 | 67.456 | 45.261 | 17.193 | 1.00 | 78.12 | sos |
| ATOM | 90 | C | ALA | 578 | 69.312 | 44.543 | 18.694 | 1.00 | 76.18 | sos |
| ATOM | 91 | O | ALA | 578 | 69.966 | 43.792 | 17.970 | 1.00 | 78.31 | sos |
| ATOM | 92 | N | GLU | 579 | 69.871 | 45.323 | 19.620 | 1.00 | 72.57 | sos |
| ATOM | 93 | CA | GLU | 579 | 71.315 | 45.300 | 19.852 | 1.00 | 71.66 | sos |
| ATOM | 94 | CB | GLU | 579 | 71.690 | 46.160 | 21.061 | 1.00 | 73.46 | sos |
| ATOM | 95 | CG | GLU | 579 | 71.215 | 47.598 | 20.977 | 0.00 | 73.77 | sos |
| ATOM | 96 | CD | GLU | 579 | 71.592 | 48.412 | 22.198 | 0.00 | 74.29 | sos |
| ATOM | 97 | OE1 | GLU | 579 | 72.686 | 49.015 | 22.198 | 0.00 | 74.50 | sos |
| ATOM | 98 | OE2 | GLU | 579 | 70.792 | 48.454 | 23.156 | 0.00 | 74.50 | sos |
| ATOM | 99 | C | GLU | 579 | 71.728 | 43.853 | 20.097 | 1.00 | 70.05 | sos |
| ATOM | 100 | O | GLU | 579 | 71.145 | 43.168 | 20.932 | 1.00 | 69.21 | sos |

TABLE 3-continued

PDB Coordinates for the Ras-Sos Structure:
DATA SET FOR REFINED COORDINATES

| ATOM | 101 | N | PRO | 580 | 72.674 | 43.342 | 19.300 | 1.00 | 70.16 | sos |
|---|---|---|---|---|---|---|---|---|---|---|
| ATOM | 102 | CD | PRO | 580 | 73.300 | 43.983 | 18.129 | 1.00 | 71.48 | sos |
| ATOM | 103 | CA | PRO | 580 | 73.136 | 41.960 | 19.453 | 1.00 | 71.03 | sos |
| ATOM | 104 | CB | PRO | 580 | 73.894 | 41.714 | 18.148 | 1.00 | 72.63 | sos |
| ATOM | 105 | CG | PRO | 580 | 74.468 | 43.067 | 17.842 | 1.00 | 72.32 | sos |
| ATOM | 106 | C | PRO | 580 | 74.022 | 41.736 | 20.675 | 1.00 | 69.79 | sos |
| ATOM | 107 | O | PRO | 580 | 74.730 | 42.638 | 21.120 | 1.00 | 69.35 | sos |
| ATOM | 108 | N | ASP | 581 | 73.967 | 40.520 | 21.208 | 1.00 | 68.02 | sos |
| ATOM | 109 | CA | ASP | 581 | 74.755 | 40.137 | 22.368 | 1.00 | 68.10 | sos |
| ATOM | 110 | CB | ASP | 581 | 74.579 | 38.643 | 22.665 | 1.00 | 66.00 | sos |
| ATOM | 111 | CG | ASP | 581 | 73.167 | 38.281 | 23.095 | 1.00 | 67.92 | sos |
| ATOM | 112 | OD1 | ASP | 581 | 72.350 | 39.188 | 23.368 | 1.00 | 64.83 | sos |
| ATOM | 113 | OD2 | ASP | 581 | 72.882 | 37.067 | 23.171 | 1.00 | 67.36 | sos |
| ATOM | 114 | C | ASP | 581 | 76.232 | 40.400 | 22.130 | 1.00 | 70.54 | sos |
| ATOM | 115 | O | ASP | 581 | 76.747 | 40.131 | 21.046 | 1.00 | 73.64 | sos |
| ATOM | 116 | N | SER | 582 | 76.902 | 40.928 | 23.151 | 1.00 | 72.53 | sos |
| ATOM | 117 | CA | SER | 582 | 78.337 | 41.211 | 23.097 | 1.00 | 72.27 | sos |
| ATOM | 118 | CB | SER | 582 | 78.613 | 42.607 | 22.517 | 1.00 | 70.00 | sos |
| ATOM | 119 | OG | SER | 582 | 78.193 | 43.638 | 23.391 | 1.00 | 64.24 | sos |
| ATOM | 120 | C | SER | 582 | 78.866 | 41.126 | 24.517 | 1.00 | 73.94 | sos |
| ATOM | 121 | O | SER | 582 | 78.137 | 40.746 | 25.432 | 1.00 | 75.37 | sos |
| ATOM | 122 | N | GLU | 583 | 80.137 | 41.458 | 24.706 | 1.00 | 77.16 | sos |
| ATOM | 123 | CA | GLU | 583 | 80.717 | 41.422 | 26.040 | 1.00 | 77.96 | sos |
| ATOM | 124 | CB | GLU | 583 | 82.232 | 41.221 | 25.971 | 1.00 | 82.27 | sos |
| ATOM | 125 | CG | GLU | 583 | 82.615 | 39.865 | 25.379 | 1.00 | 86.85 | sos |
| ATOM | 126 | CD | GLU | 583 | 84.111 | 39.613 | 25.371 | 1.00 | 91.33 | sos |
| ATOM | 127 | OE1 | GLU | 583 | 84.664 | 39.284 | 26.443 | 1.00 | 90.57 | sos |
| ATOM | 128 | OE2 | GLU | 583 | 84.728 | 39.728 | 24.289 | 1.00 | 93.09 | sos |
| ATOM | 129 | C | GLU | 583 | 80.336 | 42.686 | 26.801 | 1.00 | 76.39 | sos |
| ATOM | 130 | O | GLU | 583 | 80.553 | 42.784 | 28.002 | 1.00 | 77.91 | sos |
| ATOM | 131 | N | GLU | 584 | 79.729 | 43.633 | 26.089 | 1.00 | 75.31 | sos |
| ATOM | 132 | CA | GLU | 584 | 79.265 | 44.889 | 26.672 | 1.00 | 74.47 | sos |
| ATOM | 133 | CB | GLU | 584 | 79.508 | 46.049 | 25.710 | 1.00 | 75.89 | sos |
| ATOM | 134 | CG | GLU | 584 | 80.940 | 46.255 | 25.258 | 1.00 | 80.37 | sos |
| ATOM | 135 | CD | GLU | 584 | 81.109 | 47.532 | 24.439 | 1.00 | 82.28 | sos |
| ATOM | 136 | OE1 | GLU | 584 | 80.086 | 48.153 | 24.067 | 1.00 | 79.89 | sos |
| ATOM | 137 | OE2 | GLU | 584 | 82.269 | 47.920 | 24.176 | 1.00 | 84.81 | sos |
| ATOM | 138 | C | GLU | 584 | 77.756 | 44.817 | 26.930 | 1.00 | 74.13 | sos |
| ATOM | 139 | O | GLU | 584 | 77.140 | 45.822 | 27.289 | 1.00 | 74.42 | sos |
| ATOM | 140 | N | ASN | 585 | 77.166 | 43.640 | 26.710 | 1.00 | 73.41 | sos |
| ATOM | 141 | CA | ASN | 585 | 75.725 | 43.419 | 26.880 | 1.00 | 68.85 | sos |
| ATOM | 142 | CB | ASN | 585 | 75.108 | 42.913 | 25.575 | 1.00 | 70.58 | sos |
| ATOM | 143 | CG | ASN | 585 | 74.971 | 43.986 | 24.549 | 1.00 | 75.07 | sos |
| ATOM | 144 | OD1 | ASN | 585 | 74.410 | 45.050 | 24.819 | 1.00 | 81.03 | sos |
| ATOM | 145 | ND2 | ASN | 585 | 75.473 | 43.722 | 23.351 | 1.00 | 77.96 | sos |
| ATOM | 146 | C | ASN | 585 | 75.354 | 42.420 | 27.955 | 1.00 | 63.87 | sos |
| ATOM | 147 | O | ASN | 585 | 74.586 | 42.728 | 28.857 | 1.00 | 61.19 | sos |
| ATOM | 148 | N | ILE | 586 | 75.817 | 41.189 | 27.773 | 1.00 | 59.95 | sos |
| ATOM | 149 | CA | ILE | 586 | 75.529 | 40.101 | 28.689 | 1.00 | 58.70 | sos |
| ATOM | 150 | CB | ILE | 586 | 74.411 | 39.162 | 28.127 | 1.00 | 58.57 | sos |
| ATOM | 151 | CG2 | ILE | 586 | 74.187 | 37.971 | 29.042 | 1.00 | 59.34 | sos |
| ATOM | 152 | CG1 | ILE | 586 | 73.086 | 39.901 | 28.003 | 1.00 | 57.61 | sos |
| ATOM | 153 | CD1 | ILE | 586 | 71.901 | 38.983 | 27.761 | 1.00 | 59.39 | sos |
| ATOM | 154 | C | ILE | 586 | 76.768 | 39.251 | 28.900 | 1.00 | 58.71 | sos |
| ATOM | 155 | O | ILE | 586 | 77.625 | 39.149 | 28.024 | 1.00 | 58.57 | sos |
| ATOM | 156 | N | ILE | 587 | 76.855 | 38.661 | 30.084 | 1.00 | 58.34 | sos |
| ATOM | 157 | CA | ILE | 587 | 77.940 | 37.767 | 30.451 | 1.00 | 59.71 | sos |
| ATOM | 158 | CB | ILE | 587 | 78.862 | 38.387 | 31.513 | 1.00 | 61.79 | sos |
| ATOM | 159 | CG2 | ILE | 587 | 80.029 | 37.452 | 31.811 | 1.00 | 63.62 | sos |
| ATOM | 160 | CG1 | ILE | 587 | 79.398 | 39.728 | 31.032 | 1.00 | 60.78 | sos |
| ATOM | 161 | CD1 | ILE | 587 | 80.229 | 40.415 | 32.071 | 1.00 | 67.41 | sos |
| ATOM | 162 | C | ILE | 587 | 77.219 | 36.581 | 31.073 | 1.00 | 59.71 | sos |
| ATOM | 163 | O | ILE | 587 | 76.279 | 36.762 | 31.847 | 1.00 | 60.53 | sos |
| ATOM | 164 | N | PHE | 588 | 77.625 | 35.372 | 30.716 | 1.00 | 60.66 | sos |
| ATOM | 165 | CA | PHE | 588 | 76.975 | 34.192 | 31.264 | 1.00 | 62.04 | sos |
| ATOM | 166 | CB | PHE | 588 | 76.554 | 33.234 | 30.143 | 1.00 | 61.74 | sos |
| ATOM | 167 | CG | PHE | 588 | 75.557 | 33.826 | 29.184 | 1.00 | 62.23 | sos |
| ATOM | 168 | CD1 | PHE | 588 | 75.981 | 34.452 | 28.019 | 1.00 | 61.10 | sos |
| ATOM | 169 | CD2 | PHE | 588 | 74.198 | 33.794 | 29.466 | 1.00 | 65.02 | sos |
| ATOM | 170 | CE1 | PHE | 588 | 75.065 | 35.042 | 27.151 | 1.00 | 62.45 | sos |
| ATOM | 171 | CE2 | PHE | 588 | 73.272 | 34.383 | 28.600 | 1.00 | 64.84 | sos |
| ATOM | 172 | CZ | PHE | 588 | 73.708 | 35.007 | 27.443 | 1.00 | 62.30 | sos |
| ATOM | 173 | C | PHE | 588 | 77.857 | 33.483 | 32.271 | 1.00 | 64.51 | sos |
| ATOM | 174 | O | PHE | 588 | 79.071 | 33.685 | 32.310 | 1.00 | 62.57 | sos |
| ATOM | 175 | N | GLU | 589 | 77.226 | 32.675 | 33.110 | 1.00 | 68.76 | sos |
| ATOM | 176 | CA | GLU | 589 | 77.935 | 31.925 | 34.124 | 1.00 | 73.95 | sos |

TABLE 3-continued

PDB Coordinates for the Ras-Sos Structure:
DATA SET FOR REFINED COORDINATES

| | | | | | | | | | |
|---|---|---|---|---|---|---|---|---|---|
| ATOM | 177 | CB | GLU | 589 | 76.946 | 31.399 | 35.164 | 1.00 | 75.56 | sos |
| ATOM | 178 | CG | GLU | 589 | 77.507 | 31.326 | 36.572 | 1.00 | 80.54 | sos |
| ATOM | 179 | CD | GLU | 589 | 77.942 | 32.685 | 37.096 | 1.00 | 83.75 | sos |
| ATOM | 180 | OE1 | GLU | 589 | 77.066 | 33.548 | 37.336 | 1.00 | 84.48 | sos |
| ATOM | 181 | OE2 | GLU | 589 | 79.162 | 32.888 | 37.269 | 1.00 | 86.36 | sos |
| ATOM | 182 | C | GLU | 589 | 78.667 | 30.772 | 33.443 | 1.00 | 77.05 | sos |
| ATOM | 183 | O | GLU | 589 | 78.106 | 30.097 | 32.578 | 1.00 | 76.63 | sos |
| ATOM | 184 | N | GLU | 590 | 79.933 | 30.583 | 33.811 | 1.00 | 82.51 | sos |
| ATOM | 185 | CA | GLU | 590 | 80.769 | 29.519 | 33.250 | 1.00 | 85.84 | sos |
| ATOM | 186 | CB | GLU | 590 | 82.249 | 29.937 | 33.273 | 1.00 | 89.26 | sos |
| ATOM | 187 | CG | GLU | 590 | 82.551 | 31.333 | 32.695 | 1.00 | 93.22 | sos |
| ATOM | 188 | CD | GLU | 590 | 82.360 | 31.440 | 31.183 | 1.00 | 95.89 | sos |
| ATOM | 189 | OE1 | GLU | 590 | 82.034 | 30.423 | 30.529 | 1.00 | 98.74 | sos |
| ATOM | 190 | OE2 | GLU | 590 | 82.549 | 32.555 | 30.645 | 1.00 | 94.69 | sos |
| ATOM | 191 | C | GLU | 590 | 80.597 | 28.206 | 34.021 | 1.00 | 83.56 | sos |
| ATOM | 192 | O | GLU | 590 | 79.973 | 27.279 | 33.461 | 1.00 | 80.20 | sos |
| ATOM | 193 | OT | GLU | 590 | 9999.000 | 9999.000 | 9999.000 | 1.00 | 0.00 | sos |
| ATOM | 194 | C | GLY | 597 | 70.237 | 25.098 | 28.552 | 1.00 | 77.87 | sos |
| ATOM | 195 | O | GLY | 597 | 71.012 | 25.599 | 27.734 | 1.00 | 77.86 | sos |
| ATOM | 196 | N | GLY | 597 | 69.745 | 23.230 | 30.134 | 1.00 | 77.12 | sos |
| ATOM | 197 | CA | GLY | 597 | 70.199 | 23.597 | 28.760 | 1.00 | 77.61 | sos |
| ATOM | 198 | N | ILE | 598 | 69.396 | 25.810 | 29.302 | 1.00 | 77.50 | sos |
| ATOM | 199 | CA | ILE | 598 | 69.295 | 27.270 | 29.237 | 1.00 | 75.71 | sos |
| ATOM | 200 | CB | ILE | 598 | 68.060 | 27.772 | 30.029 | 1.00 | 74.77 | sos |
| ATOM | 201 | CG2 | ILE | 598 | 67.792 | 29.234 | 29.721 | 1.00 | 70.59 | sos |
| ATOM | 202 | CG1 | ILE | 598 | 66.825 | 26.935 | 29.684 | 1.00 | 74.32 | sos |
| ATOM | 203 | CD1 | ILE | 598 | 65.671 | 27.122 | 30.654 | 1.00 | 70.94 | sos |
| ATOM | 204 | C | ILE | 598 | 70.539 | 27.928 | 29.845 | 1.00 | 75.15 | sos |
| ATOM | 205 | O | ILE | 598 | 71.023 | 27.500 | 30.895 | 1.00 | 74.88 | sos |
| ATOM | 206 | N | PRO | 599 | 71.085 | 28.963 | 29.176 | 1.00 | 74.88 | sos |
| ATOM | 207 | CD | PRO | 599 | 70.711 | 29.418 | 27.828 | 1.00 | 75.59 | sos |
| ATOM | 208 | CA | PRO | 599 | 72.272 | 29.688 | 29.646 | 1.00 | 74.39 | sos |
| ATOM | 209 | CB | PRO | 599 | 72.595 | 30.618 | 28.470 | 1.00 | 74.55 | sos |
| ATOM | 210 | CG | PRO | 599 | 72.027 | 29.916 | 27.294 | 1.00 | 76.23 | sos |
| ATOM | 211 | C | PRO | 599 | 71.955 | 30.517 | 30.889 | 1.00 | 73.52 | sos |
| ATOM | 212 | O | PRO | 599 | 70.953 | 31.241 | 30.918 | 1.00 | 74.59 | sos |
| ATOM | 213 | N | ILE | 600 | 72.796 | 30.407 | 31.914 | 1.00 | 70.47 | sos |
| ATOM | 214 | CA | ILE | 600 | 72.594 | 31.180 | 33.135 | 1.00 | 68.92 | sos |
| ATOM | 215 | CB | ILE | 600 | 73.123 | 30.441 | 34.377 | 1.00 | 69.43 | sos |
| ATOM | 216 | CG2 | ILE | 600 | 72.898 | 31.288 | 35.622 | 1.00 | 70.41 | sos |
| ATOM | 217 | CG1 | ILE | 600 | 72.403 | 29.100 | 34.544 | 1.00 | 70.54 | sos |
| ATOM | 218 | CD1 | ILE | 600 | 72.942 | 28.253 | 35.696 | 1.00 | 71.17 | sos |
| ATOM | 219 | C | ILE | 600 | 73.292 | 32.539 | 33.012 | 1.00 | 66.64 | sos |
| ATOM | 220 | O | ILE | 600 | 74.493 | 32.607 | 32.749 | 1.00 | 66.39 | sos |
| ATOM | 221 | N | ILE | 601 | 72.523 | 33.613 | 33.178 | 1.00 | 62.89 | sos |
| ATOM | 222 | CA | ILE | 601 | 73.051 | 34.974 | 33.086 | 1.00 | 59.56 | sos |
| ATOM | 223 | CB | ILE | 601 | 71.910 | 35.988 | 32.850 | 1.00 | 58.42 | sos |
| ATOM | 224 | CG2 | ILE | 601 | 72.459 | 37.401 | 32.700 | 1.00 | 57.84 | sos |
| ATOM | 225 | CG1 | ILE | 601 | 71.136 | 35.601 | 31.597 | 1.00 | 57.80 | sos |
| ATOM | 226 | CD1 | ILE | 601 | 70.002 | 36.521 | 31.291 | 1.00 | 60.74 | sos |
| ATOM | 227 | C | ILE | 601 | 73.829 | 35.379 | 34.341 | 1.00 | 57.16 | sos |
| ATOM | 228 | O | ILE | 601 | 73.446 | 35.037 | 35.457 | 1.00 | 57.38 | sos |
| ATOM | 229 | N | LYS | 602 | 74.940 | 36.081 | 34.142 | 1.00 | 55.79 | sos |
| ATOM | 230 | CA | LYS | 602 | 75.771 | 36.550 | 35.247 | 1.00 | 54.82 | sos |
| ATOM | 231 | CB | LYS | 602 | 77.251 | 36.336 | 34.927 | 1.00 | 54.39 | sos |
| ATOM | 232 | CG | LYS | 602 | 78.208 | 36.662 | 36.058 | 1.00 | 56.18 | sos |
| ATOM | 233 | CD | LYS | 602 | 79.620 | 36.162 | 35.735 | 1.00 | 59.09 | sos |
| ATOM | 234 | CE | LYS | 602 | 80.577 | 36.319 | 36.916 | 1.00 | 60.43 | sos |
| ATOM | 235 | NZ | LYS | 602 | 81.786 | 35.452 | 36.774 | 1.00 | 60.26 | sos |
| ATOM | 236 | C | LYS | 602 | 75.492 | 38.030 | 35.432 | 1.00 | 55.34 | sos |
| ATOM | 237 | O | LYS | 602 | 75.254 | 38.495 | 36.548 | 1.00 | 57.62 | sos |
| ATOM | 238 | N | ALA | 603 | 75.479 | 38.757 | 34.320 | 1.00 | 52.61 | sos |
| ATOM | 239 | CA | ALA | 603 | 75.227 | 40.185 | 34.346 | 1.00 | 51.90 | sos |
| ATOM | 240 | CB | ALA | 603 | 76.482 | 40.920 | 34.753 | 1.00 | 54.87 | sos |
| ATOM | 241 | C | ALA | 603 | 74.757 | 40.681 | 32.991 | 1.00 | 53.33 | sos |
| ATOM | 242 | O | ALA | 603 | 74.864 | 39.969 | 31.992 | 1.00 | 53.54 | sos |
| ATOM | 243 | N | GLY | 604 | 74.248 | 41.912 | 32.968 | 1.00 | 52.47 | sos |
| ATOM | 244 | CA | GLY | 604 | 73.774 | 42.508 | 31.734 | 1.00 | 50.13 | sos |
| ATOM | 245 | C | GLY | 604 | 72.957 | 43.774 | 31.911 | 1.00 | 51.08 | sos |
| ATOM | 246 | O | GLY | 604 | 72.476 | 44.075 | 33.001 | 1.00 | 50.96 | sos |
| ATOM | 247 | N | THR | 605 | 72.813 | 44.525 | 30.826 | 1.00 | 52.63 | sos |
| ATOM | 248 | CA | THR | 605 | 72.033 | 45.759 | 30.814 | 1.00 | 56.20 | sos |
| ATOM | 249 | CB | THR | 605 | 72.111 | 46.428 | 29.419 | 1.00 | 58.46 | sos |
| ATOM | 250 | OG1 | THR | 605 | 73.484 | 46.637 | 29.071 | 1.00 | 57.02 | sos |
| ATOM | 251 | CG2 | THR | 605 | 71.383 | 47.774 | 29.418 | 1.00 | 62.73 | sos |
| ATOM | 252 | C | THR | 605 | 70.568 | 45.420 | 31.115 | 1.00 | 55.60 | sos |

TABLE 3-continued

PDB Coordinates for the Ras-Sos Structure:
DATA SET FOR REFINED COORDINATES

| ATOM | 253 | O | THR | 605 | 70.119 | 44.313 | 30.828 | 1.00 | 57.20 | sos |
|---|---|---|---|---|---|---|---|---|---|---|
| ATOM | 254 | N | VAL | 606 | 69.828 | 46.362 | 31.694 | 1.00 | 54.05 | sos |
| ATOM | 255 | CA | VAL | 606 | 68.420 | 46.128 | 32.004 | 1.00 | 53.82 | sos |
| ATOM | 256 | CB | VAL | 606 | 67.764 | 47.386 | 32.650 | 1.00 | 53.58 | sos |
| ATOM | 257 | CG1 | VAL | 606 | 67.586 | 48.497 | 31.631 | 1.00 | 52.86 | sos |
| ATOM | 258 | CG2 | VAL | 606 | 66.440 | 47.029 | 33.284 | 1.00 | 56.97 | sos |
| ATOM | 259 | C | VAL | 606 | 67.688 | 45.742 | 30.715 | 1.00 | 56.74 | sos |
| ATOM | 260 | O | VAL | 606 | 66.750 | 44.944 | 30.736 | 1.00 | 58.68 | sos |
| ATOM | 261 | N | ILE | 607 | 68.174 | 46.279 | 29.594 | 1.00 | 59.73 | sos |
| ATOM | 262 | CA | ILE | 607 | 67.628 | 46.029 | 28.259 | 1.00 | 59.05 | sos |
| ATOM | 263 | CB | ILE | 607 | 68.363 | 46.893 | 27.197 | 1.00 | 59.32 | sos |
| ATOM | 264 | CG2 | ILE | 607 | 68.048 | 46.408 | 25.801 | 1.00 | 64.10 | sos |
| ATOM | 265 | CG1 | ILE | 607 | 67.977 | 48.366 | 27.337 | 1.00 | 60.20 | sos |
| ATOM | 266 | CD1 | ILE | 607 | 66.511 | 48.643 | 27.094 | 1.00 | 58.35 | sos |
| ATOM | 267 | C | ILE | 607 | 67.797 | 44.557 | 27.890 | 1.00 | 58.65 | sos |
| ATOM | 268 | O | ILE | 607 | 66.827 | 43.858 | 27.603 | 1.00 | 58.45 | sos |
| ATOM | 269 | N | LYS | 608 | 69.044 | 44.103 | 27.904 | 1.00 | 58.82 | sos |
| ATOM | 270 | CA | LYS | 608 | 69.378 | 42.727 | 27.573 | 1.00 | 59.95 | sos |
| ATOM | 271 | CB | LYS | 608 | 70.896 | 42.577 | 27.491 | 1.00 | 63.61 | sos |
| ATOM | 272 | CG | LYS | 608 | 71.394 | 42.080 | 26.152 | 1.00 | 66.70 | sos |
| ATOM | 273 | CD | LYS | 608 | 71.068 | 43.057 | 25.045 | 1.00 | 72.38 | sos |
| ATOM | 274 | CE | LYS | 608 | 71.564 | 42.528 | 23.716 | 1.00 | 75.93 | sos |
| ATOM | 275 | NZ | LYS | 608 | 70.881 | 41.270 | 23.316 | 1.00 | 73.78 | sos |
| ATOM | 276 | C | LYS | 608 | 68.815 | 41.732 | 28.585 | 1.00 | 57.95 | sos |
| ATOM | 277 | O | LYS | 608 | 68.530 | 40.582 | 28.252 | 1.00 | 58.82 | sos |
| ATOM | 278 | N | LEU | 609 | 68.666 | 42.185 | 29.823 | 1.00 | 54.88 | sos |
| ATOM | 279 | CA | LEU | 609 | 68.148 | 41.355 | 30.899 | 1.00 | 51.61 | sos |
| ATOM | 280 | CB | LEU | 609 | 68.306 | 42.100 | 32.220 | 1.00 | 48.45 | sos |
| ATOM | 281 | CG | LEU | 609 | 68.975 | 41.392 | 33.389 | 1.00 | 47.60 | sos |
| ATOM | 282 | CD1 | LEU | 609 | 70.239 | 40.683 | 32.954 | 1.00 | 50.17 | sos |
| ATOM | 283 | CD2 | LEU | 609 | 69.280 | 42.431 | 34.449 | 1.00 | 50.18 | sos |
| ATOM | 284 | C | LEU | 609 | 66.681 | 41.049 | 30.627 | 1.00 | 51.87 | sos |
| ATOM | 285 | O | LEU | 609 | 66.249 | 39.895 | 30.692 | 1.00 | 50.36 | sos |
| ATOM | 286 | N | ILE | 610 | 65.932 | 42.097 | 30.297 | 1.00 | 52.38 | sos |
| ATOM | 287 | CA | ILE | 610 | 64.510 | 41.993 | 29.985 | 1.00 | 53.73 | sos |
| ATOM | 288 | CB | ILE | 610 | 63.866 | 43.394 | 30.002 | 1.00 | 49.31 | sos |
| ATOM | 289 | CG2 | ILE | 610 | 62.609 | 43.443 | 29.152 | 1.00 | 45.64 | sos |
| ATOM | 290 | CG1 | ILE | 610 | 63.571 | 43.770 | 31.451 | 1.00 | 47.66 | sos |
| ATOM | 291 | CD1 | ILE | 610 | 63.205 | 45.206 | 31.650 | 1.00 | 54.78 | sos |
| ATOM | 292 | C | ILE | 610 | 64.272 | 41.256 | 28.657 | 1.00 | 56.00 | sos |
| ATOM | 293 | O | ILE | 610 | 63.215 | 40.645 | 28.440 | 1.00 | 54.57 | sos |
| ATOM | 294 | N | GLU | 611 | 65.272 | 41.300 | 27.783 | 1.00 | 56.27 | sos |
| ATOM | 295 | CA | GLU | 611 | 65.191 | 40.610 | 26.511 | 1.00 | 56.64 | sos |
| ATOM | 296 | CB | GLU | 611 | 66.384 | 40.964 | 25.634 | 1.00 | 60.47 | sos |
| ATOM | 297 | CG | GLU | 611 | 66.454 | 40.193 | 24.331 | 1.00 | 62.70 | sos |
| ATOM | 298 | CD | GLU | 611 | 67.766 | 40.415 | 23.614 | 1.00 | 68.23 | sos |
| ATOM | 299 | OE1 | GLU | 611 | 68.154 | 41.594 | 23.452 | 1.00 | 74.10 | sos |
| ATOM | 300 | OE2 | GLU | 611 | 68.413 | 39.416 | 23.224 | 1.00 | 66.84 | sos |
| ATOM | 301 | C | GLU | 611 | 65.191 | 39.119 | 26.811 | 1.00 | 56.37 | sos |
| ATOM | 302 | O | GLU | 611 | 64.317 | 38.402 | 26.340 | 1.00 | 60.82 | sos |
| ATOM | 303 | N | ARG | 612 | 66.150 | 38.668 | 27.621 | 1.00 | 53.78 | sos |
| ATOM | 304 | CA | ARG | 612 | 66.262 | 37.253 | 28.000 | 1.00 | 53.05 | sos |
| ATOM | 305 | CB | ARG | 612 | 67.596 | 36.985 | 28.697 | 1.00 | 52.36 | sos |
| ATOM | 306 | CG | ARG | 612 | 68.791 | 36.994 | 27.774 | 1.00 | 56.53 | sos |
| ATOM | 307 | CD | ARG | 612 | 68.726 | 35.850 | 26.780 | 1.00 | 58.02 | sos |
| ATOM | 308 | NE | ARG | 612 | 69.817 | 35.917 | 25.812 | 1.00 | 64.18 | sos |
| ATOM | 309 | CZ | ARG | 612 | 70.646 | 34.912 | 25.537 | 1.00 | 64.70 | sos |
| ATOM | 310 | NH1 | ARG | 612 | 70.514 | 33.745 | 26.154 | 1.00 | 64.70 | sos |
| ATOM | 311 | NH2 | ARG | 612 | 71.616 | 35.076 | 24.649 | 1.00 | 63.45 | sos |
| ATOM | 312 | C | ARG | 612 | 65.123 | 36.779 | 28.901 | 1.00 | 52.66 | sos |
| ATOM | 313 | O | ARG | 612 | 64.907 | 35.578 | 29.068 | 1.00 | 52.34 | sos |
| ATOM | 314 | N | LEU | 613 | 64.422 | 37.733 | 29.505 | 1.00 | 52.72 | sos |
| ATOM | 315 | CA | LEU | 613 | 63.302 | 37.445 | 30.387 | 1.00 | 50.31 | sos |
| ATOM | 316 | CB | LEU | 613 | 63.030 | 38.653 | 31.285 | 1.00 | 51.42 | sos |
| ATOM | 317 | CG | LEU | 613 | 62.017 | 38.399 | 32.399 | 1.00 | 56.01 | sos |
| ATOM | 318 | CD1 | LEU | 613 | 62.733 | 37.628 | 33.488 | 1.00 | 58.64 | sos |
| ATOM | 319 | CD2 | LEU | 613 | 61.418 | 39.692 | 32.948 | 1.00 | 50.95 | sos |
| ATOM | 320 | C | LEU | 613 | 62.081 | 37.176 | 29.526 | 1.00 | 51.22 | sos |
| ATOM | 321 | O | LEU | 613 | 61.086 | 36.621 | 29.990 | 1.00 | 53.46 | sos |
| ATOM | 322 | N | THR | 614 | 62.176 | 37.599 | 28.269 | 1.00 | 54.70 | sos |
| ATOM | 323 | CA | THR | 614 | 61.120 | 37.466 | 27.268 | 1.00 | 55.39 | sos |
| ATOM | 324 | CB | THR | 614 | 60.425 | 38.848 | 27.062 | 1.00 | 55.34 | sos |
| ATOM | 325 | OG1 | THR | 614 | 59.732 | 39.222 | 28.258 | 1.00 | 54.40 | sos |
| ATOM | 326 | CG2 | THR | 614 | 59.423 | 38.805 | 25.945 | 1.00 | 62.65 | sos |
| ATOM | 327 | C | THR | 614 | 61.796 | 36.994 | 25.969 | 1.00 | 56.62 | sos |
| ATOM | 328 | O | THR | 614 | 61.515 | 37.490 | 24.876 | 1.00 | 56.20 | sos |

TABLE 3-continued

PDB Coordinates for the Ras-Sos Structure:
DATA SET FOR REFINED COORDINATES

| ATOM | 329 | N | TYR | 615 | 62.701 | 36.029 | 26.100 | 1.00 | 56.59 | sos |
|---|---|---|---|---|---|---|---|---|---|---|
| ATOM | 330 | CA | TYR | 615 | 63.446 | 35.518 | 24.951 | 1.00 | 58.48 | sos |
| ATOM | 331 | CB | TYR | 615 | 64.594 | 34.634 | 25.431 | 1.00 | 54.44 | sos |
| ATOM | 332 | CG | TYR | 615 | 65.784 | 34.623 | 24.506 | 1.00 | 47.69 | sos |
| ATOM | 333 | CD1 | TYR | 615 | 66.125 | 35.755 | 23.779 | 1.00 | 48.76 | sos |
| ATOM | 334 | CE1 | TYR | 615 | 67.230 | 35.767 | 22.942 | 1.00 | 48.97 | sos |
| ATOM | 335 | CD2 | TYR | 615 | 66.581 | 33.491 | 24.376 | 1.00 | 44.10 | sos |
| ATOM | 336 | CE2 | TYR | 615 | 67.692 | 33.491 | 23.545 | 1.00 | 46.56 | sos |
| ATOM | 337 | CZ | TYR | 615 | 68.013 | 34.637 | 22.826 | 1.00 | 48.62 | sos |
| ATOM | 338 | OH | TYR | 615 | 69.118 | 34.668 | 21.996 | 1.00 | 49.37 | sos |
| ATOM | 339 | C | TYR | 615 | 62.580 | 34.759 | 23.941 | 1.00 | 63.01 | sos |
| ATOM | 340 | O | TYR | 615 | 61.722 | 33.954 | 24.319 | 1.00 | 65.13 | sos |
| ATOM | 341 | N | HIS | 616 | 62.819 | 35.015 | 22.656 | 1.00 | 65.90 | sos |
| ATOM | 342 | CA | HIS | 616 | 62.060 | 34.364 | 21.588 | 1.00 | 67.88 | sos |
| ATOM | 343 | CB | HIS | 616 | 62.201 | 35.139 | 20.271 | 1.00 | 67.74 | sos |
| ATOM | 344 | CG | HIS | 616 | 63.558 | 35.040 | 19.646 | 1.00 | 70.92 | sos |
| ATOM | 345 | CD2 | HIS | 616 | 64.064 | 34.159 | 18.749 | 1.00 | 72.98 | sos |
| ATOM | 346 | ND1 | HIS | 616 | 64.574 | 35.928 | 19.924 | 1.00 | 73.67 | sos |
| ATOM | 347 | CE1 | HIS | 616 | 65.647 | 35.599 | 19.227 | 1.00 | 74.17 | sos |
| ATOM | 348 | NE2 | HIS | 616 | 65.365 | 34.529 | 18.506 | 1.00 | 72.98 | sos |
| ATOM | 349 | C | HIS | 616 | 62.454 | 32.899 | 21.388 | 1.00 | 68.65 | sos |
| ATOM | 350 | O | HIS | 616 | 61.613 | 32.065 | 21.050 | 1.00 | 67.98 | sos |
| ATOM | 351 | N | MET | 617 | 63.726 | 32.589 | 21.618 | 1.00 | 69.57 | sos |
| ATOM | 352 | CA | MET | 617 | 64.225 | 31.230 | 21.458 | 1.00 | 72.45 | sos |
| ATOM | 353 | CB | MET | 617 | 65.737 | 31.187 | 21.676 | 1.00 | 78.56 | sos |
| ATOM | 354 | CG | MET | 617 | 66.561 | 31.929 | 20.631 | 1.00 | 84.49 | sos |
| ATOM | 355 | SD | MET | 617 | 66.502 | 31.143 | 19.019 | 1.00 | 91.82 | sos |
| ATOM | 356 | CE | MET | 617 | 67.449 | 29.636 | 19.356 | 1.00 | 90.00 | sos |
| ATOM | 357 | C | MET | 617 | 63.548 | 30.243 | 22.403 | 1.00 | 72.82 | sos |
| ATOM | 358 | O | MET | 617 | 63.036 | 29.213 | 21.964 | 1.00 | 73.55 | sos |
| ATOM | 359 | N | TYR | 618 | 63.521 | 30.575 | 23.693 | 1.00 | 72.73 | sos |
| ATOM | 360 | CA | TYR | 618 | 62.920 | 29.706 | 24.710 | 1.00 | 70.75 | sos |
| ATOM | 361 | CB | TYR | 618 | 63.984 | 28.747 | 25.257 | 1.00 | 71.76 | sos |
| ATOM | 362 | CG | TYR | 618 | 65.296 | 29.428 | 25.590 | 1.00 | 74.47 | sos |
| ATOM | 363 | CD1 | TYR | 618 | 65.398 | 30.300 | 26.673 | 1.00 | 75.66 | sos |
| ATOM | 364 | CE1 | TYR | 618 | 66.588 | 30.970 | 26.950 | 1.00 | 77.18 | sos |
| ATOM | 365 | CD2 | TYR | 618 | 66.424 | 29.238 | 24.793 | 1.00 | 75.73 | sos |
| ATOM | 366 | CE2 | TYR | 618 | 67.621 | 29.903 | 25.064 | 1.00 | 75.98 | sos |
| ATOM | 367 | CZ | TYR | 618 | 67.693 | 30.768 | 26.141 | 1.00 | 76.38 | sos |
| ATOM | 368 | OH | TYR | 618 | 68.858 | 31.447 | 26.405 | 1.00 | 76.62 | sos |
| ATOM | 369 | C | TYR | 618 | 62.290 | 30.477 | 25.872 | 1.00 | 68.07 | sos |
| ATOM | 370 | O | TYR | 618 | 62.465 | 31.690 | 25.997 | 1.00 | 69.55 | sos |
| ATOM | 371 | N | ALA | 619 | 61.541 | 29.764 | 26.706 | 1.00 | 63.43 | sos |
| ATOM | 372 | CA | ALA | 619 | 60.907 | 30.359 | 27.879 | 1.00 | 59.10 | sos |
| ATOM | 373 | CB | ALA | 619 | 59.509 | 29.795 | 28.076 | 1.00 | 57.60 | sos |
| ATOM | 374 | C | ALA | 619 | 61.788 | 30.028 | 29.078 | 1.00 | 57.74 | sos |
| ATOM | 375 | O | ALA | 619 | 62.330 | 28.928 | 29.170 | 1.00 | 56.99 | sos |
| ATOM | 376 | N | ASP | 620 | 61.915 | 30.974 | 30.001 | 1.00 | 56.80 | sos |
| ATOM | 377 | CA | ASP | 620 | 62.756 | 30.788 | 31.178 | 1.00 | 53.95 | sos |
| ATOM | 378 | CB | ASP | 620 | 63.952 | 31.742 | 31.081 | 1.00 | 52.93 | sos |
| ATOM | 379 | CG | ASP | 620 | 65.210 | 31.190 | 31.725 | 1.00 | 54.68 | sos |
| ATOM | 380 | OD1 | ASP | 620 | 65.121 | 30.330 | 32.637 | 1.00 | 54.91 | sos |
| ATOM | 381 | OD2 | ASP | 620 | 66.302 | 31.636 | 31.309 | 1.00 | 52.57 | sos |
| ATOM | 382 | C | ASP | 620 | 61.966 | 31.075 | 32.455 | 1.00 | 53.26 | sos |
| ATOM | 383 | O | ASP | 620 | 62.189 | 32.097 | 33.106 | 1.00 | 50.46 | sos |
| ATOM | 384 | N | PRO | 621 | 61.051 | 30.163 | 32.844 | 1.00 | 52.73 | sos |
| ATOM | 385 | CD | PRO | 621 | 60.755 | 28.871 | 32.203 | 1.00 | 52.92 | sos |
| ATOM | 386 | CA | PRO | 621 | 60.229 | 30.331 | 34.049 | 1.00 | 53.44 | sos |
| ATOM | 387 | CB | PRO | 621 | 59.383 | 29.049 | 34.080 | 1.00 | 50.66 | sos |
| ATOM | 388 | CG | PRO | 621 | 60.221 | 28.062 | 33.360 | 1.00 | 51.48 | sos |
| ATOM | 389 | C | PRO | 621 | 61.004 | 30.547 | 35.346 | 1.00 | 53.02 | sos |
| ATOM | 390 | O | PRO | 621 | 60.503 | 31.212 | 36.249 | 1.00 | 54.53 | sos |
| ATOM | 391 | N | ASN | 622 | 62.212 | 29.989 | 35.438 | 1.00 | 54.69 | sos |
| ATOM | 392 | CA | ASN | 622 | 63.046 | 30.153 | 36.634 | 1.00 | 56.97 | sos |
| ATOM | 393 | CB | ASN | 622 | 64.146 | 29.085 | 36.707 | 1.00 | 61.77 | sos |
| ATOM | 394 | CG | ASN | 622 | 63.622 | 27.730 | 37.169 | 1.00 | 65.08 | sos |
| ATOM | 395 | OD1 | ASN | 622 | 62.787 | 27.643 | 38.076 | 1.00 | 67.33 | sos |
| ATOM | 396 | ND2 | ASN | 622 | 64.119 | 26.666 | 36.551 | 1.00 | 65.16 | sos |
| ATOM | 397 | C | ASN | 622 | 63.668 | 31.543 | 36.690 | 1.00 | 54.75 | sos |
| ATOM | 398 | O | ASN | 622 | 63.757 | 32.145 | 37.758 | 1.00 | 56.52 | sos |
| ATOM | 399 | N | PHE | 623 | 64.103 | 32.042 | 35.538 | 1.00 | 51.80 | sos |
| ATOM | 400 | CA | PHE | 623 | 64.691 | 33.373 | 35.450 | 1.00 | 52.20 | sos |
| ATOM | 401 | CB | PHE | 623 | 65.337 | 33.577 | 34.076 | 1.00 | 51.65 | sos |
| ATOM | 402 | CG | PHE | 623 | 65.909 | 34.949 | 33.862 | 1.00 | 51.14 | sos |
| ATOM | 403 | CD1 | PHE | 623 | 66.804 | 35.500 | 34.771 | 1.00 | 53.96 | sos |
| ATOM | 404 | CD2 | PHE | 623 | 65.562 | 35.685 | 32.740 | 1.00 | 51.74 | sos |

TABLE 3-continued

PDB Coordinates for the Ras-Sos Structure:
DATA SET FOR REFINED COORDINATES

| ATOM | 405 | CE1 | PHE | 623 | 67.345 | 36.767 | 34.565 | 1.00 | 54.74 | sos |
|---|---|---|---|---|---|---|---|---|---|---|
| ATOM | 406 | CE2 | PHE | 623 | 66.097 | 36.952 | 32.526 | 1.00 | 57.11 | sos |
| ATOM | 407 | CZ | PHE | 623 | 66.992 | 37.494 | 33.442 | 1.00 | 57.00 | sos |
| ATOM | 408 | C | PHE | 623 | 63.617 | 34.434 | 35.694 | 1.00 | 51.45 | sos |
| ATOM | 409 | O | PHE | 623 | 63.916 | 35.519 | 36.179 | 1.00 | 53.28 | sos |
| ATOM | 410 | N | VAL | 624 | 62.373 | 34.114 | 35.345 | 1.00 | 49.90 | sos |
| ATOM | 411 | CA | VAL | 624 | 61.249 | 35.026 | 35.539 | 1.00 | 49.19 | sos |
| ATOM | 412 | CB | VAL | 624 | 60.022 | 34.600 | 34.695 | 1.00 | 46.07 | sos |
| ATOM | 413 | CG1 | VAL | 624 | 58.781 | 35.375 | 35.121 | 1.00 | 41.56 | sos |
| ATOM | 414 | CG2 | VAL | 624 | 60.300 | 34.845 | 33.226 | 1.00 | 44.77 | sos |
| ATOM | 415 | C | VAL | 624 | 60.857 | 35.088 | 37.012 | 1.00 | 51.47 | sos |
| ATOM | 416 | O | VAL | 624 | 60.441 | 36.138 | 37.503 | 1.00 | 52.12 | sos |
| ATOM | 417 | N | ARG | 625 | 60.993 | 33.959 | 37.704 | 1.00 | 52.41 | sos |
| ATOM | 418 | CA | ARG | 625 | 60.669 | 33.864 | 39.124 | 1.00 | 53.68 | sos |
| ATOM | 419 | CB | ARG | 625 | 60.598 | 32.390 | 39.557 | 1.00 | 58.06 | sos |
| ATOM | 420 | CG | ARG | 625 | 60.669 | 32.166 | 41.071 | 1.00 | 66.44 | sos |
| ATOM | 421 | CD | ARG | 625 | 60.760 | 30.690 | 41.443 | 1.00 | 70.49 | sos |
| ATOM | 422 | NE | ARG | 625 | 59.444 | 30.052 | 41.470 | 1.00 | 78.23 | sos |
| ATOM | 423 | CZ | ARG | 625 | 59.140 | 28.979 | 42.198 | 1.00 | 78.52 | sos |
| ATOM | 424 | NH1 | ARG | 625 | 60.059 | 28.408 | 42.968 | 1.00 | 75.68 | sos |
| ATOM | 425 | NH2 | ARG | 625 | 57.909 | 28.483 | 42.169 | 1.00 | 79.21 | sos |
| ATOM | 426 | C | ARG | 625 | 61.705 | 34.612 | 39.960 | 1.00 | 51.61 | sos |
| ATOM | 427 | O | ARG | 625 | 61.367 | 35.258 | 40.950 | 1.00 | 56.36 | sos |
| ATOM | 428 | N | THR | 626 | 62.961 | 34.526 | 39.543 | 1.00 | 47.43 | sos |
| ATOM | 429 | CA | THR | 626 | 64.065 | 35.171 | 40.238 | 1.00 | 45.43 | sos |
| ATOM | 430 | CB | THR | 626 | 65.408 | 34.528 | 39.824 | 1.00 | 46.74 | sos |
| ATOM | 431 | OG1 | THR | 626 | 65.436 | 33.161 | 40.258 | 1.00 | 47.56 | sos |
| ATOM | 432 | CG2 | THR | 626 | 66.579 | 35.267 | 40.432 | 1.00 | 45.03 | sos |
| ATOM | 433 | C | THR | 626 | 64.099 | 36.678 | 39.991 | 1.00 | 44.73 | sos |
| ATOM | 434 | O | THR | 626 | 64.309 | 37.460 | 40.919 | 1.00 | 49.40 | sos |
| ATOM | 435 | N | PHE | 627 | 63.871 | 37.080 | 38.746 | 1.00 | 41.86 | sos |
| ATOM | 436 | CA | PHE | 627 | 63.867 | 38.490 | 38.361 | 1.00 | 39.24 | sos |
| ATOM | 437 | CB | PHE | 627 | 63.716 | 38.608 | 36.843 | 1.00 | 36.03 | sos |
| ATOM | 438 | CG | PHE | 627 | 63.779 | 40.017 | 36.316 | 1.00 | 34.05 | sos |
| ATOM | 439 | CD1 | PHE | 627 | 64.971 | 40.530 | 35.808 | 1.00 | 34.02 | sos |
| ATOM | 440 | CD2 | PHE | 627 | 62.640 | 40.819 | 36.284 | 1.00 | 29.53 | sos |
| ATOM | 441 | CE1 | PHE | 627 | 65.024 | 41.816 | 35.278 | 1.00 | 31.53 | sos |
| ATOM | 442 | CE2 | PHE | 627 | 62.684 | 42.107 | 35.754 | 1.00 | 30.19 | sos |
| ATOM | 443 | CZ | PHE | 627 | 63.876 | 42.605 | 35.252 | 1.00 | 31.38 | sos |
| ATOM | 444 | C | PHE | 627 | 62.746 | 39.262 | 39.051 | 1.00 | 40.68 | sos |
| ATOM | 445 | O | PHE | 627 | 62.967 | 40.357 | 39.550 | 1.00 | 43.71 | sos |
| ATOM | 446 | N | LEU | 628 | 61.544 | 38.700 | 39.089 | 1.00 | 39.71 | sos |
| ATOM | 447 | CA | LEU | 628 | 60.437 | 39.403 | 39.718 | 1.00 | 41.19 | sos |
| ATOM | 448 | CB | LEU | 628 | 59.089 | 38.839 | 39.261 | 1.00 | 38.77 | sos |
| ATOM | 449 | CG | LEU | 628 | 58.684 | 39.181 | 37.819 | 1.00 | 35.69 | sos |
| ATOM | 450 | CD1 | LEU | 628 | 57.415 | 38.447 | 37.450 | 1.00 | 39.36 | sos |
| ATOM | 451 | CD2 | LEU | 628 | 58.482 | 40.668 | 37.655 | 1.00 | 31.48 | sos |
| ATOM | 452 | C | LEU | 628 | 60.534 | 39.436 | 41.233 | 1.00 | 43.83 | sos |
| ATOM | 453 | O | LEU | 628 | 59.767 | 40.134 | 41.897 | 1.00 | 47.08 | sos |
| ATOM | 454 | N | THR | 629 | 61.494 | 38.701 | 41.779 | 1.00 | 42.92 | sos |
| ATOM | 455 | CA | THR | 629 | 61.691 | 38.669 | 43.221 | 1.00 | 43.73 | sos |
| ATOM | 456 | CB | THR | 629 | 62.046 | 37.237 | 43.711 | 1.00 | 44.20 | sos |
| ATOM | 457 | OG1 | THR | 629 | 60.879 | 36.413 | 43.680 | 1.00 | 46.48 | sos |
| ATOM | 458 | CG2 | THR | 629 | 62.584 | 37.252 | 45.132 | 1.00 | 45.85 | sos |
| ATOM | 459 | C | THR | 629 | 62.801 | 39.625 | 43.649 | 1.00 | 44.11 | sos |
| ATOM | 460 | O | THR | 629 | 62.761 | 40.168 | 44.752 | 1.00 | 45.21 | sos |
| ATOM | 461 | N | THR | 630 | 63.738 | 39.900 | 42.747 | 1.00 | 40.08 | sos |
| ATOM | 462 | CA | THR | 630 | 64.872 | 40.740 | 43.095 | 1.00 | 40.13 | sos |
| ATOM | 463 | CB | THR | 630 | 66.140 | 39.880 | 43.111 | 1.00 | 39.82 | sos |
| ATOM | 464 | OG1 | THR | 630 | 66.402 | 39.429 | 41.780 | 1.00 | 39.36 | sos |
| ATOM | 465 | CG2 | THR | 630 | 65.968 | 38.659 | 44.008 | 1.00 | 37.31 | sos |
| ATOM | 466 | C | THR | 630 | 65.193 | 41.962 | 42.233 | 1.00 | 41.28 | sos |
| ATOM | 467 | O | THR | 630 | 66.227 | 42.587 | 42.435 | 1.00 | 47.95 | sos |
| ATOM | 468 | N | TYR | 631 | 64.320 | 42.329 | 41.304 | 1.00 | 43.44 | sos |
| ATOM | 469 | CA | TYR | 631 | 64.581 | 43.457 | 40.400 | 1.00 | 42.86 | sos |
| ATOM | 470 | CB | TYR | 631 | 63.635 | 43.387 | 39.201 | 1.00 | 40.59 | sos |
| ATOM | 471 | CG | TYR | 631 | 62.279 | 44.006 | 39.464 | 1.00 | 40.71 | sos |
| ATOM | 472 | CD1 | TYR | 631 | 62.025 | 45.335 | 39.113 | 1.00 | 40.09 | sos |
| ATOM | 473 | CE1 | TYR | 631 | 60.804 | 45.926 | 39.374 | 1.00 | 37.78 | sos |
| ATOM | 474 | CD2 | TYR | 631 | 61.261 | 43.279 | 40.084 | 1.00 | 37.57 | sos |
| ATOM | 475 | CE2 | TYR | 631 | 60.029 | 43.866 | 40.344 | 1.00 | 37.78 | sos |
| ATOM | 476 | CZ | TYR | 631 | 59.812 | 45.189 | 39.987 | 1.00 | 37.58 | sos |
| ATOM | 477 | OH | TYR | 631 | 58.606 | 45.788 | 40.238 | 1.00 | 40.33 | sos |
| ATOM | 478 | C | TYR | 631 | 64.541 | 44.883 | 40.964 | 1.00 | 44.96 | sos |
| ATOM | 479 | O | TYR | 631 | 65.202 | 45.786 | 40.436 | 1.00 | 45.58 | sos |
| ATOM | 480 | N | ARG | 632 | 63.735 | 45.092 | 41.998 | 1.00 | 43.98 | sos |

TABLE 3-continued

PDB Coordinates for the Ras-Sos Structure:
DATA SET FOR REFINED COORDINATES

| ATOM | 481 | CA | ARG | 632 | 63.564 | 46.410 | 42.597 | 1.00 | 43.53 | sos |
|---|---|---|---|---|---|---|---|---|---|---|
| ATOM | 482 | CB | ARG | 632 | 62.519 | 46.330 | 43.706 | 1.00 | 39.29 | sos |
| ATOM | 483 | CG | ARG | 632 | 61.202 | 45.755 | 43.224 | 1.00 | 39.34 | sos |
| ATOM | 484 | CD | ARG | 632 | 60.322 | 45.296 | 44.364 | 1.00 | 38.22 | sos |
| ATOM | 485 | NE | ARG | 632 | 59.163 | 44.541 | 43.896 | 1.00 | 33.46 | sos |
| ATOM | 486 | CZ | ARG | 632 | 59.207 | 43.271 | 43.492 | 1.00 | 32.49 | sos |
| ATOM | 487 | NH1 | ARG | 632 | 60.353 | 42.603 | 43.490 | 1.00 | 26.44 | sos |
| ATOM | 488 | NH2 | ARG | 632 | 58.095 | 42.655 | 43.117 | 1.00 | 27.38 | sos |
| ATOM | 489 | C | ARG | 632 | 64.846 | 47.076 | 43.092 | 1.00 | 45.88 | sos |
| ATOM | 490 | O | ARG | 632 | 64.842 | 48.262 | 43.421 | 1.00 | 47.71 | sos |
| ATOM | 491 | N | SER | 633 | 65.943 | 46.324 | 43.111 | 1.00 | 47.84 | sos |
| ATOM | 492 | CA | SER | 633 | 67.233 | 46.853 | 43.554 | 1.00 | 50.15 | sos |
| ATOM | 493 | CB | SER | 633 | 68.050 | 45.780 | 44.296 | 1.00 | 50.62 | sos |
| ATOM | 494 | OG | SER | 633 | 68.441 | 44.713 | 43.449 | 1.00 | 51.12 | sos |
| ATOM | 495 | C | SER | 633 | 68.058 | 47.446 | 42.412 | 1.00 | 50.55 | sos |
| ATOM | 496 | O | SER | 633 | 69.088 | 48.070 | 42.652 | 1.00 | 52.49 | sos |
| ATOM | 497 | N | PHE | 634 | 67.619 | 47.235 | 41.172 | 1.00 | 48.98 | sos |
| ATOM | 498 | CA | PHE | 634 | 68.329 | 47.769 | 40.016 | 1.00 | 46.61 | sos |
| ATOM | 499 | CB | PHE | 634 | 69.235 | 46.700 | 39.385 | 1.00 | 46.79 | sos |
| ATOM | 500 | CG | PHE | 634 | 68.501 | 45.496 | 38.854 | 1.00 | 46.33 | sos |
| ATOM | 501 | CD1 | PHE | 634 | 67.780 | 45.564 | 37.664 | 1.00 | 45.17 | sos |
| ATOM | 502 | CD2 | PHE | 634 | 68.545 | 44.289 | 39.536 | 1.00 | 42.62 | sos |
| ATOM | 503 | CE1 | PHE | 634 | 67.118 | 44.451 | 37.169 | 1.00 | 43.98 | sos |
| ATOM | 504 | CE2 | PHE | 634 | 67.885 | 43.170 | 39.045 | 1.00 | 41.64 | sos |
| ATOM | 505 | CZ | PHE | 634 | 67.170 | 43.252 | 37.859 | 1.00 | 42.71 | sos |
| ATOM | 506 | C | PHE | 634 | 67.378 | 48.369 | 38.980 | 1.00 | 46.82 | sos |
| ATOM | 507 | O | PHE | 634 | 67.807 | 48.887 | 37.947 | 1.00 | 45.98 | sos |
| ATOM | 508 | N | CYS | 635 | 66.085 | 48.315 | 39.282 | 1.00 | 46.36 | sos |
| ATOM | 509 | CA | CYS | 635 | 65.052 | 48.844 | 38.400 | 1.00 | 44.82 | sos |
| ATOM | 510 | CB | CYS | 635 | 64.725 | 47.821 | 37.302 | 1.00 | 48.67 | sos |
| ATOM | 511 | SG | CYS | 635 | 63.444 | 48.312 | 36.122 | 1.00 | 51.68 | sos |
| ATOM | 512 | C | CYS | 635 | 63.816 | 49.122 | 39.239 | 1.00 | 41.98 | sos |
| ATOM | 513 | O | CYS | 635 | 63.499 | 48.358 | 40.153 | 1.00 | 42.11 | sos |
| ATOM | 514 | N | LYS | 636 | 63.142 | 50.232 | 38.952 | 1.00 | 41.36 | sos |
| ATOM | 515 | CA | LYS | 636 | 61.931 | 50.608 | 39.682 | 1.00 | 44.77 | sos |
| ATOM | 516 | CB | LYS | 636 | 61.806 | 52.135 | 39.743 | 1.00 | 43.56 | sos |
| ATOM | 517 | CG | LYS | 636 | 62.954 | 52.824 | 40.464 | 0.00 | 44.19 | sos |
| ATOM | 518 | CD | LYS | 636 | 62.774 | 54.331 | 40.474 | 0.00 | 44.08 | sos |
| ATOM | 519 | CE | LYS | 636 | 63.930 | 55.019 | 41.181 | 0.00 | 44.09 | sos |
| ATOM | 520 | NZ | LYS | 636 | 63.769 | 56.498 | 41.197 | 0.00 | 44.13 | sos |
| ATOM | 521 | C | LYS | 636 | 60.712 | 49.989 | 38.991 | 1.00 | 46.44 | sos |
| ATOM | 522 | O | LYS | 636 | 60.692 | 49.869 | 37.767 | 1.00 | 48.88 | sos |
| ATOM | 523 | N | PRO | 637 | 59.693 | 49.565 | 39.766 | 1.00 | 48.32 | sos |
| ATOM | 524 | CD | PRO | 637 | 59.595 | 49.623 | 41.237 | 1.00 | 48.62 | sos |
| ATOM | 525 | CA | PRO | 637 | 58.484 | 48.955 | 39.191 | 1.00 | 46.75 | sos |
| ATOM | 526 | CB | PRO | 637 | 57.504 | 48.966 | 40.367 | 1.00 | 45.79 | sos |
| ATOM | 527 | CG | PRO | 637 | 58.399 | 48.714 | 41.529 | 1.00 | 46.54 | sos |
| ATOM | 528 | C | PRO | 637 | 57.934 | 49.704 | 37.980 | 1.00 | 44.93 | sos |
| ATOM | 529 | O | PRO | 637 | 57.622 | 49.090 | 36.962 | 1.00 | 46.38 | sos |
| ATOM | 530 | N | GLN | 638 | 57.861 | 51.029 | 38.075 | 1.00 | 43.64 | sos |
| ATOM | 531 | CA | GLN | 638 | 57.360 | 51.848 | 36.974 | 1.00 | 45.35 | sos |
| ATOM | 532 | CB | GLN | 638 | 57.272 | 53.310 | 37.394 | 1.00 | 41.07 | sos |
| ATOM | 533 | CG | GLN | 638 | 56.103 | 53.612 | 38.296 | 1.00 | 41.15 | sos |
| ATOM | 534 | CD | GLN | 638 | 54.792 | 53.607 | 37.555 | 1.00 | 42.11 | sos |
| ATOM | 535 | OE1 | GLN | 638 | 54.761 | 53.669 | 36.326 | 1.00 | 44.62 | sos |
| ATOM | 536 | NE2 | GLN | 638 | 53.694 | 53.554 | 38.297 | 1.00 | 42.46 | sos |
| ATOM | 537 | C | GLN | 638 | 58.218 | 51.732 | 35.716 | 1.00 | 49.14 | sos |
| ATOM | 538 | O | GLN | 638 | 57.691 | 51.710 | 34.601 | 1.00 | 49.56 | sos |
| ATOM | 539 | N | GLU | 639 | 59.535 | 51.670 | 35.900 | 1.00 | 49.51 | sos |
| ATOM | 540 | CA | GLU | 639 | 60.471 | 51.554 | 34.786 | 1.00 | 52.29 | sos |
| ATOM | 541 | CB | GLU | 639 | 61.901 | 51.781 | 35.277 | 1.00 | 57.12 | sos |
| ATOM | 542 | CG | GLU | 639 | 62.092 | 53.094 | 36.033 | 1.00 | 63.21 | sos |
| ATOM | 543 | CD | GLU | 639 | 63.496 | 53.257 | 36.615 | 1.00 | 67.11 | sos |
| ATOM | 544 | OE1 | GLU | 639 | 64.204 | 52.237 | 36.807 | 1.00 | 65.53 | sos |
| ATOM | 545 | OE2 | GLU | 639 | 63.884 | 54.416 | 36.888 | 1.00 | 64.00 | sos |
| ATOM | 546 | C | GLU | 639 | 60.370 | 50.181 | 34.127 | 1.00 | 52.40 | sos |
| ATOM | 547 | O | GLU | 639 | 60.561 | 50.049 | 32.914 | 1.00 | 49.09 | sos |
| ATOM | 548 | N | LEU | 640 | 60.072 | 49.169 | 34.944 | 1.00 | 52.64 | sos |
| ATOM | 549 | CA | LEU | 640 | 59.938 | 47.788 | 34.485 | 1.00 | 49.13 | sos |
| ATOM | 550 | CB | LEU | 640 | 59.733 | 46.844 | 35.671 | 1.00 | 42.05 | sos |
| ATOM | 551 | CG | LEU | 640 | 60.098 | 45.358 | 35.551 | 1.00 | 38.52 | sos |
| ATOM | 552 | CD1 | LEU | 640 | 59.033 | 44.534 | 36.219 | 1.00 | 31.35 | sos |
| ATOM | 553 | CD2 | LEU | 640 | 60.274 | 44.915 | 34.123 | 1.00 | 38.01 | sos |
| ATOM | 554 | C | LEU | 640 | 58.744 | 47.669 | 33.558 | 1.00 | 51.47 | sos |
| ATOM | 555 | O | LEU | 640 | 58.842 | 47.056 | 32.501 | 1.00 | 54.80 | sos |
| ATOM | 556 | N | LEU | 641 | 57.611 | 48.232 | 33.969 | 1.00 | 51.66 | sos |

TABLE 3-continued

PDB Coordinates for the Ras-Sos Structure:
DATA SET FOR REFINED COORDINATES

| ATOM | 557 | CA | LEU | 641 | 56.406 | 48.172 | 33.157 | 1.00 | 52.31 | sos |
|---|---|---|---|---|---|---|---|---|---|---|
| ATOM | 558 | CB | LEU | 641 | 55.224 | 48.803 | 33.893 | 1.00 | 51.03 | sos |
| ATOM | 559 | CG | LEU | 641 | 53.860 | 48.693 | 33.205 | 1.00 | 49.43 | sos |
| ATOM | 560 | CD1 | LEU | 641 | 53.619 | 47.268 | 32.730 | 1.00 | 48.19 | sos |
| ATOM | 561 | CD2 | LEU | 641 | 52.763 | 49.125 | 34.159 | 1.00 | 48.61 | sos |
| ATOM | 562 | C | LEU | 641 | 56.639 | 48.864 | 31.824 | 1.00 | 54.50 | sos |
| ATOM | 563 | O | LEU | 641 | 56.204 | 48.371 | 30.785 | 1.00 | 58.19 | sos |
| ATOM | 564 | N | SER | 642 | 57.362 | 49.982 | 31.858 | 1.00 | 55.38 | sos |
| ATOM | 565 | CA | SER | 642 | 57.676 | 50.742 | 30.651 | 1.00 | 55.92 | sos |
| ATOM | 566 | CB | SER | 642 | 58.341 | 52.079 | 31.002 | 1.00 | 52.50 | sos |
| ATOM | 567 | OG | SER | 642 | 57.407 | 52.993 | 31.560 | 1.00 | 48.33 | sos |
| ATOM | 568 | C | SER | 642 | 58.570 | 49.937 | 29.708 | 1.00 | 57.93 | sos |
| ATOM | 569 | O | SER | 642 | 58.352 | 49.927 | 28.495 | 1.00 | 63.27 | sos |
| ATOM | 570 | N | LEU | 643 | 59.565 | 49.255 | 30.270 | 1.00 | 55.90 | sos |
| ATOM | 571 | CA | LEU | 643 | 60.476 | 48.435 | 29.477 | 1.00 | 55.05 | sos |
| ATOM | 572 | CB | LEU | 643 | 61.648 | 47.966 | 30.339 | 1.00 | 50.64 | sos |
| ATOM | 573 | CG | LEU | 643 | 62.634 | 49.080 | 30.683 | 1.00 | 53.66 | sos |
| ATOM | 574 | CD1 | LEU | 643 | 63.521 | 48.676 | 31.843 | 1.00 | 55.32 | sos |
| ATOM | 575 | CD2 | LEU | 643 | 63.460 | 49.424 | 29.459 | 1.00 | 51.36 | sos |
| ATOM | 576 | C | LEU | 643 | 59.744 | 47.239 | 28.868 | 1.00 | 55.37 | sos |
| ATOM | 577 | O | LEU | 643 | 60.020 | 46.846 | 27.730 | 1.00 | 55.39 | sos |
| ATOM | 578 | N | ILE | 644 | 58.808 | 46.678 | 29.633 | 1.00 | 54.04 | sos |
| ATOM | 579 | CA | ILE | 644 | 58.008 | 45.536 | 29.201 | 1.00 | 53.16 | sos |
| ATOM | 580 | CB | ILE | 644 | 57.150 | 44.990 | 30.366 | 1.00 | 53.75 | sos |
| ATOM | 581 | CG2 | ILE | 644 | 55.808 | 44.490 | 29.890 | 1.00 | 51.47 | sos |
| ATOM | 582 | CG1 | ILE | 644 | 57.896 | 43.870 | 31.075 | 1.00 | 56.44 | sos |
| ATOM | 583 | CD1 | ILE | 644 | 57.082 | 43.239 | 32.169 | 1.00 | 61.06 | sos |
| ATOM | 584 | C | ILE | 644 | 57.119 | 45.952 | 28.041 | 1.00 | 53.99 | sos |
| ATOM | 585 | O | ILE | 644 | 56.979 | 45.211 | 27.069 | 1.00 | 54.20 | sos |
| ATOM | 586 | N | ILE | 645 | 56.523 | 47.138 | 28.155 | 1.00 | 51.93 | sos |
| ATOM | 587 | CA | ILE | 645 | 55.662 | 47.671 | 27.108 | 1.00 | 50.99 | sos |
| ATOM | 588 | CB | ILE | 645 | 54.909 | 48.931 | 27.582 | 1.00 | 49.18 | sos |
| ATOM | 589 | CG2 | ILE | 645 | 54.193 | 49.601 | 26.409 | 1.00 | 44.13 | sos |
| ATOM | 590 | CG1 | ILE | 645 | 53.928 | 48.549 | 28.696 | 1.00 | 42.90 | sos |
| ATOM | 591 | CD1 | ILE | 645 | 53.021 | 49.660 | 29.140 | 1.00 | 38.51 | sos |
| ATOM | 592 | C | ILE | 645 | 56.500 | 47.974 | 25.867 | 1.00 | 53.50 | sos |
| ATOM | 593 | O | ILE | 645 | 56.079 | 47.684 | 24.746 | 1.00 | 53.68 | sos |
| ATOM | 594 | N | GLU | 646 | 57.701 | 48.517 | 26.073 | 1.00 | 55.37 | sos |
| ATOM | 595 | CA | GLU | 646 | 58.603 | 48.816 | 24.962 | 1.00 | 58.37 | sos |
| ATOM | 596 | CB | GLU | 646 | 59.831 | 49.607 | 25.430 | 1.00 | 61.55 | sos |
| ATOM | 597 | CG | GLU | 646 | 60.742 | 50.075 | 24.282 | 1.00 | 64.68 | sos |
| ATOM | 598 | CD | GLU | 646 | 62.073 | 50.678 | 24.743 | 1.00 | 69.95 | sos |
| ATOM | 599 | OE1 | GLU | 646 | 63.029 | 50.672 | 23.934 | 1.00 | 70.54 | sos |
| ATOM | 600 | OE2 | GLU | 646 | 62.169 | 51.161 | 25.897 | 1.00 | 68.67 | sos |
| ATOM | 601 | C | GLU | 646 | 59.054 | 47.516 | 24.293 | 1.00 | 58.61 | sos |
| ATOM | 602 | O | GLU | 646 | 59.388 | 47.522 | 23.114 | 1.00 | 60.61 | sos |
| ATOM | 603 | N | ARG | 647 | 59.065 | 46.413 | 25.046 | 1.00 | 58.85 | sos |
| ATOM | 604 | CA | ARG | 647 | 59.457 | 45.104 | 24.511 | 1.00 | 59.23 | sos |
| ATOM | 605 | CB | ARG | 647 | 59.861 | 44.136 | 25.632 | 1.00 | 56.11 | sos |
| ATOM | 606 | CG | ARG | 647 | 60.350 | 42.780 | 25.114 | 1.00 | 55.13 | sos |
| ATOM | 607 | CD | ARG | 647 | 61.560 | 42.991 | 24.212 | 1.00 | 58.92 | sos |
| ATOM | 608 | NE | ARG | 647 | 61.916 | 41.875 | 23.331 | 1.00 | 55.07 | sos |
| ATOM | 609 | CZ | ARG | 647 | 62.348 | 40.688 | 23.740 | 1.00 | 56.18 | sos |
| ATOM | 610 | NH1 | ARG | 647 | 62.459 | 40.422 | 25.036 | 1.00 | 60.08 | sos |
| ATOM | 611 | NH2 | ARG | 647 | 62.777 | 39.804 | 22.849 | 1.00 | 52.88 | sos |
| ATOM | 612 | C | ARG | 647 | 58.332 | 44.463 | 23.697 | 1.00 | 60.88 | sos |
| ATOM | 613 | O | ARG | 647 | 58.587 | 43.727 | 22.741 | 1.00 | 59.41 | sos |
| ATOM | 614 | N | PHE | 648 | 57.094 | 44.749 | 24.089 | 1.00 | 61.79 | sos |
| ATOM | 615 | CA | PHE | 648 | 55.909 | 44.203 | 23.435 | 1.00 | 63.84 | sos |
| ATOM | 616 | CB | PHE | 648 | 54.689 | 44.427 | 24.329 | 1.00 | 61.12 | sos |
| ATOM | 617 | CG | PHE | 648 | 53.449 | 43.729 | 23.857 | 1.00 | 61.25 | sos |
| ATOM | 618 | CD1 | PHE | 648 | 53.228 | 42.392 | 24.169 | 1.00 | 60.29 | sos |
| ATOM | 619 | CD2 | PHE | 648 | 52.476 | 44.418 | 23.139 | 1.00 | 63.20 | sos |
| ATOM | 620 | CE1 | PHE | 648 | 52.056 | 41.749 | 23.777 | 1.00 | 58.75 | sos |
| ATOM | 621 | CE2 | PHE | 648 | 51.297 | 43.782 | 22.741 | 1.00 | 61.54 | sos |
| ATOM | 622 | CZ | PHE | 648 | 51.088 | 42.445 | 23.063 | 1.00 | 61.11 | sos |
| ATOM | 623 | C | PHE | 648 | 55.661 | 44.823 | 22.065 | 1.00 | 66.88 | sos |
| ATOM | 624 | O | PHE | 648 | 55.420 | 44.110 | 21.083 | 1.00 | 66.03 | sos |
| ATOM | 625 | N | GLU | 649 | 55.712 | 46.153 | 22.017 | 1.00 | 68.68 | sos |
| ATOM | 626 | CA | GLU | 649 | 55.479 | 46.917 | 20.794 | 1.00 | 67.82 | sos |
| ATOM | 627 | CB | GLU | 649 | 55.180 | 48.370 | 21.515 | 1.00 | 66.02 | sos |
| ATOM | 628 | CG | GLU | 649 | 53.966 | 48.500 | 22.060 | 1.00 | 69.00 | sos |
| ATOM | 629 | CD | GLU | 649 | 53.696 | 49.920 | 22.516 | 1.00 | 69.98 | sos |
| ATOM | 630 | OE1 | GLU | 649 | 54.589 | 50.787 | 22.371 | 1.00 | 68.73 | sos |
| ATOM | 631 | OE2 | GLU | 649 | 52.583 | 50.163 | 23.033 | 1.00 | 70.74 | sos |
| ATOM | 632 | C | GLU | 649 | 56.634 | 46.819 | 19.803 | 1.00 | 68.63 | sos |

TABLE 3-continued

PDB Coordinates for the Ras-Sos Structure:
DATA SET FOR REFINED COORDINATES

| ATOM | 633 | O | GLU | 649 | 57.412 | 47.760 | 19.624 | 1.00 | 67.46 | sos |
|---|---|---|---|---|---|---|---|---|---|---|
| ATOM | 634 | N | ILE | 650 | 56.695 | 45.670 | 19.136 | 1.00 | 70.26 | sos |
| ATOM | 635 | CA | ILE | 650 | 57.729 | 45.362 | 18.158 | 1.00 | 71.86 | sos |
| ATOM | 636 | CB | ILE | 650 | 57.962 | 43.836 | 18.072 | 1.00 | 68.39 | sos |
| ATOM | 637 | CG2 | ILE | 650 | 59.217 | 43.545 | 17.289 | 1.00 | 65.63 | sos |
| ATOM | 638 | CG1 | ILE | 650 | 58.087 | 43.241 | 19.472 | 1.00 | 68.75 | sos |
| ATOM | 639 | CD1 | ILE | 650 | 58.156 | 41.737 | 19.495 | 1.00 | 70.35 | sos |
| ATOM | 640 | C | ILE | 650 | 57.377 | 45.861 | 16.759 | 1.00 | 75.52 | sos |
| ATOM | 641 | O | ILE | 650 | 56.288 | 45.593 | 16.249 | 1.00 | 74.42 | sos |
| ATOM | 642 | N | PRO | 651 | 58.280 | 46.640 | 16.143 | 1.00 | 79.66 | sos |
| ATOM | 643 | CD | PRO | 651 | 59.389 | 47.339 | 16.808 | 1.00 | 81.47 | sos |
| ATOM | 644 | CA | PRO | 651 | 58.078 | 47.181 | 14.796 | 1.00 | 82.25 | sos |
| ATOM | 645 | CB | PRO | 651 | 58.938 | 48.453 | 14.800 | 1.00 | 81.29 | sos |
| ATOM | 646 | CG | PRO | 651 | 59.220 | 48.721 | 16.264 | 1.00 | 84.16 | sos |
| ATOM | 647 | C | PRO | 651 | 58.611 | 46.187 | 13.759 | 1.00 | 85.37 | sos |
| ATOM | 648 | O | PRO | 651 | 59.611 | 45.505 | 14.006 | 1.00 | 85.34 | sos |
| ATOM | 649 | N | GLU | 652 | 57.938 | 46.100 | 12.611 | 1.00 | 87.40 | sos |
| ATOM | 650 | CA | GLU | 652 | 58.354 | 45.202 | 11.530 | 1.00 | 88.17 | sos |
| ATOM | 651 | CB | GLU | 652 | 57.156 | 44.857 | 10.639 | 1.00 | 87.30 | sos |
| ATOM | 652 | CG | GLU | 652 | 55.981 | 44.252 | 11.400 | 1.00 | 92.43 | sos |
| ATOM | 653 | CD | GLU | 652 | 54.732 | 44.088 | 10.545 | 1.00 | 94.97 | sos |
| ATOM | 654 | OE1 | GLU | 652 | 54.367 | 45.039 | 9.817 | 1.00 | 95.56 | sos |
| ATOM | 655 | OE2 | GLU | 652 | 54.105 | 43.008 | 10.613 | 1.00 | 93.73 | sos |
| ATOM | 656 | C | GLU | 652 | 59.459 | 45.878 | 10.707 | 1.00 | 86.89 | sos |
| ATOM | 657 | O | GLU | 652 | 59.498 | 47.105 | 10.601 | 1.00 | 85.50 | sos |
| ATOM | 658 | N | PRO | 653 | 60.386 | 45.086 | 10.138 | 1.00 | 86.96 | sos |
| ATOM | 659 | CD | PRO | 653 | 60.507 | 43.629 | 10.306 | 1.00 | 86.11 | sos |
| ATOM | 660 | CA | PRO | 653 | 61.499 | 45.601 | 9.327 | 1.00 | 87.88 | sos |
| ATOM | 661 | CB | PRO | 653 | 62.327 | 44.341 | 9.044 | 1.00 | 87.11 | sos |
| ATOM | 662 | CG | PRO | 653 | 61.989 | 43.435 | 10.187 | 1.00 | 85.53 | sos |
| ATOM | 663 | C | PRO | 653 | 61.044 | 46.270 | 8.025 | 1.00 | 88.52 | sos |
| ATOM | 664 | O | PRO | 653 | 61.835 | 47.069 | 7.475 | 1.00 | 87.36 | sos |
| ATOM | 665 | OT | PRO | 653 | 9999.000 | 9999.000 | 9999.000 | 1.00 | 0.00 | sos |
| ATOM | 666 | CB | ARG | 676 | 58.381 | 38.321 | 6.648 | 1.00 | 93.22 | sos |
| ATOM | 667 | CG | ARG | 676 | 59.077 | 39.268 | 7.619 | 0.00 | 93.71 | sos |
| ATOM | 668 | CD | ARG | 676 | 60.333 | 39.866 | 7.004 | 0.00 | 93.59 | sos |
| ATOM | 669 | NE | ARG | 676 | 60.048 | 40.625 | 5.787 | 0.00 | 93.64 | sos |
| ATOM | 670 | CZ | ARG | 676 | 60.612 | 40.392 | 4.606 | 0.00 | 93.63 | sos |
| ATOM | 671 | NH1 | ARG | 676 | 61.501 | 39.416 | 4.468 | 0.00 | 93.63 | sos |
| ATOM | 672 | NH2 | ARG | 676 | 60.284 | 41.133 | 3.557 | 0.00 | 93.63 | sos |
| ATOM | 673 | C | ARG | 676 | 57.423 | 36.520 | 8.142 | 1.00 | 95.86 | sos |
| ATOM | 674 | O | ARG | 676 | 56.518 | 35.842 | 8.637 | 1.00 | 96.59 | sos |
| ATOM | 675 | N | ARG | 676 | 56.230 | 38.689 | 7.839 | 1.00 | 92.19 | sos |
| ATOM | 676 | CA | ARG | 676 | 57.097 | 37.667 | 7.185 | 1.00 | 94.55 | sos |
| ATOM | 677 | N | PHE | 677 | 58.714 | 36.305 | 8.390 | 1.00 | 97.03 | sos |
| ATOM | 678 | CA | PHE | 677 | 59.190 | 35.255 | 9.290 | 1.00 | 97.70 | sos |
| ATOM | 679 | CB | PHE | 677 | 60.695 | 35.043 | 9.058 | 1.00 | 100.65 | sos |
| ATOM | 680 | CG | PHE | 677 | 61.238 | 33.737 | 9.597 | 1.00 | 102.75 | sos |
| ATOM | 681 | CD1 | PHE | 677 | 60.388 | 32.694 | 9.960 | 1.00 | 104.17 | sos |
| ATOM | 682 | CD2 | PHE | 677 | 62.615 | 33.554 | 9.730 | 1.00 | 103.01 | sos |
| ATOM | 683 | CE1 | PHE | 677 | 60.902 | 31.491 | 10.450 | 1.00 | 105.09 | sos |
| ATOM | 684 | CE2 | PHE | 677 | 63.138 | 32.356 | 10.218 | 1.00 | 103.49 | sos |
| ATOM | 685 | CZ | PHE | 677 | 62.280 | 31.323 | 10.579 | 1.00 | 105.45 | sos |
| ATOM | 686 | C | PHE | 677 | 58.922 | 35.665 | 10.748 | 1.00 | 97.70 | sos |
| ATOM | 687 | O | PHE | 677 | 59.220 | 34.916 | 11.682 | 1.00 | 97.24 | sos |
| ATOM | 688 | N | ARG | 678 | 58.346 | 36.855 | 10.926 | 1.00 | 96.94 | sos |
| ATOM | 689 | CA | ARG | 678 | 58.020 | 37.394 | 12.246 | 1.00 | 94.54 | sos |
| ATOM | 690 | CB | ARG | 678 | 57.927 | 38.916 | 12.184 | 1.00 | 95.28 | sos |
| ATOM | 691 | CG | ARG | 678 | 59.120 | 39.566 | 11.498 | 1.00 | 98.88 | sos |
| ATOM | 692 | CD | ARG | 678 | 60.433 | 39.231 | 12.191 | 1.00 | 99.01 | sos |
| ATOM | 693 | NE | ARG | 678 | 60.486 | 39.775 | 13.546 | 1.00 | 103.15 | sos |
| ATOM | 694 | CZ | ARG | 678 | 60.590 | 41.068 | 13.840 | 1.00 | 103.50 | sos |
| ATOM | 695 | NH1 | ARG | 678 | 60.656 | 41.977 | 12.878 | 1.00 | 105.48 | sos |
| ATOM | 696 | NH2 | ARG | 678 | 60.620 | 41.456 | 15.105 | 1.00 | 106.10 | sos |
| ATOM | 697 | C | ARG | 678 | 56.731 | 36.793 | 12.811 | 1.00 | 93.37 | sos |
| ATOM | 698 | O | ARG | 678 | 55.705 | 37.466 | 12.967 | 1.00 | 90.34 | sos |
| ATOM | 699 | N | LYS | 679 | 56.807 | 35.489 | 13.048 | 1.00 | 92.67 | sos |
| ATOM | 700 | CA | LYS | 679 | 55.743 | 34.667 | 13.613 | 1.00 | 90.06 | sos |
| ATOM | 701 | CB | LYS | 679 | 55.075 | 33.826 | 12.524 | 1.00 | 91.87 | sos |
| ATOM | 702 | CG | LYS | 679 | 54.395 | 34.654 | 11.442 | 0.00 | 91.21 | sos |
| ATOM | 703 | CD | LYS | 679 | 53.771 | 33.784 | 10.367 | 0.00 | 91.41 | sos |
| ATOM | 704 | CE | LYS | 679 | 53.111 | 34.637 | 9.295 | 0.00 | 91.36 | sos |
| ATOM | 705 | NZ | LYS | 679 | 52.486 | 33.812 | 8.226 | 0.00 | 91.44 | sos |
| ATOM | 706 | C | LYS | 679 | 56.486 | 33.768 | 14.602 | 1.00 | 88.90 | sos |
| ATOM | 707 | O | LYS | 679 | 55.892 | 33.151 | 15.486 | 1.00 | 88.37 | sos |
| ATOM | 708 | N | GLU | 680 | 57.800 | 33.686 | 14.403 | 1.00 | 86.31 | sos |

TABLE 3-continued

PDB Coordinates for the Ras-Sos Structure:
DATA SET FOR REFINED COORDINATES

| ATOM | 709 | CA | GLU | 680 | 58.694 | 32.931 | 15.265 | 1.00 | 83.50 | sos |
|---|---|---|---|---|---|---|---|---|---|---|
| ATOM | 710 | CB | GLU | 680 | 59.602 | 32.015 | 14.439 | 1.00 | 82.46 | sos |
| ATOM | 711 | CG | GLU | 680 | 58.875 | 30.818 | 13.837 | 0.00 | 82.91 | sos |
| ATOM | 712 | CD | GLU | 680 | 59.813 | 29.811 | 13.195 | 0.00 | 82.88 | sos |
| ATOM | 713 | OE1 | GLU | 680 | 60.942 | 29.627 | 13.699 | 0.00 | 82.95 | sos |
| ATOM | 714 | OE2 | GLU | 680 | 59.415 | 29.194 | 12.185 | 0.00 | 82.95 | sos |
| ATOM | 715 | C | GLU | 680 | 59.515 | 33.936 | 16.098 | 1.00 | 81.22 | sos |
| ATOM | 716 | O | GLU | 680 | 60.522 | 33.583 | 16.720 | 1.00 | 78.99 | sos |
| ATOM | 717 | N | TYR | 681 | 59.067 | 35.194 | 16.091 | 1.00 | 77.80 | sos |
| ATOM | 718 | CA | TYR | 681 | 59.702 | 36.265 | 16.855 | 1.00 | 73.84 | sos |
| ATOM | 719 | CB | TYR | 681 | 60.643 | 37.112 | 15.995 | 1.00 | 68.85 | sos |
| ATOM | 720 | CG | TYR | 681 | 61.480 | 38.058 | 16.833 | 1.00 | 65.12 | sos |
| ATOM | 721 | CD1 | TYR | 681 | 62.711 | 37.652 | 17.348 | 1.00 | 62.90 | sos |
| ATOM | 722 | CE1 | TYR | 681 | 63.463 | 38.489 | 18.162 | 1.00 | 59.90 | sos |
| ATOM | 723 | CD2 | TYR | 681 | 61.023 | 39.340 | 17.156 | 1.00 | 63.21 | sos |
| ATOM | 724 | CE2 | TYR | 681 | 61.773 | 40.189 | 17.974 | 1.00 | 58.57 | sos |
| ATOM | 725 | CZ | TYR | 681 | 62.990 | 39.753 | 18.471 | 1.00 | 59.86 | sos |
| ATOM | 726 | OH | TYR | 681 | 63.743 | 40.567 | 19.281 | 1.00 | 61.11 | sos |
| ATOM | 727 | C | TYR | 681 | 58.668 | 37.177 | 17.519 | 1.00 | 72.32 | sos |
| ATOM | 728 | O | TYR | 681 | 58.703 | 37.376 | 18.727 | 1.00 | 73.16 | sos |
| ATOM | 729 | N | ILE | 682 | 57.758 | 37.740 | 16.735 | 1.00 | 70.57 | sos |
| ATOM | 730 | CA | ILE | 682 | 56.741 | 38.624 | 17.290 | 1.00 | 68.56 | sos |
| ATOM | 731 | CB | ILE | 682 | 56.053 | 39.459 | 16.187 | 1.00 | 66.12 | sos |
| ATOM | 732 | CG2 | ILE | 682 | 54.848 | 40.196 | 16.746 | 1.00 | 64.84 | sos |
| ATOM | 733 | CG1 | ILE | 682 | 57.053 | 40.451 | 15.586 | 1.00 | 63.60 | sos |
| ATOM | 734 | CD1 | ILE | 682 | 56.444 | 41.411 | 14.591 | 1.00 | 63.42 | sos |
| ATOM | 735 | C | ILE | 682 | 55.694 | 37.880 | 18.119 | 1.00 | 69.59 | sos |
| ATOM | 736 | O | ILE | 682 | 55.278 | 38.356 | 19.173 | 1.00 | 70.79 | sos |
| ATOM | 737 | N | GLN | 683 | 55.275 | 36.709 | 17.651 | 1.00 | 71.87 | sos |
| ATOM | 738 | CA | GLN | 683 | 54.272 | 35.927 | 18.372 | 1.00 | 71.88 | sos |
| ATOM | 739 | CB | GLN | 683 | 53.724 | 34.778 | 17.500 | 1.00 | 75.52 | sos |
| ATOM | 740 | CG | GLN | 683 | 52.681 | 35.193 | 16.444 | 1.00 | 80.29 | sos |
| ATOM | 741 | CD | GLN | 683 | 51.296 | 35.457 | 17.037 | 1.00 | 84.71 | sos |
| ATOM | 742 | OE1 | GLN | 683 | 50.379 | 34.639 | 16.899 | 1.00 | 86.08 | sos |
| ATOM | 743 | NE2 | GLN | 683 | 51.141 | 36.602 | 17.695 | 1.00 | 83.82 | sos |
| ATOM | 744 | C | GLN | 683 | 54.785 | 35.412 | 19.719 | 1.00 | 67.10 | sos |
| ATOM | 745 | O | GLN | 683 | 54.093 | 35.536 | 20.731 | 1.00 | 68.22 | sos |
| ATOM | 746 | N | PRO | 684 | 55.995 | 34.822 | 19.752 | 1.00 | 62.55 | sos |
| ATOM | 747 | CD | PRO | 684 | 56.822 | 34.347 | 18.630 | 1.00 | 61.86 | sos |
| ATOM | 748 | CA | PRO | 684 | 56.523 | 34.319 | 21.025 | 1.00 | 62.04 | sos |
| ATOM | 749 | CB | PRO | 684 | 57.651 | 33.380 | 20.587 | 1.00 | 60.29 | sos |
| ATOM | 750 | CG | PRO | 684 | 58.106 | 33.961 | 19.316 | 1.00 | 60.42 | sos |
| ATOM | 751 | C | PRO | 684 | 57.005 | 35.392 | 22.007 | 1.00 | 60.47 | sos |
| ATOM | 752 | O | PRO | 684 | 56.863 | 35.218 | 23.213 | 1.00 | 61.56 | sos |
| ATOM | 753 | N | VAL | 685 | 57.568 | 36.490 | 21.504 | 1.00 | 57.77 | sos |
| ATOM | 754 | CA | VAL | 685 | 58.040 | 37.558 | 22.381 | 1.00 | 56.29 | sos |
| ATOM | 755 | CB | VAL | 685 | 58.846 | 38.636 | 21.619 | 1.00 | 54.97 | sos |
| ATOM | 756 | CG1 | VAL | 685 | 59.052 | 39.869 | 22.489 | 1.00 | 50.52 | sos |
| ATOM | 757 | CG2 | VAL | 685 | 60.200 | 38.077 | 21.222 | 1.00 | 54.54 | sos |
| ATOM | 758 | C | VAL | 685 | 56.869 | 38.199 | 23.109 | 1.00 | 57.74 | sos |
| ATOM | 759 | O | VAL | 685 | 56.925 | 38.408 | 24.320 | 1.00 | 59.80 | sos |
| ATOM | 760 | N | GLN | 686 | 55.803 | 38.497 | 22.374 | 1.00 | 58.30 | sos |
| ATOM | 761 | CA | GLN | 686 | 54.615 | 39.090 | 22.973 | 1.00 | 59.82 | sos |
| ATOM | 762 | CB | GLN | 686 | 53.570 | 39.393 | 21.900 | 1.00 | 64.80 | sos |
| ATOM | 763 | CG | GLN | 686 | 53.950 | 40.506 | 20.932 | 1.00 | 68.63 | sos |
| ATOM | 764 | CD | GLN | 686 | 52.805 | 40.877 | 20.001 | 1.00 | 72.17 | sos |
| ATOM | 765 | OE1 | GLN | 686 | 51.631 | 40.686 | 20.330 | 1.00 | 74.46 | sos |
| ATOM | 766 | NE2 | GLN | 686 | 53.142 | 41.418 | 18.837 | 1.00 | 71.83 | sos |
| ATOM | 767 | C | GLN | 686 | 54.024 | 38.133 | 24.011 | 1.00 | 59.90 | sos |
| ATOM | 768 | O | GLN | 686 | 53.440 | 38.562 | 25.006 | 1.00 | 61.22 | sos |
| ATOM | 769 | N | LEU | 687 | 54.202 | 36.836 | 23.776 | 1.00 | 59.03 | sos |
| ATOM | 770 | CA | LEU | 687 | 53.702 | 35.804 | 24.671 | 1.00 | 60.70 | sos |
| ATOM | 771 | CB | LEU | 687 | 53.884 | 34.421 | 24.042 | 1.00 | 68.03 | sos |
| ATOM | 772 | CG | LEU | 687 | 53.274 | 33.244 | 24.811 | 1.00 | 73.44 | sos |
| ATOM | 773 | CD1 | LEU | 687 | 51.768 | 33.226 | 24.571 | 1.00 | 74.75 | sos |
| ATOM | 774 | CD2 | LEU | 687 | 53.903 | 31.925 | 24.361 | 1.00 | 75.66 | sos |
| ATOM | 775 | C | LEU | 687 | 54.435 | 35.843 | 26.004 | 1.00 | 58.91 | sos |
| ATOM | 776 | O | LEU | 687 | 53.810 | 35.866 | 27.061 | 1.00 | 59.54 | sos |
| ATOM | 777 | N | ARG | 688 | 55.763 | 35.831 | 25.942 | 1.00 | 57.08 | sos |
| ATOM | 778 | CA | ARG | 688 | 56.596 | 35.863 | 27.139 | 1.00 | 56.04 | sos |
| ATOM | 779 | CB | ARG | 688 | 58.080 | 35.795 | 26.767 | 1.00 | 59.69 | sos |
| ATOM | 780 | CG | ARG | 688 | 58.468 | 34.745 | 25.739 | 1.00 | 61.07 | sos |
| ATOM | 781 | CD | ARG | 688 | 58.569 | 33.352 | 26.317 | 1.00 | 64.17 | sos |
| ATOM | 782 | NE | ARG | 688 | 59.243 | 32.466 | 25.371 | 1.00 | 69.25 | sos |
| ATOM | 783 | CZ | ARG | 688 | 58.677 | 31.418 | 24.774 | 1.00 | 73.71 | sos |
| ATOM | 784 | NH1 | ARG | 688 | 57.408 | 31.099 | 25.025 | 1.00 | 71.90 | sos |

TABLE 3-continued

PDB Coordinates for the Ras-Sos Structure:
DATA SET FOR REFINED COORDINATES

| ATOM | 785 | NH2 | ARG | 688 | 59.378 | 30.702 | 23.902 | 1.00 | 71.93 | sos |
|---|---|---|---|---|---|---|---|---|---|---|
| ATOM | 786 | C | ARG | 688 | 56.334 | 37.142 | 27.944 | 1.00 | 53.20 | sos |
| ATOM | 787 | O | ARG | 688 | 56.300 | 37.109 | 29.171 | 1.00 | 53.12 | sos |
| ATOM | 788 | N | VAL | 689 | 56.160 | 38.266 | 27.251 | 1.00 | 48.26 | sos |
| ATOM | 789 | CA | VAL | 689 | 55.889 | 39.537 | 27.916 | 1.00 | 46.29 | sos |
| ATOM | 790 | CB | VAL | 689 | 55.672 | 40.690 | 26.897 | 1.00 | 44.08 | sos |
| ATOM | 791 | CG1 | VAL | 689 | 55.065 | 41.911 | 27.581 | 1.00 | 31.99 | sos |
| ATOM | 792 | CG2 | VAL | 689 | 56.986 | 41.069 | 26.243 | 1.00 | 43.08 | sos |
| ATOM | 793 | C | VAL | 689 | 54.637 | 39.411 | 28.774 | 1.00 | 46.39 | sos |
| ATOM | 794 | O | VAL | 689 | 54.618 | 39.835 | 29.926 | 1.00 | 48.84 | sos |
| ATOM | 795 | N | LEU | 690 | 53.598 | 38.817 | 28.206 | 1.00 | 45.19 | sos |
| ATOM | 796 | CA | LEU | 690 | 52.341 | 38.648 | 28.915 | 1.00 | 45.65 | sos |
| ATOM | 797 | CB | LEU | 690 | 51.226 | 38.361 | 27.910 | 1.00 | 45.57 | sos |
| ATOM | 798 | CG | LEU | 690 | 50.939 | 39.600 | 27.050 | 1.00 | 47.07 | sos |
| ATOM | 799 | CD1 | LEU | 690 | 50.273 | 39.235 | 25.743 | 1.00 | 45.45 | sos |
| ATOM | 800 | CD2 | LEU | 690 | 50.084 | 40.587 | 27.842 | 1.00 | 47.89 | sos |
| ATOM | 801 | C | LEU | 690 | 52.395 | 37.616 | 30.050 | 1.00 | 46.47 | sos |
| ATOM | 802 | O | LEU | 690 | 51.652 | 37.732 | 31.029 | 1.00 | 44.77 | sos |
| ATOM | 803 | N | ASN | 691 | 53.284 | 36.627 | 29.933 | 1.00 | 45.71 | sos |
| ATOM | 804 | CA | ASN | 691 | 53.444 | 35.619 | 30.983 | 1.00 | 49.13 | sos |
| ATOM | 805 | CB | ASN | 691 | 54.195 | 34.386 | 30.479 | 1.00 | 52.53 | sos |
| ATOM | 806 | CG | ASN | 691 | 53.259 | 33.340 | 29.891 | 1.00 | 59.93 | sos |
| ATOM | 807 | OD1 | ASN | 691 | 52.092 | 33.236 | 30.292 | 1.00 | 58.21 | sos |
| ATOM | 808 | ND2 | ASN | 691 | 53.763 | 32.562 | 28.928 | 1.00 | 59.64 | sos |
| ATOM | 809 | C | ASN | 691 | 54.175 | 36.221 | 32.175 | 1.00 | 48.89 | sos |
| ATOM | 810 | O | ASN | 691 | 54.036 | 35.751 | 33.303 | 1.00 | 50.51 | sos |
| ATOM | 811 | N | VAL | 692 | 54.964 | 37.258 | 31.903 | 1.00 | 46.73 | sos |
| ATOM | 812 | CA | VAL | 692 | 55.705 | 37.983 | 32.928 | 1.00 | 41.82 | sos |
| ATOM | 813 | CB | VAL | 692 | 56.821 | 38.868 | 32.298 | 1.00 | 35.77 | sos |
| ATOM | 814 | CG1 | VAL | 692 | 57.197 | 39.988 | 33.228 | 1.00 | 33.35 | sos |
| ATOM | 815 | CG2 | VAL | 692 | 58.052 | 38.020 | 31.992 | 1.00 | 30.24 | sos |
| ATOM | 816 | C | VAL | 692 | 54.696 | 38.850 | 33.681 | 1.00 | 43.49 | sos |
| ATOM | 817 | O | VAL | 692 | 54.693 | 38.886 | 34.911 | 1.00 | 47.09 | sos |
| ATOM | 818 | N | CYS | 693 | 53.822 | 39.520 | 32.933 | 1.00 | 41.83 | sos |
| ATOM | 819 | CA | CYS | 693 | 52.796 | 40.367 | 33.522 | 1.00 | 40.66 | sos |
| ATOM | 820 | CB | CYS | 693 | 51.916 | 41.005 | 32.432 | 1.00 | 41.17 | sos |
| ATOM | 821 | SG | CYS | 693 | 52.735 | 42.151 | 31.247 | 1.00 | 44.94 | sos |
| ATOM | 822 | C | CYS | 693 | 51.937 | 39.515 | 34.456 | 1.00 | 43.49 | sos |
| ATOM | 823 | O | CYS | 693 | 51.617 | 39.937 | 35.563 | 1.00 | 43.89 | sos |
| ATOM | 824 | N | ARG | 694 | 51.590 | 38.305 | 34.018 | 1.00 | 47.17 | sos |
| ATOM | 825 | CA | ARG | 694 | 50.766 | 37.394 | 34.820 | 1.00 | 48.90 | sos |
| ATOM | 826 | CB | ARG | 694 | 50.453 | 36.116 | 34.033 | 1.00 | 50.18 | sos |
| ATOM | 827 | CG | ARG | 694 | 49.702 | 35.058 | 34.844 | 1.00 | 52.82 | sos |
| ATOM | 828 | CD | ARG | 694 | 49.649 | 33.715 | 34.124 | 1.00 | 59.50 | sos |
| ATOM | 829 | NE | ARG | 694 | 48.873 | 33.786 | 32.886 | 1.00 | 65.07 | sos |
| ATOM | 830 | CZ | ARG | 694 | 49.115 | 33.059 | 31.799 | 1.00 | 67.24 | sos |
| ATOM | 831 | NH1 | ARG | 694 | 50.116 | 32.186 | 31.786 | 1.00 | 72.05 | sos |
| ATOM | 832 | NH2 | ARG | 694 | 48.373 | 33.229 | 30.712 | 1.00 | 68.20 | sos |
| ATOM | 833 | C | ARG | 694 | 51.452 | 37.019 | 36.135 | 1.00 | 47.46 | sos |
| ATOM | 834 | O | ARG | 694 | 50.841 | 37.066 | 37.204 | 1.00 | 44.74 | sos |
| ATOM | 835 | N | HIS | 695 | 52.723 | 36.639 | 36.031 | 1.00 | 46.55 | sos |
| ATOM | 836 | CA | HIS | 695 | 53.544 | 36.240 | 37.173 | 1.00 | 45.44 | sos |
| ATOM | 837 | CB | HIS | 695 | 54.918 | 35.803 | 36.654 | 1.00 | 45.78 | sos |
| ATOM | 838 | CG | HIS | 695 | 55.705 | 34.966 | 37.612 | 1.00 | 49.77 | sos |
| ATOM | 839 | CD2 | HIS | 695 | 56.366 | 33.799 | 37.434 | 1.00 | 51.55 | sos |
| ATOM | 840 | ND1 | HIS | 695 | 55.912 | 35.324 | 38.927 | 1.00 | 53.47 | sos |
| ATOM | 841 | CE1 | HIS | 695 | 56.669 | 34.416 | 39.516 | 1.00 | 50.51 | sos |
| ATOM | 842 | NE2 | HIS | 695 | 56.957 | 33.480 | 38.632 | 1.00 | 52.27 | sos |
| ATOM | 843 | C | HIS | 695 | 53.689 | 37.419 | 38.148 | 1.00 | 44.09 | sos |
| ATOM | 844 | O | HIS | 695 | 53.648 | 37.243 | 39.363 | 1.00 | 45.13 | sos |
| ATOM | 845 | N | TRP | 696 | 53.844 | 38.613 | 37.594 | 1.00 | 40.28 | sos |
| ATOM | 846 | CA | TRP | 696 | 53.994 | 39.830 | 38.370 | 1.00 | 39.12 | sos |
| ATOM | 847 | CB | TRP | 696 | 54.240 | 40.997 | 37.412 | 1.00 | 42.76 | sos |
| ATOM | 848 | CG | TRP | 696 | 54.702 | 42.288 | 38.037 | 1.00 | 46.66 | sos |
| ATOM | 849 | CD2 | TRP | 696 | 55.109 | 43.471 | 37.339 | 1.00 | 44.88 | sos |
| ATOM | 850 | CE2 | TRP | 696 | 55.469 | 44.429 | 38.312 | 1.00 | 45.81 | sos |
| ATOM | 851 | CE3 | TRP | 696 | 55.205 | 43.815 | 35.984 | 1.00 | 44.24 | sos |
| ATOM | 852 | CD1 | TRP | 696 | 54.827 | 42.569 | 39.371 | 1.00 | 47.84 | sos |
| ATOM | 853 | NE1 | TRP | 696 | 55.287 | 43.852 | 39.542 | 1.00 | 49.26 | sos |
| ATOM | 854 | CZ2 | TRP | 696 | 55.919 | 45.709 | 37.974 | 1.00 | 45.03 | sos |
| ATOM | 855 | CZ3 | TRP | 696 | 55.653 | 45.092 | 35.646 | 1.00 | 45.61 | sos |
| ATOM | 856 | CH2 | TRP | 696 | 56.005 | 46.022 | 36.639 | 1.00 | 47.75 | sos |
| ATOM | 857 | C | TRP | 696 | 52.739 | 40.079 | 39.198 | 1.00 | 37.78 | sos |
| ATOM | 858 | O | TRP | 696 | 52.798 | 40.207 | 40.415 | 1.00 | 41.13 | sos |
| ATOM | 859 | N | VAL | 697 | 51.597 | 40.108 | 38.532 | 1.00 | 37.38 | sos |
| ATOM | 860 | CA | VAL | 697 | 50.323 | 40.355 | 39.191 | 1.00 | 39.69 | sos |

TABLE 3-continued

PDB Coordinates for the Ras-Sos Structure:
DATA SET FOR REFINED COORDINATES

| ATOM | 861 | CB | VAL | 697 | 49.223 | 40.568 | 38.143 | 1.00 | 40.31 | sos |
|---|---|---|---|---|---|---|---|---|---|---|
| ATOM | 862 | CG1 | VAL | 697 | 47.918 | 40.884 | 38.814 | 1.00 | 42.37 | sos |
| ATOM | 863 | CG2 | VAL | 697 | 49.615 | 41.701 | 37.211 | 1.00 | 41.66 | sos |
| ATOM | 864 | C | VAL | 697 | 49.902 | 39.244 | 40.153 | 1.00 | 39.53 | sos |
| ATOM | 865 | O | VAL | 697 | 49.224 | 39.494 | 41.150 | 1.00 | 34.79 | sos |
| ATOM | 866 | N | GLU | 698 | 50.333 | 38.024 | 39.859 | 1.00 | 41.97 | sos |
| ATOM | 867 | CA | GLU | 698 | 49.993 | 36.862 | 40.670 | 1.00 | 46.79 | sos |
| ATOM | 868 | CB | GLU | 698 | 50.133 | 35.587 | 39.818 | 1.00 | 51.41 | sos |
| ATOM | 869 | CG | GLU | 698 | 49.754 | 34.282 | 40.512 | 1.00 | 55.99 | sos |
| ATOM | 870 | CD | GLU | 698 | 48.261 | 34.151 | 40.766 | 1.00 | 60.96 | sos |
| ATOM | 871 | OE1 | GLU | 698 | 47.822 | 34.445 | 41.897 | 1.00 | 62.22 | sos |
| ATOM | 872 | OE2 | GLU | 698 | 47.525 | 33.736 | 39.843 | 1.00 | 65.34 | sos |
| ATOM | 873 | C | GLU | 698 | 50.818 | 36.729 | 41.954 | 1.00 | 47.14 | sos |
| ATOM | 874 | O | GLU | 698 | 50.262 | 36.666 | 43.048 | 1.00 | 48.55 | sos |
| ATOM | 875 | N | HIS | 699 | 52.140 | 36.713 | 41.814 | 1.00 | 47.82 | sos |
| ATOM | 876 | CA | HIS | 699 | 53.046 | 36.547 | 42.949 | 1.00 | 46.95 | sos |
| ATOM | 877 | CB | HIS | 699 | 54.187 | 35.608 | 42.557 | 1.00 | 47.42 | sos |
| ATOM | 878 | CG | HIS | 699 | 53.721 | 34.286 | 42.042 | 1.00 | 47.76 | sos |
| ATOM | 879 | CD2 | HIS | 699 | 53.895 | 33.684 | 40.842 | 1.00 | 45.49 | sos |
| ATOM | 880 | ND1 | HIS | 699 | 52.944 | 33.430 | 42.791 | 1.00 | 49.64 | sos |
| ATOM | 881 | CE1 | HIS | 699 | 52.658 | 32.358 | 42.074 | 1.00 | 46.66 | sos |
| ATOM | 882 | NE2 | HIS | 699 | 53.224 | 32.487 | 40.888 | 1.00 | 44.42 | sos |
| ATOM | 883 | C | HIS | 699 | 53.627 | 37.809 | 43.585 | 1.00 | 45.43 | sos |
| ATOM | 884 | O | HIS | 699 | 54.258 | 37.729 | 44.645 | 1.00 | 45.22 | sos |
| ATOM | 885 | N | HIS | 700 | 53.434 | 38.964 | 42.957 | 1.00 | 39.42 | sos |
| ATOM | 886 | CA | HIS | 700 | 53.978 | 40.198 | 43.512 | 1.00 | 35.64 | sos |
| ATOM | 887 | CB | HIS | 700 | 55.272 | 40.564 | 42.793 | 1.00 | 31.36 | sos |
| ATOM | 888 | CG | HIS | 700 | 56.323 | 39.505 | 42.872 | 1.00 | 35.18 | sos |
| ATOM | 889 | CD2 | HIS | 700 | 56.690 | 38.539 | 41.999 | 1.00 | 36.14 | sos |
| ATOM | 890 | ND1 | HIS | 700 | 57.083 | 39.307 | 44.005 | 1.00 | 38.78 | sos |
| ATOM | 891 | CE1 | HIS | 700 | 57.868 | 38.260 | 43.828 | 1.00 | 37.18 | sos |
| ATOM | 892 | NE2 | HIS | 700 | 57.649 | 37.776 | 42.619 | 1.00 | 35.62 | sos |
| ATOM | 893 | C | HIS | 700 | 52.990 | 41.348 | 43.459 | 1.00 | 33.92 | sos |
| ATOM | 894 | O | HIS | 700 | 53.359 | 42.479 | 43.180 | 1.00 | 39.51 | sos |
| ATOM | 895 | N | PHE | 701 | 51.746 | 41.079 | 43.823 | 1.00 | 34.30 | sos |
| ATOM | 896 | CA | PHE | 701 | 50.730 | 42.115 | 43.769 | 1.00 | 36.50 | sos |
| ATOM | 897 | CB | PHE | 701 | 49.327 | 41.554 | 44.030 | 1.00 | 33.99 | sos |
| ATOM | 898 | CG | PHE | 701 | 48.228 | 42.427 | 43.488 | 1.00 | 37.18 | sos |
| ATOM | 899 | CD1 | PHE | 701 | 48.064 | 42.584 | 42.113 | 1.00 | 39.62 | sos |
| ATOM | 900 | CD2 | PHE | 701 | 47.380 | 43.122 | 44.343 | 1.00 | 36.70 | sos |
| ATOM | 901 | CE1 | PHE | 701 | 47.068 | 43.425 | 41.598 | 1.00 | 39.69 | sos |
| ATOM | 902 | CE2 | PHE | 701 | 46.386 | 43.963 | 43.839 | 1.00 | 37.32 | sos |
| ATOM | 903 | CZ | PHE | 701 | 46.230 | 44.115 | 42.464 | 4.00 | 35.48 | sos |
| ATOM | 904 | C | PHE | 701 | 50.990 | 43.310 | 44.667 | 1.00 | 37.12 | sos |
| ATOM | 905 | O | PHE | 701 | 50.419 | 44.376 | 44.442 | 1.00 | 38.71 | sos |
| ATOM | 906 | N | TYR | 702 | 51.860 | 43.148 | 45.664 | 1.00 | 39.49 | sos |
| ATOM | 907 | CA | TYR | 702 | 52.174 | 44.249 | 46.581 | 1.00 | 37.66 | sos |
| ATOM | 908 | CB | TYR | 702 | 53.163 | 43.820 | 47.678 | 1.00 | 33.03 | sos |
| ATOM | 909 | CG | TYR | 702 | 54.454 | 43.206 | 47.180 | 1.00 | 32.53 | sos |
| ATOM | 910 | CD1 | TYR | 702 | 55.537 | 44.001 | 46.807 | 1.00 | 34.09 | sos |
| ATOM | 911 | CE1 | TYR | 702 | 56.723 | 43.432 | 46.346 | 1.00 | 33.30 | sos |
| ATOM | 912 | CD2 | TYR | 702 | 54.590 | 41.827 | 47.082 | 1.00 | 30.53 | sos |
| ATOM | 913 | CE2 | TYR | 702 | 55.764 | 41.251 | 46.625 | 1.00 | 30.66 | sos |
| ATOM | 914 | CZ | TYR | 702 | 56.826 | 42.054 | 46.257 | 1.00 | 32.87 | sos |
| ATOM | 915 | OH | TYR | 702 | 57.984 | 41.464 | 45.796 | 1.00 | 36.91 | sos |
| ATOM | 916 | C | TYR | 702 | 52.684 | 45.478 | 45.824 | 1.00 | 37.46 | sos |
| ATOM | 917 | O | TYR | 702 | 52.456 | 46.610 | 46.253 | 1.00 | 37.07 | sos |
| ATOM | 918 | N | ASP | 703 | 53.321 | 45.250 | 44.676 | 1.00 | 34.07 | sos |
| ATOM | 919 | CA | ASP | 703 | 53.819 | 46.344 | 43.852 | 1.00 | 35.59 | sos |
| ATOM | 920 | CB | ASP | 703 | 54.550 | 45.811 | 42.625 | 1.00 | 32.96 | sos |
| ATOM | 921 | CG | ASP | 703 | 56.018 | 45.555 | 42.870 | 1.00 | 33.99 | sos |
| ATOM | 922 | OD1 | ASP | 703 | 56.523 | 45.740 | 44.002 | 1.00 | 35.44 | sos |
| ATOM | 923 | OD2 | ASP | 703 | 56.679 | 45.162 | 41.897 | 1.00 | 32.69 | sos |
| ATOM | 924 | C | ASP | 703 | 52.667 | 47.218 | 43.379 | 1.00 | 38.33 | sos |
| ATOM | 925 | O | ASP | 703 | 52.817 | 48.434 | 43.266 | 1.00 | 40.68 | sos |
| ATOM | 926 | N | PHE | 704 | 51.521 | 46.591 | 43.110 | 1.00 | 37.68 | sos |
| ATOM | 927 | CA | PHE | 704 | 50.333 | 47.299 | 42.629 | 1.00 | 38.03 | sos |
| ATOM | 928 | CB | PHE | 704 | 49.510 | 46.397 | 41.696 | 1.00 | 34.72 | sos |
| ATOM | 929 | CG | PHE | 704 | 50.283 | 45.902 | 40.509 | 1.00 | 32.27 | sos |
| ATOM | 930 | CD1 | PHE | 704 | 50.928 | 44.674 | 40.548 | 1.00 | 33.00 | sos |
| ATOM | 931 | CD2 | PHE | 704 | 50.430 | 46.694 | 39.385 | 1.00 | 30.60 | sos |
| ATOM | 932 | CE1 | PHE | 704 | 51.717 | 44.245 | 39.486 | 1.00 | 33.28 | sos |
| ATOM | 933 | CE2 | PHE | 704 | 51.211 | 46.277 | 38.322 | 1.00 | 33.01 | sos |
| ATOM | 934 | CZ | PHE | 704 | 51.862 | 45.046 | 38.371 | 1.00 | 34.67 | sos |
| ATOM | 935 | C | PHE | 704 | 49.454 | 47.861 | 43.741 | 1.00 | 40.94 | sos |
| ATOM | 936 | O | PHE | 704 | 48.684 | 48.796 | 43.510 | 1.00 | 45.42 | sos |

TABLE 3-continued

PDB Coordinates for the Ras-Sos Structure:
DATA SET FOR REFINED COORDINATES

| ATOM | 937 | N | GLU | 705 | 49.543 | 47.282 | 44.937 | 1.00 | 42.08 | sos |
|---|---|---|---|---|---|---|---|---|---|---|
| ATOM | 938 | CA | GLU | 705 | 48.754 | 47.759 | 46.070 | 1.00 | 42.65 | sos |
| ATOM | 939 | CB | GLU | 705 | 48.749 | 46.731 | 47.201 | 1.00 | 44.94 | sos |
| ATOM | 940 | CG | GLU | 705 | 48.308 | 45.337 | 46.790 | 1.00 | 54.57 | sos |
| ATOM | 941 | CD | GLU | 705 | 48.372 | 44.322 | 47.935 | 1.00 | 60.40 | sos |
| ATOM | 942 | OE1 | GLU | 705 | 49.436 | 44.217 | 48.592 | 1.00 | 59.20 | sos |
| ATOM | 943 | OE2 | GLU | 705 | 47.357 | 43.624 | 48.168 | 1.00 | 57.35 | sos |
| ATOM | 944 | C | GLU | 705 | 49.392 | 49.045 | 46.572 | 1.00 | 41.53 | sos |
| ATOM | 945 | O | GLU | 705 | 48.715 | 49.925 | 47.112 | 1.00 | 38.46 | sos |
| ATOM | 946 | N | ARG | 706 | 50.697 | 49.153 | 46.337 | 1.00 | 40.41 | sos |
| ATOM | 947 | CA | ARG | 706 | 51.488 | 50.297 | 46.769 | 1.00 | 42.57 | sos |
| ATOM | 948 | CB | ARG | 706 | 52.899 | 49.827 | 47.139 | 1.00 | 39.45 | sos |
| ATOM | 949 | CG | ARG | 706 | 52.895 | 48.790 | 48.261 | 1.00 | 38.88 | sos |
| ATOM | 950 | CD | ARG | 706 | 54.275 | 48.268 | 48.610 | 1.00 | 35.98 | sos |
| ATOM | 951 | NE | ARG | 706 | 54.179 | 47.139 | 49.536 | 1.00 | 38.10 | sos |
| ATOM | 952 | CZ | ARG | 706 | 55.222 | 46.541 | 50.105 | 1.00 | 34.18 | sos |
| ATOM | 953 | NH1 | ARG | 706 | 56.450 | 46.973 | 49.855 | 1.00 | 31.53 | sos |
| ATOM | 954 | NH2 | ARG | 706 | 55.038 | 45.474 | 50.877 | 1.00 | 24.47 | sos |
| ATOM | 955 | C | ARG | 706 | 51.548 | 51.463 | 45.787 | 1.00 | 43.28 | sos |
| ATOM | 956 | O | ARG | 706 | 51.980 | 52.553 | 46.150 | 1.00 | 47.69 | sos |
| ATOM | 957 | N | ASP | 707 | 51.117 | 51.240 | 44.551 | 1.00 | 41.42 | sos |
| ATOM | 958 | CA | ASP | 707 | 51.132 | 52.291 | 43.541 | 1.00 | 42.49 | sos |
| ATOM | 959 | CB | ASP | 707 | 52.447 | 52.249 | 42.749 | 1.00 | 42.39 | sos |
| ATOM | 960 | CG | ASP | 707 | 52.600 | 53.421 | 41.778 | 1.00 | 43.12 | sos |
| ATOM | 961 | OD1 | ASP | 707 | 51.662 | 54.238 | 41.631 | 1.00 | 46.34 | sos |
| ATOM | 962 | OD2 | ASP | 707 | 53.678 | 53.525 | 41.158 | 1.00 | 40.90 | sos |
| ATOM | 963 | C | ASP | 707 | 49.942 | 52.141 | 42.605 | 1.00 | 45.28 | sos |
| ATOM | 964 | O | ASP | 707 | 50.014 | 51.432 | 41.602 | 1.00 | 45.83 | sos |
| ATOM | 965 | N | ALA | 708 | 48.865 | 52.854 | 42.921 | 1.00 | 48.09 | sos |
| ATOM | 966 | CA | ALA | 708 | 47.637 | 52.817 | 42.134 | 1.00 | 50.52 | sos |
| ATOM | 967 | CB | ALA | 708 | 46.633 | 53.821 | 42.678 | 1.00 | 50.89 | sos |
| ATOM | 968 | C | ALA | 708 | 47.872 | 53.067 | 40.651 | 1.00 | 51.13 | sos |
| ATOM | 969 | O | ALA | 708 | 47.281 | 52.399 | 39.802 | 1.00 | 54.41 | sos |
| ATOM | 970 | N | TYR | 709 | 48.746 | 54.017 | 40.339 | 1.00 | 51.70 | sos |
| ATOM | 971 | CA | TYR | 709 | 49.036 | 54.332 | 38.945 | 1.00 | 53.36 | sos |
| ATOM | 972 | CB | TYR | 709 | 49.859 | 55.623 | 38.833 | 1.00 | 51.81 | sos |
| ATOM | 973 | CG | TYR | 709 | 50.159 | 56.060 | 37.413 | 1.00 | 51.56 | sos |
| ATOM | 974 | CD1 | TYR | 709 | 49.137 | 56.222 | 36.469 | 1.00 | 53.37 | sos |
| ATOM | 975 | CE1 | TYR | 709 | 49.425 | 56.631 | 35.155 | 1.00 | 50.88 | sos |
| ATOM | 976 | CD2 | TYR | 709 | 51.468 | 56.320 | 37.013 | 1.00 | 50.88 | sos |
| ATOM | 977 | CE2 | TYR | 709 | 51.761 | 56.732 | 35.714 | 1.00 | 50.20 | sos |
| ATOM | 978 | CZ | TYR | 709 | 50.742 | 56.883 | 34.795 | 1.00 | 50.03 | sos |
| ATOM | 979 | OH | TYR | 709 | 51.062 | 57.281 | 33.525 | 1.00 | 48.29 | sos |
| ATOM | 980 | C | TYR | 709 | 49.732 | 53.168 | 38.238 | 1.00 | 52.53 | sos |
| ATOM | 981 | O | TYR | 709 | 49.524 | 52.953 | 37.045 | 1.00 | 56.26 | sos |
| ATOM | 982 | N | LEU | 710 | 50.538 | 52.403 | 38.970 | 1.00 | 48.67 | sos |
| ATOM | 983 | CA | LEU | 710 | 51.217 | 51.265 | 38.366 | 1.00 | 44.49 | sos |
| ATOM | 984 | CB | LEU | 710 | 52.143 | 50.583 | 39.369 | 1.00 | 42.56 | sos |
| ATOM | 985 | CG | LEU | 710 | 52.897 | 49.373 | 38.812 | 1.00 | 42.33 | sos |
| ATOM | 986 | CD1 | LEU | 710 | 54.102 | 49.844 | 38.014 | 1.00 | 43.81 | sos |
| ATOM | 987 | CD2 | LEU | 710 | 53.331 | 48.457 | 39.934 | 1.00 | 40.14 | sos |
| ATOM | 988 | C | LEU | 710 | 50.168 | 50.269 | 37.879 | 1.00 | 42.06 | sos |
| ATOM | 989 | O | LEU | 710 | 50.290 | 49.716 | 36.795 | 1.00 | 40.61 | sos |
| ATOM | 990 | N | LEU | 711 | 49.128 | 50.062 | 38.683 | 1.00 | 41.56 | sos |
| ATOM | 991 | CA | LEU | 711 | 48.065 | 49.136 | 38.324 | 1.00 | 42.83 | sos |
| ATOM | 992 | CB | LEU | 711 | 47.096 | 48.937 | 39.493 | 1.00 | 36.17 | sos |
| ATOM | 993 | CG | LEU | 711 | 45.982 | 47.903 | 39.257 | 1.00 | 33.63 | sos |
| ATOM | 994 | CD1 | LEU | 711 | 46.592 | 46.551 | 38.955 | 1.00 | 26.89 | sos |
| ATOM | 995 | CD2 | LEU | 711 | 45.059 | 47.815 | 40.472 | 1.00 | 29.00 | sos |
| ATOM | 996 | C | LEU | 711 | 47.318 | 49.668 | 37.106 | 1.00 | 48.70 | sos |
| ATOM | 997 | O | LEU | 711 | 47.044 | 48.919 | 36.159 | 1.00 | 49.01 | sos |
| ATOM | 998 | N | GLN | 712 | 47.019 | 50.969 | 37.126 | 1.00 | 48.39 | sos |
| ATOM | 999 | CA | GLN | 712 | 46.323 | 51.622 | 36.023 | 1.00 | 48.33 | sos |
| ATOM | 1000 | CB | GLN | 712 | 46.207 | 53.119 | 36.288 | 1.00 | 49.16 | sos |
| ATOM | 1001 | CG | GLN | 712 | 45.391 | 53.869 | 35.254 | 1.00 | 56.87 | sos |
| ATOM | 1002 | CD | GLN | 712 | 45.306 | 55.355 | 35.546 | 1.00 | 62.93 | sos |
| ATOM | 1003 | OE1 | GLN | 712 | 45.066 | 55.767 | 36.687 | 1.00 | 65.50 | sos |
| ATOM | 1004 | NE2 | GLN | 712 | 45.503 | 56.172 | 34.514 | 1.00 | 64.89 | sos |
| ATOM | 1005 | C | GLN | 712 | 47.056 | 51.375 | 34.699 | 1.00 | 47.63 | sos |
| ATOM | 1006 | O | GLN | 712 | 46.471 | 50.864 | 33.753 | 1.00 | 48.27 | sos |
| ATOM | 1007 | N | ARG | 713 | 48.344 | 51.700 | 34.654 | 1.00 | 46.21 | sos |
| ATOM | 1008 | CA | ARG | 713 | 49.147 | 51.500 | 33.452 | 1.00 | 46.35 | sos |
| ATOM | 1009 | CB | ARG | 713 | 50.608 | 51.883 | 33.697 | 1.00 | 43.47 | sos |
| ATOM | 1010 | CG | ARG | 713 | 50.876 | 53.348 | 33.957 | 1.00 | 35.81 | sos |
| ATOM | 1011 | CD | ARG | 713 | 52.367 | 53.587 | 33.962 | 1.00 | 35.68 | sos |
| ATOM | 1012 | NE | ARG | 713 | 52.949 | 53.135 | 32.704 | 1.00 | 40.74 | sos |

TABLE 3-continued

PDB Coordinates for the Ras-Sos Structure:
DATA SET FOR REFINED COORDINATES

| ATOM | 1013 | CZ  | ARG | 713 | 54.212 | 52.753 | 32.536 | 1.00 | 44.52 | sos |
|------|------|-----|-----|-----|--------|--------|--------|------|-------|-----|
| ATOM | 1014 | NH1 | ARG | 713 | 55.069 | 52.759 | 33.550 | 1.00 | 44.85 | sos |
| ATOM | 1015 | NH2 | ARG | 713 | 54.619 | 52.364 | 31.338 | 1.00 | 47.71 | sos |
| ATOM | 1016 | C   | ARG | 713 | 49.092 | 50.045 | 32.994 | 1.00 | 50.79 | sos |
| ATOM | 1017 | O   | ARG | 713 | 49.167 | 49.766 | 31.795 | 1.00 | 53.73 | sos |
| ATOM | 1018 | N   | MET | 714 | 48.999 | 49.124 | 33.955 | 1.00 | 51.70 | sos |
| ATOM | 1019 | CA  | MET | 714 | 48.924 | 47.696 | 33.658 | 1.00 | 53.37 | sos |
| ATOM | 1020 | CB  | MET | 714 | 49.147 | 46.870 | 34.917 | 1.00 | 52.18 | sos |
| ATOM | 1021 | CG  | MET | 714 | 50.419 | 46.055 | 34.891 | 1.00 | 55.86 | sos |
| ATOM | 1022 | SD  | MET | 714 | 50.334 | 44.698 | 33.742 | 1.00 | 51.90 | sos |
| ATOM | 1023 | CE  | MET | 714 | 48.874 | 43.928 | 34.369 | 1.00 | 52.55 | sos |
| ATOM | 1024 | C   | MET | 714 | 47.577 | 47.340 | 33.054 | 1.00 | 55.72 | sos |
| ATOM | 1025 | O   | MET | 714 | 47.509 | 46.552 | 32.114 | 1.00 | 55.68 | sos |
| ATOM | 1026 | N   | GLU | 715 | 46.507 | 47.916 | 33.602 | 1.00 | 57.20 | sos |
| ATOM | 1027 | CA  | GLU | 715 | 45.161 | 47.664 | 33.097 | 1.00 | 60.51 | sos |
| ATOM | 1028 | CB  | GLU | 715 | 44.107 | 48.133 | 34.108 | 1.00 | 58.42 | sos |
| ATOM | 1029 | CG  | GLU | 715 | 44.194 | 47.353 | 35.419 | 1.00 | 63.35 | sos |
| ATOM | 1030 | CD  | GLU | 715 | 42.966 | 47.483 | 36.304 | 1.00 | 63.90 | sos |
| ATOM | 1031 | OE1 | GLU | 715 | 42.110 | 46.576 | 36.270 | 1.00 | 63.21 | sos |
| ATOM | 1032 | OE2 | GLU | 715 | 42.868 | 48.470 | 37.060 | 1.00 | 67.20 | sos |
| ATOM | 1033 | C   | GLU | 715 | 44.958 | 48.296 | 31.710 | 1.00 | 62.15 | sos |
| ATOM | 1034 | O   | GLU | 715 | 44.268 | 47.727 | 30.854 | 1.00 | 60.89 | sos |
| ATOM | 1035 | N   | GLU | 716 | 45.604 | 49.440 | 31.480 | 1.00 | 63.15 | sos |
| ATOM | 1036 | CA  | GLU | 716 | 45.529 | 50.127 | 30.195 | 1.00 | 65.01 | sos |
| ATOM | 1037 | CB  | GLU | 716 | 46.118 | 51.542 | 30.279 | 1.00 | 67.96 | sos |
| ATOM | 1038 | CG  | GLU | 716 | 45.298 | 52.538 | 31.114 | 1.00 | 76.79 | sos |
| ATOM | 1039 | CD  | GLU | 716 | 45.879 | 53.961 | 31.110 | 1.00 | 82.50 | sos |
| ATOM | 1040 | OE1 | GLU | 716 | 47.122 | 54.113 | 31.115 | 1.00 | 84.75 | sos |
| ATOM | 1041 | OE2 | GLU | 716 | 45.089 | 54.933 | 31.109 | 1.00 | 84.28 | sos |
| ATOM | 1042 | C   | GLU | 716 | 46.305 | 49.304 | 29.172 | 1.00 | 64.83 | sos |
| ATOM | 1043 | O   | GLU | 716 | 45.849 | 49.128 | 28.047 | 1.00 | 68.50 | sos |
| ATOM | 1044 | N   | PHE | 717 | 47.463 | 48.786 | 29.579 | 1.00 | 62.42 | sos |
| ATOM | 1045 | CA  | PHE | 717 | 48.300 | 47.969 | 28.706 | 1.00 | 59.61 | sos |
| ATOM | 1046 | CB  | PHE | 717 | 49.641 | 47.677 | 29.362 | 1.00 | 56.95 | sos |
| ATOM | 1047 | CG  | PHE | 717 | 50.461 | 46.664 | 28.620 | 1.00 | 56.51 | sos |
| ATOM | 1048 | CD1 | PHE | 717 | 50.939 | 46.937 | 27.340 | 1.00 | 54.86 | sos |
| ATOM | 1049 | CD2 | PHE | 717 | 50.745 | 45.429 | 29.192 | 1.00 | 56.64 | sos |
| ATOM | 1050 | CE1 | PHE | 717 | 51.688 | 45.993 | 26.640 | 1.00 | 56.61 | sos |
| ATOM | 1051 | CE2 | PHE | 717 | 51.494 | 44.476 | 28.499 | 1.00 | 58.56 | sos |
| ATOM | 1052 | CZ  | PHE | 717 | 51.967 | 44.759 | 27.219 | 1.00 | 56.81 | sos |
| ATOM | 1053 | C   | PHE | 717 | 47.638 | 46.646 | 28.339 | 1.00 | 63.89 | sos |
| ATOM | 1054 | O   | PHE | 717 | 47.737 | 46.199 | 27.195 | 1.00 | 63.15 | sos |
| ATOM | 1055 | N   | ILE | 718 | 47.040 | 45.986 | 29.331 | 1.00 | 66.60 | sos |
| ATOM | 1056 | CA  | ILE | 718 | 46.347 | 44.718 | 29.111 | 1.00 | 67.17 | sos |
| ATOM | 1057 | CB  | ILE | 718 | 45.750 | 44.153 | 30.437 | 1.00 | 66.94 | sos |
| ATOM | 1058 | CG2 | ILE | 718 | 44.725 | 43.059 | 30.154 | 1.00 | 66.53 | sos |
| ATOM | 1059 | CG1 | ILE | 718 | 46.859 | 43.588 | 31.327 | 1.00 | 62.82 | sos |
| ATOM | 1060 | CD1 | ILE | 718 | 47.549 | 42.376 | 30.757 | 1.00 | 61.97 | sos |
| ATOM | 1061 | C   | ILE | 718 | 45.232 | 44.961 | 28.093 | 1.00 | 69.02 | sos |
| ATOM | 1062 | O   | ILE | 718 | 45.061 | 44.178 | 27.157 | 1.00 | 68.81 | sos |
| ATOM | 1063 | N   | GLY | 719 | 44.520 | 46.078 | 28.253 | 1.00 | 69.67 | sos |
| ATOM | 1064 | CA  | GLY | 719 | 43.442 | 46.431 | 27.340 | 1.00 | 71.55 | sos |
| ATOM | 1065 | C   | GLY | 719 | 43.898 | 46.906 | 25.965 | 1.00 | 72.80 | sos |
| ATOM | 1066 | O   | GLY | 719 | 43.076 | 47.243 | 25.118 | 1.00 | 73.22 | sos |
| ATOM | 1067 | N   | THR | 720 | 45.210 | 46.939 | 25.748 | 1.00 | 74.43 | sos |
| ATOM | 1068 | CA  | THR | 720 | 45.803 | 47.362 | 24.480 | 1.00 | 75.60 | sos |
| ATOM | 1069 | CB  | THR | 720 | 47.072 | 48.247 | 24.748 | 1.00 | 76.04 | sos |
| ATOM | 1070 | OG1 | THR | 720 | 46.669 | 49.610 | 24.939 | 1.00 | 74.75 | sos |
| ATOM | 1071 | CG2 | THR | 720 | 48.106 | 48.172 | 23.618 | 1.00 | 75.11 | sos |
| ATOM | 1072 | C   | THR | 720 | 46.122 | 46.152 | 23.583 | 1.00 | 78.01 | sos |
| ATOM | 1073 | O   | THR | 720 | 46.484 | 46.308 | 22.413 | 1.00 | 78.76 | sos |
| ATOM | 1074 | N   | VAL | 721 | 45.946 | 44.946 | 24.118 | 1.00 | 78.71 | sos |
| ATOM | 1075 | CA  | VAL | 721 | 46.215 | 43.730 | 23.357 | 1.00 | 80.46 | sos |
| ATOM | 1076 | CB  | VAL | 721 | 46.054 | 42.472 | 24.233 | 1.00 | 80.43 | sos |
| ATOM | 1077 | CG1 | VAL | 721 | 46.234 | 41.210 | 23.397 | 1.00 | 81.36 | sos |
| ATOM | 1078 | CG2 | VAL | 721 | 47.077 | 42.497 | 25.349 | 1.00 | 80.51 | sos |
| ATOM | 1079 | C   | VAL | 721 | 45.293 | 43.655 | 22.144 | 1.00 | 81.83 | sos |
| ATOM | 1080 | O   | VAL | 721 | 44.074 | 43.785 | 22.269 | 1.00 | 80.46 | sos |
| ATOM | 1081 | N   | ARG | 722 | 45.895 | 43.453 | 20.973 | 1.00 | 84.66 | sos |
| ATOM | 1082 | CA  | ARG | 722 | 45.160 | 43.393 | 19.711 | 1.00 | 88.60 | sos |
| ATOM | 1083 | CB  | ARG | 722 | 46.015 | 43.969 | 18.575 | 1.00 | 89.89 | sos |
| ATOM | 1084 | CG  | ARG | 722 | 46.496 | 45.391 | 18.809 | 0.00 | 90.39 | sos |
| ATOM | 1085 | CD  | ARG | 722 | 47.384 | 45.863 | 17.668 | 0.00 | 91.12 | sos |
| ATOM | 1086 | NE  | ARG | 722 | 47.913 | 47.205 | 17.897 | 0.00 | 91.66 | sos |
| ATOM | 1087 | CZ  | ARG | 722 | 48.957 | 47.482 | 18.674 | 0.00 | 91.94 | sos |
| ATOM | 1088 | NH1 | ARG | 722 | 49.600 | 46.510 | 19.308 | 0.00 | 92.12 | sos |

TABLE 3-continued

PDB Coordinates for the Ras-Sos Structure:
DATA SET FOR REFINED COORDINATES

| ATOM | 1089 | NH2 | ARG | 722 | 49.361 | 48.737 | 18.817 | 0.00 | 92.12 | sos |
|---|---|---|---|---|---|---|---|---|---|---|
| ATOM | 1090 | C | ARG | 722 | 44.637 | 42.017 | 19.303 | 1.00 | 89.53 | sos |
| ATOM | 1091 | O | ARG | 722 | 43.441 | 41.862 | 19.054 | 1.00 | 91.26 | sos |
| ATOM | 1092 | N | GLY | 723 | 45.536 | 41.037 | 19.206 | 1.00 | 89.38 | sos |
| ATOM | 1093 | CA | GLY | 723 | 45.161 | 39.687 | 18.802 | 1.00 | 91.07 | sos |
| ATOM | 1094 | C | GLY | 723 | 43.798 | 39.175 | 19.246 | 1.00 | 91.71 | sos |
| ATOM | 1095 | O | GLY | 723 | 43.537 | 39.048 | 20.445 | 1.00 | 91.80 | sos |
| ATOM | 1096 | N | LYS | 724 | 42.928 | 38.888 | 18.276 | 1.00 | 92.09 | sos |
| ATOM | 1097 | CA | LYS | 724 | 41.576 | 38.379 | 18.544 | 1.00 | 92.24 | sos |
| ATOM | 1098 | CB | LYS | 724 | 40.838 | 38.102 | 17.231 | 1.00 | 92.49 | sos |
| ATOM | 1099 | CG | LYS | 724 | 40.618 | 39.335 | 16.367 | 0.00 | 93.20 | sos |
| ATOM | 1100 | CD | LYS | 724 | 39.910 | 38.988 | 15.065 | 0.00 | 93.68 | sos |
| ATOM | 1101 | CE | LYS | 724 | 38.518 | 38.424 | 15.316 | 0.00 | 94.01 | sos |
| ATOM | 1102 | NZ | LYS | 724 | 37.827 | 38.071 | 14.045 | 0.00 | 94.27 | sos |
| ATOM | 1103 | C | LYS | 724 | 41.620 | 37.107 | 19.392 | 1.00 | 91.16 | sos |
| ATOM | 1104 | O | LYS | 724 | 40.727 | 36.851 | 20.204 | 1.00 | 90.41 | sos |
| ATOM | 1105 | N | ALA | 725 | 42.666 | 36.313 | 19.184 | 1.00 | 89.30 | sos |
| ATOM | 1106 | CA | ALA | 725 | 42.867 | 35.083 | 19.931 | 1.00 | 86.44 | sos |
| ATOM | 1107 | CB | ALA | 725 | 43.709 | 34.110 | 19.123 | 1.00 | 88.36 | sos |
| ATOM | 1108 | C | ALA | 725 | 43.557 | 35.414 | 21.249 | 1.00 | 84.63 | sos |
| ATOM | 1109 | O | ALA | 725 | 43.234 | 34.835 | 22.280 | 1.00 | 84.48 | sos |
| ATOM | 1110 | N | MET | 726 | 44.494 | 36.361 | 21.212 | 1.00 | 83.16 | sos |
| ATOM | 1111 | CA | MET | 726 | 45.219 | 36.766 | 22.413 | 1.00 | 83.95 | sos |
| ATOM | 1112 | CB | MET | 726 | 46.336 | 37.755 | 22.088 | 1.00 | 87.18 | sos |
| ATOM | 1113 | CG | MET | 726 | 47.613 | 37.122 | 21.592 | 1.00 | 91.73 | sos |
| ATOM | 1114 | SD | MET | 726 | 49.015 | 38.215 | 21.876 | 1.00 | 97.34 | sos |
| ATOM | 1115 | CE | MET | 726 | 48.756 | 39.472 | 20.605 | 1.00 | 96.71 | sos |
| ATOM | 1116 | C | MET | 726 | 44.333 | 37.363 | 23.497 | 1.00 | 82.55 | sos |
| ATOM | 1117 | O | MET | 726 | 44.609 | 37.187 | 24.682 | 1.00 | 82.24 | sos |
| ATOM | 1118 | N | LYS | 727 | 43.292 | 38.091 | 23.099 | 1.00 | 80.36 | sos |
| ATOM | 1119 | CA | LYS | 727 | 42.380 | 38.697 | 24.066 | 1.00 | 80.95 | sos |
| ATOM | 1120 | CB | LYS | 727 | 41.258 | 39.461 | 23.366 | 1.00 | 82.96 | sos |
| ATOM | 1121 | CG | LYS | 727 | 41.669 | 40.705 | 22.612 | 1.00 | 84.74 | sos |
| ATOM | 1122 | CD | LYS | 727 | 40.432 | 41.339 | 22.001 | 1.00 | 87.13 | sos |
| ATOM | 1123 | CE | LYS | 727 | 40.779 | 42.476 | 21.070 | 1.00 | 89.55 | sos |
| ATOM | 1124 | NZ | LYS | 727 | 39.567 | 42.952 | 20.348 | 1.00 | 93.43 | sos |
| ATOM | 1125 | C | LYS | 727 | 41.752 | 37.636 | 24.964 | 1.00 | 80.60 | sos |
| ATOM | 1126 | O | LYS | 727 | 41.663 | 37.818 | 26.176 | 1.00 | 80.84 | sos |
| ATOM | 1127 | N | LYS | 728 | 41.315 | 36.534 | 24.359 | 1.00 | 80.37 | sos |
| ATOM | 1128 | CA | LYS | 728 | 40.684 | 35.438 | 25.095 | 1.00 | 79.77 | sos |
| ATOM | 1129 | CB | LYS | 728 | 40.125 | 34.392 | 24.113 | 1.00 | 79.76 | sos |
| ATOM | 1130 | CG | LYS | 728 | 39.343 | 33.249 | 24.761 | 1.00 | 76.63 | sos |
| ATOM | 1131 | CD | LYS | 728 | 38.103 | 33.748 | 25.486 | 1.00 | 76.50 | sos |
| ATOM | 1132 | CE | LYS | 728 | 37.435 | 32.623 | 26.264 | 1.00 | 81.32 | sos |
| ATOM | 1133 | NZ | LYS | 728 | 36.263 | 33.086 | 27.066 | 1.00 | 82.40 | sos |
| ATOM | 1134 | C | LYS | 728 | 41.659 | 34.790 | 26.080 | 1.00 | 77.73 | sos |
| ATOM | 1135 | O | LYS | 728 | 41.256 | 34.299 | 27.137 | 1.00 | 79.45 | sos |
| ATOM | 1136 | N | TRP | 729 | 42.940 | 34.805 | 25.730 | 1.00 | 74.08 | sos |
| ATOM | 1137 | CA | TRP | 729 | 43.983 | 34.231 | 26.571 | 1.00 | 72.50 | sos |
| ATOM | 1138 | CB | TRP | 729 | 45.212 | 33.919 | 25.705 | 1.00 | 71.91 | sos |
| ATOM | 1139 | CG | TRP | 729 | 46.367 | 33.303 | 26.437 | 1.00 | 72.24 | sos |
| ATOM | 1140 | CD2 | TRP | 729 | 47.664 | 33.883 | 26.629 | 1.00 | 74.22 | sos |
| ATOM | 1141 | CE2 | TRP | 729 | 48.434 | 32.954 | 27.364 | 1.00 | 74.73 | sos |
| ATOM | 1142 | CE3 | TRP | 729 | 48.251 | 35.101 | 26.253 | 1.00 | 72.05 | sos |
| ATOM | 1143 | CD1 | TRP | 729 | 46.401 | 32.080 | 27.044 | 1.00 | 72.76 | sos |
| ATOM | 1144 | NE1 | TRP | 729 | 47.640 | 31.861 | 27.604 | 1.00 | 73.69 | sos |
| ATOM | 1145 | CZ2 | TRP | 729 | 49.760 | 33.205 | 27.732 | 1.00 | 73.90 | sos |
| ATOM | 1146 | CZ3 | TRP | 729 | 49.568 | 35.348 | 26.617 | 1.00 | 70.88 | sos |
| ATOM | 1147 | CH2 | TRP | 729 | 50.307 | 34.404 | 27.350 | 1.00 | 73.01 | sos |
| ATOM | 1148 | C | TRP | 729 | 44.339 | 35.211 | 27.694 | 1.00 | 71.13 | sos |
| ATOM | 1149 | O | TRP | 729 | 44.555 | 34.812 | 28.842 | 1.00 | 72.64 | sos |
| ATOM | 1150 | N | VAL | 730 | 44.356 | 36.497 | 27.347 | 1.00 | 68.50 | sos |
| ATOM | 1151 | CA | VAL | 730 | 44.676 | 37.590 | 28.267 | 1.00 | 64.02 | sos |
| ATOM | 1152 | CB | VAL | 730 | 45.012 | 38.880 | 27.453 | 1.00 | 61.57 | sos |
| ATOM | 1153 | CG1 | VAL | 730 | 44.657 | 40.145 | 28.211 | 1.00 | 59.12 | sos |
| ATOM | 1154 | CG2 | VAL | 730 | 46.491 | 38.879 | 27.095 | 1.00 | 57.17 | sos |
| ATOM | 1155 | C | VAL | 730 | 43.591 | 37.836 | 29.323 | 1.00 | 62.13 | sos |
| ATOM | 1156 | O | VAL | 730 | 43.816 | 38.530 | 30.313 | 1.00 | 61.69 | sos |
| ATOM | 1157 | N | GLU | 731 | 42.425 | 37.231 | 29.124 | 1.00 | 61.36 | sos |
| ATOM | 1158 | CA | GLU | 731 | 41.322 | 37.364 | 30.066 | 1.00 | 61.49 | sos |
| ATOM | 1159 | CB | GLU | 731 | 40.044 | 36.753 | 29.491 | 1.00 | 61.73 | sos |
| ATOM | 1160 | CG | GLU | 731 | 39.466 | 37.531 | 28.317 | 1.00 | 62.97 | sos |
| ATOM | 1161 | CD | GLU | 731 | 38.180 | 36.936 | 27.767 | 1.00 | 64.83 | sos |
| ATOM | 1162 | OE1 | GLU | 731 | 37.575 | 36.065 | 28.439 | 1.00 | 60.42 | sos |
| ATOM | 1163 | OE2 | GLU | 731 | 37.778 | 37.352 | 26.654 | 1.00 | 63.04 | sos |
| ATOM | 1164 | C | GLU | 731 | 41.685 | 36.672 | 31.370 | 1.00 | 62.16 | sos |

TABLE 3-continued

PDB Coordinates for the Ras-Sos Structure:
DATA SET FOR REFINED COORDINATES

| ATOM | 1165 | O | GLU | 731 | 41.172 | 37.020 | 32.433 | 1.00 | 59.79 | sos |
|------|------|-----|-----|-----|--------|--------|--------|------|-------|-----|
| ATOM | 1166 | N | SER | 732 | 42.577 | 35.688 | 31.275 | 1.00 | 64.99 | sos |
| ATOM | 1167 | CA | SER | 732 | 43.033 | 34.946 | 32.445 | 1.00 | 68.71 | sos |
| ATOM | 1168 | CB | SER | 732 | 43.860 | 33.730 | 32.023 | 1.00 | 71.02 | sos |
| ATOM | 1169 | OG | SER | 732 | 43.076 | 32.822 | 31.262 | 1.00 | 75.70 | sos |
| ATOM | 1170 | C | SER | 732 | 43.850 | 35.861 | 33.355 | 1.00 | 68.64 | sos |
| ATOM | 1171 | O | SER | 732 | 43.802 | 35.722 | 34.577 | 1.00 | 70.37 | sos |
| ATOM | 1172 | N | ILE | 733 | 44.578 | 36.804 | 32.749 | 1.00 | 65.31 | sos |
| ATOM | 1173 | CA | ILE | 733 | 45.396 | 37.769 | 33.490 | 1.00 | 61.66 | sos |
| ATOM | 1174 | CB | ILE | 733 | 46.348 | 38.551 | 32.547 | 1.00 | 62.26 | sos |
| ATOM | 1175 | CG2 | ILE | 733 | 47.090 | 39.638 | 33.309 | 1.00 | 58.02 | sos |
| ATOM | 1176 | CG1 | ILE | 733 | 47.348 | 37.591 | 31.897 | 1.00 | 64.07 | sos |
| ATOM | 1177 | CD1 | ILE | 733 | 48.420 | 38.283 | 31.089 | 1.00 | 65.07 | sos |
| ATOM | 1178 | C | ILE | 733 | 44.494 | 38.759 | 34.212 | 1.00 | 58.17 | sos |
| ATOM | 1179 | O | ILE | 733 | 44.720 | 39.093 | 35.374 | 1.00 | 58.75 | sos |
| ATOM | 1180 | N | THR | 734 | 43.466 | 39.216 | 33.506 | 1.00 | 58.09 | sos |
| ATOM | 1181 | CA | THR | 734 | 42.489 | 40.163 | 34.041 | 1.00 | 56.56 | sos |
| ATOM | 1182 | CB | THR | 734 | 41.445 | 40.550 | 32.952 | 1.00 | 56.88 | sos |
| ATOM | 1183 | OG1 | THR | 734 | 42.109 | 41.179 | 31.846 | 1.00 | 56.11 | sos |
| ATOM | 1184 | CG2 | THR | 734 | 40.384 | 41.485 | 33.514 | 1.00 | 49.36 | sos |
| ATOM | 1185 | C | THR | 734 | 41.766 | 39.561 | 35.251 | 1.00 | 54.23 | sos |
| ATOM | 1186 | O | THR | 734 | 41.508 | 40.254 | 36.232 | 1.00 | 52.16 | sos |
| ATOM | 1187 | N | LYS | 735 | 41.466 | 38.265 | 35.179 | 1.00 | 54.07 | sos |
| ATOM | 1188 | CA | LYS | 735 | 40.778 | 37.561 | 36.259 | 1.00 | 54.15 | sos |
| ATOM | 1189 | CB | LYS | 735 | 40.444 | 36.122 | 35.846 | 1.00 | 55.25 | sos |
| ATOM | 1190 | CG | LYS | 735 | 39.701 | 35.316 | 36.906 | 0.00 | 55.31 | sos |
| ATOM | 1191 | CD | LYS | 735 | 38.351 | 35.936 | 37.241 | 0.00 | 55.67 | sos |
| ATOM | 1192 | CE | LYS | 735 | 37.654 | 35.179 | 38.362 | 0.00 | 55.80 | sos |
| ATOM | 1193 | NZ | LYS | 735 | 38.434 | 35.211 | 39.632 | 0.00 | 56.00 | sos |
| ATOM | 1194 | C | LYS | 735 | 41.612 | 37.564 | 37.532 | 1.00 | 52.61 | sos |
| ATOM | 1195 | O | LYS | 735 | 41.074 | 37.754 | 38.621 | 1.00 | 53.85 | sos |
| ATOM | 1196 | N | ILE | 736 | 42.924 | 37.372 | 37.385 | 1.00 | 50.79 | sos |
| ATOM | 1197 | CA | ILE | 736 | 43.841 | 37.374 | 38.525 | 1.00 | 46.96 | sos |
| ATOM | 1198 | CB | ILE | 736 | 45.282 | 37.043 | 38.100 | 1.00 | 45.10 | sos |
| ATOM | 1199 | CG2 | ILE | 736 | 46.214 | 37.130 | 39.297 | 1.00 | 46.50 | sos |
| ATOM | 1200 | CG1 | ILE | 736 | 45.345 | 35.642 | 37.497 | 1.00 | 44.88 | sos |
| ATOM | 1201 | CD1 | ILE | 736 | 46.696 | 35.286 | 36.894 | 1.00 | 44.72 | sos |
| ATOM | 1202 | C | ILE | 736 | 43.828 | 38.746 | 39.193 | 1.00 | 47.19 | sos |
| ATOM | 1203 | O | ILE | 736 | 43.761 | 38.837 | 40.416 | 1.00 | 46.57 | sos |
| ATOM | 1204 | N | ILE | 737 | 43.872 | 39.808 | 38.389 | 1.00 | 46.27 | sos |
| ATOM | 1205 | CA | ILE | 737 | 43.847 | 41.168 | 38.924 | 1.00 | 47.84 | sos |
| ATOM | 1206 | CB | ILE | 737 | 43.942 | 42.234 | 37.810 | 1.00 | 45.05 | sos |
| ATOM | 1207 | CG2 | ILE | 737 | 43.766 | 43.624 | 38.388 | 1.00 | 38.43 | sos |
| ATOM | 1208 | CG1 | ILE | 737 | 45.284 | 42.128 | 37.091 | 1.00 | 44.64 | sos |
| ATOM | 1209 | CD1 | ILE | 737 | 45.575 | 43.285 | 36.180 | 1.00 | 45.58 | sos |
| ATOM | 1210 | C | ILE | 737 | 42.584 | 41.413 | 39.748 | 1.00 | 51.60 | sos |
| ATOM | 1211 | O | ILE | 737 | 42.668 | 41.834 | 40.898 | 1.00 | 54.86 | sos |
| ATOM | 1212 | N | GLN | 738 | 41.422 | 41.110 | 39.175 | 1.00 | 56.90 | sos |
| ATOM | 1213 | CA | GLN | 738 | 40.149 | 41.302 | 39.870 | 1.00 | 60.42 | sos |
| ATOM | 1214 | CG | GLN | 738 | 38.980 | 40.925 | 38.960 | 1.00 | 61.43 | sos |
| ATOM | 1215 | CG | GLN | 738 | 38.876 | 41.768 | 37.700 | 0.00 | 61.69 | sos |
| ATOM | 1216 | CD | GLN | 738 | 37.731 | 41.338 | 36.806 | 0.00 | 62.01 | sos |
| ATOM | 1217 | OE1 | GLN | 738 | 37.840 | 40.363 | 36.062 | 0.00 | 62.13 | sos |
| ATOM | 1218 | NE2 | GLN | 738 | 36.622 | 42.066 | 36.873 | 0.00 | 62.13 | sos |
| ATOM | 1219 | C | GLN | 738 | 40.079 | 40.500 | 41.170 | 1.00 | 62.11 | sos |
| ATOM | 1220 | O | GLN | 738 | 39.466 | 40.937 | 42.144 | 1.00 | 61.69 | sos |
| ATOM | 1221 | N | ARG | 739 | 40.740 | 39.345 | 41.185 | 1.00 | 64.06 | sos |
| ATOM | 1222 | CA | ARG | 739 | 40.769 | 38.471 | 42.356 | 1.00 | 67.21 | sos |
| ATOM | 1223 | CB | ARG | 739 | 41.410 | 37.131 | 41.986 | 1.00 | 71.05 | sos |
| ATOM | 1224 | CG | ARG | 739 | 41.534 | 36.117 | 43.120 | 1.00 | 73.84 | sos |
| ATOM | 1225 | CD | ARG | 739 | 42.331 | 34.893 | 42.666 | 1.00 | 79.39 | sos |
| ATOM | 1226 | NE | ARG | 739 | 41.766 | 34.287 | 41.458 | 1.00 | 86.04 | sos |
| ATOM | 1227 | CZ | ARG | 739 | 42.485 | 33.843 | 40.429 | 1.00 | 88.92 | sos |
| ATOM | 1228 | NH1 | ARG | 739 | 43.813 | 33.932 | 40.459 | 1.00 | 90.12 | sos |
| ATOM | 1229 | NH2 | ARG | 739 | 41.877 | 33.325 | 39.362 | 1.00 | 85.58 | sos |
| ATOM | 1230 | C | ARG | 739 | 41.536 | 39.106 | 43.516 | 1.00 | 67.79 | sos |
| ATOM | 1231 | O | ARG | 739 | 41.093 | 39.039 | 44.667 | 1.00 | 69.45 | sos |
| ATOM | 1232 | N | LYS | 740 | 42.669 | 39.735 | 43.199 | 1.00 | 64.96 | sos |
| ATOM | 1233 | CA | LYS | 740 | 43.532 | 40.387 | 44.189 | 1.00 | 63.69 | sos |
| ATOM | 1234 | CB | LYS | 740 | 44.883 | 40.722 | 43.561 | 1.00 | 59.37 | sos |
| ATOM | 1235 | CG | LYS | 740 | 45.653 | 39.535 | 43.020 | 1.00 | 57.16 | sos |
| ATOM | 1236 | CD | LYS | 740 | 46.112 | 38.616 | 44.131 | 1.00 | 53.16 | sos |
| ATOM | 1237 | CE | LYS | 740 | 47.139 | 37.636 | 43.613 | 1.00 | 50.16 | sos |
| ATOM | 1238 | NZ | LYS | 740 | 47.875 | 37.003 | 44.734 | 1.00 | 51.16 | sos |
| ATOM | 1239 | C | LYS | 740 | 42.955 | 41.665 | 44.796 | 1.00 | 66.36 | sos |
| ATOM | 1240 | O | LYS | 740 | 43.651 | 42.377 | 45.521 | 1.00 | 66.35 | sos |

TABLE 3-continued

PDB Coordinates for the Ras-Sos Structure:
DATA SET FOR REFINED COORDINATES

| ATOM | 1241 | N   | LYS | 741 | 41.685   | 41.948   | 44.512   | 1.00 | 70.30 | sos |
|------|------|-----|-----|-----|----------|----------|----------|------|-------|-----|
| ATOM | 1242 | CA  | LYS | 741 | 41.018   | 43.151   | 45.020   | 1.00 | 71.17 | sos |
| ATOM | 1243 | CB  | LYS | 741 | 40.865   | 44.162   | 43.873   | 1.00 | 71.10 | sos |
| ATOM | 1244 | CG  | LYS | 741 | 42.187   | 44.479   | 43.159   | 1.00 | 68.75 | sos |
| ATOM | 1245 | CD  | LYS | 741 | 42.008   | 44.834   | 41.684   | 1.00 | 67.10 | sos |
| ATOM | 1246 | CE  | LYS | 741 | 41.373   | 46.201   | 41.478   | 1.00 | 65.78 | sos |
| ATOM | 1247 | NZ  | LYS | 741 | 41.350   | 46.600   | 40.033   | 1.00 | 64.32 | sos |
| ATOM | 1248 | C   | LYS | 741 | 39.646   | 42.835   | 45.640   | 1.00 | 71.08 | sos |
| ATOM | 1249 | O   | LYS | 741 | 39.598   | 42.075   | 46.639   | 1.00 | 67.97 | sos |
| ATOM | 1250 | OT  | LYS | 741 | 9999.000 | 9999.000 | 9999.000 | 1.00 | 0.00  | sos |
| ATOM | 1251 | CB  | ILE | 752 | 46.737   | 19.718   | 55.540   | 1.00 | 83.59 | sos |
| ATOM | 1252 | CG2 | ILE | 752 | 47.927   | 18.797   | 55.260   | 1.00 | 79.74 | sos |
| ATOM | 1253 | CG1 | ILE | 752 | 46.949   | 21.082   | 54.871   | 1.00 | 85.23 | sos |
| ATOM | 1254 | CD1 | ILE | 752 | 47.082   | 21.036   | 53.356   | 1.00 | 86.58 | sos |
| ATOM | 1255 | C   | ILE | 752 | 44.953   | 18.059   | 56.094   | 1.00 | 82.97 | sos |
| ATOM | 1256 | O   | ILE | 752 | 44.854   | 18.393   | 57.276   | 1.00 | 83.53 | sos |
| ATOM | 1257 | N   | ILE | 752 | 44.347   | 20.076   | 54.818   | 1.00 | 83.95 | sos |
| ATOM | 1258 | CA  | ILE | 752 | 45.420   | 19.061   | 55.040   | 1.00 | 83.18 | sos |
| ATOM | 1259 | N   | THR | 753 | 44.650   | 16.840   | 55.653   | 1.00 | 82.13 | sos |
| ATOM | 1260 | CA  | THR | 753 | 44.195   | 15.777   | 56.549   | 1.00 | 81.07 | sos |
| ATOM | 1261 | CB  | THR | 753 | 43.154   | 14.861   | 55.848   | 1.00 | 80.20 | sos |
| ATOM | 1262 | OG1 | THR | 753 | 42.067   | 15.661   | 55.369   | 1.00 | 81.37 | sos |
| ATOM | 1263 | CG2 | THR | 753 | 42.603   | 13.810   | 56.813   | 1.00 | 76.74 | sos |
| ATOM | 1264 | C   | THR | 753 | 45.382   | 14.938   | 57.019   | 1.00 | 80.17 | sos |
| ATOM | 1265 | O   | THR | 753 | 46.034   | 14.264   | 56.221   | 1.00 | 81.94 | sos |
| ATOM | 1266 | N   | PHE | 754 | 45.669   | 14.999   | 58.315   | 1.00 | 78.70 | sos |
| ATOM | 1267 | CA  | PHE | 754 | 46.776   | 14.243   | 58.893   | 1.00 | 79.92 | sos |
| ATOM | 1268 | CB  | PHE | 754 | 47.146   | 14.796   | 60.279   | 1.00 | 79.28 | sos |
| ATOM | 1269 | CG  | PHE | 754 | 47.642   | 16.215   | 60.257   | 1.00 | 75.33 | sos |
| ATOM | 1270 | CD1 | PHE | 754 | 46.828   | 17.255   | 60.697   | 1.00 | 75.05 | sos |
| ATOM | 1271 | CD2 | PHE | 754 | 48.911   | 16.514   | 59.776   | 1.00 | 74.87 | sos |
| ATOM | 1272 | CE1 | PHE | 754 | 47.269   | 18.578   | 60.655   | 1.00 | 76.53 | sos |
| ATOM | 1273 | CE2 | PHE | 754 | 49.363   | 17.832   | 59.731   | 1.00 | 76.50 | sos |
| ATOM | 1274 | CZ  | PHE | 754 | 48.538   | 18.866   | 60.170   | 1.00 | 76.15 | sos |
| ATOM | 1275 | C   | PHE | 754 | 46.407   | 12.769   | 59.016   | 1.00 | 80.05 | sos |
| ATOM | 1276 | O   | PHE | 754 | 45.225   | 12.423   | 59.035   | 1.00 | 78.77 | sos |
| ATOM | 1277 | N   | GLN | 755 | 47.422   | 11.908   | 59.095   | 1.00 | 81.51 | sos |
| ATOM | 1278 | CA  | GLN | 755 | 47.203   | 10.471   | 59.237   | 1.00 | 83.40 | sos |
| ATOM | 1279 | CB  | GLN | 755 | 48.533   | 9.720    | 59.325   | 1.00 | 87.54 | sos |
| ATOM | 1280 | CG  | GLN | 755 | 49.396   | 9.812    | 58.080   | 1.00 | 92.89 | sos |
| ATOM | 1281 | CD  | GLN | 755 | 50.482   | 8.751    | 58.056   | 1.00 | 95.15 | sos |
| ATOM | 1282 | OE1 | GLN | 755 | 51.616   | 8.991    | 58.480   | 1.00 | 95.37 | sos |
| ATOM | 1283 | NE2 | GLN | 755 | 50.135   | 7.564    | 57.566   | 1.00 | 94.53 | sos |
| ATOM | 1284 | C   | GLN | 755 | 46.390   | 10.214   | 60.499   | 1.00 | 82.60 | sos |
| ATOM | 1285 | O   | GLN | 755 | 45.207   | 9.884    | 60.428   | 1.00 | 82.52 | sos |
| ATOM | 1286 | N   | SER | 756 | 47.033   | 10.374   | 61.653   | 1.00 | 82.24 | sos |
| ATOM | 1287 | CA  | SER | 756 | 46.369   | 10.186   | 62.939   | 1.00 | 80.01 | sos |
| ATOM | 1288 | CB  | SER | 756 | 47.336   | 9.613    | 63.982   | 1.00 | 80.76 | sos |
| ATOM | 1289 | OG  | SER | 756 | 47.651   | 8.255    | 63.712   | 1.00 | 86.46 | sos |
| ATOM | 1290 | C   | SER | 756 | 45.832   | 11.520   | 63.432   | 1.00 | 76.59 | sos |
| ATOM | 1291 | O   | SER | 756 | 46.233   | 12.582   | 62.948   | 1.00 | 76.46 | sos |
| ATOM | 1292 | N   | SER | 757 | 44.895   | 11.453   | 64.369   | 1.00 | 74.10 | sos |
| ATOM | 1293 | CA  | SER | 757 | 44.308   | 12.646   | 64.963   | 1.00 | 71.43 | sos |
| ATOM | 1294 | CB  | SER | 757 | 43.070   | 12.252   | 65.782   | 1.00 | 71.12 | sos |
| ATOM | 1295 | OG  | SER | 757 | 42.288   | 13.378   | 66.144   | 1.00 | 74.69 | sos |
| ATOM | 1296 | C   | SER | 757 | 45.393   | 13.252   | 65.872   | 1.00 | 68.88 | sos |
| ATOM | 1297 | O   | SER | 757 | 46.055   | 12.524   | 66.622   | 1.00 | 70.62 | sos |
| ATOM | 1298 | N   | PRO | 758 | 45.605   | 14.582   | 65.799   | 1.00 | 64.07 | sos |
| ATOM | 1299 | CD  | PRO | 758 | 44.779   | 15.571   | 65.089   | 1.00 | 62.90 | sos |
| ATOM | 1300 | CA  | PRO | 758 | 46.616   | 15.261   | 66.619   | 1.00 | 60.42 | sos |
| ATOM | 1301 | CB  | PRO | 758 | 46.338   | 16.741   | 66.344   | 1.00 | 60.37 | sos |
| ATOM | 1302 | CG  | PRO | 758 | 44.881   | 16.761   | 66.002   | 1.00 | 59.34 | sos |
| ATOM | 1303 | C   | PRO | 758 | 46.474   | 14.929   | 68.105   | 1.00 | 55.94 | sos |
| ATOM | 1304 | O   | PRO | 758 | 45.364   | 14.864   | 68.628   | 1.00 | 54.97 | sos |
| ATOM | 1305 | N   | PRO | 759 | 47.604   | 14.744   | 68.806   | 1.00 | 51.21 | sos |
| ATOM | 1306 | CD  | PRO | 759 | 48.969   | 14.983   | 68.307   | 1.00 | 49.38 | sos |
| ATOM | 1307 | CA  | PRO | 759 | 47.628   | 14.414   | 70.236   | 1.00 | 46.82 | sos |
| ATOM | 1308 | CB  | PRO | 759 | 49.122   | 14.472   | 70.576   | 1.00 | 46.73 | sos |
| ATOM | 1309 | CG  | PRO | 759 | 49.678   | 15.410   | 69.554   | 1.00 | 48.35 | sos |
| ATOM | 1310 | C   | PRO | 759 | 46.795   | 15.327   | 71.130   | 1.00 | 43.52 | sos |
| ATOM | 1311 | O   | PRO | 759 | 46.596   | 16.499   | 70.827   | 1.00 | 44.26 | sos |
| ATOM | 1312 | N   | THR | 760 | 46.299   | 14.762   | 72.226   | 1.00 | 41.80 | sos |
| ATOM | 1313 | CA  | THR | 760 | 45.479   | 15.483   | 73.198   | 1.00 | 43.64 | sos |
| ATOM | 1314 | CB  | THR | 760 | 45.001   | 14.537   | 74.306   | 1.00 | 44.16 | sos |
| ATOM | 1315 | OG1 | THR | 760 | 44.534   | 13.321   | 73.717   | 1.00 | 49.26 | sos |
| ATOM | 1316 | CG2 | THR | 760 | 43.885   | 15.185   | 75.133   | 1.00 | 41.92 | sos |

TABLE 3-continued

PDB Coordinates for the Ras-Sos Structure:
DATA SET FOR REFINED COORDINATES

| ATOM | 1317 | C   | THR | 760 | 46.216 | 16.617 | 73.903 | 1.00 | 43.09 | sos |
|------|------|-----|-----|-----|--------|--------|--------|------|-------|-----|
| ATOM | 1318 | O   | THR | 760 | 47.379 | 16.470 | 74.281 | 1.00 | 43.99 | sos |
| ATOM | 1319 | N   | VAL | 761 | 45.511 | 17.728 | 74.109 | 1.00 | 43.41 | sos |
| ATOM | 1320 | CA  | VAL | 761 | 46.055 | 18.889 | 74.807 | 1.00 | 43.37 | sos |
| ATOM | 1321 | CB  | VAL | 761 | 45.024 | 20.039 | 74.889 | 1.00 | 45.13 | sos |
| ATOM | 1322 | CG1 | VAL | 761 | 45.534 | 21.154 | 75.801 | 1.00 | 47.53 | sos |
| ATOM | 1323 | CG2 | VAL | 761 | 44.717 | 20.583 | 73.490 | 1.00 | 46.41 | sos |
| ATOM | 1324 | C   | VAL | 761 | 46.391 | 18.445 | 76.220 | 1.00 | 45.23 | sos |
| ATOM | 1325 | O   | VAL | 761 | 45.523 | 17.985 | 76.957 | 1.00 | 46.18 | sos |
| ATOM | 1326 | N   | GLU | 762 | 47.662 | 18.560 | 76.580 | 1.00 | 47.28 | sos |
| ATOM | 1327 | CA  | GLU | 762 | 48.131 | 18.159 | 77.898 | 1.00 | 49.55 | sos |
| ATOM | 1328 | CB  | GLU | 762 | 49.619 | 17.823 | 77.808 | 1.00 | 48.70 | sos |
| ATOM | 1329 | CG  | GLU | 762 | 50.047 | 16.606 | 78.611 | 1.00 | 56.63 | sos |
| ATOM | 1330 | CD  | GLU | 762 | 49.597 | 15.276 | 78.020 | 1.00 | 59.08 | sos |
| ATOM | 1331 | OE1 | GLU | 762 | 48.889 | 14.530 | 78.729 | 1.00 | 61.99 | sos |
| ATOM | 1332 | OE2 | GLU | 762 | 49.976 | 14.957 | 76.868 | 1.00 | 60.65 | sos |
| ATOM | 1333 | C   | GLU | 762 | 47.872 | 19.265 | 78.937 | 1.00 | 49.25 | sos |
| ATOM | 1334 | O   | GLU | 762 | 47.970 | 20.450 | 78.623 | 1.00 | 50.91 | sos |
| ATOM | 1335 | N   | TRP | 763 | 47.483 | 18.873 | 80.150 | 1.00 | 48.34 | sos |
| ATOM | 1336 | CA  | TRP | 763 | 47.213 | 19.822 | 81.235 | 1.00 | 48.11 | sos |
| ATOM | 1337 | CB  | TRP | 763 | 45.715 | 19.940 | 81.511 | 1.00 | 48.34 | sos |
| ATOM | 1338 | CG  | TRP | 763 | 44.949 | 20.637 | 80.435 | 1.00 | 52.14 | sos |
| ATOM | 1339 | CD2 | TRP | 763 | 44.849 | 22.053 | 80.226 | 1.00 | 53.95 | sos |
| ATOM | 1340 | CE2 | TRP | 763 | 44.052 | 22.250 | 79.077 | 1.00 | 52.89 | sos |
| ATOM | 1341 | CE3 | TRP | 763 | 45.359 | 23.176 | 80.896 | 1.00 | 53.73 | sos |
| ATOM | 1342 | CD1 | TRP | 763 | 44.225 | 20.053 | 79.441 | 1.00 | 50.57 | sos |
| ATOM | 1343 | NE1 | TRP | 763 | 43.685 | 21.011 | 78.621 | 1.00 | 52.45 | sos |
| ATOM | 1344 | CZ2 | TRP | 763 | 43.750 | 23.526 | 78.576 | 1.00 | 53.01 | sos |
| ATOM | 1345 | CZ3 | TRP | 763 | 45.056 | 24.451 | 80.396 | 1.00 | 54.01 | sos |
| ATOM | 1346 | CH2 | TRP | 763 | 44.259 | 24.610 | 79.247 | 1.00 | 53.15 | sos |
| ATOM | 1347 | C   | TRP | 763 | 47.913 | 19.392 | 82.515 | 1.00 | 49.46 | sos |
| ATOM | 1348 | O   | TRP | 763 | 48.130 | 18.199 | 82.734 | 1.00 | 48.08 | sos |
| ATOM | 1349 | N   | HIS | 764 | 48.247 | 20.368 | 83.363 | 1.00 | 52.66 | sos |
| ATOM | 1350 | CA  | HIS | 764 | 48.924 | 20.105 | 84.638 | 1.00 | 52.31 | sos |
| ATOM | 1351 | CB  | HIS | 764 | 50.351 | 20.668 | 84.608 | 1.00 | 51.70 | sos |
| ATOM | 1352 | CG  | HIS | 764 | 51.184 | 20.292 | 85.795 | 1.00 | 54.79 | sos |
| ATOM | 1353 | CD2 | HIS | 764 | 51.269 | 19.139 | 86.499 | 1.00 | 55.61 | sos |
| ATOM | 1354 | ND1 | HIS | 764 | 52.099 | 21.154 | 86.363 | 1.00 | 54.63 | sos |
| ATOM | 1355 | CE1 | HIS | 764 | 52.716 | 20.546 | 87.360 | 1.00 | 51.31 | sos |
| ATOM | 1356 | NE2 | HIS | 764 | 52.230 | 19.323 | 87.463 | 1.00 | 52.00 | sos |
| ATOM | 1357 | C   | HIS | 764 | 48.134 | 20.674 | 85.824 | 1.00 | 52.28 | sos |
| ATOM | 1358 | O   | HIS | 764 | 46.987 | 20.288 | 86.044 | 1.00 | 54.90 | sos |
| ATOM | 1359 | N   | ILE | 765 | 48.737 | 21.597 | 86.570 | 1.00 | 51.58 | sos |
| ATOM | 1360 | CA  | ILE | 765 | 48.097 | 22.195 | 87.736 | 1.00 | 50.96 | sos |
| ATOM | 1361 | CB  | ILE | 765 | 49.117 | 22.940 | 88.596 | 1.00 | 50.44 | sos |
| ATOM | 1362 | CG2 | ILE | 765 | 48.427 | 23.614 | 89.780 | 1.00 | 46.91 | sos |
| ATOM | 1363 | CG1 | ILE | 765 | 50.187 | 21.960 | 89.079 | 1.00 | 45.51 | sos |
| ATOM | 1364 | CD1 | ILE | 765 | 51.372 | 22.629 | 89.732 | 1.00 | 49.05 | sos |
| ATOM | 1365 | C   | ILE | 765 | 46.947 | 23.123 | 87.372 | 1.00 | 54.45 | sos |
| ATOM | 1366 | O   | ILE | 765 | 45.941 | 23.181 | 88.079 | 1.00 | 56.61 | sos |
| ATOM | 1367 | N   | SER | 766 | 47.099 | 23.858 | 86.279 | 1.00 | 55.94 | sos |
| ATOM | 1368 | CA  | SER | 766 | 46.041 | 24.752 | 85.836 | 1.00 | 56.95 | sos |
| ATOM | 1369 | CB  | SER | 766 | 46.616 | 25.892 | 84.997 | 1.00 | 58.10 | sos |
| ATOM | 1370 | OG  | SER | 766 | 47.435 | 26.735 | 85.783 | 1.00 | 58.21 | sos |
| ATOM | 1371 | C   | SER | 766 | 45.009 | 23.980 | 85.021 | 1.00 | 57.24 | sos |
| ATOM | 1372 | O   | SER | 766 | 45.354 | 23.135 | 84.193 | 1.00 | 57.67 | sos |
| ATOM | 1373 | N   | ARG | 767 | 43.739 | 24.246 | 85.296 | 1.00 | 58.66 | sos |
| ATOM | 1374 | CA  | ARG | 767 | 42.642 | 23.598 | 84.587 | 1.00 | 58.46 | sos |
| ATOM | 1375 | CB  | ARG | 767 | 41.452 | 23.386 | 85.533 | 1.00 | 57.14 | sos |
| ATOM | 1376 | CG  | ARG | 767 | 41.743 | 22.473 | 86.714 | 0.00 | 58.41 | sos |
| ATOM | 1377 | CD  | ARG | 767 | 40.512 | 22.292 | 87.588 | 0.00 | 58.76 | sos |
| ATOM | 1378 | NE  | ARG | 767 | 40.765 | 21.391 | 88.710 | 0.00 | 59.34 | sos |
| ATOM | 1379 | CZ  | ARG | 767 | 39.840 | 20.994 | 89.580 | 0.00 | 59.59 | sos |
| ATOM | 1380 | NH1 | ARG | 767 | 38.587 | 21.417 | 89.467 | 0.00 | 59.80 | sos |
| ATOM | 1381 | NH2 | ARG | 767 | 40.168 | 20.170 | 90.565 | 0.00 | 59.80 | sos |
| ATOM | 1382 | C   | ARG | 767 | 42.231 | 24.481 | 83.407 | 1.00 | 57.53 | sos |
| ATOM | 1383 | O   | ARG | 767 | 42.373 | 25.707 | 83.457 | 1.00 | 57.49 | sos |
| ATOM | 1384 | N   | PRO | 768 | 41.747 | 23.870 | 82.316 | 1.00 | 56.37 | sos |
| ATOM | 1385 | CD  | PRO | 768 | 41.533 | 22.431 | 82.096 | 1.00 | 55.30 | sos |
| ATOM | 1386 | CA  | PRO | 768 | 41.328 | 24.646 | 81.144 | 1.00 | 55.88 | sos |
| ATOM | 1387 | CB  | PRO | 768 | 40.724 | 23.582 | 80.221 | 1.00 | 55.56 | sos |
| ATOM | 1388 | CG  | PRO | 768 | 40.380 | 22.444 | 81.148 | 1.00 | 57.40 | sos |
| ATOM | 1389 | C   | PRO | 768 | 40.325 | 25.739 | 81.500 | 1.00 | 57.05 | sos |
| ATOM | 1390 | O   | PRO | 768 | 39.312 | 25.484 | 82.157 | 1.00 | 57.12 | sos |
| ATOM | 1391 | N   | GLY | 769 | 40.645 | 26.966 | 81.102 | 1.00 | 58.13 | sos |
| ATOM | 1392 | CA  | GLY | 769 | 39.779 | 28.093 | 81.392 | 1.00 | 59.78 | sos |

TABLE 3-continued

PDB Coordinates for the Ras-Sos Structure:
DATA SET FOR REFINED COORDINATES

| ATOM | 1393 | C | GLY | 769 | 40.282 | 28.995 | 82.508 | 1.00 | 62.31 | sos |
|---|---|---|---|---|---|---|---|---|---|---|
| ATOM | 1394 | O | GLY | 769 | 39.911 | 30.169 | 82.570 | 1.00 | 62.32 | sos |
| ATOM | 1395 | N | HIS | 770 | 41.119 | 28.456 | 83.392 | 1.00 | 65.22 | sos |
| ATOM | 1396 | CA | HIS | 770 | 41.662 | 29.228 | 84.509 | 1.00 | 70.02 | sos |
| ATOM | 1397 | CB | HIS | 770 | 42.010 | 28.298 | 85.673 | 1.00 | 73.45 | sos |
| ATOM | 1398 | CG | HIS | 770 | 41.030 | 28.349 | 86.803 | 1.00 | 80.04 | sos |
| ATOM | 1399 | CD2 | HIS | 770 | 40.217 | 27.398 | 87.323 | 1.00 | 82.67 | sos |
| ATOM | 1400 | ND1 | HIS | 770 | 40.814 | 29.488 | 87.550 | 1.00 | 82.69 | sos |
| ATOM | 1401 | CE1 | HIS | 770 | 39.913 | 29.237 | 88.482 | 1.00 | 84.61 | sos |
| ATOM | 1402 | NE2 | HIS | 770 | 39.533 | 27.976 | 88.367 | 1.00 | 85.45 | sos |
| ATOM | 1403 | C | HIS | 770 | 42.882 | 30.058 | 84.102 | 1.00 | 71.74 | sos |
| ATOM | 1404 | O | HIS | 770 | 44.007 | 29.792 | 84.536 | 1.00 | 71.69 | sos |
| ATOM | 1405 | N | ILE | 771 | 42.637 | 31.084 | 83.289 | 1.00 | 73.43 | sos |
| ATOM | 1406 | CA | ILE | 771 | 43.680 | 31.977 | 82.781 | 1.00 | 73.04 | sos |
| ATOM | 1407 | CB | ILE | 771 | 43.072 | 33.137 | 81.948 | 1.00 | 74.71 | sos |
| ATOM | 1408 | CG2 | ILE | 771 | 44.179 | 34.032 | 81.376 | 1.00 | 76.47 | sos |
| ATOM | 1409 | CG1 | ILE | 771 | 42.225 | 32.578 | 80.806 | 1.00 | 75.59 | sos |
| ATOM | 1410 | CD1 | ILE | 771 | 41.559 | 33.652 | 79.974 | 1.00 | 80.17 | sos |
| ATOM | 1411 | C | ILE | 771 | 44.543 | 32.583 | 83.883 | 1.00 | 71.68 | sos |
| ATOM | 1412 | O | ILE | 771 | 45.770 | 32.578 | 83.785 | 1.00 | 72.30 | sos |
| ATOM | 1413 | N | GLU | 772 | 43.893 | 33.095 | 84.924 | 1.00 | 69.35 | sos |
| ATOM | 1414 | CA | GLU | 772 | 44.568 | 33.726 | 86.056 | 1.00 | 68.16 | sos |
| ATOM | 1415 | CB | GLU | 772 | 43.576 | 33.941 | 87.191 | 1.00 | 74.89 | sos |
| ATOM | 1416 | CG | GLU | 772 | 42.158 | 34.216 | 86.750 | 1.00 | 85.41 | sos |
| ATOM | 1417 | CD | GLU | 772 | 41.157 | 33.834 | 87.821 | 1.00 | 92.40 | sos |
| ATOM | 1418 | OE1 | GLU | 772 | 40.700 | 32.666 | 87.820 | 1.00 | 94.82 | sos |
| ATOM | 1419 | OE2 | GLU | 772 | 40.844 | 34.693 | 88.674 | 1.00 | 97.12 | sos |
| ATOM | 1420 | C | GLU | 772 | 45.723 | 32.888 | 86.597 | 1.00 | 64.87 | sos |
| ATOM | 1421 | O | GLU | 772 | 46.767 | 33.422 | 86.967 | 1.00 | 66.64 | sos |
| ATOM | 1422 | N | THR | 773 | 45.521 | 31.576 | 86.634 | 1.00 | 59.53 | sos |
| ATOM | 1423 | CA | THR | 773 | 46.505 | 30.631 | 87.147 | 1.00 | 55.41 | sos |
| ATOM | 1424 | CB | THR | 773 | 45.826 | 29.305 | 87.515 | 1.00 | 56.06 | sos |
| ATOM | 1425 | OG1 | THR | 773 | 44.634 | 29.580 | 88.251 | 1.00 | 59.73 | sos |
| ATOM | 1426 | CG2 | THR | 773 | 46.735 | 28.456 | 88.385 | 1.00 | 60.66 | sos |
| ATOM | 1427 | C | THR | 773 | 47.666 | 30.313 | 86.210 | 1.00 | 52.77 | sos |
| ATOM | 1428 | O | THR | 773 | 48.707 | 29.842 | 86.661 | 1.00 | 54.52 | sos |
| ATOM | 1429 | N | PHE | 774 | 47.488 | 30.544 | 84.913 | 1.00 | 49.38 | sos |
| ATOM | 1430 | CA | PHE | 774 | 48.532 | 30.247 | 83.932 | 1.00 | 46.93 | sos |
| ATOM | 1431 | CB | PHE | 774 | 48.110 | 30.706 | 82.531 | 1.00 | 48.91 | sos |
| ATOM | 1432 | CG | PHE | 774 | 47.009 | 29.882 | 81.911 | 1.00 | 49.79 | sos |
| ATOM | 1433 | CD1 | PHE | 774 | 46.388 | 28.862 | 82.617 | 1.00 | 48.24 | sos |
| ATOM | 1434 | CD2 | PHE | 774 | 46.607 | 30.125 | 80.595 | 1.00 | 53.24 | sos |
| ATOM | 1435 | CE1 | PHE | 774 | 45.384 | 28.094 | 82.023 | 1.00 | 51.49 | sos |
| ATOM | 1436 | CE2 | PHE | 774 | 45.605 | 29.362 | 79.993 | 1.00 | 51.85 | sos |
| ATOM | 1437 | CZ | PHE | 774 | 44.993 | 28.344 | 80.709 | 1.00 | 50.82 | sos |
| ATOM | 1438 | C | PHE | 774 | 49.888 | 30.859 | 84.291 | 1.00 | 43.65 | sos |
| ATOM | 1439 | O | PHE | 774 | 49.971 | 32.029 | 84.660 | 1.00 | 43.32 | sos |
| ATOM | 1440 | N | ASP | 775 | 50.936 | 30.044 | 84.188 | 1.00 | 39.66 | sos |
| ATOM | 1441 | CA | ASP | 775 | 52.303 | 30.448 | 84.492 | 1.00 | 40.20 | sos |
| ATOM | 1442 | CB | ASP | 775 | 52.445 | 30.738 | 85.989 | 1.00 | 42.75 | sos |
| ATOM | 1443 | CG | ASP | 775 | 53.493 | 31.802 | 86.286 | 1.00 | 45.57 | sos |
| ATOM | 1444 | OD1 | ASP | 775 | 54.321 | 32.104 | 85.396 | 1.00 | 43.58 | sos |
| ATOM | 1445 | OD2 | ASP | 775 | 53.482 | 32.342 | 87.416 | 1.00 | 47.46 | sos |
| ATOM | 1446 | C | ASP | 775 | 53.245 | 29.314 | 84.069 | 1.00 | 42.02 | sos |
| ATOM | 1447 | O | ASP | 775 | 52.782 | 28.221 | 83.743 | 1.00 | 44.67 | sos |
| ATOM | 1448 | N | LEU | 776 | 54.556 | 29.554 | 84.127 | 1.00 | 40.58 | sos |
| ATOM | 1449 | CA | LEU | 776 | 55.559 | 28.567 | 83.707 | 1.00 | 39.59 | sos |
| ATOM | 1450 | CB | LEU | 776 | 56.975 | 29.141 | 83.854 | 1.00 | 37.05 | sos |
| ATOM | 1451 | CG | LEU | 776 | 58.111 | 28.179 | 83.481 | 1.00 | 34.22 | sos |
| ATOM | 1452 | CD1 | LEU | 776 | 58.062 | 27.869 | 82.008 | 1.00 | 38.01 | sos |
| ATOM | 1453 | CD2 | LEU | 776 | 59.445 | 28.766 | 83.827 | 1.00 | 41.88 | sos |
| ATOM | 1454 | C | LEU | 776 | 55.520 | 27.173 | 84.339 | 1.00 | 40.72 | sos |
| ATOM | 1455 | O | LEU | 776 | 55.928 | 26.200 | 83.704 | 1.00 | 42.54 | sos |
| ATOM | 1456 | N | LEU | 777 | 55.074 | 27.077 | 85.587 | 1.00 | 41.11 | sos |
| ATOM | 1457 | CA | LEU | 777 | 55.023 | 25.788 | 86.280 | 1.00 | 42.11 | sos |
| ATOM | 1458 | CB | LEU | 777 | 55.644 | 25.901 | 87.674 | 1.00 | 40.60 | sos |
| ATOM | 1459 | CG | LEU | 777 | 57.074 | 26.407 | 87.854 | 1.00 | 38.83 | sos |
| ATOM | 1460 | CD1 | LEU | 777 | 57.258 | 26.785 | 89.307 | 1.00 | 37.73 | sos |
| ATOM | 1461 | CD2 | LEU | 777 | 58.082 | 25.360 | 87.435 | 1.00 | 31.91 | sos |
| ATOM | 1462 | C | LEU | 777 | 53.608 | 25.257 | 86.432 | 1.00 | 44.45 | sos |
| ATOM | 1463 | O | LEU | 777 | 53.414 | 24.113 | 86.838 | 1.00 | 47.16 | sos |
| ATOM | 1464 | N | THR | 778 | 52.622 | 26.105 | 86.160 | 1.00 | 45.03 | sos |
| ATOM | 1465 | CA | THR | 778 | 51.229 | 25.707 | 86.280 | 1.00 | 45.02 | sos |
| ATOM | 1466 | CB | THR | 778 | 50.339 | 26.899 | 86.572 | 1.00 | 45.44 | sos |
| ATOM | 1467 | OG1 | THR | 778 | 50.727 | 27.984 | 85.729 | 1.00 | 51.28 | sos |
| ATOM | 1468 | OG2 | THR | 778 | 50.456 | 27.306 | 88.020 | 1.00 | 42.08 | sos |

TABLE 3-continued

PDB Coordinates for the Ras-Sos Structure:
DATA SET FOR REFINED COORDINATES

| ATOM | 1469 | C    | THR | 778 | 50.740 | 25.004 | 85.031 | 1.00 | 43.78 | sos |
|------|------|------|-----|-----|--------|--------|--------|------|-------|-----|
| ATOM | 1470 | O    | THR | 778 | 49.919 | 24.093 | 85.114 | 1.00 | 48.27 | sos |
| ATOM | 1471 | N    | LEU | 779 | 51.203 | 25.458 | 83.870 | 1.00 | 39.00 | sos |
| ATOM | 1472 | CA   | LEU | 779 | 50.821 | 24.817 | 82.620 | 1.00 | 36.61 | sos |
| ATOM | 1473 | CB   | LEU | 779 | 51.074 | 25.725 | 81.416 | 1.00 | 36.26 | sos |
| ATOM | 1474 | CG   | LEU | 779 | 50.232 | 26.987 | 81.240 | 1.00 | 36.83 | sos |
| ATOM | 1475 | CD1  | LEU | 779 | 50.645 | 27.661 | 79.961 | 1.00 | 37.53 | sos |
| ATOM | 1476 | CD2  | LEU | 779 | 48.763 | 26.650 | 81.188 | 1.00 | 39.39 | sos |
| ATOM | 1477 | C    | LEU | 779 | 51.671 | 23.572 | 82.479 | 1.00 | 36.14 | sos |
| ATOM | 1478 | O    | LEU | 779 | 52.679 | 23.419 | 83.163 | 1.00 | 35.62 | sos |
| ATOM | 1479 | N    | HIS | 780 | 51.255 | 22.674 | 81.596 | 1.00 | 36.34 | sos |
| ATOM | 1480 | CA   | HIS | 780 | 52.003 | 21.454 | 81.370 | 1.00 | 30.69 | sos |
| ATOM | 1481 | CB   | HIS | 780 | 51.122 | 20.410 | 80.683 | 1.00 | 32.54 | sos |
| ATOM | 1482 | CG   | HIS | 780 | 51.741 | 19.050 | 80.635 | 1.00 | 38.22 | sos |
| ATOM | 1483 | CD2  | HIS | 780 | 52.841 | 18.595 | 79.988 | 1.00 | 35.48 | sos |
| ATOM | 1484 | ND1  | HIS | 780 | 51.269 | 17.991 | 81.381 | 1.00 | 37.64 | sos |
| ATOM | 1485 | CE1  | HIS | 780 | 52.057 | 16.945 | 81.203 | 1.00 | 41.62 | sos |
| ATOM | 1486 | NE2  | HIS | 780 | 53.018 | 17.285 | 80.362 | 1.00 | 41.96 | sos |
| ATOM | 1487 | C    | HIS | 780 | 53.178 | 21.812 | 80.480 | 1.00 | 30.93 | sos |
| ATOM | 1488 | O    | HIS | 780 | 53.017 | 22.523 | 79.483 | 1.00 | 31.19 | sos |
| ATOM | 1489 | N    | PRO | 781 | 54.387 | 21.360 | 80.842 | 1.00 | 32.45 | sos |
| ATOM | 1490 | CD   | PRO | 781 | 54.769 | 20.578 | 82.026 | 1.00 | 27.87 | sos |
| ATOM | 1491 | CA   | PRO | 781 | 55.563 | 21.672 | 80.020 | 1.00 | 32.26 | sos |
| ATOM | 1492 | CB   | PRO | 781 | 56.693 | 20.901 | 80.712 | 1.00 | 28.92 | sos |
| ATOM | 1493 | CG   | PRO | 781 | 55.986 | 19.860 | 81.526 | 1.00 | 28.73 | sos |
| ATOM | 1494 | C    | PRO | 781 | 55.418 | 21.285 | 78.552 | 1.00 | 34.19 | sos |
| ATOM | 1495 | O    | PRO | 781 | 55.864 | 22.021 | 77.682 | 1.00 | 40.11 | sos |
| ATOM | 1496 | N    | ILE | 782 | 54.769 | 20.158 | 78.268 | 1.00 | 37.40 | sos |
| ATOM | 1497 | CA   | ILE | 782 | 54.591 | 19.724 | 76.879 | 1.00 | 38.73 | sos |
| ATOM | 1498 | CB   | ILE | 782 | 53.949 | 18.329 | 76.769 | 1.00 | 39.19 | sos |
| ATOM | 1499 | CG2  | ILE | 782 | 53.732 | 17.973 | 75.311 | 1.00 | 38.14 | sos |
| ATOM | 1500 | CG1  | ILE | 782 | 54.838 | 17.269 | 77.418 | 1.00 | 41.00 | sos |
| ATOM | 1501 | CD1  | ILE | 782 | 54.154 | 15.933 | 77.553 | 1.00 | 34.99 | sos |
| ATOM | 1502 | C    | ILE | 782 | 53.703 | 20.692 | 76.116 | 1.00 | 38.45 | sos |
| ATOM | 1503 | O    | ILE | 782 | 53.984 | 21.023 | 74.961 | 1.00 | 41.60 | sos |
| ATOM | 1504 | N    | GLU | 783 | 52.631 | 21.144 | 76.756 | 1.00 | 34.85 | sos |
| ATOM | 1505 | CA   | GLU | 783 | 51.726 | 22.071 | 76.097 | 1.00 | 38.32 | sos |
| ATOM | 1506 | CB   | GLU | 783 | 50.417 | 22.208 | 76.872 | 1.00 | 37.38 | sos |
| ATOM | 1507 | CG   | GLU | 783 | 49.239 | 22.571 | 75.983 | 1.00 | 42.65 | sos |
| ATOM | 1508 | CD   | GLU | 783 | 49.069 | 21.603 | 74.820 | 1.00 | 46.46 | sos |
| ATOM | 1509 | OE1  | GLU | 783 | 48.908 | 20.391 | 75.062 | 1.00 | 47.85 | sos |
| ATOM | 1510 | OE2  | GLU | 783 | 49.110 | 22.051 | 73.658 | 1.00 | 52.76 | sos |
| ATOM | 1511 | C    | GLU | 783 | 52.358 | 23.442 | 75.863 | 1.00 | 39.89 | sos |
| ATOM | 1512 | O    | GLU | 783 | 52.054 | 24.103 | 74.869 | 1.00 | 42.05 | sos |
| ATOM | 1513 | N    | ILE | 784 | 53.238 | 23.867 | 76.772 | 1.00 | 38.82 | sos |
| ATOM | 1514 | CA   | ILE | 784 | 53.906 | 25.157 | 76.627 | 1.00 | 35.25 | sos |
| ATOM | 1515 | CB   | ILE | 784 | 54.821 | 25.475 | 77.834 | 1.00 | 35.64 | sos |
| ATOM | 1516 | CG2  | ILE | 784 | 55.759 | 26.630 | 77.512 | 1.00 | 37.16 | sos |
| ATOM | 1517 | CG1  | ILE | 784 | 53.964 | 25.836 | 79.050 | 1.00 | 35.48 | sos |
| ATOM | 1518 | CD1  | ILE | 784 | 54.749 | 26.033 | 80.327 | 1.00 | 36.97 | sos |
| ATOM | 1519 | C    | ILE | 784 | 54.710 | 25.131 | 75.336 | 1.00 | 34.11 | sos |
| ATOM | 1520 | O    | ILE | 784 | 54.530 | 25.989 | 74.468 | 1.00 | 32.57 | sos |
| ATOM | 1521 | N    | ALA | 785 | 55.541 | 24.106 | 75.186 | 1.00 | 28.59 | sos |
| ATOM | 1522 | CA   | ALA | 785 | 56.351 | 23.958 | 73.984 | 1.00 | 31.82 | sos |
| ATOM | 1523 | CB   | ALA | 785 | 57.285 | 22.769 | 74.128 | 1.00 | 29.35 | sos |
| ATOM | 1524 | C    | ALA | 785 | 55.473 | 23.807 | 72.732 | 1.00 | 34.33 | sos |
| ATOM | 1525 | O    | ALA | 785 | 55.796 | 24.330 | 71.663 | 1.00 | 30.46 | sos |
| ATOM | 1526 | N    | ARG | 786 | 54.353 | 23.106 | 72.870 | 1.00 | 36.83 | sos |
| ATOM | 1527 | CA   | ARG | 786 | 53.445 | 22.918 | 71.744 | 1.00 | 40.76 | sos |
| ATOM | 1528 | CB   | ARG | 786 | 52.320 | 21.950 | 72.104 | 1.00 | 42.79 | sos |
| ATOM | 1529 | CG   | ARG | 786 | 52.656 | 20.492 | 71.935 | 1.00 | 37.73 | sos |
| ATOM | 1530 | CD   | ARG | 786 | 51.562 | 19.673 | 72.557 | 1.00 | 38.47 | sos |
| ATOM | 1531 | NE   | ARG | 786 | 51.806 | 18.245 | 72.408 | 1.00 | 37.64 | sos |
| ATOM | 1532 | CZ   | ARG | 786 | 51.012 | 17.299 | 72.896 | 1.00 | 34.53 | sos |
| ATOM | 1533 | NH1  | ARG | 786 | 49.914 | 17.624 | 73.574 | 1.00 | 25.27 | sos |
| ATOM | 1534 | NH2  | ARG | 786 | 51.317 | 16.027 | 72.694 | 1.00 | 35.31 | sos |
| ATOM | 1535 | C    | ARG | 786 | 52.839 | 24.233 | 71.266 | 1.00 | 41.15 | sos |
| ATOM | 1536 | O    | ARG | 786 | 52.874 | 24.542 | 70.074 | 1.00 | 45.26 | sos |
| ATOM | 1537 | N    | GLN | 787 | 52.278 | 25.003 | 72.191 | 1.00 | 40.14 | sos |
| ATOM | 1538 | CA   | GLN | 787 | 51.664 | 26.273 | 71.831 | 1.00 | 40.79 | sos |
| ATOM | 1539 | CB   | GLN | 787 | 50.812 | 26.806 | 72.978 | 1.00 | 40.49 | sos |
| ATOM | 1540 | CG   | GLN | 787 | 49.679 | 25.869 | 73.368 | 1.00 | 46.29 | sos |
| ATOM | 1541 | CD   | GLN | 787 | 48.723 | 25.561 | 72.218 | 1.00 | 49.08 | sos |
| ATOM | 1542 | OE1  | GLN | 787 | 48.464 | 26.407 | 71.358 | 1.00 | 50.00 | sos |
| ATOM | 1543 | NE2  | GLN | 787 | 48.174 | 24.349 | 72.217 | 1.00 | 45.42 | sos |
| ATOM | 1544 | C    | GLN | 787 | 52.674 | 27.315 | 71.362 | 1.00 | 39.31 | sos |

TABLE 3-continued

PDB Coordinates for the Ras-Sos Structure:
DATA SET FOR REFINED COORDINATES

| ATOM | 1545 | O   | GLN | 787 | 52.368 | 28.127 | 70.495 | 1.00 | 43.08 | sos |
|------|------|-----|-----|-----|--------|--------|--------|------|-------|-----|
| ATOM | 1546 | N   | LEU | 788 | 53.877 | 27.292 | 71.920 | 1.00 | 34.89 | sos |
| ATOM | 1547 | CA  | LEU | 788 | 54.897 | 28.235 | 71.498 | 1.00 | 33.64 | sos |
| ATOM | 1548 | CB  | LEU | 788 | 56.082 | 28.222 | 72.455 | 1.00 | 36.57 | sos |
| ATOM | 1549 | CG  | LEU | 788 | 55.901 | 29.080 | 73.704 | 1.00 | 35.94 | sos |
| ATOM | 1550 | CD1 | LEU | 788 | 57.033 | 28.827 | 74.681 | 1.00 | 30.14 | sos |
| ATOM | 1551 | CD2 | LEU | 788 | 55.838 | 30.526 | 73.279 | 1.00 | 34.86 | sos |
| ATOM | 1552 | C   | LEU | 788 | 55.358 | 27.869 | 70.101 | 1.00 | 35.31 | sos |
| ATOM | 1553 | O   | LEU | 788 | 55.767 | 28.738 | 69.324 | 1.00 | 35.36 | sos |
| ATOM | 1554 | N   | THR | 789 | 55.283 | 26.580 | 69.778 | 1.00 | 32.91 | sos |
| ATOM | 1555 | CA  | THR | 789 | 55.679 | 26.112 | 68.456 | 1.00 | 29.66 | sos |
| ATOM | 1556 | CB  | THR | 789 | 55.889 | 24.606 | 68.457 | 1.00 | 24.38 | sos |
| ATOM | 1557 | OG1 | THR | 789 | 56.876 | 24.291 | 69.441 | 1.00 | 28.48 | sos |
| ATOM | 1558 | CG2 | THR | 789 | 56.386 | 24.131 | 67.115 | 1.00 | 19.79 | sos |
| ATOM | 1559 | C   | THR | 789 | 54.645 | 26.554 | 67.414 | 1.00 | 31.44 | sos |
| ATOM | 1560 | O   | THR | 789 | 55.006 | 27.030 | 66.340 | 1.00 | 33.08 | sos |
| ATOM | 1561 | N   | LEU | 790 | 53.363 | 26.441 | 67.749 | 1.00 | 31.84 | sos |
| ATOM | 1562 | CA  | LEU | 790 | 52.309 | 26.888 | 66.846 | 1.00 | 34.52 | sos |
| ATOM | 1563 | CB  | LEU | 790 | 50.936 | 26.555 | 67.426 | 1.00 | 33.15 | sos |
| ATOM | 1564 | CG  | LEU | 790 | 50.623 | 25.060 | 67.397 | 1.00 | 37.80 | sos |
| ATOM | 1565 | CD1 | LEU | 790 | 49.348 | 24.767 | 68.177 | 1.00 | 38.42 | sos |
| ATOM | 1566 | CD2 | LEU | 790 | 50.510 | 24.583 | 65.952 | 1.00 | 30.50 | sos |
| ATOM | 1567 | C   | LEU | 790 | 52.444 | 28.403 | 66.615 | 1.00 | 36.45 | sos |
| ATOM | 1568 | O   | LEU | 790 | 52.439 | 28.868 | 65.472 | 1.00 | 35.83 | sos |
| ATOM | 1569 | N   | LEU | 791 | 52.601 | 29.156 | 67.704 | 1.00 | 36.76 | sos |
| ATOM | 1570 | CA  | LEU | 791 | 52.765 | 30.608 | 67.641 | 1.00 | 37.82 | sos |
| ATOM | 1571 | CB  | LEU | 791 | 53.008 | 31.185 | 69.036 | 1.00 | 36.78 | sos |
| ATOM | 1572 | CG  | LEU | 791 | 51.829 | 31.805 | 69.778 | 1.00 | 38.93 | sos |
| ATOM | 1573 | CD1 | LEU | 791 | 52.218 | 32.098 | 71.216 | 1.00 | 38.56 | sos |
| ATOM | 1574 | CD2 | LEU | 791 | 51.395 | 33.069 | 69.060 | 1.00 | 39.46 | sos |
| ATOM | 1575 | C   | LEU | 791 | 53.957 | 30.950 | 66.784 | 1.00 | 39.70 | sos |
| ATOM | 1576 | O   | LEU | 791 | 53.861 | 31.754 | 65.863 | 1.00 | 42.62 | sos |
| ATOM | 1577 | N   | GLU | 792 | 55.080 | 30.310 | 67.091 | 1.00 | 40.44 | sos |
| ATOM | 1578 | CA  | GLU | 792 | 56.323 | 30.546 | 66.378 | 1.00 | 39.38 | sos |
| ATOM | 1579 | CB  | GLU | 792 | 57.505 | 29.989 | 67.182 | 1.00 | 39.95 | sos |
| ATOM | 1580 | CG  | GLU | 792 | 57.846 | 30.892 | 68.379 | 1.00 | 37.88 | sos |
| ATOM | 1581 | CD  | GLU | 792 | 58.683 | 30.234 | 69.461 | 1.00 | 35.30 | sos |
| ATOM | 1582 | OE1 | GLU | 792 | 59.593 | 29.436 | 69.152 | 1.00 | 36.26 | sos |
| ATOM | 1583 | OE2 | GLU | 792 | 58.433 | 30.545 | 70.639 | 1.00 | 34.44 | sos |
| ATOM | 1584 | C   | GLU | 792 | 56.319 | 30.062 | 64.943 | 1.00 | 37.97 | sos |
| ATOM | 1585 | O   | GLU | 792 | 57.042 | 30.607 | 64.112 | 1.00 | 41.98 | sos |
| ATOM | 1586 | N   | SER | 793 | 55.497 | 29.056 | 64.645 | 1.00 | 36.85 | sos |
| ATOM | 1587 | CA  | SER | 793 | 55.398 | 28.541 | 63.278 | 1.00 | 36.16 | sos |
| ATOM | 1588 | CB  | SER | 793 | 54.730 | 27.170 | 63.234 | 1.00 | 35.06 | sos |
| ATOM | 1589 | OG  | SER | 793 | 54.742 | 26.682 | 61.899 | 1.00 | 38.63 | sos |
| ATOM | 1590 | C   | SER | 793 | 54.600 | 29.528 | 62.426 | 1.00 | 33.67 | sos |
| ATOM | 1591 | O   | SER | 793 | 54.997 | 29.860 | 61.315 | 1.00 | 31.85 | sos |
| ATOM | 1592 | N   | ASP | 794 | 53.482 | 30.006 | 62.961 | 1.00 | 30.94 | sos |
| ATOM | 1593 | CA  | ASP | 794 | 52.666 | 30.976 | 62.258 | 1.00 | 32.73 | sos |
| ATOM | 1594 | CB  | ASP | 794 | 51.449 | 31.362 | 63.098 | 1.00 | 33.18 | sos |
| ATOM | 1595 | CG  | ASP | 794 | 50.408 | 30.247 | 62.185 | 1.00 | 36.93 | sos |
| ATOM | 1596 | OD1 | ASP | 794 | 50.446 | 29.300 | 62.357 | 1.00 | 34.96 | sos |
| ATOM | 1597 | OD2 | ASP | 794 | 49.536 | 30.336 | 64.080 | 1.00 | 33.25 | sos |
| ATOM | 1598 | C   | ASP | 794 | 53.509 | 32.211 | 61.961 | 1.00 | 37.94 | sos |
| ATOM | 1599 | O   | ASP | 794 | 53.586 | 32.652 | 60.808 | 1.00 | 41.20 | sos |
| ATOM | 1600 | N   | LEU | 795 | 54.186 | 32.726 | 62.992 | 1.00 | 39.32 | sos |
| ATOM | 1601 | CA  | LEU | 795 | 55.041 | 33.904 | 62.862 | 1.00 | 36.31 | sos |
| ATOM | 1602 | CB  | LEU | 795 | 55.728 | 34.225 | 64.191 | 1.00 | 35.57 | sos |
| ATOM | 1603 | CG  | LEU | 795 | 54.843 | 34.697 | 65.351 | 1.00 | 39.55 | sos |
| ATOM | 1604 | CD1 | LEU | 795 | 55.698 | 34.920 | 66.585 | 1.00 | 32.77 | sos |
| ATOM | 1605 | CD2 | LEU | 795 | 54.083 | 35.967 | 64.985 | 1.00 | 33.97 | sos |
| ATOM | 1606 | C   | LEU | 795 | 56.082 | 33.714 | 61.767 | 1.00 | 36.51 | sos |
| ATOM | 1607 | O   | LEU | 795 | 56.326 | 34.620 | 60.961 | 1.00 | 34.84 | sos |
| ATOM | 1608 | N   | TYR | 796 | 56.671 | 32.522 | 61.726 | 1.00 | 35.48 | sos |
| ATOM | 1609 | CA  | TYR | 796 | 57.670 | 32.202 | 60.718 | 1.00 | 38.57 | sos |
| ATOM | 1610 | CB  | TYR | 796 | 58.353 | 30.877 | 61.035 | 1.00 | 33.30 | sos |
| ATOM | 1611 | CG  | TYR | 796 | 59.306 | 30.429 | 59.953 | 1.00 | 32.20 | sos |
| ATOM | 1612 | CD1 | TYR | 796 | 60.484 | 31.125 | 59.706 | 1.00 | 30.99 | sos |
| ATOM | 1613 | CE1 | TYR | 796 | 61.344 | 30.742 | 58.675 | 1.00 | 33.71 | sos |
| ATOM | 1614 | CD2 | TYR | 796 | 59.009 | 29.330 | 59.147 | 1.00 | 33.62 | sos |
| ATOM | 1615 | CE2 | TYR | 796 | 59.860 | 28.939 | 58.118 | 1.00 | 32.54 | sos |
| ATOM | 1616 | CZ  | TYR | 796 | 61.021 | 29.650 | 57.885 | 1.00 | 34.17 | sos |
| ATOM | 1617 | OH  | TYR | 796 | 61.852 | 29.281 | 56.852 | 1.00 | 34.94 | sos |
| ATOM | 1618 | C   | TYR | 796 | 57.074 | 32.126 | 59.319 | 1.00 | 41.30 | sos |
| ATOM | 1619 | O   | TYR | 796 | 57.649 | 32.651 | 58.369 | 1.00 | 46.55 | sos |
| ATOM | 1620 | N   | ARG | 797 | 55.924 | 31.469 | 59.198 | 1.00 | 43.54 | sos |

TABLE 3-continued

PDB Coordinates for the Ras-Sos Structure:
DATA SET FOR REFINED COORDINATES

| ATOM | 1621 | CA  | ARG | 797 | 55.255 | 31.297 | 57.903 | 1.00 | 44.26 | sos |
|------|------|-----|-----|-----|--------|--------|--------|------|-------|-----|
| ATOM | 1622 | CB  | ARG | 797 | 54.120 | 30.262 | 58.016 | 1.00 | 43.25 | sos |
| ATOM | 1623 | CG  | ARG | 797 | 54.519 | 28.945 | 58.657 | 1.00 | 48.61 | sos |
| ATOM | 1624 | CD  | ARG | 797 | 53.315 | 28.052 | 58.943 | 1.00 | 50.33 | sos |
| ATOM | 1625 | NE  | ARG | 797 | 52.966 | 27.228 | 57.790 | 1.00 | 53.06 | sos |
| ATOM | 1626 | CZ  | ARG | 797 | 51.729 | 27.024 | 57.357 | 1.00 | 49.86 | sos |
| ATOM | 1627 | NH1 | ARG | 797 | 50.700 | 27.583 | 57.978 | 1.00 | 50.65 | sos |
| ATOM | 1628 | NH2 | ARG | 797 | 51.525 | 26.262 | 56.295 | 1.00 | 52.23 | sos |
| ATOM | 1629 | C   | ARG | 797 | 54.683 | 32.592 | 57.321 | 1.00 | 41.37 | sos |
| ATOM | 1630 | O   | ARG | 797 | 54.302 | 32.628 | 56.154 | 1.00 | 39.16 | sos |
| ATOM | 1631 | N   | ALA | 798 | 54.624 | 33.651 | 58.123 | 1.00 | 37.11 | sos |
| ATOM | 1632 | CA  | ALA | 798 | 54.056 | 34.907 | 57.653 | 1.00 | 33.68 | sos |
| ATOM | 1633 | CB  | ALA | 798 | 53.304 | 35.591 | 58.786 | 1.00 | 27.85 | sos |
| ATOM | 1634 | C   | ALA | 798 | 55.028 | 35.879 | 56.985 | 1.00 | 33.50 | sos |
| ATOM | 1635 | O   | ALA | 798 | 54.610 | 36.862 | 56.368 | 1.00 | 37.79 | sos |
| ATOM | 1636 | N   | VAL | 799 | 56.319 | 35.595 | 57.069 | 1.00 | 31.91 | sos |
| ATOM | 1637 | CA  | VAL | 799 | 57.308 | 36.487 | 56.479 | 1.00 | 32.31 | sos |
| ATOM | 1638 | CB  | VAL | 799 | 58.707 | 36.273 | 57.098 | 1.00 | 29.54 | sos |
| ATOM | 1639 | CG1 | VAL | 799 | 59.666 | 37.326 | 56.588 | 1.00 | 27.87 | sos |
| ATOM | 1640 | CG2 | VAL | 799 | 58.625 | 36.314 | 58.611 | 1.00 | 20.72 | sos |
| ATOM | 1641 | C   | VAL | 799 | 57.392 | 36.359 | 54.964 | 1.00 | 34.13 | sos |
| ATOM | 1642 | O   | VAL | 799 | 57.570 | 35.269 | 54.424 | 1.00 | 38.42 | sos |
| ATOM | 1643 | N   | GLN | 800 | 57.253 | 37.485 | 54.282 | 1.00 | 35.08 | sos |
| ATOM | 1644 | CA  | GLN | 800 | 57.318 | 37.503 | 52.833 | 1.00 | 38.04 | sos |
| ATOM | 1645 | CB  | GLN | 800 | 56.312 | 38.505 | 52.269 | 1.00 | 40.22 | sos |
| ATOM | 1646 | CG  | GLN | 800 | 54.864 | 38.212 | 52.626 | 1.00 | 44.07 | sos |
| ATOM | 1647 | CD  | GLN | 800 | 54.478 | 36.762 | 52.386 | 1.00 | 50.52 | sos |
| ATOM | 1648 | OE1 | GLN | 800 | 54.826 | 36.162 | 51.361 | 1.00 | 52.62 | sos |
| ATOM | 1649 | NE2 | GLN | 800 | 53.763 | 36.185 | 53.343 | 1.00 | 56.05 | sos |
| ATOM | 1650 | C   | GLN | 800 | 58.714 | 37.856 | 52.355 | 1.00 | 39.57 | sos |
| ATOM | 1651 | O   | GLN | 800 | 59.458 | 38.558 | 53.037 | 1.00 | 45.69 | sos |
| ATOM | 1652 | N   | PRO | 801 | 59.101 | 37.360 | 51.174 | 1.00 | 38.94 | sos |
| ATOM | 1653 | CD  | PRO | 801 | 58.469 | 36.315 | 50.349 | 1.00 | 36.96 | sos |
| ATOM | 1654 | CA  | PRO | 801 | 60.437 | 37.675 | 50.669 | 1.00 | 35.55 | sos |
| ATOM | 1655 | CB  | PRO | 801 | 60.493 | 36.890 | 49.366 | 1.00 | 31.15 | sos |
| ATOM | 1656 | CG  | PRO | 801 | 59.671 | 35.678 | 49.694 | 1.00 | 31.47 | sos |
| ATOM | 1657 | C   | PRO | 801 | 60.652 | 39.167 | 50.447 | 1.00 | 34.71 | sos |
| ATOM | 1658 | O   | PRO | 801 | 61.789 | 39.630 | 50.422 | 1.00 | 37.18 | sos |
| ATOM | 1659 | N   | SER | 802 | 59.560 | 39.918 | 50.307 | 1.00 | 36.14 | sos |
| ATOM | 1660 | CA  | SER | 802 | 59.636 | 41.366 | 50.093 | 1.00 | 35.51 | sos |
| ATOM | 1661 | CB  | SER | 802 | 58.301 | 41.905 | 49.575 | 1.00 | 35.48 | sos |
| ATOM | 1662 | OG  | SER | 802 | 57.287 | 41.808 | 50.559 | 1.00 | 42.48 | sos |
| ATOM | 1663 | C   | SER | 802 | 60.043 | 42.106 | 51.371 | 1.00 | 34.52 | sos |
| ATOM | 1664 | O   | SER | 802 | 60.193 | 43.328 | 51.381 | 1.00 | 31.19 | sos |
| ATOM | 1665 | N   | GLU | 803 | 60.192 | 41.351 | 52.453 | 1.00 | 35.86 | sos |
| ATOM | 1666 | CA  | GLU | 803 | 60.603 | 41.906 | 53.732 | 1.00 | 38.50 | sos |
| ATOM | 1667 | CB  | GLU | 803 | 59.823 | 41.246 | 54.870 | 1.00 | 36.50 | sos |
| ATOM | 1668 | CG  | GLU | 803 | 58.340 | 41.514 | 54.823 | 1.00 | 43.32 | sos |
| ATOM | 1669 | CD  | GLU | 803 | 57.604 | 40.925 | 56.002 | 1.00 | 48.30 | sos |
| ATOM | 1670 | OE1 | GLU | 803 | 56.822 | 39.968 | 55.797 | 1.00 | 53.33 | sos |
| ATOM | 1671 | OE2 | GLU | 803 | 57.798 | 41.420 | 57.131 | 1.00 | 48.70 | sos |
| ATOM | 1672 | C   | GLU | 803 | 62.093 | 41.651 | 53.923 | 1.00 | 38.90 | sos |
| ATOM | 1673 | O   | GLU | 803 | 62.737 | 42.267 | 54.770 | 1.00 | 41.02 | sos |
| ATOM | 1674 | N   | LEU | 804 | 62.638 | 40.761 | 53.104 | 1.00 | 34.89 | sos |
| ATOM | 1675 | CA  | LEU | 804 | 64.034 | 40.399 | 53.202 | 1.00 | 32.81 | sos |
| ATOM | 1676 | CB  | LEU | 804 | 64.164 | 38.876 | 53.242 | 1.00 | 30.32 | sos |
| ATOM | 1677 | CG  | LEU | 804 | 63.196 | 38.180 | 54.200 | 1.00 | 29.48 | sos |
| ATOM | 1678 | CD1 | LEU | 804 | 63.322 | 36.694 | 54.060 | 1.00 | 25.98 | sos |
| ATOM | 1679 | CD2 | LEU | 804 | 63.452 | 38.601 | 55.628 | 1.00 | 27.46 | sos |
| ATOM | 1680 | C   | LEU | 804 | 64.879 | 40.963 | 52.076 | 1.00 | 32.25 | sos |
| ATOM | 1681 | O   | LEU | 804 | 65.965 | 41.473 | 52.309 | 1.00 | 35.65 | sos |
| ATOM | 1682 | N   | VAL | 805 | 64.374 | 40.884 | 50.856 | 1.00 | 34.37 | sos |
| ATOM | 1683 | CA  | VAL | 805 | 65.113 | 41.362 | 49.689 | 1.00 | 34.40 | sos |
| ATOM | 1684 | CB  | VAL | 805 | 64.310 | 41.099 | 48.388 | 1.00 | 29.10 | sos |
| ATOM | 1685 | CG1 | VAL | 805 | 65.081 | 41.597 | 47.184 | 1.00 | 31.84 | sos |
| ATOM | 1686 | CG2 | VAL | 805 | 64.054 | 39.610 | 48.248 | 1.00 | 24.43 | sos |
| ATOM | 1687 | C   | VAL | 805 | 65.538 | 42.832 | 49.792 | 1.00 | 33.89 | sos |
| ATOM | 1688 | O   | VAL | 805 | 64.743 | 43.705 | 50.133 | 1.00 | 31.64 | sos |
| ATOM | 1689 | N   | VAL | 805 | 66.808 | 43.093 | 49.510 | 1.00 | 33.96 | sos |
| ATOM | 1690 | CA  | GLY | 806 | 67.302 | 44.453 | 49.595 | 1.00 | 37.85 | sos |
| ATOM | 1691 | C   | GLY | 806 | 67.674 | 44.857 | 51.014 | 1.00 | 39.98 | sos |
| ATOM | 1692 | O   | GLY | 806 | 67.760 | 46.051 | 51.310 | 1.00 | 42.46 | sos |
| ATOM | 1693 | N   | SER | 807 | 67.871 | 43.866 | 51.888 | 1.00 | 37.67 | sos |
| ATOM | 1694 | CA  | SER | 807 | 68.240 | 44.081 | 53.290 | 1.00 | 35.94 | sos |
| ATOM | 1695 | CB  | SER | 807 | 69.694 | 44.530 | 53.383 | 1.00 | 35.71 | sos |
| ATOM | 1696 | OG  | SER | 807 | 70.559 | 43.526 | 52.888 | 1.00 | 41.01 | sos |

TABLE 3-continued

PDB Coordinates for the Ras-Sos Structure:
DATA SET FOR REFINED COORDINATES

| ATOM | 1697 | C   | SER | 807 | 67.339 | 45.112 | 53.945 | 1.00 | 36.28 | sos |
|------|------|-----|-----|-----|--------|--------|--------|------|-------|-----|
| ATOM | 1698 | O   | SER | 807 | 67.722 | 45.798 | 54.894 | 1.00 | 36.36 | sos |
| ATOM | 1699 | N   | VAL | 808 | 66.118 | 45.173 | 53.437 | 1.00 | 34.29 | sos |
| ATOM | 1700 | CA  | VAL | 808 | 65.105 | 46.113 | 53.868 | 1.00 | 31.50 | sos |
| ATOM | 1701 | CB  | VAL | 808 | 63.851 | 45.909 | 52.990 | 1.00 | 31.10 | sos |
| ATOM | 1702 | CG1 | VAL | 808 | 62.592 | 45.959 | 53.791 | 1.00 | 34.35 | sos |
| ATOM | 1703 | CG2 | VAL | 808 | 63.832 | 46.938 | 51.885 | 1.00 | 28.74 | sos |
| ATOM | 1704 | C   | VAL | 808 | 64.797 | 46.204 | 55.373 | 1.00 | 32.62 | sos |
| ATOM | 1705 | O   | VAL | 808 | 64.427 | 47.278 | 55.859 | 1.00 | 28.91 | sos |
| ATOM | 1706 | N   | TRP | 809 | 64.990 | 45.112 | 56.117 | 1.00 | 33.43 | sos |
| ATOM | 1707 | CA  | TRP | 809 | 64.728 | 45.124 | 57.565 | 1.00 | 30.82 | sos |
| ATOM | 1708 | CB  | TRP | 809 | 64.513 | 43.704 | 58.109 | 1.00 | 24.16 | sos |
| ATOM | 1709 | CG  | TRP | 809 | 65.776 | 42.929 | 58.317 | 1.00 | 27.11 | sos |
| ATOM | 1710 | CD2 | TRP | 809 | 66.550 | 42.269 | 57.313 | 1.00 | 27.81 | sos |
| ATOM | 1711 | CE2 | TRP | 809 | 67.695 | 41.742 | 57.948 | 1.00 | 28.87 | sos |
| ATOM | 1712 | CE3 | TRP | 809 | 66.393 | 42.076 | 55.936 | 1.00 | 26.50 | sos |
| ATOM | 1713 | CD1 | TRP | 809 | 66.456 | 42.765 | 59.492 | 1.00 | 26.39 | sos |
| ATOM | 1714 | NE1 | TRP | 809 | 67.613 | 42.061 | 59.278 | 1.00 | 21.95 | sos |
| ATOM | 1715 | CZ2 | TRP | 809 | 68.678 | 41.036 | 57.250 | 1.00 | 27.71 | sos |
| ATOM | 1716 | CZ3 | TRP | 809 | 67.370 | 41.377 | 55.246 | 1.00 | 28.78 | sos |
| ATOM | 1717 | CH2 | TRP | 809 | 68.497 | 40.866 | 55.904 | 1.00 | 27.52 | sos |
| ATOM | 1718 | C   | TRP | 809 | 65.827 | 45.829 | 58.375 | 1.00 | 32.30 | sos |
| ATOM | 1719 | O   | TRP | 809 | 65.731 | 45.930 | 59.599 | 1.00 | 32.47 | sos |
| ATOM | 1720 | N   | THR | 810 | 66.877 | 46.295 | 57.704 | 1.00 | 32.72 | sos |
| ATOM | 1721 | CA  | THR | 810 | 67.957 | 46.985 | 58.400 | 1.00 | 34.60 | sos |
| ATOM | 1722 | CB  | THR | 810 | 69.352 | 46.448 | 58.015 | 1.00 | 34.41 | sos |
| ATOM | 1723 | OG1 | THR | 810 | 69.672 | 46.844 | 56.677 | 1.00 | 38.94 | sos |
| ATOM | 1724 | CG2 | THR | 810 | 69.390 | 44.931 | 58.120 | 1.00 | 37.53 | sos |
| ATOM | 1725 | C   | THR | 810 | 67.948 | 48.494 | 58.195 | 1.00 | 35.55 | sos |
| ATOM | 1726 | O   | THR | 810 | 68.559 | 49.226 | 58.980 | 1.00 | 41.48 | sos |
| ATOM | 1727 | N   | LYS | 811 | 67.262 | 48.957 | 57.147 | 1.00 | 34.35 | sos |
| ATOM | 1728 | CA  | LYS | 811 | 67.174 | 50.389 | 56.832 | 1.00 | 31.36 | sos |
| ATOM | 1729 | CB  | LYS | 811 | 66.734 | 50.586 | 55.380 | 1.00 | 33.00 | sos |
| ATOM | 1730 | CG  | LYS | 811 | 67.352 | 49.628 | 54.380 | 1.00 | 30.80 | sos |
| ATOM | 1731 | CD  | LYS | 811 | 68.681 | 50.111 | 53.860 | 1.00 | 37.17 | sos |
| ATOM | 1732 | CE  | LYS | 811 | 69.174 | 49.209 | 52.748 | 1.00 | 43.43 | sos |
| ATOM | 1733 | NZ  | LYS | 811 | 68.164 | 49.113 | 51.639 | 1.00 | 52.12 | sos |
| ATOM | 1734 | C   | LYS | 811 | 66.208 | 51.147 | 57.760 | 1.00 | 33.21 | sos |
| ATOM | 1735 | O   | LYS | 811 | 65.470 | 50.542 | 58.544 | 1.00 | 31.41 | sos |
| ATOM | 1736 | N   | GLU | 812 | 66.181 | 52.472 | 57.630 | 1.00 | 36.64 | sos |
| ATOM | 1737 | CA  | GLU | 812 | 65.318 | 53.311 | 58.464 | 1.00 | 37.16 | sos |
| ATOM | 1738 | CB  | GLU | 812 | 65.599 | 54.798 | 58.218 | 1.00 | 35.79 | sos |
| ATOM | 1739 | CG  | GLU | 812 | 65.255 | 55.303 | 56.829 | 1.00 | 43.94 | sos |
| ATOM | 1740 | CD  | GLU | 812 | 65.452 | 56.812 | 56.678 | 1.00 | 49.71 | sos |
| ATOM | 1741 | OE1 | GLU | 812 | 64.468 | 57.511 | 56.331 | 1.00 | 56.35 | sos |
| ATOM | 1742 | OE2 | GLU | 812 | 66.586 | 57.297 | 56.896 | 1.00 | 48.88 | sos |
| ATOM | 1743 | C   | GLU | 812 | 63.818 | 53.027 | 58.363 | 1.00 | 37.58 | sos |
| ATOM | 1744 | O   | GLU | 812 | 63.075 | 53.302 | 59.305 | 1.00 | 39.37 | sos |
| ATOM | 1745 | N   | ASP | 813 | 63.370 | 52.483 | 57.234 | 1.00 | 39.99 | sos |
| ATOM | 1746 | CA  | ASP | 813 | 61.948 | 52.174 | 57.057 | 1.00 | 41.54 | sos |
| ATOM | 1747 | CB  | ASP | 813 | 61.467 | 52.559 | 55.652 | 1.00 | 41.03 | sos |
| ATOM | 1748 | CG  | ASP | 813 | 61.378 | 54.064 | 55.436 | 1.00 | 45.66 | sos |
| ATOM | 1749 | OD1 | ASP | 813 | 61.317 | 54.854 | 56.414 | 1.00 | 44.80 | sos |
| ATOM | 1750 | OD2 | ASP | 813 | 61.352 | 54.453 | 54.251 | 1.00 | 46.93 | sos |
| ATOM | 1751 | C   | ASP | 813 | 61.631 | 50.700 | 57.319 | 1.00 | 41.00 | sos |
| ATOM | 1752 | O   | ASP | 813 | 60.724 | 50.132 | 56.713 | 1.00 | 40.32 | sos |
| ATOM | 1753 | N   | LYS | 814 | 62.358 | 50.091 | 58.250 | 1.00 | 42.35 | sos |
| ATOM | 1754 | CA  | LYS | 814 | 62.146 | 48.689 | 58.578 | 1.00 | 38.25 | sos |
| ATOM | 1755 | CB  | LYS | 814 | 63.261 | 48.165 | 59.489 | 1.00 | 40.08 | sos |
| ATOM | 1756 | CG  | LYS | 814 | 63.461 | 48.912 | 60.798 | 1.00 | 43.89 | sos |
| ATOM | 1757 | CD  | LYS | 814 | 64.532 | 48.211 | 61.631 | 1.00 | 52.47 | sos |
| ATOM | 1758 | CE  | LYS | 814 | 65.033 | 49.064 | 62.783 | 1.00 | 54.54 | sos |
| ATOM | 1759 | NZ  | LYS | 814 | 65.708 | 50.298 | 62.283 | 1.00 | 60.98 | sos |
| ATOM | 1760 | C   | LYS | 814 | 60.774 | 48.380 | 59.173 | 1.00 | 36.03 | sos |
| ATOM | 1761 | O   | LYS | 814 | 60.175 | 47.364 | 58.832 | 1.00 | 31.79 | sos |
| ATOM | 1762 | N   | GLU | 815 | 60.270 | 49.252 | 60.048 | 1.00 | 36.71 | sos |
| ATOM | 1763 | CA  | GLU | 815 | 58.961 | 49.030 | 60.670 | 1.00 | 36.45 | sos |
| ATOM | 1764 | CB  | GLU | 815 | 58.609 | 50.151 | 61.656 | 1.00 | 34.50 | sos |
| ATOM | 1765 | CG  | GLU | 815 | 59.606 | 50.395 | 62.780 | 1.00 | 36.88 | sos |
| ATOM | 1766 | CD  | GLU | 815 | 59.728 | 49.256 | 62.790 | 1.00 | 38.07 | sos |
| ATOM | 1767 | OE1 | GLU | 815 | 60.710 | 49.272 | 64.560 | 1.00 | 44.19 | sos |
| ATOM | 1768 | OE2 | GLU | 815 | 58.861 | 48.363 | 63.840 | 1.00 | 38.38 | sos |
| ATOM | 1769 | C   | GLU | 815 | 57.868 | 48.945 | 59.610 | 1.00 | 36.31 | sos |
| ATOM | 1770 | O   | GLU | 815 | 56.887 | 48.221 | 59.774 | 1.00 | 39.13 | sos |
| ATOM | 1771 | N   | ILE | 816 | 58.061 | 49.692 | 58.526 | 1.00 | 32.49 | sos |
| ATOM | 1772 | CA  | ILE | 816 | 57.128 | 49.753 | 57.410 | 1.00 | 30.08 | sos |

TABLE 3-continued

PDB Coordinates for the Ras-Sos Structure:
DATA SET FOR REFINED COORDINATES

| ATOM | 1773 | CB  | ILE | 816 | 57.331 | 51.061 | 56.626 | 1.00 | 30.31 | sos |
|------|------|-----|-----|-----|--------|--------|--------|------|-------|-----|
| ATOM | 1774 | CG2 | ILE | 816 | 56.581 | 51.035 | 55.314 | 1.00 | 29.68 | sos |
| ATOM | 1775 | CG1 | ILE | 816 | 56.893 | 52.252 | 57.473 | 1.00 | 25.25 | sos |
| ATOM | 1776 | CD1 | ILE | 816 | 57.327 | 53.585 | 56.891 | 1.00 | 26.51 | sos |
| ATOM | 1777 | C   | ILE | 816 | 57.246 | 48.574 | 56.446 | 1.00 | 31.70 | sos |
| ATOM | 1778 | O   | ILE | 816 | 56.250 | 47.925 | 56.145 | 1.00 | 35.11 | sos |
| ATOM | 1779 | N   | ASN | 817 | 58.465 | 48.291 | 55.991 | 1.00 | 29.29 | sos |
| ATOM | 1780 | CA  | ASN | 817 | 58.726 | 47.219 | 55.036 | 1.00 | 29.09 | sos |
| ATOM | 1781 | CB  | ASN | 817 | 59.971 | 47.552 | 54.221 | 1.00 | 33.05 | sos |
| ATOM | 1782 | CG  | ASN | 817 | 59.799 | 48.779 | 53.342 | 1.00 | 38.44 | sos |
| ATOM | 1783 | OD1 | ASN | 817 | 58.790 | 48.933 | 52.642 | 1.00 | 42.97 | sos |
| ATOM | 1784 | ND2 | ASN | 817 | 60.798 | 49.650 | 53.356 | 1.00 | 30.19 | sos |
| ATOM | 1785 | C   | ASN | 817 | 58.852 | 45.773 | 55.526 | 1.00 | 33.20 | sos |
| ATOM | 1786 | O   | ASN | 817 | 58.654 | 44.844 | 54.739 | 1.00 | 36.73 | sos |
| ATOM | 1787 | N   | SER | 818 | 59.202 | 45.560 | 56.794 | 1.00 | 34.38 | sos |
| ATOM | 1788 | CA  | SER | 818 | 59.363 | 44.193 | 57.322 | 1.00 | 30.04 | sos |
| ATOM | 1789 | CB  | SER | 818 | 60.833 | 43.896 | 57.606 | 1.00 | 22.90 | sos |
| ATOM | 1790 | OG  | SER | 818 | 61.678 | 44.341 | 56.566 | 1.00 | 22.85 | sos |
| ATOM | 1791 | C   | SER | 818 | 58.603 | 43.998 | 58.619 | 1.00 | 30.52 | sos |
| ATOM | 1792 | O   | SER | 818 | 59.140 | 43.447 | 59.571 | 1.00 | 30.86 | sos |
| ATOM | 1793 | N   | PRO | 819 | 57.319 | 44.379 | 58.652 | 1.00 | 33.07 | sos |
| ATOM | 1794 | CD  | PRO | 819 | 56.475 | 44.859 | 57.545 | 1.00 | 31.35 | sos |
| ATOM | 1795 | CA  | PRO | 819 | 56.525 | 44.236 | 59.875 | 1.00 | 31.94 | sos |
| ATOM | 1796 | CB  | PRO | 819 | 55.189 | 44.883 | 59.492 | 1.00 | 26.86 | sos |
| ATOM | 1797 | CG  | PRO | 819 | 55.082 | 44.566 | 58.060 | 1.00 | 31.08 | sos |
| ATOM | 1798 | C   | PRO | 819 | 56.342 | 42.831 | 60.419 | 1.00 | 31.70 | sos |
| ATOM | 1799 | O   | PRO | 819 | 56.172 | 42.667 | 61.622 | 1.00 | 39.13 | sos |
| ATOM | 1800 | N   | ASN | 820 | 56.349 | 41.824 | 59.553 | 1.00 | 30.62 | sos |
| ATOM | 1801 | CA  | ASN | 820 | 56.165 | 40.445 | 60.014 | 1.00 | 31.72 | sos |
| ATOM | 1802 | CB  | ASN | 820 | 55.672 | 39.545 | 58.878 | 1.00 | 32.23 | sos |
| ATOM | 1803 | CG  | ASN | 820 | 54.338 | 39.980 | 58.332 | 1.00 | 30.27 | sos |
| ATOM | 1804 | OD1 | ASN | 820 | 53.345 | 40.036 | 59.057 | 1.00 | 27.88 | sos |
| ATOM | 1805 | ND2 | ASN | 820 | 54.304 | 40.291 | 57.045 | 1.00 | 29.05 | sos |
| ATOM | 1806 | C   | ASN | 820 | 57.439 | 39.862 | 60.605 | 1.00 | 31.97 | sos |
| ATOM | 1807 | O   | ASN | 820 | 57.390 | 39.126 | 61.590 | 1.00 | 34.79 | sos |
| ATOM | 1808 | N   | LEU | 821 | 58.567 | 40.173 | 59.972 | 1.00 | 28.78 | sos |
| ATOM | 1809 | CA  | LEU | 821 | 59.878 | 39.714 | 60.406 | 1.00 | 28.17 | sos |
| ATOM | 1810 | CB  | LEU | 821 | 60.947 | 40.268 | 59.469 | 1.00 | 25.69 | sos |
| ATOM | 1811 | CG  | LEU | 821 | 62.231 | 39.483 | 59.225 | 1.00 | 26.93 | sos |
| ATOM | 1812 | CD1 | LEU | 821 | 63.398 | 40.447 | 59.234 | 1.00 | 23.48 | sos |
| ATOM | 1813 | CD2 | LEU | 821 | 62.420 | 38.387 | 60.257 | 1.00 | 27.27 | sos |
| ATOM | 1814 | C   | LEU | 821 | 60.156 | 40.219 | 61.818 | 1.00 | 32.63 | sos |
| ATOM | 1815 | O   | LEU | 821 | 60.492 | 39.440 | 62.718 | 1.00 | 35.85 | sos |
| ATOM | 1816 | N   | LEU | 822 | 59.990 | 41.525 | 62.006 | 1.00 | 31.78 | sos |
| ATOM | 1817 | CA  | LEU | 822 | 60.230 | 42.159 | 63.298 | 1.00 | 32.96 | sos |
| ATOM | 1818 | CB  | LEU | 822 | 60.155 | 43.682 | 63.147 | 1.00 | 26.37 | sos |
| ATOM | 1819 | CG  | LEU | 822 | 61.188 | 44.237 | 62.151 | 1.00 | 27.51 | sos |
| ATOM | 1820 | CD1 | LEU | 822 | 60.863 | 45.662 | 61.751 | 1.00 | 24.75 | sos |
| ATOM | 1821 | CD2 | LEU | 822 | 62.571 | 44.157 | 62.748 | 1.00 | 20.00 | sos |
| ATOM | 1822 | C   | LEU | 822 | 59.278 | 41.647 | 64.384 | 1.00 | 33.18 | sos |
| ATOM | 1823 | O   | LEU | 822 | 59.655 | 41.498 | 65.547 | 1.00 | 31.42 | sos |
| ATOM | 1824 | N   | LYS | 823 | 58.062 | 41.316 | 63.982 | 1.00 | 33.83 | sos |
| ATOM | 1825 | CA  | LYS | 823 | 57.061 | 40.816 | 64.910 | 1.00 | 36.85 | sos |
| ATOM | 1826 | CB  | LYS | 823 | 55.708 | 40.740 | 64.194 | 1.00 | 40.57 | sos |
| ATOM | 1827 | CG  | LYS | 823 | 54.485 | 40.700 | 65.089 | 1.00 | 47.70 | sos |
| ATOM | 1828 | CD  | LYS | 823 | 53.248 | 41.222 | 64.334 | 1.00 | 55.15 | sos |
| ATOM | 1829 | CE  | LYS | 823 | 53.451 | 42.678 | 63.854 | 1.00 | 59.01 | sos |
| ATOM | 1830 | NZ  | LYS | 823 | 52.225 | 43.354 | 63.323 | 1.00 | 54.77 | sos |
| ATOM | 1831 | C   | LYS | 823 | 57.497 | 39.438 | 65.399 | 1.00 | 35.91 | sos |
| ATOM | 1832 | O   | LYS | 823 | 57.255 | 39.069 | 66.547 | 1.00 | 35.24 | sos |
| ATOM | 1833 | N   | MET | 824 | 58.179 | 38.703 | 64.524 | 1.00 | 36.31 | sos |
| ATOM | 1834 | CA  | MET | 824 | 58.654 | 37.360 | 64.839 | 1.00 | 35.97 | sos |
| ATOM | 1835 | CB  | MET | 824 | 58.956 | 36.597 | 63.548 | 1.00 | 36.40 | sos |
| ATOM | 1836 | CG  | MET | 824 | 59.380 | 35.151 | 63.733 | 1.00 | 35.54 | sos |
| ATOM | 1837 | SD  | MET | 824 | 61.144 | 35.067 | 63.983 | 1.00 | 50.50 | sos |
| ATOM | 1838 | CE  | MET | 824 | 61.739 | 35.718 | 62.410 | 1.00 | 36.08 | sos |
| ATOM | 1839 | C   | MET | 824 | 59.871 | 37.421 | 65.751 | 1.00 | 33.11 | sos |
| ATOM | 1840 | O   | MET | 824 | 59.914 | 36.757 | 66.785 | 1.00 | 32.16 | sos |
| ATOM | 1841 | N   | ILE | 825 | 60.829 | 38.270 | 65.390 | 1.00 | 33.02 | sos |
| ATOM | 1842 | CA  | ILE | 825 | 62.032 | 38.439 | 66.188 | 1.00 | 29.23 | sos |
| ATOM | 1843 | CB  | ILE | 825 | 63.060 | 39.324 | 65.487 | 1.00 | 27.67 | sos |
| ATOM | 1844 | CG2 | ILE | 825 | 64.363 | 39.289 | 66.262 | 1.00 | 24.70 | sos |
| ATOM | 1845 | CG1 | ILE | 825 | 63.312 | 38.800 | 64.068 | 1.00 | 25.91 | sos |
| ATOM | 1846 | CD1 | ILE | 825 | 64.310 | 39.608 | 63.264 | 1.00 | 20.47 | sos |
| ATOM | 1847 | C   | ILE | 825 | 61.698 | 39.000 | 67.568 | 1.00 | 28.60 | sos |
| ATOM | 1848 | O   | ILE | 825 | 62.249 | 38.547 | 68.573 | 1.00 | 32.93 | sos |

TABLE 3-continued

PDB Coordinates for the Ras-Sos Structure:
DATA SET FOR REFINED COORDINATES

| ATOM | 1849 | N | ARG | 826 | 60.763 | 39.944 | 67.631 | 1.00 | 26.29 | sos |
|---|---|---|---|---|---|---|---|---|---|---|
| ATOM | 1850 | CA | ARG | 826 | 60.359 | 40.510 | 68.915 | 1.00 | 24.09 | sos |
| ATOM | 1851 | CB | ARG | 826 | 59.478 | 41.739 | 68.728 | 1.00 | 15.92 | sos |
| ATOM | 1852 | CG | ARG | 826 | 60.314 | 42.939 | 68.361 | 1.00 | 26.19 | sos |
| ATOM | 1853 | CD | ARG | 826 | 59.600 | 43.924 | 67.494 | 1.00 | 25.33 | sos |
| ATOM | 1854 | NE | ARG | 826 | 60.530 | 44.949 | 67.043 | 1.00 | 28.97 | sos |
| ATOM | 1855 | CZ | ARG | 826 | 60.208 | 45.932 | 66.207 | 1.00 | 33.48 | sos |
| ATOM | 1856 | NH1 | ARG | 826 | 58.971 | 46.011 | 65.727 | 1.00 | 26.29 | sos |
| ATOM | 1857 | NH2 | ARG | 826 | 61.119 | 46.846 | 65.872 | 1.00 | 25.52 | sos |
| ATOM | 1858 | C | ARG | 826 | 59.725 | 39.497 | 69.858 | 1.00 | 25.27 | sos |
| ATOM | 1859 | O | ARG | 826 | 59.831 | 39.651 | 71.071 | 1.00 | 28.85 | sos |
| ATOM | 1860 | N | HIS | 827 | 59.098 | 38.456 | 69.303 | 1.00 | 28.80 | sos |
| ATOM | 1861 | CA | HIS | 827 | 58.488 | 37.383 | 70.100 | 1.00 | 28.18 | sos |
| ATOM | 1862 | CB | HIS | 827 | 57.611 | 36.475 | 69.228 | 1.00 | 26.35 | sos |
| ATOM | 1863 | CG | HIS | 827 | 57.200 | 35.191 | 69.228 | 1.00 | 26.35 | sos |
| ATOM | 1864 | CD2 | HIS | 827 | 57.776 | 33.965 | 69.899 | 1.00 | 19.17 | sos |
| ATOM | 1865 | ND1 | HIS | 827 | 56.038 | 35.068 | 70.633 | 1.00 | 26.75 | sos |
| ATOM | 1866 | CE1 | HIS | 827 | 55.914 | 33.822 | 71.054 | 1.00 | 19.14 | sos |
| ATOM | 1867 | NE2 | HIS | 827 | 56.957 | 33.132 | 70.623 | 1.00 | 22.09 | sos |
| ATOM | 1868 | C | HIS | 827 | 59.618 | 36.547 | 70.682 | 1.00 | 28.25 | sos |
| ATOM | 1869 | O | HIS | 827 | 59.594 | 36.199 | 71.861 | 1.00 | 28.05 | sos |
| ATOM | 1870 | N | THR | 828 | 60.588 | 36.205 | 69.837 | 1.00 | 24.01 | sos |
| ATOM | 1871 | CA | THR | 828 | 61.724 | 35.408 | 70.269 | 1.00 | 27.74 | sos |
| ATOM | 1872 | CB | THR | 828 | 62.716 | 35.179 | 69.107 | 1.00 | 25.58 | sos |
| ATOM | 1873 | OG1 | THR | 828 | 62.088 | 34.387 | 68.098 | 1.00 | 30.68 | sos |
| ATOM | 1874 | CG2 | THR | 828 | 63.947 | 34.456 | 69.580 | 1.00 | 25.91 | sos |
| ATOM | 1875 | C | THR | 828 | 62.419 | 36.115 | 71.432 | 1.00 | 31.88 | sos |
| ATOM | 1876 | O | THR | 828 | 62.643 | 35.519 | 72.492 | 1.00 | 32.90 | sos |
| ATOM | 1877 | N | THR | 829 | 62.688 | 37.406 | 71.246 | 1.00 | 32.17 | sos |
| ATOM | 1878 | CA | THR | 829 | 63.342 | 38.219 | 72.261 | 1.00 | 29.05 | sos |
| ATOM | 1879 | CB | THR | 829 | 63.540 | 39.661 | 71.762 | 1.00 | 23.49 | sos |
| ATOM | 1880 | OG1 | THR | 829 | 64.457 | 39.657 | 70.665 | 1.00 | 33.39 | sos |
| ATOM | 1881 | CG2 | THR | 829 | 64.099 | 40.543 | 72.858 | 1.00 | 12.28 | sos |
| ATOM | 1882 | C | THR | 829 | 62.510 | 38.241 | 73.534 | 1.00 | 31.45 | sos |
| ATOM | 1883 | O | THR | 829 | 63.028 | 38.083 | 74.641 | 1.00 | 34.90 | sos |
| ATOM | 1884 | N | ASN | 830 | 61.206 | 38.386 | 73.362 | 1.00 | 28.56 | sos |
| ATOM | 1885 | CA | ASN | 830 | 60.292 | 38.448 | 74.482 | 1.00 | 29.34 | sos |
| ATOM | 1886 | CB | ASN | 830 | 58.875 | 38.666 | 73.974 | 1.00 | 32.67 | sos |
| ATOM | 1887 | CG | ASN | 830 | 58.178 | 39.783 | 74.681 | 1.00 | 37.22 | sos |
| ATOM | 1888 | OD1 | ASN | 830 | 57.084 | 39.600 | 75.210 | 1.00 | 46.40 | sos |
| ATOM | 1889 | ND2 | ASN | 830 | 58.798 | 40.960 | 74.690 | 1.00 | 37.01 | sos |
| ATOM | 1890 | C | ASN | 830 | 60.337 | 37.190 | 75.310 | 1.00 | 30.76 | sos |
| ATOM | 1891 | O | ASN | 830 | 60.269 | 37.248 | 76.537 | 1.00 | 32.53 | sos |
| ATOM | 1892 | N | LEU | 831 | 60.445 | 36.045 | 74.646 | 1.00 | 32.45 | sos |
| ATOM | 1893 | CA | LEU | 831 | 60.473 | 34.799 | 75.379 | 1.00 | 34.32 | sos |
| ATOM | 1894 | CB | LEU | 831 | 59.978 | 33.627 | 74.545 | 1.00 | 36.69 | sos |
| ATOM | 1895 | CG | LEU | 831 | 58.562 | 33.379 | 75.060 | 1.00 | 38.32 | sos |
| ATOM | 1896 | CD1 | LEU | 831 | 57.540 | 34.044 | 74.156 | 1.00 | 34.85 | sos |
| ATOM | 1897 | CD2 | LEU | 831 | 58.319 | 31.911 | 75.195 | 1.00 | 38.04 | sos |
| ATOM | 1898 | C | LEU | 831 | 61.790 | 34.512 | 76.039 | 1.00 | 35.08 | sos |
| ATOM | 1899 | O | LEU | 831 | 61.813 | 34.036 | 77.175 | 1.00 | 39.64 | sos |
| ATOM | 1900 | N | THR | 832 | 62.885 | 34.825 | 75.354 | 1.00 | 30.32 | sos |
| ATOM | 1901 | CA | THR | 832 | 64.196 | 34.628 | 75.941 | 1.00 | 27.71 | sos |
| ATOM | 1902 | CB | THR | 832 | 65.284 | 35.170 | 75.042 | 1.00 | 26.29 | sos |
| ATOM | 1903 | OG1 | THR | 832 | 65.359 | 34.379 | 73.853 | 1.00 | 33.60 | sos |
| ATOM | 1904 | CG2 | THR | 832 | 66.615 | 35.129 | 75.749 | 1.00 | 32.62 | sos |
| ATOM | 1905 | C | THR | 832 | 64.210 | 35.406 | 77.261 | 1.00 | 32.07 | sos |
| ATOM | 1906 | O | THR | 832 | 64.570 | 34.862 | 78.306 | 1.00 | 36.74 | sos |
| ATOM | 1907 | N | LEU | 833 | 63.715 | 36.643 | 77.221 | 1.00 | 30.92 | sos |
| ATOM | 1908 | CA | LEU | 833 | 63.666 | 37.495 | 78.401 | 1.00 | 27.97 | sos |
| ATOM | 1909 | CB | LEU | 833 | 63.318 | 38.938 | 78.023 | 1.00 | 26.95 | sos |
| ATOM | 1910 | CG | LEU | 833 | 64.355 | 39.680 | 77.157 | 1.00 | 31.77 | sos |
| ATOM | 1911 | CD1 | LEU | 833 | 63.895 | 41.095 | 76.871 | 1.00 | 22.17 | sos |
| ATOM | 1912 | CD2 | LEU | 833 | 65.718 | 39.699 | 77.836 | 1.00 | 25.40 | sos |
| ATOM | 1913 | C | LEU | 833 | 62.723 | 36.997 | 79.488 | 1.00 | 30.66 | sos |
| ATOM | 1914 | O | LEU | 833 | 63.033 | 37.126 | 80.675 | 1.00 | 31.68 | sos |
| ATOM | 1915 | N | TRP | 834 | 61.583 | 36.425 | 79.102 | 1.00 | 30.81 | sos |
| ATOM | 1916 | CA | TRP | 834 | 60.624 | 35.932 | 80.093 | 1.00 | 30.70 | sos |
| ATOM | 1917 | CB | TRP | 834 | 59.306 | 35.560 | 79.419 | 1.00 | 25.41 | sos |
| ATOM | 1918 | CG | TRP | 834 | 58.271 | 34.924 | 80.315 | 1.00 | 23.44 | sos |
| ATOM | 1919 | CD2 | TRP | 834 | 57.846 | 33.555 | 80.289 | 1.00 | 22.03 | sos |
| ATOM | 1920 | CE2 | TRP | 834 | 56.763 | 33.428 | 81.205 | 1.00 | 24.35 | sos |
| ATOM | 1921 | CE3 | TRP | 834 | 58.260 | 32.423 | 79.573 | 1.00 | 22.65 | sos |
| ATOM | 1922 | CD1 | TRP | 834 | 57.477 | 35.550 | 81.234 | 1.00 | 26.60 | sos |
| ATOM | 1923 | NE1 | TRP | 834 | 56.568 | 34.659 | 81.772 | 1.00 | 24.40 | sos |
| ATOM | 1924 | CZ2 | TRP | 834 | 56.114 | 32.214 | 81.420 | 1.00 | 21.70 | sos |

TABLE 3-continued

PDB Coordinates for the Ras-Sos Structure:
DATA SET FOR REFINED COORDINATES

| ATOM | 1925 | CZ3 | TRP | 834 | 57.601 | 31.214 | 79.789 | 1.00 | 19.58 | sos |
|------|------|-----|-----|-----|--------|--------|--------|------|-------|-----|
| ATOM | 1926 | CH2 | TRP | 834 | 56.540 | 31.123 | 80.705 | 1.00 | 21.38 | sos |
| ATOM | 1927 | C | TRP | 834 | 61.211 | 34.748 | 80.869 | 1.00 | 35.00 | sos |
| ATOM | 1928 | O | TRP | 834 | 60.957 | 34.590 | 82.067 | 1.00 | 32.32 | sos |
| ATOM | 1929 | N | PHE | 835 | 62.018 | 33.938 | 80.183 | 1.00 | 35.45 | sos |
| ATOM | 1930 | CA | PHE | 835 | 62.664 | 32.791 | 80.806 | 1.00 | 31.64 | sos |
| ATOM | 1931 | CB | PHE | 835 | 63.365 | 31.929 | 79.753 | 1.00 | 31.85 | sos |
| ATOM | 1932 | CG | PHE | 835 | 62.427 | 31.052 | 78.957 | 1.00 | 31.11 | sos |
| ATOM | 1933 | CD1 | PHE | 835 | 62.640 | 30.831 | 77.602 | 1.00 | 31.59 | sos |
| ATOM | 1934 | CD2 | PHE | 835 | 61.331 | 30.447 | 79.564 | 1.00 | 28.75 | sos |
| ATOM | 1935 | CE1 | PHE | 835 | 61.770 | 30.018 | 76.860 | 1.00 | 31.83 | sos |
| ATOM | 1936 | CE2 | PHE | 835 | 60.460 | 29.633 | 78.830 | 1.00 | 31.83 | sos |
| ATOM | 1937 | CZ | PHE | 835 | 60.681 | 29.421 | 77.477 | 1.00 | 26.83 | sos |
| ATOM | 1938 | C | PHE | 835 | 63.662 | 33.302 | 81.843 | 1.00 | 32.86 | sos |
| ATOM | 1939 | O | PHE | 835 | 63.677 | 32.837 | 82.986 | 1.00 | 34.48 | sos |
| ATOM | 1940 | N | GLU | 836 | 64.456 | 34.299 | 81.458 | 1.00 | 28.18 | sos |
| ATOM | 1941 | CA | GLU | 836 | 65.433 | 34.889 | 82.365 | 1.00 | 23.70 | sos |
| ATOM | 1942 | CB | GLU | 836 | 66.206 | 36.004 | 81.668 | 1.00 | 20.91 | sos |
| ATOM | 1943 | CG | GLU | 836 | 67.080 | 35.530 | 80.526 | 1.00 | 20.46 | sos |
| ATOM | 1944 | CD | GLU | 836 | 67.789 | 36.662 | 79.825 | 1.00 | 21.62 | sos |
| ATOM | 1945 | OE1 | GLU | 836 | 67.921 | 37.755 | 80.419 | 1.00 | 26.46 | sos |
| ATOM | 1946 | OE2 | GLU | 836 | 68.229 | 36.461 | 78.673 | 1.00 | 28.51 | sos |
| ATOM | 1947 | C | GLU | 836 | 64.738 | 35.456 | 83.592 | 1.00 | 25.88 | sos |
| ATOM | 1948 | O | GLU | 836 | 65.141 | 35.183 | 84.719 | 1.00 | 26.09 | sos |
| ATOM | 1949 | N | LYS | 837 | 63.675 | 36.224 | 83.362 | 1.00 | 27.21 | sos |
| ATOM | 1950 | CA | LYS | 837 | 62.906 | 36.848 | 84.435 | 1.00 | 29.26 | sos |
| ATOM | 1951 | CB | LYS | 837 | 61.820 | 37.739 | 83.828 | 1.00 | 33.52 | sos |
| ATOM | 1952 | CG | LYS | 837 | 60.833 | 38.395 | 84.790 | 1.00 | 29.02 | sos |
| ATOM | 1953 | CD | LYS | 837 | 60.058 | 39.464 | 84.019 | 1.00 | 31.57 | sos |
| ATOM | 1954 | CE | LYS | 837 | 58.772 | 39.895 | 84.705 | 1.00 | 32.59 | sos |
| ATOM | 1955 | NZ | LYS | 837 | 59.014 | 40.772 | 85.863 | 1.00 | 38.47 | sos |
| ATOM | 1956 | C | LYS | 837 | 62.303 | 35.813 | 85.375 | 1.00 | 33.96 | sos |
| ATOM | 1957 | O | LYS | 837 | 62.309 | 36.003 | 86.589 | 1.00 | 33.19 | sos |
| ATOM | 1958 | N | CYS | 838 | 61.810 | 34.707 | 84.815 | 1.00 | 36.32 | sos |
| ATOM | 1959 | CA | CYS | 838 | 61.224 | 33.635 | 85.623 | 1.00 | 35.53 | sos |
| ATOM | 1960 | CB | CYS | 838 | 60.603 | 32.542 | 84.743 | 1.00 | 35.79 | sos |
| ATOM | 1961 | SG | CYS | 838 | 59.084 | 33.032 | 83.882 | 1.00 | 40.27 | sos |
| ATOM | 1962 | C | CYS | 838 | 62.291 | 33.022 | 86.516 | 1.00 | 35.04 | sos |
| ATOM | 1963 | O | CYS | 838 | 62.066 | 32.816 | 87.706 | 1.00 | 37.06 | sos |
| ATOM | 1964 | N | ILE | 839 | 63.459 | 32.757 | 85.940 | 1.00 | 29.20 | sos |
| ATOM | 1965 | CA | ILE | 839 | 64.566 | 32.171 | 86.685 | 1.00 | 29.27 | sos |
| ATOM | 1966 | CB | ILE | 839 | 65.758 | 31.856 | 85.744 | 1.00 | 23.78 | sos |
| ATOM | 1967 | CG2 | ILE | 839 | 66.995 | 31.500 | 86.545 | 1.00 | 17.80 | sos |
| ATOM | 1968 | CG1 | ILE | 839 | 65.391 | 30.736 | 84.781 | 1.00 | 20.67 | sos |
| ATOM | 1969 | CD1 | ILE | 839 | 66.457 | 30.465 | 83.739 | 1.00 | 29.40 | sos |
| ATOM | 1970 | C | ILE | 839 | 65.057 | 33.120 | 87.774 | 1.00 | 31.40 | sos |
| ATOM | 1971 | O | ILE | 839 | 64.945 | 32.852 | 88.969 | 1.00 | 32.73 | sos |
| ATOM | 1972 | N | VAL | 840 | 65.590 | 34.245 | 87.326 | 1.00 | 33.52 | sos |
| ATOM | 1973 | CA | VAL | 840 | 66.154 | 35.262 | 88.190 | 1.00 | 30.76 | sos |
| ATOM | 1974 | CB | VAL | 840 | 66.816 | 36.345 | 87.317 | 1.00 | 27.16 | sos |
| ATOM | 1975 | CG1 | VAL | 840 | 66.844 | 37.661 | 88.001 | 1.00 | 28.37 | sos |
| ATOM | 1976 | CG2 | VAL | 840 | 68.210 | 35.904 | 86.942 | 1.00 | 16.52 | sos |
| ATOM | 1977 | C | VAL | 840 | 65.216 | 35.832 | 89.255 | 1.00 | 31.26 | sos |
| ATOM | 1978 | O | VAL | 840 | 65.680 | 36.225 | 90.318 | 1.00 | 35.24 | sos |
| ATOM | 1979 | N | GLU | 841 | 63.912 | 35.885 | 88.990 | 1.00 | 30.34 | sos |
| ATOM | 1980 | CA | GLU | 841 | 62.980 | 36.388 | 90.005 | 1.00 | 29.58 | sos |
| ATOM | 1981 | CB | GLU | 841 | 61.784 | 37.122 | 89.396 | 1.00 | 25.11 | sos |
| ATOM | 1982 | CG | GLU | 841 | 62.115 | 38.446 | 88.714 | 1.00 | 28.61 | sos |
| ATOM | 1983 | CD | GLU | 841 | 60.870 | 39.229 | 88.310 | 1.00 | 30.25 | sos |
| ATOM | 1984 | OE1 | GLU | 841 | 59.769 | 38.640 | 88.237 | 1.00 | 28.99 | sos |
| ATOM | 1985 | OE2 | GLU | 841 | 60.994 | 40.444 | 88.065 | 1.00 | 31.14 | sos |
| ATOM | 1986 | C | GLU | 841 | 62.485 | 35.276 | 90.924 | 1.00 | 30.21 | sos |
| ATOM | 1987 | O | GLU | 841 | 61.559 | 35.485 | 91.704 | 1.00 | 35.34 | sos |
| ATOM | 1988 | N | THR | 842 | 63.029 | 34.072 | 90.760 | 1.00 | 32.01 | sos |
| ATOM | 1989 | CA | THR | 842 | 62.672 | 32.951 | 91.626 | 1.00 | 36.71 | sos |
| ATOM | 1990 | CB | THR | 842 | 62.516 | 31.612 | 90.867 | 1.00 | 37.24 | sos |
| ATOM | 1991 | OG1 | THR | 842 | 61.476 | 31.731 | 89.889 | 1.00 | 42.01 | sos |
| ATOM | 1992 | CG2 | THR | 842 | 62.127 | 30.513 | 91.831 | 1.00 | 34.88 | sos |
| ATOM | 1993 | C | THR | 842 | 63.846 | 32.899 | 92.598 | 1.00 | 39.17 | sos |
| ATOM | 1994 | O | THR | 842 | 64.874 | 32.237 | 92.359 | 1.00 | 33.40 | sos |
| ATOM | 1995 | N | GLU | 843 | 63.691 | 33.687 | 93.658 | 1.00 | 40.56 | sos |
| ATOM | 1996 | CA | GLU | 843 | 64.699 | 33.855 | 94.686 | 1.00 | 42.29 | sos |
| ATOM | 1997 | CB | GLU | 843 | 64.331 | 35.066 | 95.534 | 1.00 | 45.77 | sos |
| ATOM | 1998 | CG | GLU | 843 | 64.451 | 36.350 | 94.720 | 1.00 | 53.23 | sos |
| ATOM | 1999 | CD | GLU | 843 | 63.598 | 37.497 | 95.229 | 1.00 | 58.13 | sos |
| ATOM | 2000 | OE1 | GLU | 843 | 63.747 | 37.885 | 96.410 | 1.00 | 62.75 | sos |

TABLE 3-continued

PDB Coordinates for the Ras-Sos Structure:
DATA SET FOR REFINED COORDINATES

| ATOM | 2001 | OE2 | GLU | 843 | 62.799 | 38.033 | 94.425 | 1.00 | 54.53 | sos |
|------|------|-----|-----|-----|--------|--------|--------|------|-------|-----|
| ATOM | 2002 | C | GLU | 843 | 65.079 | 32.636 | 95.517 | 1.00 | 40.90 | sos |
| ATOM | 2003 | O | GLU | 843 | 66.241 | 32.477 | 95.876 | 1.00 | 40.87 | sos |
| ATOM | 2004 | N | ASN | 844 | 64.122 | 31.754 | 95.778 | 1.00 | 39.33 | sos |
| ATOM | 2005 | CA | ASN | 844 | 64.402 | 30.546 | 96.542 | 1.00 | 38.63 | sos |
| ATOM | 2006 | CB | ASN | 844 | 63.094 | 29.939 | 97.051 | 1.00 | 39.14 | sos |
| ATOM | 2007 | CG | ASN | 844 | 63.312 | 28.702 | 97.909 | 1.00 | 43.31 | sos |
| ATOM | 2008 | OD1 | ASN | 844 | 63.437 | 27.590 | 97.393 | 1.00 | 42.23 | sos |
| ATOM | 2009 | ND2 | ASN | 844 | 63.352 | 28.892 | 99.225 | 1.00 | 38.54 | sos |
| ATOM | 2010 | C | ASN | 844 | 65.142 | 29.547 | 95.643 | 1.00 | 39.94 | sos |
| ATOM | 2011 | O | ASN | 844 | 64.644 | 29.177 | 94.582 | 1.00 | 47.06 | sos |
| ATOM | 2012 | N | LEU | 845 | 66.313 | 29.094 | 96.081 | 1.00 | 38.22 | sos |
| ATOM | 2013 | CA | LEU | 845 | 67.126 | 28.151 | 95.314 | 1.00 | 36.15 | sos |
| ATOM | 2014 | CB | LEU | 845 | 68.375 | 27.764 | 96.097 | 1.00 | 29.74 | sos |
| ATOM | 2015 | CG | LEU | 845 | 69.338 | 26.855 | 95.340 | 1.00 | 28.22 | sos |
| ATOM | 2016 | CD1 | LEU | 845 | 69.798 | 27.555 | 94.089 | 1.00 | 34.44 | sos |
| ATOM | 2017 | CD2 | LEU | 845 | 70.523 | 26.502 | 96.193 | 1.00 | 30.09 | sos |
| ATOM | 2018 | C | LEU | 845 | 66.400 | 26.882 | 94.875 | 1.00 | 39.08 | sos |
| ATOM | 2019 | O | LEU | 845 | 66.579 | 26.425 | 93.749 | 1.00 | 39.10 | sos |
| ATOM | 2020 | N | GLU | 846 | 65.609 | 26.295 | 95.767 | 1.00 | 42.21 | sos |
| ATOM | 2021 | CA | GLU | 846 | 64.880 | 25.076 | 95.429 | 1.00 | 47.26 | sos |
| ATOM | 2022 | CB | GLU | 846 | 64.123 | 24.539 | 96.648 | 1.00 | 51.32 | sos |
| ATOM | 2023 | CG | GLU | 846 | 63.369 | 23.248 | 96.375 | 1.00 | 60.88 | sos |
| ATOM | 2024 | CD | GLU | 846 | 62.396 | 22.873 | 97.479 | 1.00 | 68.19 | sos |
| ATOM | 2025 | OE1 | GLU | 846 | 61.668 | 23.764 | 97.980 | 1.00 | 72.90 | sos |
| ATOM | 2026 | OE2 | GLU | 846 | 62.349 | 21.676 | 97.832 | 1.00 | 70.29 | sos |
| ATOM | 2027 | C | GLU | 846 | 63.910 | 25.348 | 94.275 | 1.00 | 46.86 | sos |
| ATOM | 2028 | O | GLU | 846 | 63.937 | 24.664 | 93.243 | 1.00 | 48.77 | sos |
| ATOM | 2029 | N | GLU | 847 | 63.088 | 26.377 | 94.435 | 1.00 | 42.40 | sos |
| ATOM | 2030 | CA | GLU | 847 | 62.130 | 26.741 | 93.409 | 1.00 | 41.25 | sos |
| ATOM | 2031 | CB | GLU | 847 | 61.232 | 27.885 | 93.893 | 1.00 | 40.22 | sos |
| ATOM | 2032 | CG | GLU | 847 | 60.477 | 27.600 | 95.194 | 1.00 | 38.69 | sos |
| ATOM | 2033 | CD | GLU | 847 | 59.528 | 28.723 | 95.598 | 1.00 | 44.00 | sos |
| ATOM | 2034 | OE1 | GLU | 847 | 59.879 | 29.917 | 95.431 | 1.00 | 43.40 | sos |
| ATOM | 2035 | OE2 | GLU | 847 | 58.423 | 28.407 | 96.093 | 1.00 | 46.97 | sos |
| ATOM | 2036 | C | GLU | 847 | 62.834 | 27.130 | 92.105 | 1.00 | 42.35 | sos |
| ATOM | 2037 | O | GLU | 847 | 62.375 | 26.761 | 91.016 | 1.00 | 40.50 | sos |
| ATOM | 2038 | N | ARG | 848 | 63.960 | 27.841 | 92.210 | 1.00 | 38.50 | sos |
| ATOM | 2039 | CA | ARG | 848 | 64.694 | 28.261 | 91.015 | 1.00 | 36.05 | sos |
| ATOM | 2040 | CB | ARG | 848 | 65.856 | 29.189 | 91.367 | 1.00 | 35.14 | sos |
| ATOM | 2041 | CG | ARG | 848 | 66.517 | 29.876 | 90.154 | 1.00 | 34.45 | sos |
| ATOM | 2042 | CD | ARG | 848 | 67.784 | 30.610 | 90.569 | 1.00 | 31.04 | sos |
| ATOM | 2043 | NE | ARG | 848 | 67.549 | 31.275 | 91.840 | 1.00 | 37.94 | sos |
| ATOM | 2044 | CZ | ARG | 848 | 68.424 | 31.339 | 92.834 | 1.00 | 41.45 | sos |
| ATOM | 2045 | NH1 | ARG | 848 | 69.631 | 30.794 | 92.712 | 1.00 | 35.83 | sos |
| ATOM | 2046 | NH2 | ARG | 848 | 68.047 | 31.875 | 93.985 | 1.00 | 42.13 | sos |
| ATOM | 2047 | C | ARG | 848 | 65.207 | 27.058 | 90.232 | 1.00 | 35.50 | sos |
| ATOM | 2048 | O | ARG | 848 | 65.208 | 27.071 | 89.001 | 1.00 | 36.01 | sos |
| ATOM | 2049 | N | VAL | 849 | 65.651 | 26.027 | 90.945 | 1.00 | 34.15 | sos |
| ATOM | 2050 | CA | VAL | 849 | 66.140 | 24.815 | 90.297 | 1.00 | 34.10 | sos |
| ATOM | 2051 | CB | VAL | 849 | 66.777 | 23.840 | 91.324 | 1.00 | 33.20 | sos |
| ATOM | 2052 | CG1 | VAL | 849 | 67.034 | 22.486 | 90.692 | 1.00 | 29.35 | sos |
| ATOM | 2053 | CG2 | VAL | 849 | 68.089 | 24.414 | 91.824 | 1.00 | 30.55 | sos |
| ATOM | 2054 | C | VAL | 849 | 64.966 | 24.165 | 89.559 | 1.00 | 32.68 | sos |
| ATOM | 2055 | O | VAL | 849 | 65.121 | 23.683 | 88.439 | 1.00 | 30.36 | sos |
| ATOM | 2056 | N | ALA | 850 | 62.781 | 24.233 | 90.164 | 1.00 | 31.24 | sos |
| ATOM | 2057 | CA | ALA | 850 | 62.567 | 23.687 | 89.563 | 1.00 | 33.61 | sos |
| ATOM | 2058 | CB | ALA | 850 | 61.411 | 23.774 | 90.548 | 1.00 | 29.99 | sos |
| ATOM | 2059 | C | ALA | 850 | 62.222 | 24.455 | 88.285 | 1.00 | 36.10 | sos |
| ATOM | 2060 | O | ALA | 850 | 61.820 | 23.866 | 87.278 | 1.00 | 40.05 | sos |
| ATOM | 2061 | N | VAL | 851 | 62.385 | 25.775 | 88.340 | 1.00 | 37.33 | sos |
| ATOM | 2062 | CA | VAL | 851 | 62.108 | 26.647 | 87.206 | 1.00 | 32.56 | sos |
| ATOM | 2063 | CB | VAL | 851 | 62.163 | 28.149 | 87.621 | 1.00 | 31.27 | sos |
| ATOM | 2064 | CG1 | VAL | 851 | 62.147 | 29.052 | 86.399 | 1.00 | 28.67 | sos |
| ATOM | 2065 | CG2 | VAL | 851 | 60.995 | 28.488 | 88.529 | 1.00 | 22.62 | sos |
| ATOM | 2066 | C | VAL | 851 | 63.087 | 26.374 | 86.072 | 1.00 | 32.50 | sos |
| ATOM | 2067 | O | VAL | 851 | 62.678 | 26.236 | 84.919 | 1.00 | 37.99 | sos |
| ATOM | 2068 | N | VAL | 852 | 64.371 | 26.266 | 86.392 | 1.00 | 30.98 | sos |
| ATOM | 2069 | CA | VAL | 852 | 65.371 | 26.010 | 85.353 | 1.00 | 33.50 | sos |
| ATOM | 2070 | CB | VAL | 852 | 66.826 | 26.111 | 85.883 | 1.00 | 30.46 | sos |
| ATOM | 2071 | CG1 | VAL | 852 | 67.826 | 25.747 | 84.790 | 1.00 | 20.81 | sos |
| ATOM | 2072 | CG2 | VAL | 852 | 67.098 | 27.526 | 86.357 | 1.00 | 33.84 | sos |
| ATOM | 2073 | C | VAL | 852 | 65.157 | 24.646 | 84.740 | 1.00 | 34.08 | sos |
| ATOM | 2074 | O | VAL | 852 | 65.465 | 24.430 | 83.571 | 1.00 | 33.03 | sos |
| ATOM | 2075 | N | SER | 853 | 64.573 | 23.745 | 85.522 | 1.00 | 38.05 | sos |
| ATOM | 2076 | CA | SER | 853 | 64.319 | 22.394 | 85.052 | 1.00 | 38.86 | sos |

TABLE 3-continued

PDB Coordinates for the Ras-Sos Structure:
DATA SET FOR REFINED COORDINATES

| ATOM | 2077 | CB | SER | 853 | 64.051 | 21.464 | 86.224 | 1.00 | 41.62 | sos |
|---|---|---|---|---|---|---|---|---|---|---|
| ATOM | 2078 | OG | SER | 853 | 64.460 | 20.152 | 85.903 | 1.00 | 50.46 | sos |
| ATOM | 2079 | C | SER | 853 | 63.196 | 22.307 | 84.012 | 1.00 | 39.97 | sos |
| ATOM | 2080 | O | SER | 853 | 63.382 | 21.638 | 82.995 | 1.00 | 38.79 | sos |
| ATOM | 2081 | N | ARG | 854 | 62.060 | 22.985 | 84.236 | 1.00 | 37.55 | sos |
| ATOM | 2082 | CA | ARG | 854 | 60.955 | 22.950 | 83.258 | 1.00 | 39.20 | sos |
| ATOM | 2083 | CB | ARG | 854 | 59.752 | 23.801 | 83.666 | 1.00 | 39.15 | sos |
| ATOM | 2084 | CG | ARG | 854 | 58.982 | 23.342 | 84.846 | 1.00 | 41.78 | sos |
| ATOM | 2085 | CD | ARG | 854 | 58.219 | 22.045 | 84.653 | 1.00 | 32.23 | sos |
| ATOM | 2086 | NE | ARG | 854 | 57.719 | 21.678 | 85.975 | 1.00 | 29.72 | sos |
| ATOM | 2087 | CZ | ARG | 854 | 56.557 | 22.084 | 86.471 | 1.00 | 32.83 | sos |
| ATOM | 2088 | NH1 | ARG | 854 | 55.746 | 22.832 | 85.735 | 1.00 | 31.78 | sos |
| ATOM | 2089 | NH2 | ARG | 854 | 56.280 | 21.890 | 87.755 | 1.00 | 37.02 | sos |
| ATOM | 2090 | C | ARG | 854 | 61.434 | 23.529 | 81.953 | 1.00 | 39.16 | sos |
| ATOM | 2091 | O | ARG | 854 | 61.097 | 23.027 | 80.883 | 1.00 | 42.76 | sos |
| ATOM | 2092 | N | ILE | 855 | 62.175 | 24.628 | 82.047 | 1.00 | 35.91 | sos |
| ATOM | 2093 | CA | ILE | 855 | 62.683 | 25.281 | 80.858 | 1.00 | 32.95 | sos |
| ATOM | 2094 | CB | ILE | 855 | 63.430 | 26.584 | 81.203 | 1.00 | 28.30 | sos |
| ATOM | 2095 | CG2 | ILE | 855 | 63.930 | 27.267 | 79.945 | 1.00 | 21.69 | sos |
| ATOM | 2096 | CG1 | ILE | 855 | 62.474 | 27.535 | 81.924 | 1.00 | 28.28 | sos |
| ATOM | 2097 | CD1 | ILE | 855 | 63.109 | 28.846 | 82.326 | 1.00 | 30.15 | sos |
| ATOM | 2098 | C | ILE | 855 | 63.530 | 24.306 | 80.041 | 1.00 | 33.53 | sos |
| ATOM | 2099 | O | ILE | 855 | 63.375 | 24.237 | 78.825 | 1.00 | 37.56 | sos |
| ATOM | 2100 | N | ILE | 856 | 64.360 | 23.501 | 80.702 | 1.00 | 30.79 | sos |
| ATOM | 2101 | CA | ILE | 856 | 65.167 | 22.526 | 79.972 | 1.00 | 33.67 | sos |
| ATOM | 2102 | CB | ILE | 856 | 66.246 | 21.878 | 80.869 | 1.00 | 33.05 | sos |
| ATOM | 2103 | CG2 | ILE | 856 | 67.030 | 20.847 | 80.084 | 1.00 | 29.67 | sos |
| ATOM | 2104 | CG1 | ILE | 856 | 67.222 | 22.955 | 81.357 | 1.00 | 38.46 | sos |
| ATOM | 2105 | CD1 | ILE | 856 | 68.337 | 22.454 | 82.262 | 1.00 | 36.90 | sos |
| ATOM | 2106 | C | ILE | 856 | 64.228 | 21.466 | 79.368 | 1.00 | 35.14 | sos |
| ATOM | 2107 | O | ILE | 856 | 64.429 | 20.999 | 78.250 | 1.00 | 30.98 | sos |
| ATOM | 2108 | N | GLU | 857 | 63.158 | 21.148 | 80.087 | 1.00 | 36.98 | sos |
| ATOM | 2109 | CA | GLU | 857 | 62.187 | 20.184 | 79.601 | 1.00 | 35.90 | sos |
| ATOM | 2110 | CB | GLU | 857 | 61.172 | 19.843 | 80.690 | 1.00 | 33.56 | sos |
| ATOM | 2111 | CG | GLU | 857 | 61.730 | 18.859 | 81.713 | 1.00 | 39.35 | sos |
| ATOM | 2112 | CD | GLU | 857 | 60.712 | 18.413 | 82.744 | 1.00 | 47.07 | sos |
| ATOM | 2113 | OE1 | GLU | 857 | 59.619 | 19.018 | 82.809 | 1.00 | 47.78 | sos |
| ATOM | 2114 | OE2 | GLU | 857 | 61.006 | 17.452 | 83.491 | 1.00 | 50.82 | sos |
| ATOM | 2115 | C | GLU | 857 | 61.508 | 20.738 | 78.353 | 1.00 | 36.05 | sos |
| ATOM | 2116 | O | GLU | 857 | 61.404 | 20.046 | 77.332 | 1.00 | 33.37 | sos |
| ATOM | 2117 | N | ILE | 858 | 61.103 | 22.006 | 78.425 | 1.00 | 34.08 | sos |
| ATOM | 2118 | CA | ILE | 858 | 60.470 | 22.680 | 77.298 | 1.00 | 30.12 | sos |
| ATOM | 2119 | CB | ILE | 858 | 60.076 | 24.121 | 77.656 | 1.00 | 26.79 | sos |
| ATOM | 2120 | CG2 | ILE | 858 | 59.671 | 27.897 | 76.413 | 1.00 | 24.06 | sos |
| ATOM | 2121 | CG1 | ILE | 858 | 58.935 | 24.100 | 78.672 | 1.00 | 26.97 | sos |
| ATOM | 2122 | CD1 | ILE | 858 | 58.569 | 25.462 | 79.233 | 1.00 | 26.52 | sos |
| ATOM | 2123 | C | ILE | 858 | 61.432 | 22.670 | 76.109 | 1.00 | 30.98 | sos |
| ATOM | 2124 | O | ILE | 858 | 61.003 | 22.545 | 74.965 | 1.00 | 30.92 | sos |
| ATOM | 2125 | N | LEU | 859 | 62.732 | 22.760 | 76.386 | 1.00 | 31.53 | sos |
| ATOM | 2126 | CA | LEU | 859 | 63.733 | 22.734 | 75.321 | 1.00 | 33.51 | sos |
| ATOM | 2127 | CB | LEU | 859 | 65.133 | 22.988 | 75.867 | 1.00 | 31.26 | sos |
| ATOM | 2128 | CG | LEU | 859 | 66.249 | 22.645 | 74.879 | 1.00 | 32.09 | sos |
| ATOM | 2129 | CD1 | LEU | 859 | 66.329 | 23.716 | 73.826 | 1.00 | 38.72 | sos |
| ATOM | 2130 | CD2 | LEU | 859 | 67.574 | 22.532 | 75.592 | 1.00 | 40.48 | sos |
| ATOM | 2131 | C | LEU | 859 | 63.712 | 21.366 | 74.661 | 1.00 | 37.65 | sos |
| ATOM | 2132 | O | LEU | 859 | 63.826 | 21.253 | 73.442 | 1.00 | 39.05 | sos |
| ATOM | 2133 | N | GLN | 860 | 63.599 | 20.326 | 75.473 | 1.00 | 40.83 | sos |
| ATOM | 2134 | CA | GLN | 860 | 63.531 | 18.976 | 74.948 | 1.00 | 42.80 | sos |
| ATOM | 2135 | CB | GLN | 860 | 63.466 | 17.954 | 76.076 | 1.00 | 45.25 | sos |
| ATOM | 2136 | CG | GLN | 860 | 64.350 | 16.750 | 75.810 | 1.00 | 57.32 | sos |
| ATOM | 2137 | CD | GLN | 860 | 63.578 | 15.453 | 75.725 | 1.00 | 63.55 | sos |
| ATOM | 2138 | OE1 | GLN | 860 | 63.044 | 14.965 | 76.732 | 1.00 | 64.50 | sos |
| ATOM | 2139 | NE2 | GLN | 860 | 63.524 | 14.874 | 74.523 | 1.00 | 61.86 | sos |
| ATOM | 2140 | C | GLN | 860 | 62.371 | 18.784 | 73.973 | 1.00 | 42.50 | sos |
| ATOM | 2141 | O | GLN | 860 | 62.565 | 18.249 | 72.883 | 1.00 | 41.40 | sos |
| ATOM | 2142 | N | VAL | 861 | 61.180 | 19.260 | 74.335 | 1.00 | 39.28 | sos |
| ATOM | 2143 | CA | VAL | 861 | 60.044 | 19.109 | 73.444 | 1.00 | 38.11 | sos |
| ATOM | 2144 | CB | VAL | 861 | 58.713 | 19.435 | 74.120 | 1.00 | 36.20 | sos |
| ATOM | 2145 | CG1 | VAL | 861 | 57.569 | 19.210 | 73.151 | 1.00 | 27.98 | sos |
| ATOM | 2146 | CG2 | VAL | 861 | 58.523 | 18.554 | 75.318 | 1.00 | 35.63 | sos |
| ATOM | 2147 | C | VAL | 862 | 60.230 | 19.960 | 72.197 | 1.00 | 40.53 | sos |
| ATOM | 2148 | O | VAL | 862 | 59.779 | 19.579 | 71.117 | 1.00 | 45.33 | sos |
| ATOM | 2149 | N | PHE | 862 | 60.913 | 21.094 | 72.335 | 1.00 | 39.26 | sos |
| ATOM | 2150 | CA | PHE | 862 | 61.171 | 21.952 | 71.182 | 1.00 | 37.48 | sos |
| ATOM | 2151 | CB | PHE | 862 | 61.945 | 23.221 | 71.574 | 1.00 | 37.88 | sos |
| ATOM | 2152 | CG | PHE | 862 | 61.077 | 24.345 | 72.085 | 1.00 | 38.94 | sos |

TABLE 3-continued

PDB Coordinates for the Ras-Sos Structure:
DATA SET FOR REFINED COORDINATES

| ATOM | 2153 | CD1 | PHE | 862 | 61.596 | 25.293 | 72.960 | 1.00 | 39.13 | sos |
|------|------|-----|-----|-----|--------|--------|--------|------|-------|-----|
| ATOM | 2154 | CD2 | PHE | 862 | 59.742 | 24.457 | 71.698 | 1.00 | 40.25 | sos |
| ATOM | 2155 | CE1 | PHE | 862 | 60.806 | 26.333 | 73.447 | 1.00 | 36.80 | sos |
| ATOM | 2156 | CE2 | PHE | 862 | 58.944 | 25.495 | 72.181 | 1.00 | 37.55 | sos |
| ATOM | 2157 | CZ  | PHE | 862 | 59.479 | 26.432 | 73.057 | 1.00 | 39.18 | sos |
| ATOM | 2158 | C   | PHE | 862 | 61.988 | 21.136 | 70.194 | 1.00 | 36.16 | sos |
| ATOM | 2159 | O   | PHE | 862 | 61.679 | 21.097 | 69.012 | 1.00 | 37.67 | sos |
| ATOM | 2160 | N   | GLN | 863 | 63.004 | 20.448 | 70.702 | 1.00 | 36.86 | sos |
| ATOM | 2161 | CA  | GLN | 863 | 63.866 | 19.615 | 69.874 | 1.00 | 39.30 | sos |
| ATOM | 2162 | CB  | GLN | 863 | 64.985 | 19.003 | 70.721 | 1.00 | 39.00 | sos |
| ATOM | 2163 | CG  | GLN | 863 | 66.048 | 19.999 | 71.180 | 1.00 | 44.20 | sos |
| ATOM | 2164 | CD  | GLN | 863 | 67.267 | 20.031 | 70.273 | 1.00 | 42.54 | sos |
| ATOM | 2165 | OE1 | GLN | 863 | 68.396 | 19.850 | 70.730 | 1.00 | 46.36 | sos |
| ATOM | 2166 | NE2 | GLN | 863 | 67.043 | 20.243 | 68.982 | 1.00 | 44.21 | sos |
| ATOM | 2167 | C   | GLN | 863 | 63.067 | 18.509 | 69.185 | 1.00 | 40.12 | sos |
| ATOM | 2168 | O   | GLN | 863 | 63.319 | 18.193 | 68.016 | 1.00 | 40.63 | sos |
| ATOM | 2169 | N   | GLU | 864 | 62.110 | 17.928 | 69.911 | 1.00 | 38.70 | sos |
| ATOM | 2170 | CA  | GLU | 864 | 61.266 | 16.859 | 69.371 | 1.00 | 38.97 | sos |
| ATOM | 2171 | CB  | GLU | 864 | 60.356 | 16.255 | 70.456 | 1.00 | 42.58 | sos |
| ATOM | 2172 | CG  | GLU | 864 | 61.080 | 15.441 | 71.538 | 1.00 | 49.66 | sos |
| ATOM | 2173 | CD  | GLU | 864 | 60.163 | 14.953 | 72.669 | 1.00 | 54.52 | sos |
| ATOM | 2174 | OE1 | GLU | 864 | 58.924 | 15.106 | 72.584 | 1.00 | 52.79 | sos |
| ATOM | 2175 | OE2 | GLU | 864 | 60.696 | 14.401 | 73.656 | 1.00 | 59.42 | sos |
| ATOM | 2176 | C   | GLU | 864 | 60.409 | 17.424 | 68.251 | 1.00 | 38.08 | sos |
| ATOM | 2177 | O   | GLU | 864 | 60.333 | 16.843 | 67.173 | 1.00 | 41.68 | sos |
| ATOM | 2178 | N   | LEU | 865 | 59.800 | 18.579 | 68.506 | 1.00 | 32.07 | sos |
| ATOM | 2179 | CA  | LEU | 865 | 58.946 | 19.243 | 67.543 | 1.00 | 25.81 | sos |
| ATOM | 2180 | CB  | LEU | 865 | 58.074 | 20.265 | 68.258 | 1.00 | 27.68 | sos |
| ATOM | 2181 | CG  | LEU | 865 | 57.028 | 19.709 | 69.223 | 1.00 | 34.29 | sos |
| ATOM | 2182 | CD1 | LEU | 865 | 56.338 | 20.843 | 69.971 | 1.00 | 34.50 | sos |
| ATOM | 2183 | CD2 | LEU | 865 | 56.010 | 18.894 | 68.444 | 1.00 | 38.30 | sos |
| ATOM | 2184 | C   | LEU | 865 | 59.726 | 19.938 | 66.433 | 1.00 | 29.39 | sos |
| ATOM | 2185 | O   | ASN | 866 | 59.126 | 20.549 | 65.535 | 1.00 | 26.35 | sos |
| ATOM | 2186 | N   | ASN | 866 | 61.053 | 19.831 | 66.473 | 1.00 | 28.43 | sos |
| ATOM | 2187 | CA  | ASN | 866 | 61.910 | 20.483 | 65.481 | 1.00 | 34.37 | sos |
| ATOM | 2188 | CB  | ASN | 866 | 61.690 | 19.891 | 64.088 | 1.00 | 40.28 | sos |
| ATOM | 2189 | CG  | ASN | 866 | 62.489 | 18.624 | 63.860 | 1.00 | 48.22 | sos |
| ATOM | 2190 | OD1 | ASN | 866 | 63.248 | 18.184 | 64.727 | 1.00 | 57.41 | sos |
| ATOM | 2191 | ND2 | ASN | 866 | 62.340 | 18.039 | 62.680 | 1.00 | 51.12 | sos |
| ATOM | 2192 | C   | ASN | 866 | 61.732 | 22.003 | 65.434 | 1.00 | 35.02 | sos |
| ATOM | 2193 | O   | ASN | 866 | 61.761 | 22.604 | 64.357 | 1.00 | 36.63 | sos |
| ATOM | 2194 | N   | ASN | 867 | 61.468 | 22.608 | 66.593 | 1.00 | 32.87 | sos |
| ATOM | 2195 | CA  | ASN | 867 | 61.312 | 24.056 | 66.684 | 1.00 | 32.02 | sos |
| ATOM | 2196 | CB  | ASN | 867 | 60.235 | 24.445 | 67.688 | 1.00 | 29.34 | sos |
| ATOM | 2197 | CG  | ASN | 867 | 60.066 | 25.951 | 67.783 | 1.00 | 29.91 | sos |
| ATOM | 2198 | OD1 | ASN | 867 | 60.777 | 26.702 | 67.106 | 1.00 | 23.50 | sos |
| ATOM | 2199 | ND2 | ASN | 867 | 59.128 | 26.401 | 68.613 | 1.00 | 27.52 | sos |
| ATOM | 2200 | C   | ASN | 867 | 62.648 | 24.682 | 67.093 | 1.00 | 32.97 | sos |
| ATOM | 2201 | O   | ASN | 867 | 62.921 | 24.911 | 68.281 | 1.00 | 27.37 | sos |
| ATOM | 2202 | N   | PHE | 868 | 63.463 | 24.974 | 66.088 | 1.00 | 31.22 | sos |
| ATOM | 2203 | CA  | PHE | 868 | 64.775 | 25.537 | 66.312 | 1.00 | 35.60 | sos |
| ATOM | 2204 | CB  | PHE | 868 | 65.613 | 25.420 | 65.041 | 1.00 | 36.92 | sos |
| ATOM | 2205 | CG  | PHE | 868 | 65.803 | 24.003 | 64.596 | 1.00 | 36.49 | sos |
| ATOM | 2206 | CD1 | PHE | 868 | 64.989 | 23.454 | 63.614 | 1.00 | 39.78 | sos |
| ATOM | 2207 | CD2 | PHE | 868 | 66.730 | 23.187 | 65.224 | 1.00 | 38.22 | sos |
| ATOM | 2208 | CE1 | PHE | 868 | 65.092 | 22.110 | 63.270 | 1.00 | 39.95 | sos |
| ATOM | 2209 | CE2 | PHE | 868 | 66.840 | 21.842 | 64.889 | 1.00 | 39.84 | sos |
| ATOM | 2210 | CZ  | PHE | 868 | 66.015 | 21.304 | 63.909 | 1.00 | 38.73 | sos |
| ATOM | 2211 | C   | PHE | 868 | 64.746 | 26.951 | 66.862 | 1.00 | 37.45 | sos |
| ATOM | 2212 | O   | PHE | 868 | 65.627 | 27.324 | 67.643 | 1.00 | 38.77 | sos |
| ATOM | 2213 | N   | ASN | 869 | 63.723 | 27.722 | 66.494 | 1.00 | 36.31 | sos |
| ATOM | 2214 | CA  | ASN | 869 | 63.597 | 29.084 | 66.996 | 1.00 | 32.74 | sos |
| ATOM | 2215 | CB  | ASN | 869 | 62.380 | 29.789 | 66.417 | 1.00 | 28.86 | sos |
| ATOM | 2216 | CG  | ASN | 869 | 62.206 | 31.186 | 66.974 | 1.00 | 27.76 | sos |
| ATOM | 2217 | OD1 | ASN | 869 | 62.893 | 32.127 | 66.561 | 1.00 | 29.16 | sos |
| ATOM | 2218 | ND2 | ASN | 869 | 61.308 | 31.325 | 67.938 | 1.00 | 20.45 | sos |
| ATOM | 2219 | C   | ASN | 869 | 63.446 | 28.979 | 68.496 | 1.00 | 33.00 | sos |
| ATOM | 2220 | O   | ASN | 869 | 64.120 | 29.685 | 69.243 | 1.00 | 37.32 | sos |
| ATOM | 2221 | N   | GLY | 870 | 62.581 | 28.064 | 68.920 | 1.00 | 34.36 | sos |
| ATOM | 2222 | CA  | GLY | 870 | 62.352 | 27.833 | 70.336 | 1.00 | 36.19 | sos |
| ATOM | 2223 | C   | GLY | 870 | 63.559 | 27.233 | 71.047 | 1.00 | 35.68 | sos |
| ATOM | 2224 | O   | GLY | 870 | 63.693 | 27.377 | 72.254 | 1.00 | 34.88 | sos |
| ATOM | 2225 | N   | VAL | 871 | 64.426 | 26.534 | 70.321 | 1.00 | 34.75 | sos |
| ATOM | 2226 | CA  | VAL | 871 | 65.605 | 25.950 | 70.946 | 1.00 | 35.94 | sos |
| ATOM | 2227 | CB  | VAL | 871 | 66.267 | 24.874 | 70.042 | 1.00 | 34.30 | sos |
| ATOM | 2228 | CG1 | VAL | 871 | 67.700 | 24.600 | 70.479 | 1.00 | 30.94 | sos |

TABLE 3-continued

PDB Coordinates for the Ras-Sos Structure:
DATA SET FOR REFINED COORDINATES

| ATOM | 2229 | CG2 | VAL | 871 | 65.472 | 23.593 | 70.122 | 1.00 | 34.73 | sos |
|------|------|-----|-----|-----|--------|--------|--------|------|-------|-----|
| ATOM | 2230 | C | VAL | 871 | 66.590 | 27.062 | 71.292 | 1.00 | 36.24 | sos |
| ATOM | 2231 | O | VAL | 871 | 66.966 | 27.233 | 72.458 | 1.00 | 34.39 | sos |
| ATOM | 2232 | N | LEU | 872 | 66.955 | 27.848 | 70.285 | 1.00 | 33.53 | sos |
| ATOM | 2233 | CA | LEU | 872 | 67.876 | 28.953 | 70.474 | 1.00 | 36.66 | sos |
| ATOM | 2234 | CB | LEU | 872 | 68.249 | 29.544 | 69.129 | 1.00 | 34.00 | sos |
| ATOM | 2235 | CG | LEU | 872 | 68.914 | 28.547 | 68.186 | 1.00 | 42.31 | sos |
| ATOM | 2236 | CD1 | LEU | 872 | 69.446 | 29.277 | 66.967 | 1.00 | 45.63 | sos |
| ATOM | 2237 | CD2 | LEU | 872 | 70.046 | 27.830 | 68.893 | 1.00 | 41.62 | sos |
| ATOM | 2238 | C | LEU | 872 | 67.303 | 30.033 | 71.407 | 1.00 | 40.06 | sos |
| ATOM | 2239 | O | LEU | 872 | 68.038 | 30.855 | 71.950 | 1.00 | 42.24 | sos |
| ATOM | 2240 | N | GLU | 873 | 65.990 | 29.993 | 71.606 | 1.00 | 38.54 | sos |
| ATOM | 2241 | CA | GLU | 873 | 65.270 | 30.919 | 72.475 | 1.00 | 36.06 | sos |
| ATOM | 2242 | CB | GLU | 873 | 63.780 | 30.627 | 72.335 | 1.00 | 35.86 | sos |
| ATOM | 2243 | CG | GLU | 873 | 62.873 | 31.810 | 72.266 | 1.00 | 36.06 | sos |
| ATOM | 2244 | CD | GLU | 873 | 61.522 | 31.440 | 71.694 | 1.00 | 37.01 | sos |
| ATOM | 2245 | OE1 | GLU | 873 | 60.899 | 30.486 | 72.200 | 1.00 | 36.50 | sos |
| ATOM | 2246 | OE2 | GLU | 873 | 61.089 | 32.094 | 70.721 | 1.00 | 39.69 | sos |
| ATOM | 2247 | C | GLU | 873 | 65.697 | 30.634 | 73.916 | 1.00 | 38.39 | sos |
| ATOM | 2248 | O | GLU | 873 | 66.005 | 31.547 | 74.683 | 1.00 | 37.30 | sos |
| ATOM | 2249 | N | VAL | 874 | 65.674 | 29.349 | 74.271 | 1.00 | 37.32 | sos |
| ATOM | 2250 | CA | VAL | 874 | 66.053 | 28.870 | 75.593 | 1.00 | 32.44 | sos |
| ATOM | 2251 | CB | VAL | 874 | 65.544 | 27.430 | 75.810 | 1.00 | 28.56 | sos |
| ATOM | 2252 | CG1 | VAL | 874 | 65.967 | 26.899 | 77.179 | 1.00 | 24.50 | sos |
| ATOM | 2253 | CG2 | VAL | 874 | 64.035 | 27.397 | 75.673 | 1.00 | 24.19 | sos |
| ATOM | 2254 | C | VAL | 874 | 67.576 | 28.918 | 75.756 | 1.00 | 35.18 | sos |
| ATOM | 2255 | O | VAL | 874 | 68.082 | 29.421 | 76.762 | 1.00 | 34.54 | sos |
| ATOM | 2256 | N | VAL | 875 | 68.302 | 28.424 | 74.755 | 1.00 | 34.79 | sos |
| ATOM | 2257 | CA | VAL | 875 | 69.762 | 28.431 | 74.801 | 1.00 | 35.22 | sos |
| ATOM | 2258 | CB | VAL | 875 | 70.392 | 27.951 | 73.460 | 1.00 | 31.64 | sos |
| ATOM | 2259 | CG1 | VAL | 875 | 71.887 | 28.118 | 73.500 | 1.00 | 33.87 | sos |
| ATOM | 2260 | CG2 | VAL | 875 | 70.078 | 26.498 | 73.209 | 1.00 | 28.70 | sos |
| ATOM | 2261 | C | VAL | 875 | 70.251 | 29.846 | 75.102 | 1.00 | 37.38 | sos |
| ATOM | 2262 | O | VAL | 875 | 71.122 | 30.046 | 75.948 | 1.00 | 42.10 | sos |
| ATOM | 2263 | N | SER | 876 | 69.641 | 30.828 | 74.447 | 1.00 | 36.74 | sos |
| ATOM | 2264 | CA | SER | 876 | 70.024 | 32.216 | 74.642 | 1.00 | 33.39 | sos |
| ATOM | 2265 | CB | SER | 876 | 69.321 | 33.112 | 73.630 | 1.00 | 28.63 | sos |
| ATOM | 2266 | OG | SER | 876 | 69.932 | 32.961 | 72.359 | 1.00 | 28.80 | sos |
| ATOM | 2267 | C | SER | 876 | 69.781 | 32.695 | 76.061 | 1.00 | 33.94 | sos |
| ATOM | 2268 | O | SER | 876 | 70.615 | 33.392 | 76.633 | 1.00 | 34.57 | sos |
| ATOM | 2269 | N | ALA | 877 | 68.645 | 32.312 | 76.631 | 1.00 | 33.52 | sos |
| ATOM | 2270 | CA | ALA | 877 | 68.325 | 32.692 | 77.995 | 1.00 | 32.84 | sos |
| ATOM | 2271 | CB | ALA | 877 | 66.931 | 32.242 | 78.352 | 1.00 | 29.08 | sos |
| ATOM | 2272 | C | ALA | 877 | 69.347 | 32.034 | 78.918 | 1.00 | 35.34 | sos |
| ATOM | 2273 | O | ALA | 877 | 69.870 | 32.673 | 79.831 | 1.00 | 35.43 | sos |
| ATOM | 2274 | N | MET | 878 | 69.662 | 30.769 | 78.650 | 1.00 | 34.41 | sos |
| ATOM | 2275 | CA | MET | 878 | 70.622 | 30.047 | 79.473 | 1.00 | 33.97 | sos |
| ATOM | 2276 | CB | MET | 878 | 70.711 | 28.574 | 79.070 | 1.00 | 28.48 | sos |
| ATOM | 2277 | CG | MET | 878 | 69.471 | 27.750 | 79.421 | 1.00 | 27.29 | sos |
| ATOM | 2278 | SD | MET | 878 | 69.026 | 27.925 | 81.147 | 1.00 | 34.03 | sos |
| ATOM | 2279 | CE | MET | 878 | 67.293 | 27.448 | 81.197 | 1.00 | 22.57 | sos |
| ATOM | 2280 | C | MET | 878 | 71.998 | 30.697 | 79.438 | 1.00 | 37.59 | sos |
| ATOM | 2281 | O | MET | 878 | 72.659 | 30.804 | 80.472 | 1.00 | 40.08 | sos |
| ATOM | 2282 | N | ASN | 879 | 72.409 | 31.179 | 78.269 | 1.00 | 34.80 | sos |
| ATOM | 2283 | CA | ASN | 879 | 73.715 | 31.816 | 78.151 | 1.00 | 31.61 | sos |
| ATOM | 2284 | CB | ASN | 879 | 74.335 | 31.534 | 76.785 | 1.00 | 31.29 | sos |
| ATOM | 2285 | CG | ASN | 879 | 74.888 | 30.129 | 76.683 | 1.00 | 34.71 | sos |
| ATOM | 2286 | OD1 | ASN | 879 | 75.522 | 29.633 | 77.609 | 1.00 | 35.74 | sos |
| ATOM | 2287 | ND2 | ASN | 879 | 74.644 | 29.477 | 75.558 | 1.00 | 39.42 | sos |
| ATOM | 2288 | C | ASN | 879 | 73.731 | 33.310 | 78.433 | 1.00 | 31.50 | sos |
| ATOM | 2289 | O | ASN | 879 | 74.753 | 33.966 | 78.247 | 1.00 | 31.57 | sos |
| ATOM | 2290 | N | SER | 880 | 72.089 | 33.864 | 78.874 | 1.00 | 29.56 | sos |
| ATOM | 2291 | CA | SER | 880 | 72.582 | 35.286 | 79.158 | 1.00 | 31.67 | sos |
| ATOM | 2292 | CB | SER | 880 | 71.153 | 35.768 | 79.356 | 1.00 | 31.36 | sos |
| ATOM | 2293 | OG | SER | 880 | 70.595 | 35.260 | 80.549 | 1.00 | 38.87 | sos |
| ATOM | 2294 | C | SER | 880 | 73.410 | 35.546 | 80.408 | 1.00 | 35.66 | sos |
| ATOM | 2295 | O | SER | 880 | 73.639 | 34.636 | 81.203 | 1.00 | 41.76 | sos |
| ATOM | 2296 | N | SER | 881 | 73.861 | 36.782 | 80.581 | 1.00 | 34.66 | sos |
| ATOM | 2297 | CA | SER | 881 | 74.666 | 37.132 | 81.743 | 1.00 | 32.93 | sos |
| ATOM | 2298 | CB | SER | 881 | 75.068 | 38.609 | 81.704 | 1.00 | 35.57 | sos |
| ATOM | 2299 | OG | SER | 881 | 76.054 | 38.845 | 80.715 | 1.00 | 42.33 | sos |
| ATOM | 2300 | C | SER | 881 | 74.026 | 36.820 | 83.088 | 1.00 | 28.46 | sos |
| ATOM | 2301 | O | SER | 881 | 74.661 | 36.231 | 83.947 | 1.00 | 32.27 | sos |
| ATOM | 2302 | N | PRO | 882 | 72.755 | 37.189 | 83.284 | 1.00 | 26.27 | sos |
| ATOM | 2303 | CD | PRO | 882 | 71.861 | 38.016 | 82.462 | 1.00 | 22.52 | sos |
| ATOM | 2304 | CA | PRO | 882 | 72.137 | 36.902 | 84.580 | 1.00 | 29.08 | sos |

TABLE 3-continued

PDB Coordinates for the Ras-Sos Structure:
DATA SET FOR REFINED COORDINATES

| ATOM | 2305 | CB  | PRO | 882 | 70.774 | 37.596 | 84.475 | 1.00 | 24.26 | sos |
|------|------|-----|-----|-----|--------|--------|--------|------|-------|-----|
| ATOM | 2306 | CG  | PRO | 882 | 71.016 | 38.686 | 83.505 | 1.00 | 24.18 | sos |
| ATOM | 2307 | C   | PRO | 882 | 71.966 | 35.434 | 84.928 | 1.00 | 32.67 | sos |
| ATOM | 2308 | O   | PRO | 882 | 72.069 | 35.053 | 86.092 | 1.00 | 36.85 | sos |
| ATOM | 2309 | N   | VAL | 883 | 71.719 | 34.608 | 83.922 | 1.00 | 33.62 | sos |
| ATOM | 2310 | CA  | VAL | 883 | 71.475 | 33.199 | 84.173 | 1.00 | 32.43 | sos |
| ATOM | 2311 | CB  | VAL | 883 | 70.386 | 32.663 | 83.206 | 1.00 | 31.91 | sos |
| ATOM | 2312 | CG1 | VAL | 883 | 70.110 | 31.185 | 83.450 | 1.00 | 31.78 | sos |
| ATOM | 2313 | CG2 | VAL | 883 | 69.108 | 33.460 | 83.392 | 1.00 | 31.64 | sos |
| ATOM | 2314 | C   | VAL | 883 | 72.714 | 32.319 | 84.140 | 1.00 | 31.72 | sos |
| ATOM | 2315 | O   | VAL | 883 | 72.842 | 31.392 | 84.946 | 1.00 | 29.66 | sos |
| ATOM | 2316 | N   | TYR | 884 | 73.641 | 32.652 | 83.252 | 1.00 | 29.17 | sos |
| ATOM | 2317 | CA  | TYR | 884 | 74.861 | 31.881 | 83.070 | 1.00 | 31.62 | sos |
| ATOM | 2318 | CB  | TYR | 884 | 75.747 | 32.551 | 82.020 | 1.00 | 32.40 | sos |
| ATOM | 2319 | CG  | TYR | 884 | 77.031 | 31.815 | 81.712 | 1.00 | 39.50 | sos |
| ATOM | 2320 | CD1 | TYR | 884 | 77.022 | 30.667 | 80.924 | 1.00 | 43.42 | sos |
| ATOM | 2321 | CE1 | TYR | 884 | 78.209 | 30.022 | 80.571 | 1.00 | 44.73 | sos |
| ATOM | 2322 | CD2 | TYR | 884 | 78.262 | 32.300 | 82.152 | 1.00 | 38.98 | sos |
| ATOM | 2323 | CE2 | TYR | 884 | 79.454 | 31.662 | 81.807 | 1.00 | 42.88 | sos |
| ATOM | 2324 | CZ  | TYR | 884 | 79.420 | 30.525 | 81.012 | 1.00 | 45.53 | sos |
| ATOM | 2325 | OH  | TYR | 884 | 80.591 | 29.900 | 80.632 | 1.00 | 49.39 | sos |
| ATOM | 2326 | C   | TYR | 884 | 75.668 | 31.630 | 84.331 | 1.00 | 35.09 | sos |
| ATOM | 2327 | O   | TYR | 884 | 76.129 | 30.520 | 84.549 | 1.00 | 40.22 | sos |
| ATOM | 2328 | N   | ARG | 885 | 75.824 | 32.651 | 85.166 | 1.00 | 35.68 | sos |
| ATOM | 2329 | CA  | ARG | 885 | 76.621 | 32.531 | 86.383 | 1.00 | 38.34 | sos |
| ATOM | 2330 | CB  | ARG | 885 | 77.259 | 33.880 | 86.731 | 1.00 | 40.97 | sos |
| ATOM | 2331 | CG  | ARG | 885 | 76.301 | 35.060 | 86.668 | 1.00 | 41.60 | sos |
| ATOM | 2332 | CD  | ARG | 885 | 76.743 | 36.191 | 87.564 | 1.00 | 33.91 | sos |
| ATOM | 2333 | NE  | ARG | 885 | 75.764 | 36.339 | 88.618 | 1.00 | 36.07 | sos |
| ATOM | 2334 | CZ  | ARG | 885 | 76.025 | 36.249 | 89.916 | 1.00 | 39.61 | sos |
| ATOM | 2335 | NH1 | ARG | 885 | 77.265 | 36.026 | 90.351 | 1.00 | 29.34 | sos |
| ATOM | 2336 | NH2 | ARG | 885 | 75.016 | 36.317 | 90.776 | 1.00 | 35.12 | sos |
| ATOM | 2337 | C   | ARG | 885 | 75.970 | 31.959 | 87.632 | 1.00 | 38.17 | sos |
| ATOM | 2338 | O   | ARG | 885 | 76.585 | 31.970 | 88.695 | 1.00 | 41.34 | sos |
| ATOM | 2339 | N   | LEU | 886 | 74.742 | 31.470 | 87.527 | 1.00 | 36.83 | sos |
| ATOM | 2340 | CA  | LEU | 886 | 74.066 | 30.916 | 88.695 | 1.00 | 39.59 | sos |
| ATOM | 2341 | CB  | LEU | 886 | 72.551 | 30.956 | 88.510 | 1.00 | 35.37 | sos |
| ATOM | 2342 | CG  | LEU | 886 | 71.906 | 32.326 | 88.341 | 1.00 | 35.15 | sos |
| ATOM | 2343 | CD1 | LEU | 886 | 70.403 | 32.146 | 88.146 | 1.00 | 31.82 | sos |
| ATOM | 2344 | CD2 | LEU | 886 | 72.192 | 33.160 | 89.562 | 1.00 | 38.11 | sos |
| ATOM | 2345 | C   | LEU | 886 | 74.531 | 29.493 | 89.034 | 1.00 | 42.80 | sos |
| ATOM | 2346 | O   | LEU | 886 | 73.718 | 28.565 | 89.115 | 1.00 | 42.90 | sos |
| ATOM | 2347 | N   | ASP | 887 | 75.830 | 29.358 | 89.307 | 1.00 | 43.91 | sos |
| ATOM | 2348 | CA  | ASP | 887 | 76.469 | 28.081 | 89.639 | 1.00 | 44.24 | sos |
| ATOM | 2349 | CB  | ASP | 887 | 77.902 | 28.314 | 90.118 | 1.00 | 41.57 | sos |
| ATOM | 2350 | CG  | ASP | 887 | 78.768 | 29.012 | 89.076 | 1.00 | 47.33 | sos |
| ATOM | 2351 | OD1 | ASP | 887 | 78.521 | 28.834 | 87.861 | 1.00 | 50.16 | sos |
| ATOM | 2352 | OD2 | ASP | 887 | 79.699 | 29.749 | 89.474 | 1.00 | 48.29 | sos |
| ATOM | 2353 | C   | ASP | 887 | 75.722 | 27.219 | 90.656 | 1.00 | 46.42 | sos |
| ATOM | 2354 | O   | ASP | 887 | 75.681 | 25.996 | 90.514 | 1.00 | 48.95 | sos |
| ATOM | 2355 | N   | HIS | 888 | 75.133 | 27.846 | 91.673 | 1.00 | 45.04 | sos |
| ATOM | 2356 | CA  | HIS | 888 | 74.385 | 27.109 | 92.692 | 1.00 | 46.17 | sos |
| ATOM | 2357 | CB  | HIS | 888 | 73.953 | 28.020 | 93.845 | 1.00 | 45.57 | sos |
| ATOM | 2358 | CG  | HIS | 888 | 75.069 | 28.432 | 94.748 | 1.00 | 49.49 | sos |
| ATOM | 2359 | CD2 | HIS | 888 | 75.489 | 29.656 | 95.143 | 1.00 | 50.29 | sos |
| ATOM | 2360 | ND1 | HIS | 888 | 75.891 | 27.523 | 95.376 | 1.00 | 50.17 | sos |
| ATOM | 2361 | CE1 | HIS | 888 | 76.769 | 28.170 | 96.120 | 1.00 | 50.67 | sos |
| ATOM | 2362 | NE2 | HIS | 888 | 76.547 | 29.465 | 95.997 | 1.00 | 51.38 | sos |
| ATOM | 2363 | C   | HIS | 888 | 73.138 | 26.454 | 92.120 | 1.00 | 45.58 | sos |
| ATOM | 2364 | O   | HIS | 888 | 72.674 | 25.443 | 92.637 | 1.00 | 46.41 | sos |
| ATOM | 2365 | N   | THR | 889 | 72.576 | 27.057 | 91.080 | 1.00 | 43.87 | sos |
| ATOM | 2366 | CA  | THR | 889 | 71.370 | 26.526 | 90.474 | 1.00 | 42.45 | sos |
| ATOM | 2367 | CB  | THR | 889 | 70.622 | 27.606 | 89.670 | 1.00 | 40.53 | sos |
| ATOM | 2368 | OG1 | THR | 889 | 70.437 | 28.763 | 90.491 | 1.00 | 42.54 | sos |
| ATOM | 2369 | CG2 | THR | 889 | 69.253 | 27.105 | 89.243 | 1.00 | 40.21 | sos |
| ATOM | 2370 | C   | THR | 889 | 71.683 | 25.327 | 89.592 | 1.00 | 44.38 | sos |
| ATOM | 2371 | O   | THR | 889 | 71.130 | 24.247 | 89.799 | 1.00 | 43.40 | sos |
| ATOM | 2372 | N   | PHE | 890 | 72.605 | 25.500 | 88.647 | 1.00 | 45.76 | sos |
| ATOM | 2373 | CA  | PHE | 890 | 72.971 | 24.417 | 87.740 | 1.00 | 49.27 | sos |
| ATOM | 2374 | CB  | PHE | 890 | 73.853 | 24.933 | 86.599 | 1.00 | 44.03 | sos |
| ATOM | 2375 | CG  | PHE | 890 | 73.100 | 25.768 | 85.608 | 1.00 | 47.33 | sos |
| ATOM | 2376 | CD1 | PHE | 890 | 72.980 | 27.141 | 85.783 | 1.00 | 47.33 | sos |
| ATOM | 2377 | CD2 | PHE | 890 | 72.433 | 25.173 | 84.545 | 1.00 | 49.00 | sos |
| ATOM | 2378 | CE1 | PHE | 890 | 72.203 | 27.906 | 84.920 | 1.00 | 45.68 | sos |
| ATOM | 2379 | CE2 | PHE | 890 | 71.652 | 25.931 | 83.675 | 1.00 | 49.69 | sos |
| ATOM | 2380 | CZ  | PHE | 890 | 71.538 | 27.301 | 83.867 | 1.00 | 47.29 | sos |

TABLE 3-continued

PDB Coordinates for the Ras-Sos Structure:
DATA SET FOR REFINED COORDINATES

| ATOM | 2381 | C   | PHE | 890 | 73.589 | 23.218 | 88.444 | 1.00 | 54.19 | sos |
|------|------|-----|-----|-----|--------|--------|--------|------|-------|-----|
| ATOM | 2382 | O   | PHE | 890 | 73.508 | 22.095 | 87.951 | 1.00 | 57.53 | sos |
| ATOM | 2383 | N   | GLU | 891 | 74.142 | 23.451 | 89.630 | 1.00 | 57.49 | sos |
| ATOM | 2384 | CA  | GLU | 891 | 74.750 | 22.389 | 90.425 | 1.00 | 60.15 | sos |
| ATOM | 2385 | CB  | GLU | 891 | 75.227 | 22.955 | 91.770 | 1.00 | 64.50 | sos |
| ATOM | 2386 | CG  | GLU | 891 | 75.979 | 21.969 | 92.649 | 1.00 | 67.35 | sos |
| ATOM | 2387 | CD  | GLU | 891 | 77.464 | 21.928 | 92.333 | 1.00 | 74.85 | sos |
| ATOM | 2388 | OE1 | GLU | 891 | 78.255 | 22.364 | 93.197 | 1.00 | 78.88 | sos |
| ATOM | 2389 | OE2 | GLU | 891 | 77.843 | 21.475 | 91.227 | 1.00 | 75.87 | sos |
| ATOM | 2390 | C   | GLU | 891 | 73.727 | 21.280 | 90.695 | 1.00 | 59.02 | sos |
| ATOM | 2391 | O   | GLU | 891 | 74.012 | 20.098 | 90.500 | 1.00 | 59.41 | sos |
| ATOM | 2392 | N   | GLN | 892 | 72.529 | 21.685 | 91.113 | 1.00 | 55.25 | sos |
| ATOM | 2393 | CA  | GLN | 892 | 71.463 | 20.752 | 91.446 | 1.00 | 54.27 | sos |
| ATOM | 2394 | CB  | GLN | 892 | 70.627 | 21.313 | 92.589 | 1.00 | 55.32 | sos |
| ATOM | 2395 | CG  | GLN | 892 | 71.400 | 21.434 | 93.882 | 1.00 | 63.03 | sos |
| ATOM | 2396 | CD  | GLN | 892 | 70.570 | 22.024 | 94.997 | 1.00 | 69.20 | sos |
| ATOM | 2397 | OE1 | GLN | 892 | 69.346 | 21.878 | 95.021 | 1.00 | 70.32 | sos |
| ATOM | 2398 | NE2 | GLN | 892 | 71.233 | 22.700 | 95.932 | 1.00 | 72.72 | sos |
| ATOM | 2399 | C   | GLN | 892 | 70.565 | 20.314 | 90.299 | 1.00 | 52.14 | sos |
| ATOM | 2400 | O   | GLN | 892 | 69.483 | 19.774 | 90.524 | 1.00 | 52.66 | sos |
| ATOM | 2401 | N   | ILE | 893 | 71.001 | 20.559 | 89.071 | 1.00 | 49.30 | sos |
| ATOM | 2402 | CA  | ILE | 893 | 70.229 | 20.149 | 89.906 | 1.00 | 48.65 | sos |
| ATOM | 2403 | CB  | ILE | 893 | 70.368 | 21.168 | 86.741 | 1.00 | 48.07 | sos |
| ATOM | 2404 | CG2 | ILE | 893 | 69.984 | 20.546 | 85.407 | 1.00 | 45.19 | sos |
| ATOM | 2405 | CG1 | ILE | 893 | 69.462 | 22.360 | 87.002 | 1.00 | 43.22 | sos |
| ATOM | 2406 | CD1 | ILE | 893 | 69.728 | 23.476 | 86.080 | 1.00 | 50.88 | sos |
| ATOM | 2407 | C   | ILE | 893 | 70.729 | 18.774 | 87.488 | 1.00 | 47.38 | sos |
| ATOM | 2408 | O   | ILE | 893 | 71.934 | 18.560 | 87.338 | 1.00 | 45.95 | sos |
| ATOM | 2409 | N   | PRO | 984 | 69.810 | 17.811 | 87.342 | 1.00 | 45.62 | sos |
| ATOM | 2410 | CD  | PRO | 984 | 68.372 | 17.927 | 87.617 | 1.00 | 44.81 | sos |
| ATOM | 2411 | CA  | PRO | 984 | 70.156 | 16.445 | 86.945 | 1.00 | 47.18 | sos |
| ATOM | 2412 | CB  | PRO | 984 | 68.794 | 15.792 | 86.687 | 1.00 | 45.23 | sos |
| ATOM | 2413 | CG  | PRO | 984 | 67.811 | 16.936 | 86.663 | 1.00 | 48.49 | sos |
| ATOM | 2414 | C   | PRO | 984 | 71.085 | 16.361 | 85.746 | 1.00 | 50.07 | sos |
| ATOM | 2415 | O   | PRO | 984 | 71.126 | 17.255 | 84.907 | 1.00 | 53.56 | sos |
| ATOM | 2416 | N   | SER | 895 | 71.871 | 15.294 | 85.712 | 1.00 | 54.25 | sos |
| ATOM | 2417 | CA  | SER | 895 | 72.837 | 15.061 | 84.649 | 1.00 | 56.16 | sos |
| ATOM | 2418 | CB  | SER | 895 | 73.618 | 13.775 | 84.923 | 1.00 | 59.82 | sos |
| ATOM | 2419 | OG  | SER | 895 | 74.170 | 13.781 | 86.228 | 1.00 | 64.94 | sos |
| ATOM | 2420 | C   | SER | 895 | 72.218 | 14.986 | 83.261 | 1.00 | 56.38 | sos |
| ATOM | 2421 | O   | SER | 895 | 72.675 | 15.677 | 82.353 | 1.00 | 55.87 | sos |
| ATOM | 2422 | N   | ARG | 896 | 71.180 | 14.163 | 83.094 | 1.00 | 56.53 | sos |
| ATOM | 2423 | CA  | ARG | 896 | 70.551 | 14.014 | 81.781 | 1.00 | 58.93 | sos |
| ATOM | 2424 | CB  | ARG | 896 | 69.373 | 13.024 | 81.815 | 1.00 | 62.74 | sos |
| ATOM | 2425 | CG  | ARG | 896 | 68.100 | 13.582 | 82.414 | 1.00 | 70.55 | sos |
| ATOM | 2426 | CD  | ARG | 896 | 66.877 | 12.725 | 82.117 | 1.00 | 71.37 | sos |
| ATOM | 2427 | NE  | ARG | 896 | 65.662 | 13.375 | 82.608 | 1.00 | 78.32 | sos |
| ATOM | 2428 | CZ  | ARG | 896 | 65.441 | 13.714 | 83.880 | 1.00 | 81.02 | sos |
| ATOM | 2429 | NH1 | ARG | 896 | 66.348 | 13.461 | 84.818 | 1.00 | 78.58 | sos |
| ATOM | 2430 | NH2 | ARG | 896 | 64.324 | 14.348 | 84.214 | 1.00 | 83.13 | sos |
| ATOM | 2431 | C   | ARG | 896 | 70.111 | 15.356 | 81.195 | 1.00 | 57.23 | sos |
| ATOM | 2432 | O   | ARG | 896 | 70.322 | 15.620 | 80.006 | 1.00 | 55.04 | sos |
| ATOM | 2433 | N   | GLN | 897 | 69.543 | 16.214 | 82.041 | 1.00 | 53.23 | sos |
| ATOM | 2434 | CA  | GLN | 897 | 69.093 | 17.522 | 81.597 | 1.00 | 50.14 | sos |
| ATOM | 2435 | CB  | GLN | 897 | 68.188 | 18.158 | 82.638 | 1.00 | 48.35 | sos |
| ATOM | 2436 | CG  | GLN | 897 | 66.854 | 17.442 | 82.749 | 1.00 | 49.73 | sos |
| ATOM | 2437 | CD  | GLN | 897 | 65.909 | 18.085 | 83.746 | 1.00 | 52.56 | sos |
| ATOM | 2438 | OE1 | GLN | 897 | 66.289 | 18.979 | 84.506 | 1.00 | 47.90 | sos |
| ATOM | 2439 | NE2 | GLN | 897 | 64.665 | 17.622 | 83.754 | 1.00 | 57.68 | sos |
| ATOM | 2440 | C   | GLN | 897 | 70.250 | 18.439 | 81.211 | 1.00 | 50.15 | sos |
| ATOM | 2441 | O   | GLN | 897 | 70.137 | 19.201 | 80.249 | 1.00 | 50.25 | sos |
| ATOM | 2442 | N   | LYS | 898 | 71.371 | 18.339 | 81.925 | 1.00 | 48.22 | sos |
| ATOM | 2443 | CA  | LYS | 898 | 72.546 | 19.147 | 81.606 | 1.00 | 49.84 | sos |
| ATOM | 2444 | CB  | LYS | 898 | 73.680 | 18.924 | 82.611 | 1.00 | 54.56 | sos |
| ATOM | 2445 | CG  | LYS | 898 | 73.562 | 19.670 | 83.937 | 1.00 | 60.77 | sos |
| ATOM | 2446 | CD  | LYS | 898 | 74.790 | 19.383 | 84.801 | 1.00 | 59.71 | sos |
| ATOM | 2447 | CE  | LYS | 898 | 74.668 | 19.968 | 86.189 | 1.00 | 58.47 | sos |
| ATOM | 2448 | NZ  | LYS | 898 | 75.753 | 19.471 | 87.080 | 1.00 | 60.11 | sos |
| ATOM | 2449 | C   | LYS | 898 | 73.064 | 18.774 | 80.228 | 1.00 | 49.31 | sos |
| ATOM | 2450 | O   | LYS | 898 | 73.574 | 19.625 | 79.507 | 1.00 | 52.40 | sos |
| ATOM | 2451 | N   | LYS | 899 | 72.947 | 17.496 | 79.876 | 1.00 | 48.92 | sos |
| ATOM | 2452 | CA  | LYS | 899 | 73.416 | 17.001 | 78.583 | 1.00 | 49.75 | sos |
| ATOM | 2453 | CB  | LYS | 899 | 73.561 | 15.477 | 78.615 | 1.00 | 53.80 | sos |
| ATOM | 2454 | CG  | LYS | 899 | 74.555 | 14.966 | 79.644 | 0.00 | 52.63 | sos |
| ATOM | 2455 | CD  | LYS | 899 | 74.605 | 13.448 | 79.654 | 0.00 | 53.17 | sos |
| ATOM | 2456 | CE  | LYS | 899 | 75.577 | 12.935 | 80.703 | 0.00 | 53.10 | sos |

TABLE 3-continued

PDB Coordinates for the Ras-Sos Structure:
DATA SET FOR REFINED COORDINATES

| ATOM | 2457 | NZ | LYS | 899 | 75.630 | 11.447 | 80.729 | 0.00 | 53.21 | sos |
|---|---|---|---|---|---|---|---|---|---|---|
| ATOM | 2458 | C | LYS | 899 | 72.502 | 17.432 | 77.434 | 1.00 | 47.22 | sos |
| ATOM | 2459 | O | LYS | 899 | 72.965 | 17.658 | 76.313 | 1.00 | 47.74 | sos |
| ATOM | 2460 | N | ILE | 900 | 71.207 | 17.525 | 77.722 | 1.00 | 44.71 | sos |
| ATOM | 2461 | CA | ILE | 900 | 70.204 | 17.954 | 76.749 | 1.00 | 41.05 | sos |
| ATOM | 2462 | CB | ILE | 900 | 68.799 | 17.895 | 77.371 | 1.00 | 42.02 | sos |
| ATOM | 2463 | CG2 | ILE | 900 | 67.813 | 18.727 | 76.569 | 1.00 | 41.13 | sos |
| ATOM | 2464 | CG1 | ILE | 900 | 68.349 | 16.444 | 77.535 | 1.00 | 38.96 | sos |
| ATOM | 2465 | CD1 | ILE | 900 | 67.044 | 16.311 | 78.293 | 1.00 | 39.67 | sos |
| ATOM | 2466 | C | ILE | 900 | 70.508 | 19.404 | 76.392 | 1.00 | 41.97 | sos |
| ATOM | 2467 | O | ILE | 900 | 70.456 | 19.801 | 75.225 | 1.00 | 41.45 | sos |
| ATOM | 2468 | N | LEU | 901 | 70.831 | 20.182 | 77.423 | 1.00 | 42.78 | sos |
| ATOM | 2469 | CA | LEU | 901 | 71.162 | 21.594 | 77.277 | 1.00 | 44.78 | sos |
| ATOM | 2470 | CB | LEU | 901 | 71.197 | 22.267 | 78.651 | 1.00 | 41.97 | sos |
| ATOM | 2471 | CG2 | LEU | 901 | 71.565 | 23.748 | 78.651 | 1.00 | 41.65 | sos |
| ATOM | 2472 | CD1 | LEU | 901 | 70.616 | 24.517 | 77.741 | 1.00 | 36.63 | sos |
| ATOM | 2473 | CD2 | LEU | 901 | 71.520 | 24.278 | 80.076 | 1.00 | 41.13 | sos |
| ATOM | 2474 | C | LEU | 901 | 72.503 | 21.774 | 76.568 | 1.00 | 45.37 | sos |
| ATOM | 2475 | O | LEU | 901 | 72.633 | 22.606 | 75.677 | 1.00 | 45.17 | sos |
| ATOM | 2476 | N | GLU | 902 | 73.495 | 20.988 | 76.964 | 1.00 | 49.18 | sos |
| ATOM | 2477 | CA | GLU | 902 | 74.808 | 21.068 | 76.348 | 1.00 | 53.84 | sos |
| ATOM | 2478 | CB | GLU | 902 | 75.797 | 20.144 | 77.061 | 1.00 | 58.20 | sos |
| ATOM | 2479 | CG | GLU | 902 | 77.231 | 20.276 | 76.547 | 1.00 | 69.65 | sos |
| ATOM | 2480 | CD | GLU | 902 | 78.118 | 19.100 | 76.939 | 1.00 | 74.06 | sos |
| ATOM | 2481 | OE1 | GLU | 902 | 78.111 | 18.073 | 76.217 | 1.00 | 69.06 | sos |
| ATOM | 2482 | OE2 | GLU | 902 | 78.826 | 19.211 | 77.965 | 1.00 | 77.63 | sos |
| ATOM | 2483 | C | GLU | 902 | 74.686 | 20.683 | 74.876 | 1.00 | 55.31 | sos |
| ATOM | 2484 | O | GLU | 902 | 75.262 | 21.343 | 74.008 | 1.00 | 55.16 | sos |
| ATOM | 2485 | N | GLU | 903 | 73.917 | 19.629 | 74.600 | 1.00 | 56.38 | sos |
| ATOM | 2486 | CA | GLU | 903 | 73.701 | 19.159 | 73.231 | 1.00 | 60.76 | sos |
| ATOM | 2487 | CB | GLU | 903 | 72.789 | 17.924 | 73.236 | 1.00 | 66.25 | sos |
| ATOM | 2488 | CG | GLU | 903 | 72.499 | 17.291 | 71.858 | 1.00 | 72.01 | sos |
| ATOM | 2489 | CD | GLU | 903 | 71.383 | 16.227 | 71.902 | 1.00 | 76.13 | sos |
| ATOM | 2490 | OE1 | GLU | 903 | 71.204 | 15.568 | 72.954 | 1.00 | 74.00 | sos |
| ATOM | 2491 | OE2 | GLU | 903 | 70.675 | 16.057 | 70.881 | 1.00 | 74.40 | sos |
| ATOM | 2492 | C | GLU | 903 | 73.063 | 20.292 | 72.419 | 1.00 | 59.95 | sos |
| ATOM | 2493 | O | GLU | 903 | 73.378 | 20.484 | 71.241 | 1.00 | 59.33 | sos |
| ATOM | 2494 | N | ALA | 904 | 72.193 | 21.056 | 73.080 | 1.00 | 56.64 | sos |
| ATOM | 2495 | CA | ALA | 904 | 71.506 | 22.182 | 72.457 | 1.00 | 52.32 | sos |
| ATOM | 2496 | CB | ALA | 904 | 70.358 | 22.651 | 73.339 | 1.00 | 49.36 | sos |
| ATOM | 2497 | C | ALA | 904 | 72.468 | 23.332 | 72.191 | 1.00 | 50.59 | sos |
| ATOM | 2498 | O | ALA | 904 | 72.468 | 23.909 | 71.104 | 1.00 | 51.28 | sos |
| ATOM | 2499 | N | HIS | 905 | 73.293 | 23.658 | 73.182 | 1.00 | 49.43 | sos |
| ATOM | 2500 | CA | HIS | 905 | 74.254 | 24.744 | 73.048 | 1.00 | 49.46 | sos |
| ATOM | 2501 | CB | HIS | 905 | 75.008 | 24.965 | 74.363 | 1.00 | 52.81 | sos |
| ATOM | 2502 | CG | HIS | 905 | 76.107 | 25.982 | 74.266 | 1.00 | 60.08 | sos |
| ATOM | 2503 | CD2 | HIS | 905 | 77.382 | 25.879 | 73.817 | 1.00 | 60.16 | sos |
| ATOM | 2504 | ND1 | HIS | 905 | 75.936 | 27.302 | 74.626 | 1.00 | 59.72 | sos |
| ATOM | 2505 | CE1 | HIS | 905 | 77.054 | 27.968 | 74.399 | 1.00 | 60.01 | sos |
| ATOM | 2506 | NE2 | HIS | 905 | 77.947 | 27.128 | 73.907 | 1.00 | 59.61 | sos |
| ATOM | 2507 | C | HIS | 905 | 75.241 | 24.488 | 71.916 | 1.00 | 48.69 | sos |
| ATOM | 2508 | O | HIS | 905 | 75.675 | 25.418 | 71.237 | 1.00 | 46.11 | sos |
| ATOM | 2509 | N | GLU | 906 | 75.577 | 23.221 | 71.704 | 1.00 | 50.80 | sos |
| ATOM | 2510 | CA | GLU | 906 | 76.522 | 22.848 | 70.658 | 1.00 | 51.31 | sos |
| ATOM | 2511 | CB | GLU | 906 | 76.956 | 21.398 | 70.829 | 1.00 | 56.20 | sos |
| ATOM | 2512 | CG | GLU | 906 | 77.829 | 21.168 | 72.058 | 1.00 | 63.74 | sos |
| ATOM | 2513 | CD | GLU | 906 | 78.036 | 19.695 | 72.383 | 1.00 | 69.40 | sos |
| ATOM | 2514 | OE1 | GLU | 906 | 77.836 | 18.834 | 71.489 | 1.00 | 69.83 | sos |
| ATOM | 2515 | OE2 | GLU | 906 | 78.397 | 19.405 | 73.546 | 1.00 | 68.08 | sos |
| ATOM | 2516 | C | GLU | 906 | 76.018 | 23.090 | 69.244 | 1.00 | 49.18 | sos |
| ATOM | 2517 | O | GLU | 906 | 76.793 | 23.042 | 68.294 | 1.00 | 51.45 | sos |
| ATOM | 2518 | N | LEU | 907 | 74.726 | 23.354 | 69.103 | 1.00 | 46.28 | sos |
| ATOM | 2519 | CA | LEU | 907 | 74.156 | 23.616 | 67.792 | 1.00 | 44.89 | sos |
| ATOM | 2520 | CB | LEU | 907 | 72.624 | 33.645 | 67.870 | 1.00 | 45.65 | sos |
| ATOM | 2521 | CG | LEU | 907 | 71.908 | 22.288 | 67.971 | 1.00 | 44.17 | sos |
| ATOM | 2522 | CD1 | LEU | 907 | 70.474 | 22.466 | 68.407 | 1.00 | 38.30 | sos |
| ATOM | 2523 | CD2 | LEU | 907 | 71.972 | 21.573 | 66.629 | 1.00 | 43.88 | sos |
| ATOM | 2524 | C | LEU | 907 | 74.699 | 24.934 | 67.252 | 1.00 | 46.39 | sos |
| ATOM | 2525 | O | LEU | 907 | 74.959 | 25.066 | 66.062 | 1.00 | 48.25 | sos |
| ATOM | 2526 | N | SER | 908 | 74.947 | 25.875 | 68.157 | 1.00 | 48.20 | sos |
| ATOM | 2527 | CA | SER | 908 | 75.456 | 27.200 | 67.809 | 1.00 | 47.07 | sos |
| ATOM | 2528 | CB | SER | 908 | 75.235 | 28.146 | 68.983 | 1.00 | 47.16 | sos |
| ATOM | 2529 | OG | SER | 908 | 74.020 | 27.845 | 69.645 | 1.00 | 54.65 | sos |
| ATOM | 2530 | C | SER | 908 | 76.938 | 27.224 | 67.448 | 1.00 | 48.96 | sos |
| ATOM | 2531 | O | SER | 908 | 77.355 | 27.991 | 66.584 | 1.00 | 48.06 | sos |
| ATOM | 2532 | N | GLU | 909 | 77.723 | 26.379 | 68.115 | 1.00 | 51.71 | sos |

TABLE 3-continued

PDB Coordinates for the Ras-Sos Structure:
DATA SET FOR REFINED COORDINATES

| ATOM | 2533 | CA | GLU | 909 | 79.170 | 26.313 | 67.919 | 1.00 | 52.81 | sos |
|---|---|---|---|---|---|---|---|---|---|---|
| ATOM | 2534 | CB | GLU | 909 | 79.767 | 25.161 | 68.725 | 1.00 | 57.06 | sos |
| ATOM | 2535 | CG | GLU | 909 | 79.603 | 25.302 | 70.233 | 1.00 | 64.34 | sos |
| ATOM | 2536 | CD | GLU | 909 | 80.251 | 24.161 | 71.020 | 1.00 | 70.28 | sos |
| ATOM | 2537 | OE1 | GLU | 909 | 80.379 | 23.033 | 70.480 | 1.00 | 70.28 | sos |
| ATOM | 2538 | OE2 | GLU | 909 | 80.624 | 24.397 | 72.191 | 1.00 | 72.37 | sos |
| ATOM | 2539 | C | GLU | 909 | 79.657 | 26.226 | 66.485 | 1.00 | 51.53 | sos |
| ATOM | 2540 | O | GLU | 909 | 78.952 | 25.753 | 65.601 | 1.00 | 52.93 | sos |
| ATOM | 2541 | N | ASP | 910 | 80.879 | 26.701 | 66.273 | 1.00 | 50.75 | sos |
| ATOM | 2542 | CA | ASP | 910 | 81.509 | 26.688 | 64.964 | 1.00 | 52.24 | sos |
| ATOM | 2543 | CB | ASP | 910 | 81.869 | 25.256 | 64.565 | 1.00 | 57.73 | sos |
| ATOM | 2544 | CG | ASP | 910 | 83.240 | 24.842 | 65.059 | 1.00 | 61.23 | sos |
| ATOM | 2545 | OD1 | ASP | 910 | 84.237 | 25.208 | 64.391 | 1.00 | 64.95 | sos |
| ATOM | 2546 | OD2 | ASP | 910 | 83.320 | 24.151 | 66.101 | 1.00 | 60.29 | sos |
| ATOM | 2547 | C | ASP | 910 | 80.658 | 27.338 | 63.888 | 1.00 | 50.80 | sos |
| ATOM | 2548 | O | ASP | 910 | 80.667 | 26.909 | 62.733 | 1.00 | 50.10 | sos |
| ATOM | 2549 | N | HIS | 911 | 79.938 | 28.386 | 64.278 | 1.00 | 49.45 | sos |
| ATOM | 2550 | CA | HIS | 911 | 79.070 | 29.129 | 63.372 | 1.00 | 48.32 | sos |
| ATOM | 2551 | CB | HIS | 911 | 79.868 | 29.666 | 62.174 | 1.00 | 48.45 | sos |
| ATOM | 2552 | CG | HIS | 911 | 80.918 | 30.666 | 62.547 | 1.00 | 48.50 | sos |
| ATOM | 2553 | CD2 | HIS | 911 | 81.967 | 30.582 | 63.399 | 1.00 | 48.77 | sos |
| ATOM | 2554 | ND1 | HIS | 911 | 80.947 | 31.944 | 62.031 | 1.00 | 47.75 | sos |
| ATOM | 2555 | CE1 | HIS | 911 | 81.965 | 32.604 | 62.551 | 1.00 | 44.82 | sos |
| ATOM | 2556 | NE2 | HIS | 911 | 82.600 | 31.801 | 63.384 | 1.00 | 46.54 | sos |
| ATOM | 2557 | C | HIS | 911 | 77.854 | 28.317 | 62.908 | 1.00 | 48.27 | sos |
| ATOM | 2558 | O | HIS | 911 | 77.536 | 28.259 | 61.713 | 1.00 | 47.43 | sos |
| ATOM | 2559 | N | TYR | 912 | 77.185 | 27.696 | 63.638 | 1.00 | 46.37 | sos |
| ATOM | 2560 | CA | TYR | 912 | 75.986 | 26.900 | 63.638 | 1.00 | 49.11 | sos |
| ATOM | 2561 | CB | TYR | 912 | 74.877 | 27.780 | 63.054 | 1.00 | 48.64 | sos |
| ATOM | 2562 | CG | TYR | 912 | 74.320 | 28.819 | 63.999 | 1.00 | 46.06 | sos |
| ATOM | 2563 | CD1 | TYR | 912 | 74.595 | 30.174 | 63.817 | 1.00 | 46.11 | sos |
| ATOM | 2564 | CE1 | TYR | 912 | 74.041 | 31.138 | 64.639 | 1.00 | 47.73 | sos |
| ATOM | 2565 | CD2 | TYR | 912 | 73.480 | 28.452 | 65.043 | 1.00 | 46.64 | sos |
| ATOM | 2566 | CE2 | TYR | 912 | 72.919 | 29.408 | 65.883 | 1.00 | 51.30 | sos |
| ATOM | 2567 | CZ | TYR | 912 | 73.202 | 30.747 | 65.678 | 1.00 | 48.94 | sos |
| ATOM | 2568 | OH | TYR | 912 | 72.627 | 31.688 | 66.491 | 1.00 | 53.83 | sos |
| ATOM | 2569 | C | TYR | 912 | 76.177 | 25.682 | 62.739 | 1.00 | 51.71 | sos |
| ATOM | 2570 | O | TYR | 912 | 75.199 | 25.167 | 62.194 | 1.00 | 50.47 | sos |
| ATOM | 2571 | N | LYS | 913 | 77.417 | 25.202 | 62.619 | 1.00 | 53.99 | sos |
| ATOM | 2572 | CA | LYS | 913 | 77.726 | 24.054 | 61.769 | 1.00 | 53.13 | sos |
| ATOM | 2573 | CB | LYS | 913 | 79.182 | 23.624 | 61.935 | 1.00 | 57.46 | sos |
| ATOM | 2574 | CG | LYS | 913 | 79.638 | 22.625 | 60.877 | 1.00 | 61.18 | sos |
| ATOM | 2575 | CD | LYS | 913 | 81.147 | 22.446 | 60.871 | 1.00 | 65.36 | sos |
| ATOM | 2576 | CE | LYS | 913 | 81.597 | 21.652 | 59.643 | 1.00 | 70.45 | sos |
| ATOM | 2577 | NZ | LYS | 913 | 83.082 | 21.654 | 59.456 | 1.00 | 72.56 | sos |
| ATOM | 2578 | C | LYS | 913 | 76.802 | 22.866 | 62.005 | 1.00 | 52.79 | sos |
| ATOM | 2579 | O | LYS | 913 | 76.314 | 22.259 | 61.046 | 1.00 | 51.68 | sos |
| ATOM | 2580 | N | LYS | 914 | 76.549 | 22.550 | 63.274 | 1.00 | 49.69 | sos |
| ATOM | 2581 | CA | LYS | 914 | 75.665 | 21.439 | 63.613 | 1.00 | 48.44 | sos |
| ATOM | 2582 | CB | LYS | 914 | 75.878 | 20.977 | 65.050 | 1.00 | 44.11 | sos |
| ATOM | 2583 | CG | LYS | 914 | 77.141 | 20.168 | 65.245 | 1.00 | 45.53 | sos |
| ATOM | 2584 | CD | LYS | 914 | 77.188 | 19.601 | 66.641 | 1.00 | 49.53 | sos |
| ATOM | 2585 | CE | LYS | 914 | 78.550 | 19.026 | 66.984 | 1.00 | 50.01 | sos |
| ATOM | 2586 | NZ | LYS | 914 | 78.572 | 18.663 | 68.431 | 1.00 | 54.74 | sos |
| ATOM | 2587 | C | LYS | 914 | 74.192 | 21.742 | 63.372 | 1.00 | 49.84 | sos |
| ATOM | 2588 | O | LYS | 914 | 73.439 | 20.854 | 62.972 | 1.00 | 53.26 | sos |
| ATOM | 2589 | N | TYR | 915 | 73.778 | 22.985 | 63.623 | 1.00 | 47.97 | sos |
| ATOM | 2590 | CA | TYR | 915 | 72.392 | 23.383 | 63.403 | 1.00 | 42.57 | sos |
| ATOM | 2591 | CB | TYR | 915 | 72.134 | 24.810 | 63.891 | 1.00 | 38.41 | sos |
| ATOM | 2592 | CG | TYR | 915 | 70.887 | 25.432 | 63.292 | 1.00 | 33.23 | sos |
| ATOM | 2593 | CD1 | TYR | 915 | 69.618 | 25.081 | 63.746 | 1.00 | 33.30 | sos |
| ATOM | 2594 | CE1 | TYR | 915 | 68.481 | 25.594 | 63.156 | 1.00 | 32.15 | sos |
| ATOM | 2595 | CD2 | TYR | 915 | 70.977 | 26.321 | 62.230 | 1.00 | 30.81 | sos |
| ATOM | 2596 | CE2 | TYR | 915 | 69.847 | 26.840 | 61.629 | 1.00 | 30.91 | sos |
| ATOM | 2597 | CZ | TYR | 915 | 68.602 | 26.475 | 62.095 | 1.00 | 33.16 | sos |
| ATOM | 2598 | OH | TYR | 915 | 67.478 | 27.002 | 61.505 | 1.00 | 30.46 | sos |
| ATOM | 2599 | C | TYR | 915 | 72.069 | 23.298 | 61.922 | 1.00 | 42.82 | sos |
| ATOM | 2600 | O | TYR | 915 | 71.020 | 22.794 | 61.539 | 1.00 | 44.03 | sos |
| ATOM | 2601 | N | LEU | 916 | 72.961 | 23.823 | 61.093 | 1.00 | 45.21 | sos |
| ATOM | 2602 | CA | LEU | 916 | 72.749 | 23.798 | 59.654 | 1.00 | 47.30 | sos |
| ATOM | 2603 | CB | LEU | 916 | 73.870 | 24.538 | 58.922 | 1.00 | 42.79 | sos |
| ATOM | 2604 | CG | LEU | 916 | 73.928 | 26.057 | 59.129 | 1.00 | 47.64 | sos |
| ATOM | 2605 | CD1 | LEU | 916 | 74.999 | 26.665 | 58.227 | 1.00 | 48.44 | sos |
| ATOM | 2606 | CD2 | LEU | 916 | 72.578 | 26.695 | 58.829 | 1.00 | 43.45 | sos |
| ATOM | 2607 | C | LEU | 916 | 72.647 | 22.359 | 59.170 | 1.00 | 50.76 | sos |
| ATOM | 2608 | O | LEU | 916 | 71.830 | 22.045 | 58.299 | 1.00 | 53.92 | sos |

TABLE 3-continued

PDB Coordinates for the Ras-Sos Structure:
DATA SET FOR REFINED COORDINATES

| ATOM | 2609 | N   | ALA | 917 | 73.431 | 21.481 | 59.790 | 1.00 | 49.90 | sos |
|------|------|-----|-----|-----|--------|--------|--------|------|-------|-----|
| ATOM | 2610 | CA  | ALA | 917 | 73.437 | 20.069 | 59.437 | 1.00 | 49.12 | sos |
| ATOM | 2611 | CB  | ALA | 917 | 74.621 | 19.380 | 60.077 | 1.00 | 48.74 | sos |
| ATOM | 2612 | C   | ALA | 917 | 72.144 | 19.376 | 59.847 | 1.00 | 49.95 | sos |
| ATOM | 2613 | O   | ALA | 917 | 71.562 | 18.627 | 59.064 | 1.00 | 53.14 | sos |
| ATOM | 2614 | N   | LYS | 918 | 71.685 | 19.648 | 61.064 | 1.00 | 48.98 | sos |
| ATOM | 2615 | CA  | LYS | 918 | 70.470 | 19.033 | 61.576 | 1.00 | 47.78 | sos |
| ATOM | 2616 | CB  | LYS | 918 | 70.313 | 19.313 | 63.071 | 1.00 | 46.11 | sos |
| ATOM | 2617 | CG  | LYS | 918 | 69.194 | 18.532 | 63.744 | 1.00 | 45.72 | sos |
| ATOM | 2618 | CD  | LYS | 918 | 69.346 | 18.611 | 65.252 | 1.00 | 51.11 | sos |
| ATOM | 2619 | CE  | LYS | 918 | 68.279 | 17.827 | 65.991 | 1.00 | 52.13 | sos |
| ATOM | 2620 | NZ  | LYS | 918 | 68.454 | 17.974 | 67.465 | 1.00 | 51.54 | sos |
| ATOM | 2621 | C   | LYS | 918 | 69.226 | 19.470 | 60.821 | 1.00 | 48.71 | sos |
| ATOM | 2622 | O   | LYS | 918 | 68.319 | 18.667 | 60.619 | 1.00 | 51.41 | sos |
| ATOM | 2623 | N   | LEU | 919 | 69.193 | 20.731 | 60.394 | 1.00 | 49.27 | sos |
| ATOM | 2624 | CA  | LEU | 919 | 68.053 | 21.269 | 59.652 | 1.00 | 49.27 | sos |
| ATOM | 2625 | CB  | LEU | 919 | 68.307 | 22.722 | 59.252 | 1.00 | 49.07 | sos |
| ATOM | 2626 | CG  | LEU | 919 | 67.180 | 23.749 | 59.407 | 1.00 | 49.61 | sos |
| ATOM | 2627 | CD1 | LEU | 919 | 67.473 | 24.938 | 58.499 | 1.00 | 50.70 | sos |
| ATOM | 2628 | CD2 | LEU | 919 | 65.835 | 23.159 | 59.058 | 1.00 | 50.91 | sos |
| ATOM | 2629 | C   | LEU | 919 | 67.874 | 20.437 | 58.392 | 1.00 | 50.95 | sos |
| ATOM | 2630 | O   | LEU | 919 | 66.773 | 19.983 | 58.093 | 1.00 | 49.53 | sos |
| ATOM | 2631 | N   | ARG | 920 | 68.977 | 20.224 | 57.678 | 1.00 | 52.42 | sos |
| ATOM | 2632 | CA  | ARG | 920 | 68.978 | 19.437 | 56.451 | 1.00 | 56.17 | sos |
| ATOM | 2633 | CB  | ARG | 920 | 70.383 | 19.403 | 55.836 | 1.00 | 57.65 | sos |
| ATOM | 2634 | CG  | ARG | 920 | 70.838 | 20.702 | 55.190 | 1.00 | 63.21 | sos |
| ATOM | 2635 | CD  | ARG | 920 | 72.158 | 20.529 | 54.437 | 1.00 | 62.33 | sos |
| ATOM | 2636 | NE  | ARG | 920 | 72.656 | 21.795 | 53.903 | 0.00 | 63.60 | sos |
| ATOM | 2637 | CZ  | ARG | 920 | 72.141 | 22.428 | 52.852 | 0.00 | 63.87 | sos |
| ATOM | 2638 | NH1 | ARG | 920 | 71.101 | 21.919 | 52.203 | 0.00 | 64.16 | sos |
| ATOM | 2639 | NH2 | ARG | 920 | 72.665 | 23.578 | 52.450 | 0.00 | 64.16 | sos |
| ATOM | 2640 | C   | ARG | 920 | 68.508 | 17.999 | 56.676 | 1.00 | 58.37 | sos |
| ATOM | 2641 | O   | ARG | 920 | 67.694 | 17.478 | 55.911 | 1.00 | 61.06 | sos |
| ATOM | 2642 | N   | SER | 921 | 69.002 | 17.382 | 57.747 | 1.00 | 56.83 | sos |
| ATOM | 2643 | CA  | SER | 921 | 68.686 | 15.998 | 58.082 | 1.00 | 57.26 | sos |
| ATOM | 2644 | CB  | SER | 921 | 69.661 | 15.479 | 59.144 | 1.00 | 58.43 | sos |
| ATOM | 2645 | OG  | SER | 921 | 69.105 | 15.587 | 60.448 | 1.00 | 55.03 | sos |
| ATOM | 2646 | C   | SER | 921 | 67.265 | 15.687 | 58.549 | 1.00 | 58.41 | sos |
| ATOM | 2647 | O   | SER | 921 | 66.898 | 14.512 | 58.642 | 1.00 | 61.66 | sos |
| ATOM | 2648 | N   | ILE | 922 | 66.481 | 16.706 | 58.892 | 1.00 | 55.18 | sos |
| ATOM | 2649 | CA  | ILE | 922 | 65.128 | 16.441 | 59.371 | 1.00 | 50.67 | sos |
| ATOM | 2650 | CB  | ILE | 922 | 64.764 | 17.271 | 60.639 | 1.00 | 48.00 | sos |
| ATOM | 2651 | CG2 | ILE | 922 | 65.517 | 16.748 | 61.847 | 1.00 | 48.45 | sos |
| ATOM | 2652 | CG1 | ILE | 922 | 65.006 | 18.765 | 60.417 | 1.00 | 42.40 | sos |
| ATOM | 2653 | CD1 | ILE | 922 | 63.826 | 19.508 | 59.851 | 1.00 | 40.11 | sos |
| ATOM | 2654 | C   | ILE | 922 | 64.034 | 16.596 | 58.340 | 1.00 | 49.75 | sos |
| ATOM | 2655 | O   | ILE | 922 | 64.242 | 17.169 | 57.272 | 1.00 | 48.57 | sos |
| ATOM | 2656 | N   | ASN | 923 | 62.871 | 16.049 | 58.674 | 1.00 | 50.49 | sos |
| ATOM | 2657 | CA  | ASN | 923 | 61.702 | 16.123 | 57.816 | 1.00 | 53.82 | sos |
| ATOM | 2658 | CB  | ASN | 923 | 61.089 | 14.727 | 57.593 | 1.00 | 61.32 | sos |
| ATOM | 2659 | CG  | ASN | 923 | 61.919 | 13.860 | 56.636 | 1.00 | 67.66 | sos |
| ATOM | 2660 | OD1 | ASN | 923 | 62.445 | 12.815 | 57.029 | 1.00 | 69.64 | sos |
| ATOM | 2661 | ND2 | ASN | 923 | 62.033 | 14.295 | 55.376 | 1.00 | 64.13 | sos |
| ATOM | 2662 | C   | ASN | 923 | 60.689 | 17.038 | 58.480 | 1.00 | 49.62 | sos |
| ATOM | 2663 | O   | ASN | 923 | 60.312 | 16.824 | 59.634 | 1.00 | 50.69 | sos |
| ATOM | 2664 | N   | PRO | 924 | 60.279 | 18.103 | 57.778 | 1.00 | 45.33 | sos |
| ATOM | 2665 | CD  | PRO | 924 | 60.871 | 18.569 | 56.517 | 1.00 | 46.12 | sos |
| ATOM | 2666 | CA  | PRO | 924 | 59.304 | 19.075 | 58.279 | 1.00 | 47.49 | sos |
| ATOM | 2667 | CB  | PRO | 924 | 59.075 | 20.001 | 57.071 | 1.00 | 48.41 | sos |
| ATOM | 2668 | CG  | PRO | 924 | 59.735 | 19.295 | 55.900 | 1.00 | 47.54 | sos |
| ATOM | 2669 | C   | PRO | 924 | 58.006 | 18.452 | 58.816 | 1.00 | 46.79 | sos |
| ATOM | 2670 | O   | PRO | 924 | 57.779 | 17.255 | 58.669 | 1.00 | 48.62 | sos |
| ATOM | 2671 | N   | PRO | 925 | 57.157 | 19.250 | 59.488 | 1.00 | 46.84 | sos |
| ATOM | 2672 | CD  | PRO | 925 | 55.988 | 18.666 | 60.172 | 1.00 | 44.41 | sos |
| ATOM | 2673 | CA  | PRO | 925 | 57.277 | 20.682 | 59.802 | 1.00 | 46.23 | sos |
| ATOM | 2674 | CB  | PRO | 925 | 55.934 | 20.989 | 60.451 | 1.00 | 47.40 | sos |
| ATOM | 2675 | CG  | PRO | 925 | 55.644 | 19.723 | 61.200 | 1.00 | 46.14 | sos |
| ATOM | 2676 | C   | PRO | 925 | 58.425 | 21.018 | 60.752 | 1.00 | 45.27 | sos |
| ATOM | 2677 | O   | PRO | 925 | 58.967 | 20.143 | 61.432 | 1.00 | 44.74 | sos |
| ATOM | 2678 | N   | SYS | 926 | 58.790 | 22.294 | 60.780 | 1.00 | 44.68 | sos |
| ATOM | 2679 | CA  | SYS | 926 | 59.862 | 22.785 | 61.638 | 1.00 | 40.95 | sos |
| ATOM | 2680 | CB  | SYS | 926 | 61.214 | 22.278 | 61.142 | 1.00 | 36.96 | sos |
| ATOM | 2681 | SG  | SYS | 926 | 61.805 | 23.134 | 59.673 | 1.00 | 35.53 | sos |
| ATOM | 2682 | C   | SYS | 926 | 59.885 | 24.307 | 61.620 | 1.00 | 39.14 | sos |
| ATOM | 2683 | O   | SYS | 926 | 59.323 | 24.939 | 60.722 | 1.00 | 39.53 | sos |
| ATOM | 2684 | N   | VAL | 927 | 60.508 | 24.894 | 62.634 | 1.00 | 35.38 | sos |

TABLE 3-continued

PDB Coordinates for the Ras-Sos Structure:
DATA SET FOR REFINED COORDINATES

| ATOM | 2685 | CA | VAL | 927 | 60.645 | 26.341 | 62.695 | 1.00 | 31.48 | sos |
|---|---|---|---|---|---|---|---|---|---|---|
| ATOM | 2686 | CB | VAL | 927 | 60.010 | 26.939 | 63.982 | 1.00 | 28.21 | sos |
| ATOM | 2687 | CG1 | VAL | 927 | 60.001 | 28.448 | 63.893 | 1.00 | 28.35 | sos |
| ATOM | 2688 | CG2 | VAL | 927 | 58.588 | 26.419 | 64.204 | 1.00 | 22.59 | sos |
| ATOM | 2689 | C | VAL | 927 | 62.151 | 26.652 | 62.676 | 1.00 | 34.16 | sos |
| ATOM | 2690 | O | VAL | 927 | 62.844 | 26.491 | 63.684 | 1.00 | 39.68 | sos |
| ATOM | 2691 | N | PRO | 928 | 62.701 | 27.005 | 61.508 | 1.00 | 32.22 | sos |
| ATOM | 2692 | CD | PRO | 928 | 62.151 | 27.024 | 60.143 | 1.00 | 32.76 | sos |
| ATOM | 2693 | CA | PRO | 928 | 64.135 | 27.308 | 61.497 | 1.00 | 32.49 | sos |
| ATOM | 2694 | CB | PRO | 928 | 64.455 | 27.409 | 60.002 | 1.00 | 29.58 | sos |
| ATOM | 2695 | CG | PRO | 928 | 63.186 | 27.844 | 59.406 | 1.00 | 29.45 | sos |
| ATOM | 2696 | C | PRO | 928 | 64.469 | 28.614 | 62.212 | 1.00 | 33.46 | sos |
| ATOM | 2697 | O | PRO | 928 | 63.581 | 29.425 | 62.489 | 1.00 | 32.90 | sos |
| ATOM | 2698 | N | PHE | 929 | 65.739 | 28.775 | 62.579 | 1.00 | 36.55 | sos |
| ATOM | 2699 | CA | PHE | 929 | 66.199 | 30.004 | 63.225 | 1.00 | 32.09 | sos |
| ATOM | 2700 | CB | PHE | 929 | 67.529 | 29.790 | 63.939 | 1.00 | 26.80 | sos |
| ATOM | 2701 | CG | PHE | 929 | 68.135 | 31.057 | 64.447 | 1.00 | 26.59 | sos |
| ATOM | 2702 | CD1 | PHE | 929 | 67.474 | 31.815 | 65.412 | 1.00 | 25.03 | sos |
| ATOM | 2703 | CD2 | PHE | 929 | 69.332 | 31.529 | 63.916 | 1.00 | 25.27 | sos |
| ATOM | 2704 | CE1 | PHE | 929 | 67.991 | 33.017 | 65.831 | 1.00 | 21.25 | sos |
| ATOM | 2705 | CE2 | PHE | 929 | 69.863 | 32.729 | 64.325 | 1.00 | 17.89 | sos |
| ATOM | 2706 | CZ | PHE | 929 | 69.193 | 33.482 | 65.286 | 1.00 | 27.76 | sos |
| ATOM | 2707 | C | PHE | 929 | 66.389 | 30.978 | 62.073 | 1.00 | 29.76 | sos |
| ATOM | 2708 | O | PHE | 929 | 67.164 | 30.705 | 61.154 | 1.00 | 30.77 | sos |
| ATOM | 2709 | N | PHE | 930 | 65.704 | 32.114 | 62.133 | 1.00 | 26.53 | sos |
| ATOM | 2710 | CA | PHE | 930 | 65.756 | 33.089 | 61.049 | 1.00 | 27.13 | sos |
| ATOM | 2711 | CB | PHE | 930 | 64.544 | 34.018 | 61.129 | 1.00 | 29.26 | sos |
| ATOM | 2712 | CG | PHE | 930 | 63.929 | 34.330 | 59.798 | 1.00 | 28.00 | sos |
| ATOM | 2713 | CD1 | PHE | 930 | 62.596 | 34.032 | 59.554 | 1.00 | 26.87 | sos |
| ATOM | 2714 | CD2 | PHE | 930 | 64.685 | 34.905 | 58.782 | 1.00 | 27.99 | sos |
| ATOM | 2715 | CE1 | PHE | 930 | 62.024 | 34.298 | 58.321 | 1.00 | 25.27 | sos |
| ATOM | 2716 | CE2 | PHE | 930 | 64.123 | 35.172 | 57.547 | 1.00 | 27.66 | sos |
| ATOM | 2717 | CZ | PHE | 930 | 62.789 | 34.867 | 57.316 | 1.00 | 26.15 | sos |
| ATOM | 2718 | C | PHE | 930 | 67.027 | 33.911 | 60.905 | 1.00 | 27.03 | sos |
| ATOM | 2719 | O | PHE | 930 | 67.442 | 34.230 | 59.784 | 1.00 | 25.87 | sos |
| ATOM | 2720 | N | GLY | 931 | 67.625 | 34.265 | 62.036 | 1.00 | 28.95 | sos |
| ATOM | 2721 | CA | GLY | 931 | 68.836 | 35.073 | 62.037 | 1.00 | 32.59 | sos |
| ATOM | 2722 | C | GLY | 931 | 69.902 | 34.751 | 61.004 | 1.00 | 33.38 | sos |
| ATOM | 2723 | O | GLY | 931 | 70.421 | 35.660 | 60.359 | 1.00 | 34.76 | sos |
| ATOM | 2724 | N | ILE | 932 | 70.236 | 33.470 | 60.852 | 1.00 | 30.91 | sos |
| ATOM | 2725 | CA | ILE | 932 | 71.243 | 33.051 | 59.891 | 1.00 | 28.45 | sos |
| ATOM | 2726 | CB | ILE | 932 | 71.430 | 31.542 | 59.928 | 1.00 | 27.32 | sos |
| ATOM | 2727 | CG2 | ILE | 932 | 72.561 | 31.126 | 59.011 | 1.00 | 27.12 | sos |
| ATOM | 2728 | CG1 | ILE | 932 | 71.794 | 31.116 | 61.342 | 1.00 | 30.75 | sos |
| ATOM | 2729 | CD1 | ILE | 932 | 71.880 | 29.636 | 61.524 | 1.00 | 33.98 | sos |
| ATOM | 2730 | C | ILE | 932 | 70.887 | 33.501 | 58.474 | 1.00 | 32.12 | sos |
| ATOM | 2731 | O | ILE | 932 | 71.751 | 33.960 | 57.723 | 1.00 | 34.42 | sos |
| ATOM | 2732 | N | TYR | 933 | 69.613 | 33.385 | 58.113 | 1.00 | 32.30 | sos |
| ATOM | 2733 | CA | TYR | 933 | 69.162 | 33.809 | 56.789 | 1.00 | 33.98 | sos |
| ATOM | 2734 | CB | TYR | 933 | 67.681 | 33.470 | 56.588 | 1.00 | 33.42 | sos |
| ATOM | 2735 | CG | TYR | 933 | 67.381 | 31.991 | 56.491 | 1.00 | 33.58 | sos |
| ATOM | 2736 | CD1 | TYR | 933 | 66.417 | 31.402 | 57.314 | 1.00 | 30.32 | sos |
| ATOM | 2737 | CE1 | TYR | 933 | 66.128 | 30.052 | 57.228 | 1.00 | 27.97 | sos |
| ATOM | 2738 | CD2 | TYR | 933 | 68.052 | 31.181 | 55.572 | 1.00 | 30.42 | sos |
| ATOM | 2739 | CE2 | TYR | 933 | 67.769 | 29.824 | 55.476 | 1.00 | 31.98 | sos |
| ATOM | 2740 | CZ | TYR | 933 | 66.805 | 29.269 | 56.308 | 1.00 | 35.80 | sos |
| ATOM | 2741 | OH | TYR | 933 | 66.507 | 27.931 | 56.212 | 1.00 | 45.16 | sos |
| ATOM | 2742 | C | TYR | 933 | 69.369 | 35.317 | 56.622 | 1.00 | 34.51 | sos |
| ATOM | 2743 | O | TYR | 933 | 69.807 | 35.788 | 55.566 | 1.00 | 31.15 | sos |
| ATOM | 2744 | N | LEU | 934 | 69.053 | 36.064 | 57.679 | 1.00 | 36.03 | sos |
| ATOM | 2745 | CA | LEU | 934 | 69.205 | 37.514 | 57.671 | 1.00 | 35.33 | sos |
| ATOM | 2746 | CB | LEU | 934 | 68.733 | 38.107 | 58.994 | 1.00 | 32.91 | sos |
| ATOM | 2747 | CG | LEU | 934 | 67.274 | 37.817 | 59.330 | 1.00 | 32.65 | sos |
| ATOM | 2748 | CD1 | LEU | 934 | 66.899 | 38.478 | 60.637 | 1.00 | 28.03 | sos |
| ATOM | 2749 | CD2 | LEU | 934 | 66.386 | 38.320 | 58.209 | 1.00 | 34.70 | sos |
| ATOM | 2750 | C | LEU | 934 | 70.650 | 37.905 | 57.405 | 1.00 | 34.85 | sos |
| ATOM | 2751 | O | LEU | 934 | 70.929 | 38.672 | 56.478 | 1.00 | 36.11 | sos |
| ATOM | 2752 | N | THR | 935 | 71.569 | 37.323 | 58.173 | 1.00 | 33.09 | sos |
| ATOM | 2753 | CA | THR | 935 | 72.991 | 37.618 | 58.013 | 1.00 | 34.65 | sos |
| ATOM | 2754 | CB | THR | 935 | 73.867 | 36.915 | 59.071 | 1.00 | 34.56 | sos |
| ATOM | 2755 | OG1 | THR | 935 | 73.516 | 37.391 | 60.381 | 1.00 | 32.55 | sos |
| ATOM | 2756 | OG2 | THR | 935 | 75.342 | 37.204 | 58.811 | 1.00 | 27.55 | sos |
| ATOM | 2757 | C | THR | 935 | 73.491 | 37.253 | 56.631 | 1.00 | 34.69 | sos |
| ATOM | 2758 | O | THR | 935 | 74.295 | 37.981 | 56.050 | 1.00 | 38.00 | sos |
| ATOM | 2759 | N | ASN | 936 | 72.998 | 36.143 | 56.092 | 1.00 | 36.78 | sos |
| ATOM | 2760 | CA | ASN | 936 | 73.412 | 35.714 | 54.760 | 1.00 | 38.11 | sos |

TABLE 3-continued

PDB Coordinates for the Ras-Sos Structure:
DATA SET FOR REFINED COORDINATES

| ATOM | 2761 | CB | ASN | 936 | 73.072 | 34.243 | 54.531 | 1.00 | 40.14 | sos |
|---|---|---|---|---|---|---|---|---|---|---|
| ATOM | 2762 | CG | ASN | 936 | 73.959 | 33.317 | 55.345 | 1.00 | 44.39 | sos |
| ATOM | 2763 | OD1 | ASN | 936 | 75.143 | 33.591 | 55.529 | 1.00 | 43.22 | sos |
| ATOM | 2764 | ND2 | ASN | 936 | 73.385 | 32.228 | 55.853 | 1.00 | 43.60 | sos |
| ATOM | 2765 | C | ASN | 936 | 72.884 | 36.610 | 53.637 | 1.00 | 35.72 | sos |
| ATOM | 2766 | O | ASN | 936 | 73.598 | 36.885 | 52.677 | 1.00 | 34.25 | sos |
| ATOM | 2767 | N | ILE | 937 | 71.658 | 37.103 | 53.766 | 1.00 | 33.89 | sos |
| ATOM | 2768 | CA | ILE | 937 | 71.126 | 37.993 | 52.743 | 1.00 | 33.35 | sos |
| ATOM | 2769 | CB | ILE | 937 | 69.603 | 38.220 | 52.913 | 1.00 | 34.48 | sos |
| ATOM | 2770 | CG2 | ILE | 937 | 69.108 | 39.266 | 51.928 | 1.00 | 31.14 | sos |
| ATOM | 2771 | CG1 | ILE | 937 | 68.853 | 36.905 | 52.685 | 1.00 | 32.02 | sos |
| ATOM | 2772 | CD1 | ILE | 937 | 67.409 | 36.958 | 53.088 | 1.00 | 30.48 | sos |
| ATOM | 2773 | C | ILE | 937 | 71.877 | 39.332 | 52.802 | 1.00 | 34.21 | sos |
| ATOM | 2774 | O | ILE | 937 | 72.401 | 39.797 | 51.791 | 1.00 | 34.04 | sos |
| ATOM | 2775 | N | LEU | 938 | 71.988 | 39.916 | 53.994 | 1.00 | 34.23 | sos |
| ATOM | 2776 | CA | LEU | 938 | 72.679 | 41.195 | 54.142 | 1.00 | 32.99 | sos |
| ATOM | 2777 | CB | LEU | 938 | 72.684 | 41.655 | 55.609 | 1.00 | 30.55 | sos |
| ATOM | 2778 | CG | LEU | 938 | 73.485 | 42.936 | 55.910 | 1.00 | 31.42 | sos |
| ATOM | 2779 | CD1 | LEU | 938 | 72.779 | 44.149 | 55.351 | 1.00 | 32.59 | sos |
| ATOM | 2780 | CD2 | LEU | 938 | 73.697 | 43.111 | 57.402 | 1.00 | 32.76 | sos |
| ATOM | 2781 | C | LEU | 938 | 74.111 | 41.139 | 53.597 | 1.00 | 33.32 | sos |
| ATOM | 2782 | O | LEU | 938 | 74.510 | 41.992 | 52.806 | 1.00 | 31.57 | sos |
| ATOM | 2783 | N | LYS | 939 | 74.866 | 40.117 | 53.987 | 1.00 | 31.80 | sos |
| ATOM | 2784 | CA | LYS | 939 | 76.245 | 39.982 | 53.530 | 1.00 | 33.04 | sos |
| ATOM | 2785 | CB | LYS | 939 | 76.978 | 38.928 | 54.356 | 1.00 | 34.24 | sos |
| ATOM | 2786 | CG | LYS | 939 | 77.313 | 39.373 | 55.774 | 1.00 | 31.56 | sos |
| ATOM | 2787 | CD | LYS | 939 | 77.876 | 38.225 | 55.579 | 1.00 | 32.71 | sos |
| ATOM | 2788 | CE | LYS | 939 | 78.502 | 38.680 | 57.887 | 1.00 | 35.48 | sos |
| ATOM | 2789 | NZ | LYS | 939 | 79.199 | 37.545 | 58.575 | 1.00 | 31.28 | sos |
| ATOM | 2790 | C | LYS | 939 | 76.371 | 39.692 | 52.036 | 1.00 | 36.31 | sos |
| ATOM | 2791 | O | LYS | 939 | 77.311 | 40.167 | 51.390 | 1.00 | 35.36 | sos |
| ATOM | 2792 | N | THR | 940 | 75.430 | 38.918 | 51.489 | 1.00 | 36.42 | sos |
| ATOM | 2793 | CA | THR | 940 | 75.436 | 38.602 | 50.063 | 1.00 | 37.08 | sos |
| ATOM | 2794 | CB | THR | 940 | 74.305 | 37.592 | 49.684 | 1.00 | 40.26 | sos |
| ATOM | 2795 | OG1 | THR | 940 | 74.596 | 36.304 | 50.238 | 1.00 | 44.40 | sos |
| ATOM | 2796 | CG2 | THR | 940 | 74.186 | 37.434 | 48.182 | 1.00 | 40.07 | sos |
| ATOM | 2797 | C | THR | 940 | 75.247 | 39.912 | 49.298 | 1.00 | 38.78 | sos |
| ATOM | 2798 | O | THR | 940 | 75.957 | 40.189 | 48.328 | 1.00 | 41.20 | sos |
| ATOM | 2799 | N | GLU | 941 | 74.326 | 40.746 | 49.771 | 1.00 | 38.80 | sos |
| ATOM | 2800 | CA | GLU | 941 | 74.069 | 42.026 | 49.122 | 1.00 | 40.13 | sos |
| ATOM | 2801 | CB | GLU | 941 | 72.701 | 42.575 | 49.525 | 1.00 | 34.87 | sos |
| ATOM | 2802 | CG | GLU | 941 | 71.539 | 41.680 | 49.091 | 1.00 | 42.43 | sos |
| ATOM | 2803 | CD | GLU | 941 | 70.175 | 42.360 | 49.149 | 1.00 | 46.33 | sos |
| ATOM | 2804 | OE1 | GLU | 941 | 70.022 | 43.354 | 49.896 | 1.00 | 45.38 | sos |
| ATOM | 2805 | OE2 | GLU | 941 | 69.256 | 41.894 | 48.434 | 1.00 | 47.84 | sos |
| ATOM | 2806 | C | GLU | 941 | 75.154 | 43.076 | 49.346 | 1.00 | 42.54 | sos |
| ATOM | 2807 | O | GLU | 941 | 75.501 | 43.810 | 48.428 | 1.00 | 45.91 | sos |
| ATOM | 2808 | N | GLU | 942 | 75.706 | 43.146 | 50.553 | 1.00 | 46.01 | sos |
| ATOM | 2809 | CA | GLU | 942 | 76.739 | 44.135 | 50.832 | 1.00 | 48.66 | sos |
| ATOM | 2810 | CB | GLU | 942 | 76.656 | 44.617 | 52.287 | 1.00 | 51.09 | sos |
| ATOM | 2811 | CG | GLU | 942 | 75.443 | 45.530 | 52.562 | 1.00 | 59.51 | sos |
| ATOM | 2812 | CD | GLU | 942 | 75.341 | 46.032 | 54.014 | 1.00 | 65.63 | sos |
| ATOM | 2813 | OE1 | GLU | 942 | 74.593 | 47.004 | 54.262 | 1.00 | 67.90 | sos |
| ATOM | 2814 | OE2 | GLU | 942 | 75.987 | 45.455 | 54.916 | 1.00 | 69.12 | sos |
| ATOM | 2815 | C | GLU | 942 | 78.154 | 43.679 | 50.468 | 1.00 | 49.80 | sos |
| ATOM | 2816 | O | GLU | 942 | 79.027 | 44.510 | 50.208 | 1.00 | 50.54 | sos |
| ATOM | 2817 | N | GLY | 943 | 78.359 | 42.365 | 50.381 | 1.00 | 48.00 | sos |
| ATOM | 2818 | CA | GLY | 943 | 79.672 | 41.836 | 50.045 | 1.00 | 45.15 | sos |
| ATOM | 2819 | C | GLY | 943 | 79.962 | 41.559 | 48.575 | 1.00 | 44.56 | sos |
| ATOM | 2820 | O | GLY | 943 | 81.023 | 41.033 | 48.257 | 1.00 | 46.05 | sos |
| ATOM | 2821 | N | ASN | 944 | 79.009 | 41.855 | 47.694 | 1.00 | 42.47 | sos |
| ATOM | 2822 | CA | ASN | 944 | 79.164 | 41.651 | 46.254 | 1.00 | 39.18 | sos |
| ATOM | 2823 | CB | ASN | 944 | 78.305 | 40.483 | 45.778 | 1.00 | 36.64 | sos |
| ATOM | 2824 | CG | ASN | 944 | 78.711 | 39.168 | 46.405 | 1.00 | 38.03 | sos |
| ATOM | 2825 | OD1 | ASN | 944 | 79.667 | 38.529 | 45.974 | 1.00 | 43.35 | sos |
| ATOM | 2826 | ND2 | ASN | 944 | 77.978 | 38.750 | 47.421 | 1.00 | 37.27 | sos |
| ATOM | 2827 | C | ASN | 944 | 78.727 | 42.939 | 45.563 | 1.00 | 41.08 | sos |
| ATOM | 2828 | O | ASN | 944 | 77.767 | 43.583 | 45.989 | 1.00 | 40.69 | sos |
| ATOM | 2829 | N | PRO | 945 | 79.403 | 43.316 | 44.467 | 1.00 | 41.37 | sos |
| ATOM | 2830 | CD | PRO | 945 | 80.424 | 42.530 | 43.749 | 1.00 | 44.44 | sos |
| ATOM | 2831 | CA | PRO | 945 | 79.076 | 44.542 | 43.731 | 1.00 | 43.13 | sos |
| ATOM | 2832 | CB | PRO | 945 | 80.170 | 44.595 | 42.664 | 1.00 | 42.32 | sos |
| ATOM | 2833 | CG | PRO | 945 | 80.416 | 43.153 | 42.367 | 1.00 | 41.57 | sos |
| ATOM | 2834 | C | PRO | 945 | 77.681 | 44.563 | 43.116 | 1.00 | 45.45 | sos |
| ATOM | 2835 | O | PRO | 945 | 77.085 | 43.516 | 42.864 | 1.00 | 46.67 | sos |
| ATOM | 2836 | N | GLU | 946 | 77.146 | 45.765 | 42.937 | 1.00 | 48.77 | sos |

TABLE 3-continued

PDB Coordinates for the Ras-Sos Structure:
DATA SET FOR REFINED COORDINATES

| ATOM | 2837 | CA | GLU | 946 | 75.828 | 45.947 | 42.337 | 1.00 | 56.46 | sos |
|---|---|---|---|---|---|---|---|---|---|---|
| ATOM | 2838 | CB | GLU | 946 | 75.186 | 47.248 | 42.823 | 1.00 | 61.15 | sos |
| ATOM | 2839 | CG | GLU | 946 | 74.569 | 47.178 | 44.205 | 1.00 | 71.93 | sos |
| ATOM | 2840 | CD | GLU | 946 | 73.767 | 48.424 | 44.540 | 1.00 | 79.35 | sos |
| ATOM | 2841 | OE1 | GLU | 946 | 74.381 | 49.499 | 44.742 | 1.00 | 81.51 | sos |
| ATOM | 2842 | OE2 | GLU | 946 | 72.519 | 48.328 | 44.598 | 1.00 | 80.41 | sos |
| ATOM | 2843 | C | GLU | 946 | 75.956 | 46.009 | 40.820 | 1.00 | 57.42 | sos |
| ATOM | 2844 | O | GLU | 946 | 74.971 | 45.858 | 40.092 | 1.00 | 57.27 | sos |
| ATOM | 2845 | N | VAL | 947 | 77.185 | 46.211 | 40.358 | 1.00 | 57.94 | sos |
| ATOM | 2846 | CA | VAL | 947 | 77.476 | 46.340 | 38.943 | 1.00 | 56.01 | sos |
| ATOM | 2847 | CB | VAL | 947 | 77.382 | 47.825 | 38.533 | 1.00 | 54.88 | sos |
| ATOM | 2848 | CG1 | VAL | 947 | 78.251 | 48.108 | 37.343 | 1.00 | 59.70 | sos |
| ATOM | 2849 | CG2 | VAL | 947 | 75.950 | 48.192 | 38.222 | 1.00 | 56.83 | sos |
| ATOM | 2850 | C | VAL | 947 | 78.866 | 45.820 | 38.581 | 1.00 | 56.31 | sos |
| ATOM | 2851 | O | VAL | 947 | 79.826 | 46.030 | 39.321 | 1.00 | 58.33 | sos |
| ATOM | 2852 | N | LEU | 948 | 78.948 | 45.114 | 37.456 | 1.00 | 54.54 | sos |
| ATOM | 2853 | CA | LEU | 948 | 80.211 | 44.600 | 36.943 | 1.00 | 53.27 | sos |
| ATOM | 2854 | CB | LEU | 948 | 80.060 | 43.167 | 36.442 | 1.00 | 49.68 | sos |
| ATOM | 2855 | CG | LEU | 948 | 79.860 | 42.039 | 37.451 | 1.00 | 48.63 | sos |
| ATOM | 2856 | CD1 | LEU | 948 | 79.736 | 40.731 | 36.699 | 1.00 | 46.04 | sos |
| ATOM | 2857 | CD2 | LEU | 948 | 81.035 | 41.975 | 38.414 | 1.00 | 50.15 | sos |
| ATOM | 2858 | C | LEU | 948 | 80.550 | 45.504 | 35.766 | 1.00 | 57.14 | sos |
| ATOM | 2859 | O | LEU | 948 | 79.656 | 45.890 | 35.010 | 1.00 | 60.06 | sos |
| ATOM | 2860 | N | LYS | 949 | 81.819 | 45.878 | 35.627 | 1.00 | 58.62 | sos |
| ATOM | 2861 | CA | LYS | 949 | 82.229 | 46.744 | 34.523 | 1.00 | 59.42 | sos |
| ATOM | 2862 | CB | LYS | 949 | 83.114 | 47.893 | 35.018 | 1.00 | 62.41 | sos |
| ATOM | 2863 | CG | LYS | 949 | 82.452 | 48.850 | 36.017 | 1.00 | 62.59 | sos |
| ATOM | 2864 | CD | LYS | 949 | 81.383 | 49.717 | 35.377 | 1.00 | 61.61 | sos |
| ATOM | 2865 | CE | LYS | 949 | 81.967 | 50.651 | 34.328 | 0.00 | 62.10 | sos |
| ATOM | 2866 | NZ | LYS | 949 | 80.920 | 51.502 | 33.700 | 0.00 | 62.02 | sos |
| ATOM | 2867 | C | LYS | 949 | 82.959 | 45.955 | 33.446 | 1.00 | 60.30 | sos |
| ATOM | 2868 | O | LYS | 949 | 83.829 | 45.131 | 33.737 | 1.00 | 57.71 | sos |
| ATOM | 2869 | N | ARG | 950 | 82.571 | 46.196 | 32.199 | 1.00 | 63.84 | sos |
| ATOM | 2870 | CA | ARG | 950 | 83.170 | 45.529 | 31.047 | 1.00 | 65.83 | sos |
| ATOM | 2871 | CB | ARG | 950 | 82.307 | 44.344 | 30.603 | 1.00 | 63.71 | sos |
| ATOM | 2872 | CG | ARG | 950 | 82.183 | 43.209 | 31.613 | 1.00 | 60.21 | sos |
| ATOM | 2873 | CD | ARG | 950 | 83.498 | 42.494 | 31.807 | 1.00 | 58.50 | sos |
| ATOM | 2874 | NE | ARG | 950 | 83.369 | 41.283 | 32.616 | 1.00 | 58.72 | sos |
| ATOM | 2875 | CZ | ARG | 950 | 83.474 | 41.243 | 33.943 | 1.00 | 62.20 | sos |
| ATOM | 2876 | NH1 | ARG | 950 | 83.702 | 42.355 | 34.637 | 1.00 | 65.36 | sos |
| ATOM | 2877 | NH2 | ARG | 950 | 83.390 | 40.081 | 34.578 | 1.00 | 59.20 | sos |
| ATOM | 2878 | C | ARG | 950 | 83.274 | 46.536 | 29.908 | 1.00 | 68.64 | sos |
| ATOM | 2879 | O | ARG | 950 | 82.293 | 47.215 | 29.582 | 1.00 | 65.86 | sos |
| ATOM | 2880 | N | HIS | 951 | 84.472 | 46.650 | 29.334 | 1.00 | 72.30 | sos |
| ATOM | 2881 | CA | HIS | 951 | 84.741 | 47.570 | 28.223 | 1.00 | 76.18 | sos |
| ATOM | 2882 | CB | HIS | 951 | 84.213 | 46.997 | 26.896 | 1.00 | 80.25 | sos |
| ATOM | 2883 | CG | HIS | 951 | 84.906 | 45.746 | 26.446 | 1.00 | 84.73 | sos |
| ATOM | 2884 | CD2 | HIS | 951 | 84.419 | 44.524 | 26.123 | 1.00 | 85.81 | sos |
| ATOM | 2885 | ND1 | HIS | 951 | 86.273 | 45.671 | 26.270 | 1.00 | 87.16 | sos |
| ATOM | 2886 | CE1 | HIS | 951 | 86.596 | 44.457 | 25.859 | 1.00 | 87.75 | sos |
| ATOM | 2887 | NE2 | HIS | 951 | 85.489 | 43.742 | 25.762 | 1.00 | 86.90 | sos |
| ATOM | 2888 | C | HIS | 951 | 84.171 | 48.976 | 28.439 | 1.00 | 76.14 | sos |
| ATOM | 2889 | O | HIS | 951 | 83.806 | 49.659 | 27.480 | 1.00 | 77.57 | sos |
| ATOM | 2890 | N | GLY | 952 | 84.084 | 49.393 | 29.701 | 1.00 | 76.14 | sos |
| ATOM | 2891 | CA | GLY | 952 | 83.564 | 50.714 | 30.022 | 1.00 | 74.65 | sos |
| ATOM | 2892 | C | GLY | 952 | 82.053 | 50.806 | 30.122 | 1.00 | 73.85 | sos |
| ATOM | 2893 | O | GLY | 952 | 81.506 | 51.894 | 30.299 | 1.00 | 71.91 | sos |
| ATOM | 2894 | N | LYS | 953 | 81.374 | 49.670 | 29.989 | 1.00 | 73.26 | sos |
| ATOM | 2895 | CA | LYS | 953 | 79.919 | 49.634 | 30.076 | 1.00 | 71.54 | sos |
| ATOM | 2896 | CB | LYS | 953 | 79.345 | 48.795 | 28.939 | 1.00 | 73.33 | sos |
| ATOM | 2897 | CG | LYS | 953 | 79.850 | 49.213 | 27.568 | 1.00 | 77.88 | sos |
| ATOM | 2898 | CD | LYS | 953 | 79.471 | 50.651 | 27.225 | 1.00 | 79.26 | sos |
| ATOM | 2899 | CE | LYS | 953 | 79.954 | 51.027 | 25.826 | 1.00 | 80.11 | sos |
| ATOM | 2900 | NZ | LYS | 953 | 79.511 | 52.388 | 25.403 | 1.00 | 80.55 | sos |
| ATOM | 2901 | C | LYS | 953 | 79.485 | 49.086 | 31.433 | 1.00 | 68.59 | sos |
| ATOM | 2902 | O | LYS | 953 | 80.182 | 48.267 | 32.037 | 1.00 | 66.25 | sos |
| ATOM | 2903 | N | GLU | 954 | 78.314 | 49.521 | 31.886 | 1.00 | 66.41 | sos |
| ATOM | 2904 | CA | GLU | 954 | 77.779 | 49.132 | 33.190 | 1.00 | 63.74 | sos |
| ATOM | 2905 | CB | GLU | 954 | 77.223 | 50.385 | 33.863 | 1.00 | 63.26 | sos |
| ATOM | 2906 | CG | GLU | 954 | 77.320 | 50.401 | 35.355 | 1.00 | 66.67 | sos |
| ATOM | 2907 | CD | GLU | 954 | 77.230 | 51.803 | 35.922 | 1.00 | 73.91 | sos |
| ATOM | 2908 | OE1 | GLU | 954 | 78.291 | 52.458 | 36.060 | 1.00 | 71.39 | sos |
| ATOM | 2909 | OE2 | GLU | 954 | 76.099 | 52.249 | 36.228 | 1.00 | 77.06 | sos |
| ATOM | 2910 | C | GLU | 954 | 76.722 | 48.009 | 33.170 | 1.00 | 60.57 | sos |
| ATOM | 2911 | O | GLU | 954 | 75.553 | 48.237 | 32.856 | 1.00 | 56.89 | sos |
| ATOM | 2912 | N | LEU | 955 | 77.135 | 46.800 | 33.540 | 1.00 | 58.29 | sos |

TABLE 3-continued

PDB Coordinates for the Ras-Sos Structure:
DATA SET FOR REFINED COORDINATES

| ATOM | 2913 | CA  | LEU | 955 | 76.221 | 45.660 | 33.557 | 1.00 | 58.06 | sos |
|------|------|-----|-----|-----|--------|--------|--------|------|-------|-----|
| ATOM | 2914 | CB  | LEU | 955 | 76.874 | 44.421 | 32.932 | 1.00 | 58.48 | sos |
| ATOM | 2915 | CG  | LEU | 955 | 77.830 | 44.572 | 31.748 | 1.00 | 57.76 | sos |
| ATOM | 2916 | CD1 | LEU | 955 | 78.063 | 43.206 | 31.151 | 1.00 | 54.79 | sos |
| ATOM | 2917 | CD2 | LEU | 955 | 77.263 | 45.507 | 30.704 | 1.00 | 58.49 | sos |
| ATOM | 2918 | C   | LEU | 955 | 75.777 | 45.316 | 34.975 | 1.00 | 56.28 | sos |
| ATOM | 2919 | O   | LEU | 955 | 76.600 | 45.252 | 35.890 | 1.00 | 58.79 | sos |
| ATOM | 2920 | N   | ILE | 956 | 74.482 | 45.064 | 35.137 | 1.00 | 50.43 | sos |
| ATOM | 2921 | CA  | ILE | 956 | 73.901 | 44.715 | 36.429 | 1.00 | 46.71 | sos |
| ATOM | 2922 | CB  | ILE | 956 | 72.376 | 44.868 | 36.382 | 1.00 | 42.71 | sos |
| ATOM | 2923 | CG2 | ILE | 956 | 71.739 | 44.327 | 37.645 | 1.00 | 38.41 | sos |
| ATOM | 2924 | CG1 | ILE | 956 | 72.016 | 46.335 | 36.144 | 1.00 | 41.60 | sos |
| ATOM | 2925 | CD1 | ILE | 956 | 70.579 | 46.561 | 35.727 | 1.00 | 39.13 | sos |
| ATOM | 2926 | C   | ILE | 956 | 74.266 | 43.286 | 36.843 | 1.00 | 50.82 | sos |
| ATOM | 2927 | O   | ILE | 956 | 74.059 | 42.341 | 36.085 | 1.00 | 53.08 | sos |
| ATOM | 2928 | N   | ASN | 957 | 74.819 | 43.144 | 38.047 | 1.00 | 51.69 | sos |
| ATOM | 2929 | CA  | ASN | 957 | 75.221 | 43.845 | 38.581 | 1.00 | 50.53 | sos |
| ATOM | 2930 | CB  | ASN | 957 | 76.124 | 42.041 | 39.806 | 1.00 | 52.77 | sos |
| ATOM | 2931 | CG  | ASN | 957 | 76.632 | 40.726 | 40.390 | 1.00 | 55.27 | sos |
| ATOM | 2932 | OD1 | ASN | 957 | 76.104 | 39.652 | 40.104 | 1.00 | 55.07 | sos |
| ATOM | 2933 | ND2 | ASN | 957 | 77.666 | 40.812 | 41.220 | 1.00 | 58.56 | sos |
| ATOM | 2934 | C   | ASN | 957 | 73.979 | 41.080 | 38.985 | 1.00 | 50.28 | sos |
| ATOM | 2935 | O   | ASN | 957 | 73.481 | 41.253 | 40.094 | 1.00 | 52.58 | sos |
| ATOM | 2936 | N   | PHE | 958 | 73.492 | 40.217 | 38.101 | 1.00 | 48.79 | sos |
| ATOM | 2937 | CA  | PHE | 958 | 72.289 | 39.447 | 38.404 | 1.00 | 47.01 | sos |
| ATOM | 2938 | CB  | PHE | 958 | 71.596 | 38.984 | 37.126 | 1.00 | 47.54 | sos |
| ATOM | 2939 | CG  | PHE | 958 | 70.217 | 38.463 | 37.356 | 1.00 | 43.00 | sos |
| ATOM | 2940 | CD1 | PHE | 958 | 69.184 | 39.332 | 37.662 | 1.00 | 42.75 | sos |
| ATOM | 2941 | CD2 | PHE | 958 | 69.961 | 37.099 | 37.322 | 1.00 | 44.01 | sos |
| ATOM | 2942 | CE1 | PHE | 958 | 67.912 | 38.853 | 37.940 | 1.00 | 47.07 | sos |
| ATOM | 2943 | CE2 | PHE | 958 | 68.696 | 36.609 | 37.599 | 1.00 | 45.47 | sos |
| ATOM | 2944 | CZ  | PHE | 958 | 67.667 | 37.491 | 37.911 | 1.00 | 45.82 | sos |
| ATOM | 2945 | C   | PHE | 958 | 72.566 | 38.259 | 39.309 | 1.00 | 45.59 | sos |
| ATOM | 2946 | O   | PHE | 958 | 71.724 | 37.884 | 40.124 | 1.00 | 47.48 | sos |
| ATOM | 2947 | N   | SER | 959 | 73.745 | 37.668 | 39.154 | 1.00 | 45.25 | sos |
| ATOM | 2948 | CA  | SER | 959 | 74.165 | 36.526 | 39.961 | 1.00 | 48.51 | sos |
| ATOM | 2949 | CB  | SER | 959 | 75.650 | 36.241 | 39.713 | 1.00 | 49.47 | sos |
| ATOM | 2950 | OG  | SER | 959 | 76.185 | 35.367 | 40.694 | 1.00 | 53.06 | sos |
| ATOM | 2951 | C   | SER | 959 | 73.927 | 36.769 | 41.454 | 1.00 | 48.32 | sos |
| ATOM | 2952 | O   | SER | 959 | 73.480 | 35.882 | 42.185 | 1.00 | 50.28 | sos |
| ATOM | 2953 | N   | LYS | 960 | 74.240 | 37.984 | 41.887 | 1.00 | 46.77 | sos |
| ATOM | 2954 | CA  | LYS | 960 | 74.082 | 38.416 | 43.267 | 1.00 | 42.86 | sos |
| ATOM | 2955 | CB  | LYS | 960 | 74.584 | 39.855 | 43.365 | 1.00 | 44.25 | sos |
| ATOM | 2956 | CG  | LYS | 960 | 74.189 | 40.642 | 44.582 | 1.00 | 46.06 | sos |
| ATOM | 2957 | CD  | LYS | 960 | 74.728 | 42.044 | 44.418 | 1.00 | 46.54 | sos |
| ATOM | 2958 | CE  | LYS | 960 | 74.345 | 42.943 | 45.564 | 1.00 | 47.36 | sos |
| ATOM | 2959 | NZ  | LYS | 960 | 75.046 | 44.250 | 45.438 | 1.00 | 47.00 | sos |
| ATOM | 2960 | C   | LYS | 960 | 72.618 | 38.315 | 43.671 | 1.00 | 41.85 | sos |
| ATOM | 2961 | O   | LYS | 960 | 72.294 | 37.819 | 44.754 | 1.00 | 40.54 | sos |
| ATOM | 2962 | N   | ARG | 961 | 71.738 | 38.758 | 42.775 | 1.00 | 40.96 | sos |
| ATOM | 2963 | CA  | ARG | 961 | 70.301 | 38.714 | 43.015 | 1.00 | 41.94 | sos |
| ATOM | 2964 | CB  | ARG | 961 | 69.541 | 39.547 | 41.973 | 1.00 | 46.41 | sos |
| ATOM | 2965 | CG  | ARG | 961 | 69.473 | 41.066 | 42.266 | 1.00 | 47.57 | sos |
| ATOM | 2966 | CD  | ARG | 961 | 70.803 | 41.768 | 42.001 | 1.00 | 54.33 | sos |
| ATOM | 2967 | NE  | ARG | 961 | 70.763 | 43.204 | 42.290 | 1.00 | 57.32 | sos |
| ATOM | 2968 | CZ  | ARG | 961 | 71.590 | 44.106 | 41.759 | 1.00 | 55.15 | sos |
| ATOM | 2969 | NH1 | ARG | 961 | 72.537 | 43.739 | 40.905 | 1.00 | 52.19 | sos |
| ATOM | 2970 | NH2 | ARG | 961 | 71.451 | 45.387 | 42.061 | 1.00 | 55.46 | sos |
| ATOM | 2971 | C   | ARG | 961 | 69.796 | 37.275 | 43.029 | 1.00 | 42.62 | sos |
| ATOM | 2972 | O   | ARG | 961 | 68.857 | 36.948 | 43.753 | 1.00 | 42.74 | sos |
| ATOM | 2973 | N   | ARG | 962 | 70.445 | 36.410 | 42.251 | 1.00 | 43.04 | sos |
| ATOM | 2974 | CA  | ARG | 962 | 70.065 | 35.003 | 42.203 | 1.00 | 41.95 | sos |
| ATOM | 2975 | CB  | ARG | 962 | 70.798 | 34.275 | 41.080 | 1.00 | 44.78 | sos |
| ATOM | 2976 | CG  | ARG | 962 | 70.271 | 32.854 | 40.812 | 1.00 | 47.53 | sos |
| ATOM | 2977 | CD  | ARG | 962 | 71.170 | 32.085 | 39.850 | 1.00 | 51.09 | sos |
| ATOM | 2978 | NE  | ARG | 962 | 71.624 | 32.924 | 38.741 | 1.00 | 58.29 | sos |
| ATOM | 2979 | CZ  | ARG | 962 | 70.883 | 33.258 | 37.689 | 1.00 | 61.51 | sos |
| ATOM | 2980 | NH1 | ARG | 962 | 69.630 | 32.821 | 37.564 | 1.00 | 63.81 | sos |
| ATOM | 2981 | NH2 | ARG | 962 | 71.386 | 34.079 | 36.777 | 1.00 | 61.24 | sos |
| ATOM | 2982 | C   | ARG | 962 | 70.420 | 34.353 | 43.526 | 1.00 | 41.78 | sos |
| ATOM | 2983 | O   | ARG | 962 | 69.661 | 33.541 | 44.053 | 1.00 | 44.33 | sos |
| ATOM | 2984 | N   | LYS | 963 | 71.586 | 34.707 | 44.056 | 1.00 | 42.96 | sos |
| ATOM | 2985 | CA  | LYS | 963 | 72.040 | 34.157 | 45.326 | 1.00 | 43.27 | sos |
| ATOM | 2986 | CB  | LYS | 963 | 73.477 | 34.588 | 45.630 | 1.00 | 39.82 | sos |
| ATOM | 2987 | CG  | LYS | 963 | 74.530 | 33.657 | 45.040 | 1.00 | 37.49 | sos |
| ATOM | 2988 | CD  | LYS | 963 | 75.937 | 34.080 | 45.440 | 0.00 | 38.70 | sos |

TABLE 3-continued

PDB Coordinates for the Ras-Sos Structure:
DATA SET FOR REFINED COORDINATES

| ATOM | 2989 | CE  | LYS | 963 | 76.282 | 35.464 | 44.909 | 0.00 | 38.58 | sos |
|------|------|-----|-----|-----|--------|--------|--------|------|-------|-----|
| ATOM | 2990 | NZ  | LYS | 963 | 77.650 | 35.889 | 45.314 | 0.00 | 38.88 | sos |
| ATOM | 2991 | C   | LYS | 963 | 71.096 | 34.537 | 46.462 | 1.00 | 44.33 | sos |
| ATOM | 2992 | O   | LYS | 963 | 70.875 | 33.740 | 47.382 | 1.00 | 43.72 | sos |
| ATOM | 2993 | N   | VAL | 964 | 70.510 | 35.731 | 46.375 | 1.00 | 42.38 | sos |
| ATOM | 2994 | CA  | VAL | 964 | 69.567 | 36.181 | 47.397 | 1.00 | 41.67 | sos |
| ATOM | 2995 | CB  | VAL | 964 | 69.198 | 37.679 | 47.234 | 1.00 | 41.32 | sos |
| ATOM | 2996 | CG1 | VAL | 964 | 68.243 | 38.108 | 48.324 | 1.00 | 34.58 | sos |
| ATOM | 2997 | CG2 | VAL | 964 | 70.448 | 38.536 | 47.286 | 1.00 | 44.39 | sos |
| ATOM | 2998 | C   | VAL | 964 | 68.299 | 35.338 | 47.295 | 1.00 | 41.15 | sos |
| ATOM | 2999 | O   | VAL | 964 | 67.806 | 34.815 | 48.303 | 1.00 | 39.53 | sos |
| ATOM | 3000 | N   | ALA | 965 | 67.821 | 35.171 | 46.059 | 1.00 | 41.26 | sos |
| ATOM | 3001 | CA  | ALA | 965 | 66.610 | 34.402 | 45.760 | 1.00 | 39.89 | sos |
| ATOM | 3002 | CB  | ALA | 965 | 66.311 | 34.456 | 44.281 | 1.00 | 35.28 | sos |
| ATOM | 3003 | C   | ALA | 965 | 66.655 | 32.952 | 46.243 | 1.00 | 40.61 | sos |
| ATOM | 3004 | O   | ALA | 965 | 65.621 | 32.395 | 46.620 | 1.00 | 36.39 | sos |
| ATOM | 3005 | N   | GLU | 966 | 67.844 | 32.347 | 46.235 | 1.00 | 41.19 | sos |
| ATOM | 3006 | CA  | GLU | 966 | 68.002 | 30.969 | 46.705 | 1.00 | 43.20 | sos |
| ATOM | 3007 | CB  | GLU | 966 | 69.396 | 30.434 | 46.375 | 1.00 | 46.49 | sos |
| ATOM | 3008 | CG  | GLU | 966 | 69.660 | 30.240 | 44.883 | 1.00 | 55.23 | sos |
| ATOM | 3009 | CD  | GLU | 966 | 71.132 | 29.995 | 44.549 | 1.00 | 57.37 | sos |
| ATOM | 3010 | OE1 | GLU | 966 | 71.952 | 29.772 | 45.475 | 1.00 | 52.53 | sos |
| ATOM | 3011 | OE2 | GLU | 966 | 71.466 | 30.038 | 43.345 | 1.00 | 59.09 | sos |
| ATOM | 3012 | C   | GLU | 966 | 67.757 | 30.882 | 48.212 | 1.00 | 42.86 | sos |
| ATOM | 3013 | O   | GLU | 966 | 67.128 | 29.934 | 48.692 | 1.00 | 44.23 | sos |
| ATOM | 3014 | N   | ILE | 967 | 68.250 | 31.876 | 48.953 | 1.00 | 41.38 | sos |
| ATOM | 3015 | CA  | ILE | 967 | 68.070 | 31.908 | 50.403 | 1.00 | 38.81 | sos |
| ATOM | 3016 | CB  | ILE | 967 | 68.927 | 33.002 | 51.064 | 1.00 | 34.99 | sos |
| ATOM | 3017 | CG2 | ILE | 967 | 68.854 | 32.873 | 52.572 | 1.00 | 33.20 | sos |
| ATOM | 3018 | CG1 | ILE | 967 | 70.383 | 32.851 | 50.627 | 1.00 | 31.94 | sos |
| ATOM | 3019 | CD1 | ILE | 967 | 71.280 | 33.962 | 51.080 | 1.00 | 24.81 | sos |
| ATOM | 3020 | C   | ILE | 967 | 66.595 | 32.153 | 50.680 | 1.00 | 39.08 | sos |
| ATOM | 3021 | O   | ILE | 967 | 65.981 | 31.491 | 51.520 | 1.00 | 38.84 | sos |
| ATOM | 3022 | N   | THR | 968 | 66.022 | 33.085 | 49.934 | 1.00 | 39.52 | sos |
| ATOM | 3023 | CA  | THR | 968 | 64.610 | 33.388 | 50.065 | 1.00 | 39.92 | sos |
| ATOM | 3024 | CB  | THR | 968 | 64.216 | 34.503 | 49.089 | 1.00 | 40.00 | sos |
| ATOM | 3025 | OG1 | THR | 968 | 64.371 | 35.763 | 49.744 | 1.00 | 47.85 | sos |
| ATOM | 3026 | OG2 | THR | 968 | 62.791 | 34.349 | 48.599 | 1.00 | 45.60 | sos |
| ATOM | 3027 | C   | THR | 968 | 63.817 | 32.110 | 49.788 | 1.00 | 38.89 | sos |
| ATOM | 3028 | O   | THR | 968 | 62.970 | 31.717 | 50.590 | 1.00 | 35.16 | sos |
| ATOM | 3029 | N   | GLY | 969 | 64.156 | 31.442 | 48.683 | 1.00 | 39.31 | sos |
| ATOM | 3030 | CA  | GLY | 969 | 63.489 | 30.213 | 48.290 | 1.00 | 36.56 | sos |
| ATOM | 3031 | C   | GLY | 969 | 63.532 | 29.156 | 49.371 | 1.00 | 39.29 | sos |
| ATOM | 3032 | O   | GLY | 969 | 62.507 | 28.539 | 49.681 | 1.00 | 38.99 | sos |
| ATOM | 3033 | N   | GLU | 970 | 64.708 | 28.967 | 49.968 | 1.00 | 39.85 | sos |
| ATOM | 3034 | CA  | GLU | 970 | 64.866 | 27.992 | 51.041 | 1.00 | 40.37 | sos |
| ATOM | 3035 | CB  | GLU | 970 | 66.307 | 27.971 | 51.552 | 1.00 | 46.63 | sos |
| ATOM | 3036 | CG  | GLU | 970 | 66.561 | 26.936 | 52.654 | 1.00 | 54.11 | sos |
| ATOM | 3037 | CD  | GLU | 970 | 68.026 | 26.844 | 53.089 | 1.00 | 57.16 | sos |
| ATOM | 3038 | OE1 | GLU | 970 | 68.265 | 26.435 | 54.251 | 1.00 | 50.60 | sos |
| ATOM | 3039 | OE2 | GLU | 970 | 68.929 | 27.167 | 52.273 | 1.00 | 54.40 | sos |
| ATOM | 3040 | C   | GLU | 970 | 63.912 | 28.326 | 52.181 | 1.00 | 40.45 | sos |
| ATOM | 3041 | O   | GLU | 970 | 63.261 | 27.440 | 52.722 | 1.00 | 40.70 | sos |
| ATOM | 3042 | N   | ILE | 971 | 63.808 | 29.612 | 52.516 | 1.00 | 39.96 | sos |
| ATOM | 3043 | CA  | ILE | 971 | 62.919 | 30.066 | 53.587 | 1.00 | 38.47 | sos |
| ATOM | 3044 | CB  | ILE | 971 | 62.969 | 31.617 | 53.741 | 1.00 | 39.32 | sos |
| ATOM | 3045 | CG2 | ILE | 971 | 61.824 | 32.131 | 54.595 | 1.00 | 33.01 | sos |
| ATOM | 3046 | CG1 | ILE | 971 | 64.298 | 32.044 | 54.352 | 1.00 | 37.02 | sos |
| ATOM | 3047 | CD1 | ILE | 971 | 64.531 | 33.516 | 54.262 | 1.00 | 34.62 | sos |
| ATOM | 3048 | C   | ILE | 971 | 61.489 | 29.635 | 53.297 | 1.00 | 37.74 | sos |
| ATOM | 3049 | O   | ILE | 971 | 60.846 | 29.014 | 54.136 | 1.00 | 39.30 | sos |
| ATOM | 3050 | N   | GLN | 972 | 61.020 | 29.938 | 52.089 | 1.00 | 39.14 | sos |
| ATOM | 3051 | CA  | GLN | 972 | 59.661 | 29.612 | 51.665 | 1.00 | 39.55 | sos |
| ATOM | 3052 | CB  | GLN | 972 | 59.363 | 30.220 | 50.292 | 1.00 | 40.62 | sos |
| ATOM | 3053 | CG  | GLN | 972 | 59.140 | 31.722 | 50.330 | 1.00 | 48.28 | sos |
| ATOM | 3054 | CD  | GLN | 972 | 58.877 | 32.328 | 48.958 | 1.00 | 51.83 | sos |
| ATOM | 3055 | OE1 | GLN | 972 | 59.772 | 32.394 | 48.104 | 1.00 | 50.13 | sos |
| ATOM | 3056 | NE2 | GLN | 972 | 57.650 | 32.806 | 48.752 | 1.00 | 50.20 | sos |
| ATOM | 3057 | C   | GLN | 972 | 59.347 | 28.125 | 51.664 | 1.00 | 38.20 | sos |
| ATOM | 3058 | O   | GLN | 972 | 58.217 | 27.724 | 51.941 | 1.00 | 35.92 | sos |
| ATOM | 3059 | N   | GLN | 973 | 60.349 | 27.305 | 51.375 | 1.00 | 37.71 | sos |
| ATOM | 3060 | CA  | GLN | 973 | 60.139 | 25.870 | 51.362 | 1.00 | 41.37 | sos |
| ATOM | 3061 | CB  | GLN | 973 | 61.409 | 25.146 | 50.918 | 1.00 | 45.84 | sos |
| ATOM | 3062 | CG  | GLN | 973 | 61.192 | 23.694 | 50.490 | 1.00 | 61.48 | sos |
| ATOM | 3063 | CD  | GLN | 973 | 60.289 | 23.529 | 49.255 | 1.00 | 63.88 | sos |
| ATOM | 3064 | OE1 | GLN | 973 | 59.986 | 24.490 | 48.544 | 1.00 | 66.85 | sos |

TABLE 3-continued

PDB Coordinates for the Ras-Sos Structure:
DATA SET FOR REFINED COORDINATES

| ATOM | 3065 | NE2 | GLN | 973 | 59.876 | 22.293 | 48.995 | 1.00 | 66.02 | sos |
|---|---|---|---|---|---|---|---|---|---|---|
| ATOM | 3066 | C | GLN | 973 | 59.695 | 25.404 | 52.747 | 1.00 | 42.10 | sos |
| ATOM | 3067 | O | GLN | 973 | 58.720 | 24.666 | 52.873 | 1.00 | 45.36 | sos |
| ATOM | 3068 | N | TYR | 974 | 60.351 | 25.911 | 53.788 | 1.00 | 41.97 | sos |
| ATOM | 3069 | CA | TYR | 974 | 60.015 | 25.540 | 55.161 | 1.00 | 40.25 | sos |
| ATOM | 3070 | CB | TYR | 974 | 61.167 | 25.890 | 56.104 | 1.00 | 38.89 | sos |
| ATOM | 3071 | CG | TYR | 974 | 62.407 | 25.046 | 55.906 | 1.00 | 35.61 | sos |
| ATOM | 3072 | CD1 | TYR | 974 | 63.615 | 25.624 | 55.512 | 1.00 | 33.58 | sos |
| ATOM | 3073 | CE1 | TYR | 974 | 64.749 | 24.856 | 55.333 | 1.00 | 30.13 | sos |
| ATOM | 3074 | CD2 | TYR | 974 | 62.375 | 23.671 | 56.114 | 1.00 | 30.89 | sos |
| ATOM | 3075 | CE2 | TYR | 974 | 63.504 | 22.896 | 55.934 | 1.00 | 29.51 | sos |
| ATOM | 3076 | CZ | TYR | 974 | 64.687 | 23.493 | 55.545 | 1.00 | 29.98 | sos |
| ATOM | 3077 | OH | TYR | 974 | 65.810 | 22.721 | 55.374 | 1.00 | 34.05 | sos |
| ATOM | 3078 | C | TYR | 974 | 58.701 | 26.128 | 55.688 | 1.00 | 39.49 | sos |
| ATOM | 3079 | O | TYR | 974 | 58.292 | 25.833 | 56.807 | 1.00 | 37.13 | sos |
| ATOM | 3080 | N | GLN | 975 | 58.029 | 26.934 | 54.875 | 1.00 | 41.18 | sos |
| ATOM | 3081 | CA | GLN | 975 | 56.754 | 27.536 | 55.282 | 1.00 | 45.02 | sos |
| ATOM | 3082 | CB | GLN | 975 | 56.623 | 28.950 | 54.705 | 1.00 | 46.36 | sos |
| ATOM | 3083 | CG | GLN | 975 | 57.795 | 29.874 | 54.996 | 1.00 | 47.33 | sos |
| ATOM | 3084 | CD | GLN | 975 | 57.569 | 31.270 | 54.461 | 1.00 | 49.02 | sos |
| ATOM | 3085 | OE1 | GLN | 975 | 57.488 | 31.473 | 53.249 | 1.00 | 48.89 | sos |
| ATOM | 3086 | NE2 | GLN | 975 | 57.461 | 32.247 | 55.366 | 1.00 | 45.28 | sos |
| ATOM | 3087 | C | GLN | 975 | 55.537 | 26.710 | 54.841 | 1.00 | 47.02 | sos |
| ATOM | 3088 | O | GLN | 975 | 54.398 | 27.065 | 55.157 | 1.00 | 46.13 | sos |
| ATOM | 3089 | N | ASN | 976 | 55.783 | 25.621 | 54.107 | 1.00 | 47.93 | sos |
| ATOM | 3090 | CA | ASN | 976 | 54.716 | 24.756 | 53.595 | 1.00 | 47.08 | sos |
| ATOM | 3091 | CB | ASN | 976 | 55.253 | 23.829 | 52.491 | 1.00 | 47.37 | sos |
| ATOM | 3092 | CG | ASN | 976 | 55.751 | 24.586 | 51.261 | 1.00 | 51.31 | sos |
| ATOM | 3093 | OD1 | ASN | 976 | 55.205 | 25.629 | 50.885 | 1.00 | 53.34 | sos |
| ATOM | 3094 | ND2 | ASN | 976 | 56.789 | 24.051 | 50.620 | 1.00 | 46.84 | sos |
| ATOM | 3095 | C | ASN | 976 | 54.035 | 23.909 | 54.669 | 1.00 | 48.61 | sos |
| ATOM | 3096 | O | ASN | 976 | 52.905 | 24.193 | 55.073 | 1.00 | 46.58 | sos |
| ATOM | 3097 | N | GLN | 977 | 54.742 | 22.874 | 55.118 | 1.00 | 48.44 | sos |
| ATOM | 3098 | CA | GLN | 977 | 54.257 | 21.930 | 56.118 | 1.00 | 49.81 | sos |
| ATOM | 3099 | CB | GLN | 977 | 55.325 | 20.871 | 56.374 | 1.00 | 58.19 | sos |
| ATOM | 3100 | CG | GLN | 977 | 55.482 | 19.872 | 55.251 | 1.00 | 68.58 | sos |
| ATOM | 3101 | CD | GLN | 977 | 54.218 | 19.070 | 55.035 | 1.00 | 75.31 | sos |
| ATOM | 3102 | OE1 | GLN | 977 | 53.886 | 18.184 | 55.831 | 1.00 | 76.15 | sos |
| ATOM | 3103 | NE2 | GLN | 977 | 53.485 | 19.395 | 53.968 | 1.00 | 78.10 | sos |
| ATOM | 3104 | C | GLN | 977 | 53.580 | 22.500 | 57.453 | 1.00 | 49.85 | sos |
| ATOM | 3105 | O | GLN | 977 | 54.585 | 23.095 | 58.187 | 1.00 | 54.13 | sos |
| ATOM | 3106 | N | PRO | 978 | 52.519 | 22.307 | 57.792 | 1.00 | 47.20 | sos |
| ATOM | 3107 | CD | PRO | 978 | 51.488 | 21.788 | 56.877 | 1.00 | 49.75 | sos |
| ATOM | 3108 | CA | PRO | 978 | 51.910 | 22.777 | 59.038 | 1.00 | 46.73 | sos |
| ATOM | 3109 | CB | PRO | 978 | 50.444 | 22.901 | 58.652 | 1.00 | 49.20 | sos |
| ATOM | 3110 | CG | PRO | 978 | 50.260 | 21.722 | 57.761 | 1.00 | 49.03 | sos |
| ATOM | 3111 | C | PRO | 978 | 52.100 | 21.754 | 60.159 | 1.00 | 46.41 | sos |
| ATOM | 3112 | O | PRO | 978 | 52.395 | 20.587 | 59.894 | 1.00 | 46.64 | sos |
| ATOM | 3113 | N | TYR | 979 | 51.912 | 22.190 | 61.404 | 1.00 | 46.60 | sos |
| ATOM | 3114 | CA | TYR | 979 | 52.072 | 21.315 | 62.573 | 1.00 | 43.72 | sos |
| ATOM | 3115 | CB | TYR | 979 | 52.526 | 22.117 | 63.812 | 1.00 | 39.08 | sos |
| ATOM | 3116 | CG | TYR | 979 | 54.024 | 22.262 | 63.929 | 1.00 | 32.43 | sos |
| ATOM | 3117 | CD1 | TYR | 979 | 54.677 | 23.381 | 63.417 | 1.00 | 33.41 | sos |
| ATOM | 3118 | CE1 | TYR | 979 | 56.065 | 23.485 | 63.455 | 1.00 | 35.28 | sos |
| ATOM | 3119 | CD2 | TYR | 979 | 54.796 | 21.250 | 64.494 | 1.00 | 29.89 | sos |
| ATOM | 3120 | CE2 | TYR | 979 | 56.180 | 21.343 | 64.542 | 1.00 | 33.56 | sos |
| ATOM | 3121 | CZ | TYR | 979 | 56.812 | 22.463 | 64.016 | 1.00 | 37.27 | sos |
| ATOM | 3122 | OH | TYR | 979 | 58.187 | 22.551 | 64.029 | 1.00 | 38.77 | sos |
| ATOM | 3123 | C | TYR | 979 | 50.827 | 20.521 | 62.931 | 1.00 | 43.14 | sos |
| ATOM | 3124 | O | TYR | 979 | 49.720 | 21.063 | 62.990 | 1.00 | 40.65 | sos |
| ATOM | 3125 | N | CYS | 980 | 51.014 | 19.230 | 63.176 | 1.00 | 44.31 | sos |
| ATOM | 3126 | CA | CYS | 980 | 49.895 | 18.387 | 63.562 | 1.00 | 48.01 | sos |
| ATOM | 3127 | CB | CYS | 980 | 50.149 | 16.922 | 63.193 | 1.00 | 51.99 | sos |
| ATOM | 3128 | SG | CYS | 980 | 48.742 | 15.819 | 63.546 | 1.00 | 62.82 | sos |
| ATOM | 3129 | C | CYS | 980 | 49.760 | 18.541 | 65.069 | 1.00 | 45.64 | sos |
| ATOM | 3130 | O | CYS | 980 | 50.172 | 17.664 | 65.841 | 1.00 | 44.69 | sos |
| ATOM | 3131 | N | LEU | 981 | 49.228 | 19.689 | 65.478 | 1.00 | 38.97 | sos |
| ATOM | 3132 | CA | LEU | 981 | 49.051 | 19.991 | 66.888 | 1.00 | 38.05 | sos |
| ATOM | 3133 | CB | LEU | 981 | 50.233 | 20.799 | 67.432 | 1.00 | 38.97 | sos |
| ATOM | 3134 | CG | LEU | 981 | 51.629 | 20.186 | 67.559 | 1.00 | 36.41 | sos |
| ATOM | 3135 | CD1 | LEU | 981 | 52.608 | 21.267 | 67.947 | 1.00 | 39.22 | sos |
| ATOM | 3136 | CD2 | LEU | 981 | 51.628 | 19.081 | 68.598 | 1.00 | 38.45 | sos |
| ATOM | 3137 | C | LEU | 981 | 47.791 | 20.790 | 67.098 | 1.00 | 41.09 | sos |
| ATOM | 3138 | O | LEU | 981 | 47.483 | 21.713 | 66.346 | 1.00 | 41.56 | sos |
| ATOM | 3139 | N | ARG | 982 | 47.096 | 20.458 | 68.173 | 1.00 | 45.70 | sos |
| ATOM | 3140 | CA | ARG | 982 | 45.860 | 21.120 | 68.532 | 1.00 | 48.55 | sos |

TABLE 3-continued

PDB Coordinates for the Ras-Sos Structure:
DATA SET FOR REFINED COORDINATES

| | | | | | | | | |
|---|---|---|---|---|---|---|---|---|
| ATOM | 3141 CB | ARG | 982 | 45.098 | 20.216 | 69.506 | 1.00 | 52.66 sos |
| ATOM | 3142 CG | ARG | 982 | 43.587 | 20.313 | 69.436 | 1.00 | 64.07 sos |
| ATOM | 3143 CD | ARG | 982 | 42.940 | 19.199 | 70.270 | 1.00 | 72.76 sos |
| ATOM | 3144 NE | ARG | 982 | 43.325 | 17.866 | 69.801 | 1.00 | 74.14 sos |
| ATOM | 3145 CZ | ARG | 982 | 42.485 | 16.981 | 69.265 | 1.00 | 73.64 sos |
| ATOM | 3146 NH1 | ARG | 982 | 41.198 | 17.270 | 69.127 | 1.00 | 71.98 sos |
| ATOM | 3147 NH2 | ARG | 982 | 42.938 | 15.814 | 68.830 | 1.00 | 73.04 sos |
| ATOM | 3148 C | ARG | 982 | 46.182 | 22.479 | 69.171 | 1.00 | 49.82 sos |
| ATOM | 3149 O | ARG | 982 | 47.064 | 22.580 | 70.030 | 1.00 | 53.00 sos |
| ATOM | 3150 N | VAL | 983 | 45.508 | 23.523 | 68.697 | 1.00 | 47.50 sos |
| ATOM | 3151 CA | VAL | 983 | 45.679 | 24.881 | 69.214 | 1.00 | 47.09 sos |
| ATOM | 3152 CB | VAL | 983 | 45.166 | 25.949 | 68.179 | 1.00 | 45.18 sos |
| ATOM | 3153 CG1 | VAL | 983 | 44.784 | 27.254 | 68.871 | 1.00 | 40.07 sos |
| ATOM | 3154 CG2 | VAL | 983 | 46.227 | 26.232 | 67.133 | 1.00 | 43.69 sos |
| ATOM | 3155 C | VAL | 983 | 44.864 | 25.043 | 70.493 | 1.00 | 48.14 sos |
| ATOM | 3156 O | VAL | 983 | 43.739 | 24.562 | 70.575 | 1.00 | 51.66 sos |
| ATOM | 3157 N | GLU | 984 | 45.448 | 25.671 | 71.507 | 1.00 | 49.35 sos |
| ATOM | 3158 CA | GLU | 984 | 44.718 | 25.931 | 72.743 | 1.00 | 47.44 sos |
| ATOM | 3159 CB | GLU | 984 | 45.410 | 25.335 | 73.966 | 1.00 | 46.26 sos |
| ATOM | 3160 CG | GLU | 984 | 44.441 | 24.975 | 75.104 | 1.00 | 46.87 sos |
| ATOM | 3161 CD | GLU | 984 | 43.540 | 26.129 | 75.529 | 1.00 | 47.11 sos |
| ATOM | 3162 OE1 | GLU | 984 | 42.327 | 25.913 | 75.711 | 1.00 | 50.46 sos |
| ATOM | 3163 OE2 | GLU | 984 | 44.034 | 27.257 | 75.683 | 1.00 | 49.81 sos |
| ATOM | 3164 C | GLU | 984 | 44.722 | 27.439 | 72.817 | 1.00 | 47.78 sos |
| ATOM | 3165 O | GLU | 984 | 45.720 | 28.044 | 73.183 | 1.00 | 46.26 sos |
| ATOM | 3166 N | SER | 985 | 43.593 | 28.026 | 72.438 | 1.00 | 52.10 sos |
| ATOM | 3167 CA | SER | 985 | 43.388 | 29.473 | 72.381 | 1.00 | 52.76 sos |
| ATOM | 3168 CB | SER | 985 | 41.935 | 29.773 | 71.996 | 1.00 | 54.18 sos |
| ATOM | 3169 OG | SER | 985 | 41.592 | 29.130 | 70.779 | 1.00 | 55.84 sos |
| ATOM | 3170 C | SER | 985 | 43.775 | 30.298 | 73.605 | 1.00 | 52.46 sos |
| ATOM | 3171 O | SER | 985 | 44.320 | 31.389 | 73.457 | 1.00 | 49.88 sos |
| ATOM | 3172 N | ASP | 986 | 43.472 | 29.803 | 74.802 | 1.00 | 52.58 sos |
| ATOM | 3173 CA | ASP | 986 | 43.802 | 30.536 | 76.022 | 1.00 | 54.44 sos |
| ATOM | 3174 CB | ASP | 986 | 43.009 | 29.995 | 77.213 | 1.00 | 58.68 sos |
| ATOM | 3175 CG | ASP | 986 | 41.509 | 30.195 | 77.054 | 1.00 | 64.04 sos |
| ATOM | 3176 OD1 | ASP | 986 | 41.090 | 31.291 | 76.613 | 1.00 | 66.26 sos |
| ATOM | 3177 OD2 | ASP | 986 | 40.750 | 29.251 | 77.367 | 1.00 | 67.74 sos |
| ATOM | 3178 C | ASP | 986 | 45.300 | 30.552 | 76.325 | 1.00 | 52.70 sos |
| ATOM | 3179 O | ASP | 986 | 45.852 | 31.598 | 76.656 | 1.00 | 53.82 sos |
| ATOM | 3180 N | ILE | 987 | 45.953 | 29.402 | 76.192 | 1.00 | 48.36 sos |
| ATOM | 3181 CA | ILE | 987 | 47.389 | 29.299 | 76.436 | 1.00 | 46.63 sos |
| ATOM | 3182 CB | ILE | 987 | 47.860 | 27.831 | 76.348 | 1.00 | 43.56 sos |
| ATOM | 3183 CG2 | ILE | 987 | 49.362 | 27.745 | 76.511 | 1.00 | 40.09 sos |
| ATOM | 3184 CG1 | ILE | 987 | 47.173 | 26.998 | 77.430 | 1.00 | 45.63 sos |
| ATOM | 3185 CD1 | ILE | 987 | 47.598 | 25.539 | 77.430 | 1.00 | 42.99 sos |
| ATOM | 3186 C | ILE | 987 | 48.145 | 30.136 | 75.403 | 1.00 | 46.74 sos |
| ATOM | 3187 O | ILE | 987 | 49.179 | 30.738 | 75.697 | 1.00 | 49.52 sos |
| ATOM | 3188 N | LYS | 988 | 47.597 | 30.175 | 74.196 | 1.00 | 45.85 sos |
| ATOM | 3189 CA | LYS | 988 | 48.169 | 30.911 | 73.083 | 1.00 | 44.60 sos |
| ATOM | 3190 CB | LYS | 988 | 47.382 | 30.590 | 71.813 | 1.00 | 45.12 sos |
| ATOM | 3191 CG | LYS | 988 | 47.732 | 31.425 | 70.605 | 1.00 | 50.79 sos |
| ATOM | 3192 CD | LYS | 988 | 46.543 | 31.537 | 69.662 | 1.00 | 52.63 sos |
| ATOM | 3193 CE | LYS | 988 | 46.882 | 32.357 | 68.429 | 1.00 | 53.56 sos |
| ATOM | 3194 NZ | LYS | 988 | 47.955 | 31.692 | 67.621 | 1.00 | 58.23 sos |
| ATOM | 3195 C | LYS | 988 | 48.099 | 32.400 | 73.374 | 1.00 | 46.07 sos |
| ATOM | 3196 O | LYS | 988 | 49.027 | 33.138 | 73.071 | 1.00 | 49.55 sos |
| ATOM | 3197 N | ARG | 989 | 47.004 | 32.834 | 73.988 | 1.00 | 48.10 sos |
| ATOM | 3198 CA | ARG | 989 | 46.814 | 34.243 | 74.310 | 1.00 | 51.24 sos |
| ATOM | 3199 CB | ARG | 989 | 45.353 | 34.503 | 74.677 | 1.00 | 54.21 sos |
| ATOM | 3200 CG | ARG | 989 | 44.858 | 35.887 | 74.295 | 1.00 | 66.12 sos |
| ATOM | 3201 CD | ARG | 989 | 43.327 | 35.948 | 74.278 | 1.00 | 75.02 sos |
| ATOM | 3202 NE | ARG | 989 | 42.741 | 35.092 | 73.241 | 1.00 | 78.43 sos |
| ATOM | 3203 CZ | ARG | 989 | 41.957 | 34.041 | 73.481 | 1.00 | 79.66 sos |
| ATOM | 3204 NH1 | ARG | 989 | 41.652 | 33.703 | 74.732 | 1.00 | 80.46 sos |
| ATOM | 3205 NH2 | ARG | 989 | 41.487 | 33.320 | 72.468 | 1.00 | 76.98 sos |
| ATOM | 3206 C | ARG | 989 | 47.754 | 34.673 | 75.438 | 1.00 | 50.85 sos |
| ATOM | 3207 O | ARG | 989 | 48.240 | 35.808 | 45.461 | 1.00 | 49.06 sos |
| ATOM | 3208 N | PHE | 990 | 48.037 | 33.738 | 76.341 | 1.00 | 48.35 sos |
| ATOM | 3209 CA | PHE | 990 | 48.929 | 33.977 | 77.463 | 1.00 | 48.32 sos |
| ATOM | 3210 CB | PHE | 990 | 48.998 | 32.729 | 78.350 | 1.00 | 48.04 sos |
| ATOM | 3211 CG | PHE | 990 | 49.986 | 32.836 | 79.480 | 1.00 | 47.78 sos |
| ATOM | 3212 CD1 | PHE | 990 | 49.638 | 33.475 | 80.669 | 1.00 | 43.04 sos |
| ATOM | 3213 CD2 | PHE | 990 | 51.275 | 32.313 | 79.347 | 1.00 | 44.81 sos |
| ATOM | 3214 CE1 | PHE | 990 | 50.558 | 33.597 | 81.709 | 1.00 | 40.31 sos |
| ATOM | 3215 CE2 | PHE | 990 | 52.200 | 32.430 | 80.380 | 1.00 | 45.07 sos |
| ATOM | 3216 CZ | PHE | 990 | 51.842 | 33.074 | 81.564 | 1.00 | 41.57 sos |

TABLE 3-continued

PDB Coordinates for the Ras-Sos Structure:
DATA SET FOR REFINED COORDINATES

| ATOM | 3217 | C | PHE | 990 | 50.333 | 34.346 | 76.970 | 1.00 | 50.12 | sos |
|---|---|---|---|---|---|---|---|---|---|---|
| ATOM | 3218 | O | PHE | 990 | 50.897 | 35.357 | 77.399 | 1.00 | 48.99 | sos |
| ATOM | 3219 | N | PHE | 991 | 50.887 | 33.525 | 76.077 | 1.00 | 47.76 | sos |
| ATOM | 3220 | CA | PHE | 991 | 52.225 | 33.763 | 75.538 | 1.00 | 47.68 | sos |
| ATOM | 3221 | CB | PHE | 991 | 52.809 | 32.478 | 74.923 | 1.00 | 44.16 | sos |
| ATOM | 3222 | CG | PHE | 991 | 53.087 | 31.395 | 75.933 | 1.00 | 43.00 | sos |
| ATOM | 3223 | CD1 | PHE | 991 | 52.292 | 30.259 | 75.996 | 1.00 | 43.47 | sos |
| ATOM | 3224 | CD2 | PHE | 991 | 54.117 | 31.530 | 76.853 | 1.00 | 47.07 | sos |
| ATOM | 3225 | CE1 | PHE | 991 | 52.515 | 29.281 | 76.961 | 1.00 | 39.73 | sos |
| ATOM | 3226 | CE2 | PHE | 991 | 54.347 | 30.551 | 77.827 | 1.00 | 43.11 | sos |
| ATOM | 3227 | CZ | PHE | 991 | 53.543 | 29.429 | 77.877 | 1.00 | 42.13 | sos |
| ATOM | 3228 | C | PHE | 991 | 52.249 | 34.904 | 74.530 | 1.00 | 47.41 | sos |
| ATOM | 3229 | O | PHE | 991 | 53.294 | 35.491 | 74.255 | 1.00 | 48.36 | sos |
| ATOM | 3230 | N | GLU | 992 | 51.085 | 35.240 | 73.996 | 1.00 | 49.69 | sos |
| ATOM | 3231 | CA | GLU | 992 | 50.994 | 36.317 | 73.024 | 1.00 | 48.81 | sos |
| ATOM | 3232 | CB | GLU | 992 | 49.723 | 36.149 | 72.204 | 1.00 | 49.98 | sos |
| ATOM | 3233 | CG | GLU | 992 | 49.839 | 36.573 | 70.762 | 1.00 | 53.94 | sos |
| ATOM | 3234 | CD | GLU | 992 | 48.729 | 35.992 | 69.900 | 1.00 | 57.65 | sos |
| ATOM | 3235 | OE1 | GLU | 992 | 47.569 | 35.913 | 70.374 | 1.00 | 52.43 | sos |
| ATOM | 3236 | OE2 | GLU | 992 | 49.026 | 35.610 | 68.746 | 1.00 | 58.11 | sos |
| ATOM | 3237 | C | GLU | 992 | 50.990 | 37.652 | 73.762 | 1.00 | 47.04 | sos |
| ATOM | 3238 | O | GLU | 992 | 51.459 | 38.660 | 73.243 | 1.00 | 44.61 | sos |
| ATOM | 3239 | N | ASN | 993 | 50.511 | 37.627 | 75.001 | 1.00 | 47.60 | sos |
| ATOM | 3240 | CA | ASN | 993 | 50.435 | 38.822 | 75.834 | 1.00 | 47.52 | sos |
| ATOM | 3241 | CB | ASN | 993 | 49.069 | 38.892 | 76.529 | 1.00 | 52.05 | sos |
| ATOM | 3242 | CG | ASN | 993 | 47.923 | 39.069 | 75.548 | 1.00 | 58.72 | sos |
| ATOM | 3243 | OD1 | ASN | 993 | 48.081 | 39.689 | 74.492 | 1.00 | 61.15 | sos |
| ATOM | 3244 | ND2 | ASN | 993 | 46.761 | 38.523 | 75.892 | 1.00 | 61.29 | sos |
| ATOM | 3245 | C | ASN | 993 | 51.555 | 38.985 | 76.869 | 1.00 | 44.69 | sos |
| ATOM | 3246 | O | ASN | 993 | 51.486 | 39.882 | 77.715 | 1.00 | 47.57 | sos |
| ATOM | 3247 | N | LEU | 994 | 52.568 | 38.121 | 76.825 | 1.00 | 37.93 | sos |
| ATOM | 3248 | CA | LEU | 994 | 53.680 | 38.230 | 77.763 | 1.00 | 34.34 | sos |
| ATOM | 3249 | CB | LEU | 994 | 54.686 | 37.082 | 77.590 | 1.00 | 29.91 | sos |
| ATOM | 3250 | CG | LEU | 994 | 54.336 | 35.703 | 78.106 | 1.00 | 35.00 | sos |
| ATOM | 3251 | CD1 | LEU | 994 | 55.437 | 34.722 | 77.736 | 1.00 | 30.48 | sos |
| ATOM | 3252 | CD2 | LEU | 994 | 54.109 | 35.744 | 79.616 | 1.00 | 31.54 | sos |
| ATOM | 3253 | C | LEU | 994 | 54.406 | 39.536 | 77.498 | 1.00 | 38.22 | sos |
| ATOM | 3254 | O | LEU | 994 | 54.631 | 39.919 | 76.345 | 1.00 | 36.54 | sos |
| ATOM | 3255 | N | ASN | 995 | 54.795 | 40.206 | 78.571 | 1.00 | 37.83 | sos |
| ATOM | 3256 | CA | ASN | 995 | 55.517 | 41.456 | 78.453 | 1.00 | 39.15 | sos |
| ATOM | 3257 | CB | ASN | 995 | 54.516 | 42.618 | 78.390 | 1.00 | 36.26 | sos |
| ATOM | 3258 | CG | ASN | 995 | 55.176 | 43.951 | 78.115 | 1.00 | 33.99 | sos |
| ATOM | 3259 | OD1 | ASN | 995 | 54.761 | 44.969 | 78.650 | 1.00 | 26.42 | sos |
| ATOM | 3260 | ND2 | ASN | 995 | 56.208 | 43.951 | 77.277 | 1.00 | 35.99 | sos |
| ATOM | 3261 | C | ASN | 995 | 56.457 | 41.566 | 79.660 | 1.00 | 39.02 | sos |
| ATOM | 3262 | O | ASN | 995 | 56.230 | 42.355 | 80.575 | 1.00 | 41.44 | sos |
| ATOM | 3263 | N | PRO | 996 | 57.539 | 40.768 | 79.663 | 1.00 | 37.44 | sos |
| ATOM | 3264 | CD | PRO | 996 | 57.964 | 39.935 | 78.527 | 1.00 | 34.57 | sos |
| ATOM | 3265 | CA | PRO | 996 | 58.543 | 40.733 | 80.735 | 1.00 | 34.46 | sos |
| ATOM | 3266 | CB | PRO | 996 | 59.658 | 39.884 | 80.128 | 1.00 | 33.50 | sos |
| ATOM | 3267 | CG | PRO | 996 | 58.959 | 39.023 | 79.168 | 1.00 | 37.66 | sos |
| ATOM | 3268 | C | PRO | 996 | 59.084 | 42.116 | 81.093 | 1.00 | 33.65 | sos |
| ATOM | 3269 | O | PRO | 996 | 59.207 | 42.462 | 82.265 | 1.00 | 34.12 | sos |
| ATOM | 3270 | N | MET | 997 | 59.399 | 42.895 | 80.064 | 1.00 | 31.74 | sos |
| ATOM | 3271 | CA | MET | 997 | 59.956 | 44.226 | 80.229 | 1.00 | 32.32 | sos |
| ATOM | 3272 | CB | MET | 997 | 60.517 | 44.729 | 78.900 | 1.00 | 32.89 | sos |
| ATOM | 3273 | CG | MET | 997 | 61.843 | 44.122 | 78.505 | 1.00 | 32.53 | sos |
| ATOM | 3274 | SD | MET | 997 | 62.439 | 44.734 | 76.919 | 1.00 | 43.51 | sos |
| ATOM | 3275 | CE | MET | 997 | 62.296 | 46.483 | 77.159 | 1.00 | 38.54 | sos |
| ATOM | 3276 | C | MET | 997 | 59.038 | 45.282 | 80.827 | 1.00 | 32.88 | sos |
| ATOM | 3277 | O | MET | 997 | 59.524 | 46.278 | 81.368 | 1.00 | 36.52 | sos |
| ATOM | 3278 | N | GLY | 998 | 57.727 | 45.072 | 80.746 | 1.00 | 31.92 | sos |
| ATOM | 3279 | CA | GLY | 998 | 56.792 | 46.051 | 81.282 | 1.00 | 31.78 | sos |
| ATOM | 3280 | C | GLY | 998 | 56.956 | 47.388 | 80.577 | 1.00 | 34.52 | sos |
| ATOM | 3281 | O | GLY | 998 | 56.942 | 47.441 | 79.349 | 1.00 | 35.74 | sos |
| ATOM | 3282 | N | ASN | 999 | 57.162 | 48.457 | 81.343 | 1.00 | 35.75 | sos |
| ATOM | 3283 | CA | ASN | 999 | 57.340 | 49.796 | 80.769 | 1.00 | 37.25 | sos |
| ATOM | 3284 | CB | ASN | 999 | 56.545 | 50.833 | 81.568 | 1.00 | 41.53 | sos |
| ATOM | 3285 | CG | ASN | 999 | 55.071 | 50.486 | 81.676 | 1.00 | 50.95 | sos |
| ATOM | 3286 | OD1 | ASN | 999 | 54.516 | 49.792 | 80.821 | 1.00 | 56.83 | sos |
| ATOM | 3287 | ND2 | ASN | 999 | 54.429 | 50.963 | 82.737 | 1.00 | 55.72 | sos |
| ATOM | 3288 | C | ASN | 999 | 58.806 | 50.218 | 80.732 | 1.00 | 36.50 | sos |
| ATOM | 3289 | O | ASN | 999 | 59.130 | 51.320 | 80.291 | 1.00 | 38.95 | sos |
| ATOM | 3290 | N | SER | 1000 | 59.686 | 49.337 | 81.197 | 1.00 | 34.64 | sos |
| ATOM | 3291 | CA | SER | 1000 | 61.116 | 49.611 | 81.249 | 1.00 | 34.64 | sos |
| ATOM | 3292 | CB | SER | 1000 | 61.804 | 48.615 | 82.183 | 1.00 | 33.53 | sos |

TABLE 3-continued

PDB Coordinates for the Ras-Sos Structure:
DATA SET FOR REFINED COORDINATES

| ATOM | 3293 | OG  | SER | 1000 | 61.080 | 48.449 | 83.392 | 1.00 | 39.73 | sos |
|------|------|-----|-----|------|--------|--------|--------|------|-------|-----|
| ATOM | 3294 | C   | SER | 1000 | 61.783 | 49.545 | 79.883 | 1.00 | 35.38 | sos |
| ATOM | 3295 | O   | SER | 1000 | 61.326 | 48.834 | 78.993 | 1.00 | 37.97 | sos |
| ATOM | 3296 | N   | MET | 1001 | 62.862 | 50.301 | 79.720 | 1.00 | 35.25 | sos |
| ATOM | 3297 | CA  | MET | 1001 | 63.616 | 50.292 | 78.470 | 1.00 | 35.26 | sos |
| ATOM | 3298 | CB  | MET | 1001 | 64.420 | 51.588 | 78.326 | 1.00 | 35.94 | sos |
| ATOM | 3299 | CG  | MET | 1001 | 63.588 | 52.858 | 78.368 | 1.00 | 33.04 | sos |
| ATOM | 3300 | SD  | MET | 1001 | 62.425 | 52.961 | 77.002 | 1.00 | 44.08 | sos |
| ATOM | 3301 | CE  | MET | 1001 | 60.895 | 52.453 | 77.800 | 1.00 | 36.00 | sos |
| ATOM | 3302 | C   | MET | 1001 | 64.564 | 49.093 | 78.535 | 1.00 | 35.27 | sos |
| ATOM | 3303 | O   | MET | 1001 | 64.789 | 48.533 | 79.608 | 1.00 | 33.64 | sos |
| ATOM | 3304 | N   | GLU | 1002 | 65.134 | 48.715 | 77.400 | 1.00 | 37.32 | sos |
| ATOM | 3305 | CA  | GLU | 1002 | 66.040 | 47.575 | 77.343 | 1.00 | 42.68 | sos |
| ATOM | 3306 | CB  | GLU | 1002 | 66.775 | 47.551 | 76.002 | 1.00 | 46.50 | sos |
| ATOM | 3307 | CG  | GLU | 1002 | 67.347 | 46.196 | 75.642 | 1.00 | 54.76 | sos |
| ATOM | 3308 | CD  | GLU | 1002 | 68.302 | 46.246 | 74.461 | 1.00 | 59.17 | sos |
| ATOM | 3309 | OE1 | GLU | 1002 | 69.471 | 45.839 | 74.639 | 1.00 | 60.77 | sos |
| ATOM | 3310 | OE2 | GLU | 1002 | 67.890 | 46.676 | 73.359 | 1.00 | 59.82 | sos |
| ATOM | 3311 | C   | GLU | 1002 | 67.054 | 47.558 | 78.498 | 1.00 | 45.25 | sos |
| ATOM | 3312 | O   | GLU | 1002 | 66.961 | 46.719 | 79.389 | 1.00 | 47.62 | sos |
| ATOM | 3313 | N   | LYS | 1003 | 67.964 | 48.530 | 78.515 | 1.00 | 45.39 | sos |
| ATOM | 3314 | CA  | LYS | 1003 | 69.007 | 48.626 | 79.542 | 1.00 | 42.67 | sos |
| ATOM | 3315 | CB  | LYS | 1003 | 69.882 | 49.858 | 79.295 | 1.00 | 43.73 | sos |
| ATOM | 3316 | CG  | LYS | 1003 | 70.894 | 50.117 | 80.384 | 1.00 | 46.14 | sos |
| ATOM | 3317 | CD  | LYS | 1003 | 71.761 | 51.308 | 80.074 | 1.00 | 53.73 | sos |
| ATOM | 3318 | CE  | LYS | 1003 | 72.645 | 51.635 | 81.267 | 1.00 | 62.39 | sos |
| ATOM | 3319 | NZ  | LYS | 1003 | 73.434 | 50.451 | 81.735 | 1.00 | 67.57 | sos |
| ATOM | 3320 | C   | LYS | 1003 | 68.529 | 48.628 | 80.992 | 1.00 | 39.95 | sos |
| ATOM | 3321 | O   | LYS | 1003 | 69.129 | 47.996 | 81.853 | 1.00 | 36.15 | sos |
| ATOM | 3322 | N   | GLU | 1004 | 67.480 | 49.376 | 81.275 | 1.00 | 38.13 | sos |
| ATOM | 3323 | CA  | GLU | 1004 | 66.966 | 49.428 | 82.627 | 1.00 | 42.28 | sos |
| ATOM | 3324 | CB  | GLU | 1004 | 65.766 | 50.376 | 82.668 | 1.00 | 49.59 | sos |
| ATOM | 3325 | CG  | GLU | 1004 | 65.242 | 50.729 | 84.055 | 1.00 | 55.28 | sos |
| ATOM | 3326 | CD  | GLU | 1004 | 63.916 | 51.488 | 84.003 | 1.00 | 62.38 | sos |
| ATOM | 3327 | OE1 | GLU | 1004 | 63.158 | 51.420 | 84.998 | 1.00 | 59.62 | sos |
| ATOM | 3328 | OE2 | GLU | 1004 | 63.627 | 52.138 | 82.965 | 1.00 | 63.05 | sos |
| ATOM | 3329 | C   | GLU | 1004 | 66.570 | 48.008 | 83.071 | 1.00 | 42.74 | sos |
| ATOM | 3330 | O   | GLU | 1004 | 66.919 | 47.571 | 84.170 | 1.00 | 43.63 | sos |
| ATOM | 3331 | N   | PHE | 1005 | 65.897 | 47.280 | 82.180 | 1.00 | 41.13 | sos |
| ATOM | 3332 | CA  | PHE | 1005 | 65.436 | 45.922 | 82.451 | 1.00 | 36.34 | sos |
| ATOM | 3333 | CB  | PHE | 1005 | 64.427 | 45.475 | 81.385 | 1.00 | 34.27 | sos |
| ATOM | 3334 | CG  | PHE | 1005 | 63.772 | 44.148 | 81.681 | 1.00 | 27.01 | sos |
| ATOM | 3335 | CD1 | PHE | 1005 | 62.817 | 44.039 | 82.682 | 1.00 | 21.79 | sos |
| ATOM | 3336 | CD2 | PHE | 1005 | 64.130 | 43.009 | 80.974 | 1.00 | 20.76 | sos |
| ATOM | 3337 | CE1 | PHE | 1005 | 62.229 | 42.812 | 82.976 | 1.00 | 25.20 | sos |
| ATOM | 3338 | CE2 | PHE | 1005 | 63.552 | 41.784 | 81.262 | 1.00 | 23.76 | sos |
| ATOM | 3339 | CZ  | PHE | 1005 | 62.596 | 41.683 | 82.270 | 1.00 | 20.49 | sos |
| ATOM | 3340 | C   | PHE | 1005 | 66.588 | 44.934 | 82.521 | 1.00 | 36.00 | sos |
| ATOM | 3341 | O   | PHE | 1005 | 66.647 | 44.112 | 83.428 | 1.00 | 37.43 | sos |
| ATOM | 3342 | N   | THR | 1006 | 67.489 | 44.998 | 81.549 | 1.00 | 35.34 | sos |
| ATOM | 3343 | CA  | THR | 1006 | 68.644 | 44.111 | 81.518 | 1.00 | 36.27 | sos |
| ATOM | 3344 | CB  | THR | 1006 | 69.584 | 44.449 | 80.353 | 1.00 | 37.06 | sos |
| ATOM | 3345 | OG1 | THR | 1006 | 68.911 | 44.234 | 49.112 | 1.00 | 44.33 | sos |
| ATOM | 3346 | CG2 | THR | 1006 | 70.809 | 43.572 | 80.396 | 1.00 | 48.53 | sos |
| ATOM | 3347 | C   | THR | 1006 | 69.429 | 44.253 | 82.817 | 1.00 | 37.50 | sos |
| ATOM | 3348 | O   | THR | 1006 | 69.830 | 43.254 | 83.410 | 1.00 | 44.79 | sos |
| ATOM | 3349 | N   | ASP | 1007 | 69.644 | 45.495 | 83.251 | 1.00 | 35.64 | sos |
| ATOM | 3350 | CA  | ASP | 1007 | 70.383 | 45.775 | 84.481 | 1.00 | 33.01 | sos |
| ATOM | 3351 | CB  | ASP | 1007 | 70.645 | 47.291 | 84.651 | 1.00 | 31.17 | sos |
| ATOM | 3352 | CG  | ASP | 1007 | 71.692 | 47.851 | 83.650 | 1.00 | 36.72 | sos |
| ATOM | 3353 | OD1 | ASP | 1007 | 72.264 | 47.085 | 82.843 | 1.00 | 40.67 | sos |
| ATOM | 3354 | OD2 | ASP | 1007 | 71.944 | 49.076 | 83.661 | 1.00 | 33.23 | sos |
| ATOM | 3355 | C   | ASP | 1007 | 69.641 | 45.208 | 85.694 | 1.00 | 33.20 | sos |
| ATOM | 3356 | O   | ASP | 1007 | 70.261 | 44.708 | 86.632 | 1.00 | 36.05 | sos |
| ATOM | 3357 | N   | TYR | 1008 | 68.314 | 45.250 | 85.662 | 1.00 | 31.64 | sos |
| ATOM | 3358 | CA  | TYR | 1008 | 67.514 | 44.720 | 86.763 | 1.00 | 32.10 | sos |
| ATOM | 3359 | CB  | TYR | 1008 | 66.032 | 45.030 | 86.549 | 1.00 | 27.18 | sos |
| ATOM | 3360 | CG  | TYR | 1008 | 65.093 | 44.196 | 87.394 | 1.00 | 28.35 | sos |
| ATOM | 3361 | CD1 | TYR | 1008 | 64.834 | 44.528 | 88.717 | 1.00 | 28.53 | sos |
| ATOM | 3362 | CE1 | TYR | 1008 | 63.953 | 43.779 | 89.489 | 1.00 | 28.46 | sos |
| ATOM | 3363 | CD2 | TYR | 1008 | 64.447 | 43.083 | 86.860 | 1.00 | 31.02 | sos |
| ATOM | 3364 | CE2 | TYR | 1008 | 63.568 | 42.327 | 87.624 | 1.00 | 31.72 | sos |
| ATOM | 3365 | CZ  | TYR | 1008 | 63.327 | 42.680 | 88.938 | 1.00 | 31.37 | sos |
| ATOM | 3366 | OH  | TYR | 1008 | 62.474 | 41.923 | 89.708 | 1.00 | 32.06 | sos |
| ATOM | 3367 | C   | TYR | 1008 | 67.704 | 43.213 | 86.910 | 1.00 | 33.90 | sos |
| ATOM | 3368 | O   | TYR | 1008 | 67.791 | 42.695 | 88.024 | 1.00 | 32.37 | sos |

TABLE 3-continued

PDB Coordinates for the Ras-Sos Structure:
DATA SET FOR REFINED COORDINATES

| ATOM | 3369 | N | LEU | 1009 | 67.720 | 42.512 | 85.779 | 1.00 | 34.09 | sos |
|---|---|---|---|---|---|---|---|---|---|---|
| ATOM | 3370 | CA | LEU | 1009 | 67.897 | 41.070 | 85.783 | 1.00 | 33.93 | sos |
| ATOM | 3371 | CB | LEU | 1009 | 67.797 | 40.494 | 84.369 | 1.00 | 32.28 | sos |
| ATOM | 3372 | CG | LEU | 1009 | 66.422 | 40.597 | 83.704 | 1.00 | 30.54 | sos |
| ATOM | 3373 | CD1 | LEU | 1009 | 66.497 | 39.956 | 82.322 | 1.00 | 25.84 | sos |
| ATOM | 3374 | CD2 | LEU | 1009 | 65.381 | 39.866 | 84.562 | 1.00 | 23.50 | sos |
| ATOM | 3375 | C | LEU | 1009 | 69.244 | 40.738 | 86.382 | 1.00 | 35.33 | sos |
| ATOM | 3376 | O | LEU | 1009 | 69.326 | 39.926 | 87.306 | 1.00 | 37.13 | sos |
| ATOM | 3377 | N | PHE | 1010 | 70.288 | 41.416 | 85.904 | 1.00 | 32.23 | sos |
| ATOM | 3378 | CA | PHE | 1010 | 71.634 | 41.173 | 86.409 | 1.00 | 32.78 | sos |
| ATOM | 3379 | CB | PHE | 1010 | 72.684 | 41.887 | 85.569 | 1.00 | 26.02 | sos |
| ATOM | 3380 | CG | PHE | 1010 | 74.065 | 41.348 | 85.771 | 1.00 | 27.29 | sos |
| ATOM | 3381 | CD1 | PHE | 1010 | 74.471 | 40.193 | 85.116 | 1.00 | 27.37 | sos |
| ATOM | 3382 | CD2 | PHE | 1010 | 74.956 | 41.979 | 86.633 | 1.00 | 25.11 | sos |
| ATOM | 3383 | CE1 | PHE | 1010 | 75.745 | 39.671 | 85.311 | 1.00 | 28.73 | sos |
| ATOM | 3384 | CE2 | PHE | 1010 | 76.225 | 41.471 | 86.838 | 1.00 | 26.60 | sos |
| ATOM | 3385 | CZ | PHE | 1010 | 76.626 | 40.312 | 86.175 | 1.00 | 29.00 | sos |
| ATOM | 3386 | C | PHE | 1010 | 71.817 | 41.521 | 87.892 | 1.00 | 34.21 | sos |
| ATOM | 3387 | O | PHE | 1010 | 72.541 | 40.830 | 88.610 | 1.00 | 32.67 | sos |
| ATOM | 3388 | N | ASN | 1011 | 71.183 | 42.592 | 88.352 | 1.00 | 34.52 | sos |
| ATOM | 3389 | CA | ASN | 1011 | 71.300 | 42.944 | 89.759 | 1.00 | 39.38 | sos |
| ATOM | 3390 | CB | ASN | 1011 | 70.858 | 44.387 | 90.014 | 1.00 | 37.64 | sos |
| ATOM | 3391 | CG | ASN | 1011 | 71.786 | 45.401 | 89.358 | 1.00 | 45.29 | sos |
| ATOM | 3392 | OD1 | ASN | 1011 | 73.008 | 45.228 | 89.339 | 1.00 | 47.44 | sos |
| ATOM | 3393 | ND2 | ASN | 1011 | 71.206 | 46.458 | 88.798 | 1.00 | 48.36 | sos |
| ATOM | 3394 | C | ASN | 1011 | 70.502 | 41.946 | 90.601 | 1.00 | 40.68 | sos |
| ATOM | 3395 | O | ASN | 1011 | 70.796 | 41.739 | 91.777 | 1.00 | 46.37 | sos |
| ATOM | 3396 | N | LYS | 1012 | 69.525 | 41.293 | 89.978 | 1.00 | 39.02 | sos |
| ATOM | 3397 | CA | LYS | 1012 | 68.717 | 40.295 | 90.666 | 1.00 | 36.48 | sos |
| ATOM | 3398 | CB | LYS | 1012 | 67.435 | 40.021 | 89.892 | 1.00 | 31.20 | sos |
| ATOM | 3399 | CG | LYS | 1012 | 66.188 | 40.565 | 90.537 | 1.00 | 35.86 | sos |
| ATOM | 3400 | CD | LYS | 1012 | 65.962 | 39.916 | 91.877 | 1.00 | 37.23 | sos |
| ATOM | 3401 | CE | LYS | 1012 | 64.803 | 40.556 | 92.607 | 1.00 | 35.45 | sos |
| ATOM | 3402 | NZ | LYS | 1012 | 64.698 | 39.982 | 93.974 | 1.00 | 38.71 | sos |
| ATOM | 3403 | C | LYS | 1012 | 69.532 | 39.012 | 90.790 | 1.00 | 37.79 | sos |
| ATOM | 3404 | O | LYS | 1012 | 69.437 | 38.293 | 91.788 | 1.00 | 39.45 | sos |
| ATOM | 3405 | N | SER | 1013 | 70.326 | 38.727 | 89.764 | 1.00 | 31.71 | sos |
| ATOM | 3406 | CA | SER | 1013 | 71.169 | 37.550 | 89.767 | 1.00 | 33.20 | sos |
| ATOM | 3407 | CB | SER | 1013 | 71.858 | 37.400 | 88.410 | 1.00 | 30.48 | sos |
| ATOM | 3408 | OG | SER | 1013 | 72.816 | 36.355 | 88.422 | 1.00 | 29.43 | sos |
| ATOM | 3409 | C | SER | 1013 | 72.204 | 37.683 | 90.898 | 1.00 | 37.15 | sos |
| ATOM | 3410 | O | SER | 1013 | 72.424 | 36.740 | 91.656 | 1.00 | 38.69 | sos |
| ATOM | 3411 | N | LEU | 1014 | 72.796 | 38.871 | 91.030 | 1.00 | 37.90 | sos |
| ATOM | 3412 | CA | LEU | 1014 | 73.786 | 39.140 | 92.071 | 1.00 | 34.98 | sos |
| ATOM | 3413 | CB | LEU | 1014 | 74.405 | 40.521 | 91.890 | 1.00 | 29.45 | sos |
| ATOM | 3414 | CG | LEU | 1014 | 75.317 | 40.674 | 90.673 | 1.00 | 30.45 | sos |
| ATOM | 3415 | CD1 | LEU | 1014 | 75.709 | 42.113 | 90.533 | 1.00 | 21.32 | sos |
| ATOM | 3416 | CD2 | LEU | 1014 | 76.549 | 39.783 | 90.786 | 1.00 | 23.29 | sos |
| ATOM | 3417 | C | LEU | 1014 | 73.171 | 39.040 | 93.454 | 1.00 | 37.18 | sos |
| ATOM | 3418 | O | LEU | 1014 | 73.840 | 38.629 | 94.394 | 1.00 | 42.96 | sos |
| ATOM | 3419 | N | GLU | 1015 | 71.898 | 39.412 | 93.572 | 1.00 | 33.87 | sos |
| ATOM | 3420 | CA | GLU | 1015 | 71.182 | 39.348 | 94.843 | 1.00 | 32.26 | sos |
| ATOM | 3421 | CB | GLU | 1015 | 69.888 | 40.162 | 94.755 | 1.00 | 27.02 | sos |
| ATOM | 3422 | CG | GLU | 1015 | 68.917 | 39.964 | 95.927 | 1.00 | 34.19 | sos |
| ATOM | 3423 | CD | GLU | 1015 | 67.595 | 40.713 | 95.759 | 1.00 | 43.83 | sos |
| ATOM | 3424 | OE1 | GLU | 1015 | 67.378 | 41.332 | 94.693 | 1.00 | 47.98 | sos |
| ATOM | 3425 | OE2 | GLU | 1015 | 66.766 | 40.683 | 96.696 | 1.00 | 47.33 | sos |
| ATOM | 3426 | C | GLU | 1015 | 70.852 | 37.914 | 95.285 | 1.00 | 36.90 | sos |
| ATOM | 3427 | O | GLU | 1015 | 70.851 | 37.611 | 96.485 | 1.00 | 38.20 | sos |
| ATOM | 3428 | N | ILE | 1016 | 70.549 | 37.040 | 94.326 | 1.00 | 36.35 | sos |
| ATOM | 3429 | CA | ILE | 1016 | 70.186 | 35.666 | 94.660 | 1.00 | 35.84 | sos |
| ATOM | 3430 | CB | ILE | 1016 | 69.108 | 35.099 | 93.692 | 1.00 | 36.50 | sos |
| ATOM | 3431 | CG2 | ILE | 1016 | 67.886 | 35.994 | 93.691 | 1.00 | 31.67 | sos |
| ATOM | 3432 | CG1 | ILE | 1016 | 69.661 | 34.972 | 92.276 | 1.00 | 36.56 | sos |
| ATOM | 3433 | CD1 | ILE | 1016 | 68.598 | 34.712 | 91.254 | 1.00 | 40.13 | sos |
| ATOM | 3434 | C | ILE | 1016 | 71.393 | 34.737 | 94.752 | 1.00 | 34.57 | sos |
| ATOM | 3435 | O | ILE | 1016 | 71.320 | 33.663 | 95.358 | 1.00 | 32.46 | sos |
| ATOM | 3436 | N | GLU | 1017 | 72.498 | 35.155 | 94.145 | 1.00 | 28.69 | sos |
| ATOM | 3437 | CA | GLU | 1017 | 73.738 | 34.392 | 94.188 | 1.00 | 28.48 | sos |
| ATOM | 3438 | CB | GLU | 1017 | 73.809 | 33.374 | 93.055 | 1.00 | 23.95 | sos |
| ATOM | 3439 | CG | GLU | 1017 | 72.866 | 32.190 | 93.232 | 1.00 | 32.06 | sos |
| ATOM | 3440 | CD | GLU | 1017 | 73.173 | 31.021 | 92.302 | 1.00 | 35.24 | sos |
| ATOM | 3441 | OE1 | GLU | 1017 | 74.325 | 30.915 | 91.815 | 1.00 | 41.30 | sos |
| ATOM | 3442 | OE2 | GLU | 1017 | 72.266 | 30.194 | 92.078 | 1.00 | 30.51 | sos |
| ATOM | 3443 | C | GLU | 1017 | 74.918 | 35.353 | 94.122 | 1.00 | 34.11 | sos |
| ATOM | 3444 | O | GLU | 1017 | 75.554 | 35.503 | 93.079 | 1.00 | 36.22 | sos |

TABLE 3-continued

PDB Coordinates for the Ras-Sos Structure:
DATA SET FOR REFINED COORDINATES

| ATOM | 3445 | N | PRO | 1018 | 75.210 | 36.044 | 95.242 | 1.00 | 38.86 | sos |
|---|---|---|---|---|---|---|---|---|---|---|
| ATOM | 3446 | CD | PRO | 1018 | 74.476 | 35.990 | 96.519 | 1.00 | 37.43 | sos |
| ATOM | 3447 | CA | PRO | 1018 | 76.317 | 37.005 | 95.325 | 1.00 | 38.60 | sos |
| ATOM | 3448 | CB | PRO | 1018 | 76.207 | 37.526 | 96.761 | 1.00 | 35.93 | sos |
| ATOM | 3449 | CG | PRO | 1018 | 75.522 | 36.422 | 97.486 | 1.00 | 38.41 | sos |
| ATOM | 3450 | C | PRO | 1018 | 77.668 | 36.378 | 95.029 | 1.00 | 40.60 | sos |
| ATOM | 3451 | O | PRO | 1018 | 77.822 | 35.165 | 95.172 | 1.00 | 39.54 | sos |
| ATOM | 3452 | N | ARG | 1019 | 78.624 | 37.204 | 94.595 | 1.00 | 43.68 | sos |
| ATOM | 3453 | CA | ARG | 1019 | 79.972 | 36.747 | 94.248 | 1.00 | 53.25 | sos |
| ATOM | 3454 | CB | ARG | 1019 | 80.818 | 37.900 | 93.710 | 1.00 | 53.95 | sos |
| ATOM | 3455 | CG | ARG | 1019 | 80.386 | 38.445 | 92.367 | 1.00 | 53.55 | sos |
| ATOM | 3456 | CD | ARG | 1019 | 81.494 | 39.307 | 91.765 | 1.00 | 56.28 | sos |
| ATOM | 3457 | NE | ARG | 1019 | 81.066 | 40.019 | 90.564 | 1.00 | 59.34 | sos |
| ATOM | 3458 | CZ | ARG | 1019 | 80.238 | 41.063 | 90.563 | 1.00 | 63.63 | sos |
| ATOM | 3459 | NH1 | ARG | 1019 | 79.737 | 41.530 | 91.708 | 1.00 | 58.21 | sos |
| ATOM | 3460 | NH2 | ARG | 1019 | 79.904 | 41.643 | 89.412 | 1.00 | 62.23 | sos |
| ATOM | 3461 | C | ARG | 1019 | 80.748 | 36.025 | 95.360 | 1.00 | 59.66 | sos |
| ATOM | 3462 | O | ARG | 1019 | 80.767 | 36.458 | 96.514 | 1.00 | 59.79 | sos |
| ATOM | 3463 | N | ASN | 1020 | 81.448 | 34.971 | 94.947 | 1.00 | 65.67 | sos |
| ATOM | 3464 | CA | ASN | 1020 | 82.254 | 34.074 | 95.787 | 1.00 | 72.37 | sos |
| ATOM | 3465 | CB | ASN | 1020 | 83.604 | 33.788 | 95.119 | 1.00 | 74.06 | sos |
| ATOM | 3466 | CG | ASN | 1020 | 83.597 | 32.494 | 94.323 | 1.00 | 76.63 | sos |
| ATOM | 3467 | OD1 | ASN | 1020 | 82.820 | 31.576 | 94.609 | 1.00 | 71.80 | sos |
| ATOM | 3468 | ND2 | ASN | 1020 | 84.472 | 32.400 | 93.320 | 1.00 | 78.08 | sos |
| ATOM | 3469 | C | ASN | 1020 | 82.447 | 34.228 | 97.302 | 1.00 | 75.92 | sos |
| ATOM | 3470 | O | ASN | 1020 | 81.865 | 33.453 | 98.079 | 1.00 | 76.41 | sos |
| ATOM | 3471 | N | PRO | 1021 | 83.265 | 35.206 | 97.750 | 1.00 | 75.87 | sos |
| ATOM | 3472 | CD | PRO | 1021 | 83.870 | 36.337 | 97.019 | 1.00 | 75.75 | sos |
| ATOM | 3473 | CA | PRO | 1021 | 83.468 | 35.355 | 99.198 | 1.00 | 73.46 | sos |
| ATOM | 3474 | CB | PRO | 1021 | 84.456 | 36.518 | 99.286 | 1.00 | 72.38 | sos |
| ATOM | 3475 | CG | PRO | 1021 | 84.066 | 37.367 | 98.117 | 1.00 | 76.57 | sos |
| ATOM | 3476 | C | PRO | 1021 | 82.189 | 35.623 | 99.995 | 1.00 | 72.37 | sos |
| ATOM | 3477 | O | PRO | 1021 | 82.137 | 35.370 | 101.199 | 1.00 | 76.49 | sos |
| ATOM | 3478 | N | LYS | 1022 | 81.156 | 36.109 | 99.315 | 1.00 | 66.09 | sos |
| ATOM | 3479 | CA | LYS | 1022 | 79.887 | 36.409 | 99.962 | 1.00 | 64.03 | sos |
| ATOM | 3480 | CB | LYS | 1022 | 79.168 | 37.532 | 99.200 | 1.00 | 67.17 | sos |
| ATOM | 3481 | CG | LYS | 1022 | 80.117 | 38.643 | 98.724 | 1.00 | 72.16 | sos |
| ATOM | 3482 | CD | LYS | 1022 | 79.423 | 39.780 | 97.981 | 1.00 | 70.86 | sos |
| ATOM | 3483 | CE | LYS | 1022 | 78.694 | 40.710 | 98.933 | 1.00 | 71.52 | sos |
| ATOM | 3484 | NZ | LYS | 1022 | 78.135 | 41.905 | 98.238 | 1.00 | 70.32 | sos |
| ATOM | 3485 | C | LYS | 1022 | 79.022 | 35.145 | 100.031 | 1.00 | 61.33 | sos |
| ATOM | 3486 | O | LYS | 1022 | 78.709 | 34.535 | 99.009 | 1.00 | 62.61 | sos |
| ATOM | 3487 | N | PRO | 1023 | 78.637 | 34.728 | 101.248 | 1.00 | 57.36 | sos |
| ATOM | 3488 | CD | PRO | 1023 | 78.892 | 35.438 | 102.514 | 1.00 | 53.59 | sos |
| ATOM | 3489 | CA | PRO | 1023 | 77.809 | 33.535 | 101.477 | 1.00 | 53.25 | sos |
| ATOM | 3490 | CB | PRO | 1023 | 77.680 | 33.503 | 102.999 | 1.00 | 54.32 | sos |
| ATOM | 3491 | CG | PRO | 1023 | 77.757 | 34.957 | 103.377 | 1.00 | 55.29 | sos |
| ATOM | 3492 | C | PRO | 1023 | 76.434 | 33.608 | 100.804 | 1.00 | 49.96 | sos |
| ATOM | 3493 | O | PRO | 1023 | 75.844 | 34.684 | 100.701 | 1.00 | 50.39 | sos |
| ATOM | 3494 | N | LEU | 1024 | 75.938 | 32.457 | 100.351 | 1.00 | 45.19 | sos |
| ATOM | 3495 | CA | LEU | 1024 | 74.642 | 32.367 | 99.686 | 1.00 | 38.20 | sos |
| ATOM | 3496 | CB | LEU | 1024 | 74.517 | 31.032 | 98.944 | 1.00 | 37.80 | sos |
| ATOM | 3497 | CG | LEU | 1024 | 73.177 | 30.775 | 98.240 | 1.00 | 40.96 | sos |
| ATOM | 3498 | CD1 | LEU | 1024 | 73.129 | 31.543 | 96.942 | 1.00 | 40.84 | sos |
| ATOM | 3499 | CD2 | LEU | 1024 | 72.986 | 29.301 | 97.962 | 1.00 | 42.47 | sos |
| ATOM | 3500 | C | LEU | 1024 | 73.483 | 32.500 | 100.673 | 1.00 | 37.42 | sos |
| ATOM | 3501 | O | LEU | 1024 | 73.261 | 31.621 | 101.510 | 1.00 | 37.28 | sos |
| ATOM | 3502 | N | PRO | 1025 | 72.736 | 33.611 | 100.604 | 1.00 | 33.68 | sos |
| ATOM | 3503 | CD | PRO | 1025 | 72.972 | 34.874 | 99.877 | 1.00 | 31.71 | sos |
| ATOM | 3504 | CA | PRO | 1025 | 71.624 | 33.730 | 101.549 | 1.00 | 33.72 | sos |
| ATOM | 3505 | CB | PRO | 1025 | 71.281 | 35.224 | 101.494 | 1.00 | 34.22 | sos |
| ATOM | 3506 | CG | PRO | 1025 | 71.707 | 35.647 | 100.125 | 1.00 | 29.65 | sos |
| ATOM | 3507 | C | PRO | 1025 | 70.441 | 32.848 | 101.159 | 1.00 | 32.73 | sos |
| ATOM | 3508 | O | PRO | 1025 | 70.441 | 32.230 | 100.098 | 1.00 | 35.40 | sos |
| ATOM | 3509 | N | ARG | 1026 | 69.469 | 32.749 | 102.054 | 1.00 | 32.19 | sos |
| ATOM | 3510 | CA | ARG | 1026 | 68.268 | 31.963 | 101.815 | 1.00 | 34.72 | sos |
| ATOM | 3511 | CB | ARG | 1026 | 67.920 | 31.106 | 103.034 | 1.00 | 35.94 | sos |
| ATOM | 3512 | CG | ARG | 1026 | 68.866 | 29.958 | 103.293 | 1.00 | 41.49 | sos |
| ATOM | 3513 | CD | ARG | 1026 | 68.364 | 29.105 | 104.440 | 1.00 | 38.52 | sos |
| ATOM | 3514 | NE | ARG | 1026 | 69.222 | 27.946 | 104.664 | 1.00 | 44.88 | sos |
| ATOM | 3515 | CZ | ARG | 1026 | 70.147 | 27.865 | 105.616 | 1.00 | 49.90 | sos |
| ATOM | 3516 | NH1 | ARG | 1026 | 70.352 | 28.880 | 106.448 | 1.00 | 52.41 | sos |
| ATOM | 3517 | NH2 | ARG | 1026 | 70.857 | 26.753 | 105.747 | 1.00 | 52.31 | sos |
| ATOM | 3518 | C | ARG | 1026 | 67.107 | 32.907 | 101.559 | 1.00 | 36.75 | sos |
| ATOM | 3519 | O | ARG | 1026 | 67.025 | 33.982 | 102.152 | 1.00 | 37.78 | sos |
| ATOM | 3520 | N | PHE | 1027 | 66.195 | 32.499 | 100.688 | 1.00 | 37.59 | sos |

TABLE 3-continued

PDB Coordinates for the Ras-Sos Structure:
DATA SET FOR REFINED COORDINATES

| ATOM | 3521 | CA | PHE | 1027 | 65.036 | 33.326 | 100.401 | 1.00 | 35.04 | sos |
|------|------|-----|-----|------|--------|--------|---------|------|-------|-----|
| ATOM | 3522 | CB | PHE | 1027 | 65.116 | 33.865 | 98.978 | 1.00 | 36.06 | sos |
| ATOM | 3523 | CG | PHE | 1027 | 66.331 | 34.722 | 98.720 | 1.00 | 31.03 | sos |
| ATOM | 3524 | CD1 | PHE | 1027 | 67.550 | 34.143 | 98.400 | 1.00 | 29.45 | sos |
| ATOM | 3525 | CD2 | PHE | 1027 | 66.248 | 36.107 | 98.793 | 1.00 | 24.42 | sos |
| ATOM | 3526 | CE1 | PHE | 1027 | 67.675 | 34.932 | 98.151 | 1.00 | 32.70 | sos |
| ATOM | 3527 | CE2 | PHE | 1027 | 67.354 | 36.896 | 98.552 | 1.00 | 25.93 | sos |
| ATOM | 3528 | CZ | PHE | 1027 | 68.578 | 36.306 | 98.227 | 1.00 | 31.08 | sos |
| ATOM | 3529 | C | PHE | 1027 | 63.779 | 32.501 | 100.607 | 1.00 | 35.26 | sos |
| ATOM | 3530 | O | PHE | 1027 | 63.808 | 31.278 | 100.496 | 1.00 | 35.20 | sos |
| ATOM | 3531 | N | PRO | 1028 | 62.671 | 33.153 | 100.979 | 1.00 | 36.76 | sos |
| ATOM | 3532 | CD | PRO | 1028 | 62.571 | 34.590 | 101.286 | 1.00 | 36.59 | sos |
| ATOM | 3533 | CA | PRO | 1028 | 61.388 | 32.477 | 101.213 | 1.00 | 39.55 | sos |
| ATOM | 3534 | CB | PRO | 1028 | 60.521 | 33.590 | 101.801 | 1.00 | 36.25 | sos |
| ATOM | 3535 | CG | PRO | 1028 | 61.091 | 34.826 | 101.202 | 1.00 | 36.68 | sos |
| ATOM | 3536 | C | PRO | 1028 | 60.751 | 31.871 | 99.960 | 1.00 | 42.98 | sos |
| ATOM | 3537 | O | PRO | 1028 | 61.045 | 32.283 | 98.841 | 1.00 | 42.12 | sos |
| ATOM | 3538 | N | LYS | 1029 | 59.900 | 30.868 | 100.151 | 1.00 | 49.52 | sos |
| ATOM | 3539 | CA | LYS | 1029 | 59.224 | 30.235 | 99.024 | 1.00 | 53.66 | sos |
| ATOM | 3540 | CB | LYS | 1029 | 58.517 | 28.945 | 99.456 | 1.00 | 56.78 | sos |
| ATOM | 3541 | CG | LYS | 1029 | 59.442 | 27.727 | 99.548 | 1.00 | 60.05 | sos |
| ATOM | 3542 | CD | LYS | 1029 | 58.670 | 26.449 | 99.883 | 1.00 | 60.94 | sos |
| ATOM | 3543 | CE | LYS | 1029 | 57.656 | 26.070 | 98.790 | 1.00 | 65.68 | sos |
| ATOM | 3544 | NZ | LYS | 1029 | 58.273 | 25.599 | 97.508 | 1.00 | 61.29 | sos |
| ATOM | 3545 | C | LYS | 1029 | 58.238 | 31.210 | 98.370 | 1.00 | 55.92 | sos |
| ATOM | 3546 | O | LYS | 1029 | 57.607 | 32.033 | 99.050 | 1.00 | 56.70 | sos |
| ATOM | 3547 | N | LYS | 1030 | 58.143 | 31.124 | 97.044 | 1.00 | 54.61 | sos |
| ATOM | 3548 | CA | LYS | 1030 | 57.287 | 31.985 | 96.231 | 1.00 | 51.01 | sos |
| ATOM | 3549 | CB | LYS | 1030 | 58.088 | 32.453 | 95.014 | 1.00 | 51.72 | sos |
| ATOM | 3550 | CG | LYS | 1030 | 57.459 | 33.525 | 94.149 | 1.00 | 46.27 | sos |
| ATOM | 3551 | CD | LYS | 1030 | 58.239 | 33.625 | 92.838 | 1.00 | 49.80 | sos |
| ATOM | 3552 | CE | LYS | 1030 | 58.440 | 35.061 | 92.383 | 1.00 | 51.39 | sos |
| ATOM | 3553 | NZ | LYS | 1030 | 57.161 | 35.776 | 92.112 | 1.00 | 58.17 | sos |
| ATOM | 3554 | C | LYS | 1030 | 56.045 | 31.234 | 95.766 | 1.00 | 50.24 | sos |
| ATOM | 3555 | O | LYS | 1030 | 54.939 | 31.763 | 95.814 | 1.00 | 50.83 | sos |
| ATOM | 3556 | N | TYR | 1031 | 56.237 | 29.994 | 95.326 | 1.00 | 48.18 | sos |
| ATOM | 3557 | CA | TYR | 1031 | 55.138 | 29.169 | 94.829 | 1.00 | 49.55 | sos |
| ATOM | 3558 | CB | TYR | 1031 | 55.639 | 28.274 | 93.693 | 1.00 | 42.70 | sos |
| ATOM | 3559 | CG | TYR | 1031 | 56.454 | 29.007 | 92.651 | 1.00 | 39.34 | sos |
| ATOM | 3560 | CD1 | TYR | 1031 | 57.737 | 28.589 | 92.335 | 1.00 | 34.93 | sos |
| ATOM | 3561 | CE1 | TYR | 1031 | 58.502 | 29.263 | 91.388 | 1.00 | 32.25 | sos |
| ATOM | 3562 | CD2 | TYR | 1031 | 55.946 | 30.130 | 91.989 | 1.00 | 35.70 | sos |
| ATOM | 3563 | CE2 | TYR | 1031 | 56.707 | 30.816 | 91.036 | 1.00 | 25.87 | sos |
| ATOM | 3564 | CZ | TYR | 1031 | 57.984 | 30.372 | 90.743 | 1.00 | 31.60 | sos |
| ATOM | 3565 | OH | TYR | 1031 | 58.756 | 31.018 | 89.800 | 1.00 | 31.36 | sos |
| ATOM | 3566 | C | TYR | 1031 | 54.467 | 28.313 | 95.912 | 1.00 | 52.44 | sos |
| ATOM | 3567 | O | TYR | 1031 | 55.143 | 27.616 | 96.676 | 1.00 | 54.23 | sos |
| ATOM | 3568 | N | SER | 1032 | 53.134 | 28.361 | 95.957 | 1.00 | 53.97 | sos |
| ATOM | 3569 | CA | SER | 1032 | 52.353 | 27.598 | 96.932 | 1.00 | 55.36 | sos |
| ATOM | 3570 | CB | SER | 1032 | 51.290 | 28.489 | 97.602 | 1.00 | 56.79 | sos |
| ATOM | 3571 | OG | SER | 1032 | 50.293 | 28.916 | 96.685 | 1.00 | 60.79 | sos |
| ATOM | 3572 | C | SER | 1032 | 51.695 | 26.348 | 96.342 | 1.00 | 53.81 | sos |
| ATOM | 3573 | O | SER | 1032 | 50.642 | 25.915 | 96.806 | 1.00 | 56.17 | sos |
| ATOM | 3574 | N | TYR | 1033 | 52.316 | 25.784 | 95.310 | 1.00 | 52.37 | sos |
| ATOM | 3575 | CA | TYR | 1033 | 51.824 | 24.567 | 94.655 | 1.00 | 52.43 | sos |
| ATOM | 3576 | CB | TYR | 1033 | 51.085 | 24.904 | 93.346 | 1.00 | 46.79 | sos |
| ATOM | 3577 | CG | TYR | 1033 | 51.798 | 25.881 | 92.435 | 1.00 | 43.89 | sos |
| ATOM | 3578 | CD1 | TYR | 1033 | 52.980 | 25.526 | 91.779 | 1.00 | 42.24 | sos |
| ATOM | 3579 | CE1 | TYR | 1033 | 53.632 | 26.424 | 90.930 | 1.00 | 44.77 | sos |
| ATOM | 3580 | CD2 | TYR | 1033 | 51.284 | 27.159 | 92.220 | 1.00 | 38.71 | sos |
| ATOM | 3581 | CE2 | TYR | 1033 | 51.924 | 28.063 | 91.376 | 1.00 | 37.85 | sos |
| ATOM | 3582 | CZ | TYR | 1033 | 53.095 | 27.691 | 90.732 | 1.00 | 43.47 | sos |
| ATOM | 3583 | OH | TYR | 1033 | 53.721 | 28.574 | 89.878 | 1.00 | 46.51 | sos |
| ATOM | 3584 | C | TYR | 1033 | 53.022 | 23.634 | 94.418 | 1.00 | 53.02 | sos |
| ATOM | 3585 | O | TYR | 1033 | 54.165 | 24.080 | 94.469 | 1.00 | 57.16 | sos |
| ATOM | 3586 | N | PRO | 1034 | 52.787 | 22.323 | 94.213 | 1.00 | 53.33 | sos |
| ATOM | 3587 | CD | PRO | 1034 | 51.512 | 21.584 | 94.215 | 1.00 | 55.22 | sos |
| ATOM | 3588 | CA | PRO | 1034 | 53.915 | 21.406 | 93.991 | 1.00 | 52.03 | sos |
| ATOM | 3589 | CB | PRO | 1034 | 53.231 | 20.042 | 93.847 | 1.00 | 51.71 | sos |
| ATOM | 3590 | CG | PRO | 1034 | 51.851 | 20.378 | 93.375 | 1.00 | 52.42 | sos |
| ATOM | 3591 | C | PRO | 1034 | 54.806 | 21.745 | 92.799 | 1.00 | 50.79 | sos |
| ATOM | 3592 | O | PRO | 1034 | 54.321 | 22.095 | 91.728 | 1.00 | 55.89 | sos |
| ATOM | 3593 | N | LEU | 1035 | 56.115 | 21.647 | 93.007 | 1.00 | 49.64 | sos |
| ATOM | 3594 | CA | LEU | 1035 | 57.100 | 21.949 | 91.973 | 1.00 | 48.69 | sos |
| ATOM | 3595 | CB | LEU | 1035 | 58.324 | 22.618 | 92.592 | 1.00 | 52.99 | sos |
| ATOM | 3596 | CG | LEU | 1035 | 58.040 | 23.882 | 93.388 | 1.00 | 53.80 | sos |

TABLE 3-continued

PDB Coordinates for the Ras-Sos Structure:
DATA SET FOR REFINED COORDINATES

| | | | | | | | | | |
|---|---|---|---|---|---|---|---|---|---|
| ATOM | 3597 | CD1 | LEU | 1035 | 57.790 | 23.510 | 94.838 | 1.00 | 59.44 | sos |
| ATOM | 3598 | CD2 | LEU | 1035 | 59.218 | 24.812 | 93.276 | 1.00 | 54.82 | sos |
| ATOM | 3599 | C | LEU | 1035 | 57.546 | 20.724 | 91.189 | 1.00 | 48.49 | sos |
| ATOM | 3600 | O | LEU | 1035 | 58.526 | 20.772 | 90.437 | 1.00 | 46.00 | sos |
| ATOM | 3601 | N | LYS | 1036 | 56.851 | 19.612 | 91.391 | 1.00 | 50.15 | sos |
| ATOM | 3602 | CA | LYS | 1036 | 57.194 | 18.384 | 90.688 | 1.00 | 51.26 | sos |
| ATOM | 3603 | CB | LYS | 1036 | 56.589 | 17.166 | 91.404 | 1.00 | 52.45 | sos |
| ATOM | 3604 | CG | LYS | 1036 | 57.052 | 15.819 | 90.871 | 1.00 | 50.08 | sos |
| ATOM | 3605 | CD | LYS | 1036 | 56.386 | 14.674 | 91.617 | 0.00 | 51.03 | sos |
| ATOM | 3606 | CE | LYS | 1036 | 56.838 | 13.323 | 91.084 | 0.00 | 51.10 | sos |
| ATOM | 3607 | NZ | LYS | 1036 | 58.301 | 13.108 | 91.258 | 0.00 | 51.10 | sos |
| ATOM | 3608 | C | LYS | 1036 | 56.662 | 18.490 | 89.264 | 1.00 | 48.71 | sos |
| ATOM | 3609 | O | LYS | 1036 | 55.513 | 18.870 | 89.051 | 1.00 | 47.52 | sos |
| ATOM | 3610 | N | SER | 1037 | 57.527 | 18.223 | 88.295 | 1.00 | 46.28 | sos |
| ATOM | 3611 | CA | SER | 1037 | 57.137 | 18.265 | 86.897 | 1.00 | 48.14 | sos |
| ATOM | 3612 | CB | SER | 1037 | 58.375 | 18.335 | 85.999 | 1.00 | 48.77 | sos |
| ATOM | 3613 | OG | SER | 1037 | 58.026 | 18.146 | 84.635 | 1.00 | 44.69 | sos |
| ATOM | 3614 | C | SER | 1037 | 56.345 | 17.013 | 86.540 | 1.00 | 50.68 | sos |
| ATOM | 3615 | O | SER | 1037 | 56.682 | 15.910 | 86.977 | 1.00 | 50.07 | sos |
| ATOM | 3616 | N | PRO | 1038 | 55.267 | 17.169 | 85.756 | 1.00 | 50.43 | sos |
| ATOM | 3617 | CD | PRO | 1038 | 54.632 | 18.419 | 85.305 | 1.00 | 53.61 | sos |
| ATOM | 3618 | CA | PRO | 1038 | 54.466 | 16.012 | 85.361 | 1.00 | 49.70 | sos |
| ATOM | 3619 | CB | PRO | 1038 | 53.205 | 16.652 | 84.775 | 1.00 | 51.38 | sos |
| ATOM | 3620 | CG | PRO | 1038 | 53.699 | 17.929 | 84.215 | 1.00 | 53.77 | sos |
| ATOM | 3621 | C | PRO | 1038 | 55.220 | 15.184 | 84.328 | 1.00 | 49.14 | sos |
| ATOM | 3622 | O | PRO | 1038 | 54.771 | 14.107 | 83.941 | 1.00 | 52.32 | sos |
| ATOM | 3623 | N | GLY | 1039 | 56.381 | 15.678 | 83.906 | 1.00 | 46.48 | sos |
| ATOM | 3624 | CA | GLY | 1039 | 57.174 | 14.960 | 82.928 | 1.00 | 51.54 | sos |
| ATOM | 3625 | C | GLY | 1039 | 56.982 | 15.441 | 81.500 | 1.00 | 55.26 | sos |
| ATOM | 3626 | O | GLY | 1039 | 56.078 | 16.230 | 81.209 | 1.00 | 55.05 | sos |
| ATOM | 3627 | N | VAL | 1040 | 57.808 | 14.916 | 80.598 | 1.00 | 56.00 | sos |
| ATOM | 3628 | CA | VAL | 1040 | 57.774 | 15.297 | 79.193 | 1.00 | 56.85 | sos |
| ATOM | 3629 | CB | VAL | 1040 | 59.212 | 15.641 | 78.718 | 1.00 | 55.66 | sos |
| ATOM | 3630 | CG1 | VAL | 1040 | 59.737 | 14.632 | 77.687 | 1.00 | 57.12 | sos |
| ATOM | 3631 | CG2 | VAL | 1040 | 59.250 | 17.049 | 78.197 | 1.00 | 51.43 | sos |
| ATOM | 3632 | C | VAL | 1040 | 57.107 | 14.267 | 78.268 | 1.00 | 60.22 | sos |
| ATOM | 3633 | O | VAL | 1040 | 56.887 | 14.533 | 77.082 | 1.00 | 59.88 | sos |
| ATOM | 3634 | N | ARG | 1041 | 56.787 | 13.096 | 78.814 | 1.00 | 63.28 | sos |
| ATOM | 3635 | CA | ARG | 1041 | 56.137 | 12.035 | 78.048 | 1.00 | 63.28 | sos |
| ATOM | 3636 | CB | ARG | 1041 | 56.533 | 10.671 | 78.610 | 1.00 | 66.56 | sos |
| ATOM | 3637 | CG | ARG | 1041 | 58.032 | 10.398 | 78.554 | 1.00 | 72.12 | sos |
| ATOM | 3638 | CD | ARG | 1041 | 58.409 | 9.167 | 79.369 | 1.00 | 74.84 | sos |
| ATOM | 3639 | NE | ARG | 1041 | 58.100 | 9.331 | 80.788 | 0.00 | 74.15 | sos |
| ATOM | 3640 | CZ | ARG | 1041 | 58.310 | 8.401 | 81.715 | 0.00 | 74.40 | sos |
| ATOM | 3641 | NH1 | ARG | 1041 | 58.833 | 7.228 | 81.382 | 0.00 | 74.35 | sos |
| ATOM | 3642 | NH2 | ARG | 1041 | 57.996 | 8.645 | 82.980 | 0.00 | 74.35 | sos |
| ATOM | 3643 | C | ARG | 1041 | 54.618 | 12.206 | 78.103 | 1.00 | 63.76 | sos |
| ATOM | 3644 | O | ARG | 1041 | 54.042 | 12.361 | 79.180 | 1.00 | 63.08 | sos |
| ATOM | 3645 | N | PRO | 1042 | 53.953 | 12.196 | 76.935 | 1.00 | 65.39 | sos |
| ATOM | 3646 | CD | PRO | 1042 | 54.554 | 12.027 | 75.600 | 1.00 | 63.39 | sos |
| ATOM | 3647 | CA | PRO | 1042 | 52.495 | 12.351 | 76.834 | 1.00 | 67.30 | sos |
| ATOM | 3648 | CB | PRO | 1042 | 52.265 | 12.393 | 75.323 | 1.00 | 64.74 | sos |
| ATOM | 3649 | CG | PRO | 1042 | 53.383 | 11.563 | 74.784 | 1.00 | 63.48 | sos |
| ATOM | 3650 | C | PRO | 1042 | 51.683 | 11.243 | 77.518 | 1.00 | 71.91 | sos |
| ATOM | 3651 | O | PRO | 1042 | 52.174 | 10.126 | 77.711 | 1.00 | 70.71 | sos |
| ATOM | 3652 | N | SER | 1043 | 50.438 | 11.569 | 77.868 | 1.00 | 78.21 | sos |
| ATOM | 3653 | CA | SER | 1043 | 49.521 | 10.647 | 78.552 | 1.00 | 84.35 | sos |
| ATOM | 3654 | CB | SER | 1043 | 48.125 | 11.270 | 78.673 | 1.00 | 82.31 | sos |
| ATOM | 3655 | OG | SER | 1043 | 47.546 | 11.487 | 77.396 | 1.00 | 82.51 | sos |
| ATOM | 3656 | C | SER | 1043 | 49.413 | 9.253 | 77.927 | 1.00 | 88.20 | sos |
| ATOM | 3657 | O | SER | 1043 | 49.727 | 8.251 | 78.582 | 1.00 | 87.03 | sos |
| ATOM | 3658 | N | ASN | 1044 | 48.949 | 9.195 | 76.677 | 1.00 | 90.11 | sos |
| ATOM | 3659 | CA | ASN | 1044 | 48.795 | 7.934 | 75.946 | 1.00 | 93.28 | sos |
| ATOM | 3660 | CB | ASN | 1044 | 47.445 | 7.267 | 76.272 | 1.00 | 93.92 | sos |
| ATOM | 3661 | CG | ASN | 1044 | 47.504 | 6.379 | 77.517 | 1.00 | 94.38 | sos |
| ATOM | 3662 | OD1 | ASN | 1044 | 48.099 | 5.294 | 77.499 | 1.00 | 91.81 | sos |
| ATOM | 3663 | ND2 | ASN | 1044 | 46.866 | 6.829 | 78.595 | 1.00 | 93.17 | sos |
| ATOM | 3664 | C | ASN | 1044 | 48.915 | 8.150 | 74.436 | 1.00 | 93.94 | sos |
| ATOM | 3665 | O | ASN | 1044 | 49.192 | 7.155 | 73.728 | 1.00 | 92.95 | sos |
| ATOM | 3666 | OT | ASN | 1044 | 9999.000 | 9999.000 | 9999.000 | 1.00 | 0.00 | sos |
| ATOM | 3667 | CB | MET | 1 | 98.896 | 28.177 | 63.709 | 1.00 | 64.21 | ras |
| ATOM | 3668 | CG | MET | 1 | 97.614 | 28.013 | 62.921 | 1.00 | 60.52 | ras |
| ATOM | 3669 | SD | MET | 1 | 97.711 | 28.897 | 61.353 | 1.00 | 67.68 | ras |
| ATOM | 3670 | CE | MET | 1 | 96.745 | 27.822 | 60.275 | 1.00 | 66.31 | ras |
| ATOM | 3671 | C | MET | 1 | 97.855 | 27.918 | 65.978 | 1.00 | 69.17 | ras |
| ATOM | 3672 | O | MET | 1 | 96.864 | 27.226 | 66.252 | 1.00 | 65.74 | ras |

TABLE 3-continued

PDB Coordinates for the Ras-Sos Structure:
DATA SET FOR REFINED COORDINATES

| ATOM | 3673 | N   | MET | 1  | 98.797 | 25.938 | 64.784 | 1.00 | 70.44 | ras |
|------|------|-----|-----|----|--------|--------|--------|------|-------|-----|
| ATOM | 3674 | CA  | MET | 1  | 98.937 | 27.403 | 65.030 | 1.00 | 68.67 | ras |
| ATOM | 3675 | N   | THR | 2  | 98.056 | 29.134 | 66.479 | 1.00 | 67.94 | ras |
| ATOM | 3676 | CA  | THR | 2  | 97.106 | 29.743 | 67.401 | 1.00 | 66.23 | ras |
| ATOM | 3677 | CB  | THR | 2  | 97.756 | 30.897 | 68.196 | 1.00 | 68.13 | ras |
| ATOM | 3678 | OG1 | THR | 2  | 98.957 | 30.428 | 68.820 | 1.00 | 72.20 | ras |
| ATOM | 3679 | CG2 | THR | 2  | 96.810 | 31.400 | 69.279 | 1.00 | 69.27 | ras |
| ATOM | 3680 | C   | THR | 2  | 95.858 | 30.251 | 66.676 | 1.00 | 63.62 | ras |
| ATOM | 3681 | O   | THR | 2  | 95.935 | 30.805 | 65.569 | 1.00 | 58.44 | ras |
| ATOM | 3682 | N   | GLU | 3  | 94.709 | 30.034 | 67.309 | 1.00 | 60.32 | ras |
| ATOM | 3683 | CA  | GLU | 3  | 93.431 | 30.458 | 66.764 | 1.00 | 59.63 | ras |
| ATOM | 3684 | CB  | GLU | 3  | 92.479 | 29.263 | 66.702 | 1.00 | 65.92 | ras |
| ATOM | 3685 | CG  | GLU | 3  | 91.101 | 29.577 | 66.139 | 1.00 | 73.93 | ras |
| ATOM | 3686 | CD  | GLU | 3  | 90.202 | 28.353 | 66.090 | 1.00 | 78.86 | ras |
| ATOM | 3687 | OE1 | GLU | 3  | 89.227 | 28.296 | 66.876 | 1.00 | 78.18 | ras |
| ATOM | 3688 | OE2 | GLU | 3  | 90.478 | 27.446 | 65.268 | 1.00 | 81.55 | ras |
| ATOM | 3689 | C   | GLU | 3  | 92.827 | 31.560 | 67.632 | 1.00 | 55.33 | ras |
| ATOM | 3690 | O   | GLU | 3  | 92.618 | 31.369 | 68.834 | 1.00 | 55.49 | ras |
| ATOM | 3691 | N   | TYR | 4  | 92.573 | 32.717 | 67.028 | 1.00 | 48.88 | ras |
| ATOM | 3692 | CA  | TYR | 4  | 91.979 | 33.840 | 67.752 | 1.00 | 43.76 | ras |
| ATOM | 3693 | CB  | TYR | 4  | 92.715 | 35.144 | 67.448 | 1.00 | 41.90 | ras |
| ATOM | 3694 | CG  | TYR | 4  | 94.164 | 35.151 | 67.853 | 1.00 | 42.99 | ras |
| ATOM | 3695 | CD1 | TYR | 4  | 95.168 | 35.247 | 66.895 | 1.00 | 39.72 | ras |
| ATOM | 3696 | CE1 | TYR | 4  | 96.497 | 35.267 | 67.255 | 1.00 | 42.34 | ras |
| ATOM | 3697 | CD2 | TYR | 4  | 94.533 | 35.074 | 69.195 | 1.00 | 42.32 | ras |
| ATOM | 3698 | CE2 | TYR | 4  | 95.866 | 35.093 | 69.569 | 1.00 | 43.19 | ras |
| ATOM | 3699 | CZ  | TYR | 4  | 96.845 | 35.188 | 68.593 | 1.00 | 45.54 | ras |
| ATOM | 3700 | OH  | TYR | 4  | 98.176 | 35.184 | 68.949 | 1.00 | 49.20 | ras |
| ATOM | 3701 | C   | TYR | 4  | 90.513 | 34.017 | 67.389 | 1.00 | 40.08 | ras |
| ATOM | 3702 | O   | TYR | 4  | 90.173 | 34.198 | 66.217 | 1.00 | 39.51 | ras |
| ATOM | 3703 | N   | LYS | 5  | 89.644 | 33.953 | 68.389 | 1.00 | 36.05 | ras |
| ATOM | 3704 | CA  | LYS | 5  | 88.224 | 34.145 | 68.140 | 1.00 | 39.51 | ras |
| ATOM | 3705 | CB  | LYS | 5  | 87.384 | 33.217 | 69.020 | 1.00 | 41.71 | ras |
| ATOM | 3706 | CG  | LYS | 5  | 87.517 | 31.769 | 68.592 | 1.00 | 47.56 | ras |
| ATOM | 3707 | CD  | LYS | 5  | 86.450 | 30.881 | 69.206 | 1.00 | 56.96 | ras |
| ATOM | 3708 | CE  | LYS | 5  | 86.435 | 29.514 | 68.525 | 1.00 | 60.92 | ras |
| ATOM | 3709 | NZ  | LYS | 5  | 86.206 | 29.628 | 67.047 | 1.00 | 61.12 | ras |
| ATOM | 3710 | C   | LYS | 5  | 87.831 | 35.617 | 68.297 | 1.00 | 37.04 | ras |
| ATOM | 3711 | O   | LYS | 5  | 87.789 | 36.172 | 69.399 | 1.00 | 36.97 | ras |
| ATOM | 3712 | N   | LEU | 6  | 87.586 | 36.256 | 67.164 | 1.00 | 34.50 | ras |
| ATOM | 3713 | CA  | LEU | 6  | 87.229 | 37.661 | 67.144 | 1.00 | 35.89 | ras |
| ATOM | 3714 | CB  | LEU | 6  | 88.022 | 38.374 | 66.043 | 1.00 | 31.73 | ras |
| ATOM | 3715 | CG  | LEU | 6  | 89.536 | 38.108 | 66.065 | 1.00 | 28.35 | ras |
| ATOM | 3716 | CD1 | LEU | 6  | 90.235 | 38.966 | 64.998 | 1.00 | 22.14 | ras |
| ATOM | 3717 | CD2 | LEU | 6  | 90.104 | 38.375 | 67.470 | 1.00 | 12.88 | ras |
| ATOM | 3718 | C   | LEU | 6  | 85.736 | 37.869 | 66.936 | 1.00 | 36.19 | ras |
| ATOM | 3719 | O   | LEU | 6  | 85.098 | 37.129 | 66.190 | 1.00 | 39.15 | ras |
| ATOM | 3720 | N   | VAL | 7  | 85.183 | 38.867 | 67.621 | 1.00 | 34.20 | ras |
| ATOM | 3721 | CA  | VAL | 7  | 83.765 | 39.192 | 67.507 | 1.00 | 28.91 | ras |
| ATOM | 3722 | CB  | VAL | 7  | 83.002 | 38.898 | 68.799 | 1.00 | 24.45 | ras |
| ATOM | 3723 | CG1 | VAL | 7  | 81.555 | 39.337 | 68.659 | 1.00 | 18.95 | ras |
| ATOM | 3724 | CG2 | VAL | 7  | 83.080 | 37.419 | 69.127 | 1.00 | 27.16 | ras |
| ATOM | 3725 | C   | VAL | 7  | 83.595 | 40.663 | 67.198 | 1.00 | 29.95 | ras |
| ATOM | 3726 | O   | VAL | 7  | 84.230 | 41.509 | 67.819 | 1.00 | 35.73 | ras |
| ATOM | 3727 | N   | VAL | 8  | 82.739 | 40.962 | 66.229 | 1.00 | 29.89 | ras |
| ATOM | 3728 | CA  | VAL | 8  | 82.466 | 42.337 | 65.837 | 1.00 | 25.87 | ras |
| ATOM | 3729 | CB  | VAL | 8  | 82.421 | 42.458 | 64.333 | 1.00 | 19.37 | ras |
| ATOM | 3730 | CG1 | VAL | 8  | 82.120 | 43.870 | 63.933 | 1.00 | 25.11 | ras |
| ATOM | 3731 | CG2 | VAL | 8  | 83.719 | 42.000 | 63.749 | 1.00 | 23.08 | ras |
| ATOM | 3732 | C   | VAL | 8  | 81.119 | 42.761 | 66.400 | 1.00 | 27.93 | ras |
| ATOM | 3733 | O   | VAL | 8  | 80.138 | 42.028 | 66.287 | 1.00 | 35.49 | ras |
| ATOM | 3734 | N   | VAL | 9  | 81.081 | 43.931 | 67.025 | 1.00 | 26.90 | ras |
| ATOM | 3735 | CA  | VAL | 9  | 79.851 | 44.465 | 64.602 | 1.00 | 28.06 | ras |
| ATOM | 3736 | CB  | VAL | 9  | 79.858 | 44.380 | 69.155 | 1.00 | 26.74 | ras |
| ATOM | 3737 | CG1 | VAL | 9  | 80.086 | 42.952 | 69.613 | 1.00 | 28.81 | ras |
| ATOM | 3738 | CG2 | VAL | 9  | 80.939 | 45.248 | 69.721 | 1.00 | 34.61 | ras |
| ATOM | 3739 | C   | VAL | 9  | 79.687 | 45.925 | 67.172 | 1.00 | 30.28 | ras |
| ATOM | 3740 | O   | VAL | 9  | 80.673 | 46.641 | 66.965 | 1.00 | 31.12 | ras |
| ATOM | 3741 | N   | GLY | 10 | 78.442 | 46.357 | 67.021 | 1.00 | 31.28 | ras |
| ATOM | 3742 | CA  | GLY | 10 | 78.182 | 47.723 | 66.607 | 1.00 | 30.62 | ras |
| ATOM | 3743 | C   | GLY | 10 | 76.791 | 47.876 | 66.033 | 1.00 | 32.79 | ras |
| ATOM | 3744 | O   | GLY | 10 | 76.166 | 46.888 | 65.651 | 1.00 | 32.25 | ras |
| ATOM | 3745 | N   | ALA | 11 | 76.310 | 49.113 | 65.950 | 1.00 | 31.58 | ras |
| ATOM | 3746 | CA  | ALA | 11 | 74.976 | 49.384 | 65.422 | 1.00 | 28.79 | ras |
| ATOM | 3747 | CB  | ALA | 11 | 74.672 | 50.874 | 65.486 | 1.00 | 28.24 | ras |
| ATOM | 3748 | C   | ALA | 11 | 74.802 | 48.887 | 63.996 | 1.00 | 29.83 | ras |

TABLE 3-continued

PDB Coordinates for the Ras-Sos Structure:
DATA SET FOR REFINED COORDINATES

| | | | | | | | | | |
|---|---|---|---|---|---|---|---|---|---|
| ATOM | 3749 | O | ALA | 11 | 75.758 | 48.858 | 63.217 | 1.00 | 24.58 ras |
| ATOM | 3750 | N | GLY | 12 | 73.580 | 48.461 | 63.680 | 1.00 | 32.69 ras |
| ATOM | 3751 | CA | GLY | 12 | 73.279 | 47.991 | 62.344 | 1.00 | 33.41 ras |
| ATOM | 3752 | C | GLY | 12 | 72.804 | 49.153 | 61.488 | 1.00 | 37.17 ras |
| ATOM | 3753 | O | GLY | 12 | 72.639 | 50.273 | 61.977 | 1.00 | 39.12 ras |
| ATOM | 3754 | N | GLY | 13 | 72.604 | 48.901 | 60.200 | 1.00 | 38.09 ras |
| ATOM | 3755 | CA | GLY | 13 | 72.127 | 49.944 | 59.315 | 1.00 | 36.40 ras |
| ATOM | 3756 | C | GLY | 13 | 73.152 | 50.965 | 58.877 | 1.00 | 34.79 ras |
| ATOM | 3757 | O | GLY | 13 | 72.788 | 51.969 | 58.275 | 1.00 | 37.97 ras |
| ATOM | 3758 | N | VAL | 14 | 74.424 | 50.732 | 59.181 | 1.00 | 32.97 ras |
| ATOM | 3759 | CA | VAL | 14 | 75.474 | 51.663 | 58.778 | 1.00 | 31.46 ras |
| ATOM | 3760 | CB | VAL | 14 | 75.984 | 52.508 | 59.957 | 1.00 | 29.51 ras |
| ATOM | 3761 | CG1 | VAL | 14 | 74.837 | 53.333 | 60.540 | 1.00 | 25.85 ras |
| ATOM | 3762 | CG2 | VAL | 14 | 76.603 | 51.619 | 61.024 | 1.00 | 29.24 ras |
| ATOM | 3763 | C | VAL | 14 | 76.630 | 50.933 | 58.112 | 1.00 | 33.37 ras |
| ATOM | 3764 | O | VAL | 14 | 77.726 | 51.470 | 57.979 | 1.00 | 37.97 ras |
| ATOM | 3765 | N | GLY | 15 | 76.371 | 49.691 | 57.718 | 1.00 | 34.90 ras |
| ATOM | 3766 | CA | GLY | 15 | 77.356 | 48.880 | 57.020 | 1.00 | 35.10 ras |
| ATOM | 3767 | C | GLY | 15 | 78.592 | 48.375 | 57.735 | 1.00 | 34.45 ras |
| ATOM | 3768 | O | GLY | 15 | 79.671 | 48.375 | 57.141 | 1.00 | 34.67 ras |
| ATOM | 3769 | N | LYS | 16 | 78.445 | 47.884 | 58.964 | 1.00 | 32.21 ras |
| ATOM | 3770 | CA | LYS | 16 | 79.594 | 47.375 | 59.703 | 1.00 | 33.47 ras |
| ATOM | 3771 | CB | LYS | 16 | 79.229 | 47.081 | 61.160 | 1.00 | 29.51 ras |
| ATOM | 3772 | CG | LYS | 16 | 78.315 | 45.903 | 61.341 | 1.00 | 26.74 ras |
| ATOM | 3773 | CD | LYS | 16 | 78.025 | 45.607 | 62.784 | 1.00 | 21.31 ras |
| ATOM | 3774 | CE | LYS | 16 | 76.729 | 44.824 | 62.885 | 1.00 | 23.59 ras |
| ATOM | 3775 | NZ | LYS | 16 | 76.295 | 44.522 | 64.284 | 1.00 | 24.66 ras |
| ATOM | 3776 | C | LYS | 16 | 80.169 | 46.111 | 59.064 | 1.00 | 36.18 ras |
| ATOM | 3777 | O | LYS | 16 | 81.323 | 45.774 | 59.292 | 1.00 | 40.41 ras |
| ATOM | 3778 | N | SER | 17 | 79.367 | 45.420 | 58.257 | 1.00 | 37.90 ras |
| ATOM | 3779 | CA | SER | 17 | 79.814 | 44.189 | 57.618 | 1.00 | 33.18 ras |
| ATOM | 3780 | CB | SER | 17 | 78.667 | 43.520 | 56.868 | 1.00 | 31.75 ras |
| ATOM | 3781 | OG | SER | 17 | 78.174 | 44.362 | 55.843 | 1.00 | 35.33 ras |
| ATOM | 3782 | C | SER | 17 | 80.983 | 44.416 | 56.679 | 1.00 | 32.80 ras |
| ATOM | 3783 | O | SER | 17 | 81.764 | 43.496 | 56.427 | 1.00 | 33.91 ras |
| ATOM | 3784 | N | ALA | 18 | 81.124 | 45.642 | 56.181 | 1.00 | 29.29 ras |
| ATOM | 3785 | CA | ALA | 18 | 82.225 | 45.946 | 55.264 | 1.00 | 32.79 ras |
| ATOM | 3786 | CB | ALA | 18 | 82.151 | 47.388 | 54.782 | 1.00 | 31.17 ras |
| ATOM | 3787 | C | ALA | 18 | 83.590 | 45.668 | 55.881 | 1.00 | 32.59 ras |
| ATOM | 3788 | O | ALA | 18 | 84.535 | 45.342 | 55.173 | 1.00 | 34.96 ras |
| ATOM | 3789 | N | LEU | 19 | 83.679 | 45.778 | 57.204 | 1.00 | 31.66 ras |
| ATOM | 3790 | CA | LEU | 19 | 84.928 | 45.547 | 57.915 | 1.00 | 30.79 ras |
| ATOM | 3791 | CB | LEU | 19 | 84.724 | 45.768 | 59.406 | 1.00 | 29.97 ras |
| ATOM | 3792 | CG | LEU | 19 | 85.721 | 46.656 | 60.124 | 1.00 | 31.50 ras |
| ATOM | 3793 | CD1 | LEU | 19 | 85.783 | 46.213 | 61.567 | 1.00 | 30.98 ras |
| ATOM | 3794 | CD2 | LEU | 19 | 87.083 | 46.559 | 59.477 | 1.00 | 31.11 ras |
| ATOM | 3795 | C | LEU | 19 | 85.457 | 44.131 | 57.695 | 1.00 | 32.45 ras |
| ATOM | 3796 | O | LEU | 19 | 86.482 | 43.934 | 57.054 | 1.00 | 30.89 ras |
| ATOM | 3797 | N | THR | 20 | 84.742 | 43.148 | 58.226 | 1.00 | 33.56 ras |
| ATOM | 3798 | CA | THR | 20 | 85.145 | 41.758 | 58.101 | 1.00 | 36.39 ras |
| ATOM | 3799 | CB | THR | 20 | 84.226 | 40.867 | 58.938 | 1.00 | 34.40 ras |
| ATOM | 3800 | OG1 | THR | 20 | 84.304 | 41.282 | 60.306 | 1.00 | 34.94 ras |
| ATOM | 3801 | CG2 | THR | 20 | 84.632 | 39.407 | 58.832 | 1.00 | 31.53 ras |
| ATOM | 3802 | C | THR | 20 | 85.202 | 41.256 | 56.650 | 1.00 | 40.45 ras |
| ATOM | 3803 | O | THR | 20 | 86.031 | 40.403 | 56.315 | 1.00 | 41.25 ras |
| ATOM | 3804 | N | ILE | 21 | 84.350 | 41.807 | 55.787 | 1.00 | 40.32 ras |
| ATOM | 3805 | CA | ILE | 21 | 84.319 | 41.389 | 54.391 | 1.00 | 40.25 ras |
| ATOM | 3806 | CB | ILE | 21 | 83.016 | 41.845 | 53.685 | 1.00 | 39.42 ras |
| ATOM | 3807 | CG2 | ILE | 21 | 83.137 | 41.694 | 52.171 | 1.00 | 32.60 ras |
| ATOM | 3808 | CG1 | ILE | 21 | 81.842 | 41.004 | 54.205 | 1.00 | 36.21 ras |
| ATOM | 3809 | CD1 | ILE | 21 | 80.497 | 41.447 | 53.712 | 1.00 | 34.78 ras |
| ATOM | 3810 | C | ILE | 21 | 85.555 | 41.849 | 53.639 | 1.00 | 42.12 ras |
| ATOM | 3811 | O | ILE | 21 | 86.184 | 41.057 | 52.934 | 1.00 | 43.78 ras |
| ATOM | 3812 | N | GLN | 22 | 85.931 | 43.110 | 53.829 | 1.00 | 42.34 ras |
| ATOM | 3813 | CA | GLN | 22 | 87.110 | 43.660 | 53.172 | 1.00 | 41.07 ras |
| ATOM | 3814 | CB | GLN | 22 | 87.226 | 45.163 | 53.427 | 1.00 | 41.89 ras |
| ATOM | 3815 | CG | GLN | 22 | 86.187 | 46.014 | 52.696 | 1.00 | 42.18 ras |
| ATOM | 3816 | CD | GLN | 22 | 86.419 | 47.507 | 52.887 | 1.00 | 47.35 ras |
| ATOM | 3817 | OE1 | GLN | 22 | 86.148 | 48.071 | 53.958 | 1.00 | 48.68 ras |
| ATOM | 3818 | NE2 | GLN | 22 | 86.937 | 48.154 | 51.852 | 1.00 | 49.92 ras |
| ATOM | 3819 | C | GLN | 22 | 88.388 | 42.943 | 53.614 | 1.00 | 39.88 ras |
| ATOM | 3820 | O | GLN | 22 | 89.320 | 42.796 | 52.832 | 1.00 | 43.76 ras |
| ATOM | 3821 | N | LEU | 23 | 88.430 | 42.485 | 54.859 | 1.00 | 38.90 ras |
| ATOM | 3822 | CA | LEU | 23 | 89.601 | 41.773 | 55.348 | 1.00 | 40.70 ras |
| ATOM | 3823 | CB | LEU | 23 | 89.445 | 41.424 | 56.827 | 1.00 | 37.24 ras |
| ATOM | 3824 | CG | LEU | 23 | 90.536 | 40.522 | 57.407 | 1.00 | 36.44 ras |

TABLE 3-continued

PDB Coordinates for the Ras-Sos Structure:
DATA SET FOR REFINED COORDINATES

| ATOM | 3825 | CD1 | LEU | 23 | 91.848 | 41.281 | 57.469 | 1.00 | 34.77 | ras |
|------|------|-----|-----|----|--------|--------|--------|------|-------|-----|
| ATOM | 3826 | CD2 | LEU | 23 | 90.144 | 40.043 | 58.794 | 1.00 | 37.25 | ras |
| ATOM | 3827 | C | LEU | 23 | 89.742 | 40.488 | 54.553 | 1.00 | 44.83 | ras |
| ATOM | 3828 | O | LEU | 23 | 90.774 | 40.238 | 53.929 | 1.00 | 44.30 | ras |
| ATOM | 3829 | N | ILE | 24 | 88.654 | 39.723 | 54.525 | 1.00 | 51.04 | ras |
| ATOM | 3830 | CA | ILE | 24 | 88.594 | 38.439 | 53.841 | 1.00 | 57.57 | ras |
| ATOM | 3831 | CB | ILE | 24 | 87.541 | 37.527 | 54.524 | 1.00 | 54.03 | ras |
| ATOM | 3832 | CG2 | ILE | 24 | 87.556 | 36.135 | 53.922 | 1.00 | 59.68 | ras |
| ATOM | 3833 | CG1 | ILE | 24 | 87.876 | 37.400 | 56.007 | 1.00 | 50.73 | ras |
| ATOM | 3834 | CD1 | ILE | 24 | 87.096 | 36.354 | 56.727 | 1.00 | 44.71 | ras |
| ATOM | 3835 | C | ILE | 24 | 88.349 | 38.530 | 52.330 | 1.00 | 62.59 | ras |
| ATOM | 3836 | O | ILE | 24 | 87.466 | 37.879 | 51.791 | 1.00 | 66.56 | ras |
| ATOM | 3837 | N | GLN | 25 | 89.137 | 39.350 | 51.650 | 1.00 | 69.35 | ras |
| ATOM | 3838 | CA | GLN | 25 | 89.026 | 39.513 | 50.205 | 1.00 | 75.82 | ras |
| ATOM | 3839 | CB | GLN | 25 | 87.968 | 40.555 | 49.833 | 1.00 | 74.81 | ras |
| ATOM | 3840 | CG | GLN | 25 | 86.538 | 40.046 | 49.871 | 1.00 | 74.11 | ras |
| ATOM | 3841 | CD | GLN | 25 | 85.550 | 41.024 | 49.269 | 1.00 | 76.38 | ras |
| ATOM | 3842 | OE1 | GLN | 25 | 85.746 | 42.240 | 49.317 | 1.00 | 75.82 | ras |
| ATOM | 3843 | NE2 | GLN | 25 | 84.477 | 40.493 | 48.693 | 1.00 | 77.92 | ras |
| ATOM | 3844 | C | GLN | 25 | 90.372 | 39.948 | 49.668 | 1.00 | 82.87 | ras |
| ATOM | 3845 | O | GLN | 25 | 91.159 | 40.575 | 50.379 | 1.00 | 86.41 | ras |
| ATOM | 3846 | N | ASN | 26 | 90.636 | 39.606 | 48.414 | 1.00 | 89.55 | ras |
| ATOM | 3847 | CA | ASN | 26 | 91.898 | 39.954 | 47.775 | 1.00 | 96.55 | ras |
| ATOM | 3848 | CB | ASN | 26 | 92.508 | 38.712 | 47.114 | 1.00 | 99.02 | ras |
| ATOM | 3849 | CG | ASN | 26 | 92.262 | 37.439 | 47.912 | 1.00 | 101.37 | ras |
| ATOM | 3850 | OD1 | ASN | 26 | 91.828 | 36.425 | 47.363 | 1.00 | 103.47 | ras |
| ATOM | 3851 | ND2 | ASN | 26 | 92.536 | 37.487 | 49.210 | 1.00 | 101.47 | ras |
| ATOM | 3852 | C | ASN | 26 | 91.668 | 41.033 | 46.720 | 1.00 | 994.3 | ras |
| ATOM | 3853 | O | ASN | 26 | 90.527 | 41.402 | 46.437 | 1.00 | 98.60 | ras |
| ATOM | 3854 | N | HIS | 27 | 92.758 | 41.537 | 46.142 | 1.00 | 103.37 | ras |
| ATOM | 3855 | CA | HIS | 27 | 92.668 | 42.560 | 45.102 | 1.00 | 105.64 | ras |
| ATOM | 3856 | CB | HIS | 27 | 94.072 | 42.973 | 44.625 | 1.00 | 102.92 | ras |
| ATOM | 3857 | CG | HIS | 27 | 94.983 | 43.412 | 45.732 | 0.00 | 103.19 | ras |
| ATOM | 3858 | CD2 | HIS | 27 | 96.059 | 42.811 | 46.290 | 0.00 | 102.84 | ras |
| ATOM | 3859 | ND1 | HIS | 27 | 94.829 | 44.613 | 46.395 | 0.00 | 102.84 | ras |
| ATOM | 3860 | CE1 | HIS | 27 | 95.774 | 44.728 | 47.312 | 0.00 | 102.81 | ras |
| ATOM | 3861 | NE2 | HIS | 27 | 96.533 | 43.650 | 47.269 | 0.00 | 102.81 | ras |
| ATOM | 3862 | C | HIS | 27 | 91.839 | 41.955 | 43.963 | 1.00 | 107.45 | ras |
| ATOM | 3863 | O | HIS | 27 | 91.957 | 40.761 | 43.671 | 1.00 | 109.51 | ras |
| ATOM | 3864 | N | PHE | 28 | 90.939 | 42.762 | 43.403 | 1.00 | 108.72 | ras |
| ATOM | 3865 | CA | PHE | 28 | 90.018 | 42.365 | 42.327 | 1.00 | 109.86 | ras |
| ATOM | 3866 | CB | PHE | 28 | 90.733 | 42.107 | 40.977 | 1.00 | 108.97 | ras |
| ATOM | 3867 | CG | PHE | 28 | 91.413 | 40.763 | 40.860 | 0.00 | 107.25 | ras |
| ATOM | 3868 | CD1 | PHE | 28 | 90.678 | 39.607 | 40.608 | 0.00 | 106.62 | ras |
| ATOM | 3869 | CD2 | PHE | 28 | 92.795 | 40.662 | 40.957 | 0.00 | 106.62 | ras |
| ATOM | 3870 | CE1 | PHE | 28 | 91.311 | 38.371 | 40.454 | 0.00 | 106.07 | ras |
| ATOM | 3871 | CE2 | PHE | 28 | 93.438 | 39.435 | 40.806 | 0.00 | 106.07 | ras |
| ATOM | 3872 | CZ | PHE | 28 | 92.695 | 38.287 | 40.553 | 0.00 | 105.94 | ras |
| ATOM | 3873 | C | PHE | 28 | 89.023 | 41.252 | 42.687 | 1.00 | 109.95 | ras |
| ATOM | 3874 | O | VAL | 29 | 88.266 | 40.778 | 41.833 | 1.00 | 111.13 | ras |
| ATOM | 3875 | N | VAL | 29 | 89.033 | 40.850 | 43.957 | 1.00 | 107.43 | ras |
| ATOM | 3876 | CA | VAL | 29 | 88.128 | 39.823 | 44.467 | 1.00 | 104.88 | ras |
| ATOM | 3877 | CB | VAL | 29 | 88.860 | 38.831 | 45.415 | 1.00 | 106.44 | ras |
| ATOM | 3878 | CG1 | VAL | 29 | 87.885 | 37.852 | 46.042 | 1.00 | 105.85 | ras |
| ATOM | 3879 | CG2 | VAL | 29 | 89.918 | 38.079 | 44.638 | 1.00 | 108.37 | ras |
| ATOM | 3880 | C | VAL | 29 | 86.997 | 40.549 | 45.205 | 1.00 | 102.41 | ras |
| ATOM | 3881 | O | VAL | 29 | 87.157 | 40.983 | 46.349 | 1.00 | 101.78 | ras |
| ATOM | 3882 | N | ASP | 30 | 85.891 | 40.769 | 44.503 | 1.00 | 100.00 | ras |
| ATOM | 3883 | CA | ASP | 30 | 84.736 | 41.437 | 45.089 | 1.00 | 96.73 | ras |
| ATOM | 3884 | CB | ASP | 30 | 84.296 | 42.610 | 44.211 | 1.00 | 96.24 | ras |
| ATOM | 3885 | CG | ASP | 30 | 85.360 | 43.692 | 44.119 | 0.00 | 96.14 | ras |
| ATOM | 3886 | OD1 | ASP | 30 | 85.421 | 44.554 | 45.025 | 0.00 | 95.97 | ras |
| ATOM | 3887 | OD2 | ASP | 30 | 86.151 | 43.665 | 43.153 | 0.00 | 95.97 | ras |
| ATOM | 3888 | C | ASP | 30 | 83.595 | 40.445 | 45.298 | 1.00 | 94.60 | ras |
| ATOM | 3889 | O | ASP | 30 | 82.475 | 40.833 | 45.628 | 1.00 | 96.50 | ras |
| ATOM | 3890 | N | GLU | 31 | 83.906 | 39.159 | 45.128 | 1.00 | 91.89 | ras |
| ATOM | 3891 | CA | GLU | 31 | 82.953 | 38.058 | 45.305 | 1.00 | 87.27 | ras |
| ATOM | 3892 | CB | GLU | 31 | 83.412 | 36.829 | 44.519 | 1.00 | 88.86 | ras |
| ATOM | 3893 | CG | GLU | 31 | 83.742 | 37.097 | 43.064 | 1.00 | 94.52 | ras |
| ATOM | 3894 | CD | GLU | 31 | 84.866 | 36.208 | 42.550 | 1.00 | 98.83 | ras |
| ATOM | 3895 | OE1 | GLU | 31 | 84.719 | 34.963 | 42.593 | 1.00 | 99.32 | ras |
| ATOM | 3896 | OE2 | GLU | 31 | 85.904 | 36.762 | 42.121 | 1.00 | 98.61 | ras |
| ATOM | 3897 | C | GLU | 31 | 82.901 | 37.679 | 46.785 | 1.00 | 81.60 | ras |
| ATOM | 3898 | O | GLU | 31 | 83.917 | 37.754 | 47.488 | 1.00 | 83.19 | ras |
| ATOM | 3899 | N | TYR | 32 | 81.735 | 37.246 | 47.252 | 1.00 | 71.10 | ras |
| ATOM | 3900 | CA | TYR | 32 | 81.591 | 36.866 | 48.649 | 1.00 | 62.58 | ras |

TABLE 3-continued

PDB Coordinates for the Ras-Sos Structure:
DATA SET FOR REFINED COORDINATES

| ATOM | 3901 | CB | TYR | 32 | 81.392 | 38.110 | 49.531 | 1.00 | 59.55 | ras |
|---|---|---|---|---|---|---|---|---|---|---|
| ATOM | 3902 | CG | TYR | 32 | 81.576 | 37.849 | 51.016 | 1.00 | 57.68 | ras |
| ATOM | 3903 | CD1 | TYR | 32 | 82.824 | 37.506 | 51.529 | 1.00 | 55.91 | ras |
| ATOM | 3904 | CE1 | TYR | 32 | 83.002 | 37.242 | 52.888 | 1.00 | 58.04 | ras |
| ATOM | 3905 | CD2 | TYR | 32 | 80.500 | 37.928 | 51.903 | 1.00 | 56.98 | ras |
| ATOM | 3906 | CE2 | TYR | 32 | 80.667 | 37.667 | 53.266 | 1.00 | 57.80 | ras |
| ATOM | 3907 | CZ | TYR | 32 | 81.923 | 37.322 | 53.750 | 1.00 | 59.28 | ras |
| ATOM | 3908 | OH | TYR | 32 | 82.106 | 37.034 | 55.086 | 1.00 | 57.17 | ras |
| ATOM | 3909 | C | TYR | 32 | 80.447 | 35.885 | 48.858 | 1.00 | 58.35 | ras |
| ATOM | 3910 | O | TYR | 32 | 79.314 | 36.139 | 48.456 | 1.00 | 55.09 | ras |
| ATOM | 3911 | N | ASP | 33 | 80.771 | 34.744 | 49.457 | 1.00 | 56.72 | ras |
| ATOM | 3912 | CA | ASP | 33 | 79.794 | 33.705 | 49.748 | 1.00 | 55.66 | ras |
| ATOM | 3913 | CB | ASP | 33 | 80.108 | 32.424 | 48.961 | 1.00 | 57.45 | ras |
| ATOM | 3914 | CG | ASP | 33 | 79.023 | 31.352 | 49.105 | 1.00 | 62.57 | ras |
| ATOM | 3915 | OD1 | ASP | 33 | 77.946 | 31.636 | 49.679 | 1.00 | 64.59 | ras |
| ATOM | 3916 | OD2 | ASP | 33 | 79.250 | 30.216 | 48.638 | 1.00 | 61.10 | ras |
| ATOM | 3917 | C | ASP | 33 | 79.865 | 33.457 | 51.248 | 1.00 | 53.22 | ras |
| ATOM | 3918 | O | ASP | 33 | 80.720 | 32.723 | 51.737 | 1.00 | 52.02 | ras |
| ATOM | 3919 | N | PRO | 34 | 78.957 | 34.085 | 52.000 | 1.00 | 52.62 | ras |
| ATOM | 3920 | CD | PRO | 34 | 77.890 | 34.956 | 51.475 | 1.00 | 50.65 | ras |
| ATOM | 3921 | CA | PRO | 34 | 78.869 | 33.978 | 53.457 | 1.00 | 53.48 | ras |
| ATOM | 3922 | CB | PRO | 34 | 77.798 | 35.012 | 53.790 | 1.00 | 52.62 | ras |
| ATOM | 3923 | CG | PRO | 34 | 76.901 | 34.949 | 52.591 | 1.00 | 51.04 | ras |
| ATOM | 3924 | C | PRO | 34 | 78.500 | 32.596 | 53.991 | 1.00 | 54.52 | ras |
| ATOM | 3925 | O | PRO | 34 | 77.967 | 32.474 | 55.088 | 1.00 | 55.79 | ras |
| ATOM | 3926 | N | THR | 35 | 78.813 | 31.551 | 53.244 | 1.00 | 58.47 | ras |
| ATOM | 3927 | CA | THR | 35 | 78.467 | 30.210 | 53.692 | 1.00 | 64.56 | ras |
| ATOM | 3928 | CB | THR | 35 | 77.402 | 29.593 | 52.768 | 1.00 | 64.69 | ras |
| ATOM | 3929 | OG1 | THR | 35 | 76.237 | 30.431 | 52.780 | 1.00 | 62.13 | ras |
| ATOM | 3930 | CG2 | THR | 35 | 77.010 | 28.201 | 53.248 | 1.00 | 68.96 | ras |
| ATOM | 3931 | C | THR | 35 | 79.680 | 29.295 | 53.818 | 1.00 | 67.20 | ras |
| ATOM | 3932 | O | THR | 35 | 79.670 | 28.331 | 54.586 | 1.00 | 67.05 | ras |
| ATOM | 3933 | N | ILE | 36 | 80.736 | 29.630 | 53.088 | 1.00 | 69.42 | ras |
| ATOM | 3934 | CA | ILE | 36 | 81.696 | 28.860 | 53.106 | 1.00 | 72.57 | ras |
| ATOM | 3935 | CB | ILE | 36 | 82.822 | 29.222 | 51.871 | 1.00 | 75.23 | ras |
| ATOM | 3936 | CG2 | ILE | 36 | 84.078 | 28.351 | 51.806 | 1.00 | 79.10 | ras |
| ATOM | 3937 | CG1 | ILE | 36 | 81.977 | 29.065 | 50.604 | 1.00 | 78.33 | ras |
| ATOM | 3938 | CD1 | ILE | 36 | 82.677 | 29.490 | 49.321 | 1.00 | 85.02 | ras |
| ATOM | 3939 | C | ILE | 36 | 82.759 | 29.186 | 54.379 | 1.00 | 72.69 | ras |
| ATOM | 3940 | O | ILE | 36 | 82.619 | 30.277 | 54.931 | 1.00 | 71.94 | ras |
| ATOM | 3941 | N | GLU | 37 | 83.566 | 28.240 | 54.859 | 1.00 | 72.05 | ras |
| ATOM | 3942 | CA | GLU | 37 | 84.385 | 28.484 | 56.046 | 1.00 | 71.30 | ras |
| ATOM | 3943 | CB | GLU | 37 | 85.124 | 27.219 | 56.474 | 1.00 | 74.02 | ras |
| ATOM | 3944 | CG | GLU | 37 | 84.336 | 26.301 | 57.388 | 1.00 | 81.59 | ras |
| ATOM | 3945 | CD | GLU | 37 | 85.153 | 25.109 | 57.868 | 1.00 | 86.24 | ras |
| ATOM | 3946 | OE1 | GLU | 37 | 86.402 | 25.158 | 57.777 | 1.00 | 86.76 | ras |
| ATOM | 3947 | OE2 | GLU | 37 | 84.543 | 24.121 | 58.338 | 1.00 | 88.52 | ras |
| ATOM | 3948 | C | GLU | 37 | 85.407 | 29.587 | 55.775 | 1.00 | 69.81 | ras |
| ATOM | 3949 | O | GLU | 37 | 85.855 | 30.260 | 56.697 | 1.00 | 65.94 | ras |
| ATOM | 3950 | N | ASP | 38 | 85.778 | 29.749 | 54.506 | 1.00 | 70.84 | ras |
| ATOM | 3951 | CA | ASP | 38 | 86.745 | 30.764 | 54.078 | 1.00 | 71.58 | ras |
| ATOM | 3952 | CB | ASP | 38 | 87.142 | 30.546 | 52.610 | 1.00 | 71.34 | ras |
| ATOM | 3953 | CG | ASP | 38 | 88.411 | 29.727 | 52.451 | 1.00 | 72.38 | ras |
| ATOM | 3954 | OD1 | ASP | 38 | 89.103 | 29.916 | 51.427 | 1.00 | 67.63 | ras |
| ATOM | 3955 | OD2 | ASP | 38 | 88.716 | 28.898 | 53.337 | 1.00 | 72.83 | ras |
| ATOM | 3956 | C | ASP | 38 | 86.214 | 32.183 | 54.219 | 1.00 | 71.85 | ras |
| ATOM | 3957 | O | ASP | 38 | 86.983 | 33.140 | 54.128 | 1.00 | 72.81 | ras |
| ATOM | 3958 | N | SER | 39 | 84.902 | 32.309 | 54.424 | 1.00 | 69.98 | ras |
| ATOM | 3959 | CA | SER | 39 | 84.249 | 33.609 | 54.548 | 1.00 | 66.26 | ras |
| ATOM | 3960 | CB | SER | 39 | 82.760 | 33.493 | 54.210 | 1.00 | 67.89 | ras |
| ATOM | 3961 | OG | SER | 39 | 82.053 | 32.764 | 55.198 | 1.00 | 67.90 | ras |
| ATOM | 3962 | C | SER | 39 | 84.420 | 34.284 | 55.904 | 1.00 | 63.85 | ras |
| ATOM | 3963 | O | SER | 39 | 84.245 | 35.498 | 56.014 | 1.00 | 64.22 | ras |
| ATOM | 3964 | N | TYR | 40 | 84.748 | 33.502 | 56.929 | 1.00 | 59.66 | ras |
| ATOM | 3965 | CA | TYR | 40 | 84.943 | 34.042 | 58.271 | 1.00 | 60.29 | ras |
| ATOM | 3966 | CB | TYR | 40 | 83.736 | 33.729 | 59.158 | 1.00 | 59.53 | ras |
| ATOM | 3967 | CG | TYR | 40 | 83.369 | 32.266 | 59.252 | 1.00 | 61.70 | ras |
| ATOM | 3968 | CD1 | TYR | 40 | 83.877 | 31.459 | 60.273 | 1.00 | 63.06 | ras |
| ATOM | 3969 | CE1 | TYR | 40 | 83.475 | 30.124 | 60.411 | 1.00 | 63.86 | ras |
| ATOM | 3970 | CD2 | TYR | 40 | 82.455 | 31.702 | 58.363 | 1.00 | 63.75 | ras |
| ATOM | 3971 | CE2 | TYR | 40 | 82.044 | 30.374 | 58.491 | 1.00 | 64.02 | ras |
| ATOM | 3972 | CZ | TYR | 40 | 82.554 | 29.591 | 59.517 | 1.00 | 66.19 | ras |
| ATOM | 3973 | OH | TYR | 40 | 82.127 | 28.287 | 59.649 | 1.00 | 66.63 | ras |
| ATOM | 3974 | C | TYR | 40 | 86.244 | 33.612 | 58.961 | 1.00 | 60.01 | ras |
| ATOM | 3975 | O | TYR | 40 | 86.560 | 34.089 | 60.051 | 1.00 | 61.34 | ras |
| ATOM | 3976 | N | ARG | 41 | 86.991 | 32.715 | 58.321 | 1.00 | 59.17 | ras |

TABLE 3-continued

PDB Coordinates for the Ras-Sos Structure:
DATA SET FOR REFINED COORDINATES

| ATOM | 3977 | CA | ARG | 41 | 88.261 | 32.217 | 58.846 | 1.00 | 56.28 | ras |
|---|---|---|---|---|---|---|---|---|---|---|
| ATOM | 3978 | CB | ARG | 41 | 88.185 | 30.713 | 59.110 | 1.00 | 55.38 | ras |
| ATOM | 3979 | CG | ARG | 41 | 87.273 | 30.337 | 60.267 | 1.00 | 60.83 | ras |
| ATOM | 3980 | CD | ARG | 41 | 86.991 | 28.841 | 60.304 | 1.00 | 62.22 | ras |
| ATOM | 3981 | NE | ARG | 41 | 87.171 | 28.277 | 61.639 | 1.00 | 60.37 | ras |
| ATOM | 3982 | CZ | ARG | 41 | 88.316 | 27.766 | 62.084 | 1.00 | 60.85 | ras |
| ATOM | 3983 | NH1 | ARG | 41 | 89.387 | 27.747 | 61.302 | 1.00 | 60.27 | ras |
| ATOM | 3984 | NH2 | ARG | 41 | 88.390 | 27.266 | 63.307 | 1.00 | 61.31 | ras |
| ATOM | 3985 | C | ARG | 41 | 89.382 | 32.506 | 57.859 | 1.00 | 56.73 | ras |
| ATOM | 3986 | O | ARG | 41 | 89.334 | 32.100 | 56.698 | 1.00 | 59.88 | ras |
| ATOM | 3987 | N | LYS | 42 | 90.383 | 33.239 | 58.318 | 1.00 | 56.01 | ras |
| ATOM | 3988 | CA | LYS | 42 | 91.513 | 33.580 | 57.474 | 1.00 | 54.08 | ras |
| ATOM | 3989 | CB | LYS | 42 | 91.401 | 35.034 | 57.012 | 1.00 | 51.53 | ras |
| ATOM | 3990 | CG | LYS | 42 | 92.531 | 35.472 | 56.108 | 1.00 | 51.49 | ras |
| ATOM | 3991 | CD | LYS | 42 | 92.364 | 36.892 | 55.627 | 1.00 | 50.03 | ras |
| ATOM | 3992 | CE | LYS | 42 | 93.461 | 37.238 | 54.637 | 1.00 | 52.95 | ras |
| ATOM | 3993 | NZ | LYS | 42 | 93.397 | 38.649 | 54.157 | 1.00 | 61.11 | ras |
| ATOM | 3994 | C | LYS | 42 | 92.796 | 33.385 | 58.265 | 1.00 | 54.61 | ras |
| ATOM | 3995 | O | LYS | 42 | 92.822 | 33.629 | 59.472 | 1.00 | 54.93 | ras |
| ATOM | 3996 | N | GLN | 43 | 89.832 | 32.860 | 57.615 | 1.00 | 56.41 | ras |
| ATOM | 3997 | CA | GLN | 43 | 95.108 | 32.684 | 58.297 | 1.00 | 58.18 | ras |
| ATOM | 3998 | CB | GLN | 43 | 95.732 | 31.307 | 58.026 | 1.00 | 60.23 | ras |
| ATOM | 3999 | CG | GLN | 43 | 96.551 | 31.181 | 56.750 | 1.00 | 67.52 | ras |
| ATOM | 4000 | CD | GLN | 43 | 97.766 | 30.280 | 56.935 | 1.00 | 70.11 | ras |
| ATOM | 4001 | OE1 | GLN | 43 | 97.653 | 29.159 | 57.437 | 1.00 | 69.99 | ras |
| ATOM | 4002 | NE2 | GLN | 43 | 98.939 | 30.780 | 56.548 | 1.00 | 67.33 | ras |
| ATOM | 4003 | C | GLN | 43 | 96.015 | 33.823 | 57.847 | 1.00 | 56.44 | ras |
| ATOM | 4004 | O | GLN | 43 | 96.112 | 34.122 | 56.654 | 1.00 | 55.04 | ras |
| ATOM | 4005 | N | VAL | 44 | 96.602 | 34.514 | 58.816 | 1.00 | 54.97 | ras |
| ATOM | 4006 | CA | VAL | 44 | 97.476 | 35.641 | 58.523 | 1.00 | 56.46 | ras |
| ATOM | 4007 | CB | VAL | 44 | 96.797 | 36.978 | 58.883 | 1.00 | 57.60 | ras |
| ATOM | 4008 | CG1 | VAL | 44 | 95.643 | 37.272 | 57.927 | 1.00 | 57.82 | ras |
| ATOM | 4009 | CG2 | VAL | 44 | 96.313 | 36.943 | 60.325 | 1.00 | 55.47 | ras |
| ATOM | 4010 | C | VAL | 44 | 98.806 | 35.562 | 59.262 | 1.00 | 59.75 | ras |
| ATOM | 4011 | O | VAL | 44 | 98.981 | 34.752 | 60.174 | 1.00 | 57.63 | ras |
| ATOM | 4012 | N | VAL | 45 | 99.745 | 36.403 | 58.845 | 1.00 | 57.17 | ras |
| ATOM | 4013 | CA | VAL | 45 | 101.063 | 36.457 | 59.468 | 1.00 | 61.29 | ras |
| ATOM | 4014 | CB | VAL | 45 | 102.198 | 36.347 | 58.413 | 1.00 | 62.94 | ras |
| ATOM | 4015 | CG1 | VAL | 45 | 103.521 | 36.025 | 59.097 | 1.00 | 61.07 | ras |
| ATOM | 4016 | CG2 | VAL | 45 | 101.859 | 35.300 | 57.360 | 1.00 | 62.53 | ras |
| ATOM | 4017 | C | VAL | 45 | 101.171 | 37.806 | 60.178 | 1.00 | 60.61 | ras |
| ATOM | 4018 | O | VAL | 45 | 101.246 | 38.849 | 59.528 | 1.00 | 62.86 | ras |
| ATOM | 4019 | N | ILE | 46 | 101.161 | 37.788 | 61.506 | 1.00 | 58.33 | ras |
| ATOM | 4020 | CA | ILE | 46 | 101.233 | 39.021 | 62.282 | 1.00 | 58.98 | ras |
| ATOM | 4021 | CB | ILE | 46 | 99.975 | 39.188 | 63.177 | 1.00 | 57.99 | ras |
| ATOM | 4022 | CG2 | ILE | 46 | 100.079 | 40.439 | 64.022 | 1.00 | 56.10 | ras |
| ATOM | 4023 | CG1 | ILE | 46 | 98.719 | 39.271 | 62.313 | 1.00 | 55.51 | ras |
| ATOM | 4024 | CD1 | ILE | 46 | 97.448 | 39.364 | 63.112 | 1.00 | 58.43 | ras |
| ATOM | 4025 | C | ILE | 46 | 102.486 | 39.056 | 63.148 | 1.00 | 59.99 | ras |
| ATOM | 4026 | O | ILE | 46 | 102.640 | 38.235 | 64.060 | 1.00 | 57.79 | ras |
| ATOM | 4027 | N | ASP | 47 | 103.359 | 40.031 | 62.873 | 1.00 | 61.13 | ras |
| ATOM | 4028 | CA | ASP | 47 | 104.623 | 40.200 | 63.603 | 1.00 | 60.63 | ras |
| ATOM | 4029 | CB | ASP | 47 | 104.357 | 40.551 | 65.076 | 1.00 | 59.46 | ras |
| ATOM | 4030 | CG | ASP | 47 | 103.670 | 41.894 | 65.252 | 1.00 | 59.19 | ras |
| ATOM | 4031 | OD1 | ASP | 47 | 103.669 | 42.705 | 64.299 | 1.00 | 56.94 | ras |
| ATOM | 4032 | OD2 | ASP | 47 | 103.137 | 42.135 | 66.358 | 1.00 | 56.66 | ras |
| ATOM | 4033 | C | ASP | 47 | 105.477 | 38.929 | 63.521 | 1.00 | 60.66 | ras |
| ATOM | 4034 | O | ASP | 47 | 106.049 | 38.482 | 64.520 | 1.00 | 58.61 | ras |
| ATOM | 4035 | N | GLY | 48 | 105.535 | 38.343 | 62.330 | 1.00 | 60.80 | ras |
| ATOM | 4036 | CA | GLY | 48 | 106.295 | 37.123 | 62.140 | 1.00 | 64.28 | ras |
| ATOM | 4037 | C | GLY | 48 | 105.576 | 35.865 | 62.611 | 1.00 | 66.53 | ras |
| ATOM | 4038 | O | GLY | 48 | 105.799 | 34.783 | 62.064 | 1.00 | 68.48 | ras |
| ATOM | 4039 | N | GLU | 49 | 104.724 | 35.991 | 63.625 | 1.00 | 67.16 | ras |
| ATOM | 4040 | CA | GLU | 49 | 103.999 | 34.836 | 64.146 | 1.00 | 69.14 | ras |
| ATOM | 4041 | CB | GLU | 49 | 103.741 | 34.995 | 65.644 | 1.00 | 70.93 | ras |
| ATOM | 4042 | CG | GLU | 49 | 103.246 | 33.725 | 66.313 | 1.00 | 77.78 | ras |
| ATOM | 4043 | CD | GLU | 49 | 103.031 | 33.897 | 67.804 | 1.00 | 82.68 | ras |
| ATOM | 4044 | OE1 | GLU | 49 | 101.885 | 33.708 | 68.267 | 1.00 | 87.24 | ras |
| ATOM | 4045 | OE2 | GLU | 49 | 104.009 | 34.217 | 68.514 | 1.00 | 84.60 | ras |
| ATOM | 4046 | C | GLU | 49 | 102.689 | 34.591 | 63.394 | 1.00 | 69.18 | ras |
| ATOM | 4047 | O | GLU | 49 | 101.742 | 35.373 | 63.492 | 1.00 | 72.39 | ras |
| ATOM | 4048 | N | THR | 50 | 102.656 | 33.498 | 62.638 | 1.00 | 67.02 | ras |
| ATOM | 4049 | CA | THR | 50 | 101.495 | 33.115 | 61.844 | 1.00 | 63.79 | ras |
| ATOM | 4050 | CB | THR | 50 | 101.910 | 32.105 | 60.739 | 1.00 | 64.24 | ras |
| ATOM | 4051 | OG1 | THR | 50 | 100.750 | 31.511 | 60.149 | 1.00 | 60.94 | ras |
| ATOM | 4052 | CG2 | THR | 50 | 102.819 | 31.020 | 61.308 | 1.00 | 68.55 | ras |

TABLE 3-continued

PDB Coordinates for the Ras-Sos Structure:
DATA SET FOR REFINED COORDINATES

| ATOM | 4053 | C   | THR | 50 | 100.360 | 32.557 | 62.710 | 1.00 | 62.19 | ras |
|------|------|-----|-----|----|---------|--------|--------|------|-------|-----|
| ATOM | 4054 | O   | THR | 50 | 100.610 | 31.839 | 63.683 | 1.00 | 61.68 | ras |
| ATOM | 4055 | N   | CYS | 51 | 99.118  | 32.909 | 62.362 | 1.00 | 57.84 | ras |
| ATOM | 4056 | CA  | CYS | 51 | 97.950  | 32.458 | 63.119 | 1.00 | 54.63 | ras |
| ATOM | 4057 | CB  | CYS | 51 | 97.744  | 33.337 | 64.347 | 1.00 | 51.75 | ras |
| ATOM | 4058 | SG  | CYS | 51 | 97.367  | 35.038 | 63.927 | 1.00 | 50.39 | ras |
| ATOM | 4059 | C   | CYS | 51 | 96.655  | 32.432 | 62.317 | 1.00 | 53.94 | ras |
| ATOM | 4060 | O   | CYS | 51 | 96.616  | 32.835 | 61.153 | 1.00 | 51.28 | ras |
| ATOM | 4061 | N   | LEU | 52 | 95.589  | 31.996 | 62.983 | 1.00 | 53.92 | ras |
| ATOM | 4062 | CA  | LEU | 52 | 94.265  | 31.879 | 62.380 | 1.00 | 53.64 | ras |
| ATOM | 4063 | CB  | LEU | 52 | 93.795  | 30.427 | 62.461 | 1.00 | 59.51 | ras |
| ATOM | 4064 | CG  | LEU | 52 | 92.411  | 30.096 | 61.902 | 1.00 | 63.64 | ras |
| ATOM | 4065 | CD1 | LEU | 52 | 92.448  | 30.136 | 60.382 | 1.00 | 64.77 | ras |
| ATOM | 4066 | CD2 | LEU | 52 | 91.990  | 28.719 | 62.395 | 1.00 | 66.37 | ras |
| ATOM | 4067 | C   | LEU | 52 | 93.213  | 32.781 | 63.027 | 1.00 | 50.40 | ras |
| ATOM | 4068 | O   | LEU | 52 | 92.938  | 32.688 | 64.229 | 1.00 | 47.98 | ras |
| ATOM | 4069 | N   | LEU | 53 | 92.586  | 33.604 | 62.195 | 1.00 | 46.63 | ras |
| ATOM | 4070 | CA  | LEU | 53 | 91.555  | 34.540 | 62.627 | 1.00 | 42.13 | ras |
| ATOM | 4071 | CB  | LEU | 53 | 91.707  | 35.854 | 61.849 | 1.00 | 39.29 | ras |
| ATOM | 4072 | CG  | LEU | 53 | 92.455  | 37.059 | 62.439 | 1.00 | 40.74 | ras |
| ATOM | 4073 | CD1 | LEU | 53 | 93.736  | 36.663 | 63.144 | 1.00 | 33.28 | ras |
| ATOM | 4074 | CD2 | LEU | 53 | 92.720  | 38.066 | 61.338 | 1.00 | 36.74 | ras |
| ATOM | 4075 | C   | LEU | 53 | 90.158  | 33.982 | 62.390 | 1.00 | 41.88 | ras |
| ATOM | 4076 | O   | LEU | 53 | 89.816  | 33.638 | 61.261 | 1.00 | 40.71 | ras |
| ATOM | 4077 | N   | ASP | 54 | 89.373  | 33.849 | 63.458 | 1.00 | 42.31 | ras |
| ATOM | 4078 | CA  | ASP | 54 | 87.991  | 33.370 | 63.349 | 1.00 | 41.58 | ras |
| ATOM | 4079 | CB  | ASP | 54 | 87.735  | 32.192 | 64.288 | 1.00 | 41.34 | ras |
| ATOM | 4080 | CG  | ASP | 54 | 86.407  | 31.504 | 64.012 | 1.00 | 45.99 | ras |
| ATOM | 4081 | OD1 | ASP | 54 | 85.353  | 32.128 | 64.224 | 1.00 | 48.67 | ras |
| ATOM | 4082 | OD2 | ASP | 54 | 86.407  | 30.334 | 63.580 | 1.00 | 51.70 | ras |
| ATOM | 4083 | C   | ASP | 54 | 87.109  | 34.573 | 63.712 | 1.00 | 42.80 | ras |
| ATOM | 4084 | O   | ASP | 54 | 86.997  | 34.957 | 64.878 | 1.00 | 44.58 | ras |
| ATOM | 4085 | N   | ILE | 55 | 86.455  | 35.138 | 62.705 | 1.00 | 41.61 | ras |
| ATOM | 4086 | CA  | ILE | 55 | 85.650  | 36.343 | 62.883 | 1.00 | 40.62 | ras |
| ATOM | 4087 | CB  | ILE | 55 | 86.085  | 37.374 | 61.823 | 1.00 | 39.83 | ras |
| ATOM | 4088 | CG2 | ILE | 55 | 85.603  | 38.762 | 62.197 | 1.00 | 38.10 | ras |
| ATOM | 4089 | CG1 | ILE | 55 | 87.616  | 37.359 | 61.710 | 1.00 | 33.50 | ras |
| ATOM | 4090 | CD1 | ILE | 55 | 88.138  | 37.951 | 60.456 | 1.00 | 30.99 | ras |
| ATOM | 4091 | C   | ILE | 55 | 84.125  | 36.200 | 62.857 | 1.00 | 39.70 | ras |
| ATOM | 4092 | O   | ILE | 55 | 83.550  | 35.840 | 61.829 | 1.00 | 44.14 | ras |
| ATOM | 4093 | N   | LEU | 56 | 83.480  | 36.523 | 63.982 | 1.00 | 38.25 | ras |
| ATOM | 4094 | CA  | LEU | 56 | 82.018  | 36.461 | 64.112 | 1.00 | 33.86 | ras |
| ATOM | 4095 | CB  | LEU | 56 | 81.591  | 35.958 | 65.492 | 1.00 | 31.30 | ras |
| ATOM | 4096 | CG  | LEU | 56 | 80.072  | 35.851 | 65.711 | 1.00 | 33.00 | ras |
| ATOM | 4097 | CD1 | LEU | 56 | 79.512  | 34.704 | 64.887 | 1.00 | 29.85 | ras |
| ATOM | 4098 | CD2 | LEU | 56 | 79.740  | 35.619 | 67.179 | 1.00 | 29.18 | ras |
| ATOM | 4099 | C   | LEU | 56 | 81.414  | 37.839 | 63.913 | 1.00 | 34.76 | ras |
| ATOM | 4100 | O   | LEU | 56 | 81.628  | 38.746 | 64.718 | 1.00 | 36.90 | ras |
| ATOM | 4101 | N   | ASP | 57 | 80.639  | 37.984 | 62.848 | 1.00 | 33.26 | ras |
| ATOM | 4102 | CA  | ASP | 57 | 79.990  | 39.248 | 62.546 | 1.00 | 28.29 | ras |
| ATOM | 4103 | CB  | ASP | 57 | 80.662  | 39.900 | 61.336 | 1.00 | 26.76 | ras |
| ATOM | 4104 | CG  | ASP | 57 | 80.012  | 41.200 | 60.930 | 1.00 | 28.13 | ras |
| ATOM | 4105 | OD1 | ASP | 57 | 79.118  | 41.700 | 61.642 | 1.00 | 32.83 | ras |
| ATOM | 4106 | OD2 | ASP | 57 | 80.400  | 41.738 | 59.883 | 1.00 | 35.05 | ras |
| ATOM | 4107 | C   | ASP | 57 | 78.529  | 38.954 | 62.265 | 1.00 | 27.17 | ras |
| ATOM | 4108 | O   | ASP | 57 | 78.143  | 38.750 | 61.122 | 1.00 | 29.15 | ras |
| ATOM | 4109 | N   | THR | 58 | 77.720  | 38.956 | 63.317 | 1.00 | 27.08 | ras |
| ATOM | 4110 | CA  | THR | 58 | 76.294  | 38.670 | 63.213 | 1.00 | 26.11 | ras |
| ATOM | 4111 | CB  | THR | 58 | 75.733  | 38.266 | 64.591 | 1.00 | 28.17 | ras |
| ATOM | 4112 | OG1 | THR | 58 | 75.918  | 39.332 | 65.526 | 1.00 | 28.22 | ras |
| ATOM | 4113 | CG2 | THR | 58 | 76.465  | 37.055 | 65.113 | 1.00 | 33.15 | ras |
| ATOM | 4114 | C   | THR | 58 | 75.417  | 39.771 | 62.588 | 1.00 | 26.73 | ras |
| ATOM | 4115 | O   | THR | 58 | 74.225  | 39.858 | 62.871 | 1.00 | 32.11 | ras |
| ATOM | 4116 | N   | ALA | 59 | 75.997  | 40.582 | 61.713 | 1.00 | 23.87 | ras |
| ATOM | 4117 | CA  | ALA | 59 | 75.270  | 41.655 | 61.037 | 1.00 | 28.47 | ras |
| ATOM | 4118 | CB  | ALA | 59 | 76.130  | 42.244 | 59.919 | 1.00 | 27.17 | ras |
| ATOM | 4119 | C   | ALA | 59 | 73.918  | 41.205 | 60.471 | 1.00 | 30.41 | ras |
| ATOM | 4120 | O   | ALA | 59 | 73.814  | 40.159 | 59.821 | 1.00 | 29.81 | ras |
| ATOM | 4121 | N   | GLY | 60 | 72.900  | 42.031 | 60.686 | 1.00 | 30.33 | ras |
| ATOM | 4122 | CA  | GLY | 60 | 71.568  | 41.713 | 60.213 | 1.00 | 26.72 | ras |
| ATOM | 4123 | C   | GLY | 60 | 70.714  | 41.156 | 61.335 | 1.00 | 30.07 | ras |
| ATOM | 4124 | O   | GLY | 60 | 69.480  | 41.202 | 61.264 | 1.00 | 30.03 | ras |
| ATOM | 4125 | N   | GLN | 61 | 71.362  | 40.652 | 62.385 | 1.00 | 29.87 | ras |
| ATOM | 4126 | CA  | GLN | 61 | 70.643  | 40.074 | 63.525 | 1.00 | 31.51 | ras |
| ATOM | 4127 | CB  | GLN | 61 | 71.283  | 38.754 | 63.947 | 1.00 | 30.16 | ras |
| ATOM | 4128 | CG  | GLN | 61 | 71.280  | 37.672 | 62.892 | 1.00 | 30.24 | ras |

TABLE 3-continued

PDB Coordinates for the Ras-Sos Structure:
DATA SET FOR REFINED COORDINATES

| ATOM | 4129 | CD  | GLN | 61 | 71.990 | 36.422 | 63.373 | 1.00 | 31.78 | ras |
|------|------|-----|-----|----|--------|--------|--------|------|-------|-----|
| ATOM | 4130 | OE1 | GLN | 61 | 71.628 | 35.845 | 64.396 | 1.00 | 27.94 | ras |
| ATOM | 4131 | NE2 | GLN | 61 | 73.021 | 36.010 | 62.646 | 1.00 | 32.53 | ras |
| ATOM | 4132 | C   | GLN | 61 | 70.498 | 40.981 | 64.761 | 1.00 | 30.65 | ras |
| ATOM | 4133 | O   | GLN | 61 | 70.185 | 40.494 | 65.853 | 1.00 | 30.29 | ras |
| ATOM | 4134 | N   | GLU | 62 | 70.671 | 42.289 | 64.577 | 1.00 | 26.11 | ras |
| ATOM | 4135 | CA  | GLU | 62 | 70.557 | 43.251 | 65.675 | 1.00 | 26.63 | ras |
| ATOM | 4136 | CB  | GLU | 62 | 70.781 | 44.673 | 65.168 | 1.00 | 24.29 | ras |
| ATOM | 4137 | CG  | GLU | 62 | 72.190 | 44.972 | 64.676 | 1.00 | 28.07 | ras |
| ATOM | 4138 | CD  | GLU | 62 | 72.530 | 44.266 | 63.384 | 1.00 | 31.19 | ras |
| ATOM | 4139 | OE1 | GLU | 62 | 71.660 | 44.187 | 62.489 | 1.00 | 32.48 | ras |
| ATOM | 4140 | OE2 | GLU | 62 | 73.677 | 43.803 | 63.263 | 1.00 | 32.78 | ras |
| ATOM | 4141 | C   | GLU | 62 | 69.260 | 43.235 | 66.490 | 1.00 | 27.11 | ras |
| ATOM | 4142 | O   | GLU | 62 | 69.267 | 43.618 | 67.656 | 1.00 | 32.25 | ras |
| ATOM | 4143 | N   | GLU | 63 | 68.143 | 42.841 | 65.890 | 1.00 | 25.19 | ras |
| ATOM | 4144 | CA  | GLU | 63 | 66.881 | 42.823 | 66.628 | 1.00 | 24.49 | ras |
| ATOM | 4145 | CB  | GLU | 63 | 65.673 | 42.708 | 65.693 | 1.00 | 26.72 | ras |
| ATOM | 4146 | CG  | GLU | 63 | 65.157 | 44.034 | 65.176 | 1.00 | 26.61 | ras |
| ATOM | 4147 | CD  | GLU | 63 | 64.461 | 44.853 | 66.241 | 1.00 | 41.08 | ras |
| ATOM | 4148 | OE1 | GLU | 63 | 64.746 | 46.068 | 66.299 | 1.00 | 49.94 | ras |
| ATOM | 4149 | OE2 | GLU | 63 | 63.620 | 44.302 | 67.002 | 1.00 | 37.46 | ras |
| ATOM | 4150 | C   | GLU | 63 | 66.862 | 41.709 | 67.644 | 1.00 | 23.86 | ras |
| ATOM | 4151 | O   | GLU | 63 | 66.058 | 41.722 | 68.578 | 1.00 | 25.54 | ras |
| ATOM | 4152 | N   | TYR | 64 | 67.715 | 40.717 | 67.438 | 1.00 | 20.48 | ras |
| ATOM | 4153 | CA  | TYR | 64 | 67.801 | 39.613 | 68.375 | 1.00 | 24.94 | ras |
| ATOM | 4154 | CB  | TYR | 64 | 68.430 | 38.391 | 67.701 | 1.00 | 24.96 | ras |
| ATOM | 4155 | CG  | TYR | 64 | 67.534 | 37.673 | 66.720 | 1.00 | 22.61 | ras |
| ATOM | 4156 | CD1 | TYR | 64 | 67.665 | 37.880 | 65.349 | 1.00 | 21.72 | ras |
| ATOM | 4157 | CE1 | TYR | 64 | 66.876 | 37.195 | 64.441 | 1.00 | 18.89 | ras |
| ATOM | 4158 | CD2 | TYR | 64 | 66.577 | 36.759 | 67.158 | 1.00 | 22.88 | ras |
| ATOM | 4159 | CE2 | TYR | 64 | 65.779 | 36.073 | 66.254 | 1.00 | 23.04 | ras |
| ATOM | 4160 | CZ  | TYR | 64 | 65.941 | 36.297 | 64.898 | 1.00 | 22.35 | ras |
| ATOM | 4161 | OH  | TYR | 64 | 65.187 | 35.602 | 63.990 | 1.00 | 29.93 | ras |
| ATOM | 4162 | C   | TYR | 64 | 68.690 | 40.124 | 69.512 | 1.00 | 27.20 | ras |
| ATOM | 4163 | O   | TYR | 64 | 69.792 | 39.620 | 69.742 | 1.00 | 26.43 | ras |
| ATOM | 4164 | N   | SER | 65 | 68.211 | 41.158 | 70.195 | 1.00 | 27.29 | ras |
| ATOM | 4165 | CA  | SER | 65 | 68.954 | 41.775 | 71.281 | 1.00 | 30.18 | ras |
| ATOM | 4166 | CB  | SER | 65 | 68.186 | 42.976 | 71.815 | 1.00 | 32.61 | ras |
| ATOM | 4167 | OG  | SER | 65 | 66.893 | 42.596 | 72.244 | 1.00 | 37.98 | ras |
| ATOM | 4168 | C   | SER | 65 | 69.319 | 40.822 | 72.421 | 1.00 | 29.46 | ras |
| ATOM | 4169 | O   | SER | 65 | 70.450 | 40.841 | 72.910 | 1.00 | 34.32 | ras |
| ATOM | 4170 | N   | ALA | 66 | 68.377 | 39.972 | 72.820 | 1.00 | 26.50 | ras |
| ATOM | 4171 | CA  | ALA | 66 | 68.601 | 39.023 | 73.902 | 1.00 | 21.32 | ras |
| ATOM | 4172 | CB  | ALA | 66 | 67.291 | 38.416 | 74.340 | 1.00 | 18.09 | ras |
| ATOM | 4173 | C   | ALA | 66 | 69.578 | 37.927 | 73.533 | 1.00 | 22.32 | ras |
| ATOM | 4174 | O   | ALA | 66 | 69.885 | 37.078 | 74.358 | 1.00 | 27.39 | ras |
| ATOM | 4175 | N   | MET | 67 | 70.093 | 37.969 | 72.309 | 1.00 | 24.71 | ras |
| ATOM | 4176 | CA  | MET | 67 | 71.020 | 36.948 | 71.823 | 1.00 | 27.27 | ras |
| ATOM | 4177 | CB  | MET | 67 | 70.590 | 36.525 | 70.414 | 1.00 | 25.56 | ras |
| ATOM | 4178 | CG  | MET | 67 | 70.761 | 35.061 | 70.112 | 1.00 | 32.40 | ras |
| ATOM | 4179 | SD  | MET | 67 | 69.945 | 34.548 | 68.593 | 1.00 | 34.90 | ras |
| ATOM | 4180 | CE  | MET | 67 | 68.339 | 33.964 | 69.301 | 1.00 | 37.21 | ras |
| ATOM | 4181 | C   | MET | 67 | 72.474 | 37.441 | 71.822 | 1.00 | 30.61 | ras |
| ATOM | 4182 | O   | MET | 67 | 73.403 | 36.675 | 71.565 | 1.00 | 31.76 | ras |
| ATOM | 4183 | N   | ARG | 68 | 72.660 | 38.713 | 72.161 | 1.00 | 32.17 | ras |
| ATOM | 4184 | CA  | ARG | 68 | 73.974 | 39.343 | 72.191 | 1.00 | 30.68 | ras |
| ATOM | 4185 | CB  | ARG | 68 | 73.818 | 40.837 | 72.460 | 1.00 | 29.43 | ras |
| ATOM | 4186 | CG  | ARG | 68 | 74.391 | 41.719 | 71.373 | 1.00 | 37.63 | ras |
| ATOM | 4187 | CD  | ARG | 68 | 73.557 | 42.979 | 71.183 | 1.00 | 41.31 | ras |
| ATOM | 4188 | NE  | ARG | 68 | 73.299 | 43.660 | 72.446 | 1.00 | 44.50 | ras |
| ATOM | 4189 | CZ  | ARG | 68 | 72.263 | 44.462 | 72.665 | 1.00 | 46.02 | ras |
| ATOM | 4190 | NH1 | ARG | 68 | 71.387 | 44.703 | 71.697 | 1.00 | 48.67 | ras |
| ATOM | 4191 | NH2 | ARG | 68 | 72.054 | 44.955 | 73.876 | 1.00 | 45.00 | ras |
| ATOM | 4192 | C   | ARG | 68 | 74.948 | 38.721 | 73.185 | 1.00 | 30.50 | ras |
| ATOM | 4193 | O   | ARG | 68 | 76.098 | 38.468 | 72.839 | 1.00 | 31.20 | ras |
| ATOM | 4194 | N   | ASP | 69 | 74.500 | 38.482 | 74.416 | 1.00 | 32.47 | ras |
| ATOM | 4195 | CA  | ASP | 69 | 75.369 | 37.879 | 75.430 | 1.00 | 31.42 | ras |
| ATOM | 4196 | CB  | ASP | 69 | 74.628 | 37.659 | 76.757 | 1.00 | 28.24 | ras |
| ATOM | 4197 | CG  | ASP | 69 | 74.353 | 38.947 | 77.505 | 1.00 | 32.96 | ras |
| ATOM | 4198 | OD1 | ASP | 69 | 75.000 | 39.976 | 77.207 | 1.00 | 33.92 | ras |
| ATOM | 4199 | OD2 | ASP | 69 | 73.479 | 38.930 | 78.403 | 1.00 | 34.59 | ras |
| ATOM | 4200 | C   | ASP | 69 | 75.896 | 36.547 | 74.917 | 1.00 | 32.41 | ras |
| ATOM | 4201 | O   | ASP | 69 | 77.092 | 36.294 | 74.969 | 1.00 | 33.04 | ras |
| ATOM | 4202 | N   | GLN | 70 | 75.006 | 35.723 | 74.370 | 1.00 | 35.04 | ras |
| ATOM | 4203 | CA  | GLN | 70 | 75.408 | 34.426 | 73.849 | 1.00 | 38.14 | ras |
| ATOM | 4204 | CB  | GLN | 70 | 74.235 | 33.696 | 73.198 | 1.00 | 40.88 | ras |

TABLE 3-continued

PDB Coordinates for the Ras-Sos Structure:
DATA SET FOR REFINED COORDINATES

| ATOM | 4205 | CG  | GLN | 70 | 74.566 | 32.241 | 72.898 | 1.00 | 48.54 | ras |
|------|------|-----|-----|----|--------|--------|--------|------|-------|-----|
| ATOM | 4206 | CD  | GLN | 70 | 73.596 | 31.601 | 71.949 | 1.00 | 52.73 | ras |
| ATOM | 4207 | OE1 | GLN | 70 | 72.459 | 31.315 | 72.312 | 1.00 | 60.15 | ras |
| ATOM | 4208 | NE2 | GLN | 70 | 74.039 | 31.366 | 70.716 | 1.00 | 54.95 | ras |
| ATOM | 4209 | C   | GLN | 70 | 76.526 | 34.570 | 72.827 | 1.00 | 38.95 | ras |
| ATOM | 4210 | O   | GLN | 70 | 77.591 | 33.968 | 72.978 | 1.00 | 41.60 | ras |
| ATOM | 4211 | N   | TYR | 71 | 76.274 | 35.371 | 71.795 | 1.00 | 36.90 | ras |
| ATOM | 4212 | CA  | TYR | 71 | 77.241 | 35.606 | 70.733 | 1.00 | 33.20 | ras |
| ATOM | 4213 | CB  | TYR | 71 | 76.651 | 36.550 | 69.678 | 1.00 | 35.41 | ras |
| ATOM | 4214 | CG  | TYR | 71 | 75.682 | 35.922 | 68.690 | 1.00 | 35.80 | ras |
| ATOM | 4215 | CD1 | TYR | 71 | 74.447 | 36.513 | 68.431 | 1.00 | 35.00 | ras |
| ATOM | 4216 | CE1 | TYR | 71 | 73.573 | 35.982 | 67.483 | 1.00 | 33.07 | ras |
| ATOM | 4217 | CD2 | TYR | 71 | 76.021 | 34.771 | 67.971 | 1.00 | 35.71 | ras |
| ATOM | 4218 | CE2 | TYR | 71 | 75.151 | 34.229 | 67.012 | 1.00 | 29.11 | ras |
| ATOM | 4219 | CZ  | TYR | 71 | 73.930 | 34.845 | 66.774 | 1.00 | 33.89 | ras |
| ATOM | 4220 | OH  | TYR | 71 | 73.076 | 34.354 | 65.813 | 1.00 | 25.97 | ras |
| ATOM | 4221 | C   | TYR | 71 | 78.558 | 36.188 | 71.252 | 1.00 | 32.72 | ras |
| ATOM | 4222 | O   | TYR | 71 | 79.643 | 35.743 | 70.856 | 1.00 | 27.77 | ras |
| ATOM | 4223 | N   | MET | 72 | 78.459 | 37.173 | 72.145 | 1.00 | 33.23 | ras |
| ATOM | 4224 | CA  | MET | 72 | 79.640 | 37.843 | 72.698 | 1.00 | 34.10 | ras |
| ATOM | 4225 | CB  | MET | 72 | 79.234 | 39.013 | 73.582 | 1.00 | 31.99 | ras |
| ATOM | 4226 | CG  | MET | 72 | 78.826 | 40.248 | 72.830 | 1.00 | 32.07 | ras |
| ATOM | 4227 | SD  | MET | 72 | 78.172 | 41.441 | 73.980 | 1.00 | 34.73 | ras |
| ATOM | 4228 | CE  | MET | 72 | 77.943 | 42.801 | 72.897 | 1.00 | 31.43 | ras |
| ATOM | 4229 | C   | MET | 72 | 80.524 | 36.922 | 73.497 | 1.00 | 34.87 | ras |
| ATOM | 4230 | O   | MET | 72 | 81.745 | 37.071 | 73.501 | 1.00 | 33.09 | ras |
| ATOM | 4231 | N   | ARG | 73 | 79.893 | 35.961 | 74.160 | 1.00 | 36.49 | ras |
| ATOM | 4232 | CA  | ARG | 73 | 80.599 | 35.007 | 74.995 | 1.00 | 39.03 | ras |
| ATOM | 4233 | CB  | ARG | 73 | 79.600 | 34.083 | 75.706 | 1.00 | 37.79 | ras |
| ATOM | 4234 | CG  | ARG | 73 | 80.260 | 32.948 | 76.475 | 1.00 | 47.27 | ras |
| ATOM | 4235 | CD  | ARG | 73 | 79.451 | 32.521 | 77.688 | 1.00 | 51.20 | ras |
| ATOM | 4236 | NE  | ARG | 73 | 79.364 | 33.578 | 78.690 | 1.00 | 46.38 | ras |
| ATOM | 4237 | CZ  | ARG | 73 | 78.217 | 34.051 | 79.154 | 1.00 | 46.68 | ras |
| ATOM | 4238 | NH1 | ARG | 73 | 78.204 | 35.018 | 80.056 | 1.00 | 49.23 | ras |
| ATOM | 4239 | NH2 | ARG | 73 | 77.082 | 33.539 | 78.719 | 1.00 | 43.64 | ras |
| ATOM | 4240 | C   | ARG | 73 | 81.621 | 34.194 | 74.218 | 1.00 | 38.81 | ras |
| ATOM | 4241 | O   | ARG | 73 | 82.700 | 33.891 | 74.728 | 1.00 | 40.67 | ras |
| ATOM | 4242 | N   | THR | 74 | 81.309 | 33.922 | 72.958 | 1.00 | 36.94 | ras |
| ATOM | 4243 | CA  | THR | 74 | 82.168 | 33.117 | 72.113 | 1.00 | 36.75 | ras |
| ATOM | 4244 | CB  | THR | 74 | 81.487 | 32.787 | 70.749 | 1.00 | 38.71 | ras |
| ATOM | 4245 | OG1 | THR | 74 | 81.452 | 33.952 | 69.910 | 1.00 | 41.36 | ras |
| ATOM | 4246 | CG2 | THR | 74 | 80.074 | 32.286 | 70.971 | 1.00 | 35.01 | ras |
| ATOM | 4247 | C   | THR | 74 | 83.557 | 33.666 | 71.834 | 1.00 | 36.59 | ras |
| ATOM | 4248 | O   | THR | 74 | 84.472 | 32.881 | 71.585 | 1.00 | 41.44 | ras |
| ATOM | 4249 | N   | GLY | 75 | 83.727 | 34.986 | 71.910 | 1.00 | 33.83 | ras |
| ATOM | 4250 | CA  | GLY | 75 | 85.018 | 35.581 | 71.588 | 1.00 | 37.35 | ras |
| ATOM | 4251 | C   | GLY | 75 | 86.015 | 35.931 | 72.679 | 1.00 | 41.01 | ras |
| ATOM | 4252 | O   | GLY | 75 | 85.665 | 36.038 | 73.855 | 1.00 | 43.05 | ras |
| ATOM | 4253 | N   | GLU | 76 | 87.271 | 36.121 | 72.280 | 1.00 | 40.18 | ras |
| ATOM | 4254 | CA  | GLU | 76 | 88.314 | 36.489 | 73.231 | 1.00 | 44.61 | ras |
| ATOM | 4255 | CB  | GLU | 76 | 89.449 | 35.451 | 73.253 | 1.00 | 49.52 | ras |
| ATOM | 4256 | CG  | GLU | 76 | 90.400 | 35.481 | 72.055 | 1.00 | 60.05 | ras |
| ATOM | 4257 | CD  | GLU | 76 | 91.589 | 34.525 | 72.210 | 1.00 | 67.62 | ras |
| ATOM | 4258 | OE1 | GLU | 76 | 91.878 | 33.775 | 71.248 | 1.00 | 70.96 | ras |
| ATOM | 4259 | OE2 | GLU | 76 | 92.242 | 34.529 | 73.284 | 1.00 | 68.27 | ras |
| ATOM | 4260 | C   | GLU | 76 | 88.860 | 37.885 | 72.929 | 1.00 | 42.71 | ras |
| ATOM | 4261 | O   | GLU | 76 | 89.724 | 38.391 | 73.647 | 1.00 | 42.81 | ras |
| ATOM | 4262 | N   | GLY | 77 | 88.326 | 38.504 | 71.878 | 1.00 | 36.86 | ras |
| ATOM | 4263 | CA  | GLY | 77 | 88.750 | 39.835 | 71.482 | 1.00 | 36.64 | ras |
| ATOM | 4264 | C   | GLY | 77 | 87.613 | 40.503 | 70.739 | 1.00 | 36.18 | ras |
| ATOM | 4265 | O   | GLY | 77 | 86.928 | 39.836 | 69.971 | 1.00 | 40.35 | ras |
| ATOM | 4266 | N   | PHE | 78 | 87.428 | 41.810 | 70.913 | 1.00 | 30.38 | ras |
| ATOM | 4267 | CA  | PHE | 78 | 86.318 | 42.491 | 70.254 | 1.00 | 27.89 | ras |
| ATOM | 4268 | CB  | PHE | 78 | 85.245 | 42.831 | 71.285 | 1.00 | 24.66 | ras |
| ATOM | 4269 | CG  | PHE | 78 | 84.737 | 41.648 | 72.039 | 1.00 | 23.18 | ras |
| ATOM | 4270 | CD1 | PHE | 78 | 83.526 | 41.063 | 71.700 | 1.00 | 23.43 | ras |
| ATOM | 4271 | CD2 | PHE | 78 | 85.482 | 41.093 | 73.068 | 1.00 | 21.73 | ras |
| ATOM | 4272 | CE1 | PHE | 78 | 83.066 | 39.935 | 72.375 | 1.00 | 26.18 | ras |
| ATOM | 4273 | CE2 | PHE | 78 | 85.032 | 39.968 | 73.749 | 1.00 | 20.04 | ras |
| ATOM | 4274 | CZ  | PHE | 78 | 83.827 | 39.388 | 73.403 | 1.00 | 22.43 | ras |
| ATOM | 4275 | C   | PHE | 78 | 86.613 | 43.747 | 69.438 | 1.00 | 29.88 | ras |
| ATOM | 4276 | O   | PHE | 78 | 87.522 | 44.507 | 69.748 | 1.00 | 31.55 | ras |
| ATOM | 4277 | N   | LEU | 79 | 85.837 | 43.944 | 68.374 | 1.00 | 29.54 | ras |
| ATOM | 4278 | CA  | LEU | 79 | 85.955 | 45.133 | 67.540 | 1.00 | 29.05 | ras |
| ATOM | 4279 | CB  | LEU | 79 | 86.139 | 44.776 | 66.073 | 1.00 | 28.26 | ras |
| ATOM | 4280 | CG  | LEU | 79 | 87.471 | 44.225 | 65.592 | 1.00 | 29.77 | ras |

TABLE 3-continued

PDB Coordinates for the Ras-Sos Structure:
DATA SET FOR REFINED COORDINATES

| ATOM | 4281 | CD1 | LEU | 79 | 87.354 | 42.719 | 65.469 | 1.00 | 31.86 | ras |
|---|---|---|---|---|---|---|---|---|---|---|
| ATOM | 4282 | CD2 | LEU | 79 | 87.807 | 44.843 | 64.241 | 1.00 | 23.15 | ras |
| ATOM | 4283 | C | LEU | 79 | 84.658 | 45.915 | 67.677 | 1.00 | 31.52 | ras |
| ATOM | 4284 | O | LEU | 79 | 83.625 | 45.496 | 67.150 | 1.00 | 37.59 | ras |
| ATOM | 4285 | N | CYS | 80 | 84.689 | 47.011 | 68.430 | 1.00 | 29.88 | ras |
| ATOM | 4286 | CA | CYS | 80 | 83.502 | 47.847 | 68.609 | 1.00 | 27.61 | ras |
| ATOM | 4287 | CB | CYS | 80 | 83.549 | 48.549 | 69.959 | 1.00 | 23.89 | ras |
| ATOM | 4288 | SG | CYS | 80 | 83.424 | 47.355 | 71.291 | 1.00 | 25.66 | ras |
| ATOM | 4289 | C | CYS | 80 | 83.476 | 48.828 | 67.449 | 1.00 | 26.74 | ras |
| ATOM | 4290 | O | CYS | 80 | 84.267 | 49.766 | 67.384 | 1.00 | 26.73 | ras |
| ATOM | 4291 | N | VAL | 81 | 82.570 | 48.579 | 66.516 | 1.00 | 25.28 | ras |
| ATOM | 4292 | CA | VAL | 81 | 82.484 | 49.380 | 65.313 | 1.00 | 25.48 | ras |
| ATOM | 4293 | CB | VAL | 81 | 82.357 | 48.467 | 64.084 | 1.00 | 26.03 | ras |
| ATOM | 4294 | CG1 | VAL | 81 | 82.543 | 49.264 | 62.816 | 1.00 | 33.94 | ras |
| ATOM | 4295 | CG2 | VAL | 81 | 83.357 | 47.336 | 64.157 | 1.00 | 23.51 | ras |
| ATOM | 4296 | C | VAL | 81 | 81.350 | 50.387 | 65.271 | 1.00 | 26.02 | ras |
| ATOM | 4297 | O | VAL | 81 | 80.216 | 50.080 | 65.646 | 1.00 | 32.11 | ras |
| ATOM | 4298 | N | PHE | 82 | 81.668 | 51.588 | 64.799 | 1.00 | 22.07 | ras |
| ATOM | 4299 | CA | PHE | 82 | 80.682 | 52.649 | 64.647 | 1.00 | 24.46 | ras |
| ATOM | 4300 | CB | PHE | 82 | 80.750 | 53.667 | 65.799 | 1.00 | 25.12 | ras |
| ATOM | 4301 | CG | PHE | 82 | 81.915 | 54.615 | 65.724 | 1.00 | 25.02 | ras |
| ATOM | 4302 | CD1 | PHE | 82 | 81.840 | 55.770 | 64.960 | 1.00 | 19.81 | ras |
| ATOM | 4303 | CD2 | PHE | 82 | 83.083 | 54.360 | 66.434 | 1.00 | 23.79 | ras |
| ATOM | 4304 | CE1 | PHE | 82 | 82.910 | 56.652 | 64.904 | 1.00 | 23.72 | ras |
| ATOM | 4305 | CE2 | PHE | 82 | 84.156 | 55.239 | 66.381 | 1.00 | 23.77 | ras |
| ATOM | 4306 | CZ | PHE | 82 | 84.066 | 56.388 | 65.613 | 1.00 | 22.22 | ras |
| ATOM | 4307 | C | PHE | 82 | 80.935 | 53.324 | 63.309 | 1.00 | 26.91 | ras |
| ATOM | 4308 | O | PHE | 82 | 82.019 | 53.189 | 62.733 | 1.00 | 31.81 | ras |
| ATOM | 4309 | N | ALA | 83 | 79.933 | 54.024 | 62.797 | 1.00 | 24.99 | ras |
| ATOM | 4310 | CA | ALA | 83 | 80.090 | 54.705 | 61.525 | 1.00 | 26.80 | ras |
| ATOM | 4311 | CB | ALA | 83 | 78.829 | 54.583 | 60.691 | 1.00 | 26.17 | ras |
| ATOM | 4312 | C | ALA | 83 | 80.420 | 56.167 | 61.769 | 1.00 | 31.19 | ras |
| ATOM | 4313 | O | ALA | 83 | 79.693 | 56.873 | 62.474 | 1.00 | 29.48 | ras |
| ATOM | 4314 | N | ILE | 84 | 81.509 | 56.611 | 61.152 | 1.00 | 33.20 | ras |
| ATOM | 4315 | CA | ILE | 84 | 81.992 | 57.979 | 61.252 | 1.00 | 34.13 | ras |
| ATOM | 4316 | CB | ILE | 84 | 83.335 | 58.087 | 60.509 | 1.00 | 36.54 | ras |
| ATOM | 4317 | CG2 | ILE | 84 | 83.556 | 59.464 | 59.901 | 1.00 | 40.45 | ras |
| ATOM | 4318 | CG1 | ILE | 84 | 84.454 | 57.718 | 61.472 | 1.00 | 37.91 | ras |
| ATOM | 4319 | CD1 | ILE | 84 | 85.761 | 57.530 | 60.800 | 1.00 | 43.98 | ras |
| ATOM | 4320 | C | ILE | 84 | 80.978 | 59.028 | 60.787 | 1.00 | 36.89 | ras |
| ATOM | 4321 | O | ILE | 84 | 81.094 | 60.206 | 61.130 | 1.00 | 40.46 | ras |
| ATOM | 4322 | N | ASN | 85 | 79.952 | 58.592 | 60.062 | 1.00 | 38.22 | ras |
| ATOM | 4323 | CA | ASN | 85 | 78.918 | 59.503 | 59.580 | 1.00 | 38.29 | ras |
| ATOM | 4324 | CB | ASN | 85 | 78.722 | 59.355 | 58.069 | 1.00 | 45.21 | ras |
| ATOM | 4325 | CG | ASN | 85 | 78.568 | 57.913 | 57.640 | 1.00 | 55.17 | ras |
| ATOM | 4326 | OD1 | ASN | 85 | 79.475 | 57.095 | 57.835 | 1.00 | 65.48 | ras |
| ATOM | 4327 | ND2 | ASN | 85 | 77.426 | 57.589 | 57.047 | 1.00 | 53.70 | ras |
| ATOM | 4328 | C | ASN | 85 | 77.585 | 59.339 | 60.298 | 1.00 | 35.88 | ras |
| ATOM | 4329 | O | ASN | 85 | 76.614 | 59.990 | 59.934 | 1.00 | 34.66 | ras |
| ATOM | 4330 | N | ASN | 86 | 77.543 | 58.484 | 61.322 | 1.00 | 34.66 | ras |
| ATOM | 4331 | CA | ASN | 86 | 76.324 | 58.249 | 62.101 | 1.00 | 30.45 | ras |
| ATOM | 4332 | CB | ASN | 86 | 75.774 | 56.846 | 61.819 | 1.00 | 23.84 | ras |
| ATOM | 4333 | CG | ASN | 86 | 74.356 | 56.648 | 62.349 | 1.00 | 29.04 | ras |
| ATOM | 4334 | OD1 | ASN | 86 | 74.145 | 56.140 | 63.458 | 1.00 | 32.05 | ras |
| ATOM | 4335 | ND2 | ASN | 86 | 73.375 | 57.027 | 61.548 | 1.00 | 28.73 | ras |
| ATOM | 4336 | C | ASN | 86 | 76.665 | 58.394 | 63.589 | 1.00 | 34.94 | ras |
| ATOM | 4337 | O | ASN | 86 | 77.196 | 57.469 | 64.208 | 1.00 | 38.78 | ras |
| ATOM | 4338 | N | THR | 87 | 76.340 | 59.550 | 64.165 | 1.00 | 35.03 | ras |
| ATOM | 4339 | CA | THR | 87 | 76.629 | 59.834 | 65.572 | 1.00 | 31.23 | ras |
| ATOM | 4340 | CB | THR | 87 | 76.187 | 61.269 | 65.950 | 1.00 | 31.51 | ras |
| ATOM | 4341 | OG1 | THR | 87 | 76.898 | 62.216 | 65.149 | 1.00 | 37.29 | ras |
| ATOM | 4342 | CG2 | THR | 87 | 76.478 | 61.560 | 67.391 | 1.00 | 26.65 | ras |
| ATOM | 4343 | C | THR | 87 | 75.991 | 58.845 | 66.537 | 1.00 | 31.90 | ras |
| ATOM | 4344 | O | THR | 87 | 76.601 | 58.474 | 67.542 | 1.00 | 33.13 | ras |
| ATOM | 4345 | N | LYS | 88 | 74.770 | 58.406 | 66.239 | 1.00 | 31.12 | ras |
| ATOM | 4346 | CA | LYS | 88 | 74.087 | 57.467 | 67.218 | 1.00 | 28.19 | ras |
| ATOM | 4347 | CB | LYS | 88 | 72.639 | 57.248 | 66.693 | 1.00 | 26.48 | ras |
| ATOM | 4348 | CG | LYS | 88 | 71.644 | 57.101 | 67.842 | 1.00 | 27.73 | ras |
| ATOM | 4349 | CD | LYS | 88 | 71.475 | 55.673 | 68.319 | 1.00 | 34.43 | ras |
| ATOM | 4350 | CE | LYS | 88 | 70.424 | 55.601 | 69.431 | 1.00 | 41.39 | ras |
| ATOM | 4351 | NZ | LYS | 88 | 70.234 | 54.215 | 69.984 | 1.00 | 42.22 | ras |
| ATOM | 4352 | C | LYS | 88 | 74.833 | 56.137 | 67.215 | 1.00 | 29.90 | ras |
| ATOM | 4353 | O | LYS | 88 | 74.840 | 55.508 | 68.276 | 1.00 | 26.26 | ras |
| ATOM | 4354 | N | SER | 89 | 75.480 | 55.725 | 66.118 | 1.00 | 24.30 | ras |
| ATOM | 4355 | CA | SER | 89 | 76.232 | 54.479 | 66.143 | 1.00 | 24.94 | ras |
| ATOM | 4356 | CB | SER | 89 | 76.613 | 53.999 | 64.732 | 1.00 | 26.40 | ras |

TABLE 3-continued

PDB Coordinates for the Ras-Sos Structure:
DATA SET FOR REFINED COORDINATES

| ATOM | 4357 | OG   | SER | 89 | 77.645 | 54.768 | 64.140 | 1.00 | 28.35 | ras |
|------|------|------|-----|----|--------|--------|--------|------|-------|-----|
| ATOM | 4358 | C    | SER | 89 | 77.465 | 54.680 | 67.015 | 1.00 | 26.50 | ras |
| ATOM | 4359 | O    | SER | 89 | 78.008 | 53.727 | 67.560 | 1.00 | 31.98 | ras |
| ATOM | 4360 | N    | PHE | 90 | 77.881 | 55.932 | 67.173 | 1.00 | 26.48 | ras |
| ATOM | 4361 | CA   | PHE | 90 | 79.027 | 56.252 | 68.010 | 1.00 | 29.25 | ras |
| ATOM | 4362 | CB   | PHE | 90 | 79.606 | 57.616 | 67.648 | 1.00 | 29.36 | ras |
| ATOM | 4363 | CG   | PHE | 90 | 80.826 | 57.989 | 68.432 | 1.00 | 27.23 | ras |
| ATOM | 4364 | CD1  | PHE | 90 | 80.812 | 59.102 | 69.277 | 1.00 | 28.08 | ras |
| ATOM | 4365 | CD2  | PHE | 90 | 81.996 | 57.250 | 68.314 | 1.00 | 30.70 | ras |
| ATOM | 4366 | CE1  | PHE | 90 | 81.951 | 59.483 | 69.996 | 1.00 | 22.23 | ras |
| ATOM | 4367 | CE2  | PHE | 90 | 83.149 | 57.617 | 69.027 | 1.00 | 35.26 | ras |
| ATOM | 4368 | CZ   | PHE | 90 | 83.119 | 58.742 | 69.872 | 1.00 | 31.38 | ras |
| ATOM | 4369 | C    | PHE | 90 | 78.608 | 56.248 | 69.466 | 1.00 | 30.19 | ras |
| ATOM | 4370 | O    | PHE | 90 | 79.251 | 55.603 | 70.293 | 1.00 | 31.67 | ras |
| ATOM | 4371 | N    | GLU | 91 | 77.510 | 56.933 | 69.774 | 1.00 | 30.50 | ras |
| ATOM | 4372 | CA   | GLU | 91 | 77.028 | 56.997 | 71.159 | 1.00 | 32.87 | ras |
| ATOM | 4373 | CB   | GLU | 91 | 75.874 | 57.993 | 71.294 | 1.00 | 33.18 | ras |
| ATOM | 4374 | CG   | GLU | 91 | 76.214 | 59.398 | 70.815 | 1.00 | 39.61 | ras |
| ATOM | 4375 | CD   | GLU | 91 | 74.991 | 60.287 | 70.610 | 1.00 | 45.97 | ras |
| ATOM | 4376 | OE1  | GLU | 91 | 75.188 | 61.512 | 70.431 | 1.00 | 45.72 | ras |
| ATOM | 4377 | OE2  | GLU | 91 | 73.845 | 59.768 | 70.618 | 1.00 | 47.57 | ras |
| ATOM | 4378 | C    | GLU | 91 | 76.605 | 55.636 | 71.702 | 1.00 | 30.20 | ras |
| ATOM | 4379 | O    | GLU | 91 | 76.537 | 55.454 | 72.908 | 1.00 | 32.09 | ras |
| ATOM | 4380 | N    | ASP | 92 | 76.344 | 54.685 | 70.805 | 1.00 | 28.72 | ras |
| ATOM | 4381 | CA   | ASP | 92 | 75.940 | 53.329 | 71.179 | 1.00 | 27.86 | ras |
| ATOM | 4382 | CB   | ASP | 92 | 75.345 | 52.598 | 69.971 | 1.00 | 30.79 | ras |
| ATOM | 4383 | CG   | ASP | 92 | 73.861 | 52.871 | 69.768 | 1.00 | 30.60 | ras |
| ATOM | 4384 | OD1  | ASP | 92 | 73.254 | 53.654 | 70.528 | 1.00 | 27.98 | ras |
| ATOM | 4385 | OD2  | ASP | 92 | 73.299 | 52.279 | 68.825 | 1.00 | 33.59 | ras |
| ATOM | 4386 | C    | ASP | 92 | 77.102 | 52.494 | 71.699 | 1.00 | 28.76 | ras |
| ATOM | 4387 | O    | ASP | 92 | 76.896 | 51.460 | 72.341 | 1.00 | 31.38 | ras |
| ATOM | 4388 | N    | ILE | 93 | 78.320 | 52.925 | 71.387 | 1.00 | 29.13 | ras |
| ATOM | 4389 | CA   | ILE | 93 | 79.524 | 52.213 | 71.793 | 1.00 | 24.79 | ras |
| ATOM | 4390 | CB   | ILE | 93 | 80.789 | 52.944 | 71.331 | 1.00 | 20.41 | ras |
| ATOM | 4391 | CG2  | ILE | 93 | 82.021 | 52.310 | 71.950 | 1.00 | 16.70 | ras |
| ATOM | 4392 | CG1  | ILE | 93 | 80.873 | 52.917 | 69.804 | 1.00 | 19.72 | ras |
| ATOM | 4393 | CD1  | ILE | 93 | 80.860 | 51.509 | 69.207 | 1.00 | 14.18 | ras |
| ATOM | 4394 | C    | ILE | 93 | 79.621 | 51.963 | 73.281 | 1.00 | 27.14 | ras |
| ATOM | 4395 | O    | ILE | 93 | 79.861 | 50.830 | 73.710 | 1.00 | 28.78 | ras |
| ATOM | 4396 | N    | HIS | 94 | 79.408 | 53.006 | 74.074 | 1.00 | 27.42 | ras |
| ATOM | 4397 | CA   | HIS | 94 | 79.508 | 52.851 | 75.515 | 1.00 | 28.70 | ras |
| ATOM | 4398 | CB   | HIS | 94 | 79.119 | 54.135 | 76.250 | 1.00 | 30.71 | ras |
| ATOM | 4399 | CG   | HIS | 94 | 79.336 | 54.055 | 77.727 | 1.00 | 36.51 | ras |
| ATOM | 4400 | CD2  | HIS | 94 | 78.480 | 53.781 | 78.741 | 1.00 | 38.54 | ras |
| ATOM | 4401 | ND1  | HIS | 94 | 80.587 | 54.149 | 78.297 | 1.00 | 38.15 | ras |
| ATOM | 4402 | CE1  | HIS | 94 | 80.495 | 53.925 | 79.595 | 1.00 | 39.37 | ras |
| ATOM | 4403 | NE2  | HIS | 94 | 79.227 | 53.698 | 79.890 | 1.00 | 42.28 | ras |
| ATOM | 4404 | C    | HIS | 94 | 78.728 | 51.664 | 76.070 | 1.00 | 27.17 | ras |
| ATOM | 4405 | O    | HIS | 94 | 79.265 | 50.878 | 76.840 | 1.00 | 29.71 | ras |
| ATOM | 4406 | N    | GLN | 95 | 77.488 | 51.492 | 75.636 | 1.00 | 30.36 | ras |
| ATOM | 4407 | CA   | GLN | 95 | 76.679 | 50.389 | 76.136 | 1.00 | 32.04 | ras |
| ATOM | 4408 | CB   | GLN | 95 | 75.201 | 50.614 | 75.806 | 1.00 | 31.39 | ras |
| ATOM | 4409 | CG   | GLN | 95 | 74.257 | 49.550 | 76.347 | 1.00 | 44.63 | ras |
| ATOM | 4410 | CD   | GLN | 95 | 74.437 | 49.249 | 77.842 | 1.00 | 50.89 | ras |
| ATOM | 4411 | OE1  | GLN | 95 | 74.808 | 50.128 | 78.644 | 1.00 | 49.09 | ras |
| ATOM | 4412 | NE2  | GLN | 95 | 74.159 | 47.995 | 78.221 | 1.00 | 46.16 | ras |
| ATOM | 4413 | C    | GLN | 95 | 77.174 | 49.014 | 75.667 | 1.00 | 32.52 | ras |
| ATOM | 4414 | O    | GLN | 95 | 77.135 | 48.035 | 76.431 | 1.00 | 26.20 | ras |
| ATOM | 4415 | N    | TYR | 96 | 77.665 | 48.939 | 74.431 | 1.00 | 32.01 | ras |
| ATOM | 4416 | CA   | TYR | 96 | 78.180 | 47.670 | 73.923 | 1.00 | 31.34 | ras |
| ATOM | 4417 | CB   | TYR | 96 | 78.611 | 47.785 | 72.461 | 1.00 | 34.45 | ras |
| ATOM | 4418 | CG   | TYR | 96 | 77.460 | 47.839 | 71.488 | 1.00 | 37.62 | ras |
| ATOM | 4419 | CD1  | TYR | 96 | 76.487 | 46.844 | 71.478 | 1.00 | 37.68 | ras |
| ATOM | 4420 | CE1  | TYR | 96 | 75.415 | 46.897 | 70.596 | 1.00 | 41.39 | ras |
| ATOM | 4421 | CD2  | TYR | 96 | 77.335 | 48.891 | 70.584 | 1.00 | 39.08 | ras |
| ATOM | 4422 | CE2  | TYR | 96 | 76.264 | 48.952 | 69.698 | 1.00 | 39.51 | ras |
| ATOM | 4423 | CZ   | TYR | 96 | 75.306 | 47.954 | 69.712 | 1.00 | 40.78 | ras |
| ATOM | 4424 | OH   | TYR | 96 | 74.219 | 48.028 | 68.866 | 1.00 | 43.01 | ras |
| ATOM | 4425 | C    | TYR | 96 | 79.356 | 47.234 | 74.785 | 1.00 | 31.83 | ras |
| ATOM | 4426 | O    | TYR | 96 | 79.403 | 46.086 | 75.238 | 1.00 | 28.42 | ras |
| ATOM | 4427 | N    | ARG | 97 | 80.270 | 48.169 | 75.062 | 1.00 | 30.31 | ras |
| ATOM | 4428 | CA   | ARG | 97 | 81.433 | 47.859 | 75.890 | 1.00 | 30.06 | ras |
| ATOM | 4429 | CB   | ARG | 97 | 82.374 | 49.057 | 75.989 | 1.00 | 28.86 | ras |
| ATOM | 4430 | CG   | ARG | 97 | 83.635 | 48.791 | 76.799 | 1.00 | 27.81 | ras |
| ATOM | 4431 | CD   | ARG | 97 | 84.519 | 50.014 | 76.840 | 1.00 | 31.48 | ras |
| ATOM | 4432 | NE   | ARG | 97 | 85.164 | 50.159 | 78.141 | 1.00 | 40.53 | ras |

TABLE 3-continued

PDB Coordinates for the Ras-Sos Structure:
DATA SET FOR REFINED COORDINATES

| ATOM | 4433 | CZ  | ARG | 97  | 86.275 | 49.523 | 78.504 | 1.00 | 48.88 | ras |
|------|------|-----|-----|-----|--------|--------|--------|------|-------|-----|
| ATOM | 4434 | NH1 | ARG | 97  | 86.780 | 49.715 | 79.716 | 1.00 | 50.67 | ras |
| ATOM | 4435 | NH2 | ARG | 97  | 86.894 | 48.708 | 77.653 | 1.00 | 49.76 | ras |
| ATOM | 4436 | C   | ARG | 97  | 81.023 | 47.358 | 77.281 | 1.00 | 30.07 | ras |
| ATOM | 4437 | O   | ARG | 97  | 81.546 | 46.354 | 77.757 | 1.00 | 32.73 | ras |
| ATOM | 4438 | N   | GLU | 98  | 80.054 | 48.020 | 77.906 | 1.00 | 27.73 | ras |
| ATOM | 4439 | CA  | GLU | 98  | 79.577 | 47.596 | 79.219 | 1.00 | 30.13 | ras |
| ATOM | 4440 | CB  | GLU | 98  | 78.449 | 48.501 | 79.718 | 1.00 | 33.28 | ras |
| ATOM | 4441 | CG  | GLU | 98  | 78.864 | 49.924 | 80.081 | 1.00 | 44.17 | ras |
| ATOM | 4442 | CD  | GLU | 98  | 79.895 | 49.977 | 81.195 | 1.00 | 44.23 | ras |
| ATOM | 4443 | OE1 | GLU | 98  | 80.986 | 50.543 | 80.961 | 1.00 | 45.22 | ras |
| ATOM | 4444 | OE2 | GLU | 98  | 79.614 | 49.439 | 82.290 | 1.00 | 43.73 | ras |
| ATOM | 4445 | C   | GLU | 98  | 79.043 | 46.185 | 79.141 | 1.00 | 32.04 | ras |
| ATOM | 4446 | O   | GLU | 98  | 79.082 | 45.452 | 80.113 | 1.00 | 38.13 | ras |
| ATOM | 4447 | N   | GLN | 99  | 78.512 | 45.816 | 77.981 | 1.00 | 36.53 | ras |
| ATOM | 4448 | CA  | GLN | 99  | 77.953 | 44.485 | 77.793 | 1.00 | 35.89 | ras |
| ATOM | 4449 | CB  | GLN | 99  | 77.015 | 44.473 | 76.595 | 1.00 | 38.24 | ras |
| ATOM | 4450 | CG  | GLN | 99  | 75.973 | 43.392 | 76.662 | 1.00 | 41.78 | ras |
| ATOM | 4451 | CD  | GLN | 99  | 74.896 | 43.566 | 75.630 | 1.00 | 44.64 | ras |
| ATOM | 4452 | OE1 | GLN | 99  | 74.762 | 44.633 | 75.022 | 1.00 | 46.06 | ras |
| ATOM | 4453 | NE2 | GLN | 99  | 74.104 | 42.518 | 75.429 | 1.00 | 45.44 | ras |
| ATOM | 4454 | C   | GLN | 99  | 79.052 | 43.449 | 77.620 | 1.00 | 35.19 | ras |
| ATOM | 4455 | O   | GLN | 99  | 78.973 | 42.356 | 78.177 | 1.00 | 36.49 | ras |
| ATOM | 4456 | N   | ILE | 100 | 80.073 | 43.792 | 76.845 | 1.00 | 30.37 | ras |
| ATOM | 4457 | CA  | ILE | 100 | 81.188 | 42.886 | 76.643 | 1.00 | 31.19 | ras |
| ATOM | 4458 | CB  | ILE | 100 | 82.190 | 43.472 | 75.638 | 1.00 | 30.53 | ras |
| ATOM | 4459 | CG2 | ILE | 100 | 83.362 | 42.529 | 75.448 | 1.00 | 27.62 | ras |
| ATOM | 4460 | CG1 | ILE | 100 | 81.495 | 43.710 | 74.298 | 1.00 | 33.21 | ras |
| ATOM | 4461 | CD1 | ILE | 100 | 82.282 | 44.567 | 73.336 | 1.00 | 33.34 | ras |
| ATOM | 4462 | C   | ILE | 100 | 81.869 | 42.627 | 78.002 | 1.00 | 33.76 | ras |
| ATOM | 4463 | O   | ILE | 100 | 82.098 | 41.470 | 78.375 | 1.00 | 36.80 | ras |
| ATOM | 4464 | N   | LYS | 101 | 82.128 | 43.698 | 78.757 | 1.00 | 28.56 | ras |
| ATOM | 4465 | CA  | LYS | 101 | 82.764 | 43.596 | 80.074 | 1.00 | 29.64 | ras |
| ATOM | 4466 | CB  | LYS | 101 | 82.896 | 44.983 | 80.716 | 1.00 | 29.57 | ras |
| ATOM | 4467 | CG  | LYS | 101 | 84.083 | 45.806 | 80.229 | 1.00 | 32.63 | ras |
| ATOM | 4468 | CD  | LYS | 101 | 83.869 | 47.294 | 80.472 | 1.00 | 39.41 | ras |
| ATOM | 4469 | CE  | LYS | 101 | 83.726 | 47.620 | 81.954 | 1.00 | 44.50 | ras |
| ATOM | 4470 | NZ  | LYS | 101 | 83.340 | 49.041 | 82.177 | 1.00 | 46.05 | ras |
| ATOM | 4471 | C   | LYS | 101 | 81.977 | 42.678 | 81.007 | 1.00 | 28.98 | ras |
| ATOM | 4472 | O   | LYS | 101 | 82.541 | 41.847 | 81.709 | 1.00 | 27.85 | ras |
| ATOM | 4473 | N   | ARG | 102 | 80.662 | 42.833 | 80.997 | 1.00 | 28.49 | ras |
| ATOM | 4474 | CA  | ARG | 102 | 79.800 | 42.022 | 81.828 | 1.00 | 26.91 | ras |
| ATOM | 4475 | CB  | ARG | 102 | 78.375 | 42.569 | 81.795 | 1.00 | 23.08 | ras |
| ATOM | 4476 | CG  | ARG | 102 | 77.375 | 41.695 | 82.513 | 1.00 | 24.75 | ras |
| ATOM | 4477 | CD  | ARG | 102 | 76.545 | 42.490 | 83.493 | 1.00 | 35.90 | ras |
| ATOM | 4478 | NE  | ARG | 102 | 75.557 | 43.346 | 82.853 | 1.00 | 42.73 | ras |
| ATOM | 4479 | CZ  | ARG | 102 | 75.035 | 44.433 | 83.415 | 1.00 | 49.72 | ras |
| ATOM | 4480 | NH1 | ARG | 102 | 74.136 | 45.148 | 82.758 | 1.00 | 58.43 | ras |
| ATOM | 4481 | NH2 | ARG | 102 | 75.420 | 44.822 | 84.622 | 1.00 | 48.40 | ras |
| ATOM | 4482 | C   | ARG | 102 | 79.799 | 40.537 | 81.461 | 1.00 | 29.95 | ras |
| ATOM | 4483 | O   | ARG | 102 | 79.853 | 39.700 | 82.351 | 1.00 | 34.44 | ras |
| ATOM | 4484 | N   | VAL | 103 | 79.768 | 40.200 | 80.171 | 1.00 | 30.73 | ras |
| ATOM | 4485 | CA  | VAL | 103 | 79.722 | 38.788 | 79.789 | 1.00 | 37.32 | ras |
| ATOM | 4486 | CB  | VAL | 103 | 79.224 | 38.564 | 78.339 | 1.00 | 37.36 | ras |
| ATOM | 4487 | CG1 | VAL | 103 | 77.974 | 39.367 | 78.097 | 1.00 | 45.16 | ras |
| ATOM | 4488 | CG2 | VAL | 103 | 80.290 | 38.916 | 77.334 | 1.00 | 46.10 | ras |
| ATOM | 4489 | C   | VAL | 103 | 81.016 | 38.034 | 80.011 | 1.00 | 36.20 | ras |
| ATOM | 4490 | O   | VAL | 103 | 81.003 | 36.857 | 80.367 | 1.00 | 35.19 | ras |
| ATOM | 4491 | N   | LYS | 104 | 82.132 | 38.717 | 79.817 | 1.00 | 38.07 | ras |
| ATOM | 4492 | CA  | LYS | 104 | 83.427 | 38.096 | 80.007 | 1.00 | 40.22 | ras |
| ATOM | 4493 | CB  | LYS | 104 | 84.423 | 38.657 | 78.993 | 1.00 | 39.84 | ras |
| ATOM | 4494 | CG  | LYS | 104 | 83.934 | 38.579 | 77.544 | 1.00 | 43.17 | ras |
| ATOM | 4495 | CD  | LYS | 104 | 84.771 | 37.627 | 76.690 | 1.00 | 44.51 | ras |
| ATOM | 4496 | CE  | LYS | 104 | 84.602 | 36.174 | 77.104 | 1.00 | 46.30 | ras |
| ATOM | 4497 | NZ  | LYS | 104 | 85.511 | 35.270 | 76.341 | 1.00 | 45.22 | ras |
| ATOM | 4498 | C   | LYS | 104 | 83.916 | 38.310 | 81.443 | 1.00 | 41.88 | ras |
| ATOM | 4499 | O   | LYS | 104 | 85.043 | 37.943 | 81.774 | 1.00 | 44.68 | ras |
| ATOM | 4500 | N   | ASP | 105 | 83.052 | 38.890 | 82.283 | 1.00 | 40.36 | ras |
| ATOM | 4501 | CA  | ASP | 105 | 83.338 | 39.172 | 83.697 | 1.00 | 42.95 | ras |
| ATOM | 4502 | CB  | ASP | 105 | 83.101 | 37.914 | 84.535 | 1.00 | 43.72 | ras |
| ATOM | 4503 | CG  | ASP | 105 | 83.095 | 38.195 | 86.031 | 1.00 | 48.68 | ras |
| ATOM | 4504 | OD1 | ASP | 105 | 82.581 | 39.254 | 86.454 | 1.00 | 51.36 | ras |
| ATOM | 4505 | OD2 | ASP | 105 | 83.590 | 37.341 | 86.792 | 1.00 | 52.22 | ras |
| ATOM | 4506 | C   | ASP | 105 | 84.759 | 39.703 | 83.925 | 1.00 | 43.92 | ras |
| ATOM | 4507 | O   | ASP | 105 | 85.551 | 39.093 | 84.646 | 1.00 | 43.78 | ras |
| ATOM | 4508 | N   | SER | 106 | 85.058 | 40.851 | 83.324 | 1.00 | 42.62 | ras |

TABLE 3-continued

PDB Coordinates for the Ras-Sos Structure:
DATA SET FOR REFINED COORDINATES

| ATOM | 4509 | CA  | SER | 106 | 86.383 | 41.454 | 83.406 | 1.00 | 44.60 | ras |
|------|------|-----|-----|-----|--------|--------|--------|------|-------|-----|
| ATOM | 4510 | CB  | SER | 106 | 87.352 | 40.660 | 82.519 | 1.00 | 41.74 | ras |
| ATOM | 4511 | OG  | SER | 106 | 88.526 | 41.409 | 82.238 | 1.00 | 50.25 | ras |
| ATOM | 4512 | C   | SER | 106 | 86.382 | 42.915 | 82.963 | 1.00 | 45.68 | ras |
| ATOM | 4513 | O   | SER | 106 | 85.709 | 43.270 | 81.995 | 1.00 | 45.22 | ras |
| ATOM | 4514 | N   | ASP | 107 | 87.159 | 43.751 | 83.651 | 1.00 | 47.39 | ras |
| ATOM | 4515 | CA  | ASP | 107 | 87.239 | 45.165 | 83.300 | 1.00 | 50.41 | ras |
| ATOM | 4516 | CB  | ASP | 107 | 87.566 | 46.036 | 84.514 | 1.00 | 56.56 | ras |
| ATOM | 4517 | CG  | ASP | 107 | 86.378 | 46.201 | 85.452 | 1.00 | 65.47 | ras |
| ATOM | 4518 | OD1 | ASP | 107 | 86.594 | 46.243 | 86.680 | 1.00 | 70.32 | ras |
| ATOM | 4519 | OD2 | ASP | 107 | 85.225 | 46.285 | 84.969 | 1.00 | 68.20 | ras |
| ATOM | 4520 | C   | ASP | 107 | 88.212 | 45.434 | 82.169 | 1.00 | 50.18 | ras |
| ATOM | 4521 | O   | ASP | 107 | 88.189 | 46.511 | 81.580 | 1.00 | 51.60 | ras |
| ATOM | 4522 | N   | ASP | 108 | 89.094 | 44.481 | 81.883 | 1.00 | 49.01 | ras |
| ATOM | 4523 | CA  | ASP | 108 | 90.017 | 44.666 | 80.771 | 1.00 | 52.07 | ras |
| ATOM | 4524 | CB  | ASP | 108 | 91.441 | 45.093 | 81.211 | 1.00 | 57.29 | ras |
| ATOM | 4525 | CG  | ASP | 108 | 92.236 | 43.980 | 81.880 | 1.00 | 64.88 | ras |
| ATOM | 4526 | OD1 | ASP | 108 | 91.729 | 43.353 | 82.835 | 1.00 | 73.22 | ras |
| ATOM | 4527 | OD2 | ASP | 108 | 93.393 | 43.751 | 81.463 | 1.00 | 64.57 | ras |
| ATOM | 4528 | C   | ASP | 108 | 89.989 | 43.458 | 79.843 | 1.00 | 50.11 | ras |
| ATOM | 4529 | O   | ASP | 108 | 90.569 | 42.404 | 80.121 | 1.00 | 51.00 | ras |
| ATOM | 4530 | N   | VAL | 109 | 89.182 | 43.608 | 78.795 | 1.00 | 46.58 | ras |
| ATOM | 4531 | CA  | VAL | 109 | 88.974 | 42.596 | 77.769 | 1.00 | 38.54 | ras |
| ATOM | 4532 | CB  | VAL | 109 | 87.462 | 42.420 | 77.483 | 1.00 | 36.56 | ras |
| ATOM | 4533 | CG1 | VAL | 109 | 87.226 | 41.340 | 76.456 | 1.00 | 39.60 | ras |
| ATOM | 4534 | CG2 | VAL | 109 | 86.733 | 42.072 | 78.750 | 1.00 | 40.29 | ras |
| ATOM | 4535 | C   | VAL | 109 | 89.645 | 43.129 | 76.524 | 1.00 | 33.51 | ras |
| ATOM | 4536 | O   | VAL | 109 | 89.540 | 44.311 | 76.229 | 1.00 | 36.22 | ras |
| ATOM | 4537 | N   | PRO | 110 | 90.381 | 42.280 | 75.798 | 1.00 | 31.92 | ras |
| ATOM | 4538 | CD  | PRO | 110 | 90.717 | 40.869 | 76.052 | 1.00 | 31.46 | ras |
| ATOM | 4539 | CA  | PRO | 110 | 91.043 | 42.758 | 74.589 | 1.00 | 32.74 | ras |
| ATOM | 4540 | CB  | PRO | 110 | 91.750 | 41.506 | 74.065 | 1.00 | 28.50 | ras |
| ATOM | 4541 | CG  | PRO | 110 | 91.997 | 40.710 | 75.283 | 1.00 | 29.23 | ras |
| ATOM | 4542 | C   | PRO | 110 | 90.016 | 43.265 | 73.576 | 1.00 | 36.53 | ras |
| ATOM | 4543 | O   | PRO | 110 | 89.223 | 42.496 | 73.040 | 1.00 | 40.80 | ras |
| ATOM | 4544 | N   | MET | 111 | 89.980 | 44.574 | 73.377 | 1.00 | 38.62 | ras |
| ATOM | 4545 | CA  | MET | 111 | 89.065 | 45.147 | 72.415 | 1.00 | 34.61 | ras |
| ATOM | 4546 | CB  | MET | 111 | 87.697 | 45.461 | 73.032 | 1.00 | 36.33 | ras |
| ATOM | 4547 | CG  | MET | 111 | 87.577 | 46.718 | 73.877 | 1.00 | 41.05 | ras |
| ATOM | 4548 | SD  | MET | 111 | 85.827 | 46.981 | 74.348 | 1.00 | 42.89 | ras |
| ATOM | 4549 | CE  | MET | 111 | 85.554 | 45.562 | 75.348 | 1.00 | 33.81 | ras |
| ATOM | 4550 | C   | MET | 111 | 89.684 | 46.372 | 71.791 | 1.00 | 34.96 | ras |
| ATOM | 4551 | O   | MET | 111 | 90.652 | 46.929 | 72.317 | 1.00 | 37.97 | ras |
| ATOM | 4552 | N   | VAL | 112 | 89.134 | 46.758 | 70.647 | 1.00 | 31.93 | ras |
| ATOM | 4553 | CA  | VAL | 112 | 89.605 | 47.905 | 69.904 | 1.00 | 28.79 | ras |
| ATOM | 4554 | CB  | VAL | 112 | 90.528 | 47.428 | 68.758 | 1.00 | 26.36 | ras |
| ATOM | 4555 | CG1 | VAL | 112 | 89.726 | 46.958 | 67.561 | 1.00 | 26.90 | ras |
| ATOM | 4556 | CG2 | VAL | 112 | 91.495 | 48.498 | 68.385 | 1.00 | 36.07 | ras |
| ATOM | 4557 | C   | VAL | 112 | 88.385 | 48.660 | 69.369 | 1.00 | 28.06 | ras |
| ATOM | 4558 | O   | VAL | 112 | 87.345 | 48.061 | 69.125 | 1.00 | 34.41 | ras |
| ATOM | 4559 | N   | LEU | 113 | 88.476 | 49.983 | 69.294 | 1.00 | 28.07 | ras |
| ATOM | 4560 | CA  | LEU | 113 | 87.386 | 50.819 | 68.781 | 1.00 | 25.02 | ras |
| ATOM | 4561 | CB  | LEU | 113 | 87.283 | 52.107 | 69.595 | 1.00 | 21.40 | ras |
| ATOM | 4562 | CG  | LEU | 113 | 86.373 | 53.212 | 69.069 | 1.00 | 19.88 | ras |
| ATOM | 4563 | CD1 | LEU | 113 | 84.932 | 52.850 | 69.288 | 1.00 | 23.94 | ras |
| ATOM | 4564 | CD2 | LEU | 113 | 86.671 | 54.478 | 69.817 | 1.00 | 23.55 | ras |
| ATOM | 4565 | C   | LEU | 113 | 87.701 | 51.156 | 67.327 | 1.00 | 27.33 | ras |
| ATOM | 4566 | O   | LEU | 113 | 88.722 | 51.791 | 67.047 | 1.00 | 28.89 | ras |
| ATOM | 4567 | N   | VAL | 114 | 86.839 | 50.708 | 66.412 | 1.00 | 26.31 | ras |
| ATOM | 4568 | CA  | VAL | 114 | 87.014 | 50.935 | 64.974 | 1.00 | 24.24 | ras |
| ATOM | 4569 | CB  | VAL | 114 | 86.936 | 49.613 | 64.189 | 1.00 | 24.54 | ras |
| ATOM | 4570 | CG1 | VAL | 114 | 87.212 | 49.859 | 62.715 | 1.00 | 28.38 | ras |
| ATOM | 4571 | CG2 | VAL | 114 | 87.896 | 48.598 | 64.759 | 1.00 | 22.17 | ras |
| ATOM | 4572 | C   | VAL | 114 | 85.962 | 51.878 | 64.386 | 1.00 | 24.95 | ras |
| ATOM | 4573 | O   | VAL | 114 | 84.764 | 51.636 | 64.512 | 1.00 | 28.31 | ras |
| ATOM | 4574 | N   | GLY | 115 | 86.418 | 52.936 | 63.725 | 1.00 | 23.90 | ras |
| ATOM | 4575 | CA  | GLY | 115 | 85.506 | 53.890 | 63.121 | 1.00 | 28.42 | ras |
| ATOM | 4576 | C   | GLY | 115 | 85.557 | 53.719 | 61.620 | 1.00 | 34.16 | ras |
| ATOM | 4577 | O   | GLY | 115 | 86.563 | 54.015 | 60.988 | 1.00 | 35.95 | ras |
| ATOM | 4578 | N   | ASN | 116 | 84.462 | 53.240 | 61.047 | 1.00 | 40.31 | ras |
| ATOM | 4579 | CA  | ASN | 116 | 84.379 | 52.973 | 59.617 | 1.00 | 42.55 | ras |
| ATOM | 4580 | CB  | ASN | 116 | 83.526 | 51.716 | 59.421 | 1.00 | 44.24 | ras |
| ATOM | 4581 | CG  | ASN | 116 | 83.240 | 51.414 | 57.970 | 1.00 | 50.67 | ras |
| ATOM | 4582 | OD1 | ASN | 116 | 84.141 | 51.426 | 57.116 | 1.00 | 51.53 | ras |
| ATOM | 4583 | ND2 | ASN | 116 | 81.973 | 51.128 | 57.679 | 1.00 | 50.47 | ras |
| ATOM | 4584 | C   | ASN | 116 | 83.844 | 54.164 | 58.819 | 1.00 | 42.65 | ras |

TABLE 3-continued

PDB Coordinates for the Ras-Sos Structure:
DATA SET FOR REFINED COORDINATES

| ATOM | 4585 | O | ASN | 116 | 82.916 | 54.843 | 59.252 | 1.00 | 45.11 | ras |
|---|---|---|---|---|---|---|---|---|---|---|
| ATOM | 4586 | N | LYS | 117 | 84.431 | 54.414 | 57.654 | 1.00 | 43.03 | ras |
| ATOM | 4587 | CA | LYS | 117 | 84.015 | 55.536 | 56.822 | 1.00 | 48.43 | ras |
| ATOM | 4588 | CB | LYS | 117 | 85.196 | 56.478 | 56.592 | 1.00 | 48.89 | ras |
| ATOM | 4589 | CG | LYS | 117 | 84.844 | 57.734 | 55.812 | 1.00 | 53.86 | ras |
| ATOM | 4590 | CD | LYS | 117 | 86.032 | 58.206 | 55.002 | 1.00 | 57.77 | ras |
| ATOM | 4591 | CE | LYS | 117 | 85.610 | 59.182 | 53.914 | 1.00 | 63.27 | ras |
| ATOM | 4592 | NZ | LYS | 117 | 86.665 | 59.297 | 52.858 | 1.00 | 63.79 | ras |
| ATOM | 4593 | C | LYS | 117 | 83.403 | 55.154 | 55.475 | 1.00 | 53.12 | ras |
| ATOM | 4594 | O | LYS | 117 | 83.916 | 54.295 | 54.758 | 1.00 | 53.06 | ras |
| ATOM | 4595 | N | CYS | 118 | 82.305 | 55.822 | 55.140 | 1.00 | 61.54 | ras |
| ATOM | 4596 | CA | CYS | 118 | 81.594 | 55.610 | 53.880 | 1.00 | 71.48 | ras |
| ATOM | 4597 | CB | CYS | 118 | 80.132 | 55.253 | 54.162 | 1.00 | 74.52 | ras |
| ATOM | 4598 | SG | CYS | 118 | 79.058 | 55.239 | 52.716 | 1.00 | 80.85 | ras |
| ATOM | 4599 | C | CYS | 118 | 81.686 | 56.917 | 53.087 | 1.00 | 76.03 | ras |
| ATOM | 4600 | O | CYS | 118 | 81.141 | 57.944 | 53.505 | 1.00 | 79.63 | ras |
| ATOM | 4601 | N | ASP | 119 | 82.362 | 56.869 | 51.941 | 1.00 | 79.14 | ras |
| ATOM | 4602 | CA | ASP | 119 | 82.576 | 58.050 | 51.100 | 1.00 | 82.11 | ras |
| ATOM | 4603 | CB | ASP | 119 | 83.403 | 57.677 | 49.864 | 1.00 | 86.58 | ras |
| ATOM | 4604 | CG | ASP | 119 | 84.342 | 58.796 | 49.430 | 1.00 | 90.60 | ras |
| ATOM | 4605 | OD1 | ASP | 119 | 85.500 | 58.810 | 49.908 | 1.00 | 91.32 | ras |
| ATOM | 4606 | OD2 | ASP | 119 | 83.924 | 58.659 | 48.622 | 1.00 | 89.50 | ras |
| ATOM | 4607 | C | ASP | 119 | 81.331 | 58.825 | 50.668 | 1.00 | 81.94 | ras |
| ATOM | 4608 | O | ASP | 119 | 81.433 | 59.969 | 50.228 | 1.00 | 81.54 | ras |
| ATOM | 4609 | N | LEU | 120 | 80.163 | 58.209 | 50.807 | 1.00 | 82.74 | ras |
| ATOM | 4610 | CA | LEU | 120 | 78.909 | 58.847 | 50.423 | 1.00 | 82.51 | ras |
| ATOM | 4611 | CB | LEU | 120 | 77.766 | 57.822 | 50.433 | 1.00 | 84.98 | ras |
| ATOM | 4612 | CG | LEU | 120 | 77.922 | 56.578 | 49.545 | 1.00 | 89.71 | ras |
| ATOM | 4613 | CD1 | LEU | 120 | 76.701 | 55.676 | 49.693 | 1.00 | 87.10 | ras |
| ATOM | 4614 | CD2 | LEU | 120 | 78.119 | 56.981 | 48.085 | 1.00 | 89.88 | ras |
| ATOM | 4615 | C | LEU | 120 | 78.529 | 60.056 | 51.287 | 1.00 | 80.53 | ras |
| ATOM | 4616 | O | LEU | 120 | 78.412 | 61.172 | 50.776 | 1.00 | 82.27 | ras |
| ATOM | 4617 | N | ALA | 121 | 78.370 | 59.837 | 52.593 | 1.00 | 75.55 | ras |
| ATOM | 4618 | CA | ALA | 121 | 77.968 | 60.896 | 53.522 | 1.00 | 68.08 | ras |
| ATOM | 4619 | CB | ALA | 121 | 77.020 | 60.329 | 54.572 | 1.00 | 69.04 | ras |
| ATOM | 4620 | C | ALA | 121 | 79.081 | 61.714 | 54.195 | 1.00 | 63.21 | ras |
| ATOM | 4621 | O | ALA | 121 | 80.273 | 61.488 | 53.966 | 1.00 | 62.81 | ras |
| ATOM | 4622 | N | ALA | 122 | 78.658 | 62.672 | 55.020 | 1.00 | 54.57 | ras |
| ATOM | 4623 | CA | ALA | 122 | 79.553 | 63.570 | 55.744 | 1.00 | 47.69 | ras |
| ATOM | 4624 | CB | ALA | 122 | 78.927 | 64.949 | 55.847 | 1.00 | 46.58 | ras |
| ATOM | 4625 | C | ALA | 122 | 79.908 | 63.077 | 57.133 | 1.00 | 43.56 | ras |
| ATOM | 4626 | O | ALA | 122 | 79.070 | 62.530 | 57.842 | 1.00 | 47.26 | ras |
| ATOM | 4627 | N | ARG | 123 | 81.145 | 63.335 | 57.534 | 1.00 | 38.05 | ras |
| ATOM | 4628 | CA | ARG | 123 | 81.646 | 62.939 | 58.840 | 1.00 | 36.68 | ras |
| ATOM | 4629 | CB | ARG | 123 | 83.157 | 63.184 | 58.901 | 1.00 | 33.60 | ras |
| ATOM | 4630 | CG | ARG | 123 | 83.783 | 62.983 | 60.264 | 1.00 | 33.76 | ras |
| ATOM | 4631 | CD | ARG | 123 | 85.244 | 63.380 | 60.261 | 1.00 | 25.51 | ras |
| ATOM | 4632 | NE | ARG | 123 | 86.078 | 62.421 | 59.540 | 1.00 | 29.08 | ras |
| ATOM | 4633 | CZ | ARG | 123 | 86.543 | 61.283 | 60.055 | 1.00 | 29.44 | ras |
| ATOM | 4634 | NH1 | ARG | 123 | 86.268 | 60.939 | 61.309 | 1.00 | 24.21 | ras |
| ATOM | 4635 | NH2 | ARG | 123 | 87.259 | 60.465 | 59.298 | 1.00 | 33.23 | ras |
| ATOM | 4636 | C | ARG | 123 | 80.941 | 63.738 | 59.931 | 1.00 | 38.95 | ras |
| ATOM | 4637 | O | ARG | 123 | 80.821 | 64.956 | 59.825 | 1.00 | 41.45 | ras |
| ATOM | 4638 | N | THR | 124 | 80.445 | 63.050 | 60.958 | 1.00 | 37.94 | ras |
| ATOM | 4639 | CA | THR | 124 | 79.765 | 63.716 | 62.064 | 1.00 | 36.74 | ras |
| ATOM | 4640 | CB | THR | 124 | 78.284 | 63.345 | 62.129 | 1.00 | 37.25 | ras |
| ATOM | 4641 | OG1 | THR | 124 | 78.151 | 61.938 | 62.369 | 1.00 | 42.57 | ras |
| ATOM | 4642 | CG2 | THR | 124 | 77.599 | 63.699 | 60.826 | 1.00 | 33.15 | ras |
| ATOM | 4643 | C | THR | 124 | 80.432 | 63.375 | 63.392 | 1.00 | 38.85 | ras |
| ATOM | 4644 | O | THR | 124 | 80.005 | 63.845 | 64.454 | 1.00 | 42.61 | ras |
| ATOM | 4645 | N | VAL | 125 | 81.452 | 62.520 | 63.327 | 1.00 | 35.36 | ras |
| ATOM | 4646 | CA | VAL | 125 | 82.221 | 62.124 | 64.503 | 1.00 | 34.45 | ras |
| ATOM | 4647 | CB | VAL | 125 | 82.115 | 60.622 | 64.811 | 1.00 | 32.97 | ras |
| ATOM | 4648 | CG1 | VAL | 125 | 82.910 | 60.296 | 66.058 | 1.00 | 32.27 | ras |
| ATOM | 4649 | CG2 | VAL | 125 | 80.672 | 60.205 | 64.977 | 1.00 | 32.25 | ras |
| ATOM | 4650 | C | VAL | 125 | 83.657 | 62.411 | 64.130 | 1.00 | 36.78 | ras |
| ATOM | 4651 | O | VAL | 125 | 84.219 | 61.733 | 63.267 | 1.00 | 37.16 | ras |
| ATOM | 4652 | N | GLU | 126 | 84.234 | 63.443 | 64.740 | 1.00 | 39.83 | ras |
| ATOM | 4653 | CA | GLU | 126 | 85.613 | 63.824 | 64.449 | 1.00 | 37.95 | ras |
| ATOM | 4654 | CB | GLU | 126 | 85.904 | 65.237 | 64.949 | 1.00 | 39.78 | ras |
| ATOM | 4655 | CG | GLU | 126 | 85.064 | 66.334 | 64.303 | 1.00 | 43.78 | ras |
| ATOM | 4656 | CD | GLU | 126 | 85.229 | 66.426 | 62.787 | 1.00 | 47.47 | ras |
| ATOM | 4657 | OE1 | GLU | 126 | 86.386 | 66.438 | 62.294 | 1.00 | 46.50 | ras |
| ATOM | 4658 | OE2 | GLU | 126 | 84.188 | 66.501 | 62.092 | 1.00 | 48.25 | ras |
| ATOM | 4659 | C | GLU | 126 | 86.582 | 62.846 | 65.081 | 1.00 | 36.49 | ras |
| ATOM | 4660 | O | GLU | 126 | 86.282 | 62.239 | 66.108 | 1.00 | 38.33 | ras |

TABLE 3-continued

PDB Coordinates for the Ras-Sos Structure:
DATA SET FOR REFINED COORDINATES

| ATOM | 4661 | N | SER | 127 | 87.738 | 62.683 | 64.451 | 1.00 | 35.17 | ras |
|---|---|---|---|---|---|---|---|---|---|---|
| ATOM | 4662 | CA | SER | 127 | 88.758 | 61.775 | 64.952 | 1.00 | 35.51 | ras |
| ATOM | 4663 | CB | SER | 127 | 90.021 | 61.855 | 64.090 | 1.00 | 37.90 | ras |
| ATOM | 4664 | OG | SER | 127 | 90.225 | 63.160 | 63.564 | 1.00 | 46.43 | ras |
| ATOM | 4665 | C | SER | 127 | 89.085 | 62.005 | 66.426 | 1.00 | 35.79 | ras |
| ATOM | 4666 | O | SER | 127 | 89.164 | 61.043 | 67.201 | 1.00 | 35.46 | ras |
| ATOM | 4667 | N | ARG | 128 | 89.204 | 63.273 | 66.825 | 1.00 | 35.69 | ras |
| ATOM | 4668 | CA | ARG | 128 | 89.511 | 63.620 | 68.214 | 1.00 | 37.26 | ras |
| ATOM | 4669 | CB | ARG | 128 | 89.639 | 65.139 | 68.384 | 1.00 | 42.71 | ras |
| ATOM | 4670 | CG | ARG | 128 | 90.005 | 65.607 | 69.801 | 1.00 | 50.29 | ras |
| ATOM | 4671 | CD | ARG | 128 | 91.320 | 64.998 | 70.289 | 1.00 | 56.35 | ras |
| ATOM | 4672 | NE | ARG | 128 | 91.672 | 65.452 | 71.634 | 1.00 | 60.48 | ras |
| ATOM | 4673 | CZ | ARG | 128 | 92.727 | 66.218 | 71.928 | 1.00 | 61.33 | ras |
| ATOM | 4674 | NH1 | ARG | 128 | 92.957 | 66.574 | 73.188 | 1.00 | 55.18 | ras |
| ATOM | 4675 | NH2 | ARG | 128 | 93.556 | 66.619 | 70.968 | 1.00 | 57.47 | ras |
| ATOM | 4676 | C | ARG | 128 | 88.508 | 63.052 | 69.227 | 1.00 | 37.08 | ras |
| ATOM | 4677 | O | ARG | 128 | 88.914 | 62.441 | 70.215 | 1.00 | 32.60 | ras |
| ATOM | 4678 | N | GLN | 129 | 87.208 | 63.215 | 68.982 | 1.00 | 38.36 | ras |
| ATOM | 4679 | CA | GLN | 129 | 86.230 | 62.682 | 69.930 | 1.00 | 39.21 | ras |
| ATOM | 4680 | CB | GLN | 129 | 87.810 | 63.217 | 69.698 | 1.00 | 37.59 | ras |
| ATOM | 4681 | CG | GLN | 129 | 84.336 | 63.287 | 68.270 | 1.00 | 43.52 | ras |
| ATOM | 4682 | CD | GLN | 129 | 82.969 | 63.952 | 68.151 | 1.00 | 43.31 | ras |
| ATOM | 4683 | OE1 | GLN | 129 | 82.677 | 64.634 | 67.164 | 1.00 | 45.38 | ras |
| ATOM | 4684 | NE2 | GLN | 129 | 82.127 | 63.751 | 69.157 | 1.00 | 35.28 | ras |
| ATOM | 4685 | C | GLN | 129 | 86.254 | 61.172 | 70.044 | 1.00 | 37.78 | ras |
| ATOM | 4686 | O | GLN | 129 | 86.002 | 60.632 | 71.127 | 1.00 | 39.32 | ras |
| ATOM | 4687 | N | ALA | 130 | 86.622 | 60.495 | 68.957 | 1.00 | 35.54 | ras |
| ATOM | 4688 | CA | ALA | 130 | 86.708 | 59.032 | 68.963 | 1.00 | 35.96 | ras |
| ATOM | 4689 | CB | ALA | 130 | 86.615 | 58.484 | 67.559 | 1.00 | 34.63 | ras |
| ATOM | 4690 | C | ALA | 130 | 88.036 | 58.647 | 69.595 | 1.00 | 36.61 | ras |
| ATOM | 4691 | O | ALA | 130 | 88.172 | 57.596 | 70.225 | 1.00 | 31.58 | ras |
| ATOM | 4692 | N | GLN | 131 | 89.014 | 59.531 | 69.429 | 1.00 | 40.59 | ras |
| ATOM | 4693 | CA | GLN | 131 | 90.341 | 59.334 | 69.991 | 1.00 | 40.20 | ras |
| ATOM | 4694 | CB | GLN | 131 | 91.293 | 60.393 | 69.440 | 1.00 | 43.47 | ras |
| ATOM | 4695 | CG | GLN | 131 | 92.753 | 60.014 | 69.499 | 1.00 | 54.26 | ras |
| ATOM | 4696 | CD | GLN | 131 | 93.175 | 59.119 | 68.354 | 1.00 | 58.42 | ras |
| ATOM | 4697 | OE1 | GLN | 131 | 93.139 | 59.530 | 67.190 | 1.00 | 59.02 | ras |
| ATOM | 4698 | NE2 | GLN | 131 | 93.604 | 57.895 | 68.677 | 1.00 | 55.27 | ras |
| ATOM | 4699 | C | GLN | 131 | 90.217 | 59.451 | 71.512 | 1.00 | 37.26 | ras |
| ATOM | 4700 | O | GLN | 131 | 90.677 | 58.568 | 72.236 | 1.00 | 37.81 | ras |
| ATOM | 4701 | N | ASP | 132 | 89.533 | 60.501 | 71.981 | 1.00 | 36.13 | ras |
| ATOM | 4702 | CA | ASP | 132 | 89.318 | 60.730 | 73.420 | 1.00 | 35.75 | ras |
| ATOM | 4703 | CB | ASP | 132 | 88.556 | 62.036 | 73.681 | 1.00 | 34.78 | ras |
| ATOM | 4704 | CG | ASP | 132 | 89.405 | 63.287 | 73.445 | 1.00 | 41.42 | ras |
| ATOM | 4705 | OD1 | ASP | 132 | 88.811 | 64.377 | 73.302 | 1.00 | 39.44 | ras |
| ATOM | 4706 | OD2 | ASP | 132 | 90.653 | 63.193 | 73.397 | 1.00 | 45.68 | ras |
| ATOM | 4707 | C | ASP | 132 | 88.560 | 59.585 | 74.079 | 1.00 | 33.84 | ras |
| ATOM | 4708 | O | ASP | 132 | 88.904 | 59.152 | 75.180 | 1.00 | 35.32 | ras |
| ATOM | 4709 | N | LEU | 133 | 87.540 | 59.084 | 73.392 | 1.00 | 31.84 | ras |
| ATOM | 4710 | CA | LEU | 133 | 86.739 | 57.986 | 73.909 | 1.00 | 28.69 | ras |
| ATOM | 4711 | CB | LEU | 133 | 85.537 | 57.724 | 72.995 | 1.00 | 29.78 | ras |
| ATOM | 4712 | CG | LEU | 133 | 84.615 | 56.586 | 73.451 | 1.00 | 32.23 | ras |
| ATOM | 4713 | CD1 | LEU | 133 | 83.897 | 56.985 | 74.725 | 1.00 | 26.55 | ras |
| ATOM | 4714 | CD2 | LEU | 133 | 83.620 | 56.236 | 72.363 | 1.00 | 32.38 | ras |
| ATOM | 4715 | C | LEU | 133 | 87.568 | 56.716 | 74.043 | 1.00 | 27.76 | ras |
| ATOM | 4716 | O | LEU | 133 | 87.387 | 55.939 | 74.988 | 1.00 | 27.92 | ras |
| ATOM | 4717 | N | ALA | 134 | 88.467 | 56.498 | 73.090 | 1.00 | 23.60 | ras |
| ATOM | 4718 | CA | ALA | 134 | 89.303 | 55.312 | 73.114 | 1.00 | 25.39 | ras |
| ATOM | 4719 | CB | ALA | 134 | 90.066 | 55.177 | 71.809 | 1.00 | 22.66 | ras |
| ATOM | 4720 | C | ALA | 134 | 90.262 | 55.367 | 74.296 | 1.00 | 29.43 | ras |
| ATOM | 4721 | O | ALA | 134 | 90.508 | 54.360 | 74.965 | 1.00 | 31.72 | ras |
| ATOM | 4722 | N | ARG | 135 | 90.784 | 56.556 | 74.564 | 1.00 | 30.99 | ras |
| ATOM | 4723 | CA | ARG | 135 | 91.711 | 56.731 | 75.663 | 1.00 | 32.98 | ras |
| ATOM | 4724 | CB | ARG | 135 | 92.427 | 58.074 | 75.539 | 1.00 | 36.31 | ras |
| ATOM | 4725 | CG | ARG | 135 | 93.291 | 58.429 | 76.722 | 1.00 | 34.04 | ras |
| ATOM | 4726 | CD | ARG | 135 | 94.375 | 59.391 | 76.317 | 1.00 | 36.97 | ras |
| ATOM | 4727 | NE | ARG | 135 | 95.647 | 58.694 | 76.150 | 1.00 | 39.27 | ras |
| ATOM | 4728 | CZ | ARG | 135 | 96.251 | 58.512 | 74.984 | 1.00 | 40.93 | ras |
| ATOM | 4729 | NH1 | ARG | 135 | 97.407 | 57.867 | 74.943 | 1.00 | 35.06 | ras |
| ATOM | 4730 | NH2 | ARG | 135 | 95.700 | 58.978 | 73.859 | 1.00 | 45.53 | ras |
| ATOM | 4731 | C | ARG | 135 | 91.028 | 56.587 | 77.017 | 1.00 | 33.49 | ras |
| ATOM | 4732 | O | ARG | 135 | 91.649 | 56.133 | 77.978 | 1.00 | 36.94 | ras |
| ATOM | 4733 | N | SER | 136 | 89.751 | 56.950 | 77.099 | 1.00 | 31.27 | ras |
| ATOM | 4734 | CA | SER | 136 | 89.040 | 56.821 | 78.367 | 1.00 | 30.97 | ras |
| ATOM | 4735 | CB | SER | 136 | 87.744 | 57.632 | 78.368 | 1.00 | 26.61 | ras |
| ATOM | 4736 | OG | SER | 136 | 86.707 | 59.966 | 77.681 | 1.00 | 39.64 | ras |

TABLE 3-continued

PDB Coordinates for the Ras-Sos Structure:
DATA SET FOR REFINED COORDINATES

| ATOM | 4737 | C   | SER | 136 | 88.776 | 55.347 | 78.688 | 1.00 | 30.12 | ras |
|------|------|-----|-----|-----|--------|--------|--------|------|-------|-----|
| ATOM | 4738 | O   | SER | 136 | 88.577 | 54.991 | 79.842 | 1.00 | 27.40 | ras |
| ATOM | 4739 | N   | TYR | 137 | 88.805 | 54.496 | 77.660 | 1.00 | 33.73 | ras |
| ATOM | 4740 | CA  | TYR | 137 | 88.601 | 53.049 | 77.823 | 1.00 | 35.00 | ras |
| ATOM | 4741 | CB  | TYR | 137 | 87.793 | 52.453 | 76.661 | 1.00 | 33.68 | ras |
| ATOM | 4742 | CG  | TYR | 137 | 86.362 | 52.934 | 76.565 | 1.00 | 36.06 | ras |
| ATOM | 4743 | CD1 | TYR | 137 | 85.683 | 53.386 | 77.693 | 1.00 | 33.29 | ras |
| ATOM | 4744 | CE1 | TYR | 137 | 84.381 | 53.850 | 77.606 | 1.00 | 34.15 | ras |
| ATOM | 4745 | CD2 | TYR | 137 | 85.692 | 52.954 | 75.339 | 1.00 | 35.98 | ras |
| ATOM | 4746 | CE2 | TYR | 137 | 84.380 | 53.418 | 75.242 | 1.00 | 35.22 | ras |
| ATOM | 4747 | CZ  | TYR | 137 | 83.735 | 53.866 | 76.381 | 1.00 | 35.02 | ras |
| ATOM | 4748 | OH  | TYR | 137 | 82.458 | 54.354 | 76.311 | 1.00 | 34.03 | ras |
| ATOM | 4749 | C   | TYR | 137 | 89.942 | 52.340 | 77.881 | 1.00 | 34.41 | ras |
| ATOM | 4750 | O   | TYR | 137 | 90.011 | 51.161 | 78.225 | 1.00 | 38.75 | ras |
| ATOM | 4751 | N   | GLY | 138 | 91.002 | 53.056 | 77.524 | 1.00 | 30.33 | ras |
| ATOM | 4752 | CA  | GLY | 138 | 92.328 | 52.467 | 77.524 | 1.00 | 29.39 | ras |
| ATOM | 4753 | C   | GLY | 138 | 92.511 | 51.438 | 76.423 | 1.00 | 27.77 | ras |
| ATOM | 4754 | O   | GLY | 138 | 93.130 | 50.392 | 76.632 | 1.00 | 25.61 | ras |
| ATOM | 4755 | N   | ILE | 139 | 91.948 | 51.731 | 75.255 | 1.00 | 25.41 | ras |
| ATOM | 4756 | CA  | ILE | 139 | 92.033 | 50.841 | 74.109 | 1.00 | 24.60 | ras |
| ATOM | 4757 | CB  | ILE | 139 | 90.706 | 50.084 | 73.852 | 1.00 | 26.61 | ras |
| ATOM | 4758 | CG2 | ILE | 139 | 90.316 | 49.281 | 75.068 | 1.00 | 23.18 | ras |
| ATOM | 4759 | CG1 | ILE | 139 | 89.589 | 51.053 | 73.454 | 1.00 | 27.23 | ras |
| ATOM | 4760 | CD1 | ILE | 139 | 88.328 | 50.350 | 72.995 | 1.00 | 26.53 | ras |
| ATOM | 4761 | C   | ILE | 139 | 92.371 | 51.665 | 72.885 | 1.00 | 25.85 | ras |
| ATOM | 4762 | O   | ILE | 139 | 92.152 | 52.878 | 72.871 | 1.00 | 30.51 | ras |
| ATOM | 4763 | N   | PRO | 140 | 92.931 | 51.022 | 71.846 | 1.00 | 23.26 | ras |
| ATOM | 4764 | CD  | PRO | 140 | 93.374 | 49.619 | 71.854 | 1.00 | 20.40 | ras |
| ATOM | 4765 | CA  | PRO | 140 | 93.319 | 51.681 | 70.593 | 1.00 | 23.44 | ras |
| ATOM | 4766 | CB  | PRO | 140 | 94.129 | 50.600 | 69.871 | 1.00 | 19.82 | ras |
| ATOM | 4767 | CG  | PRO | 140 | 94.562 | 49.678 | 70.965 | 1.00 | 23.28 | ras |
| ATOM | 4768 | C   | PRO | 140 | 92.127 | 52.104 | 69.732 | 1.00 | 27.00 | ras |
| ATOM | 4769 | O   | PRO | 140 | 91.046 | 51.515 | 69.825 | 1.00 | 26.80 | ras |
| ATOM | 4770 | N   | TYR | 141 | 92.329 | 53.135 | 68.912 | 1.00 | 25.97 | ras |
| ATOM | 4771 | CA  | TYR | 141 | 91.298 | 53.611 | 68.003 | 1.00 | 27.64 | ras |
| ATOM | 4772 | CB  | TYR | 141 | 90.997 | 55.089 | 68.222 | 1.00 | 28.94 | ras |
| ATOM | 4773 | CG  | TYR | 141 | 90.091 | 55.682 | 67.157 | 1.00 | 26.44 | ras |
| ATOM | 4774 | CD1 | TYR | 141 | 88.832 | 55.140 | 66.905 | 1.00 | 26.23 | ras |
| ATOM | 4775 | CE1 | TYR | 141 | 87.996 | 55.676 | 65.946 | 1.00 | 22.47 | ras |
| ATOM | 4776 | CD2 | TYR | 141 | 90.490 | 56.784 | 66.412 | 1.00 | 25.52 | ras |
| ATOM | 4777 | CE2 | TYR | 141 | 89.660 | 57.332 | 65.447 | 1.00 | 26.83 | ras |
| ATOM | 4778 | CZ  | TYR | 141 | 88.414 | 56.770 | 65.222 | 1.00 | 27.46 | ras |
| ATOM | 4779 | OH  | TYR | 141 | 87.586 | 57.308 | 64.268 | 1.00 | 27.03 | ras |
| ATOM | 4780 | C   | TYR | 141 | 91.859 | 53.441 | 66.613 | 1.00 | 31.51 | ras |
| ATOM | 4781 | O   | TYR | 141 | 93.005 | 53.802 | 66.371 | 1.00 | 36.56 | ras |
| ATOM | 4782 | N   | ILE | 142 | 91.054 | 52.913 | 65.692 | 1.00 | 35.13 | ras |
| ATOM | 4783 | CA  | ILE | 142 | 91.504 | 52.699 | 64.317 | 1.00 | 31.73 | ras |
| ATOM | 4784 | CB  | ILE | 142 | 91.846 | 51.228 | 64.081 | 1.00 | 27.10 | ras |
| ATOM | 4785 | CG2 | ILE | 142 | 92.480 | 51.050 | 62.706 | 1.00 | 15.67 | ras |
| ATOM | 4786 | CG1 | ILE | 142 | 92.792 | 50.750 | 65.179 | 1.00 | 23.98 | ras |
| ATOM | 4787 | CD1 | ILE | 142 | 92.821 | 49.289 | 65.356 | 1.00 | 31.23 | ras |
| ATOM | 4788 | C   | ILE | 142 | 90.445 | 53.099 | 63.307 | 1.00 | 33.54 | ras |
| ATOM | 4789 | O   | ILE | 142 | 89.350 | 52.549 | 63.317 | 1.00 | 40.35 | ras |
| ATOM | 4790 | N   | GLU | 143 | 90.764 | 54.070 | 62.458 | 1.00 | 30.75 | ras |
| ATOM | 4791 | CA  | GLU | 143 | 89.831 | 54.510 | 61.436 | 1.00 | 30.42 | ras |
| ATOM | 4792 | CB  | GLU | 143 | 89.993 | 55.994 | 61.127 | 1.00 | 31.06 | ras |
| ATOM | 4793 | CG  | GLU | 143 | 89.275 | 56.869 | 62.106 | 1.00 | 33.85 | ras |
| ATOM | 4794 | CD  | GLU | 143 | 88.853 | 58.222 | 61.550 | 1.00 | 39.08 | ras |
| ATOM | 4795 | OE1 | GLU | 143 | 89.075 | 58.501 | 60.353 | 1.00 | 34.80 | ras |
| ATOM | 4796 | OE2 | GLU | 143 | 88.272 | 59.012 | 62.324 | 1.00 | 42.20 | ras |
| ATOM | 4797 | C   | GLU | 143 | 90.076 | 53.689 | 60.191 | 1.00 | 32.43 | ras |
| ATOM | 4798 | O   | GLU | 143 | 91.212 | 53.357 | 59.883 | 1.00 | 38.54 | ras |
| ATOM | 4799 | N   | THR | 144 | 89.005 | 53.379 | 59.472 | 1.00 | 33.98 | ras |
| ATOM | 4800 | CA  | THR | 144 | 89.084 | 52.565 | 58.270 | 1.00 | 34.43 | ras |
| ATOM | 4801 | CB  | THR | 144 | 88.642 | 51.116 | 58.566 | 1.00 | 34.35 | ras |
| ATOM | 4802 | OG1 | THR | 144 | 87.222 | 51.083 | 58.767 | 1.00 | 36.77 | ras |
| ATOM | 4803 | CG2 | THR | 144 | 89.313 | 50.597 | 59.823 | 1.00 | 28.88 | ras |
| ATOM | 4804 | C   | THR | 144 | 88.154 | 53.099 | 57.188 | 1.00 | 37.34 | ras |
| ATOM | 4805 | O   | THR | 144 | 87.166 | 53.774 | 57.483 | 1.00 | 39.02 | ras |
| ATOM | 4806 | N   | SER | 145 | 88.470 | 52.772 | 55.940 | 1.00 | 40.33 | ras |
| ATOM | 4807 | CA  | SER | 145 | 87.654 | 53.175 | 54.798 | 1.00 | 44.04 | ras |
| ATOM | 4808 | CB  | SER | 145 | 88.523 | 53.853 | 53.739 | 1.00 | 42.89 | ras |
| ATOM | 4809 | OG  | SER | 145 | 87.746 | 54.281 | 52.632 | 1.00 | 39.80 | ras |
| ATOM | 4810 | C   | SER | 145 | 86.980 | 51.936 | 54.198 | 1.00 | 47.52 | ras |
| ATOM | 4811 | O   | SER | 145 | 87.613 | 50.897 | 54.026 | 1.00 | 49.05 | ras |
| ATOM | 4812 | N   | ALA | 146 | 85.689 | 52.032 | 53.906 | 1.00 | 51.96 | ras |

TABLE 3-continued

PDB Coordinates for the Ras-Sos Structure:
DATA SET FOR REFINED COORDINATES

| ATOM | 4813 | CA  | ALA | 146 | 84.968 | 50.908 | 53.307 | 1.00 | 54.95 | ras |
|------|------|-----|-----|-----|--------|--------|--------|------|-------|-----|
| ATOM | 4814 | CB  | ALA | 146 | 83.490 | 50.995 | 53.645 | 1.00 | 51.70 | ras |
| ATOM | 4815 | C   | ALA | 146 | 85.159 | 50.879 | 51.787 | 1.00 | 56.42 | ras |
| ATOM | 4816 | O   | ALA | 146 | 84.939 | 49.863 | 51.141 | 1.00 | 58.52 | ras |
| ATOM | 4817 | N   | LYS | 147 | 85.598 | 52.000 | 51.232 | 1.00 | 60.15 | ras |
| ATOM | 4818 | CA  | LYS | 147 | 85.799 | 52.149 | 49.797 | 1.00 | 62.34 | ras |
| ATOM | 4819 | CB  | LYS | 147 | 85.394 | 53.575 | 49.392 | 1.00 | 64.73 | ras |
| ATOM | 4820 | CG  | LYS | 147 | 85.666 | 53.942 | 47.939 | 1.00 | 70.11 | ras |
| ATOM | 4821 | CD  | LYS | 147 | 85.674 | 55.447 | 47.737 | 1.00 | 72.20 | ras |
| ATOM | 4822 | CE  | LYS | 147 | 85.966 | 55.793 | 46.285 | 1.00 | 77.40 | ras |
| ATOM | 4823 | NZ  | LYS | 147 | 86.125 | 57.261 | 46.077 | 1.00 | 80.49 | ras |
| ATOM | 4824 | C   | LYS | 147 | 87.224 | 51.862 | 49.299 | 1.00 | 62.91 | ras |
| ATOM | 4825 | O   | LYS | 147 | 87.409 | 51.476 | 48.139 | 1.00 | 64.68 | ras |
| ATOM | 4826 | N   | THR | 148 | 88.222 | 52.045 | 50.162 | 1.00 | 58.14 | ras |
| ATOM | 4827 | CA  | THR | 148 | 89.616 | 51.857 | 49.766 | 1.00 | 52.41 | ras |
| ATOM | 4828 | CB  | THR | 148 | 90.411 | 53.164 | 49.959 | 1.00 | 51.99 | ras |
| ATOM | 4829 | OG1 | THR | 148 | 90.455 | 53.491 | 51.353 | 1.00 | 48.72 | ras |
| ATOM | 4830 | OG2 | THR | 148 | 89.765 | 54.307 | 49.203 | 1.00 | 51.18 | ras |
| ATOM | 4831 | C   | THR | 148 | 90.374 | 50.761 | 50.502 | 1.00 | 50.64 | ras |
| ATOM | 4832 | O   | THR | 148 | 91.540 | 50.502 | 50.203 | 1.00 | 52.35 | ras |
| ATOM | 4833 | N   | ARG | 149 | 89.722 | 50.134 | 51.472 | 1.00 | 48.50 | ras |
| ATOM | 4834 | CA  | ARG | 149 | 90.332 | 49.083 | 52.290 | 1.00 | 45.39 | ras |
| ATOM | 4835 | CB  | ARG | 149 | 90.841 | 47.905 | 51.438 | 1.00 | 46.80 | ras |
| ATOM | 4836 | CG  | ARG | 149 | 90.911 | 46.595 | 52.232 | 1.00 | 53.56 | ras |
| ATOM | 4837 | CD  | ARG | 149 | 91.602 | 45.426 | 51.513 | 1.00 | 55.50 | ras |
| ATOM | 4838 | NE  | ARG | 149 | 91.660 | 44.241 | 52.382 | 1.00 | 52.88 | ras |
| ATOM | 4839 | CZ  | ARG | 149 | 92.776 | 43.704 | 52.871 | 1.00 | 46.33 | ras |
| ATOM | 4840 | NH1 | ARG | 149 | 92.717 | 42.641 | 53.660 | 1.00 | 46.20 | ras |
| ATOM | 4841 | NH2 | ARG | 149 | 93.955 | 44.208 | 52.553 | 1.00 | 46.94 | ras |
| ATOM | 4842 | C   | ARG | 149 | 91.446 | 49.624 | 53.206 | 1.00 | 43.06 | ras |
| ATOM | 4843 | O   | ARG | 149 | 92.101 | 48.856 | 53.917 | 1.00 | 43.99 | ras |
| ATOM | 4844 | N   | GLN | 150 | 91.637 | 50.945 | 53.216 | 1.00 | 39.08 | ras |
| ATOM | 4845 | CA  | GLN | 150 | 92.648 | 51.565 | 54.077 | 1.00 | 34.98 | ras |
| ATOM | 4846 | CB  | GLN | 150 | 92.753 | 53.071 | 53.816 | 1.00 | 33.52 | ras |
| ATOM | 4847 | CG  | GLN | 150 | 93.352 | 53.487 | 52.491 | 1.00 | 34.22 | ras |
| ATOM | 4848 | CD  | GLN | 150 | 93.448 | 55.000 | 52.349 | 1.00 | 37.95 | ras |
| ATOM | 4849 | OE1 | GLN | 150 | 92.553 | 55.649 | 51.798 | 1.00 | 37.26 | ras |
| ATOM | 4850 | NE2 | GLN | 150 | 94.539 | 55.568 | 52.845 | 1.00 | 38.50 | ras |
| ATOM | 4851 | C   | GLN | 150 | 92.267 | 51.371 | 55.545 | 1.00 | 33.31 | ras |
| ATOM | 4852 | O   | GLN | 150 | 91.135 | 51.652 | 55.939 | 1.00 | 32.99 | ras |
| ATOM | 4853 | N   | GLY | 151 | 93.206 | 50.874 | 56.342 | 1.00 | 33.35 | ras |
| ATOM | 4854 | CA  | GLY | 151 | 92.960 | 50.680 | 57.761 | 1.00 | 30.37 | ras |
| ATOM | 4855 | C   | GLY | 151 | 92.410 | 49.341 | 58.206 | 1.00 | 33.41 | ras |
| ATOM | 4856 | O   | GLY | 151 | 92.566 | 48.985 | 59.367 | 1.00 | 33.92 | ras |
| ATOM | 4857 | N   | VAL | 152 | 91.779 | 48.594 | 57.301 | 1.00 | 36.30 | ras |
| ATOM | 4858 | CA  | VAL | 152 | 91.192 | 47.296 | 57.643 | 1.00 | 33.95 | ras |
| ATOM | 4859 | CB  | VAL | 152 | 90.542 | 46.630 | 56.424 | 1.00 | 33.22 | ras |
| ATOM | 4860 | CG1 | VAL | 152 | 89.924 | 45.300 | 56.812 | 1.00 | 33.95 | ras |
| ATOM | 4861 | CG2 | VAL | 152 | 89.474 | 47.528 | 55.868 | 1.00 | 31.32 | ras |
| ATOM | 4862 | C   | VAL | 152 | 92.134 | 46.315 | 58.334 | 1.00 | 36.15 | ras |
| ATOM | 4863 | O   | VAL | 152 | 91.797 | 45.789 | 59.396 | 1.00 | 35.10 | ras |
| ATOM | 4864 | N   | GLU | 153 | 93.305 | 46.066 | 57.749 | 1.00 | 39.86 | ras |
| ATOM | 4865 | CA  | GLU | 153 | 94.264 | 45.150 | 58.368 | 1.00 | 41.52 | ras |
| ATOM | 4866 | CB  | GLU | 153 | 95.539 | 45.030 | 57.541 | 1.00 | 45.51 | ras |
| ATOM | 4867 | CG  | GLU | 153 | 95.360 | 44.441 | 56.156 | 1.00 | 58.86 | ras |
| ATOM | 4868 | CD  | GLU | 153 | 96.527 | 43.547 | 55.748 | 1.00 | 64.28 | ras |
| ATOM | 4869 | OE1 | GLU | 153 | 97.671 | 43.784 | 56.221 | 1.00 | 63.29 | ras |
| ATOM | 4870 | OE2 | GLU | 153 | 96.285 | 42.595 | 54.968 | 1.00 | 62.65 | ras |
| ATOM | 4871 | C   | GLU | 153 | 94.636 | 45.663 | 59.751 | 1.00 | 41.05 | ras |
| ATOM | 4872 | O   | GLU | 153 | 94.426 | 44.987 | 60.756 | 1.00 | 40.07 | ras |
| ATOM | 4873 | N   | ASP | 154 | 95.166 | 46.881 | 59.783 | 1.00 | 41.55 | ras |
| ATOM | 4874 | CA  | ASP | 154 | 95.585 | 47.535 | 61.017 | 1.00 | 41.98 | ras |
| ATOM | 4875 | CB  | ASP | 154 | 95.772 | 49.033 | 60.742 | 1.00 | 45.25 | ras |
| ATOM | 4876 | CG  | ASP | 154 | 96.554 | 49.752 | 61.828 | 1.00 | 51.92 | ras |
| ATOM | 4877 | OD1 | ASP | 154 | 97.264 | 49.091 | 62.625 | 1.00 | 51.51 | ras |
| ATOM | 4878 | OD2 | ASP | 154 | 96.471 | 51.004 | 61.862 | 1.00 | 57.26 | ras |
| ATOM | 4879 | C   | ASP | 154 | 94.561 | 47.290 | 62.137 | 1.00 | 39.90 | ras |
| ATOM | 4880 | O   | ASP | 154 | 94.919 | 46.888 | 63.242 | 1.00 | 39.23 | ras |
| ATOM | 4881 | N   | ALA | 155 | 93.285 | 47.437 | 61.808 | 1.00 | 36.72 | ras |
| ATOM | 4882 | CA  | ALA | 155 | 92.214 | 47.226 | 62.765 | 1.00 | 35.26 | ras |
| ATOM | 4883 | CB  | ALA | 155 | 90.880 | 47.435 | 62.095 | 1.00 | 40.16 | ras |
| ATOM | 4884 | C   | ALA | 155 | 92.283 | 45.835 | 63.378 | 1.00 | 34.56 | ras |
| ATOM | 4885 | O   | ALA | 155 | 92.394 | 45.692 | 64.595 | 1.00 | 33.83 | ras |
| ATOM | 4886 | N   | PHE | 156 | 92.236 | 44.812 | 62.529 | 1.00 | 35.79 | ras |
| ATOM | 4887 | CA  | PHE | 156 | 92.297 | 43.427 | 62.992 | 1.00 | 33.23 | ras |
| ATOM | 4888 | CB  | PHE | 156 | 91.925 | 42.473 | 61.873 | 1.00 | 27.57 | ras |

TABLE 3-continued

PDB Coordinates for the Ras-Sos Structure:
DATA SET FOR REFINED COORDINATES

| ATOM | 4889 | CG  | PHE | 156 | 90.471  | 42.482 | 61.547 | 1.00 | 27.45 | ras |
|------|------|-----|-----|-----|---------|--------|--------|------|-------|-----|
| ATOM | 4890 | CD1 | PHE | 156 | 89.979  | 43.292 | 60.531 | 1.00 | 28.01 | ras |
| ATOM | 4891 | CD2 | PHE | 156 | 89.591  | 41.662 | 62.239 | 1.00 | 27.64 | ras |
| ATOM | 4892 | CE1 | PHE | 156 | 88.631  | 43.286 | 60.201 | 1.00 | 24.89 | ras |
| ATOM | 4893 | CE2 | PHE | 156 | 88.239  | 41.643 | 61.922 | 1.00 | 28.91 | ras |
| ATOM | 4894 | CZ  | PHE | 156 | 87.758  | 42.458 | 60.897 | 1.00 | 30.70 | ras |
| ATOM | 4895 | C   | PHE | 156 | 93.629  | 43.027 | 63.612 | 1.00 | 32.93 | ras |
| ATOM | 4896 | O   | PHE | 156 | 93.650  | 42.460 | 64.695 | 1.00 | 34.20 | ras |
| ATOM | 4897 | N   | TYR | 157 | 94.739  | 43.338 | 62.953 | 1.00 | 34.46 | ras |
| ATOM | 4898 | CA  | TYR | 157 | 96.046  | 42.994 | 63.514 | 1.00 | 38.67 | ras |
| ATOM | 4899 | CB  | TYR | 157 | 97.186  | 43.390 | 62.566 | 1.00 | 39.66 | ras |
| ATOM | 4900 | CG  | TYR | 157 | 97.276  | 42.563 | 61.295 | 1.00 | 43.32 | ras |
| ATOM | 4901 | CD1 | TYR | 157 | 96.302  | 41.621 | 60.972 | 1.00 | 42.37 | ras |
| ATOM | 4902 | CE1 | TYR | 157 | 96.398  | 40.857 | 59.812 | 1.00 | 46.60 | ras |
| ATOM | 4903 | CD2 | TYR | 157 | 98.349  | 42.719 | 60.419 | 1.00 | 45.75 | ras |
| ATOM | 4904 | CE2 | TYR | 157 | 98.457  | 41.960 | 59.256 | 1.00 | 44.00 | ras |
| ATOM | 4905 | CZ  | TYR | 157 | 97.481  | 41.032 | 58.956 | 1.00 | 49.74 | ras |
| ATOM | 4906 | OH  | TYR | 157 | 97.581  | 40.289 | 57.794 | 1.00 | 51.25 | ras |
| ATOM | 4907 | C   | TYR | 157 | 96.231  | 43.652 | 64.891 | 1.00 | 38.80 | ras |
| ATOM | 4908 | O   | TYR | 157 | 96.768  | 43.028 | 65.813 | 1.00 | 40.75 | ras |
| ATOM | 4909 | N   | THR | 158 | 95.758  | 44.891 | 65.047 | 1.00 | 35.11 | ras |
| ATOM | 4910 | CA  | THR | 158 | 95.880  | 45.570 | 66.335 | 1.00 | 31.71 | ras |
| ATOM | 4911 | CB  | THR | 158 | 95.316  | 47.016 | 66.332 | 1.00 | 27.49 | ras |
| ATOM | 4912 | OG1 | THR | 158 | 96.108  | 47.851 | 65.484 | 1.00 | 30.09 | ras |
| ATOM | 4913 | CG2 | THR | 158 | 95.369  | 47.599 | 67.722 | 1.00 | 23.73 | ras |
| ATOM | 4914 | C   | THR | 158 | 95.159  | 44.772 | 67.412 | 1.00 | 32.12 | ras |
| ATOM | 4915 | O   | THR | 158 | 95.709  | 44.576 | 68.489 | 1.00 | 34.06 | ras |
| ATOM | 4916 | N   | LEU | 159 | 93.948  | 44.290 | 67.123 | 1.00 | 31.36 | ras |
| ATOM | 4917 | CA  | LEU | 159 | 93.205  | 43.521 | 68.119 | 1.00 | 30.98 | ras |
| ATOM | 4918 | CB  | LEU | 159 | 91.801  | 43.158 | 67.627 | 1.00 | 27.46 | ras |
| ATOM | 4919 | CG  | LEU | 159 | 90.983  | 42.311 | 68.615 | 1.00 | 31.35 | ras |
| ATOM | 4920 | CD1 | LEU | 159 | 90.868  | 43.012 | 69.950 | 1.00 | 33.01 | ras |
| ATOM | 4921 | CD2 | LEU | 159 | 89.612  | 41.993 | 68.072 | 1.00 | 31.71 | ras |
| ATOM | 4922 | C   | LEU | 159 | 93.968  | 42.267 | 68.536 | 1.00 | 33.71 | ras |
| ATOM | 4923 | O   | LEU | 159 | 94.016  | 41.923 | 69.723 | 1.00 | 32.03 | ras |
| ATOM | 4924 | N   | VAL | 160 | 94.588  | 41.605 | 67.560 | 1.00 | 35.72 | ras |
| ATOM | 4925 | CA  | VAL | 160 | 95.358  | 40.399 | 67.829 | 1.00 | 37.53 | ras |
| ATOM | 4926 | CB  | VAL | 160 | 95.924  | 39.812 | 66.533 | 1.00 | 37.45 | ras |
| ATOM | 4927 | CG1 | VAL | 160 | 96.971  | 38.754 | 66.837 | 1.00 | 42.21 | ras |
| ATOM | 4928 | CG2 | VAL | 160 | 94.806  | 39.200 | 65.727 | 1.00 | 40.43 | ras |
| ATOM | 4929 | C   | VAL | 160 | 96.481  | 40.717 | 68.816 | 1.00 | 39.35 | ras |
| ATOM | 4930 | O   | VAL | 160 | 96.661  | 40.016 | 69.817 | 1.00 | 36.57 | ras |
| ATOM | 4931 | N   | ARG | 161 | 97.198  | 41.806 | 68.547 | 1.00 | 39.14 | ras |
| ATOM | 4932 | CA  | ARG | 161 | 98.286  | 42.249 | 69.409 | 1.00 | 40.11 | ras |
| ATOM | 4933 | CB  | ARG | 161 | 98.957  | 43.501 | 68.821 | 1.00 | 35.29 | ras |
| ATOM | 4934 | CG  | ARG | 161 | 99.609  | 43.256 | 67.473 | 1.00 | 30.12 | ras |
| ATOM | 4935 | CD  | ARG | 161 | 100.321 | 44.486 | 66.931 | 1.00 | 31.35 | ras |
| ATOM | 4936 | NE  | ARG | 161 | 101.023 | 44.166 | 65.687 | 1.00 | 36.97 | ras |
| ATOM | 4937 | CZ  | ARG | 161 | 100.716 | 44.650 | 64.482 | 1.00 | 38.66 | ras |
| ATOM | 4938 | NH1 | ARG | 161 | 99.707  | 45.505 | 64.334 | 1.00 | 37.06 | ras |
| ATOM | 4939 | NH2 | ARG | 161 | 101.403 | 44.250 | 63.413 | 1.00 | 32.26 | ras |
| ATOM | 4940 | C   | ARG | 161 | 97.770  | 42.513 | 70.831 | 1.00 | 42.84 | ras |
| ATOM | 4941 | O   | ARG | 161 | 98.427  | 42.167 | 71.810 | 1.00 | 45.27 | ras |
| ATOM | 4942 | N   | GLU | 162 | 96.572  | 43.082 | 70.938 | 1.00 | 43.77 | ras |
| ATOM | 4943 | CA  | GLU | 162 | 95.972  | 43.358 | 72.239 | 1.00 | 45.50 | ras |
| ATOM | 4944 | CB  | GLU | 162 | 94.657  | 44.117 | 72.073 | 1.00 | 45.29 | ras |
| ATOM | 4945 | CG  | GLU | 162 | 94.828  | 45.572 | 71.666 | 1.00 | 49.28 | ras |
| ATOM | 4946 | CD  | GLU | 162 | 95.393  | 46.433 | 72.783 | 1.00 | 49.96 | ras |
| ATOM | 4947 | OE1 | GLU | 162 | 94.893  | 46.306 | 73.919 | 1.00 | 50.13 | ras |
| ATOM | 4948 | OE2 | GLU | 162 | 96.322  | 47.235 | 72.526 | 1.00 | 45.47 | ras |
| ATOM | 4949 | C   | GLU | 162 | 95.729  | 42.065 | 73.012 | 1.00 | 45.57 | ras |
| ATOM | 4950 | O   | GLU | 162 | 95.812  | 42.049 | 74.238 | 1.00 | 49.62 | ras |
| ATOM | 4951 | N   | ILE | 163 | 95.441  | 40.985 | 72.291 | 1.00 | 43.63 | ras |
| ATOM | 4952 | CA  | ILE | 163 | 95.199  | 39.689 | 72.912 | 1.00 | 43.70 | ras |
| ATOM | 4953 | CB  | ILE | 163 | 94.518  | 38.721 | 71.929 | 1.00 | 42.08 | ras |
| ATOM | 4954 | CG2 | ILE | 163 | 94.293  | 37.369 | 72.586 | 1.00 | 39.47 | ras |
| ATOM | 4955 | CG1 | ILE | 163 | 93.195  | 39.313 | 71.452 | 1.00 | 38.60 | ras |
| ATOM | 4956 | CD1 | ILE | 163 | 92.460  | 38.442 | 70.479 | 1.00 | 40.43 | ras |
| ATOM | 4957 | C   | ILE | 163 | 96.515  | 39.073 | 73.389 | 1.00 | 46.62 | ras |
| ATOM | 4958 | O   | ILE | 163 | 96.614  | 38.592 | 74.519 | 1.00 | 46.18 | ras |
| ATOM | 4959 | N   | ARG | 164 | 97.521  | 39.089 | 72.519 | 1.00 | 49.07 | ras |
| ATOM | 4960 | CA  | ARG | 164 | 98.835  | 38.543 | 72.846 | 1.00 | 48.45 | ras |
| ATOM | 4961 | CB  | ARG | 164 | 99.784  | 38.670 | 71.653 | 1.00 | 46.05 | ras |
| ATOM | 4962 | CG  | ARG | 164 | 99.500  | 37.700 | 70.529 | 1.00 | 45.27 | ras |
| ATOM | 4963 | CD  | ARG | 164 | 100.329 | 38.016 | 69.297 | 1.00 | 45.53 | ras |
| ATOM | 4964 | NE  | ARG | 164 | 100.096 | 37.039 | 68.239 | 1.00 | 44.23 | ras |

TABLE 3-continued

PDB Coordinates for the Ras-Sos Structure:
DATA SET FOR REFINED COORDINATES

| ATOM | 4965 | CZ  | ARG | 164 | 100.571  | 37.135   | 67.002   | 1.00 | 44.50 | ras |
|------|------|-----|-----|-----|----------|----------|----------|------|-------|-----|
| ATOM | 4966 | NH1 | ARG | 164 | 101.320  | 38.175   | 66.648   | 1.00 | 43.21 | ras |
| ATOM | 4967 | NH2 | ARG | 164 | 100.277  | 36.195   | 66.112   | 1.00 | 43.19 | ras |
| ATOM | 4968 | C   | ARG | 164 | 99.441   | 39.239   | 74.056   | 1.00 | 48.10 | ras |
| ATOM | 4969 | O   | ARG | 164 | 99.888   | 38.581   | 74.989   | 1.00 | 49.06 | ras |
| ATOM | 4970 | N   | GLN | 165 | 99.415   | 40.568   | 74.049   | 1.00 | 49.21 | ras |
| ATOM | 4971 | CA  | GLN | 165 | 99.972   | 41.360   | 45.141   | 1.00 | 55.72 | ras |
| ATOM | 4972 | CB  | GLN | 165 | 100.255  | 42.780   | 74.661   | 1.00 | 58.53 | ras |
| ATOM | 4973 | CG  | GLN | 165 | 101.227  | 42.844   | 73.500   | 1.00 | 66.52 | ras |
| ATOM | 4974 | CD  | GLN | 165 | 101.412  | 44.249   | 72.960   | 1.00 | 70.16 | ras |
| ATOM | 4975 | OE1 | GLN | 165 | 102.113  | 44.450   | 71.965   | 1.00 | 73.83 | ras |
| ATOM | 4976 | NE2 | GLN | 165 | 100.784  | 45.231   | 73.610   | 1.00 | 69.19 | ras |
| ATOM | 4977 | C   | GLN | 165 | 99.068   | 41.401   | 76.366   | 1.00 | 57.35 | ras |
| ATOM | 4978 | O   | GLN | 165 | 99.171   | 42.300   | 77.201   | 1.00 | 58.59 | ras |
| ATOM | 4979 | N   | HIS | 166 | 98.199   | 40.407   | 76.480   | 1.00 | 59.52 | ras |
| ATOM | 4980 | CA  | HIS | 166 | 97.269   | 40.321   | 77.595   | 1.00 | 63.45 | ras |
| ATOM | 4981 | CB  | HIS | 166 | 95.834   | 40.359   | 77.055   | 1.00 | 66.59 | ras |
| ATOM | 4982 | CG  | HIS | 166 | 94.782   | 40.297   | 78.115   | 1.00 | 70.68 | ras |
| ATOM | 4983 | CD2 | HIS | 166 | 93.954   | 41.249   | 78.604   | 1.00 | 72.45 | ras |
| ATOM | 4984 | ND1 | HIS | 166 | 94.486   | 39.140   | 78.802   | 1.00 | 73.34 | ras |
| ATOM | 4985 | CE1 | HIS | 166 | 93.521   | 39.382   | 79.671   | 1.00 | 75.61 | ras |
| ATOM | 4986 | NE2 | HIS | 166 | 93.181   | 40.655   | 79.571   | 1.00 | 75.70 | ras |
| ATOM | 4987 | C   | HIS | 166 | 97.522   | 39.031   | 78.378   | 1.00 | 63.34 | ras |
| ATOM | 4988 | O   | HIS | 166 | 97.543   | 39.110   | 79.621   | 1.00 | 59.29 | ras |
| ATOM | 4989 | OT  | HIS | 166 | 9999.000 | 9999.000 | 9999.000 | 1.00 | 0.00  | ras |
| ATOM | 4990 | O   | HOH | 1   | 69.299   | 32.369   | 96.154   | 1.00 | 25.14 | wat |
| ATOM | 4991 | O   | HOH | 2   | 55.542   | 23.355   | 83.075   | 1.00 | 41.80 | wat |
| ATOM | 4992 | O   | HOH | 3   | 63.755   | 32.926   | 64.057   | 1.00 | 39.83 | wat |
| ATOM | 4993 | O   | HOH | 4   | 73.092   | 45.998   | 59.527   | 1.00 | 24.81 | wat |
| ATOM | 4994 | O   | HOH | 5   | 74.894   | 61.523   | 62.272   | 1.00 | 31.78 | wat |
| ATOM | 4995 | O   | HOH | 6   | 82.477   | 43.373   | 59.812   | 1.00 | 33.10 | wat |
| ATOM | 4996 | O   | HOH | 7   | 81.024   | 40.935   | 57.522   | 1.00 | 32.28 | wat |
| ATOM | 4997 | O   | HOH | 8   | 77.096   | 40.473   | 68.317   | 1.00 | 31.48 | wat |
| ATOM | 4998 | O   | HOH | 9   | 68.149   | 28.273   | 59.475   | 1.00 | 25.69 | wat |
| ATOM | 4999 | O   | HOH | 10  | 66.815   | 33.640   | 28.729   | 1.00 | 53.77 | wat |
| ATOM | 5000 | O   | HOH | 11  | 65.439   | 51.704   | 26.104   | 1.00 | 40.04 | wat |
| ATOM | 5001 | O   | HOH | 12  | 61.946   | 44.526   | 49.630   | 1.00 | 29.31 | wat |
| ATOM | 5002 | O   | HOH | 13  | 63.194   | 49.565   | 54.927   | 1.00 | 28.90 | wat |
| ATOM | 5003 | O   | HOH | 14  | 43.364   | 25.822   | 87.328   | 1.00 | 60.71 | wat |
| ATOM | 5004 | O   | HOH | 15  | 41.602   | 26.163   | 72.376   | 1.00 | 35.06 | wat |
| ATOM | 5005 | O   | HOH | 16  | 49.525   | 28.716   | 70.468   | 1.00 | 43.22 | wat |
| ATOM | 5006 | O   | HOH | 17  | 78.124   | 23.228   | 66.046   | 1.00 | 35.79 | wat |
| ATOM | 5007 | O   | HOH | 18  | 79.663   | 55.785   | 72.976   | 1.00 | 35.57 | wat |
| ATOM | 5008 | O   | HOH | 19  | 58.528   | 42.327   | 77.044   | 1.00 | 34.00 | wat |
| ATOM | 5009 | O   | HOH | 20  | 77.367   | 40.161   | 94.623   | 1.00 | 29.24 | wat |
| ATOM | 5010 | O   | HOH | 21  | 60.209   | 17.900   | 88.460   | 1.00 | 36.53 | wat |
| ATOM | 5011 | O   | HOH | 22  | 77.995   | 41.999   | 64.087   | 1.00 | 47.66 | wat |
| ATOM | 5012 | O   | HOH | 23  | 76.550   | 44.191   | 67.484   | 1.00 | 38.12 | wat |
| ATOM | 5013 | O   | HOH | 24  | 75.990   | 48.437   | 60.460   | 1.00 | 32.28 | wat |
| ATOM | 5014 | O   | HOH | 25  | 81.857   | 38.271   | 57.371   | 1.00 | 34.53 | wat |
| ATOM | 5015 | O   | HOH | 26  | 89.482   | 37.565   | 76.274   | 1.00 | 38.75 | wat |
| END  |      |     |     |     |          |          |          |      |       |     |

What is claimed is:

1. A crystal of a Ras-Son of sevenless (Ras-Sos) complex that effectively diffracts X-rays for the determination of the atomic coordinates of the complex to a resolution of better than 5.0 Angstroms; wherein the Ras-Sos complex consists of a fragment of Ras consisting of amino acids 1 to 166 of SEQ ID NO:1 and a fragment of Sos consisting of amino acids 564 to 1049 of SEQ ID NO:2; wherein said crystal has a space group selected from the group consisting of I422 with unit cell dimensions of a=142.7, b=142.7 and c=207.9, and I4 with unit cell dimensions of a=124.6Å, b=124.6Å and c=314.9 Å.

2. The crystal of claim 1 that has a space group of I422 with unit cell dimensions of a=142.7, b=142.7 and c=207.9.

3. A method of growing a crystal of the Ras-Sos complex comprising:
   (a) contacting The Ras fragment with the Sos fragment of claim 2 under conditions in which a Ras-Sos complex is formed; and
   (b) growing the crystal by vapor diffusion using a reservoir buffer containing 2.7-3.2 M sodium formate and 100 mM Tris buffer, pH=8.0, at 4° C.

4. The crystal of claim 1 that has a space group of I4 with unit cell dimensions of a=124.6Å, b=124.6Å and c=314.9 Å.

5. A soluble polypeptide that consists of about 500 or fewer amino acids comprising the nucleotide exchange domain of Sos comprising amino acid residues 781 to 1017 of SEQ ID NO:2 or amino acid residues 781 to 1017 comprising one or more conservative amino acid substitutions; wherein said soluble polypeptide binds to Ras and promotes its activation.

6. A chimeric protein comprising the polypeptide of claim 5.

7. The soluble polypeptide of claim 5 further comprising amino acid residues 568–741 of SEQ ID NO:2 or amino acid residues 568–741 of SEQ ID NO:2 comprising one or more conservative amino acid substitutions.

8. A chimeric protein comprising the polypeptide of claim 7.

9. The soluble polypeptide of claim 7 that further comprises the amino acid residues 564 to 567, 742 to 780, and 1018 to 1049 of SEQ ID NO:2, or the amino acid residues 564 to 567, 742 to 780 and 1018 to 1049 of SEQ ID NO:2 comprising one or more conservative amino acid substitutions.

10. A chimeric protein comprising the polypeptide of claim 9.

* * * * *

UNITED STATES PATENT AND TRADEMARK OFFICE
CERTIFICATE OF CORRECTION

PATENT NO.    : 6,117,663
DATED         : September 12, 2000
INVENTOR(S)   : Ann-Boriack-Sjodin, S. Mariana Margarit, Dafna Bar-Sagi, Philip Cole and John Kuriyan It is certified that error appears in the above-identified patent and that said Letters Patent is hereby corrected as shown below:

<u>Title page, Item [54], and Column 1, line 1,</u>
Please change the Title from "CRYSTAL OF A RAS-SOS COMPLEX" to read
-- CRYSTAL OF A RAS-SOS COMPLEX AND METHODS OF USE THEREOF --

<u>Column 1,</u>
Lines 14-17, please change the Governmental Support from "The research leading to the present invention was supported, at least in part, by a grant from National Institutes of Health, Grant No. F32 Dk09664-1. Accordingly the Government may have certain rights in the invention." to read -- The research leading to the present invention was supported, at least in part, by a grants from National Institutes of Health, Grant No. F32 Dk09664-1, Grant No. 5P01 CA2814618, and Grant No. 5R01 CA5536008. Accordingly, the Government may have certain rights in the invention. --

Signed and Sealed this

Eleventh Day of June, 2002

*Attest:*

*Attesting Officer*

JAMES E. ROGAN
*Director of the United States Patent and Trademark Office*

SEQUENCE LISTING

<160> NUMBER OF SEQ ID NOS: 14

<210> SEQ ID NO 1
<211> LENGTH: 189
<212> TYPE: PRT
<213> ORGANISM: Homo sapiens

<400> SEQUENCE: 1

Met Thr Glu Tyr Lys Leu Val Val Val Gly Ala Gly Gly Val Gly Lys
 1               5                  10                  15

Ser Ala Leu Thr Ile Gln Leu Ile Gln Asn His Phe Val Asp Glu Tyr
            20                  25                  30

-continued

```
Asp Pro Thr Ile Glu Asp Ser Tyr Arg Lys Gln Val Val Ile Asp Gly
         35                  40                  45

Glu Thr Cys Leu Leu Asp Ile Leu Asp Thr Ala Gly Gln Glu Glu Tyr
 50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His Gln Tyr
                 85                  90                  95

Arg Glu Gln Ile Lys Arg Val Lys Asp Ser Asp Val Pro Met Val
            100                 105                 110

Leu Val Gly Asn Lys Cys Asp Leu Ala Ala Arg Thr Val Glu Ser Arg
            115                 120                 125

Gln Ala Gln Asp Leu Ala Arg Ser Tyr Gly Ile Pro Tyr Ile Glu Thr
        130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185

<210> SEQ ID NO 2
<211> LENGTH: 1333
<212> TYPE: PRT
<213> ORGANISM: Homo sapiens

<400> SEQUENCE: 2

Met Gln Ala Gln Gln Leu Pro Tyr Glu Phe Phe Ser Glu Glu Asn Ala
 1               5                  10                  15

Pro Lys Trp Arg Gly Leu Leu Val Pro Ala Leu Lys Lys Val Gln Gly
             20                  25                  30

Gln Val His Pro Thr Leu Glu Ser Asn Asp Asp Ala Leu Gln Tyr Val
         35                  40                  45

Glu Glu Leu Ile Leu Gln Leu Leu Asn Met Leu Cys Gln Ala Gln Pro
 50                  55                  60

Arg Ser Ala Ser Asp Val Glu Glu Arg Val Gln Lys Ser Phe Pro His
 65                  70                  75                  80

Pro Ile Asp Lys Trp Ala Ile Ala Asp Ala Gln Ser Ala Ile Glu Lys
                 85                  90                  95

Arg Lys Arg Arg Asn Pro Leu Ser Leu Pro Val Glu Lys Ile His Pro
            100                 105                 110

Leu Leu Lys Glu Val Leu Gly Tyr Lys Ile Asp His Gln Val Ser Val
            115                 120                 125

Tyr Ile Val Ala Val Leu Glu Tyr Ile Ser Ala Asp Ile Leu Lys Leu
        130                 135                 140

Val Gly Asn Tyr Val Arg Asn Ile Arg His Tyr Glu Ile Thr Lys Gln
145                 150                 155                 160

Asp Ile Lys Val Ala Met Cys Ala Asp Lys Val Leu Met Asp Met Phe
                165                 170                 175

His Gln Asp Val Glu Asp Ile Asn Ile Leu Ser Leu Thr Asp Glu Glu
            180                 185                 190

Pro Ser Thr Ser Gly Glu Gln Thr Tyr Tyr Asp Leu Val Lys Ala Phe
            195                 200                 205

Met Ala Glu Ile Arg Gln Tyr Ile Arg Glu Leu Asn Leu Ile Ile Lys
        210                 215                 220
```

-continued

```
Val Phe Arg Glu Pro Phe Val Ser Asn Ser Lys Leu Phe Ser Ala Asn
225                 230                 235                 240

Asp Val Glu Asn Ile Phe Ser Arg Ile Val Asp Ile His Glu Leu Ser
                245                 250                 255

Val Lys Leu Leu Gly His Ile Glu Asp Thr Val Glu Met Thr Asp Glu
                260                 265                 270

Gly Ser Pro His Pro Leu Val Gly Ser Cys Phe Glu Asp Leu Ala Glu
            275                 280                 285

Glu Leu Ala Phe Asp Pro Tyr Glu Ser Tyr Ala Arg Asp Ile Leu Arg
        290                 295                 300

Pro Gly Phe His Asp Arg Phe Leu Ser Gln Leu Ser Lys Pro Gly Ala
305                 310                 315                 320

Ala Leu Tyr Leu Gln Ser Ile Gly Glu Gly Phe Lys Glu Ala Val Gln
                325                 330                 335

Tyr Val Leu Pro Arg Leu Leu Leu Ala Pro Val Tyr His Cys Leu His
                340                 345                 350

Tyr Phe Glu Leu Leu Lys Gln Leu Glu Glu Lys Ser Glu Asp Gln Glu
            355                 360                 365

Asp Lys Glu Cys Leu Lys Gln Ala Ile Thr Ala Leu Leu Asn Val Gln
        370                 375                 380

Ser Gly Met Glu Lys Ile Cys Ser Lys Ser Leu Ala Lys Arg Arg Leu
385                 390                 395                 400

Ser Glu Ser Ala Cys Arg Phe Tyr Ser Gln Gln Met Lys Gly Lys Gln
                405                 410                 415

Leu Ala Ile Lys Lys Met Asn Glu Ile Gln Lys Asn Ile Asp Gly Trp
                420                 425                 430

Glu Gly Lys Asp Ile Gly Gln Cys Cys Asn Glu Phe Ile Met Glu Gly
            435                 440                 445

Thr Leu Thr Arg Val Gly Ala Lys His Glu Arg His Ile Phe Leu Phe
        450                 455                 460

Asp Gly Leu Met Ile Cys Cys Lys Ser Asn His Gly Gln Pro Arg Leu
465                 470                 475                 480

Pro Gly Ala Ser Asn Ala Glu Tyr Arg Leu Lys Glu Lys Phe Phe Met
                485                 490                 495

Arg Lys Val Gln Ile Asn Asp Lys Asp Asp Thr Asn Glu Tyr Lys His
                500                 505                 510

Ala Phe Glu Ile Ile Leu Lys Asp Glu Asn Ser Val Ile Phe Ser Ala
            515                 520                 525

Lys Ser Ala Glu Glu Lys Asn Asn Trp Met Ala Ala Leu Ile Ser Leu
        530                 535                 540

Gln Tyr Arg Ser Thr Leu Glu Arg Met Leu Asp Val Thr Met Leu Gln
545                 550                 555                 560

Glu Glu Lys Glu Glu Gln Met Arg Leu Pro Ser Ala Asp Val Tyr Arg
                565                 570                 575

Phe Ala Glu Pro Asp Ser Glu Glu Asn Ile Ile Phe Glu Glu Asn Met
                580                 585                 590

Gln Pro Lys Ala Gly Ile Pro Ile Ile Lys Ala Gly Thr Val Ile Lys
            595                 600                 605

Leu Ile Glu Arg Leu Thr Tyr His Met Tyr Ala Asp Pro Asn Phe Val
        610                 615                 620

Arg Thr Phe Leu Thr Thr Tyr Arg Ser Phe Cys Lys Pro Gln Glu Leu
625                 630                 635                 640
```

-continued

```
Leu Ser Leu Ile Ile Glu Arg Phe Glu Ile Pro Glu Pro Thr
                645                 650             655

Glu Ala Asp Arg Ile Ala Ile Glu Asn Gly Asp Gln Pro Leu Ser Ala
            660                 665             670

Glu Leu Lys Arg Phe Arg Lys Glu Tyr Ile Gln Pro Val Gln Leu Arg
            675                 680             685

Val Leu Asn Val Cys Arg His Trp Val Glu His Phe Tyr Asp Phe
690             695                 700

Glu Arg Asp Ala Tyr Leu Leu Gln Arg Met Glu Glu Phe Ile Gly Thr
705             710                 715                 720

Val Arg Gly Lys Ala Met Lys Lys Trp Val Glu Ser Ile Thr Lys Ile
                725             730                 735

Ile Gln Arg Lys Lys Ile Ala Arg Asp Asn Gly Pro Gly His Asn Ile
            740                 745             750

Thr Phe Gln Ser Ser Pro Pro Thr Val Glu Trp His Ile Ser Arg Pro
            755             760                 765

Gly His Ile Glu Thr Phe Asp Leu Leu Thr Leu His Pro Ile Glu Ile
770             775                 780

Ala Arg Gln Leu Thr Leu Leu Glu Ser Asp Leu Tyr Arg Ala Val Gln
785             790                 795                 800

Pro Ser Glu Leu Val Gly Ser Val Trp Thr Lys Glu Asp Lys Glu Ile
            805                 810             815

Asn Ser Pro Asn Leu Leu Lys Met Ile Arg His Thr Thr Asn Leu Thr
            820                 825             830

Leu Trp Phe Glu Lys Cys Ile Val Glu Thr Glu Asn Leu Glu Glu Arg
        835                 840             845

Val Ala Val Val Ser Arg Ile Ile Glu Ile Leu Gln Val Phe Gln Glu
850                 855                 860

Leu Asn Asn Phe Asn Gly Val Leu Glu Val Val Ser Ala Met Asn Ser
865                 870             875                 880

Ser Pro Val Tyr Arg Leu Asp His Thr Phe Glu Gln Ile Pro Ser Arg
            885             890             895

Gln Lys Lys Ile Leu Glu Glu Ala His Glu Leu Ser Glu Asp His Tyr
            900                 905             910

Lys Lys Tyr Leu Ala Lys Leu Arg Ser Ile Asn Pro Pro Cys Val Pro
        915                 920             925

Phe Phe Gly Ile Tyr Leu Thr Asn Ile Leu Lys Thr Glu Glu Gly Asn
930                 935             940

Pro Glu Val Leu Lys Arg His Gly Lys Glu Leu Ile Asn Phe Ser Lys
945             950                 955                 960

Arg Arg Lys Val Ala Glu Ile Thr Gly Glu Ile Gln Gln Tyr Gln Asn
                965             970                 975

Gln Pro Tyr Cys Leu Arg Val Glu Ser Asp Ile Lys Arg Phe Phe Glu
            980             985                 990

Asn Leu Asn Pro Met Gly Asn Ser Met Glu Lys Glu Phe Thr Asp Tyr
        995             1000                1005

Leu Phe Asn Lys Ser Leu Glu Ile Glu Pro Arg Asn Pro Lys Pro Leu
    1010                1015            1020

Pro Arg Phe Pro Lys Lys Tyr Ser Tyr Pro Leu Lys Ser Pro Gly Val
1025                1030            1035                1040

Arg Pro Ser Asn Pro Arg Pro Gly Thr Met Arg His Pro Thr Pro Leu
            1045            1050                1055
```

Gln Gln Glu Pro Arg Lys Ile Ser Tyr Ser Arg Ile Pro Glu Ser Glu
            1060                1065                1070

Thr Glu Ser Thr Ala Ser Ala Pro Asn Ser Pro Arg Thr Pro Leu Thr
        1075                1080                1085

Pro Pro Pro Ala Ser Gly Ala Ser Ser Thr Thr Asp Val Cys Ser Val
    1090                1095                1100

Phe Asp Ser Asp His Ser Ser Pro Phe His Ser Asn Asp Thr Val
1105                1110                1115                1120

Phe Ile Gln Val Thr Leu Pro His Gly Pro Arg Ser Ala Ser Val Ser
            1125                1130                1135

Ser Ile Ser Leu Thr Lys Gly Thr Asp Glu Val Pro Val Pro Pro Pro
        1140                1145                1150

Val Pro Pro Arg Arg Pro Glu Ser Ala Pro Ala Glu Ser Ser Pro
    1155                1160                1165

Ser Lys Ile Met Ser Lys His Leu Asp Ser Pro Ala Ile Pro Pro
    1170                1175                1180

Arg Gln Pro Thr Ser Lys Ala Tyr Ser Pro Arg Tyr Ser Ile Ser Asp
1185                1190                1195                1200

Arg Thr Ser Ile Ser Asp Pro Pro Glu Ser Pro Pro Leu Leu Pro Pro
            1205                1210                1215

Arg Glu Pro Val Arg Thr Pro Asp Val Phe Ser Ser Pro Leu His
        1220                1225                1230

Leu Gln Pro Pro Pro Leu Gly Lys Lys Ser Asp His Gly Asn Ala Phe
    1235                1240                1245

Phe Pro Asn Ser Pro Ser Pro Phe Thr Pro Pro Pro Gln Thr Pro
    1250                1255                1260

Ser Pro His Gly Thr Arg Arg His Leu Pro Ser Pro Pro Leu Thr Gln
1265                1270                1275                1280

Glu Val Asp Leu His Ser Ile Ala Gly Pro Pro Val Pro Pro Arg Gln
            1285                1290                1295

Ser Thr Ser Gln His Ile Pro Lys Leu Pro Pro Lys Thr Tyr Lys Arg
        1300                1305                1310

Glu His Thr His Pro Ser Met His Arg Asp Gly Pro Pro Leu Leu Glu
    1315                1320                1325

Asn Ala His Ser Ser
    1330

<210> SEQ ID NO 3
<211> LENGTH: 1596
<212> TYPE: PRT
<213> ORGANISM: Drosophila melanogaster

<400> SEQUENCE: 3

Met Phe Ser Gly Pro Ser Gly His Ala His Thr Ile Ser Tyr Gly Gly
 1               5                  10                  15

Gly Ile Gly Leu Gly Thr Gly Gly Gly Gly Ser Gly Gly Ser Gly
            20                  25                  30

Ser Gly Ser Gln Gly Gly Gly Gly Gly Ile Gly Ile Gly Gly Gly
        35                  40                  45

Val Ala Gly Leu Gln Asp Cys Asp Gly Tyr Asp Phe Thr Lys Cys Glu
    50                  55                  60

Asn Ala Ala Arg Trp Arg Gly Leu Phe Thr Pro Ser Leu Lys Lys Val
65                  70                  75                  80

Leu Glu Gln Val His Pro Arg Val Thr Ala Lys Glu Asp Ala Leu Leu
            85                  90                  95

-continued

```
Tyr Val Glu Lys Leu Cys Leu Arg Leu Leu Ala Met Leu Cys Ala Lys
            100                 105                 110

Pro Leu Pro His Ser Val Gln Asp Val Glu Glu Lys Val Asn Lys Ser
            115                 120                 125

Phe Pro Ala Pro Ile Asp Gln Trp Ala Leu Asn Glu Ala Lys Glu Val
            130                 135                 140

Ile Asn Ser Lys Lys Arg Lys Ser Val Leu Pro Thr Glu Lys Val His
145                 150                 155                 160

Thr Leu Leu Gln Lys Asp Val Leu Gln Tyr Lys Ile Asp Ser Ser Val
                165                 170                 175

Ser Ala Phe Leu Val Ala Val Leu Glu Tyr Ile Ser Ala Asp Ile Leu
            180                 185                 190

Lys Met Ala Gly Asp Tyr Val Ile Lys Ile Ala His Cys Glu Ile Thr
            195                 200                 205

Lys Glu Asp Ile Glu Val Val Met Asn Ala Asp Arg Val Leu Met Asp
210                 215                 220

Met Leu Asn Gln Ser Glu Ala His Ile Leu Pro Ser Pro Leu Ser Leu
225                 230                 235                 240

Pro Ala Gln Arg Ala Ser Ala Thr Tyr Glu Glu Thr Val Lys Glu Leu
                245                 250                 255

Ile His Asp Glu Lys Gln Tyr Gln Arg Asp Leu His Met Ile Ile Arg
            260                 265                 270

Val Phe Arg Glu Glu Leu Val Lys Ile Val Ser Asp Pro Arg Glu Leu
            275                 280                 285

Glu Pro Ile Phe Ser Asn Ile Met Asp Ile Tyr Glu Val Thr Val Thr
290                 295                 300

Leu Leu Gly Ser Leu Glu Asp Val Ile Glu Met Ser Gln Glu Gln Ser
305                 310                 315                 320

Ala Pro Cys Val Gly Ser Cys Phe Glu Glu Leu Ala Glu Ala Glu Glu
                325                 330                 335

Phe Asp Val Tyr Lys Lys Tyr Ala Tyr Asp Val Thr Ser Gln Ala Ser
            340                 345                 350

Arg Asp Ala Leu Asn Asn Leu Leu Ser Lys Pro Gly Ala Ser Ser Leu
            355                 360                 365

Thr Thr Ala Gly His Gly Phe Arg Asp Ala Val Lys Tyr Tyr Leu Pro
370                 375                 380

Lys Leu Leu Leu Val Pro Ile Cys His Ala Phe Val Tyr Phe Asp Tyr
385                 390                 395                 400

Ile Lys His Leu Lys Asp Leu Ser Ser Gln Asp Ile Glu Ser
                405                 410                 415

Phe Glu Gln Val Gln Gly Leu Leu His Pro Leu His Cys Asp Leu Glu
            420                 425                 430

Lys Val Met Ala Ser Leu Ser Lys Glu Arg Gln Val Pro Val Ser Gly
            435                 440                 445

Arg Val Arg Arg Gln Leu Ala Ile Glu Arg Thr Arg Glu Leu Gln Met
450                 455                 460

Lys Val Glu His Trp Glu Asp Lys Asp Val Gly Gln Asn Cys Asn Glu
465                 470                 475                 480

Phe Ile Arg Glu Asp Ser Leu Ser Lys Leu Gly Ser Gly Lys Arg Ile
                485                 490                 495

Trp Ser Glu Arg Lys Val Phe Leu Phe Asp Gly Leu Met Val Leu Cys
            500                 505                 510
```

-continued

```
Lys Ala Asn Thr Lys Lys Gln Thr Pro Ser Ala Gly Ala Thr Ala Tyr
        515                 520                 525

Asp Tyr Arg Leu Lys Glu Lys Tyr Phe Met Arg Arg Val Asp Ile Asn
        530                 535                 540

Asp Arg Pro Asp Ser Asp Asp Leu Lys Asn Ser Phe Glu Leu Ala Pro
545                 550                 555                 560

Arg Met Gln Pro Pro Ile Val Leu Thr Ala Lys Asn Ala Gln His Lys
                565                 570                 575

His Asp Trp Met Ala Asp Leu Leu Met Val Ile Thr Lys Ser Met Leu
                580                 585                 590

Asp Arg His Leu Asp Ser Ile Leu Gln Asp Ile Glu Arg Lys His Pro
        595                 600                 605

Leu Arg Met Pro Ser Pro Glu Ile Tyr Lys Phe Ala Val Pro Asp Ser
610                 615                 620

Gly Asp Asn Ile Val Leu Glu Glu Arg Glu Ser Ala Gly Val Pro Met
625                 630                 635                 640

Ile Lys Gly Ala Thr Leu Cys Lys Leu Ile Glu Arg Leu Thr Tyr His
                645                 650                 655

Ile Tyr Ala Asp Pro Thr Phe Val Arg Thr Phe Leu Thr Thr Tyr Arg
                660                 665                 670

Tyr Phe Cys Ser Pro Gln Gln Leu Leu Gln Leu Leu Val Glu Arg Phe
        675                 680                 685

Asn Ile Pro Asp Pro Ser Leu Val Tyr Gln Asp Thr Gly Thr Ala Gly
        690                 695                 700

Ala Gly Gly Met Gly Gly Val Gly Gly Asp Lys Glu His Lys Asn Ser
705                 710                 715                 720

His Arg Glu Asp Trp Lys Arg Tyr Arg Lys Glu Tyr Val Gln Pro Val
                725                 730                 735

Gln Phe Arg Val Leu Asn Val Leu Arg His Trp Val Asp His His Phe
                740                 745                 750

Tyr Asp Phe Glu Lys Asp Pro Met Leu Leu Glu Lys Leu Leu Asn Phe
        755                 760                 765

Leu Glu His Val Asn Gly Lys Ser Met Arg Lys Trp Val Asp Ser Val
        770                 775                 780

Leu Lys Ile Val Gln Arg Lys Asn Glu Gln Glu Lys Ser Asn Lys Lys
785                 790                 795                 800

Ile Val Tyr Ala Tyr Gly His Asp Pro Pro Ile Glu His His Leu
                805                 810                 815

Ser Val Pro Asn Asp Glu Ile Thr Leu Leu Thr Leu His Pro Leu Glu
                820                 825                 830

Leu Ala Arg Gln Leu Thr Leu Leu Glu Phe Glu Met Tyr Lys Asn Val
        835                 840                 845

Lys Pro Ser Glu Leu Val Gly Ser Pro Trp Thr Lys Lys Asp Lys Glu
850                 855                 860

Val Lys Ser Pro Asn Leu Leu Lys Ile Met Lys His Thr Thr Asn Val
865                 870                 875                 880

Thr Arg Trp Ile Glu Lys Ser Ile Thr Glu Ala Glu Asn Tyr Glu Glu
                885                 890                 895

Arg Leu Ala Ile Met Gln Arg Ala Ile Glu Val Met Met Val Met Leu
                900                 905                 910

Glu Leu Asn Asn Phe Asn Gly Ile Leu Ser Ile Val Ala Ala Met Gly
        915                 920                 925
```

```
Thr Ala Ser Val Tyr Arg Leu Arg Trp Thr Phe Gln Gly Leu Pro Glu
    930                 935                 940

Arg Tyr Arg Lys Phe Leu Glu Glu Cys Arg Glu Leu Ser Asp Asp His
945                 950                 955                 960

Leu Lys Lys Tyr Gln Glu Arg Leu Arg Ser Ile Asn Pro Pro Cys Val
                965                 970                 975

Pro Phe Phe Gly Arg Tyr Leu Thr Asn Ile Leu His Leu Glu Glu Gly
            980                 985                 990

Asn Pro Asp Leu Leu Ala Asn Thr Glu Leu Ile Asn Phe Ser Lys Arg
        995                 1000                1005

Arg Lys Val Ala Glu Ile Ile Gly Glu Ile Gln Gln Tyr Gln Asn Gln
    1010                1015                1020

Pro Tyr Cys Leu Asn Glu Ser Thr Ile Arg Gln Phe Phe Glu Gln
1025                1030                1035                1040

Leu Asp Pro Phe Asn Gly Leu Ser Asp Lys Gln Met Ser Asp Tyr Leu
                1045                1050                1055

Tyr Asn Glu Ser Leu Arg Ile Glu Pro Arg Gly Cys Lys Thr Val Pro
            1060                1065                1070

Lys Phe Pro Arg Lys Trp Pro His Ile Pro Leu Lys Ser Pro Gly Ile
        1075                1080                1085

Lys Pro Arg Arg Gln Asn Gln Thr Asn Ser Ser Ser Lys Leu Ser Asn
    1090                1095                1100

Ser Thr Ser Ser Val Ala Ala Ala Ala Ala Ser Ser Thr Ala Thr
1105                1110                1115                1120

Ser Ile Ala Thr Ala Ser Ala Pro Ser Leu His Ala Ser Ser Ile Met
            1125                1130                1135

Asp Ala Pro Thr Ala Ala Ala Ala Asn Ala Gly Ser Gly Thr Leu Ala
        1140                1145                1150

Gly Glu Gln Ser Pro Gln His Asn Pro His Ala Phe Ser Val Phe Ala
            1155                1160                1165

Pro Val Ile Ile Pro Glu Arg Asn Thr Ser Ser Trp Ser Gly Thr Pro
    1170                1175                1180

Gln His Thr Arg Thr Asp Gln Asn Asn Gly Glu Val Ser Val Pro Ala
1185                1190                1195                1200

Pro His Leu Pro Lys Lys Pro Gly Ala His Val Trp Ala Asn Asn Asn
            1205                1210                1215

Ser Thr Leu Ala Ser Ala Ser Ala Met Asp Val Val Phe Ser Pro Ala
        1220                1225                1230

Leu Pro Glu His Leu Pro Pro Gln Ser Leu Pro Asp Ser Asn Pro Phe
        1235                1240                1245

Ala Ser Asp Thr Glu Ala Pro Pro Ser Pro Leu Pro Lys Leu Val Val
    1250                1255                1260

Ser Pro Arg His Glu Thr Gly Asn Arg Ser Pro Phe His Gly Arg Met
1265                1270                1275                1280

Gln Asn Ser Pro Thr His Ser Thr Ala Ser Thr Val Thr Leu Thr Gly
                1285                1290                1295

Met Ser Thr Ser Gly Gly Glu Glu Phe Cys Ala Gly Gly Phe Tyr Phe
            1300                1305                1310

Asn Ser Ala His Gln Gly Gln Pro Gly Ala Val Pro Ile Ser Pro His
            1315                1320                1325

Val Asn Val Pro Met Ala Thr Asn Met Glu Tyr Arg Ala Val Pro Pro
    1330                1335                1340
```

-continued

```
Pro Leu Pro Pro Arg Arg Lys Glu Arg Thr Glu Ser Cys Ala Asp Met
1345                1350                1355                1360

Ala Gln Lys Arg Gln Ala Pro Asp Ala Pro Thr Leu Pro Pro Arg Asp
            1365                1370                1375

Gly Glu Leu Ser Pro Pro Ile Pro Pro Arg Leu Asn His Ser Thr
        1380                1385                1390

Gly Ile Ser Tyr Leu Arg Gln Ser His Gly Lys Ser Lys Glu Phe Val
        1395                1400                1405

Gly Asn Ser Ser Leu Leu Leu Pro Asn Thr Ser Ser Ile Met Ile Arg
    1410                1415                1420

Arg Asn Ser Ala Ile Glu Lys Arg Ala Ala Thr Ser Gln Pro Asn
1425                1430                1435                1440

Gln Ala Ala Ala Gly Pro Ile Ser Thr Thr Leu Val Thr Val Ser Gln
            1445                1450                1455

Ala Val Ala Thr Asp Glu Pro Leu Pro Leu Pro Ile Ser Pro Ala Ala
            1460                1465                1470

Ser Ser Ser Thr Thr Thr Ser Pro Leu Thr Pro Ala Met Ser Pro Met
        1475                1480                1485

Ser Pro Asn Ile Pro Ser His Pro Val Glu Ser Thr Ser Ser Ser Tyr
    1490                1495                1500

Ala His Gln Leu Arg Met Arg Gln Gln Gln Gln Gln Thr His Pro
1505                1510                1515                1520

Ala Ile Tyr Ser Gln His His Gln His His Ala Thr His Leu Pro His
            1525                1530                1535

His Pro His Gln His His Ser Asn Pro Thr Gln Ser Arg Ser Ser Pro
        1540                1545                1550

Lys Glu Phe Phe Pro Ile Ala Thr Ser Leu Glu Gly Thr Pro Lys Leu
    1555                1560                1565

Pro Pro Lys Pro Ser Leu Ser Ala Asn Phe Tyr Asn Asn Pro Asp Lys
1570                1575                1580

Gly Thr Met Phe Leu Tyr Pro Ser Thr Asn Glu Glu
1585                1590                1595

<210> SEQ ID NO 4
<211> LENGTH: 1589
<212> TYPE: PRT
<213> ORGANISM: Saccharomyces cerevisiae

<400> SEQUENCE: 4

Met Ser Asp Thr Asn Thr Ser Ile Pro Asn Thr Ser Ser Ala Arg Glu
  1               5                  10                  15

Ala Gly Asn Ala Ser Gln Thr Pro Ser Ile Ser Ser Ser Asn Thr
            20                  25                  30

Ser Thr Thr Thr Asn Thr Glu Ser Ser Ser Ala Ser Leu Ser Ser Ser
        35                  40                  45

Pro Ser Thr Ser Glu Leu Thr Ser Ile Arg Pro Ile Gly Ile Val Val
    50                  55                  60

Ala Ala Tyr Asp Phe Asn Tyr Pro Ile Lys Lys Asp Ser Ser Ser Gln
 65                  70                  75                  80

Leu Leu Ser Val Gln Gln Gly Glu Thr Ile Tyr Ile Leu Asn Lys Asn
                85                  90                  95

Ser Ser Gly Trp Trp Asp Gly Leu Val Ile Asp Asp Ser Asn Gly Lys
            100                 105                 110

Val Asn Arg Gly Trp Phe Pro Gln Asn Phe Gly Arg Pro Leu Arg Asp
        115                 120                 125
```

-continued

```
Ser His Leu Arg Lys His Ser His Pro Met Lys Lys Tyr Ser Ser Ser
    130                 135                 140
Lys Ser Ser Arg Arg Ser Ser Leu Asn Ser Leu Gly Asn Ser Ala Tyr
145                 150                 155                 160
Leu His Val Pro Arg Asn Pro Ser Lys Ser Arg Arg Gly Ser Ser Thr
                165                 170                 175
Leu Ser Ala Ser Leu Ser Asn Ala His Asn Ala Glu Thr Ser Ser Gly
            180                 185                 190
His Asn Asn Thr Val Ser Met Asn Asn Ser Pro Phe Ser Ala Pro Asn
        195                 200                 205
Asp Ala Ser His Ile Thr Pro Gln Ser Ser Asn Phe Asn Ser Asn Ala
    210                 215                 220
Ser Leu Ser Gln Asp Met Thr Lys Ser Ala Asp Gly Ser Ser Glu Met
225                 230                 235                 240
Asn Thr Asn Ala Ile Met Asn Asn Asn Glu Thr Asn Leu Gln Thr Ser
                245                 250                 255
Gly Glu Lys Ala Gly Pro Pro Leu Val Ala Glu Thr Ile Lys Ile
                260                 265                 270
Leu Pro Leu Glu Glu Ile Glu Met Ile Ile Asn Gly Ile Arg Ser Asn
            275                 280                 285
Ile Ala Ser Thr Trp Ser Pro Ile Pro Leu Ile Thr Lys Thr Ser Asp
    290                 295                 300
Tyr Lys Leu Val Tyr Tyr Asn Lys Asp Leu Asp Ile Tyr Cys Ser Glu
305                 310                 315                 320
Leu Pro Leu Ile Ser Asn Ser Ile Met Glu Ser Asp Ile Cys Asp
                325                 330                 335
Ser Glu Pro Lys Phe Pro Pro Asn Asp His Leu Val Asn Leu Tyr Thr
            340                 345                 350
Arg Asp Leu Arg Lys Asn Ala Asn Ile Glu Asp Ser Ser Thr Arg Ser
        355                 360                 365
Lys Gln Ser Glu Ser Glu Gln Asn Arg Ser Ser Leu Leu Met Glu Lys
    370                 375                 380
Gln Asp Ser Lys Glu Thr Asp Gly Asn Asn Ser Ile Asn Asp Asp
385                 390                 395                 400
Asp Asn Asn Asn Glu Asn Asn Lys Asn Glu Phe Asn Glu Ala Gly Pro
                405                 410                 415
Ser Ser Leu Asn Ser Leu Ser Ala Pro Asp Leu Thr Gln Asn Ile Gln
            420                 425                 430
Ser Arg Val Val Ala Pro Ser Arg Ser Ser Ile Leu Ala Lys Ser Asp
        435                 440                 445
Ile Phe Tyr His Tyr Ser Arg Asp Ile Lys Leu Trp Thr Glu Leu Gln
    450                 455                 460
Asp Leu Thr Val Tyr Tyr Thr Lys Thr Ala His Lys Met Phe Leu Lys
465                 470                 475                 480
Glu Asn Arg Leu Asn Phe Thr Lys Tyr Phe Asp Leu Ile Ser Asp Ser
                485                 490                 495
Ile Val Phe Thr Gln Leu Gly Cys Arg Leu Met Gln His Glu Ile Lys
            500                 505                 510
Ala Lys Ser Cys Ser Lys Glu Ile Lys Lys Ile Phe Lys Gly Leu Ile
        515                 520                 525
Ser Ser Leu Ser Arg Ile Ser Ile Asn Ser His Leu Tyr Phe Asp Ser
    530                 535                 540
```

-continued

```
Ala Phe His Arg Lys Lys Met Asp Thr Met Asn Asp Lys Asp Asn Asp
545                 550                 555                 560

Asn Gln Glu Asn Asn Cys Ser Arg Thr Glu Gly Asp Asp Gly Lys Ile
                565                 570                 575

Glu Val Asp Ser Val His Asp Leu Val Ser Val Pro Leu Ser Gly Lys
                580                 585                 590

Arg Asn Val Ser Thr Ser Thr Thr Asp Thr Leu Thr Pro Met Arg Ser
                595                 600                 605

Ser Phe Ser Thr Val Asn Glu Asn Asp Met Glu Asn Phe Ser Val Leu
                610                 615                 620

Gly Pro Arg Asn Ser Val Asn Ser Val Val Thr Pro Arg Thr Ser Ile
625                 630                 635                 640

Gln Asn Ser Thr Leu Glu Asp Phe Ser Pro Ser Asn Lys Asn Phe Lys
                645                 650                 655

Ser Ala Lys Ser Ile Tyr Glu Met Val Asp Val Glu Phe Ser Lys Phe
                660                 665                 670

Leu Arg His Val Gln Leu Leu Tyr Phe Val Leu Gln Ser Ser Val Phe
                675                 680                 685

Ser Asp Asp Asn Thr Leu Pro Gln Leu Leu Pro Arg Phe Phe Lys Gly
690                 695                 700

Ser Phe Ser Gly Gly Ser Trp Thr Asn Pro Phe Ser Thr Phe Ile Thr
705                 710                 715                 720

Asp Glu Phe Gly Asn Ala Thr Lys Asn Lys Ala Val Thr Ser Asn Glu
                725                 730                 735

Val Thr Ala Ser Ser Ser Lys Asn Ser Ser Ile Ser Arg Ile Pro Pro
                740                 745                 750

Lys Met Ala Asp Ala Ile Ala Ser Ala Ser Gly Tyr Ser Ala Asn Ser
                755                 760                 765

Glu Thr Asn Ser Gln Ile Asp Leu Lys Ala Ser Ser Ala Ala Ser Gly
                770                 775                 780

Ser Val Phe Thr Pro Phe Asn Arg Pro Ser His Asn Arg Thr Phe Ser
785                 790                 795                 800

Arg Ala Arg Val Ser Lys Arg Lys Lys Tyr Pro Leu Thr Val Asp
                805                 810                 815

Thr Leu Asn Thr Met Lys Lys Ser Ser Gln Ile Phe Glu Lys Leu
                820                 825                 830

Asn Asn Ala Thr Gly Glu His Leu Lys Ile Ile Ser Lys Pro Lys Ser
                835                 840                 845

Arg Ile Arg Asn Leu Glu Ile Asn Ser Ser Thr Tyr Glu Gln Ile Asn
850                 855                 860

Gln Asn Val Leu Leu Leu Glu Ile Leu Glu Asn Leu Asp Leu Ser Ile
865                 870                 875                 880

Phe Ile Asn Leu Lys Asn Leu Ile Lys Thr Pro Ser Ile Leu Leu Asp
                885                 890                 895

Leu Glu Ser Glu Glu Phe Leu Val His Ala Met Ser Ser Val Ser Ser
                900                 905                 910

Val Leu Thr Glu Phe Phe Asp Ile Lys Gln Ala Phe His Asp Ile Val
                915                 920                 925

Ile Arg Leu Ile Met Thr Thr Gln Gln Thr Thr Leu Asp Asp Pro Tyr
                930                 935                 940

Leu Phe Ser Ser Met Arg Ser Asn Phe Pro Val Gly His Glu Pro
945                 950                 955                 960
```

-continued

Phe Lys Asn Ile Ser Asn Thr Pro Leu Val Lys Gly Pro Phe His Lys
                965                 970                 975

Lys Asn Glu Gln Leu Ala Leu Ser Leu Phe His Val Leu Val Ser Gln
            980                 985                 990

Asp Val Glu Phe Asn Asn Leu Glu Phe Leu Asn Asn Ser Asp Asp Phe
        995                1000                1005

Lys Asp Ala Cys Glu Lys Tyr Val Glu Ile Ser Asn Leu Ala Cys Ile
    1010                1015                1020

Ile Val Asp Gln Leu Ile Glu Glu Arg Glu Asn Leu Leu Asn Tyr Ala
1025                1030                1035                1040

Ala Arg Met Met Lys Asn Asn Leu Thr Ala Glu Leu Leu Lys Gly Glu
            1045                1050                1055

Gln Glu Lys Trp Phe Asp Ile Tyr Ser Glu Asp Tyr Ser Asp Asp Asp
        1060                1065                1070

Ser Glu Asn Asp Glu Ala Ile Ile Asp Asp Glu Leu Gly Ser Glu Asp
        1075                1080                1085

Tyr Ile Glu Arg Lys Ala Ala Asn Ile Glu Lys Asn Leu Pro Trp Phe
1090                1095                1100

Leu Thr Ser Asp Tyr Glu Thr Ser Leu Val Tyr Asp Ser Arg Gly Lys
1105                1110                1115                1120

Ile Arg Gly Gly Thr Lys Glu Ala Leu Ile Glu His Leu Thr Ser His
            1125                1130                1135

Glu Leu Val Asp Ala Ala Phe Asn Val Thr Met Leu Ile Thr Phe Arg
        1140                1145                1150

Ser Ile Leu Thr Thr Arg Glu Phe Phe Tyr Ala Leu Ile Tyr Arg Tyr
        1155                1160                1165

Asn Leu Tyr Pro Pro Glu Gly Leu Ser Tyr Asp Asp Tyr Asn Ile Trp
    1170                1175                1180

Ile Glu Lys Lys Ser Asn Pro Ile Lys Cys Arg Val Val Asn Ile Met
1185                1190                1195                1200

Arg Thr Phe Leu Thr Gln Tyr Trp Thr Arg Asn Tyr Tyr Glu Pro Gly
            1205                1210                1215

Ile Pro Leu Ile Leu Asn Phe Ala Lys Met Val Val Ser Glu Lys Ile
        1220                1225                1230

Pro Gly Ala Glu Asp Leu Leu Gln Lys Ile Asn Glu Lys Leu Ile Asn
    1235                1240                1245

Glu Asn Glu Lys Glu Pro Val Asp Pro Lys Gln Gln Asp Ser Val Ser
1250                1255                1260

Ala Val Val Gln Thr Thr Lys Arg Asp Asn Lys Ser Pro Ile His Met
1265                1270                1275                1280

Ser Ser Ser Ser Leu Pro Ser Ser Ala Ser Ser Ala Phe Phe Arg Leu
            1285                1290                1295

Lys Lys Leu Lys Leu Leu Asp Ile Asp Pro Tyr Thr Tyr Ala Thr Gln
        1300                1305                1310

Leu Thr Val Leu Glu His Asp Leu Tyr Leu Arg Ile Thr Met Phe Glu
    1315                1320                1325

Cys Leu Asp Arg Ala Trp Gly Thr Lys Tyr Cys Asn Met Gly Gly Ser
    1330                1335                1340

Pro Asn Ile Thr Lys Phe Ile Ala Asn Ala Asn Thr Leu Thr Asn Phe
1345                1350                1355                1360

Val Ser His Thr Ile Val Lys Gln Ala Asp Val Lys Thr Arg Ser Lys
            1365                1370                1375

-continued

```
Leu Thr Gln Tyr Phe Val Thr Val Ala Gln His Cys Lys Glu Leu Asn
        1380                1385                1390

Asn Phe Ser Ser Met Thr Ala Ile Val Ser Ala Leu Tyr Ser Ser Pro
    1395                1400                1405

Ile Tyr Arg Leu Lys Lys Thr Trp Asp Leu Val Ser Thr Glu Ser Lys
1410                1415                1420

Asp Leu Leu Lys Asn Leu Asn Asn Leu Met Asp Ser Lys Arg Asn Phe
1425                1430                1435                1440

Val Lys Tyr Arg Glu Leu Leu Arg Ser Val Thr Asp Val Ala Cys Val
            1445                1450                1455

Pro Phe Phe Gly Val Tyr Leu Ser Asp Leu Thr Phe Thr Phe Val Gly
        1460                1465                1470

Asn Pro Asp Phe Leu His Asn Ser Thr Asn Ile Ile Asn Phe Ser Lys
    1475                1480                1485

Arg Thr Lys Ile Ala Asn Ile Val Glu Glu Ile Ile Ser Phe Lys Arg
1490                1495                1500

Phe His Tyr Lys Leu Lys Arg Leu Asp Asp Ile Gln Thr Val Ile Glu
1505                1510                1515                1520

Ala Ser Leu Glu Asn Val Pro His Ile Glu Lys Gln Tyr Gln Leu Ser
            1525                1530                1535

Leu Gln Val Glu Pro Arg Ser Gly Asn Thr Lys Gly Ser Thr His Ala
        1540                1545                1550

Ser Ser Ala Ser Gly Thr Lys Thr Ala Lys Phe Leu Ser Glu Phe Thr
    1555                1560                1565

Asp Asp Lys Asn Gly Asn Phe Leu Lys Leu Gly Lys Lys Pro Pro
   1570                1575                1580

Ser Arg Leu Phe Arg
1585

<210> SEQ ID NO 5
<211> LENGTH: 1048
<212> TYPE: PRT
<213> ORGANISM: Saccharomyces cerevisiae

<400> SEQUENCE: 5

Met Pro Ile Thr Ser Ser Pro Asp Leu Phe Tyr Leu Asn Asp Cys Asp
 1               5                  10                  15

Val Val Tyr Trp Tyr Asp Leu Thr Arg Leu Val Cys His Tyr Val Asn
            20                  25                  30

Leu Thr Glu Arg Asp Leu Leu Ala Asn Glu Arg Glu Lys Phe Leu Thr
        35                  40                  45

Ser Leu Asp Leu Leu Thr Ala Gln Ile Thr Tyr Val Tyr Met Leu Phe
    50                  55                  60

Arg Asn Leu Arg Leu Val Glu Asp Ser Phe Lys Lys Thr Leu Lys Lys
65                  70                  75                  80

Leu Ile Tyr Thr Leu Ser Arg Phe Ser Ile Asn Ala Asn Ile Trp Phe
                85                  90                  95

His Ser Thr Leu Phe Glu Glu Arg Glu Ala Ile Ala Ser Gln Lys Asp
            100                 105                 110

Pro Glu Arg Arg Ser Pro Leu Leu Gln Ser Ile Leu Gly Thr Phe Gln
        115                 120                 125

Lys Phe His Phe Leu Leu Arg Leu Leu His Phe Leu Ser Asn Pro Asn
    130                 135                 140

Glu Leu Thr Ile Leu Pro Gln Leu Thr Pro Arg Phe Lys Asp Ser
145                 150                 155                 160
```

-continued

```
Phe Asn Thr Ile Ser Trp Asn Asn Pro Phe Leu Arg Lys Arg Leu Asn
                165                 170                 175

Gln His Met Ser His Asp Leu Pro Arg Gln Met Ile Lys Ala Val Ala
            180                 185                 190

Gly Ala Ser Gly Ile Val Ala Glu Asn Ile Asp Glu Ile Pro Ala Ser
            195                 200                 205

Lys Gln Gly Thr Ser Cys Ser Ser Glu Thr Ser His His Ser Pro Ser
        210                 215                 220

Ala Pro Phe Gln Arg Arg Arg Arg Gly Thr Ile Phe Ser Asn Val Ser
225                 230                 235                 240

Gly Ser Ser Asp Glu Ser Asp Thr Ile Trp Ser Lys Arg Lys Lys Pro
                245                 250                 255

Tyr Pro Leu Asn Glu Glu Thr Leu Ser Leu Val Arg Ala Arg Lys Lys
                260                 265                 270

Gln Leu Asp Gly Lys Leu Lys Gln Met Ile Lys Ser Ala Asn Glu Tyr
            275                 280                 285

Leu Ser Asn Thr Ala Asn Phe Ser Lys Met Leu Asn Phe Glu Met Asn
        290                 295                 300

Phe Lys Thr Tyr Glu Glu Val Ser Gly Thr Ile Pro Ile Ile Asp Ile
305                 310                 315                 320

Leu Glu Asn Leu Asp Leu Thr Ile Phe Leu Asn Leu Arg Glu Leu Gly
                325                 330                 335

Asp Glu Asn Arg Val Phe Asp Glu Asp Val Ala Ile Asp Asp Glu Asp
                340                 345                 350

Glu Glu Phe Leu Lys His Ser Leu Ser Ser Leu Ser Tyr Ile Leu Ser
            355                 360                 365

Asp Tyr Phe Asn Met Lys Gln Tyr Phe His Asp Val Val Lys Phe
        370                 375                 380

Ile Ile Val Ala Gln His Leu Thr Leu Glu Asp Pro Phe Val Phe Ser
385                 390                 395                 400

Pro Met Gln Asn Asp Leu Pro Thr Gly Tyr Tyr Glu Pro Met Lys Pro
                405                 410                 415

Ser Ser Leu Asn Leu Asp Asn Ala Lys Asp Lys Lys Asn Gly Ser Gln
                420                 425                 430

Asn Thr Asp Ile Gln Glu Glu Glu Asp Glu Tyr Glu Pro Asp Pro Asp
            435                 440                 445

Ser Leu Ile Leu Phe His Asn Leu Ile Asn Gln Asp Ser Asp Phe Asn
        450                 455                 460

Asp Leu Lys Phe Phe Asn Leu Ala His Val Phe Lys Lys Ser Cys Asp
465                 470                 475                 480

Asp Tyr Phe Asp Val Leu Lys Leu Ala Ile Glu Phe Val Asn Gln Leu
                485                 490                 495

Ile Leu Glu Arg Glu Asn Leu Leu Asn Tyr Ala Ala Arg Met Met Lys
                500                 505                 510

Asn Asn Ile Thr Glu Leu Leu Leu Arg Gly Glu Glu Gly Tyr Gly Ser
            515                 520                 525

Tyr Asp Gly Gly Glu Thr Ala Glu Lys Ser Asp Thr Asn Ala Val Tyr
        530                 535                 540

Ala Asp Ser Asp Thr Lys Asp Asn Asp Glu Trp Arg Asp Ser Gln Val
545                 550                 555                 560

Lys Leu Pro Arg Tyr Leu Gln Arg Glu Tyr Asp Ser Glu Leu Ile Trp
                565                 570                 575
```

-continued

```
Gly Ser Asn Asn Arg Ile Lys Gly Gly Ser Lys His Ala Leu Ile Ser
            580                 585                 590

Tyr Leu Thr Asp Asn Glu Lys Lys Asp Leu Phe Phe Asp Ile Thr Phe
        595                 600                 605

Leu Ile Thr Phe Arg Ser Ile Phe Thr Thr Thr Glu Phe Leu Ser Tyr
        610                 615                 620

Leu Ile Ser Gln Tyr Asn Leu Asp Pro Pro Glu Asp Leu Cys Phe Glu
625                 630                 635                 640

Glu Tyr Asn Glu Trp Val Thr Lys Lys Leu Ile Pro Val Lys Cys Arg
                645                 650                 655

Val Val Glu Ile Met Thr Thr Phe Phe Lys Gln Tyr Trp Phe Leu Gly
                660                 665                 670

Tyr Asp Glu Pro Asp Leu Ala Thr Leu Asn Leu Asp Tyr Phe Ala Gln
                675                 680                 685

Val Ala Ile Lys Glu Asn Ile Thr Gly Ser Val Glu Leu Leu Lys Glu
            690                 695                 700

Val Asn Gln Lys Phe Lys His Gly Asn Ile Gln Glu Ala Thr Ala Pro
705                 710                 715                 720

Met Lys Thr Leu Asp Gln Gln Ile Cys Gln Asp His Tyr Ser Gly Thr
                725                 730                 735

Leu Tyr Ser Thr Thr Glu Ser Ile Leu Ala Val Asp Pro Val Leu Phe
                740                 745                 750

Ala Thr Gln Leu Thr Ile Leu Glu His Glu Ile Tyr Cys Glu Ile Thr
            755                 760                 765

Ile Phe Asp Cys Leu Gln Lys Ile Trp Lys Asn Lys Tyr Thr Lys Ser
            770                 775                 780

Tyr Gly Ala Ser Pro Gly Leu Asn Glu Phe Ile Ser Phe Ala Asn Lys
785                 790                 795                 800

Leu Thr Asn Phe Ile Ser Tyr Ser Val Val Lys Glu Ala Asp Lys Ser
                805                 810                 815

Lys Arg Ala Lys Leu Leu Ser His Phe Ile Phe Ile Ala Glu Tyr Cys
                820                 825                 830

Arg Lys Phe Asn Asn Phe Ser Ser Met Thr Ala Ile Ile Ser Ala Leu
                835                 840                 845

Tyr Ser Ser Pro Ile Tyr Arg Leu Glu Lys Thr Trp Gln Ala Val Ile
            850                 855                 860

Pro Gln Thr Arg Asp Leu Leu Gln Ser Leu Asn Lys Leu Met Asp Pro
865                 870                 875                 880

Lys Lys Asn Phe Ile Asn Tyr Arg Asn Glu Leu Lys Ser Leu His Ser
                885                 890                 895

Ala Pro Cys Val Pro Phe Phe Gly Val Tyr Leu Ser Asp Leu Thr Phe
            900                 905                 910

Thr Asp Ser Gly Asn Pro Asp Tyr Leu Val Leu Glu His Gly Leu Lys
        915                 920                 925

Gly Val His Asp Glu Lys Lys Tyr Ile Asn Phe Asn Lys Arg Ser Arg
        930                 935                 940

Leu Val Asp Ile Leu Gln Glu Ile Ile Tyr Phe Lys Lys Thr His Tyr
945                 950                 955                 960

Asp Phe Thr Lys Asp Arg Thr Val Ile Glu Cys Ile Ser Asn Ser Leu
                965                 970                 975

Glu Asn Ile Pro His Ile Glu Lys Gln Tyr Gln Leu Ser Leu Ile Ile
                980                 985                 990
```

-continued

```
Glu Pro Lys Pro Arg Lys Val Pro Asn Ser Asn Ser Asn Asn
        995                 1000                1005

Lys Ser Gln Glu Lys Ser Arg Asp Asp Gln Thr Asp Glu Gly Lys Thr
    1010                1015                1020

Ser Thr Lys Lys Asp Arg Phe Pro Lys Phe Gln Leu His Lys Thr Lys
1025                1030                1035                1040

Lys Lys Ala Pro Lys Val Ser Lys
                1045
```

<210> SEQ ID NO 6
<211> LENGTH: 911
<212> TYPE: PRT
<213> ORGANISM: Schizosaccharomyces pombe

<400> SEQUENCE: 6

```
Met Arg Phe Gln Thr Thr Ala Ile Ser Asp Tyr Glu Asn Ser Ser Asn
  1               5                  10                  15

Pro Ser Phe Leu Lys Phe Ser Ala Gly Asp Thr Ile Ile Val Ile Glu
             20                  25                  30

Val Leu Glu Asp Gly Trp Cys Asp Gly Ile Cys Ser Glu Lys Arg Gly
         35                  40                  45

Trp Phe Pro Thr Ser Cys Ile Asp Ser Ser Lys Ile Gln Asn Phe Phe
     50                  55                  60

Ser Ser Phe His Ser Ser Asn Glu Lys Asp Pro Asn Ala Gln Cys Cys
 65                  70                  75                  80

Ala Pro Phe His Val Glu Ala His Leu Gln Asp Ser Ala Trp Phe Glu
                 85                  90                  95

Lys His Gly Val Gln Ala Ile Asn Ser Ile Pro Ser Ser Glu Glu Phe
            100                 105                 110

Leu Arg Lys Asn Leu Gln Asn Asp Ile His His Leu Val Lys Gly Ile
        115                 120                 125

Leu Thr Thr Ala Ala Ala Val Ser Gln Ser Ile Lys Lys Glu Gly Thr
    130                 135                 140

Gln Val Ile Val Phe Gly Ile Glu Thr Val Arg Ser Met Val Leu Ser
145                 150                 155                 160

Phe Pro Leu Ile Ile Leu Ser Thr Leu Asp Glu Asn Phe Leu Ser Glu
                165                 170                 175

Val Ala Gln Val Phe Ser Ser Leu Asn Leu Leu Pro Glu Leu Ser Arg
            180                 185                 190

Met Gly Cys Thr Tyr Gly Glu Leu Cys Ile Arg Phe Thr Lys Leu Leu
        195                 200                 205

Lys Gln Leu Ala Asn Lys Phe Leu Phe Phe Arg Pro Asp Val Ser
    210                 215                 220

Phe Pro Ser Tyr Phe Leu Gly Ser Leu Ile Ala His Glu Ile His Phe
225                 230                 235                 240

Leu Pro Trp Asp Phe Asn Met Leu Cys Ser Asn Ser Val Gln Ser Ala
                245                 250                 255

His Thr Asn Leu Gln Pro Asp Ile Thr Ser Phe Val Ala Ile Leu Ser
            260                 265                 270

Leu Ser His Glu Ala Tyr His Cys Thr Glu Asn Glu Phe Trp Asn Leu
        275                 280                 285

Glu Ala Gln Lys Leu Thr Glu Asn Thr Thr Gln Lys Val Leu Gln Leu
    290                 295                 300

Val Ala Glu Asp Ala Leu Glu Ala Trp Lys Leu Asp Ile Leu Glu Asp
305                 310                 315                 320
```

-continued

```
Ile Asp Arg Cys Ile Gln Cys Cys Arg Arg Phe Leu Ser Ala Asn Gln
            325                 330                 335

Arg Ile Asn Tyr Ser Ser Ser Glu Asn Asn Pro Phe Ser Phe Thr Ser
            340                 345                 350

Gln Asp Val Glu Ala Leu Lys Asp Glu Leu Ser Ser Asn Leu Cys Asp
            355                 360                 365

Leu Tyr Leu Trp Ser Ile Asp Leu Glu Gln Ile Ser Pro Ser Asp Cys
            370                 375                 380

Leu Leu Asp Asn Tyr Ser Leu Phe Val Asp Leu Val Thr Leu Lys
385                 390                 395                 400

Val Ser Leu Leu Arg Ile Lys Ser Ile Ile Val Gln Phe Ser Glu Arg
                405                 410                 415

Ile Val Phe Leu Ser Leu Glu Tyr Lys Phe Leu Thr Asn Ile Gln Pro
                420                 425                 430

Glu Leu Asn Asp Ala Glu Lys Ser Gln Leu Asp Gly Phe Asp Leu Asn
                435                 440                 445

Lys Thr Asn Trp Phe Asp Ser Lys Gly Leu Val Cys Tyr Leu Met Lys
                450                 455                 460

Gln Thr Ser Pro Glu Pro Leu Leu Ile Arg Asn Leu Leu Phe Ser Phe
465                 470                 475                 480

Trp Ser Cys Asn Gly Lys Ile Glu Gln Asp Gly Lys Ile Lys Thr Ala
                485                 490                 495

Thr Leu Val Phe Ile Ile Asn Tyr Leu Leu Arg Thr Asp Ile Asp Ser
                500                 505                 510

Thr Phe Phe Thr Thr Ile Phe Leu Asn Thr Tyr Ala Ser Met Ile Ser
                515                 520                 525

Ser Ser Asp Leu Phe Ser Ile Leu Gly Ala His Phe Arg Phe Ile Cys
    530                 535                 540

Ser Leu Asn Phe Gly Lys Ile Ser Phe Ile Ser His Glu Phe Tyr Arg
545                 550                 555                 560

Val Ser Lys Arg Phe Leu Asp Ile Leu Leu Ile Trp Phe Glu Ser Tyr
                565                 570                 575

Leu Val Glu Glu Leu Asp Asn Ser Ser Ile Phe Phe Leu Phe Lys
                580                 585                 590

Ile Tyr Lys Val Phe Glu Val Phe Val Pro His Phe Ala Ser Ala
                595                 600                 605

Glu Glu Leu Leu His Ser Leu Ser His Leu Leu His His Pro Ser Thr
    610                 615                 620

Lys Arg Ser His Lys Met Leu Glu Gly Lys Glu Leu Ser Gln Glu Leu
625                 630                 635                 640

Glu Asp Leu Ser Leu His Asn Ser Pro Asp Pro Ile Ile Tyr Lys Asp
                645                 650                 655

Glu Leu Val Leu Leu Pro Pro Arg Glu Ile Ala Lys Gln Leu Cys
                660                 665                 670

Ile Leu Glu Phe Gln Ser Phe Ser His Ile Ser Arg Ile Gln Phe Leu
                675                 680                 685

Thr Lys Ile Trp Asp Asn Leu Asn Arg Phe Ser Pro Lys Glu Lys Thr
                690                 695                 700

Ser Thr Phe Tyr Leu Ser Asn His Leu Val Asn Phe Val Thr Glu Thr
705                 710                 715                 720

Ile Val Gln Glu Glu Pro Arg Arg Thr Asn Val Leu Ala Tyr
                725                 730                 735
```

```
Phe Ile Gln Val Cys Asp Tyr Leu Arg Glu Leu Asn Asn Phe Ala Ser
            740                 745                 750

Leu Phe Ser Ile Ile Ser Ala Leu Asn Ser Ser Pro Ile His Arg Leu
            755                 760                 765

Arg Lys Thr Trp Ala Asn Leu Asn Ser Lys Thr Leu Ala Ser Phe Glu
            770                 775                 780

Leu Leu Asn Asn Leu Thr Glu Ala Arg Lys Asn Phe Ser Asn Tyr Arg
785                 790                 795                 800

Asp Cys Leu Glu Asn Cys Val Leu Pro Cys Val Pro Phe Leu Gly Val
                    805                 810                 815

Tyr Phe Thr Asp Leu Thr Phe Leu Lys Thr Gly Asn Lys Asp Asn Phe
            820                 825                 830

Gln Asn Met Ile Asn Phe Asp Lys Arg Thr Lys Val Thr Arg Ile Leu
            835                 840                 845

Asn Glu Ile Lys Lys Phe Gln Ser Val Gly Tyr Met Phe Asn Pro Ile
850                 855                 860

Asn Glu Val Gln Glu Leu Leu Asn Glu Val Ile Ser Arg Glu Arg Asn
865                 870                 875                 880

Thr Asn Asn Ile Tyr Gln Arg Ser Leu Thr Val Glu Pro Arg Glu Ser
            885                 890                 895

Glu Asp Gln Ala Leu Gln Arg Leu Leu Ile Asp Ser Gly Ile Phe
            900                 905                 910

<210> SEQ ID NO 7
<211> LENGTH: 1244
<212> TYPE: PRT
<213> ORGANISM: Rattus rattus

<400> SEQUENCE: 7

Met Gln Lys Ala Ile Arg Leu Asn Asp Gly His Val Val Ser Leu Gly
  1               5                  10                  15

Leu Leu Ala Gln Arg Asp Gly Thr Arg Lys Gly Tyr Leu Ser Lys Arg
                 20                  25                  30

Ser Ser Asp Asn Pro Lys Trp Gln Thr Lys Trp Phe Ala Leu Leu Gln
             35                  40                  45

Asn Leu Leu Phe Tyr Phe Glu Ser Asp Ser Ser Arg Pro Ser Gly
 50                  55                  60

Leu Tyr Leu Leu Glu Gly Ser Ile Cys Lys Arg Met Pro Ser Pro Lys
 65                  70                  75                  80

Arg Gly Thr Ser Ser Lys Glu Ser Asp Lys Gln His His Tyr Phe Thr
                 85                  90                  95

Val Asn Phe Ser Asn Asp Ser Gln Lys Ser Leu Glu Leu Arg Thr Asp
            100                 105                 110

Asp Ser Lys Asp Cys Asp Glu Trp Val Ala Ala Ile Ala Arg Ala Ser
            115                 120                 125

Tyr Lys Ile Leu Ala Thr Glu His Glu Ala Leu Met Gln Lys Tyr Leu
            130                 135                 140

His Leu Leu Gln Val Val Glu Thr Glu Lys Thr Val Ala Lys Gln Leu
145                 150                 155                 160

Arg Gln Gln Leu Glu Asp Gly Glu Val Glu Ile Glu Arg Leu Lys Ala
                165                 170                 175

Glu Ile Ala Asn Leu Ile Lys Asp Asn Glu Arg Ile Gln Ser Asn Gln
            180                 185                 190

Leu Val Ala Pro Glu Asp Glu Asp Ser Asp Ile Lys Lys Ile Lys Lys
            195                 200                 205
```

```
Val Gln Ser Phe Leu Arg Gly Trp Leu Cys Arg Arg Lys Trp Lys Asn
    210                 215                 220
Ile Ile Gln Asp Tyr Ile Arg Ser Pro His Ala Asp Ser Met Arg Lys
225                 230                 235                 240
Arg Asn Gln Val Val Phe Ser Met Leu Glu Ala Glu Ala Glu Tyr Val
                245                 250                 255
Gln Gln Leu His Ile Leu Val Asn Asn Phe Leu Arg Pro Leu Arg Met
            260                 265                 270
Ala Ala Ser Ser Lys Lys Pro Pro Ile Thr His Asp Asp Val Ser Ser
        275                 280                 285
Ile Phe Leu Asn Ser Glu Thr Ile Met Phe Leu His Gln Ile Phe Tyr
290                 295                 300
Gln Gly Leu Lys Ala Arg Ile Ala Ser Trp Pro Thr Leu Val Leu Ala
305                 310                 315                 320
Asp Leu Phe Asp Ile Leu Leu Pro Met Leu Asn Ile Tyr Gln Glu Phe
                325                 330                 335
Val Arg Asn His Gln Tyr Ser Leu Gln Ile Leu Ala His Cys Lys Gln
            340                 345                 350
Asn Arg Asp Phe Asp Lys Leu Leu Lys Gln Tyr Glu Ala Lys Pro Asp
        355                 360                 365
Cys Glu Glu Arg Thr Leu Glu Thr Phe Leu Thr Tyr Pro Met Phe Gln
370                 375                 380
Ile Pro Arg Tyr Ile Leu Thr Leu His Glu Leu Leu Ala His Thr Pro
385                 390                 395                 400
His Glu His Val Glu Arg Asn Ser Leu Asp Tyr Ala Lys Ser Lys Leu
                405                 410                 415
Glu Glu Leu Ser Arg Val Met His Asp Glu Val Ser Glu Thr Glu Asn
            420                 425                 430
Ile Arg Lys Asn Leu Ala Ile Glu Arg Met Ile Thr Glu Gly Cys Glu
        435                 440                 445
Ile Leu Leu Asp Thr Ser Gln Thr Phe Val Arg Gln Gly Ser Leu Ile
450                 455                 460
Gln Val Pro Met Ser Glu Lys Gly Lys Ile Asn Lys Gly Arg Leu Gly
465                 470                 475                 480
Ser Leu Ser Leu Lys Lys Glu Gly Glu Arg Gln Cys Phe Leu Phe Ser
                485                 490                 495
Lys His Leu Ile Ile Cys Thr Arg Gly Ser Gly Ser Lys Leu His Leu
            500                 505                 510
Thr Lys Asn Gly Val Ile Ser Leu Ile Asp Cys Thr Leu Leu Asp Asp
        515                 520                 525
Pro Glu Asn Met Asp Asp Gly Lys Gly Gln Glu Val Asp His Leu
530                 535                 540
Asp Phe Lys Ile Trp Val Glu Pro Lys Asp Ser Pro Pro Phe Thr Val
545                 550                 555                 560
Ile Leu Val Ala Ser Ser Arg Gln Glu Lys Ala Ala Trp Thr Ser Asp
                565                 570                 575
Ile Ile Gln Cys Val Asp Asn Ile Arg Cys Asn Gly Leu Met Met Asn
            580                 585                 590
Ala Phe Glu Glu Asn Ser Lys Val Thr Val Pro Gln Met Ile Lys Ser
        595                 600                 605
Asp Ala Ser Leu Tyr Cys Asp Asp Val Asp Ile Arg Phe Ser Lys Thr
610                 615                 620
```

-continued

```
Met Asn Ser Cys Lys Val Leu Gln Ile Arg Tyr Ala Ser Val Glu Arg
625                 630                 635                 640

Leu Leu Glu Arg Leu Thr Asp Leu Arg Phe Leu Ser Ile Asp Phe Leu
                645                 650                 655

Asn Thr Phe Leu His Ser Tyr Arg Val Phe Thr Asp Ala Val Val Val
                660                 665                 670

Leu Asp Lys Leu Ile Ser Ile Tyr Lys Lys Pro Ile Thr Ala Ile Pro
                675                 680                 685

Ala Arg Ser Leu Glu Leu Leu Phe Ser Ser His Asn Thr Lys Leu
690                 695                 700

Leu Tyr Gly Asp Ala Pro Lys Ser Pro Arg Ala Ser Arg Lys Phe Ser
705                 710                 715                 720

Ser Pro Pro Leu Ala Ile Gly Thr Ser Pro Val Arg Arg Arg
                725                 730                 735

Lys Leu Ser Leu Asn Ile Pro Ile Ile Thr Gly Gly Lys Ala Leu Glu
                740                 745                 750

Leu Ala Ser Leu Gly Cys Pro Ser Asp Gly Tyr Thr Asn Ile His Ser
                755                 760                 765

Pro Ile Ser Pro Phe Gly Lys Thr Thr Leu Asp Thr Ser Lys Leu Cys
770                 775                 780

Val Ala Ser Ser Leu Thr Arg Thr Pro Glu Glu Ile Asp Met Thr Thr
785                 790                 795                 800

Leu Glu Glu Ser Ser Gly Phe Arg Lys Pro Thr Ser Asp Ile Leu Lys
                805                 810                 815

Glu Glu Ser Asp Asp Asp Gln Ser Asp Val Asp Asp Thr Glu Val Ser
                820                 825                 830

Pro Pro Thr Pro Lys Ser Phe Arg Asn Arg Ile Thr Gln Glu Phe Pro
                835                 840                 845

Leu Phe Asn Tyr Asn Ser Gly Ile Met Met Thr Cys Arg Asp Leu Met
                850                 855                 860

Asp Ser Asn Arg Ser Pro Leu Ser Ala Thr Ser Ala Phe Ala Ile Ala
865                 870                 875                 880

Thr Ala Gly Ala Asn Glu Ser Pro Ala Asn Lys Glu Ile Tyr Arg Arg
                885                 890                 895

Met Ser Leu Ala Asn Thr Gly Tyr Ser Ser Asp Gln Arg Asn Ile Asp
                900                 905                 910

Lys Glu Phe Val Ile Arg Arg Ala Thr Asn Arg Val Leu Asn Val
                915                 920                 925

Leu Arg His Trp Val Thr Lys His Ser Gln Asp Phe Glu Thr Asp Asp
                930                 935                 940

Leu Leu Lys Tyr Lys Val Ile Cys Phe Leu Glu Glu Val Met His Asp
945                 950                 955                 960

Pro Asp Leu Leu Pro Gln Glu Arg Lys Ala Ala Ala Asn Ile Met Arg
                965                 970                 975

Thr Leu Thr Gln Glu Glu Ile Thr Glu Asn His Ser Met Leu Asp Glu
                980                 985                 990

Leu Leu Leu Met Thr Glu Gly Val Lys Thr Glu Pro Phe Glu Asn His
                995                 1000                1005

Ser Ala Met Glu Ile Ala Glu Gln Leu Thr Leu Leu Asp His Leu Val
        1010                1015                1020

Phe Lys Ser Ile Pro Tyr Glu Glu Phe Phe Gly Gln Gly Trp Met Lys
1025                1030                1035                1040
```

Ala Asp Lys Asn Glu Arg Thr Pro Tyr Ile Met Lys Thr Thr Arg His
          1045                1050                1055

Phe Asn His Ile Ser Asn Leu Ile Ala Ser Glu Ile Leu Arg Asn Glu
          1060                1065                1070

Glu Val Ser Ala Arg Ala Ser Thr Ile Glu Lys Trp Val Ala Val Ala
          1075                1080                1085

Asp Ile Cys Arg Cys Leu His Asn Tyr Asn Ala Val Leu Glu Ile Thr
     1090                1095                1100

Ser Ser Ile Asn Arg Ser Ala Ile Phe Arg Leu Lys Lys Thr Trp Leu
1105                1110                1115                1120

Lys Val Ser Lys Gln Thr Lys Ser Leu Phe Asp Lys Leu Gln Lys Leu
          1125                1130                1135

Val Ser Ser Asp Gly Arg Phe Lys Asn Leu Arg Glu Thr Leu Arg Asn
          1140                1145                1150

Cys Asp Pro Pro Cys Val Pro Tyr Leu Gly Met Tyr Leu Thr Asp Leu
          1155                1160                1165

Ala Phe Leu Glu Glu Gly Thr Pro Asn Tyr Thr Glu Asp Gly Leu Val
          1170                1175                1180

Asn Phe Ser Lys Met Arg Met Ile Ser His Ile Ile Arg Glu Ile Arg
1185                1190                1195                1200

Gln Phe Gln Gln Thr Thr Tyr Lys Ile Glu Pro Gln Pro Lys Val Thr
          1205                1210                1215

Gln Tyr Leu Val Asp Glu Thr Phe Val Leu Asp Asp Glu Ser Leu Tyr
          1220                1225                1230

Glu Ala Ser Leu Arg Ile Glu Pro Lys Leu Pro Thr
          1235                1240

<210> SEQ ID NO 8
<211> LENGTH: 6453
<212> TYPE: DNA
<213> ORGANISM: Homo sapiens

<400> SEQUENCE: 8
ggatcccagc ctttccccag cccgtagccc cgggacctcc gcggtgggcg gcgccgcgct      60
gccggcgcag ggagggcctc tggtgcaccg gcaccgctga gtcgggttct ctcgccggcc    120
tgttcccggg agagcccggg gccctgctcg agatgccgcc cccgggcccc cagacaccgg    180
ctccctggcc ttcctcgagc aaccccgagc tcggctccgg tctccagcca agcccaaccc    240
cgagaggccg cggccctact ggctccgcct ccgcgttgc tccggaagc cccgcccgac      300 cgcggctcct gacagacggg ccgctcagcc aaccggggtg gggcggggcc cgatggcgcg    360
cagccaatgg taggccgcgc ctggcagacg gacgggcgcg gggcggggcg tgcgcaggcc    420
cgcccgagtc tccgccgccc gtgccctgcg cccgcaaccc gagccgcacc cgccgcggac    480
ggagcccatg cgcggggcga accgcgcgcc cccgccccg cccgcccg gcctcggccc       540 cggccctggc cccgggggca gtcgcgcctg tgaacggtga gtgcgggcag ggatcggccg    600
ggccgcgcgc cctcctcgcc cccaggcggc agcaatacgc gcggcgcggg ccggggcgc    660 ggggccggcg ggcgtaagcg gcggcggcgg cggcgggtgg gtgggccgg gcggggcccg    720 cgggcacagg tgagcgggcg tcggggggctg cggcgggcg gggccccttc ctccctgggg    780
cctgcgggaa tccgggcccc accgtggcc tcgcgctggg cacggtcccc acgccggcgt    840
acccgggagc tcgggcccg gcgccctcac acccgggggc gtctgggagg aggcggccgc    900
ggccacggca cgcccgggca ccccgattc agcatcacag gtcgcggacc aggccggggg    960

-continued

```
cctcagcccc agtgccttt  ccctctccgg gtctcccgcg ccgcttctcg gcccttcct   1020
gtcgctcagt ccctgcttcc caggagctcc tctgtcttct ccagctttct gtggctgaaa  1080
gatgcccccg gttccccgcc gggggtgcgg ggcgctgccc gggtctgccc tccctcggc   1140
ggcgcctagt acgcagtagg cgctcagcaa atacttgtcg gaggcaccag cgccgcgggg  1200
cctgcaggct ggcactagcc tgcccgggca cgccgtggcg cgctccgccg tggcagacc   1260
tgttctggag gacggtaacc tcagccctcg ggcgcctccc tttagccttt ctgccgaccc  1320
agcagcttct aatttgggtg cgtggttgag agcgctcagc tgtcagccct gcctttgagg  1380
gctgggtccc tttccccatc actgggtcat taagagcaag tgggggcgag gcgacagccc  1440
tcccgcacgc tggttgcag ctgcacaggt aggcacgctg cagtccttgc tgcctggcgt   1500
tggggcccag ggaccgctgt gggtttgccc ttcagatggc cctgccagca gctgccctgt  1560
ggggcctggg gctgggcctg gcctggctg agcagggccc tccttggcag gtggggcagg   1620
agaccctgta ggaggacccc gggccgcagg cccctgagga gcgatgacgg aatataagct  1680
ggtggtggtg ggcgccggcg gtgtgggcaa gagtgcgctg accatccagc tgatccagaa  1740
ccattttgtg gacgaatacg accccactat agaggtgagc ctagcgccgc cgtccaggtg  1800
ccagcagctg ctgcgggcga gcccaggaca cagccaggat agggctggct gcagcccctg  1860
gtcccctgca tggtgctgtg gccctgtctc ctgcttcctc tagaggaggg gagtccctcg  1920
tctcagcacc ccaggagagg aggggcatg aggggcatga gaggtaccag ggagaggctg   1980
gctgtgtgaa ctcccccac ggaaggtcct gaggggtcc ctgagccctg tcctcctgca    2040
ggattcctac cggaagcagg tggtcattga tggggagacg tgcctgttgg acatcctgga  2100
taccgccggc caggaggagt acagcgccat gcgggaccag tacatgcgca ccggggaggg  2160
cttcctgtgt gtgtttgcca tcaacaacac caagtctttt gaggacatcc accagtacag  2220
gtgaaccccg tgaggctggc ccgggagccc acgccgcaca ggtggggcca ggccggctgc  2280
gtccaggcag gggcctcctg tcctctctgc gcatgtcctg gatgccgctg cgcctgcagc  2340
ccccgtagcc agctctcgct ttccacctct cagggagcag atcaaacggg tgaaggactc  2400
ggatgacgtg cccatggtgc tggtggggaa caagtgtgac ctggctgcac gcactgtgga  2460
atctcggcag gctcaggacc tcgcccgaag ctacggcatc ccctacatcg agacctcggc  2520
caagacccgg caggtgaggc agctctccac cccacagcta gccagggacc cgccccgccc  2580
cgccccagcc agggagcagc actcactgac cctctcccct gacacagggc agccgctctg  2640
gctctagctc cagctccggg accctctggg accccccggg acccatgtga cccagcggcc  2700
cctcgcactg taggtctccc gggacggcag ggcagtgagg gaggcgaggg ccgggtctg   2760
ggctcacgcc ctgcagtcct gggccgacac agctccgggg aaggcggagg tccttgggga  2820
gagctgccct gagccaggcc ggagcggtga ccctggggcc cggcccctct tgtccccaga  2880
gtgtcccacg ggcacctgtt ggttctgagt cttagtgggg ctactgggga cacgggccgt  2940
agctgagtcg agagctgggt gcaggtggt caaaccctgg ccagacctgg agttcaggag   3000
ggccccgggc caccctgacc tttgagggc tgctgtagca tgatgcgggt ggccctgggc   3060
acttcgagat ggccagagtc cagcttcccg tgtgtgtggt gggcctgggg aagtggctgg  3120
tggagtcggg agcttcgggc caggcaaggc ttgatcccac agcagggagc ccctcaccca  3180
ggcaggcggc cacaggccgg tcctcctga tcccatccct cctttcccag ggagtggagg   3240
atgccttcta cacgttggtg cgtgagatcc ggcagcacaa gctgcggaag ctgaaccctc  3300
ctgatgagag tggccccggc tgcatgagct gcaagtgtgt gctctcctga cgcaggtgag  3360
```

```
ggggactccc agggcggccg ccacgcccac cggatgaccc cggctcccccg cccctgccgg  3420 tctcctggcc tgcggtcagc agcctccctt gtgccccgcc cagcacaagc tcaggacatg  3480
gaggtgccgg atgcaggaag gaggtgcaga cggaaggagg aggaaggaag gacggaagca  3540
aggaaggaag gaagggctgc tggagcccag tcaccccggg accgtgggcc gaggtgactg  3600
cagaccctcc cagggaggct gtgcacagac tgtcttgaac atcccaaatg ccaccggaac  3660
cccagcccct agctcccctc ccaggcctct gtgggcccct gtcgggcaca gatgggatca  3720
cagtaaatta ttggatggtc ttgatcttgg ttttcggctg agggtgggac acggtgcgcg  3780
tgtggcctgg catgaggtat gtcggaacct caggcctgtc cagccctggg ctctccatag  3840
cctttgggag gggaggttg ggagaggccg gtcagggtc tgggctgtgg tgctctctcc  3900
tcccgcctgc cccagtgtcc acggcttctg gcagagagct ctggacaagc aggcagatca  3960
taaggacaga gagcttactg tgcttctacc aactaggagg gcgtcctggt cctccagagg  4020
gaggtggttt caggggttgg ggatctgtgc cggtggctct ggtctctgct gggagccttc  4080
ttggcggtga gaggcatcac ctttcctgac ttgctcccag cgtgaaatgc acctgccaag  4140
aatggcagac atagggaccc cgcctcctgg gccttcacat gcccagtttt cttcggctct  4200
gtggcctgaa gcggtctgtg gaccttggaa gtagggctcc agcaccgact ggcctcaggc  4260
ctctgcctca ttggtggtcg ggtagcggcc agtagggcgt gggagcctgg ccatccctgc  4320
ctcctggagt ggacgaggtt ggcagctggt ccgtctgctc ctgccccact ctcccccgcc  4380
cctgccctca ccctacccct gccccacgcc tgcctcatgg ctggttgctc ttggagcctg  4440
gtagtgtcac tggctcagcc ttgctgggta tacacaggct ctgccaccca ctctgctcca  4500
aggggcttgc cctgccttgg gccaagttct aggtctggcc acagccacag acagctcagt  4560
cccctgtgtg gtcatcctgg cttctgctgg gggcccacag cgcccctggt gcccctcccc  4620
tcccagggcc cggggttgagg ctgggccagg ccctctggga cggggacttg tgccctgtca  4680
gggttcccta tccctgaggt tgggggagag ctagcagggc atgccgctgg ctggccaggg  4740
ctgcagggac actcccccctt ttgtccaggg aataccacac tcgcccttct ctccagcgaa  4800
caccacactc gcccttctct ccaggggacg ccacactccc ccttctgtcc aggggacgcc  4860
acactccccc ttctctccag gggacgccac actcgcccctt ctctcagggg acgccacac  4920 tcgcccttct ctcagggga cgccacactc gcccttctgt ccagggacg ccacactcgc  4980 ccttctctcc aggggacgcc acactcgccc ttctctccag gggacgccac actccccctt  5040
ctgtccaggg gacgccacac tccccttcct ctccaggga cgccacactc cccttctct  5100 ccaggggacg ccacactcgc ccttctctcc agggacgcc acactccccc ttctgtccag  5160
gggacgccac actcgcccctt ctctccaggg gacgccacac tcgcccttct ctcagggga  5220 cgccacactc cccttctct ccaggggacg ccacactccc ccttctctcc aggggacgcc  5280
acactccccc ttctgtccag gggacgccac actcgcccctt ctctccaggg gacgccacac  5340 tccccccttct ctcagggga cgccacactc cccccttctct ccaggggacg ccacactccc  5400
ccttctgtcc aggggacgcc acactcgccc ttctctccag gggacgccac actcgcccctt  5460 ctctccaggg gacgccacac tcgcccctttct ccaggggga cgccacactt gcccttctgt  5520
ccaggggatg ccacactccc ccctttctccc agcagcctcc gagtgaccag cttccccatc  5580
gatagacttc ccgaggccag gagccctcta gggctgccgg gtgccaccct ggctccttcc  5640
acaccgtgct ggtcactgcc tgctgggggc gtcagatgca ggtgaccctg tgcaggaggt  5700
atctctggac ctgcctcttg gtcattacgg ggctgggcag ggcctggtat cagggccccg  5760
```

```
ctggggttgc agggctgggc ctgtgctgtg gtcctgggdt gtccaggaca gacgtggagg      5820
ggtcagggcc cagcacccct gctccatgct gaactgtggg aagcatccag gtccctgggt      5880
ggcttcaaca ggagttccag cacgggaacc actggacaac ctgggdtgtg tcctgatctg      5940
gggacaggcc agccacaccc cgagtcctag ggactccaga gagcagccca ctgccctggg      6000
ctccacggaa gccccctcat gccgctaggc cttggcctcg gggacagccc agctaggcca      6060
gtgtgtggca ggaccaggcc cccatgtggg agctgacccc ttgggattct ggagctgtgc      6120
tgatgggcag gggagagcca gctcctcccc ttgagggagg gtcttgatgc ctggggttac      6180
ccgcagaggc ctgggtgccg ggacgctccc cggtttggct gaaaggaaag cagatgtggt      6240
cagcttctcc actgagccca tctggtcttc ccggggctgg gccccataga tctgggtccc      6300
tgtgtggccc ccctggtctg atgccgagga taccccctgca aactgccaat cccagaggac      6360
aagactggga gtccctgca gggagagccc atccccgcac cctgacccac aagagggact      6420
cctgctgccc accaggcatc cctccaggga tcc                                  6453
```

<210> SEQ ID NO 9
<211> LENGTH: 4002
<212> TYPE: DNA
<213> ORGANISM: Homo sapiens

<400> SEQUENCE: 9

```
atgcaggcgc agcagctgcc ctacgagttt ttcagcgaag agaacgcgcc caagtggcgg      60
ggactactgg tgcctgcgct gaaaaaggtc caggggcaag ttcatcctac tctcgagtct     120
aatgatgatg ctcttcagta tgttgaagaa ttaattttgc aattattaaa tatgctatgc     180
caagctcagc cccgaagtgc ttcagatgta gaggaacgtg ttcaaaaaag tttccctcat     240
ccaattgata aatgggcaat agctgatgcc caatcagcta ttgaaaagag gaagcgaaga     300 aacccttat ctctcccagt agaaaaaatt catccttat taaggaggt cctaggttat        360 aaaattgacc accaggtttc tgtttacata gtagcagtct tagaatacat ttctgcagac     420
attttaaagc tggttgggaa ttatgtaaga aatatacggc attatgaaat tacaaaacaa     480
gatattaaag tggcaatgtg tgctgacaag gtattgatgg atatgtttca tcaagatgta     540
gaagatatta atatattatc tttaactgac gaagagcctt ccacctcagg agaacaaact     600
tactatgatt tggtaaaagc atttatggca gaaattcgac aatatataag ggaactaaat     660
ctaattataa aagttttag agagcccttt gtctccaatt caaaattgtt tcagctaat      720 gatgtagaaa atatatttag tcgcatagta gatatacatg aacttagtgt aaagttactg     780
ggccatatag aagatacagt agaaatgaca gatgaaggca gtccccatcc actagtagga     840
agctgctttg aagacttagc agaggaactg gcatttgatc catatgaatc gtatgctcga     900
gatattttgc gacctggttt tcatgatcgt ttccttagtc agttatcaaa gcctggggca     960
gcactttatt tgcagtcaat aggcgaaggt ttcaaagaag ctgttcaata tgttttaccc    1020
aggctgcttc tggcccctgt ttaccactgt ctccattact ttgaactttt gaagcagtta    1080
gaagaaaaaa gtgaagatca agaagacaag gaatgtttaa acaagcaat aacagctttg    1140 cttaatgttc agagtggtat ggaaaaaata tgttctaaaa gtcttgcaaa acgaagactg    1200
agtgaatctg catgtcggtt ttatagtcag caaatgaagg ggaaacaact agcaatcaag    1260
aagatgaacg agattcagaa gaatattgat ggttgggagg gaaaagacat tggacagtgt    1320
tgtaatgaat ttataatgga aggaactctt acacgtgtag gagccaaaca tgagagacac    1380
atatttctct ttgatggctt aatgatttgc tgtaaatcaa atcatgggca gccaagactt    1440
```

```
cctggtgcta gcaatgcaga atatcgtctt aaagaaaagt tttttatgcg aaaggtacaa    1500
attaatgata aagatgacac caatgaatac aagcatgctt ttgaaataat tttaaaagat    1560
gaaaatagtg ttatattttc tgccaagtca gctgaagaga aaacaattg gatggcagca     1620 ttgatatctt tacagtaccg gagtacactg gaaaggatgc ttgatgtaac aatgctacag    1680
gaagagaaag aggagcagat gaggctgcct agtgctgatg tttatagatt tgcagagcct    1740
gactctgaag agaatattat atttgaagag aacatgcagc ccaaggctgg aattccaatt    1800
atcaaagcag gaactgttat taaacttata gagaggctta cgtaccatat gtacgcagat    1860
cccaattttg ttcggacatt tcttacaaca tacagatcct tttgcaaacc tcaagaacta    1920
ctgagtctta aatagaaag gtttgaaatt ccagagcctg agccaacaga agctgatcgc     1980
atagctatag agaatggaga tcaacccttg agtgcagaac tgaaaagatt tagaaaagaa    2040
tatatacagc ctgtgcaact gcgagtatta atgtatgtc ggcactgggt agagcaccac     2100
ttctatgatt ttgaaagaga tgcatatctt ttgcaacgaa tggaagaatt tattggaaca    2160
gtaagaggta aagcaatgaa aaatggggtt gaatccatca ctaaaataat ccaaaggaaa    2220
aaaattgcaa gagacaatgg accaggtcat aatattacat ttcagagttc acctcccaca    2280
gttgagtggc atataagcag acctgggcac atagagactt ttgacctgct caccttacac    2340
ccaatagaaa ttgctcgaca actcacttta cttgaatcag atctataccg agctgtacag    2400
ccatcagaat tagttggaag tgtgtggaca aagaagaca aagaaattaa ctctcctaat     2460
cttctgaaaa tgattcgaca taccaccaac ctcactctgt ggtttgagaa atgtattgta    2520
gaaactgaaa atttagaaga aagagtagct gtggtgagtc gaattattga gattctacaa    2580
gtctttcaag agttgaacaa ctttaatggt gtccttgagg ttgtcagtgc tatgaattca    2640
tcacctgttt acagactaga ccacacattt gagcaaatac caagtcgcca gaagaaaatt    2700
ttagaagaag ctcatgaatt gagtgaagat cactataaga aatatttggc aaaactcagg    2760
tctattaatc caccatgtgt gcctttcttt ggaatttatc tcactaatat cttgaaaaca    2820
gaagaaggca ccctgaggt cctaaaaaga catggaaaag agcttataaa ctttagcaaa     2880
aggaggaaag tagcagaaat aacaggagag atccagcagt accaaaatca gccttactgt    2940
ttacgagtag aatcagatat caaaaggttc tttgaaaact tgaatccgat gggaaatagc    3000
atggagaagg aatttacaga ttatcttttc aacaaatccc tagaaataga accacgaaac    3060
cctaagcctc tcccaagatt tccaaaaaaa tatagctatc ccctaaaatc tcctggtgtt    3120
cgtccatcaa acccaagacc aggtaccatg aggcatccca cacctctgca gcaggagcca    3180
aggaaaatta gttatagtag gatccctgaa agtgaaacag aaagtacagc atctgcacca    3240
aattctccaa gaacaccgtt aacacctccg cctgcttctg gtgcttccag taccacagat    3300
gtttgcagtg tatttgattc cgatcattcg agcccttttc actcaagcaa tgataccgtc    3360
tttatccaag ttactctgcc ccatggccca agatctgctt ctgtatcatc tataagttta    3420
accaaaggca ctgatgaagt gcctgtccct cctcctgttc ctccacgaag acgaccagaa    3480
tctgccccag cagaatcttc accatctaag attatgtcta agcatttgga cagtccccca    3540
gccattcctc ctaggcaacc cacatcaaaa gcctattcac cacgatattc aatatcagac    3600
cggacctcta tctcagaccc tcctgaaagc cctccttat taccaccacg agaacctgtg     3660
aggacacctg atgttttctc aagctccacca ctacatctcc aacctccccc tttgggcaaa   3720
aaaagtgacc atgcaatgc cttcttccca aacagccctt cccccttttac accacctcct    3780 cctcaaacac cttctcctca cggcacaaga aggcatctgc catcaccacc attgacacaa    3840
```

```
gaagtggacc ttcattccat tgctgggccg cctgttcctc cacgacaaag cacttctcaa    3900
catatcccta aactccctcc aaaaacttac aaaagggagc acacacaccc atccatgcac    3960
agagatggac caccactgtt ggagaatgcc cattcttcct ga                       4002

<210> SEQ ID NO 10
<211> LENGTH: 6601
<212> TYPE: DNA
<213> ORGANISM: Drosophila melanogaster

<400> SEQUENCE: 10
aagcttcgac ttctggaagc tagctcccta actgttttg gtttttgtat tctgttgcat      60
tgcattgctt tcatatgttt aattgtttca actgaacaca ttgtacttgt tttcgattta   120
gaagcgttga agcggatgt atcttacatt atccaagtaa ataagggat gagtcgatat     180 gtatgttgca tatctcctta cgattttaga taaggaaaga cattttataa atataaatat   240
aaatttcttg aaatataaac attgaagaga taattaaatt cattttttt gggtaaatta   300 taatatattt taaacctgct cgttgcaatt taaattcaaa atgcttcttc ttctgctaaa   360
aaagccattc aacacgaatg ctctctacat tggattttt agtacattct taagcatcga   420
atcagggctg gtcgcgagca tttactggat ttaggcagtg ccgcactctg gtcacaccgc   480
gaaaaatatt atattgagtt gaagattata ttatacatat atatatcgaa gatacatatt   540
ctgaaaacaa gtgctgaagc ccaagcgatt tgcaaacgaa acggacgcgc gagccccgtt   600
caagattcga aacgagttca gtgcgtgcgc ttgagtgtgt gtgactgcca tgcgacgttc   660
gcccgggtga tccggctgtg ccaggtgccc cacggttcca ggtttccagt ttccaggttc   720
cgctccactc cactcgtcgc tggattcagt gcacaacaca gcgggcgggg aggcggaggg   780
caggcggcca acgaaggtgc tccacggcag gctctcgtcg gctactccac ggcgcacaga   840
atgttctcgg ggcccagcgg ccatgcccac accattagct acggggcgg gatcggtctg   900 ggcactggag gcggcggcgg cagcggtggt agtggtagtg gctcacaggg cggaggcggt   960
ggtattggca ttggcggcgg tggcgtggct gggctgcagg attgcgatgg ctatgacttc  1020
accaagtgcg agaatgctgc gagatggagg ggcttgttta cgccatcgct aaagaaggtg  1080
ctggagcaag tgcatccacg ggttaccgcc aaggaggacg cactgctgta tgtggagaaa  1140
ctctgtctgc ggcttctggc catgctgtgc gccaagccgc tgcccattc cgtgcaggat   1200 gtggaggaga aggtgaacaa gtcctttcca gcgcccatcg atcagtgggc cctgaacgag  1260
gccaaggagg tgatcaactc gaagaaacgc aagtctgtcc tgcccacgga aaaggtgcac  1320
acgctgctcc agaaggatgt gttgcagtac aagatcgata gctccgtgtc cgccttcctg  1380
gtggccgtgc tcgagtacat ctcagcggac atactcaaaa tggccggcga ctatgtgatc  1440
aagatcgccc actgcgagat caccaaggag gacatcgagg tggtgatgaa cgccgatcgt  1500
gtgctaatgg acatgctcaa ccagagcgaa gcccacatcc tgcccagtcc cctgtcactt  1560
cccgcgcagc gtgcaagtgc cacctacgag gagacggtca aggagctgat ccacgacgag  1620
aagcagtacc aacgcgacct gcacatgatc atacgcgtct tcgtgagga gctggtgaag  1680 atcgtgtccg atccgcgcga gctggaaccg atattctcca acataatgga catttacgag  1740
gtgacggtca ctctgctcgg ctccctggag gacgtcatcg agatgtccca ggagcagagt  1800
gccccctgcg tcggtagctg cttgaggaa ctggccgagg ccgaggagtt cgatgtgtac  1860
aagaagtacg cctacgacgt tacctcgcag gcctcacggg atgctctcaa caatctcctg  1920
tctaagccag gggtaagtat tgataccttc tgtgcgaaga attctactaa aatccctgct  1980
```

-continued

```
tttaggcctc atctctgacc acagccggcc atggcttccg cgatgcggtc aaatactatt    2040
tgcccaagct gcttctggtg cccatttgcc atgccttcgt gtatttcgac tacatcaagc    2100
atctcaagga tctcagctct tcgcaggacg acatcgagag cttcgaacag gtacagggac    2160
tgttgcatcc actccactgc gatctcgaaa aggtaatggc cagcctgtcc aaggagcgac    2220
aagttccggt tagcggtcga gtgcgccgcc agctggcaat cgagcggaca cgggagctcc    2280
aaatgaaggt ggagcactgg gaggacaagg acgtgggcca gaattgcaat gaatttattc    2340
gcggtaagtg ctggcaacga aagttacttg catcctccaa ctaaaatggt atttcaaatt    2400
tacagaggat tcgctgagca aacttggatc gggaaaacga atctggagcg agcgcaaggt    2460
attcctcttc gacgggctaa tggtgctatg caaggcaaac accaagaaac aaacaccatc    2520
ggcaggagca acggcctacg actaccgact gaaggagaag tatttcatgc gacgcgtgga    2580
tatcaacgat cgaccggaca gcgatgatct gaagaacagt tttgagttgg cacccggat    2640 gcagccgccc attgtgctga ccgccaagaa tgcacagcac aagcacgact ggatggcaga    2700
cctgctgatg gttatcacca gtcgatgct ggaccggcac ttggacagca tattgcaaga    2760
catcgagcga aagcatccgc tgcggatgcc cagtccggag atttacaagt tcgcggtgcc    2820
ggacagcggt gacaatatcg tgttggagga gcgcgaaagc gcaggagtgc cgatgatcaa    2880
gggagcgacg ctttgcaagc taatcgagcg cctcacctat cacatctacg ccgatccgac    2940
ttttgtgcgc accttcctca ccacatatcg ctacttctgc tcgccgcagc aattgctgca    3000
actgctggtg gaacgcttta acataccgga tcccagcctg gtctatcaag acacgggcac    3060
agcaggtgcg ggtggaatgg gcggcgttgg cggtgacaag gagcacaaga actcgcatcg    3120
cgaggactgg aaacgatatc gcaaggagta cgtgcagcca gtgcagtttc gagtgctcaa    3180
cgtactgcgc cattgggtcg accatcattt ttacgatttc gagaaggatc ccatgttgct    3240
ggagaagctg ctgaactttc tggagcacgt gaatggcaaa tcgatgcgca agtgggtgga    3300
ttccgtgctt aagattgttc agagaaaggt gagtagttgg tcaacagcat aatgtggaag    3360
tatcgttatc atttttcaaa tattatttac agaacgagca ggagaaaagc aataaaaaga    3420
ttgtatacgc ctatggccac gatccgccgc ccattgagca tcaccttagt gtacccaacg    3480
acgagataac gctcctcacc ctgcacccac tggaactggc ccgtcagctc actctactgg    3540
aattcgagat gtacaagaat gtaaagccgt ctgagttggt cggatcaccc tggacgaaaa    3600
aggacaagga ggtgaagagc cctaatctac tgaagataat gaagcacacc acgaacgtca    3660
cccgctggat tgaaaaatcc atcaccgaag cggagaacta cgaggaacgc ctggctatta    3720
tgcaacgcgc aatcgaagtg atgatggtga tgctggaatt gaacaatttt aatggaatcc    3780
tctcgattgt cgcggctatg ggcacggcat ctgtttatcg actgcggtgg acattccagg    3840
gattgcccga acgctacaga aaattcttgg aggaatgccg cgagctcagc gacgatcatc    3900
tcaaaaagta tcaggagcga ttgcgatcca tcaatccgcc ttgtgtgcca tttttcggtc    3960
gctacttgac caaacatactc cacttggagg agggtaaccc cgacctgcta gccaacacag    4020
agctaattaa cttttccaaa cgacggaaag tggccgagat tattggcgag attcaacagt    4080
accagaacca gccatactgc ctcaacgagg agtccacaat acgacagttc ttcgagcaac    4140
tggatccgtt taacggactg tccgacaaac agatgtccga ctatctctat aacgaaagcc    4200
tgcgcattga gccaagggc tgcaagacag tgccgaaatt cgtaagtata atgcttcaaa    4260
gtttacaagt catataggaa atttaaccat tttcctttcg tagcctcgaa aatggccgca    4320
cattccgctc aaatcgccgg gcatcaagcc gcgtcgccag aatcagacca acagcagtag    4380
```

```
caagctgtcg aacagcacgt cgtccgtggc ggcggcagcg gcagcatcgt caacggccac    4440
ctcaatagct acggcatcgg cgccatcttt gcacgcctcc agcataatgg atgcgccaac    4500
agcagcagca gctaatgctg gatctggaac tctcgctggc gagcaaagtc cgcagcacaa    4560
tccgcacgct ttctccgttt tcgcccctgt tattataccc gaacggaaca ccagcagctg    4620
gagtggaacg ccacagcaca ctcgaacgga ccagaacaac ggggaggttt cggtgccggc    4680
gccacatctc cccaagaaac cgggcgcgca tgtctgggct aacaacaact cgacactggc    4740
cagtgcgtcg gcaatggatg ttgtgttcag tccagcgctg ccggagcatc tgccaccgca    4800
gtccctgccg gacagcaatc cattcgcatc ggacacggaa gctccaccgt cgccgctgcc    4860
caagctagtg gtcagtccgc gtcacgaaac cggcaatcga tcaccattcc atgggcgcat    4920
gcagaacagc ccaacgcata gcactgccag taccgtgacc cttacaggca tgtctacatc    4980
gggcggggag gaattctgcg cgggtggatt ctactttaac agtgcccatc agggacagcc    5040
gggggcagtg cccatctcgc cgcatgtcaa cgttccgatg ccaccaata tggagtaccg    5100 agcagtgccg cctccactgc cacccagacg caaggagcgc actgagagct gtgcggacat    5160
ggcgcaaaag cgtcaggcgc cagacgcacc cacagtaagt agcctcactt acttctaatt    5220
tgtagtagca gatgacagca atcattttac gtatccttgc agttaccccc gcgtgatggc    5280
gaactcagtc cgccgccgat accgccacgg ctcaaccatt ccacgggcat cagctacttg    5340
cgacaaagcc acggcaagag caaggagttt gtgggcaaca gcagtctgct cctgcccaac    5400
accagcagta ttatgatacg ccgcaactcg gcgatcgaga agcgggcagc ggcaactagc    5460
cagccaaacc aggcggcggc gggacccatc agcacgacac tagtgaccgt gtcgcaggca    5520
gtggcgacgg acgaaccgct gccgctaccg atctcgccag cggcaagctc ctcgacgacc    5580
acatcaccgc tgacacccgc catgtcgccc atgtctccca acattcccag ccatccggtg    5640
gagagcacgt cgagcagcta tgcccaccaa ctgcgaatgc ggcagcagca gcagcagcag    5700
acgcatccag cgatctactc gcagcaccat caacatcatg ccacccatct gccgcaccat    5760
ccgcaccagc accattcgaa tccgacgcag tcgcgctcgt cccccaagga gttctttccg    5820
attgccacga gcctcgaggg cacacccaaa cttccaccaa aacctagtct aagcgctaac    5880
ttctataaca atccaggtga gtgctaccaa ctcggcccgt gataacgtgt ttcctaaccc    5940
aaccatccta tccgtttgca gataaaggta cgatgtttct ttacccaagt acaaacgaag    6000
aataatttaa attgcctggc gatgtgataa ggacgaaaac tacgagtatg atccgtaaga    6060
ttcaaagttg cgagcactgc ttgagtgcag atatatatat gagagaacgg aacgtgagat    6120
atatatatat atatatacat atacgctag gcgcagttta tgtattctag tatgaaacga    6180
gttggaaccg ctgatttaga ttattcgcca ctcatttaac aaggtagaac agacagacg    6240 acaaaatacg ctctcattta cacacaacag gcacgcgcat atggatagga atgcaggaca    6300
cacaaaccaa gcaagcaacc aagcaaccaa caagaaatgc aaacaagaaa ttatgttatt    6360 ataaattac tattataaat atttgtaaat atcgagaaca ttgtattgat cgtagaacgt    6420
aaaacaataa agtataaccc tattgttaga cacttggcga catctttcga tgaccagaaa    6480
tatagagtat tgtagccaaa gtcaaggcaa tctgagcaaa tagcatagat tatcaaggct    6540
tttccaacgt ttaaagatcg tgggtattct ttatgtgccc agtggccttg atgaagtcga    6600
c                                                                    6601
```

-continued

<210> SEQ ID NO 11
<211> LENGTH: 5398
<212> TYPE: DNA
<213> ORGANISM: Saccharomyces cerevisiae

<400> SEQUENCE: 11

```
gtcgacgtca gtcacctcca ggttattatg taattcgcta aaacgacttt taaacatcgc      60
gggagacgga tctttgacag agacctggag gaaaaaataa aatagaaaaa taagctcaaa     120
agttacagaa aaaactgcat caccaacacg gcggagacag ttatagtgac ttgatcaccg     180
tgaagcaatt cctttagtta gatagactgt ttcttttttcg gaaagaaatt gaataaaaag     240
agccacattt ttcttcgaat aaatactaaa aaataaaacg aaaaagcaag gtggatattg     300
gatagttgta tcatgtccga tactaacacg tctattccca atacaagttc tgcaagggag     360
gcaggcaatg cttcacaaac tccatcgatc agctcttcat ctaacacttc cactaccact     420
aacacagaat catcctcagc ttctctttct tcttcccccct cgacaagtga gttgaccagc     480
attcgtccaa ttggaatagt agtcgctgct tatgacttta attatcccat taaaaaagac     540
agttcttcgc aacttttgtc tgtacaacaa ggggaaacca tttatatact taacaaaaac     600
tcatctgggt ggtgggatgg attagttatt gacgacagta atgggaaagt taacagaggc     660
tggtttcctc aaaacttcgg tagacctttaa agagacagtc atctcagaaa gcacagtcat     720
ccgatgaaaa aatatagttc cagtaagagc tcaaggcgca gcagcttaaa tagcttgggc     780
aatagtgcat atttacatgt gcctagaaat ccgagcaaga gcaggagggg gagttctact     840
ttatcagcgt ctttatcaaa tgcccacaat gcagaaacaa gttccggcca caataacacc     900
gtatcgatga ataattctcc cttttcagcg ccaaacgatg cttcccacat aaacccctcaa    960
tcttcgaact ttaattccaa tgctagtcta tcccaggata tgacaaagag tgcagatggc    1020
tcatctgaga tgaatacaaa cgcaattatg aataacaatg aaacaaattt acaaacttct    1080
ggtgagaaag caggtccccc actagtagca gaagaaacaa ttaagatatt accgttggaa    1140
gagatagaaa tgattattaa tggtatacgt tcgaacattg cttcgacttg gtcccccata    1200
ccactgataa cgaaaacatc cgattacaag ttggtatact ataacaaaga ccttgatata    1260
tactgttcag aattacccctt gatttctaac tcaattatgg aatccgatga catttgtgac    1320
agcgaaccaa aattcccgcc caatgatcat cttgttaacc tatatactag agatctgagg    1380
aaaaatgcga atattgagga cagttctacg agatcgaagc aatcggaaag tgaacaaaat    1440
agatcaagcc ttctaatgga aaaacaggat tcaaagaaa ctgatggaaa taataacagt    1500
attaatgatg atgataataa taacgaaaat aacaaaaacg aattcaatga ggctggtcct    1560
tcatcattaa attctttatc tgctccagat ttaacgcaga atattcaatc aagggtagtt    1620
gccccaagtc gctcttctat actggccaag agtgacatct tttatcacta ttcaagagat    1680
ataaaattgt ggacagaatt acaagaccta acagtttatt atactaaaac ggctcacaag    1740
atgttcctta aagagaatcg tctcaatttc acgaaatact ttgatttgat atcagattca    1800
atagtcttca cacagttagg ctgcaggcta atgcaacatg aaattaaagc caaaagttgc    1860
agcaaggaga ttaagaagat tttcaaaggt ctaatctctt cattgtcaag gataagtatc    1920
aattctcatt tatatttcga ttcagctttt cacagaaaaa aaatggatac tatgaatgac    1980
aaggataacg ataatcagga aaataattgt tctaggacgg aagggggatga tggtaaaatt    2040
gaagtagata gtgtacatga tctagtttca gttccattgt ccggtaaacg taatgtaagt    2100
accagtacaa cggatacatt gactccaatg agatcatcat tcagtacagt caatgagaac    2160
```

```
gatatggaaa atttctcagt cttaggtcca agaaatagtg ttaattctgt cgtaacacca    2220
aggacttcaa tacaaaattc tactttggaa gattttttcac cgtccaacaa aaattttaag   2280
tcagctaaat cgatttacga aatggttgat gtggaattct cgaaattttt aaggcatgtt    2340
cagttacttt attttgtgtt acagagctca gtcttctcag atgataatac tttaccacag    2400
ttgctcccaa gattttttaa aggttcattt agcggtggtt cttggacaaa tccattttcg    2460
actttattta cggatgaatt tggtaatgcg acaaagaaca aagctgtcac atctaatgaa    2520
gtgaccgctt cgtcgtccaa aaattcctca atatcaagga ttccaccaaa gatggcagat    2580
gctattgcct ctgcgtcagg atatagcgct aattcagaaa caaattccca aattgattta    2640
aaagcaagca gtgccgcgtc tggttcagtt tttacacctt tcaaccgtcc ttctcataac    2700 agaaccttttt caagagcaag agtttcaaaa aggaagaaaa aatatccatt aactgtagac   2760
actttgaata caatgaagaa gaaatcctcg caaattttttg aaaaattaaa taatgctaca   2820
ggtgaacact taaaaattat aagtaaaccc aaaagcagaa ttaggaattt ggaaataaat    2880
tcaagcacat acgaacaaat aaatcagaat gttttactat ggagatact ggagaattta     2940 gatctgtcaa ttttcatcaa tttgaaaaac ctgattaaga cacccagtat tttgttggat    3000
ttggaaagcg aggaattttt agttcacgcc atgtcttcgg tctcctcagt actaacagag    3060
ttttttgata taaagcaggc ttttcatgac atcgtcatca gattaataat gacaacgcaa    3120
caaacgacct tagacgaccc gtatttgttt tcctcaatga ggtccaattt ccctgtcgga    3180
catcatgaac ctttcaagaa tatctctaat acacctttgg tcaagggccc cttccataaa   3240
aaaaatgaac aattggcact ctccttattt cacgtattgg tgagtcaaga tgtggagttc    3300
aataaccttg aattttttaaa caactccgac gattttaaag atgcttgtga aaagtatgtc    3360
gagatttcta atcttgcgtg tattattgtt gatcaattga ttgaagaaag agaaaatttg    3420
ctgaactacg cagcaagaat gatgaagaat aatttgactg cagaactatt gaaaggtgag    3480
caagaaaaat ggtttgatat ttattccgag gactatagtg atgacgattc agaaaatgat    3540
gaagctatca tcgatgacga attaggatct gaggactata ttgaacgcaa agctgcgaac    3600
atagagaaaa accttccatg gttttttaact tcagattatg aaactagtct tgtctatgac    3660
tcaagaggaa aaattcgtgg cgggacaaaa gaggcactga ttgaacattt aaccagtcat    3720
gaacttgttg atgcggcttt caatgttaca atgttaataa cttttcagaag tatattaacc    3780 acaagagagt ttttttatgc cctgatttac aggtacaact tgtatcctcc tgaagggctg    3840
agttacgatg attacaatat ttggatagaa aaaagtcaa acccgattaa atgccgtgtg     3900
gtcaacatta tgagaacatt tttgacgcag tattggacaa gaaattatta tgaacctggc    3960
ataccactga ttctaaattt tgccaagatg gttgtatcgg agaaaatacc gggggcagag    4020
gatcttttgc aaaagataaa tgaaaaactg ataaatgaga atgagaaaga accagtggat    4080
cctaagcaac aagattcggt atcggcagtc gtacagacaa ctaaacgtga caataaatca    4140
ccgatacaca tgtcttcgtc ttcttttacca tcttctgctt cttcagcgtt ttttagattg    4200
aagaaattga agctcttgga tattgaccca tacacatatg ccacacaatt gactgtactt    4260
gaacatgact tatacctcag gatcactatg tttgaatgct tggataggggc atgggggtacc   4320 aagtattgta atatgggtgg ttctccgaac attacgaaat ttatagctaa tgctaatacg    4380
ctaactaatt ttgtttctca taccattgta aaacaggcag atgtcaagac acgttcaaaa    4440
ttaacgcaat atttttgttac cgttgcccag cattgtaaag agttgaataa ttttttcttca   4500 atgactgcca tagtgtccgc tttgtattcc tccccaatct accgactgaa aaagacatgg    4560
```

```
gatttagttt ccactgagtc gaaggacctt ctgaagaacc taaacaacct tatggattcc    4620
aagagaaatt tgtgaagta tagagagctg ttgcgatccg tgacggacgt tgcatgtgtt    4680
cccttttttg gtgtatacct atctgattta acatttacgt tgtcggaaa cccagatttt    4740 cttcacaatt caaccaacat aataaacttc agcaagagga ctaaaatcgc aaatatagtg    4800
gaggaaatta taagctttaa aagattccat tacaagctga aacgattgga tgatattcag    4860
accgttatag aagcgtcttt ggaaaatgtc ccccacattg aaaagcagta tcaattatca    4920
ctgcaagtgg aaccgagatc aggaaacacc aaaggcagta cgcatgcttc ttctgctagc    4980
ggtacaaaaa ctgcaaaatt cctaagtgaa tttacagatg ataaaaatgg caatttttg    5040 aagctaggta agaaaaaacc tccttctagg ttatttcgat aaaagtttat acaatttgct    5100
aatcaagaag aaccttagct ttatgtttga ttgctacact ctattattta agatggctgc    5160
ttttacttaa tattcttcgt gataatactg tactggtgga gtgttttcg ttttcgagga    5220 tttgagagta cgcttcattt gcagttcttc ttgataaagt tcgttttata tatatatatc    5280
tattttatat ctttatatat tttattacac ccagtttaagt tatcgatcca agattttaaa    5340
tgcccgatta gaggaaactt attacctgaa aaaatatcaa ttagtgattc tatgaaaa    5398

<210> SEQ ID NO 12
<211> LENGTH: 43676
<212> TYPE: DNA
<213> ORGANISM: Saccharomyces cerevisiae

<400> SEQUENCE: 12
gatcaatggc aacttaccgt agttgtcctt tgcggtgtct tcggcagcgg ctttcttttc      60
acgggcttct ctttcagctt ccaactggag agctcttttcc tccttctttc tctgtttctc    120
ttgctctttc tgcaatttct tcaaggcctt cttggacaat ggcttaccat cttccccaag    180
aataacttga gcaggttctg cggattcttc aacagctttg acaatatttt cgtcttgaga    240
catcacgtaa aatgtttctt tttttctttt acaattaacc ttaagaggcc gttccagcca    300
atgatcgaaa acttaaacaa atcggttgtc ttgcttcatc cttatatgac attaaataat    360
ttttcatttc ttctttttttc acgaaaatgc gtcataaggt actcgtcact gatgatttca    420
tagacaataa agcaacagca caacgtaaaa gagttcttat ggatgagtcc caatcctatt    480
gttttctgta gcctaatggt acaaaatgtg acggtaatag aatatatact ttcataatat    540
cataggaaca tcttcagctt ggcctgtctc tttgagaaac aaaaactgca tgtgcacaat    600
tactgcagat gaacttcaag gaaacatatg tcctgcttgg aggaccagaa gcaaaccatt    660
ctagctgtat ttgcaacgct tttgtaccaa atgtacgtta ttatgttatg tcgtcagtgt    720
agatatatta gatttacatg cggctgtacc gcatcattgg aaaataatgt ctgcaggctc    780
gcaaaattta agggttccct tctacaatag tagtcaaaat tgcttttttg catataacaa    840
agtgaaaaaa aaaaaaaata tgagagacat atctaaaaga catatataat ctgccaccag    900
aatgagttgc actgcgtcat atgccggcat gacaactccg gtgaaggata aggaaggcca    960
cgggattcca tgcttacaac ctatcgatgt agtggaatgt acctatcaat attttacaaa   1020
atcacggaat aaactgtctt taagggtagg cgatttgatt tacgtactca ctaaaggttc   1080
taatggctgg tgggatggtg ttcttatcag acacagcgct aataataata ataattcgtt   1140
gatactagac agaggttggt tccccccttc tttttacacg gtccattcta acgaactac   1200 acggggtgcc tgacatcggt aatgaattgg aaatatttca agcgggtctt aatcttaaac   1260
```

-continued

```
tggaattatc aagcaaccca gtgatcttat cattggaaga cttttagac tgctgtcgcg    1320 atattgaatt caaggaacaa ctggcttggt cacctactcc cgtccacgaa aggaaaggct    1380
gctgtgagct gctgtactat aaccaggatt tagatgttta ttgtcgcacg ttaccatatt    1440
taccacaaaa tcaagttgaa accgtgaacg actattcgtc ttttcctgca atatcgaaga    1500
tagctggtaa aaagatgcct ataacgtcaa gccccgatct gttctatctc aatgattgtg    1560
atgtcgtcta ttggtatgac ctcactcgct tagtgtgtca ttatgttaat ttaacagagc    1620
gcgacctatt ggcaaatgaa cgggaaaagt ttctaacttc cttggattta ttaacagctc    1680
aaataaccta tgtttatatg cttttcagga atctccgttt agttgaagat agtttcaaaa    1740
aaaccctcaa aaaactaatt tacaccttgt ctaggttttc aataaatgca atatttggt    1800 ttcattccac attgtttgaa gaaagagaag ccatagcctc ccagaaggat ccagaaagaa    1860
gatcccctct tctacagtca atcctaggaa ccttccaaaa atttcatttt ctactgcgtt    1920
tactacattt cctctcaaat cctaacgaac ttacaatact gcctcaattg actcctcgat    1980
ttttcaagga ttcttcaat acaatttcat ggaataaccc gttttgcgt aagcgtctca    2040 accagcatat gtcccatgac ctaccgagac agatgattaa agccgttgct ggtgcttcag    2100
gaattgttgc ggaaaatatt gatgaaattc cagcttccaa acagggcact tcatgctcgt    2160
cagaaacgtc tcaccattca ccatcagccc cgtttcaaag aaggagaaga ggtaccattt    2220
tctctaatgt gtcaggaagt tccgatgagt ctgacaccat atggtccaaa aggaaaaaac    2280
catacccgct aaatgaagaa actctaagcc ttgtaagggc caggaagaag cagcttgatg    2340
gtaaactaaa acaaatgatc aaaagtgcta atgaatatct cagtaacacg gctaattttt    2400
caaaaatgtt gaattttgaa atgaatttca aaacctacga agaagtaagc ggaacaattc    2460
ctataattga tattctggaa aacctagatt taactattt tctaaacttg agagagttgg    2520
gagatgagaa tagagttttt gacgaagatg tcgctattga tgatgaagat gaagagtttt    2580
tgaaacattc tttatcatcc ctatcgtata tcttatccga ctattttaat atgaagcaat    2640
attttcatga tgtagtagtg aaatttataa ttgtcgccca gcatttgaca ttagaggatc    2700
ctttcgtttt ctcgccaatg caaaacgact tgcctaccgg ttattatgaa ccaatgaaac    2760
cttcatcctt gaatttagat aatgccaagg ataagaagaa tgggagccaa atactgata    2820 tccaagagga ggaagatgaa tatgagccag acccggatag tcttattctc ttccacaacc    2880
tcatcaatca agattctgat ttcaatgatt taaagttttt taatctcgcc cacgttttta    2940 aaaatcctg tgatgactat tttgatgtgc ttaaactagc cattgagttc gtgaatcaat    3000
taattctaga aagagagaat ttgttaaatt atgctgctag aatgatgaaa acaatatca    3060 cggaattgct attgcgcggg gaagaaggct atgggtccta tgacggcggt gaaactgccg    3120 aaaaagtga cacgaatgct gtttatgcag attcagatac taaagacaat gacgaatggc    3180
gtgacagcca agtcaaatta ccgaggtatt tgcagcgcga gtatgacagt gaactgattt    3240
ggggctctaa caataggatt aaaggtggtt ctaaacacgc actgatctct tacttgacag    3300
ataatgaaaa gaaggatcta ttttcgata ttactttttt aatcactttc agaagcatct    3360
ttactacaac ggagttttta agctacttga tttcgcaata taatttggat ccaccagagg    3420
atttgtgctt tgaagaatac aatgaatggg tgacgaaaaa gcttataccg gttaaatgta    3480
gggtggttga gattatgaca accttttttca agcaatattg gttcctgggc tatgatgagc    3540
ccgatcttgc gaccctaaat ctggattatt ttgcgcaagt agcaatcaag gaaaatataa    3600
caggatctgt ggaattacta aaggaggtca atcagaagtt taaacatggt aatatacaag    3660
```

-continued

```
aagcgactgc accaatgaaa acgttagatc aacagatctg ccaggaccat tactcgggca    3720
ctttatactc taccacggaa tccatttttgg ccgtcgatcc agttttattt gccactcaat    3780
taacgatact agagcatgaa atttattgtg agataaccat ttttgattgt ttacaaaaaa    3840
tttggaagaa caagtataca aaatcgtatg gggcttcacc gggtttgaac gagtttatca    3900
gttttgccaa taaactgaca aatttcatat cctactctgt tgtaaaggag gctgataaaa    3960
gtaagcgcgc caagctactc tctcatttta tttttatcgc agaatattgt aggaaattca    4020
ataacttttc ttccatgact gcaatcattt cagcattata ttcttcacca atttatcgtt    4080
tagagaaaac ctggcaggca gttattcctc aaacgagaga tctattgcag tcactgaaca    4140
agttgatgga tcccaagaaa aatttcataa attacagaaa cgagctgaaa tctttacata    4200
gcgctccctg cgtaccgttt ttcggcgttt atttatctga tctaacccttt actgattccg    4260 gaaatccgga ttatcttgtc ttggaacatg gtttaaaggg tgtccatgat gagaagaaat    4320
atataaactt caacaaaagg agcagacttg ttgatatctt acaagagatc atatatttca    4380
agaaaacaca ttatgatttc actaaagatc ggacggtaat tgaatgtata tcaaattcat    4440
tggaaaacat cccccatatt gagaaacaat accaattatc attaattatt gaaccaaaac    4500
caagaaagaa agtcgttccg aattccaatt cgaataataa atcacaagaa aaatccaggg    4560
atgaccaaac cgatgaagga aaaacatcca ctaagaaaga cagatttcca aaatttcaat    4620
tacataagac aaagaaaaaa gctcccaagg tttctaagta acggcgccgt atgttcgatt    4680
tccttctctc ggtggattaa ttattttgtt tgttttctcc tgttatatta tttattgatc    4740
actatagtaa actatgtccg tcatcaagcc cgacggctgc tatcccacaa tgttgatcgt    4800
attgtttgcc tagtttatta tatatttgct tatttatagc ataccataat atttaaatgc    4860
cctcaaattt ttggccgtag cgacatcgcg ataattccaa ttccctttaa aaaattgcgc    4920
ctgagtataa gttaattcag ccagttctcc aaattaaaat cgcatactcc tgaacctatc    4980
aacagattgt cctcgcatac ttttctatac caaggtctct tctgaacata tattagcagt    5040 ggttaattttt aaagagatca taagaaaat tttgtctaaa aaagattaat ataaagacaa    5100
tgtcttcact agaagtggta gatgggtgcc cctatggata ccgaccatat ccagatagtg    5160
gcacaaatgc attaaatcca tgttttatat cagtaatatc cgcctggcaa gccgtctttt    5220
tcctattgat tggtagctat caattgtgga aactttataa gaacaataaa gtaccaccca    5280
gatttaagaa ctttcctaca ttaccaagta aaatcaacag tcgacatcta acgcatttga    5340
ccaatgtttg ctttcagtcc acgcttataa tttgtgaact ggccttggta tcccaatcta    5400
gcgatagggt ttatccattt atactaaaga aggctctgta cttgaatctc cttttcaatt    5460
tgggtatttc tctccctact caatacttag cttatttttaa aagtacattt tcaatgggca    5520
accagctttt ctattacatg tttcaaattc ttctacagct cttcttgata ttgcagaggt    5580
actatcatgg ttctagtaac gaaaggctta ctgttattag cggacaaact gctatgattt    5640
tagaagtgct ccttcttttc aattctgtgg caatttttat ttatgatcta tgcatttttg    5700
agccaattaa cgaattatct gaatactaca agaaaaatgg gtggtatccc cccgttcatg    5760
tactatccta tattacattt atctggatga acaaactgat tgtggaaact taccgtaaca    5820
agaaaatcaa agatcctaac cagttaccat tgccgccagt agatctgaat attaagtcga    5880
taagtaagga atttaaggct aactgggaat tggaaaaatg gttgaataga aattctcttt    5940
ggagggccat ttggaagtca tttggtagga ctatttctgt ggctatgctg tatgaaacga    6000
catctgattt actttctgta gtacagcccc agtttctacg gatattcata gatggtttga    6060
```

```
acccggaaac atcttctaaa tatcctcctt taaatggtgt atttattgct ctaaccctttt     6120 tcgtaatcag cgtggtttct gtgttcctca ccaatcaatt ttatattgga attttttgagg    6180 ctggtttggg gataagaggc tctttagctt ctttagtgta tcagaagtcc ttaagattga    6240
cgctagcaga gcgtaacgaa aaatctactg gtgacatctt aaatttgatg tctgtggatg    6300
tgttaaggat ccagcggttt ttcgaaaatg cccaaaccat tattggcgct cctattcaga    6360
ttattgttgt attaacttcc ctgtactggt tgctaggaaa ggctgttatt ggagggttgg    6420
ttactatggc tattatgatg cctatcaatg ccttcttatc tagaaaggta aaaaagctat    6480
caaaaactca aatgaagtat aaggacatga gaatcaagac tattacagag cttttgaatg    6540
ctataaaatc tattaaatta tacgcctggg aggaacctat gatggcaaga ttgaatcatg    6600
ttcgtaatga tatggagttg aaaaattttc ggaaaattgg tatagtgagc aatctgatat    6660
attttgcgtg gaattgtgta cctttaatgg tgacatgttc cacattttggc ttattttctt    6720 tatttagtga ttctccgtta tctcctgcca ttgtcttccc ttcattatct ttatttaata    6780
ttttgaacag tgccatctat tccgttccat ccatgataaa taccattata gagacaagcg    6840
tttctatgga aagattaaag tcattcctac ttagtgacga aattgatgat tcgttcatcg    6900
aacgtattga tccttcagcg gatgaaagag cgttacctgc tatagagatg aataatatta    6960 cattttatg gaaatcaaaa gaagtattaa catctagcca atctggagat aatttgagga    7020
cagatgaaga gtctattatc ggatcttctc aaattgcgtt gaagaatatc gatcattttg    7080
aagcaaaaag gggtgattta gtttgtgttg ttggtcgggt aggagctggt aaatcaacat    7140
ttttgaaggc aattcttggt caacttcctt gcatgagtgg ttctagggac tcgataccac    7200
ctaaactgat cattagatca tcgtctgtag cctactgttc acaagaatcc tggataatga    7260
acgcatctgt aagagaaaac attctatttg gtcacaagtt cgaccaagat tattatgacc    7320
tcactattaa agcatgtcaa ttgctacccg atttgaaaat actaccagat ggtgatgaaa    7380
ctttggtagg tgaaaagggc atttccctat caggcggtca aaggcccgt ctttcattag    7440 ccagagcggt gtactcgaga gcagatattt atttgttgga tgcatttta tctgctgttg    7500 atgcagaagt tagtaaaaat attattgaat atgttttgat cggaaagacg gctttattaa    7560
aaaataaaac aattattta actaccaata ctgtatcaat tttaaaacat tcgcagatga    7620
tatatgcgct agaaaacggt gaaattgttg aacaagggaa ttatgaggat gtaatgaacc    7680
gtaagaacaa tacttcaaaa ctgaaaaaat tactagagga atttgattct ccgattgata    7740
atggaaatga aagcgatgtc caaactgaac accgatccga aagtgaagtg gatgaacctc    7800
tgcagcttaa agtaactgaa tcagaaactg aggatgaggt tgttactgag agtgaattag    7860
aactaatcaa agccaattct agaagagctt ctctagctac gctaagacct agacccttg    7920 tgggagcaca attggattcc gtgaagaaaa cggcgcaaaa ggccgagaag acagaggtgg    7980
gaagagtcaa aacaaagatt tatcttgcgt atattaaggc ttgtggagtt ttaggtgttg    8040 ttttatttt cttgtttatg atattaacaa gggttttcga cttagcagag aattttttggt    8100 taaagtactg gtcagaatct aatgaaaaaa atggttcaaa tgaaagggtt tggatgtttg    8160
ttggtgtgta ttccttaatc ggagtagcat cggccgcatt caataattta cggagtatta    8220
tgatgctact gtattgttct attaggggtt ctaagaaact gcatgaaagc atggccaaat    8280
ctgtaattag aagtcctatg actttctttg agactacacc agttggaagg atcataaaca    8340
ggttctcatc tgatatggat gcagtggaca gtaatctaca gtacattttc tccttttttt    8400
tcaaatcaat actaacctat ttggttactg ttatattagt cgggtacaat atgccatggt    8460
```

-continued

| | | | | | |
|---|---|---|---|---|---|
| ttttagtgtt | caatatgttt | ttggtggtta | tctatattta | ctatcaaaca | ttttacattg | 8520 |
| tgctatctag | ggagctaaaa | agattgatca | gtatatctta | ctctccgatt | atgtccttaa | 8580 |
| tgagtgagag | cttgaacggt | tattctatta | ttgatgcata | cgatcatttt | gagagattca | 8640 |
| tctatctaaa | ttatgaaaaa | atccaataca | acgttgattt | tgtcttcaac | tttagatcaa | 8700 |
| cgaatagatg | gttatccgtg | agattgcaaa | ctattggtgc | tacaattgtt | ttggctactg | 8760 |
| caatcttagc | actagcaaca | atgaatacta | aaaggcaact | aagttcgggt | atggttggtc | 8820 |
| tactaatgag | ctattcatta | gaggttacag | gttcattgac | ttggattgta | aggacaactg | 8880 |
| tgacgattga | aaccaacatt | gtatcagtgg | agagaattgt | tgagtactgc | gaattaccac | 8940 |
| ctgaagcaca | gtccattaac | cctgaaaaga | ggccagatga | aaattggcca | tcaaagggtg | 9000 |
| gtattgaatt | caaaaactat | tccacaaaat | acagagaaaa | tttggatcca | gtgctgaata | 9060 |
| atattaacgt | gaagattgag | ccatgtgaaa | aggttgggat | tgttggcaga | acaggtgcag | 9120 |
| ggaagtctac | actgagcctg | gcattattta | gaatactaga | acctaccgaa | ggtaaaatta | 9180 |
| ttattgacgg | cattgatata | tccgacatag | gtctgttcga | tttaagaagc | catttggcaa | 9240 |
| ttattcctca | ggatgcacaa | gcttttgaag | gtacagtaaa | gaccaatttg | gaccctttca | 9300 |
| atcgttattc | agaagatgaa | cttaaaaggg | ctgttgagca | ggcacattta | aagcctcatc | 9360 |
| tggaaaaaat | gctgcacagt | aaaccaagag | gtgatgattc | taatgaagag | gatggcaatg | 9420 |
| ttaatgatat | tctggatgtc | aagattaatg | agaacggtag | taacttgtca | gtggggcaaa | 9480 |
| gacaactact | atgtttggca | agagcgctgc | taaaccgttc | caaatattg | gtccttgatg | 9540 |
| aagcaacggc | ttctgtggat | atggaaaccg | ataaaattat | ccaagacact | ataagaagag | 9600 |
| aatttaagga | ccgtaccatc | ttaacaattg | cacatcgtat | cgacactgta | ttggacagtg | 9660 |
| ataagataat | tgttcttgac | cagggtagtg | tgagggaatt | cgattcaccc | tcgaaattgt | 9720 |
| tatccgataa | aacgtctatt | ttttacagtc | tttgtgagaa | aggtgggtat | ttgaaataat | 9780 |
| gacattgatt | attatatatg | aagatataga | acatttaatg | cgctgcaata | tgtacggtca | 9840 |
| cgccaattct | ttttctttct | atatgctttc | tagtaacccg | ggtaatcaca | aatgaagcta | 9900 |
| gtagagatat | aactaaatac | aacttaattt | taaccttatg | ttggattgct | caagcagtgt | 9960 |
| tcgagaaaga | cagcggcaga | cagatagaaa | tgagctcaaa | tgaagaggta | tttactcaga | 10020 |
| taaacgcaac | tgcgaatgtg | gttgataata | agaagcgttt | acttttcgtg | caagatagct | 10080 |
| cagcacttgt | tctagggctt | gttgcaggat | ttttgcaaat | cgagtcagtc | catgggttta | 10140 |
| tttggttcct | gattctgtac | aacttgatta | atgtcattta | cattgttttgg | atctgtcaac | 10200 |
| ttcaaccagg | aaagttctac | caaagcccac | ttcatgacat | ttttttcgaa | tcgtttttta | 10260 |
| gagagataac | tggttttgtc | atggcatgga | catttggata | cgccctaatc | ggatgaacat | 10320 |
| ataagaacta | cttctataaa | cggttagaaa | caggcttgat | ttattatgta | cagtaaatat | 10380 |
| aatgttatttt | gtgttttttt | tttttaaatt | tttttagttc | cttctatgta | aaaagacatg | 10440 |
| acaacagtat | tctcagtcaa | atgatttcaa | atacacaatg | ttaaattctc | tatctgttgc | 10500 |
| agaaataaga | agagcgtaag | agcgcaaaga | tttttgcaga | aaaatagaga | tgaggtacaa | 10560 |
| aaagtaggta | atggaaaaaa | gcaaataatg | aatatagggg | aacataaatg | ttatggacaa | 10620 |
| gagtagatat | caaaataaaa | caaaataaaa | tagagtaagt | gaaagacaaa | tggaggaaaa | 10680 |
| aaaaaaaaaa | aaaaaaaaaa | aaaaaatagt | aaaaagtgaa | aggagaacga | tgataacact | 10740 |
| aatcacacct | ccgcattttc | aaccaatgct | gcaagtttct | caacactggc | taaatgtcta | 10800 |
| tttcctaggg | agttagattt | gtttagttta | tccaaatatg | ctctaatggc | aatgacgatc | 10860 |

-continued

```
aatttcttac cctcaccctc agagacatta actaattttt gaatcacata gttggcaaat    10920
tgatccttga tcattaaaat cattggagaa tcgtcttcca gattcaaagc atgattttg    10980 tctcttggta aaatcttaga aattattaaa tccttctgat ttttagagcc ataaagaata    11040 gattttttcga ccacgttgga ggcaaattta tgtttagagt attcgacaac attattggcc    11100
acagtttcta tgatttcctg tttgatatcg accatttcct tattggtgaa ctgatcttgt    11160
tgcaaaacat attgaatgac atagttacca tattggtctt gaattagata tggtatgaaa    11220
tctttcaatt cgtttaaaat gctttcctga tcttcgctcg aaccaaattc taacaatctt    11280
tgaatgaccc tacagccgta ggagtgggta gatagatggt aaatgtggcc agttaaagaa    11340
cttaagataa aaggtaattt ttcgatagga attgtttcga tggccttttg aattacgtga    11400
ttaccgttct gatctttgat catttgcaaa acggagtcag ataattccag gactaactca    11460
attctttgat tggaatcaat atattctaac gccttttgaa ttacacgaca tgcgtacatt    11520
tgtagagata actgtttcat gttaccttta aattgatcaa ccaaagtatt tttttgaatt    11580
ttgctaccaa attcaaaaaa cttctgaatg acgtaattac caaatacatc gttcgaaagc    11640
tcaatggcgt catcgcgaat ttcattgaat atgacctcct tttctgaggc tggtgaggtg    11700
gccaactcgc gctgaatgaa ccgtgaacca tgttgatctt tgcaaaactc taaggaatgg    11760
ccaaagatgt cttttagtga catgttcgag tttgaatttt tgtcagaact actgtttctt    11820
agttgctcta acaacggcga tcgatgatac gtttgctgct gttgctgtag actttgagaa    11880
tgaggatgag aatgagagtg agattatgg ttgttggccg ttgactcatt agatttggaa    11940
gaagcattct ttttagaggt attctttgtg ggtatagaat tttctagata aggatttgcc    12000
tgtttgttgg cgttgttgga gttatttgca ggatgattct tgttatttct tttcttgaag    12060 gtttttttcgt ccttgggcat tttgacaggt ataggatttg gagtagggta gtaaatataa    12120
ggattctcct gttgctgttg ctgttgttgg tcttcttgtt gttgttgttg ttgctgttgc    12180
tgttgttgct ggggagcaga gagtggtgga ggtggcataa acatcattgg gttggggtag    12240
gcaaacggga acggagaatt gtttggaggg gacgaaggtg aagaaacaga agaaggtctg    12300
tttgccttct tctttttctt accatttgag tcttcggtgt cttcatttgc tggaatctgt    12360
actgaaatca tctgggagat gaaatttgaa ggagatccga tcaagtagtt ggggaagttt    12420
tggtaatgag ggccctgatg aaactgattg ggtgggaagc cgttcatgta gggggggaaa    12480
ttgttatttg caggcccatc ttgttggtta ggaagcgcga catttgtggc cccaacagcg    12540
gctggattgt tactaggtct aaatactggt gtgttggcta cgttccagat atttctcttg    12600
gggtaatgag cattttcgga ctctaaagac gcagatgagc ctgaatttga actggagtgg    12660
taaagcgaac cactgttagt agtgttccta ttcaatttgt tgaagttttt gtcagactcg    12720
acattttgct cgaaagtatt ctgtgtgtct aagctggcgt tagagacgct ttttgatatg    12780
aattgggact gagtattgac agcgtcgggt ctatcttgag attccagttc ccttgtaccg    12840
tcaatcaaag atttttccgaa cttctcaaaa aacccttccc caccagagtt gttgttgtca    12900
ttgccattgt agtaaacggg accagcaatg gaagctgaat actggcccag aagatggttg    12960
accttgttgt ttttcccgag attagccgca gtatgatgag tatgatagtt attgtacgat    13020
gcggatgaca gggaggcagt gtcggttgat ctgtactggt aataattgcc gccgttacca    13080 aaaaacttt tcgagttcgt ggagaatggc ggagcagtac caactgatag ggcggttttc    13140
ttgaagatcg gtgaagattc actggaaccg tgaagcagca agatctctga atctacttca    13200
tttgccgtgg tgaaactcga ccttctgaag ccgccaattt gctgtgatcc agcagcaccg    13260
```

-continued

```
ccgttcacaa tgccggccgc ggcggcctga ccgccgttgt tgttactatg ggacagggcg  13320
cttaaagaag aaactatgga tgcgagttcc atatccatat ccatatccat gttcatttcc  13380
atttataccc gcaatattgc gttattcaga agaaatttaa atgcgtagtt cttgtttgtt  13440
ttcttgtttg cttgcgtact tctatgctta tagatatatc agtagcaagg aagtttcctt  13500
ttcaccgcct ttcaatgttc ctatctttt cttatgtttc tctttagaga ccagatgacc  13560
agaaaaaaat tagctaagca gtgttatact atttacagta gatattcaaa tatgtgcagg  13620
caccacttat ttttctttt ccttcttttc tttgttttt tttttctcct attcatcaag  13680
cttcatacat ccaatataca ttctcaagtg tgctaatggt acatttggga aattatcttc  13740
ctctctccac aattttaga aggaaaaag aaatgcagtt cagggtaaca gagtgcgcaa  13800
ttaccgtaga tagcgatcgg atgtttatct ttagccctct ttttctagct caaaccccgg  13860
cacgaatttt ttaggtcttg ctgctctgcc ctcgggcact tttcttcgag aagttctggg  13920
gcggtctgat cgggaaaaaa cgttcccttt tcggacgtat cgcaggcaat gtgcaaaagc  13980
ttattatata cgagaaaaga aacgcgaagg aacgaaagaa gatgaaaaaa atgcagcgat  14040
aaaatgatat tgtggttaat ctaaatttat atatatatat atatatacat atatatatag  14100
aaatctattg ttatacacaa aaatacttat tttttaatat agatggctgc agataaagta  14160
atagttttat atataggtat atttactgca caattcacac gatgggtgtt tctgcggtgt  14220 tgaaagagc taggaattta ctagcaacgt tcatagtctg ctgttttatg gcagtagtgc  14280
ttgttctggc gctggcacac catttttataa atgagcacag agacactagg agttcatcga  14340
cccaaatcga agttgatgac gaaagtaaaa gaaacgtaca ccatgaccat gttctcacta  14400
gaaccaatgc atacgcgacg ccatacctcg atctggaaca tgacaagaaa aacggtatcg  14460
tctacgatca tacaagaacg gttgtccgta aaagaaacca cgaagtgggg tcctcgtcac  14520
tgcataaaaa ccttttcac aaattttga caaagcttat ttttaggttt atcgagaagg  14580
aaaaagttac cgaaggcgta acgcaaggaa agttcaataa tagtagcaat gaaattgcca  14640
atcatgaacc ggttttgaa aaaattcctg tacagtgcga caatccatta cagaatctaa  14700
tcttatcgga agacttgaca ttagttgcgg atcttaatta ttatttaac cagtacaata  14760 ttcaaataga ggaatttaga ttggagaccg aagatgggtt tgttatagat ttgtggcact  14820
tgataccaaa atatagaacg acagattctg acaagaagaa gaggccaccc attttgatgc  14880
tacatggcct tttgcaaagc agtggttcgt tcgcatccaa tggtagaaaa tctctggcat  14940 atttttctgta tcaatccggt tacgacatat ggttagggaa taacagatgc gggtttaggc  15000
cggaatggaa cgaagcgaaa gtaccgcacac tagcttccag gtgggactgg gaccttcgcg  15060
agatggttaa gtacgatctg accctttga ttgataccgt gttagctaag acgcagtttg  15120
aaaagcttac tttgatctcg cattctcagg gcactacaca ggggtttatg ggcttggtca  15180
acgaagataa gttttcct cccggttcgg gatctaaaga atctttttc acttctaaga  15240 tcgcaaacta tattgccttg gccccgcag tgtatcctgg tcccttactt aacgagaaat  15300
tgtttgttaa gctatgaca aaggaaatcg aaaatccctg gttcttggt gaaacgagct  15360 tttttgagat aatgatgatt gtaagaaact tgtgcgttgg tgagagcttg ttctccttg  15420 tttgttacac catcttcaat tacctgtttg attggaacga tacccttgg gataccgcat  15480 taagagatcg ccatttcctg ttttcgccag tccatgtttc agtgaagttg atgcaatggt  15540
ggctgtcacc cgaccccaac aaggtaagtt ttaaatttgg ttcccataag atgttccccg  15600
acaatgttaa gtggttttca gacgcatcaa aggccccaaa tatctacttg tttgttccaa  15660
```

```
agcaagatag attggtggac ggagaaagac taatcaatca tttcgtcaat gtggagtcga   15720
atgtcaacta caagatctgg tacattgatg agtatgccca tattgatgtc ctatgggcac   15780
atgatgtcat agagagaatt ggtaaaccaa ttttacagaa tttgaacaac tattactcca   15840
agaagccatc cagcgccttt gaaagtgatt gttcggacac agaggtggaa acggagctgg   15900
aaatggttgc tgagaaggct tgaagaggaa gcatgatata taggttaata taaattatac   15960
ttgggaatac atagatagag ggctagtaaa tttttagttt ttaattgttc ttttttttg    16020 aagtattgtg tcacaaattg tcgggagttg ggacatcacc gtgcataacg atacattttt   16080
ttgaaaaatt tgatattgaa aaaaaatcga tgagtttgaa ttacattaca gttgtataaa   16140
gcaaccgcat ttcattaacg tagtttgact cgcgaagata aggcgttaaa atgaagatta   16200
agaccattaa aagaagtgct gatgactatg tccctgttaa aagtacgcag gaatctcaaa   16260
tgcccaggaa tttgaaccct gaattgcatc cttttgaaag ggcacgtgaa tatactaaag   16320
ctttgaatgc caccaaattg gaaagaatgt ttgctaaacc ctttgtgggt cagttaggat    16380
acggtcatag agatggtgtt tatgctattg ccaaaaatta tggtagtctg ataaaattgg    16440
ctactggttc tgcagatggt gtgattaaat actggaacat gtctactaga gaagaatttg    16500
tttcctttaa ggcgcattat ggactcgtta ctggtctttg tgtgacacag cctcgttttc    16560
atgacaagaa gccagatttg aagagccaaa attttatgtt atcttgcagt gatgacaaaa    16620
ctgtcaagct atggtcaata aatgttgatg attactccaa taaaaactcc agtgataacg    16680
actccgttac taacgaggaa ggtttgattc gtacttttga cggtgaatct gcatttcaag    16740
gtatcgattc gcacagagaa aactccacgt ttgccacagg tggggccaag atccatcttt    16800
gggacgttaa cagattgaag ccagtttccg atctatcatg gggagcagac aacattacta    16860
gtttaaaatt caatcaaaat gaaacagata tcttggccag tactggtagt gataattcta    16920
ttgttcttta cgacttgaga accaactccc ccacacaaaa gattgttcaa acaatgagga    16980
cgaatgctat ttgctggaat ccaatggagg ccttcaactt tgtaactgcc aatgaagatc    17040
ataacgccta ctattatgat atgaggaatt tatcacgttc attgaatgta ttcaaagatc    17100
acgtcagcgc agtaatggat gttgactttt ctcctacggg ggatgagatt gttactggtt    17160
cgtacgataa gagtatcaga atatataaga cgaatcacgg acattcgaga gaaatttatc    17220
atacgaagag aatgcagcat gttttccagg ttaaatattc catggattct aaatatatta    17280
tcagtggatc tgatgatggg aatgttaggc tatggagaag taaagcttgg gagaggtcta    17340
atgtcaaaac tactcgtgaa aagaataaat tagaatatga cgaaaaatta aagaaagat    17400 ttagacatat gccggagatc aaaagaatca gtagacatag acacgtgcca caagtcatca    17460
aaaaggctca ggaaattaag aacattgagt tgagttctat taagagaaga gaagctaatg    17520
aaaggcgtac tagaaaggat atgccataca tttccgaaag gaagaaacaa atcgttggta    17580
ccgtgcacaa atatgaagat tcaggaagag ataggaaaag aagaaaggaa gatgacaaac    17640
gtgatactca agaaagtag ttattctgtt ttatgttgtc tgtatataca catatgtaca     17700
atatttgcat ttttttaatt tttaattcac atgtatttga taaatgttca cgccagtccc    17760
gttaaattaa aattaccatt ttattagatt atgaatttat atatgaatac attgtgtcgt    17820
aatggtagaa gaagttgaaa aaaaaaatgt caagggacag catgggtaca gtgtgttgag    17880
ccaaaaaaaa aaagaaaaaa aagaaaaaaa cttttttgttc tctggttctt ttcttcatct    17940
tcttcatctt cattctttgg tagcgggggc cacaagaaat tcgggcgaaa gtgctcatta    18000
tattgttaca tccaaaattt tgcccacatc cagtgaggtt ttcacagaaa ggtcttctaa    18060
```

```
aagaggaata atatctaata attcgttatc atgagtatct gagaaccagg acgaaatcgg    18120
tattgcatgt tggggatgaa aaatataaga tgccggagag ttatcgagaa tgatgatatc    18180
tgataacggc cttccaatct gggataagtt ttttatatag tttccttcat agttatagca    18240
agcctctctg aataatctgt gatgaatgac tttatctgtg tctaatatat caagcaaagg    18300
atcaccgtat cgagagacac tagccgtgaa gactacaacc tcgaataatt ttccgactct    18360
ttccaaaaat tcttccacac caggtctttt aatgacatag acattgtgta cttggtcatc    18420
tatttccaca gacaaaacaa aatccgcaga tcgtaagtat ttgaaagaag agtgtaccaa    18480
ggtttcatcc aggtccagta ttaggcattt cttgccctttt gtactttcat cttgtggggg    18540
gagcagagtg ttgtaacctg gtgcatgata ctggccctgc tgcaaaagcg ttagatcaat    18600
atattcttca tcttcatcgt cttcgtcgtc ggcatcgttg gaagtttcac tggcttgaga    18660
gctgctactt accctactca aattcatatc ttggataaga tggtcagacg atacttgtac    18720
agtaggccct cgctgctgcg actgcgactg cgactgtgac tgtgactgtg actggggttg    18780
tggttgtggt tgtgactgtt gttgttgttg ctgctgttgt tttttctgcc tggaagtatc    18840
tttcacagca tctccttttt cctgtacaat gccacgactg cgacggttat cttcatcgtc    18900
gatctcttca tcttcgtcaa cctcgtattt ttcctcgtaa agatcatctt tactaattcg    18960
cttctctact tttgtcatat tattagtagt agtggcggtg acggctgcag tcggcgacga    19020
tggcttcttt ttttcattat cgttcgtgct tatcccagat ttaccggtgg atcgttcagt    19080
ggaactgaaa gtagcggctg aatttgtctt agaaggagga gagtttgtct gatgtacgcc    19140
acgggttcgg cttttcgtgt tggaatgttt aacgcttctg ttttttattga gagaactgct    19200
ctgttgttgc cgataagcag aattggaatt ggattgtgtc gtctcggaag agcagcacag    19260
tattgacgat atgaaaccca tactgttttg ctacttattg ttgttaaagc ttacgaacac    19320
gaatgtaggc aaataaaaag cttggataaa cgcacaatga aggggaagt gcgattgatt    19380
atgctataag gaatgacacg aagagagcag actataggct aggcaggcga taaggaagg    19440
agttgtactt gacgacaacg taataaagag ttcaatgaaa gagtattgtg agcagtatgg    19500
ttcaacgagc acttcttctc gacacctatt tctatacttt ttcacttaat atacactaac    19560
taatcccaga cttttttttt tttccgttct tccagaaaaa aaaagaaaca aagcaagcgt    19620
gccctgactt agggtttcct aaaaaagtta ttaggtttgt gtcacgtgat acgtcctttt    19680
ctggtcacgt ggtcttagaa cactcttaag gggccaagca caagaggaca gtgctagcag    19740
tagaagtggt gtagtagtga tgaggtaatg ttaattgtgc atcgcacata tttacaggta    19800
gtatatacta tagtttgtga atacctattc ttatatatac aagaaatggt tgtcggcaga    19860
ctgtcagtaa gactaatttg cacttggaac ttcgaagcca taaccettca tgcactcttt    19920
gtactttttca atgaattcct tgcatttttc agagtcttgt ccattgaata agatgcatgt    19980
atcccgctcc tcctttctg gcttacaaac gcaacatggc ttaggtttgt cctcgcactc    20040
cgcgtggttt tcttgttctt gtttcttgtc agtttcagtc attgggtata attgattgtg    20100
tagttatctg attgtgtaca ctaaaatttt gtttagttgt actagagaca agtagttagg    20160
tggttactag attctgattc gccgctatat atcgtcattt tatctttttt tgaaggagat    20220
aggtagggtt ataacattat ccgggtaatg atttgaaaaa aaattttcaa aaaatgcgat    20280
gagatgaggt tgaaaattgt aagttagaat atgcttagat agtatgagta tttacgttgg    20340
taacttgggt ttcgaattgg agctgtgtgc ctacaacagc gtcttatata tatactatgg    20400
tggtaggaac taaaaaatac tctaatttgg actttgtccc tacaatcagt gacagtgaag    20460
```

```
acgatgttcc aattctagat tcttctgatg acgaaaagt cgaggctaag aagactacga   20520
agaagcggaa gggtaagaat aacaagaaaa aggttagtga gggggataac ctcgatgagg   20580
atgttcatga ggacttggac gcggggttta agtttgattt ggacgccgat gataccactt   20640
cgaacttcca aggctggaac tttctagcag agggcgagtc aataaggac gatgccgaag    20700 cttttgtgaa gaaggacgtt gacttggata agattattag aagaaaggt gggctggtga    20760 aaatggccca tattgatagt aaacaagaag aagaaaccga gaaagaaaaa gtagaaaaag   20820
aaaacgatag cgacgatgag gaattagcaa tggacgggtt cggtatggga gctcccatga   20880
acaatggaga cgaaaatcag tcagaagaag aagaagaaga ggaggaaaag aagaggaag    20940 aggaggaaga ggaggaacaa gaagagatga cgttagaaaa aggcggcaaa gatgacgaaa   21000
tagatgaaga agacgattct gaagaggcaa aagccgattt ctatgcgcct gaaactgagg   21060
gagatgaagc taaaagcaa atgtacgaaa atttcaacag tttgtcttta tctcgtccgg    21120
ttcttaaggg ccttgcaagt ttgggttacg tcaagccttc ccctattcaa agcgccacaa   21180
tccccattgc cttattgggt aaagacatca ttgccggtgc tgtgactggt tccggtaaga   21240
ctgctgcgtt tatgattccc ataatcgagc gtttgttgta taaaccagcc aaaatcgctt   21300
ccaccagagt tattgttcta ttgcccactc gtgagttagc tatccaagtc gctgacgttg   21360
gtaaacaaat tgcacgtttc gtctccggta taaccttggg tctggccgtt ggtggtttga   21420
acttgagaca acaagaacaa atgttgaaat ctcgtccgga catcgtcatt gctaccccag   21480
gtagattcat tgatcatatc aggaactcag caagttttaa tgtggactca gtagagattc   21540
tggttatgga tgaagccgat agaatgttag aagaaggttt tcaagatgaa ctgaacgaaa   21600
ttatgggcct attccaagc aatagacaga acctattgtt ttctgctaca atgaactcca   21660
aaattaaaag tttagttagt ctttctctaa aaaaccagt aaggattatg attgatcctc    21720
caaagaaagc tgctactaag ttgacacaag aattcgttcg tattcgtaaa agagaccatt   21780
tgaagcctgc cttgttattt aatttgatta ggaaattgga tccaacgggt caaagagga    21840 ttgtcgtttt tgtggctaga aaagaaactg ctcataggtt aaggattatc atgggtcttt   21900
taggtatgag tgtgggtgaa ttacacggtt ctttaaccca agaacagcgt ttagattccg   21960
ttaataaatt caaaaatttg gaagttcctg tacttatctg tacggatttg gcctccagag   22020
gtcttgatat ccccaagatt gaggttgtta tcaactacga tatgcccaag agttatgaga   22080
tctacctgca tagagttggt cgtaccgcca gagctggtag ggaaggtcgt tccgtcacct   22140
tcgtcggtga atcatctcaa gatagaagta ttgtacgtgc tgctataaag agtgtagaag   22200
aaaataagtc cctaactcaa ggtaaagcac ttggtagaaa cgtagactgg gttcaaatcg   22260
aagaaacaaa caaacttgtt gaatccatga acgatacgat tgaagatatt ctggtggaag   22320
aaaaggagga gaaggaaata ttaagggctg aaatgcaatt aagaaagggt gaaaatatgt   22380
tgaagcataa aaaggaaatc caggcaagac caagaaggac atggttccaa agcgaatcag   22440
ataagaaaaa ttccaaagta ttaggtgctt tatcaaggaa caagaaagtc actaacagca   22500 aaagagaaa gcgtgaagaa gctaaggcag atggcaatgg tgcacgttct tatagaaaaa   22560
ccaaaaccga ccgtattgca gatcaagaaa gaacttttaa aaagcagaag agtacaaatt   22620
caaataagaa gaagggcttc aaaagccgta ggtaataatt ttcatcgtca ttatcataaa   22680
atatcaacat acttatcact gtcattatat tattaatact ttgtatttaa atatcattaa   22740
ttcatctaat aaacagggga ttagtcaaaa attccttttt ttttgttgaa tctgtagaag   22800
tgagtattaa taaactgcaa gctatatgct atattaaaag gattttcaa gtacaaacga    22860
```

```
actgaatgga gactcaagct acttgcggga aagaattaca aaattacatt ccattctagt    22920 aaaaaaagt tataaataaa aaaaaatcgt ctgacgacaa atttgtatct taatcaaaat     22980
aaaaattttg ggttactttc tttaacgttt ccaagttata aaattcttca tcttcgtcct    23040
cgtcgcttgg ttcaggtgga ggcactatga tgtcctgacg aacgttcaaa tttatcatct    23100
gaacattttt cctcaaatca aataaagtgt ctatttgttc tttcgtgtct tctgatatat    23160
cttcatgctg gaatggagat atcaatttca atccgtctag ccatatatat cttccctctt    23220
ctgtgtctaa ataaaatttc aaaactgtcc tgtcgttacg atcttttaat tcaactccag    23280
tgtacacatt ggcttcatct aatttgatgt aaacattact gctcgtccga cgactcggtg    23340
tagtaagttc tatgcttttg aaagaggtta tatgtttcaa acaacaact tttgttctgc     23400 cattagctaa tgcctcagaa cctggacttg ttaaaatttt attgtcgaat agataaggta    23460
aatcgtttgt ttgtgtttcg aattctctgg ctaataaatt tgcgtggtta tctgaaacta    23520
tgaggaagta gactttaggc gtgccagctt caggattcag tgggttctct gcgtaaaccc    23580
acgttccctt ttgcaattga agaagtcttt gatgacgaac gtaatcacga acctggcctg    23640
atagcatggt atcgaagcta gcgatactag atgaccaggt tcgatactgt tctttttttga   23700 ttgagtctaa ttgtaatgtt cttgcaaatt tatatctcat agagtcaagt gcaacaactt    23760
gggtcttgag aagggatttc gtctgtattg ctgcttccaa atcactggat gacaaacaaa    23820
catattttaa agtgataata gctaaattta acagtgaaac caaatcactt tgcgattttg    23880
ctaatgattc tatccaaaat ctcaaaaaca actcgagtgt tttgtaaaaa catgtttgtc    23940
gattgagaac agcggtagca atttgtaatt ttaaatcacg ctctgagtct gagtattggt    24000
tctctttttt cccacttaga ttgaaaagtc ttctaaattg gtctgaaagt ttaaatattg    24060
cttcataaag agggaaatcg ttctcgccaa acaacaattg ttcagtgtaa agtctcttga    24120
aagacccatt aggactgttt aagaatgtga atgtatcata cgcatttaat aaatttatac    24180
tgggaagatc gcccatttcc atttctaacc cttttttggaa tacggagtta tctttgatgg   24240
ctgtaagaag atcagcttta agcgaacagg aataatcatc aatactaacc gaagatagaa    24300
aatttattag cctctgcttt aacggtacaa attcttcaag gattagtggt tgcaagtctt    24360
ctatgtaaag taattcagac atggaagctg gaaagtttata ctgaaatagc aaaatgagga   24420
ttctgggtac aaattctacg gcgtgtgata gtgatgtctc acataatgta agtgagcatt    24480
ttaaaaatag ggttatgcat agtatagtgt ccgtaaacaa cggtatatga ataggtcttt    24540
gggacaaaag ttgtaaaagt attccaatga gctgagagtt ctctctggag atgtggcaga    24600
tgctcacaat aacttcattc ttattagaat cttggcattt aagggctaca ttaaaaatcc    24660
taatgagatt tgctaccaac gtttctgacc ttagcttttg gcaattatca cacaatatag    24720
cccaaaatcg ggaatctgga attacggttt tacataggta ttttttcatca caaggagga   24780 tatagtttgc caataacttt tcgtattcat cacttgtctt gttcaaattt ttattactga    24840
tcagcgtatg atagcaagct tttgattgtg cactcgtaag tgacttgact ggcttttccta   24900 atttaggatt cagtagcact tttatgtttt ccaagctttc atctggcatc tgcctgttat    24960
gcttcattgc ttatgccgtt atttgaggtt actttaatct attttcctac tgatgacaca    25020
attgagtcaa tccaacgtgg aacgggttgc ccttgtatac atttcagttt acttcttttc    25080
atgtatttcc ttaatagttt attttttcac tttctgccta tccgtttcaa ttccgaagaa    25140
ccgtcaacat ccaataaaga tcatctacaa caataagtgc ccctcataat tttctcaatg    25200
agatgaaaga actttgagag agtcaatata atacctgtag ccttttttctg aaaatgactg   25260
```

```
atagtgagaa tgaatccacc gaaacggatt cgttaatgac gtttgacgat tatataagca   25320
aagagctacc tgaacattta cagagactaa tcatggagaa tttgaagggt tctactacta   25380
atgacttaaa gcaaacttca aacaactcag agtttaatgt cagtaaaaac gggagcttca   25440
aaggtctcga tgatgcaatt caagctttgc aaatgcaaag cgtgttgcat ccttcttcgt   25500
taggatcgtt agcaacgtcc tccaaatttt ctggatggtc gtttgctcaa gggttttttg   25560
taggacagct aagcatagtg ttgttgttca tcttttcct aaagttcttt atattcagtg    25620
atgagccatc taaaagtaag aatccgaaac ctgcagcctc ccgtcacaga tcaaaattta   25680
aagaatatcc ctttatatct cgcgaattcc tgacttctct tgttaggaag ggtgctaaac   25740
aacactacga gctcaatgaa gaggcagaaa atgaacatct tcaagaacta gctcttattt   25800
tagagaaaac ctattataat gtcgacgtgc accctgcaga gtcattggac tggttcaacg   25860
ttttagttgc ccaaataata cagcaattcc gcagtgaggc ttggcacagg gacaatatcc   25920
ttcattcctt gaatgatttt attggaagaa atcacccga tctgcctgaa tatttggata    25980
ccataaaaat aactgaactg gatacaggtg atgatttccc catttctcg aattgcagaa     26040 tacaatattc gccaaattca ggaaataaaa agctagaggc taaaattgat atagatttaa   26100
atgaccactt aactttagga gtagaaacaa aactattact taactatcca aagcctggta   26160
ttgccgcact ccccataaat ctagtagtgt caattgtgag gtttcaggcg tgtttgaccg   26220
tatctttaac taatgcagag gagtttgctt ctacttcgaa cggtagcagt agtgaaaacg   26280
gtatggaggg caattcagga tacttttga tgttttcttt ttctcctgaa tatagaatgg     26340
aatttgaaat caagtcgcta attggctcac ggtctaaact tgaaaatatt cccaagatcg   26400
gcagtgtcat tgaataccaa ataaaaaaat ggttcgttga acgatgcgtt gaaccaagat   26460
tccaatttgt caggttacca agtatgtggc cacgtagtaa aaatacgaga gaagaaaagc   26520
ctacagagtt ataaatattt atgtacaaat tttttgttct atcttttcc tatcttctct     26580 gcctcatttt tggtgttcca gttttggtta gtgcaagtgg ctattctcca agtgacaatc   26640
accaaataaa ttcattgaat acatattaag atcgaatttc aggtgatacg acttctccaa   26700
aaatgattgt tcttcttcag aaattcctag tttgtccctt ggtagccaaa tttcatccga   26760
atttctacaa atggagaaaa tatcatgaa agtataactt tcttgacaga attggtcctt     26820
cctttcctct gttagattcg acaagtattc caaagttggt atgcgttgag gcttcgattt   26880
tatttgtttg gagattttgg agtgcgtgat tactgttaga gcaaagacaa caagcattat   26940
agttgacaat gtgtattgat caaaagagt gaacagcccg agtaaacaaa attccatgaa     27000
ataaatgccc gcgtacaatt gcataagggc ctgtatgtac aatttaccga acgtttcaga   27060
atagttctct ttgttatatt ggtatttgaa caagtaactg aaagaaaaga aaaccatcga   27120
aaatgagatg caacataata ataatataat aggagcaaca acactgtata tgataccaat   27180
acagcccaac actgagaata taggataaat agatcctagt tggaaaaata aagatgtctt   27240
taacctctta aattgagcat gtggagtact ccttttccat ttatagtaga acaattcaaa   27300
aagtagctct tttattctta acaaattacc gcctgcataa gccattcccc taatcaaaac   27360
aaaagaacag aaaaagtttg cgcatttagg caagtcgttg gccaggagag cagggatact   27420
gacaggattg ttaagaagcc tctcaataat tatagaaaat ccagaagata ttgtaacaac   27480
tacgaaaaga tgaatgaaga caaagacgaa ataccaattc tggacatcag cttctatttg   27540
cgctccagtt ttcaacccatc gaaggtaact cagccaacgg aaaaagtagg gtacgatttc   27600
tattattatt attaaggtta ctattggaat caaattcttt gccacttctc ttataaatgg   27660
```

-continued

```
agattggaaa tgaattattt ttgtaaacgg tattagtgag gaaatatttg gtatttgtga    27720
tattaaccca aggaacgcga caggcaaaat ccagcctata atcacaaaaa ttcgcaatat    27780
atttgccgag aaatatttgg cacttttcca aagggtgat gaatcgagga tatttctcca    27840
aataatgtca ttaacattgg ggcctattat tacttttaaa ttttgggtgg gtagtctata    27900
cgaaagcaac tcacctataa cgtttgacaa taatgtggac ttgaaggtaa tgaacatctt    27960
atccatataa atgtctgtgc ccgacgataa atcgtcgggc agtgcctgct tggtttctga    28020
agttgctttc aaggaattta cttggaattt aatgagtttt tccttgcgta ttattttatc    28080
aaggattctg tatttccttt ctaatattgt ttctgtattt acatacagtt tagggtaata    28140
taacggaaag atgcttgact ttttccagcg cagacgaatt tttgtgcaat agtatgaaat    28200
tctaaattga gttaaaaata ccaattttt gtactgaaat aatagatggt ttttcaactt    28260
tgaaaagaaa atcttttgt gatttgctat caaatgcctg tgtattgaaa ctcttctaaa    28320
atatttctct aaaataatct caaagataat ttgttctttt gattttgta atttatttaa    28380 ctttatttct aatttgtgga cttcttcaa attttttgga atgaaatgcg tcacgccaaa    28440
gcaatcactg tgtagcggct gaaaaaaagt ttctaaagaa atactttggg taaccaattt    28500
acttgagaat ccttccaaat atagaatgtt ttggtattta cttttcgtca aaacggaata    28560
tcctagtcga ttaacgaacc tcagttccga agaaagaatg aagtgaaacc agagtacaac    28620
aaagatactc aaaaacaagt gacagattaa agtattcgat gaattaggtg atagatttga    28680
catggtccac ttgtcaagtt tacttgtcgt cctgaaactt tgctcataac gttcaccttc    28740
attttctttc aaaatatccc tggaaaaata atggattgga attagtattg gaatgttgat    28800
aattgataac actgcaaaaa agaatatcaa aagtttgaga aaccgtaaaa atagataatt    28860
gtctaggcca taccttcgt ttcgttcgaa ttttccata ggatctaaca ttcttccggg    28920
aagttgcttg agaaatgcaa ataatgacca ataattttt atttttttct tagcaaaaca    28980
aactttagaa cctggatgga ttttcagaac gacattggcc tgatatatag tcttgaatct    29040
tgatcttaaa ataataaga gtgacagctg aaataaaaag tacaaaaag aaaacaatat    29100 accagatatg aaccctttta gtgagattcc agcatgtctt tgcgcagatc caaatctttc    29160
tttgtcttga aatttattca gtaaattaaa agtcagttct ttagtagcat tcatcttctt    29220
ggtaagtctt tttcttgttt ttgaaaaaga gttcctgaag tttgtctact gtgaatatac    29280
tttgcacatt tgtttaattt ttaaacacgc tataatttgt gtcataaaga atttttgta    29340 gaatagcttt ttttttaata ggaaaaaaaa ataaaaaaag gtggaaaaga caatcttttc    29400
cagaaacttg aaactatact ggagatgaag ggttgtcgtt ggttgcgtta cgagacaggc    29460
ttgacaattt cacaagagta atgtttcatt acctgctgtt ttattatctt tatatttagt    29520
aagaccagca gaaacgctac acgtgatgat aatggaacta agcattctgt tagatggtaa    29580 gaatttttt taccttccat taccactaac gcctttttta gtgtcttttt gatatttact    29640
gacgtatttt tccgcaccgt aatttgaaga aaaagaaaag tgacaaaaga tggcattgtt    29700
tacatacaga gtcgtagtat cacaagagta gtccaacagg atgagcgacc ttaaccaatc    29760 caaaagatg aacgtcagcg agtttgctga cgcccaaagg agccactata cagtataccc    29820
cagtttgcct caaagtaaca aaaatgataa acacattccc tttgtcaaac ttctatcagg    29880
caaagaatcg gaagtgaacg tggaaaaaag atgggaattg tatcatcagt tacattccca    29940 cttttcatgat caagtagatc atattatcga taatattgaa gcagacttga aagcagagat    30000
ttcagacctt ttatatagtg aaactactca gaaaaggcga tgctttaaca ctatttttcct    30060
```

```
attaggttca gatagtacga caaaaattga acttaaagac gaatcttctc gctacaacgt    30120
tttgattgaa ttgactccga aagaatctcc gaatgtaaga atgatgcttc gtaggtctat    30180
gtacaaactt tacagcgcag ctgatgcaga agaacatcca actatcaagt atgaagacat    30240
taacgatgaa gatggcgatt ttaccgagca aaacaatgat gtatcatacg atctgtcact    30300
tgtggaaaac ttcaaaaggc ttttttggaaa agacttagca atggtattta attttaaaga    30360
tgtagattct attaacttca acacattgga taacttcata attctattga aaagtgcctt    30420
caagtatgac catgttaaaa taagtttaat ctttaatatt aatacaaact tgtcaaatat    30480
tgagaaaaat ttgagacaat caaccatacg acttctgaag agaaattatc ataaactaga    30540
cgtgtcgagt aataaaggat ttaagtacgg aaaccaaatc tttcaaagct ttttggatac    30600
ggttgatggc aaactaaatc tttcagatcg ttttgtggaa ttcattctca gcaagatggc    30660
aaataatact aatcacaact tacaattatt gacgaagatg ctggattatt cgttgatgtc    30720
gtactttttc cagaatgcct tttcagtatt cattgaccct gtaaatgttg attttttgaa    30780
cgacgactac ttaaaaatac tgagcagatg tcctacattc atgttctttg tcgaaggtct    30840
tataaagcag catgctcctg ctgacgaaat tctttcatta ttgacaaaca aaacagagg    30900 cctagaagag tttttttgttg agttttggt aagagagaac ccgattaacg ggcatgctaa    30960
gtttgttgct cgattcctcg aagaagaatt gaatataacc aatttttaatc tgatagaatt    31020 atatcataat ttgcttattg gcaaactaga ctcctatcta gatcgttggt cagcatgtaa    31080
agagtataag gatcggcttc atttttgaacc cattgataca attttttcaag agctatttac    31140 tttggacaac agaagtggat tacttaccca gtcgattttc ccttcttaca agtcaaatat    31200
cgaagataac ttactaagtt gggagcaggt gctgccttcg cttgataaag aaaattatga    31260
tactctttct ggagatttgg ataaaataat ggctccggta ctgggtcagc tattcaagct    31320
ttatcgtgag gcgaatatga ctatcaacat ttacgatttc tacattgcgt tcagagaaac    31380
attaccaaaa gaggaaatat taaatttcat aagaaaagat ccctccaaca ccaaactctt    31440
agaactagca gaaacaccgg acgcatttga caaagtagca ctaattttat tcatgcaagc    31500
aatcttcgcc tttgaaaaca tgggtctcat taagtttcaa agcaccaaga gttacgatct    31560
ggtagaaaaa tgtgtctgga gaggaattta gataaagaat gcacggataa ataagtaaat    31620
aaataaccat acatatatag aaccatagaa ccacgttttt gtaatgaaca gtctacctgt    31680
atctcatcat ttttctgtgt taactattat tattattat atcgaatgga gggtaatatt    31740
atgtataggt aaaataaata gatagtgcca tgatgcgcga agattggcaa tgggaaactc    31800
aagaaggcag caacaaaaaa ataaaggtgg cctattaatc acaatctatt gcctatatgt    31860
gctaggttat gggcaaattc ggcacgacaa ataaatcaac ggagaatctt ctgcgtgata    31920
aattcgtacc cgagacatct ccaactaata ttcccactga tgtactcatc aagcaagggc    31980
aaataacgga ttccaccgaa tcactaattc atggaggcgc agaaaggtat attgttaacg    32040
ctttaaagcc tatagaatta aataaaactg aaggcttttt cgaagacccg ccgttccatc    32100
ttccttctcc accggttgat tcgacaaatc tggagtatga agacgttacc gatcttccta    32160
agaatggttt acgatatgat ttgaatgata tatcgttga ggtaatcgaa gatttatacc    32220
gccagattga agcttttttg gttcatttca aactatccag aagtttttta caaattttca    32280
aaaactatgt caatattctt attcaagaag gcatcaatcc tttacgcgat gagtacttca    32340
caatattgga agatgaactg aaaggttttt tcactttcaa ttctgttata gaagagattt    32400
tagaaatatt tttaatccac cctcgcaaca aattcattgc attgtcccct gcagaatata    32460
```

```
cctacgctaa gaacaaaatc agaagacatt ttaatcactg gaagactgta tgtgaattga    32520
atgaagaggc aaacaggttt gcaaatcaag caaagctgag ggtacaggaa gccgtcttct    32580
atatttggag tgataaaaca ttaaaatact cacagatggc caacgatgaa gctgaaagtt    32640
ttaggaatac ttggctacta tttcgctcgt tccaacaatg gataacttta acacaaactc    32700
ttaaggagca gtcaaggtta gcagatcagg cctttttgaa taagatgttt aggaaaattt    32760
taaaggcaca agagcattgg aaacacttag aaactgttaa cactgacaac attaagaaga    32820
tatttttacg aacaacattt catatatgga agctaagaca taaagaaata aactaccacg    32880
ggttggaaag aaggattttc gaaagaataa aacagaaagt tataaactat gaatacaata    32940
agagcattgc agaaaaagtg aggtcgtttt ctctacaaag aaaatatctg aataaatggg    33000
aaaagaaaaa cattgaaaac gaagataaac ttggggcact ttatgaactg gagaataaat    33060
tcatcaaaca aaagtttttt cgcaaattaa accggtcatt tcaacatagt caacaagagg    33120
caattgcaaa gagtaaacta aatcagacac ttttgaggtg cgttttgag aagatgtggc    33180 tgaaaagatt cgaagaccat ctgcatttgt attcaattgt aagtctaaaa gaggctaacc    33240
tcgtgaagcg tattttcat tcatggaaaa aacttctata tattgacctc aaagcaagcg    33300
attattcgag gactaatttg ctcaagtcat cattgcgaag ttggaaactt gaagtaaagt    33360
taaaaatatt tgagcagaaa tgtaaaaaga gtattcaagc aagcgcgtat cgtacatgga    33420
ggaaaagaat acagtatggg aaaatatcga gcgaacatgt taaaacggca ttttgtgcaa    33480
aatatcttgg tgtgtggaaa aggaggatgc tacaaatgaa ttctatgaat gacgaagcat    33540 ccaaattta cgaagagggt ctcgtaaatg agtgtctagc tatatggaaa gaacgcctga    33600
ttaaaactaa ggaattggag gatagataca atttcttatg taagacacat gcaattttga    33660
ctgtaaaacg gacgctaatg catattgata atgttcattt gctatatacg aaactggcgc    33720
cctctatgga tagagtaaag ctttctaagg cctttttaaa gtggcggaaa gccacaaggt    33780
tcaaagtcag gcataagtta aacgatattt tacacgttta tgaaaagagt aaagagcgcg    33840
aacttcaaag ccaactgttc aacgcttggc gaaatagatt ttgcttctac acagaagaat    33900
gtaacattca ggctatttca aagagaaact accagcttga aaaaatggtg ctgaagaaat    33960
ttagagaaag acttttagag atagtaaaat cagaagaatt agcagacgaa gttcgcgaag    34020
aatttgtgtt agtcaagacg tttttatattt ggaaaactca tctagacgaa atattttata    34080
tgagtacatt attggaacaa tcggaagcta ataacaatt cataattaca tccaaattct    34140
tgaaaatgtg gagtcttcga ttcctaaaaa ttaagcgtaa tgatgagaca gtcgaggtgt    34200
ttcgtcatcg gtgggacagg gccactgtaa ggggattgtt attattatgg aaaaatcgtt    34260
cagacagttc tccaaagaga aggaaggact tcaatcttaa acatgaacta aaaactccca    34320
taagatcaga ctctcaaaac gcctcaacca taccaggctc agaaagaata aagcagcaca    34380
gaatggaagc gatgaagtcg cattatagca gggcaagaag agccatacca agtccggtga    34440
aatcttccag tgttcttgat tctacagcta aaaaacagat caaccttgaa agtacgacag    34500
gcttaaacgg atctccgacg cgaggaaaac ctctaaggta ttctcctagg cgtaccacta    34560
gaaacatgcc atccaaagtt gaccatattg attttggcag aatacccgct gtacctttta    34620
gcctaagcgc caattctcct aaaatcgatc aagatatgga ttatataaga gagcatgata    34680
aatccccgtt aagtcgtaaa cgtcaataga tatatatatt atgtacgtat gtatgtgtgc    34740
atatgtagtc gtaaccttc ttgcttctga gatgcataca attactaata atattctcca    34800
```

```
ggtctatgaa aacatcacaa catactatac ttttcgtgtt cgcgttgtaa gctataatgg    34860
aaaatggacg ccataacgca ttacttaaca aactacagtt tgtcaataga gttgtccagt    34920
agagttaaaa ggtcaattca accggtcttc aataagacat gtcactgaat gacttcctaa    34980
gttccgtgct acctgtcagt gaacaatttg aatacttatc gttgcaatct attccgttag    35040
aaacccatgc tgtcgtaacc ccaaataagg acgacaaaag ggtcccaaaa agcacgatca    35100
agactcaaca cttctttagt ctatttcacc aaggaaaagt ttttttttca ttagaagtgt    35160
atgtgtatgt cacgctttgg gatgaagcag atgccgaacg gttaatattt gtatcaaagg    35220
cagacactaa tggttattgt aatacgaggg taagcgttag agatattaca aaataatat    35280 tagaatttat attatcaatc gacccgaatt actatcttca aaagtaaaa ccggcaataa    35340 gatcatataa gaagatatcc cccgagctga ttagcgcagc cagtacgcca gcaagaactt    35400
taaggatttt ggctagaagg cttaaacagt caggcagcac cgttttgaaa gaaatagaat    35460
ctccacgttt tcaacaagat ctttatctct cattcacctg tcctcgtgag attttgacca    35520
aaatttgttt atttactaga cctgcatccc agtacctctt cccagattct tcaaaaaaca    35580
gcaaaaagca tatactaaat ggcgaggaac taatgaaatg gtgggcgttt atttttggata   35640 gattactaat tgaatgcttt caaaatgata cacaagcaaa attaaggata ccgggcgaag    35700
atcctgctcg agtaagatca tacctaagag ggatgaaata tccactatgg caagtgggtg    35760
atatatttac ctctaaagaa aattctcttg cggtatataa tattccatta ttcccagacg    35820
atcctaaggc tagatttata caccaattgg cagaggaaga tcgcctcctc aaagtaagct    35880
tatcatcctt ctggattgaa ctacaagagc gtcaagagtt caaattaagt gtcacatcat    35940
ctgtaatggg tatttcggga tactctcttg ccactccatc tttatttcca tctagtgccg    36000
atgttattgt accgaagtca aggaagcagt ttagggcaat caagaagtac attactggag    36060
aggaatacga tacagaggaa ggcgcaatag aagctttcac caatattcgt gattttctat    36120
tgctcagaat ggcaacaaat cttcaatctt taacagggaa gagggagcat cgggagagaa    36180
atcagccggt tcctgcaagc aacatcaaca cgttggcgat aacaatgcta aaaccgcgta    36240
aaaaagctaa agccttgcct aaaacttgat acatattgat atttattatt tagtacacgt    36300
atgtagcatc gatcttagaa aatgcatgtt tgtatttatt gttagtacct tgatcgccac    36360 cttttctaggt aatgataggt cctcaacttt tactacgcgg tgcacgcctg taaggtcggg    36420
caaaacaaag tgtgggaaca ataaataaga gggtaggatg aaatattacc tttactctac    36480
tgctcaggtt ggccacaatt tgctaaagag tttatcatta agtagctacc agcgaatcta    36540
aatacgacga ataaagaatg gctagtttag aagatcttat tcctactgtc aacaagctgc    36600
aggatgttat gtacgactcc gggatcgata cactcgattt gcccatttta gctgttgttg    36660
ggtcacaatc ctccgggaaa tcctcgatat tggaaacgtt agttggaaga gatttttac    36720 ctaggggtac tggtattgtc acaagaagac cgttagttct tcaacttaat aacatatctc    36780
caaattctcc tctaatagag gaagatgata actcagttaa tccacatgat gaagttacaa    36840
aaatatcagg attcgaagct ggtacgaagc ccttggagta tagggcaag gaaagaaatc     36900 atgcagatga gtgggggaa ttcctgcata taccaggaaa acggttttat gatttcgacg    36960
atatcaaaag agaaatcgaa aacgaaacag cgaggatagc cggtaaggat aagggcatca    37020
gtaagattcc gattaatttg aaagtgtttt cccctcatgt tttgaatcta acgctagtag    37080
atttgcctgg gattacaaag gttcctattg gggaacaacc acctgatatt gaaaagcaaa    37140
tcaagaattt gatcctagac tatatagcca ctccaaattg tttaatcttg gccgtctctc    37200
```

```
cagctaacgt tgatcttgtt aattctgaat ccttaaagtt ggccagagag gtagaccctc    37260
agggcaaaag gactattggt gtcattacca aattagattt gatggattct gggactaatg    37320
ctctagatat cttgtctgga aaaatgtatc ctctgaaatt ggggtttgtt ggtgtagtga    37380
atcgctcgca acaggatatt caattgaaca aaaccgttga agaatcattg acaaagaag     37440 aggactattt caggaaacat ccagtctaca gaactatttc aacaaagtgt ggtacgcgtt    37500
atttagctaa attgctaaac cagacattat taagccacat tagagacaag cttccggata    37560
ttaaaaccaa gttaaatacc ctgatctctc aaaccgaaca agagctcgct agatacggtg    37620
gcgtaggagc tactactaat gaaagcagag ctagccttgt tcttcaacta atgaataagt    37680
tttctacaaa cttcatttca tctatagatg gtacatcctc cgacattaat acgaaggaac    37740
tctgtggtgg tgcccgtatt tattacattt acaataatgt ttttgggaat tctttgaagt    37800
cgattgatcc aacttctaat ttatccgttc ttgatgttag aacagcgatt agaaattcta    37860
ctggtccccg tcctacatta tttgtacctg agttggcttt tgacctattg gttaaacctc    37920
aaattaaact tttactagaa ccatctcaac gttgcgtcga gttagtttac gaggagctga    37980
tgaaaatatg ccataaatgt ggctccgctg agctagctag atatcctaaa ttgaagagta    38040
tgttaataga agttataagc gaactactta gagaaaggtt acaacctact cgctcttacg    38100
ttgaaagctt gattgacata catcgagcct acatcaaatac taatcatcct aatttttttaa    38160 gtgcaacaga agcaatggat gacatcatga aaacgcgtag aaaacggaat caagagttat    38220
tgaaaagtaa gttgtctcaa caggagaatg gacaaaccaa cggtattaat ggtacttcat    38280
ctatctcttc gaatatagat caagattctg ctaaaaacag tgactacgat gatgatggta    38340
tcgacgcaga atcgaagcaa acgaaggaca aattttttaaa ttatttcttt ggcaaggata    38400
aaaagggtca acctgtgttc gatgcatcag acaagaaaag atccattgcc ggtgatggaa    38460
atattgaaga ttttagaaat ttacaaatat cagattttttc actgggcgat atagatgacc    38520
ttgaaaacgc tgaacctcca ctgaccgaga gagaagaatt ggagtgcgaa ttaattaaac    38580
gtctgattgt ttcatacttt gatattataa gagaaatgat tgaagatcaa gtaccaaagg    38640
cagttatgtg tttactcgtc aattattgta aggattctgt tcaaaacaga ttggtaacca    38700
aactctacaa agaaacactg tttgaagaac ttttagttga ggatcaaact ttagctcaag    38760
atagagaact atgtgtgaaa tcactcggag tttataaaaa ggctgcaacc cttattagta    38820
atattctgta attgcataat tcatctcatt tttgatctta cttcaacatt gcgggcgtga    38880
ttataggtca gtgtttattc ctttactcag ttgatgattt caaatgtgct ctcctctcca    38940 ttcttttttct tgttaataaa aatccataac taaataaata acaaatatta gcaatcgcaa    39000
aagtattaac taagctagag aaccttcact agagaagctc tacctaaagg tatagaacag    39060 gaaaagtgt ttttatttttg gcggacttcg tggaagattg ccttccatca ataataagcg    39120
tagtccatag gtacgatcat ttcctttttta accgttaagc aagcgacaag atgtattttg    39180
tttaccagcg aatgctctta tttatcttct gcgccttttcc aataatctaa ttatcaatgc    39240
tacgaatgat tatagttttta actagatgaa cgaaatttct aggttattaa agagtacgtt    39300
atgcatcaaa agaatatcag tcataataag cagatagacc ttctacatgg tttgtagaca    39360
accaaactgg tgtatgctaa tatcaacgag taaacgctta cttttctaaa gttgaatatt    39420
tgaagtacac acccgcgtaa agagttttta ccccgaaaac aaatttttat gcttgaaaaa    39480
tagctaataa aatgttttta ttgttcggat aacaaataca atagtgttat taaaaaataa    39540 aacttatttta aaaatagtaa tttaaattat tatttttattt taataaactt tttaataata    39600
```

```
tttattacac gtgatttaat atatcctgtt ttttttcat cattctcttt ctttcttatg    39660
ttaacctcgt actacaagtt ttctccttat aaaaagctga ctaaaattag agattgataa    39720
tcataaataa atttagtagc catttccatt tttacatttt gatttaatcg acactcaaag    39780
ttcttatttg aaagctagtt tagaacttat ttgtttgctc cttgatgaat ataatgagaa    39840
gaaattccac tcagattaaa tatgaagatt gttaacggca agacgctaaa agaaaaggaa    39900
aggaagtaga tgatggcaaa taaggtcact ttcttgttag ttacatatac tttcacagaa    39960
acttgaaaat aaccacaaaa cttaaaacga acgttatttt gttcaattgc ttaatttgtg    40020
aagatattat ctactactta aatgatatat taacacttat gaggtactga cactgcgacc    40080
gcccttttga tctgatccca cccttcgtat atctctgggg gtttgtatag cgttcacaga    40140
atatgaacct tcaaaagtgg gttgagaaag tggtgataaa tgcgctgttg ccgagtaaga    40200
agggttgtgg attatcggag agtgttgaat cagtggtgtt gttgctcgat catttctccc    40260
tctttgattt ttgtctttta cttttccacc cctggtaatt attatgcaaa acaataaaga    40320
aatggctatg gtaacaccta ttataacccc aaatccaacc gctatccctg gcaagcgcag    40380
atggtatttc tcgctgttta gccaagataa ggatatgggt ttgtcgatca gaaatatgca    40440
tgaacttttc aaattagtag tgcatcctgt tttaagaact ctaacttcct tggtccagtc    40500
gccctgtatg ctaacaaaaa cgttgtccag atgatctttt ctgcagttta gttttgtacc    40560
tagtttagtg ctaatggagc cattgcagtc tagtaggttt tgcgttacat tagcaggaat    40620
caaatggagt tcgaggaatt ttcttaagtt tgtcgagttc gccgtgatgc cacttaatgg    40680
aatagaagaa gccgttggaa ctaaaagcga gtactcttcg ttattccaaa tgattgaaga    40740
aaggtcataa aacaagttaa aaaagtcaaa tatttctttt gttccagtag tttctatcag    40800
ctcttttagg gatatctcca aatcgactgg aaaatccaat tggtctatag gatggataac    40860
tccctggttg aaaaatatat cggaactctc ctcaataata atactttcct ttatagtact    40920
cactgagatt ttcgtaaggt tttggcttcc cacaattttt tgtacgccaa tagatacaga    40980
atttccgtat aaattcttga cagtagtcga aatactataa ttgttggaat aaataaggtc    41040
ttcgaagatt aggttcctca taagtaaatt tagggcggtt ttgtttgacc tcaaatagtc    41100
tatagtcaaa tcattattgt cccatgaatt catacatgga agaagtatcg tgtacccctt    41160
atgatttgat ggtagatcca aaaggttaag ttccttcaag agcattaggg aaatagaaca    41220
gtggttttct ggtgctaatg acaacactaa gtcgcccggt aattgaagat catcgtcaat    41280
agaataaatg gacgtattac caatctcata aggttttgtg tttaaaatct tgaagcgacc    41340
attgatgtaa taacctttat tagaccttgt gattttgaac ttttggcagt gtccacctag    41400
tcttttagct gaagagcaaa aggcggagtc ataaatttgg gtaggtgcgt attgaatcgg    41460
gcgcaatgag gaaaagtcct gttcaaggtc aattttacct tctacaaaat ggtacagaag    41520
tgatggtttt gtgtacccac gatcctcatt aaaagaggct tgtggtacaa atatggtgat    41580
tttccttccg ttttgaatga atttttcaag gtctctgaag tataactcct ttacgaattc    41640
tgagcagttc aaaccgtgca agtacttttc agcatcaaac tgtatatgcg ttcgtaaaaa    41700
gtctaagtca gaaaatccat gcacgacgcc tatttcaaaa attctgtttg atatgggtga    41760
gtaatctgaa ttatttacac ttactgatgt accttctgaa ttactcttca taaaagtttt    41820
tcgattgttt ttattttcta aaattagttc cttgggtaaa ataccaccat acacgtcatc    41880
aataatgagt tcttgaagaa gggaagttct atctgcggcc catttggcct gagaaattgt    41940
attagattta cccaatttat tatatttgtc aagtagatag tttatttcga ttgtattgaa    42000
```

-continued

| | |
|---|---|
| gaattttcga aaattaacat ctaagggcac taaaactgtg gatgagtttg tatatgcatt | 42060 |
| atagtttgaa aaactgctga taaaatcact aaatatcttt aaatcttggg tttcttcatc | 42120 |
| tagttgtacc agcaactcat ttatttgagg ttgaattagt aaaagattgt taataccttg | 42180 |
| taatgaagca ttctggaaac taggcagcaa atcgggttcg acaacagcaa tttcattgac | 42240 |
| aaagcaatgg cgctcatgct ttctcagcaa taaaggtgct tttgcagctc ttttctccag | 42300 |
| gtaggtaccg ttttcaaggt ctctcacttg caatacccta tcatgaataa ggaaatcttc | 42360 |
| aatatggaaa tgctcctcaa attggtctgt ggtttggtcc cccttaataa atgctgaatt | 42420 |
| aatcggagca aaaagtgtaa agttctgtag ctcatttaag tactgtacgt gaccagtttt | 42480 |
| ctgaataatc cttaaaaaag ttgagaattc aacattttct gagaggatat ctattactgt | 42540 |
| gctaaatgga aaatcgtccc ctgggttttg tagaagtgct tgtgtaagcc ctaatatcgg | 42600 |
| cagtagccaa aaaatgtatt taattgtttg gattgccatg ttcatcaaag ggctccgttt | 42660 |
| gattcagtta atacatgctg tcactcacag cagcttagat aagaagccgt tttgtcttat | 42720 |
| tttctaggcc cttaatatac gcctaatggg gaagtccgac cgaacaaaat tctcctaccg | 42780 |
| ggttttcacg gtaatgttct tccataaaaa aagacaatat agtaagctgt taatattgat | 42840 |
| ttggtgaact tgaatctgat atttgtttct attgcttacg tataatactt ttgcggtaat | 42900 |
| tcattcaaat ttcatacaat gctaatattt atacaattct actcgacacg gcaaaaatga | 42960 |
| ttggctaacg ataatcgtgg ctctttatat acttaatata taggatctag ctatttagaa | 43020 |
| cactctttag atctagatga tagagagcgt agccccttg taactacagg acaataatgc | 43080 |
| ttttcaagaa gagcattatc ccataaggtt gctgcctctg ggttactcct tgaaggatta | 43140 |
| tcggcttcca ttatgaaatg accgttgcct attctatcct cggaagagta aaggcctgaa | 43200 |
| atttctggat atctattcat taatttatca ataaatttaa gaatggcaat acttgttttt | 43260 |
| tctggggtat ggctgatgca catgtacaat cttttggtaa acgccgtagc cctttcttta | 43320 |
| gtccctgatt tagagcggaa aaatacatgg tccagagcct ttagcagaag ttctgctttg | 43380 |
| gtagaaacgt taactgatgg ttttattatt tcgttattga gtgggtcagc caaccttagc | 43440 |
| gatctataag ataattcgat gtctgcatca agacagatat aaggtaatag cgcgtaaagc | 43500 |
| ccatcgacga atttggacaa atccacatta actttcatat attgtgtatt tgaaataagt | 43560 |
| gagaatgcac taacgataca aagcaaagcc ttacggacct cagcagagga aaggttatcg | 43620 |
| aattcagtgt cactaataag ttctttcatt acttcgagga agtcccctaa tagatc | 43676 |

SEQ ID NO 13
LENGTH: 3268
TYPE: DNA
ORGANISM: Schizosaccharomyces pombe

SEQUENCE: 13

| | |
|---|---|
| gaattcaact ttttttttta gaaaaacgct accagaagga caatctgttt tattttttcag | 60 |
| gaagaacatt tttctttctg tatttattga atagcgaagg atagggttga atagtgaaaa | 120 |
| caacgaagta ttactgtatt gcggaatagt cgcatacca caggttttag gtgagtccat | 180 |
| tgtgaaagtg attgacaaca tagtctagtg aaatactgta tgtaatatta cagttgcgta | 240 |
| gtgacaaaac gcgacgcgcc aaattcacag gtaatttcta ttgtagtagc ccattgttag | 300 |
| taaacaaaga aattcccaaa atggctaata atgggaaaac aagctttttt tttaaataaa | 360 |
| cgggtgtttt ctttatttta aaagcaggaa atactgaaa taacttaaga aggtatattt | 420 |
| cctcttttct ttcaaaaata aatgaatcgt ggaattgata gcattcatgg acccttacga | 480 |

-continued

```
aaatgaggtt tcaaacgacc gcaataagtg attatgagaa cagctctaat ccttcatttt    540
taaaattttc tgcaggagac actatcatag ttatagaagt gctcgaggac ggttggtgcg    600
acggaatttg ctcagaaaaa cgaggttggt tccccacgtc gtgcattgat tcttcaaaaa    660
ttcaaaattt tttttcaagt tttcattcat cgaatgagaa agacccaaat gctcaatgtt    720
gtgcgccgtt tcacgtagag gctcatcttc aagattctgc atggtttgag aaacacggag    780
tgcaagcgat aaatagtatc ccttcttcag aagagttctt aagaaaaaat cttcaaaatg    840
acattcacca ccttgtaaaa gggattctca ccaccgctgc cgctgtgtca caatctataa    900
aaaaggaagg cactcaagtg atcgttttttg gaattgaaac tgttcgtagt atggttctttt   960 catttccctt gataatcctt tctacattag atgaaaattt tctctcagaa gtcgcgcaag   1020
tgttctcctc attaaattta ttgccagagt tgagccgaat gggttgcact tatggtgaac   1080
tttgcatcag atttactaag cttttgaagc aattggctaa taagtttttg tttttcttca   1140
ggcccgatgt ttccttccct tcttactttt tgggctcttt gatagcgcat gaaatacatt   1200
tcttgccatg ggattttaat atgctctgtt ccaattctgt acaatcagca catacaaatc   1260
tccaacctga tattacttcc tttgttgcaa ttttgtcact ttcacacgaa gcttaccatt   1320
gcactgagaa tgaattttgg aatttagaag cacagaagct aactgaaaat acaacccaaa   1380
aagtactaca gctagttgcg gaagatgcac tagaagcttg gaaactagat attctagagg   1440
acatcgatag atgcattcaa tgttgtaggc gattcttgtc tgcaaatcaa gaataaaatt   1500
attcttcctc tgaaaataac ccttttttctt tcacttctca agatgttgaa gccttgaagg   1560
atgaactgtc ttctaactta tgtgatttat atttgtggag tatcgacttg gagcaaatct   1620
cacctagcga ttgtttactg gacaattatt ccctttttgt tgatttacta gtaaccttga   1680
aagtatccct tcttcggatc aagtcaataa ttgttcaatt ttcagaaaga attgtgtttc   1740
tttctctaga atacaaattc ctcacaaata tccaaccaga attgaatgat gcggagaagt   1800
cccaacttga tggttttgac ctcaataaaa ccaactggtt cgactctaaa ggattagttt   1860
gttatttaat gaaacagact tcaccagagc cattattgat ccgaaacctt ttgtttttcat   1920 tttggtcatg taatggtaaa attgaacaag atggaaaaat aaaaacagcc actttagtgt   1980
tcattataaa ttaccttcta aggacagata tagatagtac attttttact actatctttt   2040
taaacacata cgctagtatg atcagttctt cagatttatt ttccatactt ggagcacatt   2100
ttcggttcat ctgctcatta aattttggaa aaatttcttt tatttctcac gaattttacc   2160
gagttagtaa gaggttttttg gatatacttc ttatttggtt cgaatcgtat cttgttgaag   2220
agttggacaa ttccaagtca atattctttt tgtttaaaat ttataaagtt tttgaagtct   2280
ttgtagttcc acattttgca tctgctgaag aattattgca ttctttatca cacctacttc   2340
atcatccctc tacaaaaaga tcacataaaa tgctagaggg aaaagagcta tcccaagaat   2400
tagaggatct ttctctccat aattcccctg atccaattat atataaggat gaattggttt   2460
tacttctacc tcctcgtgaa attgcaaagc agttatgtat cttagagttt caatcatttt   2520
cacacatatc aaggattcag ttcctaacta aaatctggga caatcttaac agattctcac   2580
ccaaagaaaa aacttcgacc ttttatttgt cgaatcatct ggttaacttt gtgaccgaaa   2640
ccatcgtgca agaagaagaa cctcgcagac gtaccaatgt gctagcatat tttattcagg   2700
tctgtgatta tttgagagag cttaacaatt ttgctagttt attttccatc atttctgcgt   2760
taaattcctc acccattcat cggctgcgta agacatggga aaatttgaat agtaaaacat   2820
tggctagttt tgagcttcta aacaatttga cagaggcaag gaaaaatttc agtaattata   2880
```

-continued

```
gagattgtct ggagaactgt gtcttgccat gtgtcccttt cttaggtgtt tacttcactg      2940
atctgacttt ccttaaaact ggaaataaag ataactttca aaacatgatc aatttcgata      3000
agcgcaccaa agtcactaga attttgaatg agataaaaaa gtttcaatct gttgggtaca      3060
tgtttaatcc catcaacgaa gttcaagagc ttcttaatga agttatatcg agagagcgaa      3120
acacgaataa catctatcaa agaagtttaa ctgtagaacc acgtgaatct gaagatcaag      3180
ccttacaacg cttgctaatt gattctggca ttttttgaag cgtgaacgtt aacagtgatt      3240
taagttttta tgagcttgct tcgaattc                                         3268

<210> SEQ ID NO 14
<211> LENGTH: 3804
<212> TYPE: DNA
<213> ORGANISM: Rattus rattus

<400> SEQUENCE: 14
ccgacgaggg gcagtcgggt gcctctcgga gatgtttagt gcgtgaggtc tctctggcct        60
ccaagcacca tgcagaaagc catccgactg aacgatggcc acgtcgtgtc cctgggactg       120
ctggcccaga gagacggtac gcgcaaaggc tacctgagca agaggagttc ggacaaccca       180
aaatggcaaa ccagtggtt tgcgctgctg cagaacctgc tcttctactt cgaaagtgac       240
tcgagctctc ggccctcggg gctctacctg ctggaggca gtatctgcaa acgcatgccc       300
tcccccaagc gagggacctc ctccaaggag tccgacaaac agcatcatta cttcacagtg       360
aacttctcca atgacagcca gaagtcccta gagctgagga ccgatgactc caaggactgt       420
gacgagtggg tggcagcgat tgctcgcgcc agctacaaga tactggccac agagcatgag       480
gcgctcatgc agaagtacct gcacctgctg caggtggtgg agacagagaa gaccgtgggct      540 aagcagctgc gacagcagct cgaggatggc gaggtcgaga tcgagcgcct gaaggcagag       600
attgcaaacc tgatcaagga caatgaacgt atccagtcca accagctggt tgcccctgag       660
gatgaggaca gtgacatcaa gaaaattaag aaggtacaga gtttccttcg cggatggctg       720
tgccggcgaa agtggaagaa catcatccag gactacatcc ggtctcctca tgccgacagc       780
atgcgcaaga ggaaccaggt ggtgttcagc atgctggaag ctgaggccga gtacgtgcag       840
caactacaca tccttgtcaa caattttctg cgcccactgc gcatggccgc cagctctaag       900
aaacccccta taacacatga cgacgtcagc agtatctttc tgaacagtga gaccatcatg       960
ttcctgcacc agatcttcta ccaaggcctg aaggcccgta tcgccagctg gcccaccctg      1020
gttctggcgg acctgttcga catcctgctg ccaatgctta acatctacca ggagttcgtc      1080
cgcaaccacc agtacagtct ccagatccta gcacactgca agcaaaaccg ggactttgac      1140
aagctcctca agcagtatga ggccaagcca gactgcgagg agcgcacact ggagaccttc      1200
ctcacctatc caatgttcca gatccccagg tacatcctga cactccatga gctgctggcc      1260
cacacacctc atgagcatgt ggagcgcaac agcctggact atgccaaatc caaactagag      1320
gagctgtcca gggtcatgca cgacgaagtc agtgagaccg agaacatccg caaaaacctg      1380
gccattgagc gtatgatcac cgagggctgt gagatcctcc ttgacaccag ccagaccttt      1440
gtgcgccaag gttccctcat ccaggtgccc atgtcagaaa agggcaagat caacaagggc      1500
cgcctggggt ctctgtccct taagaaagaa ggtgagcgcc agtgtttcct gttctccaag      1560
catctcatca tctgcaccag aggctctggt agcaaactgc acctaaccaa gaatggcgtg      1620
atttccctca ttgactgcac tctactggat gatccagaaa acatggatga tgacggcaaa      1680
ggacaagagg tagatcacct ggactttaag atttgggtgg agccaaagga ttccccaccc      1740
```

```
ttcacagtca tcctggtggc ctcatccagg caggagaagg cggcatggac cagtgacatc      1800
atccagtgcg tggataatat ccgctgcaac gggctcatga tgaatgcctt tgaagaaaat      1860
tccaaggtca ccgtgccgca gatgatcaag tctgatgctt ccttatactg tgatgatgtt      1920
gacattcgct tcagcaaaac catgaattct tgcaaagtgc tgcagatccg ctatgccagc      1980
gtggagcgcc tgctggagcg cctgactgat cttcgcttcc tgagtattga ctttctcaac      2040
accttcctgc actcctatcg agtcttcacc gatgctgtgg tggtcctaga caagctgatc      2100
agcatctaca aaaagcccat cactgcgatt cctgccaggt cactggaact cctgttctcc      2160
agtagccaca acaccaaact tctgtacgga gatgcccca agtcgcctcg tgccagccgc        2220
aagttctcct cgccgccgcc cttggccatc ggcacttcgt ccccagtccg ccgccggaag      2280
ttgtctctca acattcccat catcacaggc ggcaaggcgc tggaactggc ttcgctcggg      2340
tgcccctccg acggctacac caacatacac tcgcccatat ctcccttcgg caaaaccacg      2400
ctggacacca gcaagctctg tgtggccagc agcttgacca gaacgccgga ggagattgat      2460
atgaccactc tagaggagtc atcaggcttc aggaagccga cctcagacat cttgaaagaa      2520
gagtctgatg atgaccagag tgatgtagac gacacagaag tgtctccacc aacaccgaaa      2580
tcattcagaa acagaatcac tcaagagttc ccactcttta actacaacag tggaatcatg      2640
atgacatgtc gcgatctgat ggacagtaac cgcagccctc tgtcagctac ctctgccttt      2700
gccatagcga ctgcaggagc caatgaaagc cccgcaaaca aggagatata tcgaaggatg      2760
tctttggcca acacagggta ttcctctgac cagagaaata tcgacaaaga gttcgtgatc      2820
cgcagagcgg ccaccaaccg tgtactgaat gtgttgcgcc actgggtcac caagcactcc      2880
caggactttg aaactgacga cctcctcaaa tacaaggtga tctgctttct ggaagaggtc      2940
atgcatgacc cagaccttct accacaagag cgaaaggcag cagccaacat catgaggact      3000
ctgacccagg aagaaataac tgaaaaccat agcatgctgg atgagctctt actaatgacg      3060
gagggtgtga agactgagcc cttcgaaaac cactcagcca tggagatagc agagcagctg      3120
accctgctgg atcaccttgt cttcaagagt attccttatg aggaattctt tggccagggc      3180
tggatgaagg cagataagaa tgaaaggaca ccttacatta tgaaaaccac cagacatttc      3240
aaccatatca gtaacttgat cgcttcagaa attctccgaa acgaggaggt cagtgcaagg      3300
gcaagcacca tcgagaagtg ggtggctgtt gccgacattt gccgctgcct gcacaactac      3360
aatgctgtgc tggagatcac ttcctccatc aaccgcagcg caatcttccg actcaagaag      3420
acatggctca aagtttctaa gcagacgaaa tctctgtttg acaagctcca aaagcttgtg      3480
tcatcagatg gccgatttaa gaacctcaga gaaactttgc gaaattgtga tccaccctgt      3540
gtcccttacc tggggatgta cctgaccgac ttggcattcc tcgaggaagg aacacccaat      3600
tacacagagg acggcctggt caacttctcc aagatgagga tgatctccca tattatccgc      3660
gagattcgcc agtttcagca gactacttac aaaatcgagc cccagccaaa ggtaactcag      3720
tacttagtgg atgaaacctt tgtgttggac gacgaaagtc tgtatgaggc ctccctccga      3780
attgaaccaa aactccccac atga                                             3804
```